United States Patent
Veidal et al.

(10) Patent No.: US 9,606,130 B2
(45) Date of Patent: Mar. 28, 2017

(54) FIBROSIS BIOMARKER ASSAY

(71) Applicants: Sanne S. Veidal, Olstykke (DK); Morten A. Karsdal, Kobenhavn O (DK); Diana J. Oersnes-Leeming, Klampenborg (DK); Natasha Barascuk Michaelsen, Gentofte (DK); Helene Skjot-Arkil, Kolding (DK); Antonio Segovia-Silvestre, Copenhagen (DK); Efstathios Vassiliadis, Hammel (DK)

(72) Inventors: Sanne S. Veidal, Olstykke (DK); Morten A. Karsdal, Kobenhavn O (DK); Diana J. Oersnes-Leeming, Klampenborg (DK); Natasha Barascuk Michaelsen, Gentofte (DK); Helene Skjot-Arkil, Kolding (DK); Antonio Segovia-Silvestre, Copenhagen (DK); Efstathios Vassiliadis, Hammel (DK)

(73) Assignee: Nordic Bioscience A/S, Herlev (DK)

( * ) Notice: Subject to any disclaimer, the term of this patent is extended or adjusted under 35 U.S.C. 154(b) by 0 days.

(21) Appl. No.: 14/960,713

(22) Filed: Dec. 7, 2015

(65) Prior Publication Data

US 2016/0091502 A1    Mar. 31, 2016

Related U.S. Application Data

(60) Division of application No. 12/749,652, filed on Mar. 30, 2010, now Pat. No. 9,206,464, which is a continuation-in-part of application No. PCT/EP2008/064946, filed on Nov. 4, 2008.

(60) Provisional application No. 61/289,081, filed on Dec. 22, 2009, provisional application No. 61/211,467, filed on Mar. 30, 2009.

(30) Foreign Application Priority Data

Nov. 5, 2007 (GB) .................................. 0721713.6
Nov. 20, 2007 (GB) .................................. 0722748.1
Feb. 15, 2008 (GB) .................................. 0802814.4

(51) Int. Cl.
*G01N 31/00* (2006.01)
*G01N 33/53* (2006.01)
*G01N 33/68* (2006.01)
*C12Q 1/37* (2006.01)

(52) U.S. Cl.
CPC .......... *G01N 33/6893* (2013.01); *C12Q 1/37* (2013.01); *G01N 2333/4737* (2013.01); *G01N 2333/78* (2013.01); *G01N 2800/085* (2013.01); *G01N 2800/32* (2013.01); *G01N 2800/50* (2013.01)

(58) Field of Classification Search
CPC ...... A61K 38/00; A61K 39/00; G01N 33/582; G01N 22/6893; C07K 14/705; C07K 16/18
See application file for complete search history.

(56) References Cited

PUBLICATIONS

Bigg et al., (The FEBS Journal, Mar. 2007; 274(5) pp. 1246-1255).*
Tascilar et al. (Annals of Oncology 10,Suppl. 4:S107-S110, 1999).*
Tockman et al. (Cancer Research 52:2711s-2718s, 1992).*

* cited by examiner

Primary Examiner — Lisa Cook
(74) Attorney, Agent, or Firm — Benjamin Aaron Adler

(57) ABSTRACT

Provided herein are methods of diagnosis or of quantitation of fibrosis. An immunoassay is conducted to measure neo-epitope containing protein fragments of collagen type III, collagen type I, collagen type IV, collagen type V, or collagen type VI, elastin, biglycan, decorin, lumican, versican, perlecan, neurocan, brevican, fibromodulin, serglycin, syndecan, betaglycan, vimentin, or C-reactive protein naturally present in a biofluid sample obtained from a patient. An above normal elevation of the measured protein fragments in the patient is associated with the presence or extent of fibrosis.

5 Claims, 14 Drawing Sheets

FIBROSIS BIOMARKER ASSAY

CROSS REFERENCE TO RELATED APPLICATIONS

This application is a divisional of pending application U.S. Ser. No. 12/749,652 which is a continuation-in-part of PCT/EP2008/064946 filed on Nov. 4, 2008 which claims Convention priority from GB0721713.6 filed in the United Kingdom on Nov. 5, 2007, GB0722748.1 filed in the United Kingdom on Nov. 20, 2007 and GB0802814.4 filed in the United Kingdom on Feb. 15, 2008, and also claims the benefit under 35 U.S.C. §1.119(e) of U.S. Provisional application No. 61/211,467 filed on Mar. 30, 2009 and U.S. Provisional application No. 61/289,081 filed on Dec. 22, 2009. The entire contents of each of the aforementioned patent applications are incorporated herein by this references.

BACKGROUND OF THE INVENTION

Field of the Invention

The present invention relates to assays for biomarkers useful in the diagnosis of fibrosis disease and prognosis of its development, including biomarkers indicative of the risk of developing fibrosis after a chronic injury. In particular, according to the present invention, biomarkers relating to degradation fragments of Collagen type I, III, IV, V, and VI, elastin, C-reactive protein, and proteoglycans including Biglycan, Decorin, Versican, and Perlecan are found to be useful.

Description of Related Art

Fibrotic diseases (including those listed in Table 1) are a leading cause of morbidity and mortality, e.g. cirrhosis with 800,000 death per year worldwide[1].

TABLE 1

Different fibrotic diseases[2]

| Tissue | Examples of Causes |
| --- | --- |
| Liver | Viral hepatitis, Schistosomiasis, Steatohepatitis (Alcoholic or non-alcoholic) |
| Lung | Idiopathic pulmonary fibrosis (IPF), Systemic sclerosis (Scleroderma) |
| Kidney | Nephrogenic systemic fibrosis (NSF), Diabetes, Untreated hypertension |
| Heart | Heart attack, Hypertension, Atherosclerosis, Restenosis |
| Eye | Macular degeneration, retinal and vitreal retinopathy |
| Skin | Systemic sclerosis and scleroderma, keloids, hypertrophic scars, burns, genetic factors, NFS |
| Pancreas | Autoimmune/hereditary causes |
| Intestine | Crohn's disease/inflammatory bowl disease |
| Brain | Alzheimer's disease, AIDS |
| Bone marrow | Cancer, ageing |
| Multi-organ fibrosis | Surgical complications, chemotherapeutic drug-induced fibrosis, radiation-induced fibrosis, mechanical injuries |

A 'fibrotic disease' is any disease giving rise to fibrosis, whether as a main or a secondary symptom. Fibrosis is the end result of chronic inflammatory reactions induced by a variety of stimuli including persistent infections, autoimmune reactions, allergic responses, chemical insults, radiation, and tissue injury. Fibrosis is characterized by the accumulation and reorganization of the extracellular matrix (ECM). Despite having obvious etiological and clinical distinctions, most chronic fibrotic disorders have in common a persistent irritant that sustains the production of growth factors, proteolytic enzymes, angiogenic factors, and fibrogenic cytokines, which together stimulate the deposition of connective tissue elements, especially collagens and proteoglycans, which progressively remodel and destroy normal tissue architecture [3, 4]. Despite its enormous impact on human health, there are currently no approved treatments that directly target the mechanisms of fibrosis [5]. The key cellular mediator of fibrosis is the myofibroblast, which when activated serves as the primary collagen-producing cell.

Extracellular Matrix (ECM)

Fibrogenesis is a dynamic process involving complex cellular and molecular mechanisms that usually originates from tissue injury [6]. Fibrogenesis is the result of an imbalance in normal ECM regulation that alters the concentration of macromolecules leading to increased tissue size and density, with progressively impaired function. These macromolecules are mainly fibrous proteins with structural and adhesive functions, such as collagens and proteoglycans.

Collagen

Collagens are widely distributed in the human body, i.e. ~30% of the protein mass in the human body is composed of collagens. Collagens are responsible for the structural integrity of the ECM of most connective tissues. The ECM content results from a fine balance between synthesis and degradation tightly controlled through regulation of gene expression and protein secretion, but also through endogenous protease inhibition and protein degradation by metalloproteinases and cysteine proteases[7-9]. Table 2 lists the major collagen types with their major tissue distribution.

TABLE 2

Major collagen types and their tissue distribution.

| Collagen type | Tissue distribution |
| --- | --- |
| I | Most connective tissues |
| II | Cartilage, vitreous humor |
| III | Extensible connective tissues, e.g. liver, skin, lung, vascular system |
| IV | Basement membranes |
| V | Tissues containing collagen I |
| VI | Most connective tissues |
| VII | Skin, bladder, oral mucosa, umbilical cord, amnion |
| VIII | Many tissues, especially endothelium |
| XIII | Endothelial cells, skin, eye, heart, skeletal muscle |
| XIV | Vessel, bone, skin, cartilage, eye, nerve, tendon, uterus |
| XXI | Vessel, heart, stomach, kidney, skeletal muscle, placenta |

Type I collagen is the most abundant collagen and is found in most connective tissues. It is especially important for the structure of bone and skin where the major collagenous components are type I and III collagens [10]. Collagen type I and III are the major components of liver and lung in a 1:1 ratio in healthy tissue. In addition, collagen type IV and VI are found in the basement membranes in most tissues. The most common localization of type V collagen is within the characteristic collagen fibrils, in association with the collagen type I and III [10]. Some collagens have a restricted tissue distribution: for example, type II, which is found almost exclusively in cartilage [11]. During fibrogenesis the net amount of collagens increases[12-14].

Table 3 shows by way of example the collagen increase during liver fibrosis.

TABLE 3

Changes of the composition of collagen from normal to cirrhotic human liver [15].

| Collagen type | Chains | Collagen normal liver (mg/g) | Collagen cirrhotic liver (mg/g) | Times in-creased | Distribution normal liver (%) | Distribution cirrhotic liver (%) |
|---|---|---|---|---|---|---|
| I | $\alpha_1(I)\ \alpha_2(I)$ | 2 | 16 | 8 | 37 | 42 |
| III | $\alpha_1(III)$ | 2 | 8 | 4 | 37 | 21 |
| IV | $\alpha_1(IV)$ $\alpha_2(IV)$ | 0.5 | 7 | 14 | 9 | 18 |
| V | $\alpha_1(V)$ $\alpha_2(V)$ $\alpha_3(V)$ | 0.9 | 7 | 8 | 17 | 18 |
| VI | $\alpha_1(VI)$ $\alpha_2(VI)$ | 0.01 | 0.1 | 10 | 0.2 | 0.3 |

Elastin

Elastin is a protein present in many connective tissues, primarily those that are elastic. It has a very high content of the amino acids glycine, valine, alanine, and proline, and has a molecular weight of 64 to 66 kDa. It is organised in an irregular or random coil conformation made up of 830 amino acids. Elastin is made by linking many soluble tropoelastin protein molecules, in a reaction catalyzed by lysyl oxidase, to make a massive insoluble, durable cross-linked array.

Elastin serves an important function in arteries as a medium for pressure wave propagation to help blood flow and is particularly abundant in large elastic blood vessels such as the aorta. Elastin is also very important in the lungs, elastic ligaments and the skin. Despite much efforts devoted to the understanding of elastin synthesis and turnover, neo-epitopes originating from the proteolytic cleavage of this matrix molecules have until now not been associated with disease development in fibrosis.

Vimentin

Vimentin is a member of the intermediate filament family of proteins. Intermediate filaments are an important structural feature of eukaryotic cells. They, along with microtubules and actin microfilaments, make up the cytoskeleton. Although most intermediate filaments are stable structures, in fibroblasts, vimentin exists as a dynamic structure. This filament is used as a marker for mesodermally derived tissues, and as such has been used as an immunohistochemical marker for sarcomas.

Hertig and coworkers (Hertig et al., J Am Soc Nephrol. 2008 August; 19(8):1584-91) investigated if epithelial-to-mesenchymal transition in renal tubular epithelial cells of subjects with chronic allograft nephropathy could predict the progression of fibrosis in the allograft and measured vimentin expression in 83 biopsies from these. They did find an association between elevated vimentin expression and the intestinal fibrosis score at 1 year after surgery. In another study of hepatic fibrosis, Meriden and colleagues (Meriden et al., Clin Gastro & Hepatol 2010; 8:289-296) found a significant association between vimentin expression (in biopsies obtained at F0 stage) and fibrosis progression, with elevated levels predicting rapid progression of the hepatic fibrosis. Accordingly, we wanted to investigate if circulating fragments of vimentin could serve as sensitive and specific biomarkers of fibrosis.

Proteoglycans

Proteoglycans are a diverse group of macromolecules, which covalently link a variable number of glycosaminoglycan (GAG) side chains to a core protein [16]. These GAGs are polymers of disaccharide repeats (e.g. N-acetyl glucosamine or N-acetyl galactosamine), which are acidic (negatively charged) due to hydroxyl, carboxylated and sulfated side groups on the disaccharide units. This makes them highly hydrophilic, thus aiding the diffusion of water and positive ions (e.g. sodium from extracellular fluids) [17]. Furthermore, GAGs have the ability to form non-covalent links with for example hyaluronic acid chains to form even larger molecular complexes [16]. Table 4 lists the most studied proteoglycans associated with connective tissue.

TABLE 4

Proteoglycans of the extracellular matrix of connective tissue

| Group | Proteoglycans | Origin | Function |
|---|---|---|---|
| Large extracellular proteoglycans (aggregating and hyaluronan-binding) | Aggrecan (18) | Articular cartilage chondrocytes, intervertebral disc, nasal cartilage | Extracellular matrix stability (hyaluronan binding) |
| | Versican (19, 20) | Connective tissue: fibroblast, keratinocytes, smooth muscle cells, mesangial cells | Cell-cell and cell-matrix interactions Binding of sugars in Ca-dependent manner |
| | Neurocan (20) | Nervous tissue | Binds to neural cell adhesion molecules |
| | Brevican (22) | Nervous tissue | Extracellular matrix stability |
| Small Leucine-rich proteoglycans (collagen-binding) | Decorin (23) | Connective tissue, cartilage, bone | Binds to and connect collagen molecules (matrix stabilization and thickness) Organogenesis Binding of TGFβ |
| | Biglycans [24] | Capillary endothelium, skin (keratinocytes), epithelium of kidney | Cell differentiation Binds and connect collagen fibrils |

TABLE 4-continued

Proteoglycans of the extracellular matrix of connective tissue

| Group | Proteoglycans | Origin | Function |
|---|---|---|---|
| | Fibromodulin [17] | Connective tissue, bone, cartilage | Regulate orientation of collagen fibers |
| | Lumican [23] | Cornea, muscle, cartilage, kidney, lung, intestine | Controls spacing and thickness of collagen fibers |
| Cell-associated proteoglycans | Serglycins [25] | Widely distributed to endothelium-intercellular compartments | Hemopoietic cell differentiation Adhesion and activation of lymphoid cells |
| | Syndecans [26] | Widely distributed-often cell membrane bound | Binds collagens, fibronectin, thrombospondin, tenascin and bFGF |
| | Betaglycan [27] | Widely distributed | TGFβ receptor and signaling Possible reservoir of TGFβ |
| Basement membrane proteoglycans | Perlecan [28] | All basement membranes | Selective barrier for macromolecules Cell-adhesion |

C-Reactive Protein

C-reactive protein (CRP) is an acute phase serum protein produced by the liver in response to different clinical conditions such as, inflammation, infection, or trauma[29]. The production of CRP is induced by cytokines such as IL-6, released from the affected or damaged tissues. The physiological role of CRP is yet unknown and discussions on its pro- or anti-inflammatory actions are ongoing.

Proteases

The imbalance between synthesis and degradation of ECM during fibrogenesis, results from conversion of the low-density subendothelial matrix into matrix rich in interstitial collagens. The increase in collagen and proteoglycans may be due to one or both of (1) a decrease in protein production and (2) impaired protein degradation, and hence less matrix degradation. The decreased protein degradation has recently received increased attention. In the regulation of this process matrix metalloproteinases (MMPs) and their tissue inhibitors (TIMPs) play important roles, as well as other proteases and their inhibitors, such as cystein proteases and the cystatins.

MMPs

MMPs are a large group of endopeptidases, capable of degrading most if not all components of the ECM. Presently, more than 25 MMPs have been found. MMPs are characterized by an active site containing a metal atom, typically zinc, and are secreted as zymogens. Different MMPs are expressed in different tissues. In Table 5 MMPs in the liver are shown.

TABLE 5

MMPs in the liver[30-32]

| Family | Protease | Source | Substrate |
|---|---|---|---|
| Collagenases | MMP-1 | HSC | I, II, III, VII, VIII, X, gelatin |
| | MMP-8 | Neutrophil | I, II, III, V, VII, X, gelatin |
| | MMP-13 | HSC, MFB, KC | I, II, III, VII, X, gelatin |
| Stromelysins | MMP-3 | HSC | III, IV, V, IX, X, XI, gelatin, laminin, fibronectin, proteoglycans, glycoproteins, elastin, pro-MMP-1/13 |
| | MMP-10 | HSC | III, IV, V, gelatin, elastin, aggrecan |
| | MMP-11 | HC | PAI-1, week activity against matrix proteins |
| Gelatinases | MMP-2 | HSC, MBF | I, II, III, IV, V, VII, X, XI, gelagin, elastin, laminin |
| | MMP-9 | KC, HSC, HC | I, II, III, IV, V, VII, X, XI, gelagin, elastin, laminin |
| | MMP-7 | HSC | Entactin, gelatin, elastin, fibronectin, vitronectin, laminin, fibrinogen |
| Metalloelastase | MMP-12 | Macrophages | Elastin, gelatins, IV, laminin, fibronectin, entactin, vitronectin, proteoglycan, myelin basic protein, α1-antitripsin |
| MT-MMPs | MMP-14 | HSC, MFB, KC | I, II, III, gelatin, fibronectin, vitronectin, laminin, fibrinogen, pro-MMP-2, pro-MMP-13 |
| | MMP-15 | HC, BDEC | Pro-MMP-2, fibronectin, tenascin, laminin, aggrecan, perlecan |

TIMPs block MMPs' proteolytic activity by binding in a substrate- and tissue-specific manner to MMP and membrane-type 1 metalloproteinase in a trimolecular complex (Table 6). During fibrosis TIMP levels increase dramatically, and MMP levels increase modestly or remain relatively static (except MMP-2) which in all gives a decrease in degradation of collagens.

TABLE 6

TIMPs in the liver[31]

| Name | Sources | Metalloproteinase inhibited |
|---|---|---|
| TIMP-1 | HSC, MFB, KC, HC | Pro-MMP-9, MMP-1, MMP-2, MMP-3, MMP-13 |
| TIMP-2 | KC, HSC | MT-MMP-1, MT-MMP-2, proMMP-2, MMP-3, MMP-13, MMP-7 |
| TIMP-3 | HC | MT-MMP-1, MT-MMP-2, TACE, MMP-13 |

Fibroblast Activation Protein

Fibroblast Activation Protein alpha subunit (FAPa or FAP, alpha) is an integral membrane gelatinase belonging to the serine protease family. FAPa is the alpha subunit and DPP4 (CD26) the beta subunit of a heterodimeric membrane-bound proteinase complex also known as 170 kDa Melanoma Membrane Gelatinase, Integral Membrane Serine Proteinase and Seprase. Some cells make only FAPa homodimers, some only DPP4 homodimers. The monomer is inactive. FAP, alpha is selectively expressed in reactive stromal fibroblasts of epithelial cancers, granulation tissue of healing wounds, and malignant cells of bone and soft tissue sarcomas[33]. This protein is thought to be involved in the control of fibroblast growth or epithelial-mesenchymal interactions during development, tissue repair, and epithelial carcinogenesis. It has been shown that expression of FAP increase with the stage of fibrosis[34, 35].

Fibrosis Biomarkers

A number of biochemical markers have been suggested for fibrotic diseases, although not specific product of the disease. In Table 7 is an example of biochemical markers of liver fibrosis used in clinical trial. In addition there are a lot of examples of biomarkers of other fibrotic diseases[12, 36-42]. Table 7 summarizes some of the known markers of liver fibrosis.

| Biomarker | Parameters | Chronic liver disease | Reference |
|---|---|---|---|
| One parameter | | | |
| CRP | | NASH | 43 |
| Hyaluronan | | HCV | 44-47 |
| IGF-I | | HCV | 48 |
| Leptin | | HCV | 49 |
| PIIIP | | HCV | 50 |
| Several parameters | Parameters | Chronic liver disease | References |
| MP3 | PIIINP, MMP1 | HCV | 51, 52 |
| Zheng et al index | HA, PIIICP, PIIINP, Laminin, C-IV | Chronic hepatitis | 53 |
| Lebensztjen et al index | Laminin-2, C-IV, MMP2, MMP9-TIMP1 index | HBV | 54 |
| | Tenascin, hyaluronana, Colalegn VI, TIMP-1 | HBV | 55 |
| Tsochatzis et al index | Leptin, adiponectin, resistin | HCV, HBC, NASH | 56 |
| Patel et al index | Hyaluronan, TIMP-1, α$_2$-macroglobulin | HCV | 57 |
| | TIMP-1, tenascin, collagen IV, PIIINP, MMP2, laminin, Hyaluronan | NASH | 58 |
| Foms-index (76, 77) | Age, platelet count, γGT, cholesterol | HCV HIV/HCV | 51, 59-62 |
| FibroTest (76, 78) | Haptoglobin, α$_2$-macroglobulin, apolipoprotein A1, γGT, bilirubin | HCV HIV/HCV NAFLD NAFLD in diabetes patients | 45, 51, 60, 61, 63-75 |
| Actitest | FibroTest + ALT | HCV | 65, 76-78 |
| APRI (Wai-index) | AST, platelet count | HIV/HCV HCV NAFLD | 45, 51, 60, 61, 64, 66, 79-87 |
| Hepascore | Bilirubin, γGT, hyaluronan, α$_2$-macroglobulin, age, gender | HCV HIV/HCV | 51, 61, 64, 66, 88 |
| FIB-4 | Platelet count, AST, ALT, age | HIV/HCV | 61, 83 |
| SHASTA | Hyaluronan, albumin, AST | HIV/HCV | 61 |
| Fibroindex | FORN + APRI | HCV | 89 |
| Fibrometer test | Platelet count, prothrombin index, AST, α$_2$-macroglobulin, hyaluronan, urea, age | HIV/HCV HCV NAFLD | 51, 61, 64, 66, 81 |
| NFSA | Age, hyperglycaemia, body mass index, platelets, albumin, AST/ALT | NAFLD | 81 |
| Ultrasound + APRI | | HCV | 82 |
| Metwally et al index | Platelet count, albumin, AST, history of blood transfusion, HBV core antibody | HCV | 90 |
| Mohamadnejad et al index | Age, HBV DNA levels, alkaline phosphatase, albumin, platelet counts, AST | HCV | 91 |

-continued

| | | | |
|---|---|---|---|
| FibroSpect II | Hyaluronan, TIMP-1, $\alpha_2$-macroglobulin | HCV | 85, 92, 93 |
| Stepwise combination algorithms | Combination of APRI and Fibrotest | HCV | 94 |
| Imbert-Bismut index | $\alpha_2$ macroglobulin, AST, ALT $\gamma$GT, total bilirubin, albumin, $\alpha_1$ globulin, $\alpha_2$ globulin, $\beta$ globulin, $\gamma$ globulin, apolipoprotein A1 | HCV | 95 |
| Nunes et al | Age, Platelets, INR, CD4, AST/ALT, Hyaluronan, YKL-40, PIIINP | HCV/HIV HCV | 96 |
| Fibroscan +++ | Fibroscan, Fibrotest, APRI, | HCV | 97 |

U.S. Pat. No. 5,387,504 describes the neo-epitope VDIPEN released by the action of stromelysin at the aggrecan site $N_{341}$-$F_{342}$ and an RIA assay employing a monoclonal antibody specific for this neo-epitope. More generally the use of monospecific antibodies specific for fragments of aggrecan, generated by specific stromelysin cleavage are described. Elevations of stromelysin occur in osteoarthritis, rheumatoid arthritis, atherosclerotic lesions, gout, inflammatory bowel disease (IBD), idiopathic pulmonary fibrosis (IPF), certain cancers, joint injuries, and numerous inflammatory diseases. Stromelysin is reported to be elevated in idiopathic pulmonary fibrosis, and it is alleged that the assay can be conducted on blood or other biological fluids to detect stromelysin cleavage products of aggrecan and that quantitation of such fragments can be used diagnostically in respect of IPF as well as other conditions. However, no evidence for this is provided and there have to our knowledge been no subsequent publications validating this prediction. Such RIA assays have been commercially available for many years and no reports of their successful use in diagnosing or monitoring any fibrotic disease have appeared.

U.S. Pat. No. 7,225,080 discloses a method for diagnosis of an inflammatory, a fibrotic or a cancerous disease in a patient by measuring the values of at least four biochemical markers selected from the group consisting of $\alpha$2-macroglobulin, AST (aspartate aminotransferase), ALT (alanine aminotransferase), GGT (gammaglutamyl transpeptidase), $\gamma$-globulin, total bilirubin, albumin, $\alpha$1-globulin, $\alpha$2-globulin, haptoglobin, $\beta$-globulin, apoA1, IL-10, TGF-$\beta$1, apoA2, and apoB in the serum or plasma of said patient, and subsequently combining said values in order to determine the presence of liver fibrosis and/or liver necroinflammatory lesions in said patient. The patent does not teach the quantitative measurement of peptide fragment carrying neo-epitopes generated during fibrotic disease.

U.S. Pat. No. 6,060,255 describes a method for diagnosing the degree of liver fibrosis, comprising the steps of measuring the concentration of type IV collagen high molecular weight form in a sample using an antibody that specifically binds to type IV collagen, and relating the measurement to the degree of liver fibrosis. Again, no use is made of neo-epitopes produced by proteolytic enzymes acting in the body. The sample is actually digested with pepsin, which may obscure the natural pattern of collagen cleavage in the sample.

U.S. Pat. No. 4,628,027 (Gay) discloses the production of antibodies specific for connective tissue proteins and, more particularly, the production of monoclonal antibodies by fused cell hybrids against human collagens and enzymes involved in collagen degradation. The use of monoclonal antibodies against connective tissue proteins to establish the collagen profile of histological, cytological and biological fluid samples is described. However, the patent does not describe the measurement of connective tissue proteins based on the binding of antibodies to neo-epitopes on said connective tissue proteins.

Guañabens N et al, J Bone Miner Res, 1998 [98] evaluated the bone turnover markers N-telopeptide of type I collagen (NTX), C-telopeptide of type I collagen (CTX) and N-terminal pro-peptide of collagen type I (PINP) in patients with primary biliary cirrhosis, a disease with increased hepatic fibrosis. The level of NTX, CTX and PINP were elevated in patients compared to controls and correlated with the histological stage of the disease. The antibodies employed in the NTX were raised against a cathepsin K cleaved site in the N-terminal of collagen type I and are dependent on the neoepitope JYDGKGVG↓(SEQ ID NO2249). The antibodies employed in the CTX were raised against a cathepsin K cleaved site in the C-terminal of collagen type I and are dependent on the neoepitope EKAHDGGR↓(SEQ ID NO2250). These markers are located in telopeptides of collagen type I and not in the internal part (the triple helical part) of collagen type I. The monoclonal antibodies employed for the PINP assay were raised against an internal epitope in the PINP sequence which is not a neo-epitope.

Møller S et al, Gut., 1999 [99] demonstrated that the C-terminal cross linked telopeptide of type I collagen (ICTP) was elevated in alcoholic cirrhosis patients compared to controls. The study described showed that a biochemical marker can reflect hepatic fibrosis. The ICTP polyclonal antibody has been raised against trypsin and collagenase cleaved collagen type I. However, the antibodies are not binding to a neo-epitope.

Rosen H N et al, Calcif Tissue Int, 2004 [100] assessed the bone turnover markers N-telopeptide of type I collagen (NTX) and C-telopeptide of type I collagen (CTX) in women receiving hormone replacement treatment (HRT). In the study it was observed that the bone turnover markers decreased with treatment. The antibodies employed in the NTX were raised against a cathepsin K cleaved site in the N-terminal of collagen type I and are dependent on the neoepitope JYDGKGVG↓. The antibodies employed in the CTX were raised against a cathepsin K cleaved site in the C-terminal of collagen type I and are dependent on the neoepitope EKAHDGGR↓. In contrast to the present invention, these antibodies were used for evaluation of bone metabolism and not fibrosis.

Lein M et al, Eur Urol, 2007 [101] evaluated the use of the neo-epitope specific bone turnover markers N-telopeptide of type I collagen (NTX) and C-telopeptide of type I collagen (CTX) in prostate cancer patients receiving zoledronic acid. In the study it was observed that the bone turnover markers decreased with treatment. The antibodies employed in the NTX were raised against a cathepsin K cleaved site in the N-terminal of collagen type I and are dependent on the neoepitope JYDGKGVG↓. The antibodies employed in the CTX were raised against a cathepsin K cleaved site in the C-terminal of collagen type I and are dependent on the neoepitope EKAHDGGR↓. In contrast to the present invention, these antibodies were used for evaluation of the bone metabolism during invasion of bone metastases and not fibrosis.

PIIINP has been used in a number of studies to assess the severity of fibrotic disease [102], in patients with skin fibrosis following severe burn trauma [103], for disease progression in noncirrhotic primary biliary cirrhosis [104] in primary biliary cirrhosis and chronic viral hepatitis C [105]. PIIINP and ICTP were measured in patients with fibrosis of the myocardium [106].

Many reports combine a set of biochemical markers to improve the predictive value of the biochemical index. Eleven different serum markers were measured in 205 patients with fibrotic staging from F0 to F4, and the most informative markers were alpha2 macroglobulin, alpha2 globulin (or haptoglobin), gamma globulin, apolipoprotein A1, gamma glutamyltranspeptidase, and total bilirubin [107]. An index of these markers had a negative predictive value (100% certainty of absence of F2, F3, or F4) was obtained for scores ranging from zero to 0.10 (12% [41] of all patients), and high positive predictive value (>90% certainty of presence of F2, F3, or F4) for scores ranging from 0.60 to 1.00 (34% [115] of all patients). However, in none of the above mentioned reports is it suggested that measurements of peptide fragments based on antibodies binding to neo-epitopes as now claimed might be useful for the assessment of patients with fibrotic disease.

SUMMARY OF THE INVENTION

The present invention now provides a method of diagnosis of fibrosis comprising, conducting an immunoassay to measure neo-epitope containing protein fragments naturally present in a patient biofluid sample, and associating an elevation of said measure in said patient above a normal level with the presence of fibrosis, wherein said immunoassay is conducted by a method comprising: contacting protein fragments naturally present in said sample with an immunological binding partner reactive with a neo-epitope formed by cleavage of a protein by a proteinase and measuring the extent of binding of peptide fragments to said immunological binding partner to measure therein protein fragments comprising said neo-epitope, and wherein said protein is collagen type I, collagen type III, collagen type IV, collagen type V or collagen type VI, biglycan, decorin, lumican, versican, perlecan, neurocan, brevican, fibromodulin, serglycin, syndecan, betaglycan, CRP, or vimentin subject to the proviso that when the neo-epitopes are formed by cleavage of type I collagen, the cleavage is not at a site at which collagen type I is cleaved by cathepsin K. WO2009/059972 published on 14 May 2009 (after the priority date hereof) discloses assays for neo-epitopes of collagen III, but does not disclose that an elevated level of such a measure is to be associated with the presence or extent of fibrosis. Optionally, an assay according to this invention is based on one of the proteins named above other than collagen Type III or if based on collagen Type III utilises an immunological binding partner against one of the neoepitopes formed at the cleavage sites PGIPGRNGDP* SEQ ID NO1, *ESCPTG-PQNY SEQ ID NO2, or PKGDTGPRGP* SEQ ID NO3 (where * marks the cleavage site).

For these purposes, cardiovascular disease may not be regarded as fibrosis, or the fibrosis detected according to the invention may be other than fibrosis accompanying cardiovascular disease. Optionally, an elevated result in an immunoassay according to this invention is associated with skin fibrosis, lung fibrosis, or liver fibrosis.

The method may comprise the preliminary step of obtaining a patient biofluid sample.

The invention includes a method of immunoassay to measure neo-epitope containing protein fragments naturally present in body fluid sample, wherein said immunoassay is conducted by a method comprising: contacting protein fragments naturally present in said sample with an immunological binding partner reactive with a neo-epitope formed by cleavage of a protein by a proteinase and measuring the extent of binding of peptide fragments to said immunological binding partner to measure therein protein fragments comprising said neo-epitope, and wherein said protein is neurocan, brevican, fibromodulin, serglycin, syndecan, betaglycan, collagen type I, collagen type IV, collagen type V, collagen type VI, CRP, or vimentin subject to the proviso that when the neo-epitopes are formed by cleavage of type I collagen, the cleavage is not at a site at which collagen type I is cleaved by cathepsin K.

Optionally, an assay according to this invention is based on one of the proteins named above other than collagen Type III or if based on collagen Type III utilises an immunological binding partner against one of the neoepitopes formed at the cleavage sites PGIPGRNGDP* SEQ ID NO1, *ESCPTG-PQNY SEQ ID NO2, or PKGDTGPRGP* SEQ ID NO3 (where * marks the cleavage site).

Said immunological binding partner may have specific binding affinity for peptide fragments comprising a C-terminal neoepitope or an N-terminal neoepitope.

Specific reactivity with or immunological affinity for a neo-epitope will imply that the relevant immunological binding partner is not reactive with intact protein from which the neo-epitope derives. Preferably, said immunological binding partner is not reactive with a neo-epitope sequence, such as a sequence listed below, if the sequence is prolonged past the respective cleavage site.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

Preferably, said peptide fragments are fragments of Type I, III, IV, V, or VI collagen, elastin, C-reactive protein, or one of the proteoglycans Biglycan, Decorin, Versican, and Perlecan. The connective tissue proteins are preferred. Preferably, the neo-epitope sequence to which the immunological binding partner binds is not found in any other protein or is not found in any of the other proteins to which the method of the invention relates.

Several candidate proteases may be responsible for the digestion of proteins in the fibrotic tissues. Most likely, this is the result of the large range of complicated processes resulting in different neo-epitope profiles dependent on the levels of disease.

BRIEF DESCRIPTION OF THE SEVERAL VIEWS OF THE DRAWINGS

The invention will be further described and illustrated with reference to the following examples and the accompanying drawings.

FIG. 5A shows MMP-9 mediated CO3 degradation serum levels in bile duct ligated BDL- or sham-operated rats. FIG. 5B shows CO3-610C delta values (termination-baseline paired) 2 weeks post-surgery P<0.0001 and 4 weeks post-surgery P=0.0016. FIG. 5C shows ctx-II levels in BDL- or sham-operated rats.

FIG. 7A shows Western blot 2 and 4 weeks post-surgery and FIG. 7B shows bands from Western Blot quantified by densitometry.

FIG. 8A shows histology sections from BDL- or sham-operated rats stained with Sirius Red (top) and masked histology sections for quantifying total collagen content in the liver (bottom). FIG. 8B shows total collagen quantified by Visiopharm software 2 weeks post-surgery P=0.0081 and 4 weeks post-surgery P=0.0047.

FIG. 9A shows a correlation of Col3a1 to CO3-610C was found. FIG. 9B shows a correlation of CO3-610C to % collagen was found. FIG. 9C shows that a correlation of Col3a1 to % collagen was found.

FIG. 18A shows a skin section from a PBS treated mouse at 8 weeks of treatment. FIG. 18B shows a skin section from Bleomycin treated mouse at 8 weeks of treatment. FIGS. 18C-18D are plots of skin thickness increase between P/bs (n=7/time point) and Bleomycin (n=13/time point) treated mice for 2 weeks (P=0.0029), 4 weeks (P=0.0004), 6 weeks (P<0.0001) and 8 weeks ((P<0.0001).

DETAILED DESCRIPTION OF THE INVENTION

Figure 1:
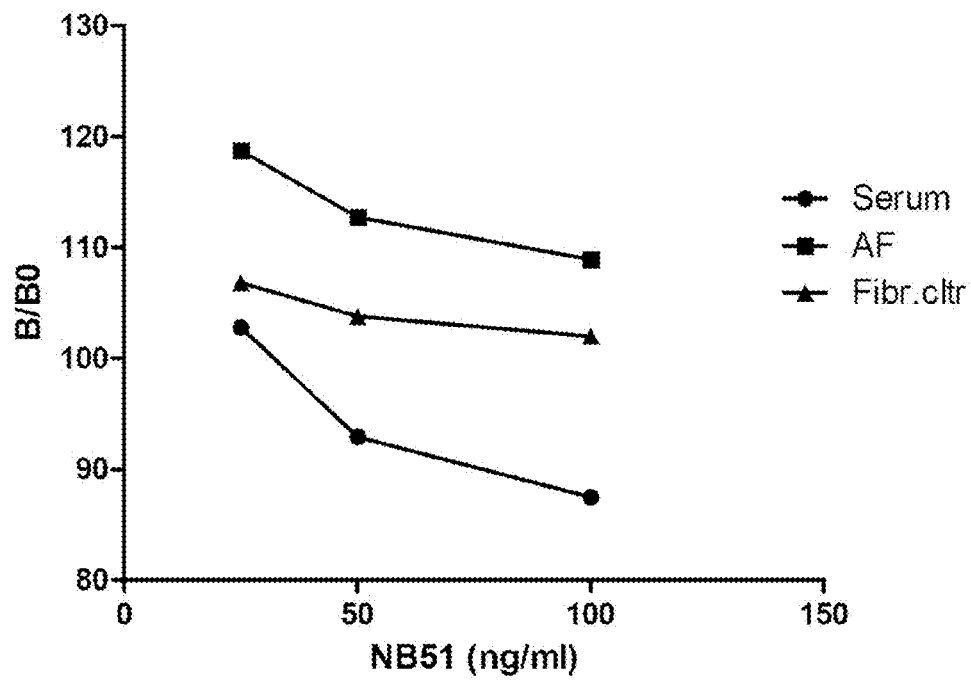
FIG. 1 shows a graph showing CO3 ELISA results of different biological samples: Pooled human serum samples (Serum); Human amniotic fluid (AF); Human fibroblast culture media (Fibr. Cltr.).

Collagen Assays
Collagen Type I

We have determined that the enzymes listed in the following table cleave type I collagen at least the following cleavage sites (marked "."):

TABLE 8

Collagen type I cleavage sites.

| Protease | Collagen type I |
|---|---|
| MMP-2 | V.PGPMGPSGPRGLPGPPGAPGPQG.F SEQ ID NO: 4 |
| MMP-2 | S.VPGPMGPSGPRGLPGPPGAPGPQG.F SEQ ID NO: 5 |
| MMP-2 | G.ISVPGPMGPSGPRGLPGPPGAPGPQG.F SEQ ID NO: 6 |
| MMP-9 | G.ISVPGPMGPSGPRGLPGPPGAPGPQG.F SEQ ID NO: 6 |
| MMP-13 | G.FQGPPGEPGEPGASGPMGPRGPPGPPG.K SEQ ID NO: 7 |
| MMP-13 | V.PGPMGPSGPRGLPGPPGAPGPQG.F SEQ ID NO: 8 |
| MMP-2 | F.SGLDGAKGDAGPAGPKGEPGSPGENGAPGQMGPRG.L SEQ ID NO: 9 |
| MMP-9 | F.SGLDGAKGDAGPAGPKGEPGSPGENGAPGQMGPRG.L SEQ ID NO: 9 |
| MMP-13 | F.SGLDGAKGDAGPAGPKGEPGSPGENGAPGQMGPRG.L SEQ ID NO: 9 |
| MMP-9 | G.LPGERGRPGAPGPAG.A SEQ ID NO: 10 |
| MMP-13 | G.LPGERGRPGAPGPAG.A SEQ ID NO: 10 |
| MMP-2 | G.LTGSPGSPGPDGKTGPPGPAG.Q SEQ ID NO: 11 |
| MMP-2 | E.RGSPGPAGPKGSPGEAGRPGEAGLPGAKG.L SEQ ID NO: 12 |

TABLE 8-continued

Collagen type I cleavage sites.

| Protease | Collagen type I |
|---|---|
| MMP-2 | G.ERGSPGPAGPKGSPGEAGRPGEAGLPGAKG.L SEQ ID NO: 13 |
| MMP-9 | G.LTGSPGSPGPDGKTGPPGPAG.Q SEQ ID NO: 14 |
| MMP-9 | G.LTGSPGSPGPDGKTGPPGPAGQDGRPGPPGPPG.A SEQ ID NO: 15 |
| MMP-9 | G.LTGSPGSPGPDGKTGPPGPAGQDGRPGPPGPPGARG.Q SEQ ID NO: 16 |
| MMP-13 | G.LTGSPGSPGPDGKTGPPGPAG.Q SEQ ID NO: 14 |
| MMP-13 | G.ERGSPGPAGPKGSPGEAGRPGEAGLPGAKG.L SEQ ID NO: 13 |
| MMP-9 | G.QDGRPGPPGPPGARG.Q SEQ ID NO: 17 |
| MMP-9 | G.LTGSPGSPGPDGKTGPPGPAGQDGRPGPPGPPGARG.Q SEQ ID NO: 18 |

TABLE 8-continued

Collagen type I cleavage sites.

| Protease | Collagen type I |
|---|---|
| MMP-2 | G.KDGEAGAQGPPGPAGPAGERGEQGPAGSPGF.Q SEQ ID NO: 19 |
| MMP-2 | G.ERGEQGPAGSPGF.Q SEQ ID NO: 20 |
| MMP-3 | E.RGVPGPPGAVGPAGKDGEAGAQGPPGPAGPAGERGEQGPAGSPGF.Q SEQ ID NO: 21 |
| MMP-8 | E.RGVPGPPGAVGPAGKDGEAGAQGPPGPAGPAGERGEQGPAGSPGF.Q SEQ ID NO: 21 |
| — | 113 PKGDTGPRGP.122 SEQ ID NO: 22 |

P indicates hydroxyproline, M indicates oxidised methionine, and K indicates hydroxylysine.

The immunological binding partner may be one specifically reactive with a C-terminal or N-terminal neoepitope formed by cleavage of type I collagen, excluding cleavage at a cathepsin K type I collagen site. Suitable immunological binding partners may therefore be specifically reactive with any of the following sequences at the N terminal of a peptide:

TABLE 9

N-terminal sequences of protease generated peptide fragments of Collagen type I. (The symbol '.' Indicates the cleavage site) Collagen I, alpha1

| | | |
|---|---|---|
| .ISVPGP SEQ ID NO: 23 | .VPGPMG SEQ ID NO: 24 | .PGPMGP SEQ ID NO: 25 |
| .LPGPGG SEQ ID NO: 26 | .FQGPPG SEQ ID NO: 27 | .KNGDDG SEQ ID NO: 28 |
| .ARGLPG SEQ ID NO: 29 | .SGLDGA SEQ ID NO: 30 | .LDGAKG SEQ ID NO: 31 |
| .LPGERG SEQ ID NO: 32 | .VRGEPG SEQ ID NO: 33 | .PGAKGA SEQ ID NO: 34 |
| .GGPPGP SEQ ID NO: 35 | .NSGEPG SEQ ID NO: 36 | .DGVAGP SEQ ID NO: 37 |
| .ERGSPG SEQ ID NO: 38 | .LTGSPG SEQ ID NO: 39 | .QDGRPG SEQ ID NO: 40 |
| .RGVPGP SEQ ID NO: 41 | .VGPAGK SEQ ID NO: 42 | .ERGEQG SEQ ID NO: 43 |
| .RGEQGP SEQ ID NO: 44 | .PGERGV SEQ ID NO: 45 | .ANGAPG SEQ ID NO: 46 |
| .ARGAPG SEQ ID NO: 47 | .PGDRGE SEQ ID NO: 48 | .AKGDAG SEQ ID NO: 49 |
| .PIGNVG SEQ ID NO: 50 | .AAGRVG SEQ ID NO: 51 | .PPGPAG SEQ ID NO: 52 |
| .GADGPA SEQ ID NO: 53 | .GPQGIA SEQ ID NO: 54 | .GQRGVV SEQ ID NO: 55 |
| .QRGVVG SEQ ID NO: 56 | .GLPGQR SEQ ID NO: 57 | .PGLPGP SEQ ID NO: 58 |
| .PMGPPG SEQ ID NO: 59 | .MGPPGL SEQ ID NO: 60 | .DKGETG SEQ ID NO: 61 |
| .LQGPPG SEQ ID NO: 62 | .SAGAPG SEQ ID NO: 63 | .RTGDAG SEQ ID NO: 64 |
| .FDFSF SEQ ID NO: 65 | .DFSF SEQ ID NO: 66 | .ATGAAG SEQ ID NO: 67 |
| .AKGEAG SEQ ID NO: 68 | .GIAGAP SEQ ID NO: 69 | .IAGAPG SEQ ID NO: 70 |
| .VQGPPG SEQ ID NO: 71 | .LPGPPG SEQ ID NO: 72 | .AGPKGS SEQ ID NO: 73 |
| .RGSPGP SEQ ID NO: 74 | .FAGPPG SEQ ID NO: 75 | .QAGVMG SEQ ID NO: 76 |
| .ARGQAG SEQ ID NO: 77 | .NVGAPG SEQ ID NO: 78 | .PAGERG SEQ ID NO: 79 |
| .KDGEAG SEQ ID NO: 80 | .GEVGPP SEQ ID NO: 81 | .ARGERG SEQ ID NO: 82 |
| .QGLPGP SEQ ID NO: 83 | .IAGQRG SEQ ID NO: 84 | .LTGPIG SEQ ID NO: 85 |
| .AGLPGP SEQ ID NO: 86 | .RGVVGL SEQ ID NO: 87 | .AGPPGA SEQ ID NO: 88 |
| .LAGPPG SEQ ID NO: 89 | .EPGKQG SEQ ID NO: 90 | .ATGFPG SEQ ID NO: 91 |

TABLE 9-continued

N-terminal sequences of protease generated peptide fragments of Collagen type I. (The symbol '.' Indicates the cleavage site)
Collagen I, alpha1

| | | |
|---|---|---|
| .PSGASG SEQ ID NO: 92 | .GKQGPS SEQ ID NO: 93 | .GPPGPA SEQ ID NO: 94 |
| .AGQRGV SEQ ID NO: 95 | .ARGPAG SEQ ID NO: 96 | .ASGPAG SEQ ID NO: 97 |
| .VVGLPG SEQ ID NO: 98 | .VGPPGP SEQ ID NO: 99 | .GPPGPP SEQ ID NO: 100 |
| .TGDAGP SEQ ID NO: 175 | | |

Alternatively, suitable immunological binding partners 15 may be specifically reactive with any of the following sequences at the C terminal of a peptide:

TABLE 10

C-terminal sequences of protease generated peptide fragments of Collagen type I (The symbol '.' Indicates the cleavage site).
Collagen I, alpha1

| | | |
|---|---|---|
| QLSYGY. SEQ ID NO: 101 | EKSTGG. SEQ ID NO: 102 | PPGPQG. SEQ ID NO: 103 |
| KGHRGF. SEQ ID NO: 104 | PSGPRG. SEQ ID NO: 105 | APGPQG. SEQ ID NO: 106 |
| APGPAG. SEQ ID NO: 107 | FPGAVG. SEQ ID NO: 108 | SEGPQG. SEQ ID NO: 109 |
| GANGAP. SEQ ID NO: 110 | ANGAPG. SEQ ID NO: 46 | SGPQGP. SEQ ID NO: 112 |
| EPGPVG. SEQ ID NO: 113 | EPGPTG. SEQ ID NO: 114 | RGFPGA. SEQ ID NO: 115 |
| KGPAGE. SEQ ID NO: 116 | RGSPGP. SEQ ID NO: 74 | LPGAKG. SEQ ID NO: 118 |
| PPGPPG. SEQ ID NO: 119 | PPGARG. SEQ ID NO: 120 | PGKAGE. SEQ ID NO: 121 |
| AVGPAG. SEQ ID NO: 122 | PAGPAG. SEQ ID NO: 123 | AGPAGE. SEQ ID NO: 124 |
| APGPDG. SEQ ID NO: 125 | RGERGF. SEQ ID NO: 126 | PAGPRG. SEQ ID NO: 127 |
| KDGVRG. SEQ ID NO: 128 | PAGPTG. SEQ ID NO: 129 | TGARGA. SEQ ID NO: 130 |
| PGPAGF. SEQ ID NO: 131 | EPGDAG. SEQ ID NO: 132 | PAGPPG. SEQ ID NO: 133 |
| SAGPPG. SEQ ID NO: 134 | ATGFPG. SEQ ID NO: 91 | NAGPPG. SEQ ID NO: 136 |
| GEVGPP. SEQ ID NO: 81 | GEKGSP. SEQ ID NO: 138 | GAPGTP. SEQ ID NO: 139 |
| PGPQGI. SEQ ID NO: 140 | GPQGIA. SEQ ID NO: 54 | PQGIAG. SEQ ID NO: 142 |
| IAGQRG. SEQ ID NO: 84 | GQRGVV. SEQ ID NO: 55 | |
| GPSGEP. SEQ ID NO: 146 | ERGPPG. SEQ ID NO: 147 | RGPPGP. SEQ ID NO: 148 |
| PVGPVG. SEQ ID NO: 149 | PQGPRG. SEQ ID NO: 150 | HRGFSG. SEQ ID NO: 151 |
| EQGPSG. SEQ ID NO: 152 | PRGPPG. SEQ ID NO: 153 | PPGPRG. SEQ ID NO: 154 |
| GPPGPP. SEQ ID NO: 100 | GPPSAG. SEQ ID NO: 156 | PPSAGF. SEQ ID NO: 157 |
| PPGPAG. SEQ ID NO: 52 | TPGPQG. SEQ ID NO: 160 | |
| QMGPRG. SEQ ID NO: 161 | PGPPGA. SEQ ID NO: 162 | QGIAGQ. SEQ ID NO: 163 |
| PGADGQ. SEQ ID NO: 164 | AGSPGF. SEQ ID NO: 165 | LPGPSG. SEQ ID NO: 166 |
| PPGPKG. SEQ ID NO: 167 | PGERGA. SEQ ID NO: 168 | PMGPPG. SEQ ID NO: 59 |
| PKGPAG. SEQ ID NO: 170 | GRNGDP. SEQ ID NO: 171 | SPGEQG. SEQ ID NO: 172 |
| GPAGRP. SEQ ID NO: 173 | PPGPIG. SEQ ID NO: 174 | TGDAGP. SEQ ID NO: 175 |
| TGPRGP. SEQ ID NO: 177 | | |

Collagen Type III

We have determined that the enzymes listed in the following table cleave type III collagen at least the following cleavage sites (marked *):

TABLE 11

Cleavage sites in collagen type III.

| Protease | Neo-Epitope |
|---|---|
| MMP-1 | A*GIPGAPGLMGARGPPGPA*G SEQ ID NO: 178 |
| MMP-1 | K*GDPGPPGIPGRNGDPGI*P SEQ ID NO: 179 |
| MMP-1 | G*LAGPPGMPGPRGSPGPQG*V SEQ ID NO: 180 |
| MMP-1 | G*ERGLPGPPGIKGPAGIPGF*P SEQ ID NO: 181 |
| MMP-1 | G*IAGITGARGLAGPPGMPGPR*G SEQ ID NO: 182 |
| MMP-1 | G*IKGHRGFPGNPGAPGSPGPAG*Q SEQ ID NO: 183 |
| MMP-1 | A*RGLAGPPGMPGPRGSPGPQGV*K SEQ ID NO: 184 |
| MMP-1 | I*TGARGLAGPPGMPGPRGSPGPQG*V SEQ ID NO: 185 |
| MMP-1 | I*TGARGLAGPPGMPGPRGSPGPQGV*K SEQ ID NO: 186 |
| MMP-1 | G*ITGARGLAGPPGMPGPRGSPGPQG*V SEQ ID NO: 187 |
| MMP-1 | G*VKGESGKPGANGLSGERGPPGPQG*L SEQ ID NO: 188 |
| MMP-1 | G*SRGAPGPQGPRGDKGETGERGAAG*I SEQ ID NO: 189 |
| MMP-1 | P*KGDAGQPGEKGSPGAQGPPGAPGPLG*I SEQ ID NO: 190 |
| MMP-1 | G*ITGARGLAGPPGMPGPRGSPGPQGV*K SEQ ID NO: 191 |
| MMP-1 | G*LRGGAGPPGPEGGKGAAGPPGPPGAAGTPG*L SEQ ID NO: 192 |
| MMP-1 | G*HAGAQGPPGPPGINGSPGGKGEMGPAGIPGAPG*L SEQ ID NO: 193 |
| MMP-1 | A*GKSGDRGESGPAGPAGAPGPAGSRGAPGPQGPRGDKGETGERGAAG*I SEQ ID NO: 194 |
| MMP-1 | G*LQGLPGTGGPPGENGKPGEPGPKGDAGAPGAPGGKGDAGAPGERGPPG*L SEQ ID NO: 195 |
| MMP-3 | G*ERGLPGPPGIKGPAGIPGF*P SEQ ID NO: 196 |
| MMP-3 | A*VGGLAGYPGPAGPPGPPGPGT*S SEQ ID NO: 197 |
| MMP-3 | K*DGTSGHPGPIGPPGPRGNRGER*G SEQ ID NO: 198 |
| MMP-3 | A*VGGLAGYPGPAGPPGPPGPPGTSGHPG*S SEQ ID NO: 199 |
| MMP-3 | G*IAGITGARGLAGPPGMPGPRGSPGPQG*V SEQ ID NO: 200 |
| MMP-3 | A*PGAPGGKGDAGAPGERGPPGLAGAPGLRG*G SEQ ID NO: 201 |
| MMP-3 | A*VGGLAGYPGPAGPPGPPGPPGTSGHPGSPG*S SEQ ID NO: 202 |
| MMP-2 | A*IGSPGPAGPRGPVGPSGPPG*K SEQ ID NO: 203 |
| MMP-3 & -8 | G*AIGSPGPAGPRGPVGPSGPPG*K SEQ ID NO: 204 |
| MMP-8 | P*AGQQGAIGSPGPA*G SEQ ID NO: 205 |
| MMP-8 | G*GPPGVAGPPGGSGPAGPP*G SEQ ID NO: 206 |
| MMP-8 | L*AGPPGMPGPRGSPGPQG*V SEQ ID NO: 207 |
| MMP-8 | G*LSGERGPPGPQGLPGLA*G SEQ ID NO: 208 |
| MMP-8 | R*GLAGPPGMPGPRGSPGPQG*V SEQ ID NO: 209 |
| MMP-8 | G*LAGPPGMPGPRGSPGPQGV*K SEQ ID NO: 210 |
| MMP-8 | R*GLAGPPGMPGPRGSPGPQGV*K SEQ ID NO: 211 |

TABLE 11-continued

Cleavage sites in collagen type III.

| Protease | Neo-Epitope |
|---|---|
| MMP-8 | G*PQGPPGKNGETGPQGPPGP*T SEQ ID NO: 212 |
| MMP-8 | G*VKGERGSPGGPGAAGFPGAR*G SEQ ID NO: 213 |
| MMP-8 | A*RGLAGPPGMPGPRGSPGPQG*V SEQ ID NO: 214 |
| MMP-8 | N*GLSGERGPPGPQGLPGLAGTA*G SEQ ID NO: 215 |
| MMP-8 | A*VGGLAGYPGPAGPPGPPGPPGT*S SEQ ID NO: 216 |
| MMP-8 | G*SPGGKGEMGPAGIPGAPGLMGA*R SEQ ID NO: 217 |
| MMP-8 | T*GARGLAGPPGMPGPRGSPGPQG*V SEQ ID NO: 218 |
| MMP-8 | V*KGESGKPGANGLSGERGPPGPQG*L SEQ ID NO: 219 |
| MMP-8 | G*VKGERGSPGGPGAAGFPGARGLPGPPGSNGNPGPPGPSGSPGKDGPPGPAG*N SEQ ID NO: 220 |
| MMP-8 | G*SPGAQGPPGAPGPLGIAGITGARGLAGPPG*M SEQ ID NO: 221 |
| MMP-8 | R*GAPGEKGEGGPPGVAGPPGGSGPAGPPGPQ*G SEQ ID NO: 222 |
| MMP-8 | R*GAPGEKGEGGPPGVAGPPGGSGPAGPPGPQ*G SEQ ID NO: 223 |
| MMP-8 | G*IAGITGARGLAGPPGMPGPRGSPGPQG*V SEQ ID NO: 224 |
| MMP-9 | G*IKGPAGIPGFPG*M SEQ ID NO: 225 |
| MMP-9 | G*QPGVMGFPGPKG*N SEQ ID NO: 226 |
| MMP-9 | G*IKGPAGIPGFPGMK*G SEQ ID NO: 227 |
| MMP-9 | G*IKGPAGIPGFPGMKG*H SEQ ID NO: 228 |
| MMP-9 | I*PGAPGLMGARGPPGPAG*A SEQ ID NO: 229 |
| MMP-9 | G*ERGLPGPPGIKGPAGIP*G SEQ ID NO: 230 |
| MMP-9 | G*IPGAPGLMGARGPPGPAG*A SEQ ID NO: 231 |
| MMP-9 | G*FRGPAGPNGIPGEKGPAG*E SEQ ID NO: 232 |
| MMP-9 | P*GIPGQPGSPGSPGPPGIC*E SEQ ID NO: 233 |
| MMP-9 | G*ERGLPGPPGIKGPAGIPGF*P SEQ ID NO: 234 |
| MMP-9 | A*VGGLAGYPGPAGPPGPPGPPG*T SEQ ID NO: 235 |
| MMP-9 | G*VKGERGSPGGPGAAGFPGARG*L SEQ ID NO: 236 |
| MMP-9 | G*DAGAPGAPGGKGDAGAPGERGPPG*L SEQ ID NO: 237 |
| MMP-9 | Q*GPPGPTGPGGDKGDTGPPGPQGL*Q SEQ ID NO: 238 |
| MMP-9 | G*INGSPGGKGEMGPAGIPGAPGLM*G SEQ ID NO: 239 |
| MMP-9 | Q*GPPGEPGQAGPSGPPGPPGAIGPS*G SEQ ID NO: 240 |
| MMP-9 | P*GPPGINGSPGGKGEMGPAGIPGAP*G SEQ ID NO: 241 |
| MMP-9 | R*GLPGPPGSNGNPGPPGPSGSPGKDGPPGPAG*N SEQ ID NO: 242 |
| MMP-9 | G*KNGETGPQGPPGPTGPGGDKGDTGPPGPQG*L SEQ ID NO: 243 |
| MMP-9 | G*LPGIAGPRGSPGERGETGPPGPAGFPGAPG*Q SEQ ID NO: 244 |
| MMP-9 | G*INGSPGGKGEMGPAGIPGAPGLMGARGPPGPAG*A SEQ ID NO: 245 |
| MMP-9 | P*GINGSPGGKGEMGPAGIPGAPGLMGARGPPGPAG*A SEQ ID NO: 246 |
| MMP-9 | P*PGENGKPGEPGPKGDAGAPGAPGGKGDAGAPGERGPPG*L SEQ ID NO: 247 |
| MMP-9 | G*LKGENGLPGENGAPGPMGPRGAPGERGRPGLPGAAG*A SEQ ID NO: 248 |

TABLE 11-continued

Cleavage sites in collagen type III.

| Protease | Neo-Epitope |
|---|---|
| MMP-9 | G*NTGAPGSPGVSGPKGDAGQPGEKGSPGAQGPPGAPGPLG*I SEQ ID NO: 249 |
| MMP-9 | G*LMGARGPPGPAGANGAPGLRGGAGEPGKNGAKGEPGPRG*E SEQ ID NO: 250 |
| MMP-9 | G*LRGGAGPPGPEGGKGAAGPPGPPGAAGTPGLQGMPGERGGLGSPGPKG*D SEQ ID NO: 251 |
| MMP-8 & -9 | G*QQGAIGSPGPAGPRGPVGPSGPPG*K SEQ ID NO: 252 |
| MMP-9 | K*GDPGPPGIPGRNGDPGIPGQPG*S SEQ ID NO: 253 |
| MMP-9 | G*LRGGAGPPGPEGGKGAAGPPGPPG*A SEQ ID NO: 254 |
| MMP-9 | G*KNGETGPQGPPGPTGPGGDKGDTGPPGPQG*L SEQ ID NO: 255 |
| MMP-9 | G*YQGPPGEPGQAGPSGPPGPPG*A SEQ ID NO: 256 |
| MMP-9 | G*VAGPPGGSGPAGPPGPQG*V SEQ ID NO: 257 |
| MMP-8, -9 & -13 | G*DKGEPGGPGADGVPGKDGPRGPTGPIGPPGPAG*Q SEQ ID NO: 258 |
| ADAMTS-5 | Q*GHAGAQGPPGPPGIN*G SEQ ID NO: 259 |
| CathepsinK | A*GERGAPGPA*G SEQ ID NO: 260 |
| CathepsinK | A*GIPGFPGMK*G SEQ ID NO: 261 |
| CathepsinK | F*PGMKGHRGFD*G SEQ ID NO: 262 |
| CathepsinK | G*FPGARGLPGPPG*S SEQ ID NO: 263 |
| CathepsinK | A*GFPGARGLPGPPG*S SEQ ID NO: 264 |
| CathepsinK | P*PGPPGPPGTSGHP*G SEQ ID NO: 265 |
| CathepsinK | G*FPGMKGHRGFD*G SEQ ID NO: 266 |
| CathepsinK | Q*PGDKGEGGAPGLPGI*A SEQ ID NO: 267 |
| CathepsinK | R*GDKGETGERGAAGIK*G SEQ ID NO: 268 |
| CathepsinK | D*GRNGEKGETGAPGLK*G SEQ ID NO: 269 |
| CathepsinK | A*GQPGDKGEGGAPGLPGIA*G SEQ ID NO: 270 |
| CathepsinK | G*PPGENGKPGEPGPKGD*A SEQ ID NO: 271 |
| CathepsinK | A*GIPGFPGMKGHRGFD*G SEQ ID NO: 272 |
| CathepsinK | R*GGAGEPGKNGAKGEPGPR*G SEQ ID NO: 273 |
| CathepsinK | K*GERGSPGGPGAAGFPGARGLPGPP*G SEQ ID NO: 274 |
| CathepsinK | EDGKDGSPGEPGANGLP*G SEQ ID NO: 275 |
| CathepsinK | G*AAGFPGARGLPGPPGSNGNPGPPGPS*G SEQ ID NO: 276 |
| CathepsinK | R*PGPPGPSGPRGQPGVMGFPGPKGN*D SEQ ID NO: 277 |
| CathepsinK | Q*GPPGPPGINGSPGGKGEMGPAGIPGAP*G SEQ ID NO: 278 |
| CathepsinK | A*GKDGESGRPGRPGERGLPGPPGIK*G SEQ ID NO: 279 |
| CathepsinK | A*GARGNDGARGSDGQPGPPGPPGTAGFPG*S SEQ ID NO: 280 |
| CathepsinK | S*PGVSGPKGDAGQPGEKGSPGAQGPPGAPG*P SEQ ID NO: 281 |
| CathepsinK | R*GSDGQPGPPGPPGTAGFPGSPGAKGEVGPA*G SEQ ID NO: 282 |
| CathepsinK | Q*GPPGPPGINGSPGGKGEMGPAGIPGAPGLM*G SEQ ID NO: 283 |
| CathepsinK | A*GPPGPPGPPGTSGHPGSPGSPGYQGPPGEPG*Q SEQ ID NO: 284 |

TABLE 11-continued

Cleavage sites in collagen type III.

| Protease | Neo-Epitope |
|---|---|
| CathepsinK | F*PGAPGQNGEPGGKGERGAPGEKGEGGPPGVA*G SEQ ID NO: 285 |
| CathepsinK | A*GFPGAPGQNGEPGGKGERGAPGEKGEGGPPG*V SEQ ID NO: 286 |
| CathepsinK | A*GARGNDGARGSDGQPGPPGPPGTAGFPGSPGAKGEVGPA*G SEQ ID NO: 287 |
| CathepsinK | R*GAAGEPGRDGVPGGPGMRGMPGSPGGPGSDGKPGPPGSQGESGRPGPPGPS*G SEQ ID NO: 288 |
| CathepsinS | G*IAGITGARGL*A SEQ ID NO: 289 |
| CathepsinS | A*GPPGPPGAAGTPGLQG*M SEQ ID NO: 290 |
| CathepsinS | N*GLSGERGPPGPQGLPG*L SEQ ID NO: 291 |
| CathepsinS | M*GARGPPGPAGANGAPGLR*G SEQ ID NO: 292 |
| CathepsinS | N*GLSGERGPPGPQGLPGLA*G SEQ ID NO: 293 |
| CathepsinS | G*IAGITGARGLAGPPGMPGPRG*S SEQ ID NO: 294 |
| CathepsinS | G*IAGITGARGLAGPPGMPGPRGSPGPQG*V SEQ ID NO: 295 |
| CathepsinS | R*GGAGPPGPEGGKGAAGPPGPPGAAGTPGLQ*G SEQ ID NO: 296 |
| CathepsinS | S*GPKGDAGQPGEKGSPGAQGPPGAPGPLG*I SEQ ID NO: 297 |
| CathepsinS | G*IAGITGARGLAGPPGMPGPRGSPGPQGVK*G SEQ ID NO: 298 |
| CathepsinS | S*GPKGDAGQPGEKGSPGAQGPPGAPGPLG*I SEQ ID NO: 299 |
| CathepsinS | G*IAGITGARGLAGPPGMPGPRGSPGPQGVK*G SEQ ID NO: 300 |
| CathepsinS | A*VGGLAGYPGPAGPGPPGPPGTSGHPGSPGSPGYQ*G SEQ ID NO: 301 |
| CathepsinS | E*PGPQGHAGAQGPPGPPGINGSPGGKGEMGPAGIPGAPG*L SEQ ID NO: 302 |
| ADAMTS1 | I*PGFPGMKGHR*G SEQ ID NO: 303 |
| ADAMTS1 | R*GSPGGPGAAGFPGAR*G SEQ ID NO: 304 |
| ADAMTS1 | K*GPAGIPGFPGMKGHR*G SEQ ID NO: 305 |
| ADAMTS1 | R*GLAGPPGMPGPRGSPGPQ*G SEQ ID NO: 306 |
| ADAMTS1 | A*GITGARGLAGPPGMPGPR*G SEQ ID NO: 307 |
| ADAMTS1 | L*GIAGITGARGLAGPPGMPGPR*G SEQ ID NO: 308 |
| ADAMTS1 | T*GARGLAGPPGMPGPRGSPGPQ*G SEQ ID NO: 309 |
| ADAMTS1 | Q*GPPGPPGINGSPGGKGEMGPAG*I SEQ ID NO: 310 |
| ADAMTS1 | L*PGPPGIKGPAGIPGFPGMKGHR*G SEQ ID NO: 311 |
| ADAMTS1 | A*GITGARGLAGPPGMPGPRGSPGPQ*G SEQ ID NO: 312 |
| ADAMTS1 | T*GARGLAGPPGMPGPRGSPGPQGVK*G SEQ ID NO: 313 |
| ADAMTS1 | R*GLPGPPGIKGPAGIPGFPGMKGHR*G SEQ ID NO: 314 |
| ADAMTS1 | G*RPGLPGAAGARGNDGARGSDGQPGPPG*P SEQ ID NO: 315 |
| ADAMTS1 | N*GAPGPMGPRGAPGERGRPGLPGAAGAR*G SEQ ID NO: 316 |
| ADAMTS1 | A*GSRGAPGPQGPRGDKGETGERGAAGIK*G SEQ ID NO: 317 |
| ADAMTS1 | R*GLAGPPGMPGPRGSPGPQGVKGESGKPGAN*G SEQ ID NO: 318 |
| ADAMTS1 | R*GLAGPPGMPGPRGSPGPQGVKGESGKPGANGL*S SEQ ID NO: 319 |
| ADAMTS1 | P*GPPGSNGNPGPPGPSGSPGKDGPPGPAGNTGAPGS*P SEQ ID NO: 320 |
| ADAMTS1 | T*GARGLAGPPGMPGPRGSPGPQGVKGESGKPGAN*G SEQ ID NO: 321 |

TABLE 11-continued

Cleavage sites in collagen type III.

| Protease | Neo-Epitope |
|---|---|
| ADAMTS1 | R*GAPGEKGEGGPPGVAGPPGGSGPAGPPGPQGVKGER*G SEQ ID NO: 322 |
| ADAMTS1 | G*GPPGVAGPPGGSGPAGPPGPQGVKGERGSPGGPGAAGF*P SEQ ID NO: 323 |
| ADAMTS1 | K*SGDRGESGPAGPAGAPGPAGSRGAPGPQGPRGDKGETGERGAAGIK*G SEQ ID NO: 324 |
| ADAMTS4 | I*PGFPGMKGHR*G SEQ ID NO: 325 |
| ADAMTS4 | R*GLAGPPGMPGPR*G SEQ ID NO: 326 |
| ADAMTS4 | G*PQGLQGLPGTGGPP*G SEQ ID NO: 327 |
| ADAMTS4 | K*GPAGIPGFPGMKGHR*G SEQ ID NO: 328 |
| ADAMTS4 | R*GLAGPPGMPGPRGSPGPQG*V SEQ ID NO: 329 |
| ADAMTS4 | G*PPGENGKPGEPGPKGDAGAP*G SEQ ID NO: 330 |
| ADAMTS4 | A*PGFRGPAGPNGIPGEKGPAGER*G SEQ ID NO: 331 |
| ADAMTS4 | E*KGSPGAQGPPGAPGPLGIAGITGAR*G SEQ ID NO: 332 |
| ADAMTS4 | L*PGPPGIKGPAGIPGFPGMKGHR*G SEQ ID NO: 333 |
| ADAMTS4 | R*GAPGFRGPAGPNGIPGEKGPAGER*G SEQ ID NO: 334 |
| ADAMTS4 | R*GLPGPPGIKGPAGIPGFPGMKGHR*G SEQ ID NO: 335 |
| ADAMTS4 | R*GPVGPSGPPGKDGTSGHPGPIGPPGPR*G SEQ ID NO: 336 |
| ADAMTS4 | A*PGPQGPRGDKGETGERGAAGIKGHR*G SEQ ID NO: 337 |
| ADAMTS4 | R*GAPGPQGPRGDKGETGERGAAGIKGHR*G SEQ ID NO: 338 |
| ADAMTS4 | R*GFPGNPGAPGSPGPAGQQGAIGSPGPAGPR*G SEQ ID NO: 339 |
| ADAMTS4 | L*PGPPGIKGPAGIPGFPGMKGHRGFDGR*N SEQ ID NO: 340 |
| ADAMTS4 | D*AGQPGEKGSPGAQGPPGAPGPLGIAGITGAR*G SEQ ID NO: 341 |
| ADAMTS4 | R*GPTGPIGPPGPAGQPGDKGEGGAPGLPGIAGPR*G SEQ ID NO: 342 |
| ADAMTS4 | K*GDAGQPGEKGSPGAQGPPGAPGPLGIAGITGAR*G SEQ ID NO: 343 |
| ADAMTS4 | R*NGEKGETGAPGLKGENGLPGENGAPGPMGPR*G SEQ ID NO: 344 |
| ADAMTS4 | A*PGFRGPAGPNGIPGEKGPAGERGAPGPAGPRGA*A SEQ ID NO: 345 |
| ADAMTS4 | R*GAPGFRGPAGPNGIPGEKGPAGERGAPGPAGPR*G SEQ ID NO: 346 |
| ADAMTS4 | R*GSPGERGETGPPGPAGFPGAPGQNGEPGGKGER*G SEQ ID NO: 347 |
| ADAMTS4 | G*HAGAQGPPGPPGINGSPGGKGEMGPAGIPGAPGLMG*A SEQ ID NO: 348 |
| ADAMTS4 | R*GLAGPPGMPGPRGSPGPQGVKGESGKPGANGLSGER*G SEQ ID NO: 349 |
| ADAMTS8 | L*GIAGITGARGL*A SEQ ID NO: 350 |
| ADAMTS8 | I*PGFPGMKGHR*G SEQ ID NO: 351 |
| ADAMTS8 | R*GLAGPPGMPGPR*G SEQ ID NO: 352 |
| ADAMTS8 | Q*GPPGAPGPLGIAGITGAR*G SEQ ID NO: 353 |
| ADAMTS8 | A*GITGARGLAGPPGMPGPR*G SEQ ID NO: 354 |
| ADAMTS8 | A*GIPGAPGLMGARGPPGPAGAN*G SEQ ID NO: 355 |
| ADAMTS8 | R*GLAGPPGMPGPRGSPGPQGVKG*E SEQ ID NO: 356 |
| ADAMTS8 | K*GSPGAQGPPGAPGPLGIAGITGAR*G SEQ ID NO: 357 |
| ADAMTS8 | L*PGPPGIKGPAGIPGFPGMKGHR*G SEQ ID NO: 358 |
| ADAMTS8 | K*DGTSGHPGPIGPPGPRGNRGER*G SEQ ID NO: 359 |

TABLE 11-continued

Cleavage sites in collagen type III.

| Protease | Neo-Epitope |
|---|---|
| ADAMTS8 | A*GITGARGLAGPPGMPGPRGSPGPQ*G SEQ ID NO: 360 |
| ADAMTS8 | R*GLAGPPGMPGPRGSPGPQGVKGESG*K SEQ ID NO: 361 |
| ADAMTS8 | R*GLAGPPGMPGPRGSPGPQGVKGESGKPGAN*G SEQ ID NO: 362 |
| ADAMTS8 | R*GLAGPPGMPGPRGSPGPQGVKGESGKPGANGL*S SEQ ID NO: 363 |
| ADAMTS8 | P*GPPGSNGNPGPPGPSGSPGKDGPPGPAGNTGAPGS*P SEQ ID NO: 364 |
| ADAMTS8 | R*GAPGEKGEGGPPGVAGPPGGSGPAGPPGPQGVKGER*G SEQ ID NO: 365 |
| ADAMTS8 | K*SGDRGESGPAGPAGAPGPAGSRGAPGPQGPRGDKGETGERGA*A SEQ ID NO: 366 |
| ADAMTS8 | R*GAPGEKGEGGPPGVAGPPGGSGPAGPPGPQGVKGERGSPGGPGAAGFPGAR*G SEQ ID NO: 367 |
| MMP9 | _*AIGPSG_____*_ SEQ ID NO: 368 |
| MMP9 | 117' PGIPGRNGDP*. 124' SEQ ID NO: 369 |
| MMP9 | 142' .*ESCPTGPQNY 151' SEQ ID NO: 370 |
| MMP9 | 113' PKGDTGPRGP*. '122 SEQ ID NO: 371 |

The immunological binding partner may be one specifically reactive with a C-terminal or N-terminal neoepitope formed by cleavage of type III collagen. Suitable immunological binding partners may therefore be specifically reactive with any of the following sequences at the N terminal of a peptide:

TABLE 12

N-terminal sequences of protease generated peptide fragments of Collagen type III.
Collagen type III

| | | |
|---|---|---|
| GIPGAP SEQ ID NO: 372 | GDPGPP SEQ ID NO: 373 | LAGPPG SEQ ID NO: 89 |
| IAGITG SEQ ID NO: 375 | IKGHRG SEQ ID NO: 376 | RGLAGP SEQ ID NO: 377 |
| TGARGL SEQ ID NO: 378 | ITGARG SEQ ID NO: 379 | VKGESG SEQ ID NO: 380 |
| KGDAGQ SEQ ID NO: 381 | LRGGAG SEQ ID NO: 382 | ERGLPG SEQ ID NO: 385 |
| GKSGDR SEQ ID NO: 383 | LQGLPG SEQ ID NO: 384 | AIGSPG SEQ ID NO: 143 |
| DGTSGH SEQ ID NO: 135 | VGGLAG SEQ ID NO: 155 | LSGERG SEQ ID NO: 176 |
| GPPGVA SEQ ID NO: 158 | AGPPGM SEQ ID NO: 145 | IGSPGP SEQ ID NO: 386 |
| GLSGER SEQ ID NO: 387 | GLAGPP SEQ ID NO: 388 | PQGPPG SEQ ID NO: 389 |
| GARGLA SEQ ID NO: 111 | KGESGK SEQ ID NO: 374 | VKGERG SEQ ID NO: 159 |
| GAPGEK SEQ ID NO: 141 | QPGVMG SEQ ID NO: 144 | IKGPAG SEQ ID NO: 169 |
| IPGAPG SEQ ID NO: 117 | FRGPAG SEQ ID NO: 137 | QQGAIG SEQ ID NO: 390 |
| GPPGPT SEQ ID NO: 391 | INGSPG SEQ ID NO: 392 | GPPGEP SEQ ID NO: 393 |
| GLPGPP SEQ ID NO: 394 | KNGETG SEQ ID NO: 395 | LPGIAG SEQ ID NO: 396 |
| GINGSP SEQ ID NO: 397 | PGENGK SEQ ID NO: 398 | LKGENG SEQ ID NO: 399 |
| LMGARG SEQ ID NO: 400 | YQGPPG SEQ ID NO: 401 | GERGAP SEQ ID NO: 402 |
| DKGEPG SEQ ID NO: 403 | GHAGAQ SEQ ID NO: 404 | GSDGQP SEQ ID NO: 405 |
| PGMKGH SEQ ID NO: 406 | FPGARG SEQ ID NO: 407 | GFPGAR SEQ ID NO: 408 |
| FPGMKG SEQ ID NO: 409 | PGDKGE SEQ ID NO: 410 | GDKGET SEQ ID NO: 411 |

TABLE 12-continued

N-terminal sequences of protease generated peptide fragments of Collagen type III.
Collagen type III

| | | | | | |
|---|---|---|---|---|---|
| GQPGDK | SEQ ID NO: 412 | GPPGEN | SEQ ID NO: 413 | GIPGFP | SEQ ID NO: 414 |
| GERGSP | SEQ ID NO: 415 | PGVPGA | SEQ ID NO: 416 | AAGFPG | SEQ ID NO: 417 |
| GPPGPP | SEQ ID NO: 100 | GKDGES | SEQ ID NO: 418 | GARGND | SEQ ID NO: 419 |
| GFPGAP | SEQ ID NO: 420 | NTGAPG | SEQ ID NO: 437 | GAAGEP | SEQ ID NO: 421 |
| IAGITG | SEQ ID NO: 375 | GLSGER | SEQ ID NO: 387 | GARGPP | SEQ ID NO: 422 |
| GPPGSN | SEQ ID NO: 423 | GPKGDA | SEQ ID NO: 424 | GGAGPP | SEQ ID NO: 425 |
| PGPQGH | SEQ ID NO: 426 | PGFPGM | SEQ ID NO: 427 | GSPGGP | SEQ ID NO: 428 |
| SGDRGE | SEQ ID NO: 429 | GITGAR | SEQ ID NO: 430 | GIAGIT | SEQ ID NO: 431 |
| PGPPGI | SEQ ID NO: 432 | ESCPTG | SEQ ID NO: 433 | HAGAQG | SEQ ID NO: 434 |
| GAPGFR | SEQ ID NO: 435 | RPGLPG | SEQ ID NO: 436 | GAPGPM | SEQ ID NO: 438 |
| GSPGER | SEQ ID NO: 439 | PQGLQG | SEQ ID NO: 440 | GPAGIP | SEQ ID NO: 441 |
| AIGPSG | SEQ ID NO: 368 | PGFRGP | SEQ ID NO: 443 | KGSPGA | SEQ ID NO: 444 |
| GAPGPQ | SEQ ID NO: 445 | GFPGNP | SEQ ID NO: 446 | GPVGPS | SEQ ID NO: 447 |
| GPTGPI | SEQ ID NO: 448 | GDAGQP | SEQ ID NO: 449 | NGEKGE | SEQ ID NO: 450 |
| SRGAPG | SEQ ID NO: 451 | VAGPPG | SEQ ID NO: 452 | PGPQGP | SEQ ID NO: 453 |
| AGQPGE | SEQ ID NO: 454 | PGAPGG | SEQ ID NO: 455 | PGAPGQ | SEQ ID NO: 456 |
| AGQQGA | SEQ ID NO: 457 | PGPPGP | SEQ ID NO: 458 | SPGGKG | SEQ ID NO: 459 |
| GARGLA | SEQ ID NO: 111 | GRNGEK | SEQ ID NO: 460 | GPPGAP | SEQ ID NO: 461 |
| GSRGAP | SEQ ID NO: 462 | GGAGEP | SEQ ID NO: 463 | GSPGAQ | SEQ ID NO: 464 |
| SPGAQG | SEQ ID NO: 465 | PGVSGP | SEQ ID NO: 466 | PGAPGL | SEQ ID NO: 467 |
| GIPGQP | SEQ ID NO: 468 | DAGAPG | SEQ ID NO: 469 | GPPGIN | SEQ ID NO: 470 | or with any of the following sequences at the C-terminal of a peptide:

TABLE 13

C-terminal sequences of protease generated peptide fragments of Collagen type III.
Collagen type III

| | | | | | |
|---|---|---|---|---|---|
| GPPGPA | SEQ ID NO: 94 | NGDPGI | SEQ ID NO: 471 | SPGPQG | SEQ ID NO: 472 |
| GMPGPR | SEQ ID NO: 473 | SPGPAG | SEQ ID NO: 474 | PGPQGV | SEQ ID NO: 475 |
| ERGAAG | SEQ ID NO: 476 | PGPLGI | SEQ ID NO: 477 | AAGTPG | SEQ ID NO: 478 |
| ERGPPG | SEQ ID NO: 147 | PGPPGT | SEQ ID NO: 479 | GNRGER | SEQ ID NO: 480 |
| | | APGLRG | SEQ ID NO: 481 | HPGSPG | SEQ ID NO: 482 |
| PSGPPG | SEQ ID NO: 483 | GSPGPA | SEQ ID NO: 484 | GPAGPP | SEQ ID NO: 485 |
| GLPGLA | SEQ ID NO: 486 | GPPGPQ | SEQ ID NO: 490 | QGPPGP | SEQ ID NO: 487 |
| GLAGTA | SEQ ID NO: 488 | FPGPKG | SEQ ID NO: 491 | PGLMGA | SEQ ID NO: 489 |
| LAGPPG | SEQ ID NO: 89 | GPAGIP | SEQ ID NO: 441 | FPGARG | SEQ ID NO: 407 |
| IPGFPG | SEQ ID NO: 492 | PPGPPG | SEQ ID NO: 119 | GFPGMK | SEQ ID NO: 493 |
| FPGAPG | SEQ ID NO: 494 | GAIGPS | SEQ ID NO: 495 | AGIPGF | SEQ ID NO: 496 |

TABLE 13-continued

C-terminal sequences of protease generated peptide fragments of Collagen type III.
Collagen type III

| | | | | | |
|---|---|---|---|---|---|
| GPPGIC | SEQ ID NO: 2187 | LPGAAG | SEQ ID NO: 2188 | APGPLG | SEQ ID NO: 2189 |
| PGPQGL | SEQ ID NO: 497 | GAPGLM | SEQ ID NO: 498 | GPPGIN | SEQ ID NO: 470 |
| SPGPKG | SEQ ID NO: 499 | GEPGPR | SEQ ID NO: 500 | IPGQPG | SEQ ID NO: 501 |
| TGAPGS | SEQ ID NO: 502 | GHRGFD | SEQ ID NO: 503 | LPGPPG | SEQ ID NO: 72 |
| PGPKGD | SEQ ID NO: 506 | PGLPGI | SEQ ID NO: 504 | GAAGIK | SEQ ID NO: 505 |
| GLPGIA | SEQ ID NO: 507 | PQGLPG | SEQ ID NO: 508 | GAPGLR | SEQ ID NO: 509 |
| GLPGPP | SEQ ID NO: 394 | GANGLP | SEQ ID NO: 510 | GPPGPS | SEQ ID NO: 511 |
| IPGAPG | SEQ ID NO: 117 | GPPGIK | SEQ ID NO: 512 | TAGFPG | SEQ ID NO: 513 |
| GEVGPA | SEQ ID NO: 514 | PPGPQG | SEQ ID NO: 103 | GPPGVA | SEQ ID NO: 158 |
| GEVGPA | SEQ ID NO: 499 | GFPGAR | SEQ ID NO: 408 | TGARGL | SEQ ID NO: 378 |
| EKGPAG | SEQ ID NO: 515 | EPGPRG | SEQ ID NO: 516 | PPGAPG | SEQ ID NO: 517 |
| TSGHPG | SEQ ID NO: 518 | GAPGPA | SEQ ID NO: 519 | TPGLQG | SEQ ID NO: 520 |
| GTPGLQ | SEQ ID NO: 521 | GTSGHP | SEQ ID NO: 522 | MPGPRG | SEQ ID NO: 523 |
| GPQGVK | SEQ ID NO: 524 | GAPGLK | SEQ ID NO: 525 | GSPGYQ | SEQ ID NO: 526 |
| PPGPAG | SEQ ID NO: 52 | PGPKGN | SEQ ID NO: 527 | GAAGAR | SEQ ID NO: 528 |
| FPGMKG | SEQ ID NO: 409 | PGANGL | SEQ ID NO: 529 | GTGGPP | SEQ ID NO: 530 |
| GLSGER | SEQ ID NO: 387 | TGPRGP | SEQ ID NO: 177 | GITGAR | SEQ ID NO: 430 |
| GMKGHR | SEQ ID NO: 531 | EGGPPG | SEQ ID NO: 532 | GSPGPQ | SEQ ID NO: 533 |
| EMGPAG | SEQ ID NO: 534 | GIAGPR | SEQ ID NO: 535 | QPGPPG | SEQ ID NO: 536 |
| GRNGDP | SEQ ID NO: 171 | GKPGAN | SEQ ID NO: 537 | VKGESG | SEQ ID NO: 380 |
| GVKGER | SEQ ID NO: 538 | PGAAGF | SEQ ID NO: 539 | TGERGA | SEQ ID NO: 540 |
| PQGVKG | SEQ ID NO: 541 | GDAGAP | SEQ ID NO: 542 | GPAGER | SEQ ID NO: 543 |
| GPPGPR | SEQ ID NO: 544 | GPAGPR | SEQ ID NO: 545 | RGFDGR | SEQ ID NO: 546 |
| AGPRGA | SEQ ID NO: 547 | GGKGER | SEQ ID NO: 548 | APGLMG | SEQ ID NO: 549 |
| GPAGAN | SEQ ID NO: 550 | | | | |

Collagen IV

We have determined that the enzymes listed in the following table cleave type IV collagen at least the following cleavage sites (marked "."):

TABLE 14

Cleavage fragments of collagen type IV

| Protease | Neo-Epitope |
|---|---|
| FAP | D.IDGYRGPPGP.Q SEQ ID NO: 551 |
| FAP | S.MGPPGTPSVDHGF.L SEQ ID NO: 552 |
| FAP | P.DGLPGSMGPPGTPSVDHG.F SEQ ID NO: 553 |
| FAP | P.DGLPGSMGPPGTPSVDHGF.L SEQ ID NO: 554 |
| FAP | P.DGLPGSMGPPGTPSVDHGFL.V SEQ ID NO: 555 |
| FAP | P.SGRDGLPGPPGSPGPPGQPGY.T SEQ ID NO: 556 |

TABLE 14-continued

Cleavage fragments of collagen type IV

| Protease | Neo-Epitope |
|---|---|
| FAP | P.SGRDGLPGPPGSPGPPGQPGYTN.G SEQ ID NO: 557 |
| FAP | P.SGRDGLPGPPGSPGPPGQPGYTNG.I SEQ ID NO: 558 |
| FAP | I.PGSKGEQGFMGPPGPQGQPGLPGS.P SEQ ID NO: 559 |
| FAP | P.RGFPGPPGPDGLPGSMGPPGTPSVD.H SEQ ID NO: 560 |
| FAP | E.PGPPGLPGSVGSPG.V SEQ ID NO: 561 |
| FAP | I.DGYRGPPGPQGP.P SEQ ID NO: 562 |
| FAP | P.RGFPGPPGPDGLPGSMG.P SEQ ID NO: 563 |
| FAP | D.GLPGSMGPPGTPSVDHGF.L SEQ ID NO: 564 |
| FAP | D.GLPGSMGPPGTPSVDHGFL.V SEQ ID NO: 565 |
| FAP | P.GLPGQQGAPGIPGFPGSKGEMGVMGTP.G SEQ ID NO: 566 |
| FAP | I.GIPGMPGSPGLKGSPGSVGYPGSPGLPGE.K SEQ ID NO: 567 |
| FAP | P.GPPGPPGEKGQMGLSFQGPKGDKGDQGVSGPPGVP.G SEQ ID NO: 568 |
| FAP | P.GIGPPGARGPPGGQGPPGLSGPPGIKGEKGFPGFPGL.D SEQ ID NO: 569 |
| FAP | E.PGLPGIPGVSGPK.G SEQ ID NO: 570 |
| FAP | G.EKGQKGDTGPPGPPGLV.I SEQ ID NO: 571 |
| FAP | L.PGIGVQGPPGPPGIPGPIGQPGLHGIPGEKGDPGPP.G SEQ ID NO: 572 |
| FAP | G.SPGIPGHQGEMG.P SEQ ID NO: 573 |
| FAP | E.PGMQGEPGPPGP.P SEQ ID NO: 574 |
| FAP | G.PPGRLGAPGTPGLPGP.R SEQ ID NO: 575 |
| FAP | P.PGPKGFPGIPGP.P SEQ ID NO: 576 |
| FAP | A.KGQPGLPGFPGT.P SEQ ID NO: 577 |
| FAP | D.RGPPGPPGIRGPPGP.P SEQ ID NO: 578 |
| FAP | P.GPPGEKGKPGQDGIPGP.A SEQ ID NO: 579 |
| FAP | L.LGSKGEKGEPGLPGIPGVSGPKGY.Q SEQ ID NO: 580 |
| MMP-9 | D.GLPGSMGPPGTPSVDHG.F SEQ ID NO: 581 |
| MMP-9 | D.GLPGSMGPPGTPSVDHGF.L SEQ ID NO: 564 |
| MMP-9 | T.GPLGEKGERGYPGTPGPRGE.P SEQ ID NO: 582 |
| MMP-9 | G.LQGIRGEPGPPGLPGSVGSPGVPGIGPPGARGPPGGQGPPG.L SEQ ID NO: 583 |
| MMP-9 | P.DGLPGSMGPPGTPSVDHGFL.V SEQ ID NO: 555 |
| MMP-9 | D.PGLKGDKGDVGLPGKPGSMDKVDMGS.M SEQ ID NO: 584 |
| MMP-9 | L.PGPMGPPGLPGIDGV.K SEQ ID NO: 585 |
| MMP-9 | D.GLPGSMGPPGTPSVDHGFL.V SEQ ID NO: 565 |
| MMP-9 | G.IRGEPGPPGLPGSVGSPGVPGIGPPG.A SEQ ID NO: 586 |
| MMP-9 | G.FPGPPGPDGLPGSMGPPGTPSVDHGF.L SEQ ID NO: 587 |
| MMP-9 | G.LQGIRGEPGPPGLPGSVGSPGVPGIGPPG.A SEQ ID NO: 588 |
| MMP-9 | G.IRGEPGPPGLPGSVGSPGVPGIGPPGARGPPGGQGPPG.L SEQ ID NO: 589 |

TABLE 14-continued

Cleavage fragments of collagen type IV

| Protease | Neo-Epitope |
|---|---|
| MMP-9 | E.DGVIGMMGFPGAIGP.P SEQ ID NO: 590 |
| MMP-9 | Y.PGNPGILGPPGEDGVIGMMGFPGAIGPPGPPG.N SEQ ID NO: 591 |
| MMP-9 | I.PPSDEICEPGPPGP.P SEQ ID NO: 592 |
| MMP-9 | L.PGLPGPKGEPGLPGYPGNPGIKGS.V SEQ ID NO: 593 |
| MMP-9 | G.IKGDKGSMGHPGPKGPP.G SEQ ID NO: 594 |
| MMP-9 | T.PGSPGCAGSPGLPGSPGPPG.P SEQ ID NO: 595 |
| MMP-9 | P.GAPGPQGLPGPPGFPGPVGPPGPPGFFGFPGAMGPRGPKGHMGE.R SEQ ID NO: 596 |
| MMP-9 | G.LPGFAGNPGP SEQ ID NO: 597 |
| MMP-9 + FAP | G.AEGLPGSPGFPGPQG.D SEQ ID NO: 598 |
| MMP-9 + FAP | M.GPPGVPGFQGPKGLP.G SEQ ID NO: 599 |
| MMP-9 + FAP | D.IDGYRGPPGPQGPPG.E SEQ ID NO: 600 |
| MMP-9 + FAP | G.DQGDQGVPGAKGLPGP.P SEQ ID NO: 601 |
| MMP-9 + FAP | G.DRGPQGQPGLPGLPGP.M SEQ ID NO: 602 |
| MMP-9 + FAP | P.DGLPGSMGPPGTPSVDHGF.L SEQ ID NO: 554 |
| MMP-9 + FAP | E.KGSIGIPGMPGSPGLKGSPGSVGYP.G SEQ ID NO: 603 |
| MMP-9 + FAP | G.LQGIRGEPGPPGLPGSVGSPGVPGIGPPG.A SEQ ID NO: 588 |
| MMP-9 + FAP | G.IRGEPGPPGLPGSVGSPGVPGIGPPGARGPPGGQGPPG.L SEQ ID NO: 589 |
| MMP-9 + FAP | G.LQGIRGEPGPPGLPGSVGSPGVPGIGPPGARGPPGGQGPPG.L SEQ ID NO: 583 |
| MMP-9 + FAP | G.LQGIRGEPGPPGLPGSVGSPGVPGIGPPGARGPPGGQGPPGLSGPPG.I SEQ ID NO: 604 |
| MMP-9 + FAP | I.PPSDEICEPGPPGP.P SEQ ID NO: 592 |
| MMP-9 + FAP | P.GPPGLMGPPGPPGLPGP.K SEQ ID NO: 605 |
| MMP-9 + FAP | G.ERGSPGIPGAPGPIGPPGSPG.L SEQ ID NO: 606 |
| MMP-9 + FAP | P.GIPGAPGAPGFPGSKGEPGDILTFPGMKGDKGELGSPGAPGL.P SEQ ID NO: 607 |
| MMP-9 + FAP | C.DGGVPNTGPPGEPGPP.G SEQ ID NO: 608 |
| MMP12, Alpha1 | .ILGHVPGML. SEQ ID NO: 2190 |
| MMP12, Alpha1 | .PGLPGQPGPPGLPVPGQ. SEQ ID NO: 2191 |
| MMP12, Alpha1 | .SGYPGNPGLPGIPGQDGPPGPPGPIPGCNGTKGERGPLGPPGL. SEQ ID NO: 2192 |
| MMP12, Alpha1 | .VSGPPGVPGQA. SEQ ID NO: 2193 |
| MMP12, Alpha1 | .VSGPPGVPGQAQ. SEQ ID NO: 2194 |
| MMP12, Alpha2 | .KRGPPGPPGLPGPPGPDGFL. SEQ ID NO: 2195 |
| MMP12, Alpha2 | .LHGFPGAPGQEGPLG. SEQ ID NO: 2196 |
| MMP12, Alpha2 | .LPGPDGPPGERGLPGEVL. SEQ ID NO: 2197 |
| MMP12, Alpha2 | .LRGIPGF. SEQ ID NO: 2198 |
| MMP12, Alpha2 | .PGFPGAPGTVGAPGIAGIPQK. SEQ ID NO: 2199 |
| MMP12, Alpha2 | .QQGNRGLGF. SEQ ID NO: 2200 |

TABLE 14-continued

Cleavage fragments of collagen type IV

| Protease | Neo-Epitope |
|---|---|
| MMP12, Alpha2 | .VGQPGPNGIPSDTL. SEQ ID NO: 2201 |
| MMP12, Alpha3 | .GEPGMQGEPGPPGPPGNLGPCGPRGKPGKDGKPGTPGPAGEKG. SEQ ID NO: 2202 |
| MMP12, Alpha3 | .GEPGPPGPPGNLGPCGPRGKPGKDGKPGTPGPAGEKGNK. SEQ ID NO: 2203 |
| MMP12, Alpha3 | .PGIPGTPGPPGLPGLQGPVGPPG. SEQ ID NO: 2204 |
| MMP12, Alpha3 | .PGDIVFRK. SEQ ID NO: 2205 |
| MMP12, Alpha4 | .GNKGDPASHFGPPGPPKG. SEQ ID NO: 2206 |
| MMP12, Alpha4 | .PGPRGKPGM. SEQ ID NO: 2207 |
| MMP12, Alpha5 | .PGLPGQPGTRGL. SEQ ID NO: 2208 |
| MMP12, Alpha5 | .PGPPGPLGIPGRSGVPGLKGDDGLQGQPGLPGPTGEKGSK. SEQ ID NO: 2209 |
| MMP12, Alpha5 | .PGPPGPLGIPGRSGVPGLKGDDGLQGQPGLPGPTGEKGSKG. SEQ ID NO: 2210 |
| MMP12, Alpha5 | .SKGEKGEPGLPGIPGVSGPKGYQGLPGDPGQPGLSGQPGL. SEQ ID NO: 2211 |

The immunological binding partner may be one specifically reactive with a C-terminal or N-terminal neoepitope formed by cleavage of type IV collagen. Suitable immunological binding partners may therefore be specifically reactive with any of the following sequences at the N terminal of a peptide:

TABLE 15

N-terminal sequences of protease generated peptide fragments of Collagen type IV.
Collagen type IV

| | | |
|---|---|---|
| IDGYRG SEQ ID NO: 609 | MGPPGT SEQ ID NO: 610 | DGLPGS SEQ ID NO: 611 |
| PGSKGE SEQ ID NO: 612 | RGFPGP SEQ ID NO: 613 | PGPPGL SEQ ID NO: 614 |
| GPPGPP SEQ ID NO: 100 | GLPGSM SEQ ID NO: 615 | GLPGQQ SEQ ID NO: 616 |
| LGSKGE SEQ ID NO: 617 | GIGPPG SEQ ID NO: 611 | PGLPGI SEQ ID NO: 504 |
| PGIGVQ SEQ ID NO: 618 | SPGIPG SEQ ID NO: 619 | PGMQGE SEQ ID NO: 620 |
| PGPKGF SEQ ID NO: 621 | KGQPGL SEQ ID NO: 622 | RGPPGP SEQ ID NO: 148 |
| PPSDEI SEQ ID NO: 623 | PGLKGD SEQ ID NO: 624 | GPLGEK SEQ ID NO: 625 |
| IRGEPG SEQ ID NO: 626 | FPGPPG SEQ ID NO: 627 | LQGIRG SEQ ID NO: 628 |
| DGVIGM SEQ ID NO: 629 | PGNPGI SEQ ID NO: 630 | PGLPGP SEQ ID NO: 58 |
| IKGDKG SEQ ID NO: 631 | PGSPGC SEQ ID NO: 632 | GAPGPQ SEQ ID NO: 445 |
| GPPGVP SEQ ID NO: 633 | DQGDQG SEQ ID NO: 634 | DRGPQG SEQ ID NO: 442 |
| KGSIGI SEQ ID NO: 635 | PPGRLG SEQ ID NO: 636 | EKGQKG SEQ ID NO: 637 |
| ERGSPG SEQ ID NO: 38 | GIPGAP SEQ ID NO: 372 | DGGVPN SEQ ID NO: 638 |
| SGRDGL SEQ ID NO: 639 | GPPGEK SEQ ID NO: 640 | AEGLPG SEQ ID NO: 641 |
| DGYRGP SEQ ID NO: 642 | GPPGLM SEQ ID NO: 643 | LPGFAG SEQ ID NO: 644 |
| GIPGMP SEQ ID NO: 645 | PGPMGP SEQ ID NO: 25 | .PGIPGT SEQ ID NO: 2227 |
| .ILGHVP SEQ ID NO: 2212 | .LPGPDG SEQ ID NO: 2214 | .PGDIVF SEQ ID NO: 2215 |
| .PGLPGQ SEQ ID NO: 2213 | .LRGIPG SEQ ID NO: 760 | .GNKGDP SEQ ID NO: 2216 |

TABLE 15-continued

N-terminal sequences of protease generated peptide fragments of Collagen type IV.
Collagen type IV

| | | |
|---|---|---|
| .SGYPGN SEQ ID NO: 2217 | .PGFPGA SEQ ID NO: 2218 | .PGPRGK SEQ ID NO: 2219 |
| .VSGPPG SEQ ID NO: 2220 | .QQGNRG SEQ ID NO: 2221 | .PGPPGP SEQ ID NO: 458 |
| .KRGPPG SEQ ID NO: 2223 | .VGQPGP SEQ ID NO: 2222 | .SKGEKG SEQ ID NO: 2226 |
| .LHGFPG SEQ ID NO: 2225 | .GEPGMQ SEQ ID NO: 2224 | .GEPGPP SEQ ID NO: 675 | or with any of the following sequences at the C-terminal of a peptide:

TABLE 16

C-terminal sequences of protease generated peptide fragments of Collagen type IV.
Collagen type IV

| | | |
|---|---|---|
| RGPPGP SEQ ID NO: 148 | SVDHGF SEQ ID NO: 646 | PSVDHG SEQ ID NO: 647 |
| VDHGFL SEQ ID NO: 648 | PGQPGY SEQ ID NO: 649 | QPGYTN SEQ ID NO: 650 |
| PGLPGS SEQ ID NO: 651 | GTPSVD SEQ ID NO: 652 | SVGSPG SEQ ID NO: 653 |
| LPGSMG SEQ ID NO: 654 | GPPGVP SEQ ID NO: 633 | PGFPGL SEQ ID NO: 655 |
| PGLPGE SEQ ID NO: 656 | GDPGPP SEQ ID NO: 373 | HQGEMG SEQ ID NO: 657 |
| GPPGLV SEQ ID NO: 658 | PGIPGP SEQ ID NO: 659 | PGFPGT SEQ ID NO: 660 |
| PGLPGP SEQ ID NO: 58 | DGIPGP SEQ ID NO: 661 | SGPKGY SEQ ID NO: 662 |
| PGPRGE SEQ ID NO: 663 | GQGPPG SEQ ID NO: 664 | KVDMGS SEQ ID NO: 665 |
| GIGPPG SEQ ID NO: 611 | PGIDGV SEQ ID NO: 666 | KGHMGE SEQ ID NO: 667 |
| PGAIGP SEQ ID NO: 668 | PPGPPG SEQ ID NO: 119 | KGLPGP SEQ ID NO: 669 |
| GPKGPP SEQ ID NO: 671 | SPGPPG SEQ ID NO: 672 | GPKGLP SEQ ID NO: 670 |
| GSVGYP SEQ ID NO: 673 | PQGPPG SEQ ID NO: 389 | PPGSPG SEQ ID NO: 674 |
| GEPGPP SEQ ID NO: 675 | AGNPGP SEQ ID NO: 676 | PGIKGS SEQ ID NO: 677 |
| PGYTNG SEQ ID NO: 678 | FPGPQG SEQ ID NO: 679 | PGPQGP SEQ ID NO: 453 |
| LSGPPG SEQ ID NO: 680 | PGAPGL SEQ ID NO: 467 | GVMGTP SEQ ID NO: 681 |
| GVSGPK SEQ ID NO: 682 | PGPPGP SEQ ID NO: 458 | |
| HVPGML. SEQ ID NO: 2228 | LPVPGQ. SEQ ID NO: 2229 | LGPPGL. SEQ ID NO: 2230 |
| GVPGQA. SEQ ID NO: 2231 | VPGQAQ. SEQ ID NO: 2232 | GPDGFL. SEQ ID NO: 2233 |
| QEGPLG. SEQ ID NO: 2234 | LPGEVL. SEQ ID NO: 2235 | RGIPGF. SEQ ID NO: 2236 |
| NRGLGF. SEQ ID NO: 2238 | IPSDTL. SEQ ID NO: 2239 | PAGEKG. SEQ ID NO: 2240 |
| GEKGNK. SEQ ID NO: 2241 | PVGPPG. SEQ ID NO: 2242 | DIVFRK. SEQ ID NO: 2243 |
| PPGPKG. SEQ ID NO: 167 | RGKPGM. SEQ ID NO: 2244 | PGTRGL. SEQ ID NO: 2245 |
| GEKGSK. SEQ ID NO: 2246 | EKGSKG. SEQ ID NO: 2247 | SGQPGL. SEQ ID NO: 2248 |
| AGIPQK. SEQ ID NO: 2237 | | |

Collagen V

We have determined that the enzymes listed in the following table cleave type v collagen at least the following cleavage sites (marked "." or in the absence of a '.', at the end of the sequence):

TABLE 14A

Cleavage fragments of collagen type V

| Protease | Neo-epitope (COV) |
|---|---|
| MMP2, Alpha3 | K.GDPGPPGPIGSLG.H SEQ ID NO: 683 |
| MMP2, Alpha3 | G.LRGIPGPVGEPG.L SEQ ID NO: 684 |
| MMP2, Alpha3 | V.IGPPGLQGLPGPPGE.K SEQ ID NO: 685 |
| MMP2, Alpha3 | G.KDGIPGPLGPLGPPG.A SEQ ID NO: 686 |
| MMP2, Alpha3 | G.LRGIPGPVGEPGLL.G SEQ ID NO: 687 |
| MMP2, Alpha3 | G.VLGPQGKTGEVGPLG.E SEQ ID NO: 688 |
| MMP2, Alpha3 | K.DGIPGPLGPLGPPGAA.G SEQ ID NO: 689 |
| MMP2, Alpha3 | G.EDGERGAEGPPGPTG.Q SEQ ID NO: 690 |
| MMP2, Alpha3 | G.LQGPPGFPGPKGPPG.H SEQ ID NO: 691 |
| MMP2, Alpha3 | P.IGSLGHPGPPGVAGPLG.Q SEQ ID NO: 692 |
| MMP2, Alpha3 | G.IRGPPGTVIMMPFQ.F SEQ ID NO: 693 |
| MMP2, Alpha3 | G.QMGPPGPLGPSGLPGLK.G SEQ ID NO: 694 |
| MMP2, Alpha3 | G.LLGAPGQMGPPGPLGPSG.L SEQ ID NO: 695 |
| MMP2, Alpha3 | G.LRGIPGPVGEPGLLGAPG.Q SEQ ID NO: 696 |
| MMP2, Alpha3 | G.LLGPRGSPGPTGRPGVTG.I SEQ ID NO: 697 |
| MMP2, Alpha3 | G.IRGPPGTVIMMPFQF.A SEQ ID NO: 698 |
| MMP2, Alpha3 | G.KDGIPGPLGPLGPPGAAGP.S SEQ ID NO: 699 |
| MMP2, Alpha3 | G.KDGIPGPLGPLGPPGAAGPSG.E SEQ ID NO: 700 |
| MMP2, Alpha3 | Q.GLPGLEGREGAKGELGPPGPLG.K SEQ ID NO: 701 |
| MMP2, Alpha3 | L.GPIGEKGKSGKTGQPGLEGERGPPGSRG.E SEQ ID NO: 702 |
| MMP2, Alpha3 | G.LRGIPGPVGEPGLLGAPGQMGPPGPLGPSG.L SEQ ID NO: 703 |
| MMP2, Alpha3 | G.ANGSPGERGPLGPAGGIGLPGQSGSEGPVGPAG.K SEQ ID NO: 704 |
| MMP2, Alpha3 | G.LIGTPGEKGPPGNPGIPGLPGSDGPLGHPGHEGPTG.E SEQ ID NO: 705 |
| MMP2, Alpha1 | G.LPGEPGPRG.L SEQ ID NO: 706 |
| MMP2, Alpha1 | L.ALRGPAGPMG.L SEQ ID NO: 707 |
| MMP2, Alpha1 | R.LALRGPAGPMG.L SEQ ID NO: 708 |
| MMP2, Alpha1 | G.LTGRPGPVGPPGSGG.L SEQ ID NO: 709 |
| MMP2, Alpha1 | G.LLGPKGPPGPPGPPG.V SEQ ID NO: 710 |
| MMP2, Alpha1 | G.IPGRPGPQGPPGPAG.E SEQ ID NO: 711 |
| MMP2, Alpha1 | P.GPDGPPGPMGPPGLP.G SEQ ID NO: 712 |
| MMP2, Alpha1 | G.QPGPSGADGEPGPRG.Q SEQ ID NO: 713 |
| MMP2, Alpha1 | G.ETGFQGKTGPPGPPG.V SEQ ID NO: 714 |
| MMP2, Alpha1 | G.LRGFPGDRGLPGPV.G SEQ ID NO: 715 |
| MMP2, Alpha1 | G.LRGFPGDRGLPGPVG.A SEQ ID NO: 716 |
| MMP2, Alpha1 | G.KTGPIGPQGAPGKPGPDG.L SEQ ID NO: 717 |
| MMP2, Alpha1 | G.PPGRPGLPGADGLPGPPG.T SEQ ID NO: 718 |
| MMP2, Alpha1 | G.LKGNEGPPGPPGPAGSPGE.R SEQ ID NO: 719 |
| MMP2, Alpha1 | G.LRGFPGDRGLPGPVGALG.L SEQ ID NO: 720 |

TABLE 14A-continued

Cleavage fragments of collagen type V

| Protease | Neo-epitope (COV) | |
|---|---|---|
| MMP2, Alpha1 | G.ERGHPGPPGPPGEQGLPG.L | SEQ ID NO: 721 |
| MMP2, Alpha1 | I.GPPGEQGEKGDRGLPGPQG.S | SEQ ID NO: 722 |
| MMP2, Alpha1 | G.EAGHPGPPGPPGPPGEVIQPLP.I | SEQ ID NO: 723 |
| MMP2, Alpha1 | K.PGPKGNSGGDGPAGPPGERGPNGP.Q | SEQ ID NO: 724 |
| MMP2, Alpha1 | G.EQGLPGSPGPDGPPGPMGPPGLPG.L | SEQ ID NO: 725 |
| MMP2, Alpha1 | E.GPPGEKGGQGPPGPQGPIGYPGPRG.V | SEQ ID NO: 726 |
| MMP2, Alpha1 | G.FPGPKGPPGPPGKDGLPGHPGQRG.E | SEQ ID NO: 727 |
| MMP2 | L.PFRFGGGDA | SEQ ID NO: 728 |
| MMP2 and 9 | GSKGPMVSAQ.E | SEQ ID NO: 729 |
| MMP2 and 9 | Q.ESQAQAILQQ | SEQ ID NO: 730 |
| MMP9, Alpha1 | L.ALRGPAGPMG.L | SEQ ID NO: 707 |
| MMP9, Alpha1 | G.AIGPPGEKGPLG.K | SEQ ID NO: 731 |
| MMP9, Alpha1 | G.GPNGDPGPLGPPG.E | SEQ ID NO: 732 |
| MMP9, Alpha1 | P.PGPPGEQGLPGL.A | SEQ ID NO: 733 |
| MMP9, Alpha1 | G.LLGPKGPPGPPGPPG.V | SEQ ID NO: 734 |
| MMP9, Alpha1 | G.IPGRPGPQGPPGPAG.E | SEQ ID NO: 711 |
| MMP9, Alpha1 | G.QPGPSGADGEPGPRG.Q | SEQ ID NO: 713 |
| MMP9, Alpha1 | G.QQGNPGAQGLPGPQG.A | SEQ ID NO: 735 |
| MMP9, Alpha1 | G.KEGPPGEKGGQGPPG.P | SEQ ID NO: 736 |
| MMP9, Alpha1 | G.ETGFQGKTGPPGPPG.V | SEQ ID NO: 737 |
| MMP9, Alpha1 | G.EKGHPGLIGLIGPPG.E | SEQ ID NO: 738 |
| MMP9, Alpha1 | G.LRGFPGDRGLPGPVG.A | SEQ ID NO: 716 |
| MMP9, Alpha1 | G.KTGPIGPQGAPGKPGPDG.L | SEQ ID NO: 739 |
| MMP9, Alpha1 | P.GPDGPPGPMGPPGLPGLK.G | SEQ ID NO: 740 |
| MMP9, Alpha1 | G.ERGHPGPPGPPGEQGLPG.L | SEQ ID NO: 721 |
| MMP9, Alpha1 | G.ERGPNGPQGPTGFPGPKGPPGPPG.K | SEQ ID NO: 741 |
| MMP9, Alpha1 | L.IGLIGPPGEQGEKGDRGLPGPQGS.S | SEQ ID NO: 742 |
| MMP9, Alpha1 | E.GPPGEKGGQGPPGPQGPIGYPGPRG.V | SEQ ID NO: 726 |
| MMP9, Alpha1 | I.GPPGPPGLPGPPGPKGAKGSSGPTGPKGE.A | SEQ ID NO: 743 |
| MMP9, Alpha1 | P.LGPPGEKGKLGVPGLPGYPGRQGPKGSI.G | SEQ ID NO: 744 |
| MMP9, Alpha1 | Q.GPKGSIGFPGFPGANGEKGGRGTPGKPGPRG.Q | SEQ ID NO: 745 |
| MMP9, Alpha3 | P.GPKGDPGPPGPIG.S | SEQ ID NO: 746 |
| MMP9, Alpha3 | K.GDPGPPGPIGSLG.H | SEQ ID NO: 683 |
| MMP9, Alpha3 | A.PGIPGEKGLPGL.Q | SEQ ID NO: 747 |
| MMP9, Alpha3 | Q.GPPGPKGDPGPPGP.I | SEQ ID NO: 748 |
| MMP9, Alpha3 | G.SLGHPGPPGVAGPLG.Q | SEQ ID NO: 749 |
| MMP9, Alpha3 | G.KDGIPGPLGPLGPPG.A | SEQ ID NO: 686 |
| MMP9, Alpha3 | G.VLGPQGKTGEVGPLG.E | SEQ ID NO: 688 |

TABLE 14A-continued

Cleavage fragments of collagen type V

| Protease | Neo-epitope (COV) | |
|---|---|---|
| MMP9, Alpha3 | G.ELGFQGQTGPPGPAG.V | SEQ ID NO: 750 |
| MMP9, Alpha3 | G.EDGERGAEGPPGPTG.Q | SEQ ID NO: 690 |
| MMP9, Alpha3 | G.LQGPPGFPGPKGPPG.H | SEQ ID NO: 691 |
| MMP9, Alpha3 | G.EKGHIGLIGLIGPPG.E | SEQ ID NO: 751 |
| MMP9, Alpha3 | G.QMGPPGPLGPSGLPGLK.G) | SEQ ID NO: 694 |
| MMP9, Alpha3 | G.PVGEPGLLGAPGQMGPPG.P | SEQ ID NO: 752 |
| MMP9, Alpha3 | G.LRGIPGPVGEPGLLGAPG.Q | SEQ ID NO: 696 |
| MMP9, Alpha3 | G.LLGPRGSPGPTGRPGVTG.I | SEQ ID NO: 697 |
| MMP9, Alpha3 | G.KDGIPGPLGPLGPPGAAGPSG.E | SEQ ID NO: 700 |
| MMP9, Alpha3 | Q.GLPGLEGREGAKGELGPPGPLG.K | SEQ ID NO: 701 |
| MMP9, Alpha3 | G.SRGERGPPGPTGKDGIPGPLGPLG.P | SEQ ID NO: 753 |
| MMP9, Alpha3 | G.EKGKSGKTGQPGLEGERGPPGSRG.E | SEQ ID NO: 754 |
| MMP9, Alpha3 | L.GPIGEKGKSGKTGQPGLEGERGPPGSRG.E | SEQ ID NO: 702 |
| MMP9, Alpha3 | G.ANGSPGERGPLGPAGGIGLPGQSGSEGPVGPAG.K | SEQ ID NO: 704 |
| MMP9, Alpha3 | G.LIGTPGEKGPPGNPGIPGLPGSDGPLGHPGHEGPTG.E | SEQ ID NO: 705 |
| MMP13, Alpha1 | L.PGEPGPRG.L | SEQ ID NO: 755 |
| MMP13, Alpha1 | A.LRGPAGPMG.L | SEQ ID NO: 756 |
| MMP13, Alpha1 | G.LPGEPGPRG.L | SEQ ID NO: 706 |
| MMP13, Alpha1 | L.ALRGPAGPMG.L | SEQ ID NO: 707 |
| MMP13, Alpha1 | R.LALRGPAGPMG.L | SEQ ID NO: 708 |
| MMP13, Alpha1 | G.LRGFPGDRGLPGPVG.A | SEQ ID NO: 716 |
| MMP13, Alpha1 | Q.ESQAQAILQQARLA.L | SEQ ID NO: 730 |
| MMP13, Alpha1 | P.GPDGPPGPMGPPGLPGLK.G | SEQ ID NO: 740 |
| MMP13, Alpha1 | G.PQGAIGPPGEKGPLGKPGLPGMPGADGPPGHPG.K | SEQ ID NO: 757 |
| MMP13, Alpha1 | A.GPMGLTGRPGPVGPPGSGGLKGEPGDVGPQGPRG.V | SEQ ID NO: 758 |
| MMP13, Alpha3 | G.VLGPQGKTGEVGPLG.E | SEQ ID NO: 688 |
| MMP13, Alpha3 | G.LRGIPGPVGEPGLLGAPG.Q | SEQ ID NO: 696 |
| MMP13, Alpha3 | G.LRGIPGPVGEPGLLGAPGQMGPPGPLGPSG.L | SEQ ID NO: 703 |
| MMP13, Alpha3 | G.LRGIPGPVGEPGLLGAPGQMGPPGPLGPSGLPG.L | SEQ ID NO: 759 |

P is hydroxyproline, K indicates hydroxylysine, glycosylation, lipoxidation or cross linking.

The immunological binding partner may be one specifically reactive with a C-terminal or N-terminal neoepitope formed by cleavage of type v collagen. Suitable immunological binding partners may therefore be specifically reactive with any of the following sequences at the N terminal of a peptide:

TABLE 15a

N-terminal sequences of protease generated peptide fragments of Collagen type V.
Collagen type V

| | | |
|---|---|---|
| GDPGPP SEQ ID NO: 373 | LRGIPG SEQ ID NO: 760 | IGPPGI SEQ ID NO: 761 |
| LQGPPG SEQ ID NO: 62 | IGSLGH SEQ ID NO: 762 | IRGPPG SEQ ID NO: 763 |

TABLE 15a-continued

N-terminal sequences of protease generated peptide fragments of Collagen type V.
Collagen type V

| | | | | | |
|---|---|---|---|---|---|
| ANGSPG | SEQ ID NO: 764 | LIGTPG | SEQ ID NO: 765 | LPGEPG | SEQ ID NO: 766 |
| IPGRPG | SEQ ID NO: 767 | GPDGPP | SEQ ID NO: 768 | QPGPSG | SEQ ID NO: 769 |
| LKGNEG | SEQ ID NO: 770 | ERGHPG | SEQ ID NO: 771 | GPPGEQ | SEQ ID NO: 772 |
| FPGPKG | SEQ ID NO: 491 | PFRFGG | SEQ ID NO: 773 | ESQAQA | SEQ ID NO: 774 |
| LLGPKG | SEQ ID NO: 775 | QQGNPG | SEQ ID NO: 776 | KEGPPG | SEQ ID NO: 777 |
| IGLIGP | SEQ ID NO: 778 | GPPGPP | SEQ ID NO: 100 | LGPPGE | SEQ ID NO: 779 |
| GPPGPK | SEQ ID NO: 780 | SLGHPG | SEQ ID NO: 781 | KDGIPG | SEQ ID NO: 782 |
| PVGEPG | SEQ ID NO: 783 | LRGIPG | SEQ ID NO: 760 | KDGIPG | SEQ ID NO: 782 |
| ANGSPG | SEQ ID NO: 764 | LIGTPG | SEQ ID NO: 765 | PGEPGP | SEQ ID NO: 784 |
| LLGAPG | SEQ ID NO: 785 | GLPGLE | SEQ ID NO: 786 | GIPGEK | SEQ ID NO: 787 |
| LALRGP | SEQ ID NO: 788 | LTGRPG | SEQ ID NO: 789 | LLGPKG | SEQ ID NO: 775 |
| LRGFPG | SEQ ID NO: 790 | KTGPIG | SEQ ID NO: 791 | PPGRPG | SEQ ID NO: 792 |
| PGPKGN | SEQ ID NO: 527 | EQGLPG | SEQ ID NO: 793 | GPPGEK | SEQ ID NO: 640 |
| AIGGPP | SEQ ID NO: 794 | GPNGDP | SEQ ID NO: 795 | PGPPGE | SEQ ID NO: 796 |
| LLGPRG | SEQ ID NO: 797 | GPDGPP | SEQ ID NO: 768 | ERGPNG | SEQ ID NO: 798 |
| GPKGDP | SEQ ID NO: 799 | GDPGPP | SEQ ID NO: 373 | PGIPGE | SEQ ID NO: 800 |
| LQGPPG | SEQ ID NO: 62 | EKGHIG | SEQ ID NO: 801 | QMGPPG | SEQ ID NO: 802 |
| SRGERG | SEQ ID NO: 803 | EKGKSG | SEQ ID NO: 804 | GPIGEK | SEQ ID NO: 805 |
| LPGEPG | SEQ ID NO: 766 | PQGAIG | SEQ ID NO: 806 | GPMGLT | SEQ ID NO: 807 |
| QMGPPG | SEQ ID NO: 802 | ETGFQG | SEQ ID NO: 808 | GSKGPM | SEQ ID NO: 809 |
| ALRGPA | SEQ ID NO: 810 | EAGHPG | SEQ ID NO: 811 | EKGHPG | SEQ ID NO: 812 |
| KDGIP | SEQ ID NO: 813 | VLGPQG | SEQ ID NO: 814 | EDGERG | SEQ ID NO: 815 |
| GPKGSI | SEQ ID NO: 816 | ELGFQG | SEQ ID NO: 817 | LRGPAG | SEQ ID NO: 818 |

P is hydroxyproline, K indicates hydroxylysine, glycosylation, lipoxidation or cross linking.

or with any of the following sequences at the C-terminal of a peptide:

TABLE 16a

C-terminal sequences of protease generated peptide fragments of Collagen type V.
Collagen type V

| | | | | | |
|---|---|---|---|---|---|
| PIGSLG | SEQ ID NO: 819 | PVGEPG | SEQ ID NO: 783 | PGPPGE | SEQ ID NO: 796 |
| PPGPTG | SEQ ID NO: 820 | PKGPPG | SEQ ID NO: 821 | VAGPLG | SEQ ID NO: 822 |
| RPGVTG | SEQ ID NO: 823 | MMPFQF | SEQ ID NO: 824 | PGAAGP | SEQ ID NO: 825 |
| PVGPAG | SEQ ID NO: 826 | HEGPTG | SEQ ID NO: 827 | EPGPRG | SEQ ID NO: 516 |
| GPPGLP | SEQ ID NO: 828 | GQGPPG | SEQ ID NO: 664 | PPGPPG | SEQ ID NO: 119 |
| AGSPGE | SEQ ID NO: 829 | PVGALG | SEQ ID NO: 830 | EQGLPG | SEQ ID NO: 793 |
| YPGPRG | SEQ ID NO: 831 | HPGQRG | SEQ ID NO: 832 | GGGGDA | SEQ ID NO: 833 |

TABLE 16a-continued

C-terminal sequences of protease generated peptide fragments of Collagen type V.
Collagen type V

LIGPPG SEQ ID NO: 834   GLPGLK SEQ ID NO: 835   PPGPPG SEQ ID NO: 119

PPGPIG SEQ ID NO: 174   KGLPGL SEQ ID NO: 836   PGPPGP SEQ ID NO: 458

QMGPPG SEQ ID NO: 802   LLGAPG SEQ ID NO: 785   RPGVTG SEQ ID NO: 823

QQARLA SEQ ID NO: 837   PPGHPG SEQ ID NO: 838   PQGPRG SEQ ID NO: 150

PLGPPG SEQ ID NO: 839   GEPGLL SEQ ID NO: 840   EVGPLG SEQ ID NO: 841

IMMPFQ SEQ ID NO: 842   GLPGLK SEQ ID NO: 835   PLGPSG SEQ ID NO: 843

AAGPSG SEQ ID NO: 844   PPGPLG SEQ ID NO: 845   PPGSRG SEQ ID NO: 846

PAGPMG SEQ ID NO: 847   PPGSGG SEQ ID NO: 848   PPGPPG SEQ ID NO: 119

GLPGPV SEQ ID NO: 849   LPGPVG SEQ ID NO: 850   KPGPDG SEQ ID NO: 851

LPGPQG SEQ ID NO: 852   VIQPLP SEQ ID NO: 853   RGPNGP SEQ ID NO: 854

PGPQGS SEQ ID NO: 855   EKGPLG SEQ ID NO: 856   PLGPPG SEQ ID NO: 839

GPPGAA SEQ ID NO: 857   TGPKGE SEQ ID NO: 858   GPKGSI SEQ ID NO: 816

PPGPAG SEQ ID NO: 52    PPGPAG SEQ ID NO: 52    PPGPTG SEQ ID NO: 820

QGLPGL SEQ ID NO: 859   PSGLPG SEQ ID NO: 860   LLGAPG SEQ ID NO: 785

PPGSRG SEQ ID NO: 846   LPGPPG SEQ ID NO: 72    PPGLPG SEQ ID NO: 861

PPGPLG SEQ ID NO: 845   KPGPRG SEQ ID NO: 862   PKGPPG SEQ ID NO: 821

PLGPLG SEQ ID NO: 863   PPGSRG SEQ ID NO: 846

P is hydroxyproline, K indicates hydroxylysine, glycosylation, lipoxidation or cross linking.

Collagen VI

We have determined that the enzymes listed in the following table cleave type vi collagen at least the following cleavage sites (marked "." or in the absence of a '.', at the end of the sequence):

TABLE 14b

Cleavage fragments of collagen type VI

| Protease | Neoepitope |
|---|---|
| MMP2 | G.YRGPEGPQGPPG.H SEQ ID NO: 864 |
| MMP2 | G.PIGPKGYRGDEGPP.G SEQ ID NO: 865 |
| MMP2, (a3) | I.GIGIGNADIT.E SEQ ID NO: 866 |
| MMP2, (a3) | G.AQGPAGPAGPPG.L SEQ ID NO: 867 |
| MMP9 | G.LIGEQGISGPRG.S SEQ ID NO: 868 |
| MMP9 | P.PGLIGEQGISGPR.G SEQ ID NO: 869 |
| MMP9 | E.PGEPGPKGGIGNRG.P SEQ ID NO: 870 |
| MMP9 | G.ISGPRGSGGAAGAPGERGRTGPLG.R SEQ ID NO: 871 |
| MMP13 | PGPAGPPGDPGLMG SEQ ID NO: 872 |
| FAP-1 | VAAKPAAVRPPAAAAAKPVATKPEVPRP SEQ ID NO: 873 |
| FAP-1 | GEPGLNGTTGPKGI SEQ ID NO: 874 |
| FAP-1 | IGPKGIPGEDGYRGYPG SEQ ID NO: 875 |
| FAP-1 | VAVVQHAPSESVDNASMPPVKVEFSL SEQ ID NO: 876 |
| FAP-2 | LGPMGVPGRD SEQ ID NO: 877 |
| FAP-2 | GEPGPPGEKGEAGDEGNPGPDGAPGERG SEQ ID NO: 878 |
| FAP-2 | RGPIGSIGPKGIPGEDGYRGYPGDEGGP SEQ ID NO: 879 |
| FAP-2 | PPPPQPARSAS SEQ ID NO: 880 |
| FAP-2 | FGPSAATPAPPG SEQ ID NO: 881 |
| FAP-2 | GPKGETGDLGPMGVPGRDGVPGGPGETGK SEQ ID NO: 882 |

The immunological binding partner may be one specifically reactive with a C-terminal or N-terminal neoepitope formed by cleavage of type v collagen. Suitable immunological binding partners may therefore be specifically reactive with any of the following sequences at the N terminal of a peptide:

TABLE 15B

N-terminal sequences of protease generated peptide fragments of Collagen type VI.
Collagen type VI

| | | |
|---|---|---|
| YRGPEG SEQ ID NO: 883 | PIGPKG SEQ ID NO: 865 | GIGIGN SEQ ID NO: 885 |
| ISGPRG SEQ ID NO: 886 | PGPAGP SEQ ID NO: 887 | VAAKPA SEQ ID NO: 888 |
| GEPGPP SEQ ID NO: 675 | RGPIGS SEQ ID NO: 889 | PPPPQP SEQ ID NO: 890 |
| AQGPAG SEQ ID NO: 891 | LIGEQG SEQ ID NO: 892 | PGLIGE SEQ ID NO: 893 |
| GEPGLN SEQ ID NO: 894 | IGPKGI SEQ ID NO: 895 | VAVVQH SEQ ID NO: 896 |
| FGPSAA SEQ ID NO: 897 | GPKGET SEQ ID NO: 898 | PGEPGP SEQ ID NO: 784 |
| LGPMGV SEQ ID NO: 899 | | | or with any of the following sequences at the C-terminal of a peptide:

TABLE 16B

C-terminal sequences of protease generated peptide fragments of Collagen type VI.
Collagen type VI

| | | |
|---|---|---|
| GDEGPP SEQ ID NO900 | GNADIT SEQ ID NO901 | PAGPPG SEQ ID NO 133 |
| DPGLMG SEQ ID NO902 | PEVPRP SEQ ID NO903 | TGPKGI SEQ ID NO904 |
| GDEGGP SEQ ID NO905 | PARSAS SEQ ID NO906 | TPAPPG SEQ ID NO915 |
| ISGPRG SEQ ID NO886 | GISGPR SEQ ID NO907 | GIGNRG SEQ ID NO908 |
| YRGYPG SEQ ID NO909 | KVEFSL SEQ ID NO910 | GVPGRD SEQ ID NO911 |
| PGETGK SEQ ID NO912 | RTGPLG SEQ ID NO913 | APGERG SEQ ID NO914 |

Proteoglycans

In another aspect of the invention, said peptide fragments are fragments of proteoglycans versican, lumican, perlecan, biglycan and decorin, which are all identified in fibrotic tissue. Several candidate proteases may be responsible for the digestion of proteoglycans in fibrotic lesions We have determined that the enzymes listed in table 17 generate lumican, versican, biglycan, perlecan and decorin resulting in at least following cleavage products:

TABLE 17

Cleavage fragments of biglycan, decorin, versican, lumican, and perlecan.

| Protease | |
|---|---|
| | Biglycan |
| MMP-3 | SVPKEISPDTTLLDLQNNDISE SEQ ID NO: 916 |
| MMP-3 | KSVPKEISPDTTLLDLQNNDISE SEQ ID NO: 917 |
| MMP-9 | NSGFEPGAFDGLKLNYLRISEAK SEQ ID NO: 918 |
| MMP-9 | LKSVPKEISPDTTLLDLQNNDISE SEQ ID NO: 919 |
| MMP-12 | LRISEAKLTGIPKDLPET SEQ ID NO: 920 |
| MMP-13 | LKSVPKEISPDTTLLDLQNNDISE SEQ ID NO: 919 |
| MMP-13 | LTGIPKDLPETLNELHLDHNKIQAIE SEQ ID NO: 921 |

TABLE 17-continued

Cleavage fragments of biglycan, decorin, versican, lumican, and perlecan.

| Protease | |
|---|---|
| ADAMTS4 | RISEAKLTGIPKDLPETLNE SEQ ID NO: 922 |
| ADAMTS4 | AIELEDLLRYSK SEQ ID NO: 923 |
| ADAMTS4 | AIELEDLLRY SEQ ID NO: 924 |
| ADAMTS4 | EAKLTGIPKDLPETLNE SEQ ID NO: 925 |
| ADAMTS4 | LKAVPKEISPDTTLLDLQNNDISE SEQ ID NO: 926 |
| MMP-8 | LLDLQNNDISELRKDD SEQ ID NO: 927 |
| MMP-8 | IELEDLLRYS SEQ ID NO: 928 |
| CathepsinS | NSGFEPGAFDGLK SEQ ID NO: 929 |
| | Decorin |
| MMP-12 | IVIELGTNPLK SEQ ID NO: 930 |
| MMP-3 | DEASGIGPEVPDDR SEQ ID NO: 931 |
| MMP-3 | LHLDGNKISRVDAAS SEQ ID NO: 932 |
| MMP-3 | VNNKISKVSPGAFTPL SEQ ID NO: 933 |
| MMP-3 | LILVNNKISKVSPGAFTPLVKLER SEQ ID NO: 934 |
| MMP-9 | SNPVQYWEIQPSTFR SEQ ID NO: 935 |

TABLE 17-continued

Cleavage fragments of biglycan, decorin, versican, lumican, and perlecan.

| Protease | | |
|---|---|---|
| CathepsinK | SSGIENGAFQGMK | SEQ ID NO: 884 |
| CathepsinK | SSGIENGAFQGMKKLS | SEQ ID NO: 946 |
| ADAMTS1 | KITEIKDGDFK | SEQ ID NO: 936 |
| ADAMTS1 | GLPPSLTELHLDGNK | SEQ ID NO: 937 |
| Versican | | |
| Unknown | LLASDAGLYR | SEQ ID NO: 938 |
| Unknown | LATVGELQAAWR | SEQ ID NO: 939 |
| Unknown | ETTVLVAQNGNIK | SEQ ID NO: 940 |
| Lumican | | |
| Unknown | SLEDLQLTHNK | SEQ ID NO: 941 |
| Unknown | LKEDAVSAAFK | SEQ ID NO: 942 |
| Perlecan | | |
| Unknown | SIEYSPQLEDAGSR | SEQ ID NO: 943 |
| Unknown | LEGDTLIIPR | SEQ ID NO: 944 |
| ADAMTS4 | VSEAVVEKLEPEYR | SEQ ID NO: 945 |
| ADAMTS4 | EVSEAVVEKLEPEYR | SEQ ID NO: 947 |
| ADAMTS4 | SIEYSPQLEDASAKEFR | SEQ ID NO: 948 |

The immunological binding partner may be one specifically reactive with a C-terminal or N-terminal neo-epitope formed by cleavage of type versican, lumican, decorin, perlecan, and biglycan.

Suitable immunological binding partners may therefore be specifically reactive with any of the following at the N terminal of a peptide:

TABLE 18

N-terminal sequences of protease generated peptide fragments of biglycan, decorin, lumican, versican, and perlecan.

Biglycan

SVPKEI SEQ ID NO: 949  GLKLNY SEQ ID NO: 950  RISEAK SEQ ID NO: 951

NSGFEP SEQ ID NO: 952  LKSVPK SEQ ID NO: 953  AIELED SEQ ID NO: 954

IELEDL SEQ ID NO: 957  QCSDLG SEQ ID NO: 955  EAKLTG SEQ ID NO: 956

LRISEA SEQ ID NO: 958  LTGIPK SEQ ID NO: 959  LKAVPK SEQ ID NO: 960

LLDLQN SEQ ID NO: 961

Decorin

IVIELG SEQ ID NO: 962  DEASGI SEQ ID NO: 963  VNNKIS SEQ ID NO: 964

NGLNQM SEQ ID NO: 965  LHLDGN SEQ ID NO: 966  LILVNN SEQ ID NO: 967

SSGIEN SEQ ID NO: 968  KITEIK SEQ ID NO: 969  GLPPSL SEQ ID NO: 970

SNPVQY SEQ ID NO: 971

Versican

LLASDA SEQ ID NO: 972  LATVGE SEQ ID NO: 973  ETTVLV SEQ ID NO: 974

ENQDAR SEQ ID NO: 975  NGFDQC SEQ ID NO: 976  SLTVVK SEQ ID NO: 977

Lumican

SLEDLQ SEQ ID NO: 978  LKEDAV SEQ ID NO: 979  HLQHNR SEQ ID NO: 980

LQHNRL SEQ ID NO: 985

Perlecan

SIEYSP SEQ ID NO: 981  LVNFTR SEQ ID NO: 982  VSEAVV SEQ ID NO: 983

EVSEAV SEQ ID NO: 984 or with any of the following sequences in table 19, at the C-terminal of a peptide:

TABLE 19

C-terminal sequences of protease generated peptide fragments of biglycan, decorin, lumican, versican, and perlecan.

Biglycan

NNDISE SEQ ID NO: 986    YWEVQP SEQ ID NO: 987    EDLLRY SEQ ID NO: 988

RISEAK SEQ ID NO: 951    KIQAIE SEQ ID NO: 989    PETLNE SEQ ID NO: 990

LRKDDF SEQ ID NO: 991    LLRYSK SEQ ID NO: 992    ELRKDD SEQ ID NO: 993

KDLPET SEQ ID NO: 994    DLLRYS SEQ ID NO: 995    AFDGLK SEQ ID NO: 996

LNELHL SEQ ID NO: 997

Decorin

GTNPLK SEQ ID NO: 998    EVPDDR SEQ ID NO: 999    GAFTPL SEQ ID NO: 1000

SSGIEN SEQ ID NO: 968    RVDAAS SEQ ID NO: 1001   LVKLER SEQ ID NO: 1002

GMKKLS SEQ ID NO: 1003   KDGDFK SEQ ID NO: 1004   HLDGNK SEQ ID NO: 1005

QPSTFR SEQ ID NO: 1006   AFQGMK SEQ ID NO: 1007

Versican

CDVMYG SEQ ID NO: 1008   NGFDQC SEQ ID NO: 976    QNGINK SEQ ID NO: 1009

IGQDYK SEQ ID NO: 1010

Lumican

QLTHNK SEQ ID NO: 1011   VSAAFK SEQ ID NO: 1012   GLKSLE SEQ ID NO: 1013

Perlecan

EDAGSR SEQ ID NO: 1014   EFREVS SEQ ID NO: 1015   VAQQDS SEQ ID NO: 1016

SAKEFR SEQ ID NO: 1017   LEPEYR SEQ ID NO: 1018

CRP

Several candidate proteases may be responsible for the digestion of CRP in fibrotic tissue the literature reports many different proteases in fibrotic tissue. Most likely, this is the result of the large range of complicated processes eventually leading to fibrosis. However, in our assessment, early phases may consist of a range of MMPs, whereas later stages may rely more on cathepsin K degradation of the matrix, resulting in different neo-epitope profiles dependent on the levels of disease. We have through a range of in vitro cleavages of pure native proteins determined that the enzymes listed in the following tables of cleaved CRP at least following cleavage sites (marked * in Table 20, but at the ends of each sequence in Table 21):

TABLE 20

CRP fragments generated by specific proteases.

| Protease/Protein | Neo-epitope |
|---|---|
| CRP + CatK | K*ESDTSYVSLKAPLT*K SEQ ID NO: 1019 |
| CRP + CatK | G*GNFEGSQSLVGDIG*N SEQ ID NO: 1020 |
| CRP + MMP9 | A*LKYEVQGEVFTKPQ*L SEQ ID NO: 1021 |
| CRP + MMP9 | G*IVEFWVDGKPRV*R SEQ ID NO: 1022 |

TABLE 20-continued

CRP fragments generated by specific proteases.

| Protease/Protein | Neo-epitope |
|---|---|
| CRP + MMP1/MMP3 | R*KAFVFPKE*S SEQ ID NO: 1023 |
| CRP + MMP3 | K*YEVQGEVFTKPQLWP*- SEQ ID NO: 1024 |
| CRP + MMP3 | D*SFGGNFEGSQS*L SEQ ID NO: 1025 |
| CRP + MMP3 | D*FVLSPDEINT*I SEQ ID NO: 1026 |
| CRP + MMP3 | S*LKKGYTVGAEA*S SEQ ID NO: 1027 |
| CRP + MMP3 | A*FGQTDMSRKA*F SEQ ID NO: 1028 |
| CRP + MMP3 | S*LKKGYTVGAEAS*I SEQ ID NO: 1029 |
| CRP + MMP3 | G*EVFTKPQLWP*- SEQ ID NO: 1030 |
| CRP + MMP3 | S*IILGQEQDSFGGN.F SEQ ID NO: 1031 |
| CRP + MMP3 | K*YEVQGEVFTKPQ.L SEQ ID NO: 1032 |

TABLE 21

CRP fragments generated by specific proteases.

| Protease | Neoepitope | Aminoacid Nos* |
|---|---|---|
| MMP9 | AFVFPK SEQ ID NO: 1033 | 026-031 |
| MMP9 | FGQTDMSR SEQ ID NO: 1034 | 017-024 |
| MMP9 | FGQTDMSRK SEQ ID NO: 1035 | 017-025 |
| MMP9 | FGQTDMSRKA SEQ ID NO: 1036 | 017-026 |
| MMP9 | FGQTDMSRKAF SEQ ID NO: 1037 | 017-027 |
| MMP9 | FGQTDMSRKAFVFPKE SEQ ID NO: 1038 | 017-032 |
| MMP9 | FGQTDMSRKAFVFPKESDTS SEQ ID NO: 1039 | 017-036 |
| MMP9 | FGQTDMSRKAFVFPKESDTSYV SEQ ID NO: 1040 | 017-038 |
| MMP9 | FGQTDMSRKAFVFPKESDTSYVS SEQ ID NO: 1041 | 017-039 |
| MMP9 | TDMSRKAFVFPKESDTSYV SEQ ID NO: 1042 | 020-038 |
| MMP9 | MSRKAFVFPKESDTS SEQ ID NO: 1043 | 022-036 |
| MMP9 | SRKAFVFPKESDTSYV SEQ ID NO: 1044 | 023-038 |
| MMP9 | RKAFVFPKE SEQ ID NO: 1045 | 024-032 |
| MMP9 | RKAFVFPKESDTSYV SEQ ID NO: 1046 | 024-038 |
| MMP9 | RKAFVFPKESDTSYVS SEQ ID NO: 1047 | 024-039 |
| MMP9 | KAFVFPKE SEQ ID NO: 1048 | 025-032 |
| MMP9 | KAFVFPKESD SEQ ID NO: 1049 | 025-034 |
| MMP9 | KAFVFPKESDT SEQ ID NO: 1050 | 025-035 |
| MMP9 | KAFVFPKESDTS SEQ ID NO: 1051 | 025-036 |
| MMP9 | KAFVFPKESDTSYV SEQ ID NO: 1052 | 025-038 |
| MMP9 | KAFVFPKESDTSYVS SEQ ID NO: 1053 | 025-039 |
| MMP9 | AFVFPKE SEQ ID NO: 1054 | 026-032 |
| MMP9 | AFVFPKESDT SEQ ID NO: 1055 | 026-035 |
| MMP9 | AFVFPKESDTSYV SEQ ID NO: 1056 | 026-038 |
| MMP9 | AFVFPKESDTSYVS SEQ ID NO: 1057 | 026-039 |
| MMP9 | AFVFPKESDTSYVSL SEQ ID NO: 1058 | 026-040 |
| MMP9 | FVFPK SEQ ID NO: 1059 | 027-031 |
| MMP9 | FVFPKE SEQ ID NO: 1060 | 027-032 |
| MMP9 | FVFPKESD SEQ ID NO: 1061 | 027-034 |
| MMP9 | FVFPKESDTS SEQ ID NO: 1062 | 027-036 |
| MMP9 | FVFPKESDTSY SEQ ID NO: 1063 | 027-037 |
| MMP9 | FVFPKESDTSYV SEQ ID NO: 1064 | 027-038 |
| MMP9 | FVFPKESDTSYVS SEQ ID NO: 1065 | 027-039 |
| MMP9 | FVFPKESDTSYVSL SEQ ID NO: 1066 | 027-040 |
| MMP9 | VFPKESDTS SEQ ID NO: 1067 | 028-036 |
| MMP9 | VFPKESDTSYV SEQ ID NO: 1068 | 028-038 |
| MMP9 | VFPKESDTSYVS SEQ ID NO: 1069 | 028-039 |
| MMP9 | VFPKESDTSYVSL SEQ ID NO: 1070 | 028-040 |

TABLE 21-continued

CRP fragments generated by specific proteases.

| Protease | Neoepitope | Aminoacid Nos* |
|---|---|---|
| MMP9 | FPKESDTSYVS SEQ ID NO: 1071 | 029-039 |
| MMP9 | KESDTSYVSLKAPLTKP SEQ ID NO: 1072 | 031-047 |
| MMP9 | SDTSYVSLKAPLTKP SEQ ID NO: 1073 | 033-047 |
| MMP9 | SLKAPLTKP SEQ ID NO: 1074 | 039-047 |
| MMP9 | SLKAPLTKPLK SEQ ID NO: 1075 | 039-049 |
| MMP9 | LKAPLTKPLK SEQ ID NO: 1076 | 040-049 |
| MMP9 | FYTELSSTRGYS SEQ ID NO: 1077 | 057-068 |
| MMP9 | LSSTRGYS SEQ ID NO: 1078 | 061-068 |
| MMP9 | SSTRGYS SEQ ID NO: 1079 | 062-068 |
| MMP9 | STRGYS SEQ ID NO: 1080 | 063-068 |
| MMP9 | IFSYATKRQ SEQ ID NO: 1081 | 069-077 |
| MMP9 | IFSYATKRQDNEILI SEQ ID NO: 1082 | 069-083 |
| MMP9 | SYATKRQDNEILI SEQ ID NO: 1083 | 071-083 |
| MMP9 | YATKRQDNEIL SEQ ID NO: 1084 | 072-082 |
| MMP9 | YATKRQDNEILI SEQ ID NO: 1085 | 072-083 |
| MMP9 | YATKRQDNEILIF SEQ ID NO: 1086 | 072-084 |
| MMP9 | TKRQDNEILI SEQ ID NO: 1087 | 074-083 |
| MMP9 | TKRQDNEILIF SEQ ID NO: 1088 | 074-084 |
| MMP9 | TKRQDNEILIFWSKDI SEQ ID NO: 1089 | 074-089 |
| MMP9 | KRQDNEILI SEQ ID NO: 1090 | 075-083 |
| MMP9 | KRQDNEILIF SEQ ID NO: 1091 | 075-084 |
| MMP9 | WSKDIGYS SEQ ID NO: 1092 | 085-092 |
| MMP9 | SKDIGYS SEQ ID NO: 1093 | 086-092 |
| MMP9 | IVEFWVDGKPRV SEQ ID NO: 1094 | 124-135 |
| MMP9 | EFWVDGKPR SEQ ID NO: 1095 | 126-134 |
| MMP9 | VVVDGKPRV SEQ ID NO: 1096 | 128-135 |
| MMP9 | VDGKPRV SEQ ID NO: 1097 | 129-135 |
| MMP9 | SLKKGYTVGAE SEQ ID NO: 1098 | 138-148 |
| MMP9 | SLKKGYTVGAEA SEQ ID NO: 1099 | 138-149 |
| MMP9 | SLKKGYTVGAEAS SEQ ID NO: 1100 | 138-150 |
| MMP9 | LKKGYTV SEQ ID NO: 1101 | 139-145 |
| MMP9 | LKKGYTVG SEQ ID NO: 1102 | 139-146 |
| MMP9 | LKKGYTVGA SEQ ID NO: 1103 | 139-147 |
| MMP9 | LKKGYTVGAE SEQ ID NO: 1104 | 139-148 |
| MMP9 | LKKGYTVGAEA SEQ ID NO: 1105 | 139-149 |
| MMP9 | LKKGYTVGAEAS SEQ ID NO: 1106 | 139-150 |
| MMP9 | LKKGYTVGAEASI SEQ ID NO: 1107 | 139-151 |
| MMP9 | SIILGQEQDSFGGN SEQ ID NO: 1108 | 150-163 |

TABLE 21-continued

CRP fragments generated by specific proteases.

| Protease | Neoepitope | Aminoacid Nos* |
|---|---|---|
| MMP9 | SIILGQEQDSFGGNFEGSQ SEQ ID NO: 1109 | 150-168 |
| MMP9 | SIILGQEQDSFGGNFEGSQS SEQ ID NO: 1110 | 150-169 |
| MMP9 | IILGQEQDSFGGNFEGS SEQ ID NO: 1111 | 151-067 |
| MMP9 | IILGQEQDSFGGNFEGSQS SEQ ID NO: 1112 | 151-169 |
| MMP9 | ILGQEQDSFGGN SEQ ID NO: 1113 | 152-163 |
| MMP9 | ILGQEQDSFGGNFEGSQ SEQ ID NO: 1114 | 152-168 |
| MMP9 | ILGQEQDSFGGNFEGSQS SEQ ID NO: 1115 | 152-169 |
| MMP9 | LGQEQDSFGGNFEGSQ SEQ ID NO: 1116 | 153-168 |
| MMP9 | LGQEQDSFGGNFEGSQS SEQ ID NO: 1117 | 153-169 |
| MMP9 | GQEQDSFGGNFEGSQS SEQ ID NO: 1118 | 154-169 |
| MMP9 | SFGGNFEGSQS SEQ ID NO: 1119 | 159-169 |
| MMP9 | QSLVGDIGNVN SEQ ID NO: 1120 | 168-178 |
| MMP9 | INTIYLGGPFSPNV SEQ ID NO: 1121 | 189-202 |
| MMP9 | INTIYLGGPFSPNVLN SEQ ID NO: 1122 | 189-204 |
| MMP9 | IYLGGPFSPNVLN SEQ ID NO: 1123 | 192-204 |
| MMP9 | YLGGPFSPNVLN SEQ ID NO: 1124 | 193-204 |
| MMP9 | LGGPFSPN SEQ ID NO: 1125 | 194-201 |
| MMP9 | SPNVLNWRALKYEVQGEVFTKPQLWP SEQ ID NO: 1126 | 199-224 |
| MMP9 | LNWRA SEQ ID NO: 1127 | 203-207 |
| MMP9 | LNWRAL SEQ ID NO: 1128 | 203-208 |
| MMP9 | LNWRALK SEQ ID NO: 1129 | 203-209 |
| MMP9 | WRALKYE SEQ ID NO: 1130 | 205-211 |
| MMP9 | WRALKYEV SEQ ID NO: 1131 | 205-212 |
| MMP9 | WRALKYEVQGE SEQ ID NO: 1132 | 205-215 |
| MMP9 | ALKYEV SEQ ID NO: 1133 | 207-212 |
| MMP9 | LKYEVQ SEQ ID NO: 1134 | 208-213 |
| MMP9 | LKYEVQG SEQ ID NO: 1135 | 208-214 |
| MMP9 | LKYEVQGE SEQ ID NO: 1136 | 208-215 |
| MMP9 | LKYEVQGEVFTKP SEQ ID NO: 1137 | 208-220 |
| MMP9 | LKYEVQGEVFTKPQ SEQ ID NO: 1138 | 208-221 |
| MMP9 | LKYEVQGEVFTKPQLWP SEQ ID NO: 1139 | 208-224 |
| MMP9 | KYEVQGE SEQ ID NO: 1140 | 209-215 |
| MMP9 | KYEVQGEVFTKPQ SEQ ID NO: 1141 | 209-221 |
| MMP9 | KYEVQGEVFTKPQLWP SEQ ID NO: 1142 | 209-224 |
| MMP9 | YEVQGEVFTKP SEQ ID NO: 1143 | 210-220 |
| MMP9 | YEVQGEVFTKPQ SEQ ID NO: 1144 | 210-221 |
| MMP9 | YEVQGEVFTKPQLWP SEQ ID NO: 1145 | 210-224 |
| MMP9 | VQGEVFTKPQ SEQ ID NO: 1146 | 212-221 |

TABLE 21-continued

CRP fragments generated by specific proteases.

| Protease | Neoepitope | Aminoacid Nos* |
|---|---|---|
| MMP9 | VQGEVFTKPQLWP SEQ ID NO: 1147 | 212-224 |
| MMP9 | QGEVFTKPQ SEQ ID NO: 1148 | 213-221 |
| MMP9 | GEVFTKP SEQ ID NO: 1149 | 214-220 |
| MMP9 | GEVFTKPQ SEQ ID NO: 1150 | 214-221 |
| MMP9 | EVFTKPQ SEQ ID NO: 1151 | 215-221 |
| MMP9 | EVFTKPQLWP SEQ ID NO: 1152 | 215-224 |
| MMP9 | VFTKPQ SEQ ID NO: 1153 | 216-221 |
| MMP9 | FTKPQ SEQ ID NO: 1154 | 217-221 |
| MMP9 | FTKPQLWP SEQ ID NO: 1155 | 217-224 |
| MMP9 | TKPQLWP SEQ ID NO: 1156 | 218-224 |
| MMP9 | KPQLWP SEQ ID NO: 1157 | 219-224 |
| MMP12 | FGQTDMSRKA SEQ ID NO: 1036 | 017-026 |
| MMP12 | MSRKAFVFP SEQ ID NO: 1158 | 022-030 |
| MMP12 | MSRKAFVFPKE SEQ ID NO: 1159 | 022-032 |
| MMP12 | MSRKAFVFPKESD SEQ ID NO: 1160 | 022-034 |
| MMP12 | MSRKAFVFPKESDTS SEQ ID NO: 1043 | 022-036 |
| MMP12 | MSRKAFVFPKESDTSYVS SEQ ID NO: 1161 | 022-039 |
| MMP12 | SRKAFVFP SEQ ID NO: 1162 | 023-030 |
| MMP12 | SRKAFVFPKESD SEQ ID NO: 1163 | 023-034 |
| MMP12 | SRKAFVFPKESDTS SEQ ID NO: 1164 | 023-036 |
| MMP12 | RKAFVFP SEQ ID NO: 1165 | 024-030 |
| MMP12 | RKAFVFPKESD SEQ ID NO: 1166 | 024-034 |
| MMP12 | KAFVFP SEQ ID NO: 1167 | 025-030 |
| MMP12 | KAFVFPKE SEQ ID NO: 1048 | 025-032 |
| MMP12 | KAFVFPKESD SEQ ID NO: 1049 | 025-034 |
| MMP12 | AFVFPKE SEQ ID NO: 1054 | 026-032 |
| MMP12 | AFVFPKESDTS SEQ ID NO: 1168 | 026-036 |
| MMP12 | AFVFPKESDTSYVS SEQ ID NO: 1057 | 026-039 |
| MMP12 | FVFPKE SEQ ID NO: 1060 | 027-032 |
| MMP12 | FVFPKESD SEQ ID NO: 1061 | 027-034 |
| MMP12 | FVFPKESDTS SEQ ID NO: 1062 | 027-036 |
| MMP12 | FVFPKESDTSY SEQ ID NO: 1063 | 027-037 |
| MMP12 | FVFPKESDTSYVS SEQ ID NO: 1065 | 027-039 |
| MMP12 | VFPKESD SEQ ID NO: 1169 | 028-034 |
| MMP12 | KESDTSY SEQ ID NO: 1170 | 031-037 |
| MMP12 | KESDTSYVS SEQ ID NO: 1171 | 031-039 |
| MMP12 | VSLKAP SEQ ID NO: 1172 | 038-043 |
| MMP12 | LKAPLT SEQ ID NO: 1173 | 040-045 |

TABLE 21-continued

CRP fragments generated by specific proteases.

| Protease | Neoepitope | Aminoacid Nos* |
|---|---|---|
| MMP12 | LKAPLTKP SEQ ID NO: 1174 | 040-047 |
| MMP12 | YTELSSTRGYS SEQ ID NO: 1175 | 058-068 |
| MMP12 | LSSTRGYS SEQ ID NO: 1078 | 061-068 |
| MMP12 | STRGYS SEQ ID NO: 1080 | 063-068 |
| MMP12 | YATKRQDNE SEQ ID NO: 1176 | 072-080 |
| MMP12 | YATKRQDNEI SEQ ID NO: 1177 | 072-081 |
| MMP12 | YATKRQDNEIL SEQ ID NO: 1084 | 072-082 |
| MMP12 | TKRQDNEIL SEQ ID NO: 1178 | 074-082 |
| MMP12 | KRQDNEIL SEQ ID NO: 1179 | 075-082 |
| MMP12 | ILIFWSKD SEQ ID NO: 1180 | 081-088 |
| MMP12 | IFWSKD SEQ ID NO: 1181 | 083-088 |
| MMP12 | SKDIGYS SEQ ID NO: 1093 | 086-092 |
| MMP12 | WVDGKPRV SEQ ID NO: 1096 | 128-135 |
| MMP12 | WVDGKPRVR SEQ ID NO: 1182 | 128-136 |
| MMP12 | VRKSLKKGYTVGAEAS SEQ ID NO: 1183 | 135-150 |
| MMP12 | SLKKGYT SEQ ID NO: 1184 | 138-144 |
| MMP12 | SLKKGYTVG SEQ ID NO: 1185 | 138-146 |
| MMP12 | SLKKGYTVGA SEQ ID NO: 1186 | 138-147 |
| MMP12 | SLKKGYTVGAE SEQ ID NO: 1098 | 138-148 |
| MMP12 | SLKKGYTVGAEA SEQ ID NO: 1099 | 138-149 |
| MMP12 | SLKKGYTVGAEAS SEQ ID NO: 1100 | 138-150 |
| MMP12 | SLKKGYTVGAEASI SEQ ID NO: 1187 | 138-151 |
| MMP12 | LKKGYTV SEQ ID NO: 1101 | 139-145 |
| MMP12 | LKKGYTVG SEQ ID NO: 1102 | 139-146 |
| MMP12 | LKKGYTVGA SEQ ID NO: 1103 | 139-147 |
| MMP12 | LKKGYTVGAE SEQ ID NO: 1104 | 139-148 |
| MMP12 | LKKGYTVGAEA SEQ ID NO: 1105 | 139-149 |
| MMP12 | LKKGYTVGAEAS SEQ ID NO: 1106 | 139-150 |
| MMP12 | LKKGYTVGAEASI SEQ ID NO: 1107 | 139-151 |
| MMP12 | KKGYTVGAEAS SEQ ID NO: 1188 | 140-150 |
| MMP12 | KGYTVGAEAS SEQ ID NO: 1189 | 141-150 |
| MMP12 | KGYTVGAEASI SEQ ID NO: 1190 | 141-151 |
| MMP12 | SIILGQEQDSFGGN SEQ ID NO: 1108 | 150-163 |
| MMP12 | IILGQEQD SEQ ID NO: 1191 | 151-158 |
| MMP12 | IILGQEQDSFGGN SEQ ID NO: 1192 | 151-163 |
| MMP12 | IILGQEQDSFGGNFEGSQS SEQ ID NO: 1112 | 151-169 |
| MMP12 | ILGQEQDSFGGN SEQ ID NO: 1113 | 152-163 |
| MMP12 | LVGDIGNVNMWD SEQ ID NO: 1193 | 170-181 |

TABLE 21-continued

CRP fragments generated by specific proteases.

| Protease | Neoepitope | Aminoacid Nos* |
|---|---|---|
| MMP12 | INTIYLGGPFSPNVLN SEQ ID NO: 1122 | 189-204 |
| MMP12 | IYLGGPFSPN SEQ ID NO: 1194 | 192-201 |
| MMP12 | IYLGGPFSPNV SEQ ID NO: 1195 | 192-202 |
| MMP12 | IYLGGPFSPNVLN SEQ ID NO: 1123 | 192-204 |
| MMP12 | LGGPFSPNVLN SEQ ID NO: 1196 | 194-204 |
| MMP12 | WRALKYE SEQ ID NO: 1130 | 205-210 |
| MMP12 | YEVQGEVFTKP SEQ ID NO: 1143 | 210-220 |
| MMP12 | YEVQGEVFTKPQ SEQ ID NO: 1144 | 210-221 |
| MMP12 | YEVQGEVFTKPQLWP SEQ ID NO: 1145 | 210-224 |
| MMP12 | EVQGEVFTKP SEQ ID NO: 1197 | 211-220 |
| MMP12 | EVQGEVFTKPQLWP SEQ ID NO: 1198 | 211-224 |
| MMP12 | VQGEVFTKP SEQ ID NO: 1199 | 212-220 |
| MMP12 | VQGEVFTKPQ SEQ ID NO: 1146 | 212-221 |
| MMP12 | VQGEVFTKPQLWP SEQ ID NO: 1147 | 212-224 |
| MMP12 | GEVFTKPQLWP SEQ ID NO: 1200 | 214-224 |
| MMP12 | EVFTKP SEQ ID NO: 1201 | 215-220 |
| MMP12 | EVFTKPQLWP SEQ ID NO: 1152 | 215-224 |
| MMP12 | VFTKPQ SEQ ID NO: 1153 | 216-221 |
| MMP12 | VFTKPQL SEQ ID NO: 1202 | 216-222 |
| MMP12 | VFTKPQLWP SEQ ID NO: 1203 | 216-224 |
| MMP12 | FTKPQLWP SEQ ID NO: 1155 | 217-224 |
| MMP12 | TKPQLWP SEQ ID NO: 1156 | 218-224 |
| MMP1 | AFVFPK SEQ ID NO: 1033 | 006-031 |
| MMP1 | KAFVFPK SEQ ID NO: 1204 | 025-031 |
| MMP1 | VRKSLK SEQ ID NO: 1205 | 135-140 |
| MMP1 | YEVQGEVFTKPQLWP SEQ ID NO: 1145 | 210-224 |
| MMP3 | FGQTDMSRKA SEQ ID NO: 1036 | 017-026 |
| MMP3 | FGQTDMSRKAF SEQ ID NO: 1037 | 017-027 |
| MMP3 | MSRKAFVFPKESDTSYV SEQ ID NO: 1206 | 022-038 |
| MMP3 | MSRKAFVFPKESDTSYVS SEQ ID NO: 1161 | 022-039 |
| MMP3 | SRKAFVFPKESDTSYV SEQ ID NO: 1044 | 023-038 |
| MMP3 | SRKAFVFPKESDTSYVS SEQ ID NO: 1207 | 023-039 |
| MMP3 | RKAFVFPKESDTSYV SEQ ID NO: 1046 | 024-038 |
| MMP3 | RKAFVFPKESDTSYVS SEQ ID NO: 1047 | 024-039 |
| MMP3 | KAFVFPKE SEQ ID NO: 1048 | 025-032 |
| MMP3 | KAFVFPKESDTS SEQ ID NO: 1051 | 025-036 |
| MMP3 | KAFVFPKESDTSYVS SEQ ID NO: 1053 | 025-039 |
| MMP3 | KAFVFPKESDTSYVSL SEQ ID NO: 1208 | 025-040 |

TABLE 21-continued

CRP fragments generated by specific proteases.

| Protease | Neoepitope | | Aminoacid Nos* |
|---|---|---|---|
| MMP3 | KAFVFPKESDTSYVSLK | SEQ ID NO: 1209 | 025-041 |
| MMP3 | AFVFPKESDTSYVS | SEQ ID NO: 1057 | 026-039 |
| MMP3 | AFVFPKESDTSYVSL | SEQ ID NO: 1058 | 026-040 |
| MMP3 | AFVFPKESDTSYVSLKAP | SEQ ID NO: 1210 | 026-043 |
| MMP3 | FVFPKESDTSYV | SEQ ID NO: 1064 | 027-038 |
| MMP3 | FVFPKESDTSYVSLK | SEQ ID NO: 1211 | 027-041 |
| MMP3 | VFPKESDTSYVSLK | SEQ ID NO: 1212 | 028-041 |
| MMP3 | KESDTSYVSLKAP | SEQ ID NO: 1213 | 031-043 |
| MMP3 | TKRQDNEILIFW | SEQ ID NO: 1214 | 074-085 |
| MMP3 | IVEFWVDGKPRVRKS | SEQ ID NO: 1215 | 124-138 |
| MMP3 | SLKKGYTVGAEA | SEQ ID NO: 1099 | 138-149 |
| MMP3 | SLKKGYTVGAEAS | SEQ ID NO: 1100 | 138-150 |
| MMP3 | LKKGYTVGAEA | SEQ ID NO: 1105 | 139-149 |
| MMP3 | LKKGYTVGAEAS | SEQ ID NO: 1106 | 139-150 |
| MMP3 | LKKGYTVGAEASI | SEQ ID NO: 1107 | 139-151 |
| MMP3 | LKKGYTVGAEASII | SEQ ID NO: 1216 | 139-152 |
| MMP3 | SIILGQEQDSFGGNFEGSQS | SEQ ID NO: 1110 | 150-169 |
| MMP3 | IILGQEQDSFGGN | SEQ ID NO: 1192 | 151-163 |
| MMP3 | IILGQEQDSFGGNFEGSQS | SEQ ID NO: 1112 | 151-169 |
| MMP3 | ILGQEQDSFGGNFEGSQS | SEQ ID NO: 1115 | 152-169 |
| MMP3 | LGQEQDSFGGNFEGSQS | SEQ ID NO: 1117 | 153-169 |
| MMP3 | QEQDSFGGNFEGSQS | SEQ ID NO: 1217 | 155-169 |
| MMP3 | SFGGNFEGSQS | SEQ ID NO: 1119 | 159-169 |
| MMP3 | LVGDIGNVNMWD | SEQ ID NO: 1193 | 170-181 |
| MMP3 | FVLSPDEINT | SEQ ID NO: 1218 | 182-191 |
| MMP3 | YLGGPFSPNVLN | SEQ ID NO: 1124 | 193-204 |
| MMP3 | LKYEVQGEVFTKPQ | SEQ ID NO: 1138 | 208-221 |
| MMP3 | KYEVQGEVFTKPQ | SEQ ID NO: 1141 | 209-221 |
| MMP3 | KYEVQGEVFTKPQLWP | SEQ ID NO: 1142 | 209-224 |
| MMP3 | YEVQGEVFTKPQ | SEQ ID NO: 1144 | 210-221 |
| MMP3 | YEVQGEVFTKPQLWP | SEQ ID NO: 1145 | 210-224 |
| MMP3 | EVQGEVFTKPQLWP | SEQ ID NO: 1198 | 211-224 |
| MMP3 | VQGEVFTKPQLWP | SEQ ID NO: 1147 | 212-224 |
| MMP3 | GEVFTKPQLWP | SEQ ID NO: 1200 | 214-224 |
| MMP3 | EVFTKPQLWP | SEQ ID NO: 1152 | 215-224 |
| MMP3 | SKDIGYSFTVGGSEI | SEQ ID NO: 1219 | 86-100 |
| MMP8 | FGQTDMSR | SEQ ID NO: 1034 | 017-024 |
| MMP8 | FGQTDMSRK | SEQ ID NO: 1035 | 017-025 |

TABLE 21-continued

CRP fragments generated by specific proteases.

| Protease | Neoepitope | Aminoacid Nos* |
|---|---|---|
| MMP8 | FGQTDMSRKA SEQ ID NO: 1036 | 017-026 |
| MMP8 | FGQTDMSRKAF SEQ ID NO: 1037 | 017-027 |
| MMP8 | FGQTDMSRKAFV SEQ ID NO: 1220 | 017-028 |
| MMP8 | FGQTDMSRKAFVFPKESDTSYV SEQ ID NO: 1040 | 017-038 |
| MMP8 | MSRKAFVFPKESDTSYV SEQ ID NO: 1206 | 022-038 |
| MMP8 | SRKAFVFPKESDTSYV SEQ ID NO: 1044 | 023-038 |
| MMP8 | RKAFVFPKESDTSYV SEQ ID NO: 1046 | 024-038 |
| MMP8 | KAFVFPKESDT SEQ ID NO: 1050 | 025-035 |
| MMP8 | KAFVFPKESDTS SEQ ID NO: 1051 | 025-036 |
| MMP8 | KAFVFPKESDTSYV SEQ ID NO: 1052 | 025-038 |
| MMP8 | KAFVFPKESDTSYVS SEQ ID NO: 1053 | 025-039 |
| MMP8 | AFVFPKESDTSYV SEQ ID NO: 1056 | 026-038 |
| MMP8 | FVFPKESDTSYV SEQ ID NO: 1064 | 027-038 |
| MMP8 | VFPKESDTSYV SEQ ID NO: 1068 | 028-038 |
| MMP8 | FPKESDTSYV SEQ ID NO: 1221 | 029-038 |
| MMP8 | SLKAPL SEQ ID NO: 1222 | 039-044 |
| MMP8 | SLKAPLTKP SEQ ID NO: 1074 | 039-047 |
| MMP8 | SLKAPLTKPLKA SEQ ID NO: 1223 | 039-050 |
| MMP8 | RGYSIFSYA SEQ ID NO: 1224 | 065-073 |
| MMP8 | FSYATKRQDNEILI SEQ ID NO: 1225 | 070-083 |
| MMP8 | SYATKRQDNEILI SEQ ID NO: 1083 | 071-083 |
| MMP8 | YATKRQDNEILI SEQ ID NO: 1085 | 072-083 |
| MMP8 | ATKRQDNEILI SEQ ID NO: 1226 | 073-083 |
| MMP8 | TKRQDNEILI SEQ ID NO: 1087 | 074-083 |
| MMP8 | TKRQDNEILIF SEQ ID NO: 1088 | 074-084 |
| MMP8 | FWSKDIGYS SEQ ID NO: 1227 | 084-092 |
| MMP8 | FWSKDIGYSFT SEQ ID NO: 1228 | 084-094 |
| MMP8 | FWSKDIGYSFTV SEQ ID NO: 1229 | 084-095 |
| MMP8 | WSKDIGYSFTV SEQ ID NO: 1230 | 085-095 |
| MMP8 | KSLKKGYTVGAEA SEQ ID NO: 1231 | 137-149 |
| MMP8 | SLKKGYTVGAEA SEQ ID NO: 1099 | 138-149 |
| MMP8 | LKKGYTV SEQ ID NO: 1101 | 139-145 |
| MMP8 | LKKGYTVGAEA SEQ ID NO: 1105 | 139-149 |
| MMP8 | LKKGYTVGAEAS SEQ ID NO: 1106 | 139-150 |
| MMP8 | KKGYTVGAEA SEQ ID NO: 1232 | 140-149 |
| MMP8 | GAEASIILGQE SEQ ID NO: 1233 | 146-156 |
| MMP8 | GAEASIILGQEQD SEQ ID NO: 1234 | 146-158 |
| MMP8 | SIILGQEQD SEQ ID NO: 1235 | 150-158 |

TABLE 21-continued

CRP fragments generated by specific proteases.

| Protease | Neoepitope | Aminoacid Nos* |
|---|---|---|
| MMP8 | SIILGQEQDSFGGNFEGSQ SEQ ID NO: 1109 | 150-168 |
| MMP8 | SIILGQEQDSFGGNFEGSQS SEQ ID NO: 1110 | 150-169 |
| MMP8 | IILGQEQDSFGGN SEQ ID NO: 1192 | 151-163 |
| MMP8 | IILGQEQDSFGGNFEGSQ SEQ ID NO: 1236 | 151-168 |
| MMP8 | IILGQEQDSFGGNFEGSQS SEQ ID NO: 1112 | 151-169 |
| MMP8 | ILGQEQDSFGGN SEQ ID NO: 1113 | 152-163 |
| MMP8 | ILGQEQDSFGGNFEGS SEQ ID NO: 1237 | 152-167 |
| MMP8 | ILGQEQDSFGGNFEGSQ SEQ ID NO: 1114 | 152-168 |
| MMP8 | ILGQEQDSFGGNFEGSQS SEQ ID NO: 1115 | 152-169 |
| MMP8 | LGQEQDSFGGN SEQ ID NO: 1238 | 153-163 |
| MMP8 | LGQEQDSFGGNFEGS SEQ ID NO: 1239 | 153-167 |
| MMP8 | LGQEQDSFGGNFEGSQ SEQ ID NO: 1116 | 153-168 |
| MMP8 | LGQEQDSFGGNFEGSQS SEQ ID NO: 1117 | 153-169 |
| MMP8 | LGQEQDSFGGNFEGSQSL SEQ ID NO: 1240 | 153-170 |
| MMP8 | LGQEQDSFGGNFEGSQSLV SEQ ID NO: 1241 | 153-171 |
| MMP8 | QDSFGGNFEGSQS SEQ ID NO: 1242 | 157-169 |
| MMP8 | SFGGNFEGSQ SEQ ID NO: 1243 | 159-168 |
| MMP8 | SFGGNFEGSQS SEQ ID NO: 1119 | 159-169 |
| MMP8 | SFGGNFEGSQSLV SEQ ID NO: 1244 | 159-171 |
| MMP8 | LVGDIGNVNMW SEQ ID NO: 1245 | 170-180 |
| MMP8 | INTIYLGGPFSPN SEQ ID NO: 1246 | 189-201 |
| MMP8 | TIYLGGPFSPN SEQ ID NO: 1247 | 191-201 |
| MMP8 | IYLGGPFSPN SEQ ID NO: 1194 | 192-201 |
| MMP8 | YLGGPFSPNV SEQ ID NO: 1248 | 193-202 |
| MMP8 | YLGGPFSPNVLN SEQ ID NO: 1124 | 193-204 |
| MMP8 | LGGPFSPNVLN SEQ ID NO: 1196 | 194-204 |
| MMP8 | VLNWRA SEQ ID NO: 1249 | 202-207 |
| MMP8 | VLNWRAL SEQ ID NO: 1250 | 202-208 |
| MMP8 | VLNWRALK SEQ ID NO: 1251 | 202-209 |
| MMP8 | LNWRAL SEQ ID NO: 1128 | 203-208 |
| MMP8 | LNWRALK SEQ ID NO: 1129 | 203-209 |
| MMP8 | LNWRALKYEV SEQ ID NO: 1252 | 203-212 |
| MMP8 | NWRAL SEQ ID NO: 1253 | 204-208 |
| MMP8 | NWRALKY SEQ ID NO: 1254 | 204-210 |
| MMP8 | NWRALKYEV SEQ ID NO: 1255 | 204-212 |
| MMP8 | NWRALKYEVQ SEQ ID NO: 1256 | 204-213 |
| MMP8 | WRALKYE SEQ ID NO: 1130 | 205-211 |
| MMP8 | WRALKYEVQ SEQ ID NO: 1257 | 205-213 |

TABLE 21-continued

CRP fragments generated by specific proteases.

| Protease | Neoepitope | Aminoacid Nos* |
|---|---|---|
| MMP8 | WRALKYEVQGE SEQ ID NO: 1132 | 205-215 |
| MMP8 | RALKYEV SEQ ID NO: 1258 | 206-212 |
| MMP8 | RALKYEVQ SEQ ID NO: 1259 | 206-213 |
| MMP8 | RALKYEVQGE SEQ ID NO: 1260 | 206-215 |
| MMP8 | ALKYEV SEQ ID NO: 1133 | 207-212 |
| MMP8 | ALKYEVQGEVFTKPQ SEQ ID NO: 1261 | 207-221 |
| MMP8 | LKYEVQGE SEQ ID NO: 1136 | 208-215 |
| MMP8 | LKYEVQGEVFTKPQ SEQ ID NO: 1138 | 208-221 |
| MMP8 | KYEVQGEVFTKPQ SEQ ID NO: 1141 | 209-221 |
| MMP8 | KYEVQGEVFTKPQLWP SEQ ID NO: 1142 | 209-224 |
| MMP8 | YEVQGEVFTKPQ SEQ ID NO: 1144 | 210-221 |
| MMP8 | YEVQGEVFTKPQLWP SEQ ID NO: 1145 | 210-224 |
| MMP8 | EVQGEVFTKPQ SEQ ID NO: 1262 | 211-221 |
| MMP8 | EVQGEVFTKPQLWP SEQ ID NO: 1198 | 211-224 |
| MMP8 | VQGEVFTKPQ SEQ ID NO: 1146 | 212-221 |
| MMP8 | VQGEVFTKPQLWP SEQ ID NO: 1147 | 212-224 |
| MMP8 | QGEVFTKPQ SEQ ID NO: 1148 | 213-221 |
| MMP8 | QGEVFTKPQL SEQ ID NO: 1263 | 213-222 |
| MMP8 | QGEVFTKPQLWP SEQ ID NO: 1264 | 213-224 |
| MMP8 | GEVFTKPQ SEQ ID NO: 1150 | 214-221 |
| MMP8 | GEVFTKPQLWP SEQ ID NO: 1200 | 214-224 |
| MMP8 | VFTKPQ SEQ ID NO: 1153 | 216-221 |
| MMP8 | VFTKPQLWP SEQ ID NO: 1203 | 216-224 |
| MMP8 | FTKPQLWP SEQ ID NO: 1155 | 217-224 |
| MMP8 | TKPQLWP SEQ ID NO: 1156 | 218-224 |
| ADAMTS-1 | ESDTSYVSLK SEQ ID NO: 1265 | 032-041 |
| ADAMTS-1 | QEQDSFGGNFEGSQ SEQ ID NO: 1266 | 155-168 |
| ADAMTS-1 | QEQDSFGGNFEGSQSLVG SEQ ID NO: 1267 | 155-172 |
| ADAMTS-1 | GNFEGSQSLVG SEQ ID NO: 1268 | 162-172 |
| ADAMTS-1 | YEVQGEVFT SEQ ID NO: 1269 | 210-218 |
| ADAMTS-1 | YEVQGEVFTKPQ SEQ ID NO: 1144 | 210-221 |
| ADAMTS-1 | GEVFTKPQ SEQ ID NO: 1150 | 214-221 |
| ADAMTS-8 | VFPKESDTSYVS SEQ ID NO: 1069 | 028-039 |
| ADAMTS-8 | QEQDSFGGNFEGSQSLVG SEQ ID NO: 1267 | 155-172 |
| ADAMTS-8 | EINTIYL SEQ ID NO: 1270 | 188-194 |
| ADAMTS-8 | KYEVQ SEQ ID NO: 1271 | 209-213 |
| ADAMTS-8 | KYEVQGE SEQ ID NO: 1140 | 209-215 |

TABLE 21-continued

CRP fragments generated by specific proteases.

| Protease | Neoepitope | Aminoacid Nos* |
|---|---|---|
| Cat K | FGQTDMSR SEQ ID NO: 1034 | 017-024 |
| Cat K | AFVFPK SEQ ID NO: 1033 | 026-031 |
| Cat K | FVFPK SEQ ID NO: 1059 | 027-031 |
| Cat K | ESDTSYVSLK SEQ ID NO: 1265 | 032-041 |
| Cat K | ESDTSYVSLKAPLT SEQ ID NO: 1272 | 032-045 |
| Cat K | SDTSYVSLK SEQ ID NO: 1273 | 033-041 |
| Cat K | DTSYVSLK SEQ ID NO: 1274 | 034-041 |
| Cat K | STRGYS SEQ ID NO: 1080 | 063-068 |
| Cat K | IFWSKDIG SEQ ID NO: 1275 | 083-090 |
| Cat K | KGYTVGAE SEQ ID NO: 1276 | 141-148 |
| Cat K | AEASIILGQEQDSFG SEQ ID NO: 1277 | 147-161 |
| Cat K | LGQEQDSFG SEQ ID NO: 1278 | 153-161 |
| Cat K | LGQEQDSFGGNFE SEQ ID NO: 1279 | 153-165 |
| Cat K | GQEQDSFG SEQ ID NO: 1280 | 154-161 |
| Cat K | GQEQDSFGGNFE SEQ ID NO: 1281 | 154-165 |
| Cat K | GQEQDSFGGNFEGSQ SEQ ID NO: 1282 | 154-168 |
| Cat K | GQEQDSFGGNFEGSQS SEQ ID NO: 1118 | 154-169 |
| Cat K | QEQDSFGGN SEQ ID NO: 1283 | 155-163 |
| Cat K | QEQDSFGGNFE SEQ ID NO: 1284 | 155-165 |
| Cat K | QEQDSFGGNFEG SEQ ID NO: 1285 | 155-166 |
| Cat K | QEQDSFGGNFEGS SEQ ID NO: 1286 | 155-167 |
| Cat K | QEQDSFGGNFEGSQ SEQ ID NO: 1266 | 155-168 |
| Cat K | QEQDSFGGNFEGSQS SEQ ID NO: 1217 | 155-169 |
| Cat K | GNFEGSQSLV SEQ ID NO: 1287 | 162-171 |
| Cat K | GNFEGSQSLVG SEQ ID NO: 1268 | 162-172 |
| Cat K | GNFEGSQSLVGDIG SEQ ID NO: 1288 | 162-175 |
| Cat K | GSQSLVGDIG SEQ ID NO: 1289 | 166-175 |
| Cat K | GSQSLVGDIGNVN SEQ ID NO: 1290 | 166-178 |
| Cat K | DFVLSPDEIN SEQ ID NO: 1291 | 181-190 |
| Cat K | FVLSPDEINT SEQ ID NO: 1218 | 182-191 |
| Cat K | VLSPDEINT SEQ ID NO: 1291 | 183-191 |
| Cat K | GPFSPNVLN SEQ ID NO: 1292 | 196-204 |
| Cat K | SPNVLNWR SEQ ID NO: 1293 | 199-206 |
| Cat K | KYEVQG SEQ ID NO: 1294 | 209-214 |
| Cat K | YEVQGEVFT SEQ ID NO: 1269 | 210-218 |
| Cat K | YEVQGEVFTKPQ SEQ ID NO: 1144 | 210-221 |
| Cat K | VQGEVFTKPQ SEQ ID NO: 1146 | 212-221 |
| Cat K | GEVFTKPQ SEQ ID NO: 1150 | 214-221 |

TABLE 21-continued

CRP fragments generated by specific proteases.

| Protease | Neoepitope | Aminoacid Nos* |
|---|---|---|
| Cat K | EVFTKPQ SEQ ID NO: 1151 | 215-221 |
| Cat S | FGQTDMSR SEQ ID NO: 1034 | 017-024 |
| Cat S | AFVFPKESDTSYVS SEQ ID NO: 1057 | 026-039 |
| Cat S | FVFPKESDTSYVS SEQ ID NO: 1065 | 027-039 |
| Cat S | VFPKESDTSYVS SEQ ID NO: 1069 | 028-039 |
| Cat S | FPKESDTSYVS SEQ ID NO: 1071 | 029-039 |
| Cat S | ESDTSYVSLK SEQ ID NO: 1265 | 032-041 |
| Cat S | TSWESASGIVE SEQ ID NO: 1295 | 116-126 |
| Cat S | KGYTVG SEQ ID NO: 1296 | 141-146 |
| Cat S | QEQDSFGGNFE SEQ ID NO: 1284 | 155-165 |
| Cat S | QEQDSFGGNFEG SEQ ID NO: 1285 | 155-166 |
| Cat S | QEQDSFGGNFEGSQ SEQ ID NO: 1266 | 155-168 |
| Cat S | QEQDSFGGNFEGSQS SEQ ID NO: 1217 | 155-169 |
| Cat S | QEQDSFGGNFEGSQSLV SEQ ID NO: 1297 | 155-171 |
| Cat S | QEQDSFGGNFEGSQSLVG SEQ ID NO: 1267 | 155-172 |
| Cat S | SFGGNFEGSQSLVG SEQ ID NO: 1298 | 159-172 |
| Cat S | GNFEGSQSLVG SEQ ID NO: 1268 | 162-172 |
| Cat S | GNFEGSQSLVGDIG SEQ ID NO: 1288 | 162-175 |
| Cat S | SPDEINTIYL SEQ ID NO: 1299 | 185-194 |
| Cat S | SPDEINTIYLG SEQ ID NO: 1300 | 185-195 |
| Cat S | LGGPFSPNVLN SEQ ID NO: 1196 | 194-204 |
| Cat S | GGPFSPNVLN SEQ ID NO: 1301 | 195-204 |
| Cat S | GPFSPNVLN SEQ ID NO: 1292 | 196-204 |
| Cat S | ALKYE SEQ ID NO: 1302 | 207-211 |
| Cat S | ALKYEVQ SEQ ID NO: 1303 | 207-213 |
| Cat S | YEVQGEVF SEQ ID NO: 1304 | 210-217 |
| Cat S | YEVQGEVFT SEQ ID NO: 1269 | 210-218 |
| Cat S | YEVQGEVFTKPQ SEQ ID NO: 1144 | 210-221 |
| Cat S | YEVQGEVFTKPQLWP SEQ ID NO: 1145 | 210-224 |
| Cat S | VQGEVFTKPQLWP SEQ ID NO: 1147 | 212-224 |
| Cat S | GEVFTKPQ SEQ ID NO: 1150 | 214-221 |
| Cat S | GEVFTKPQLWP SEQ ID NO: 1200 | 214-224 |
| Cat S | EVFTKPQLWP SEQ ID NO: 1152 | 215-224 |
| Cat S | TKPQLWP SEQ ID NO: 1156 | 218-224 |
| Cat S | KPQLWP SEQ ID NO: 1157 | 219-224 |

*numbers in the sequence of CRP

Accordingly, in a method of the invention, said peptide fragments preferably comprise a neo-epitope formed by cleavage of CRP by a protease at a site marked by the sign * in any one of the above partial sequences of CRP in Table 20 or at either end of any partial sequence of CRP in Table 21.

The immunological binding partner may be one specifically reactive with a C-terminal or N-terminal neo-epitope formed by cleavage of CRP.

Suitable immunological binding partners may therefore be specifically reactive with any of the following sequences at the N terminal of a peptide:

TABLE 22

N-terminal sequences of protease generated peptide fragments of CRP. CRP

| | | | | | |
|---|---|---|---|---|---|
| AFVFPK SEQ ID NO: 1033 | SFGGNF SEQ ID NO: 1305 | FGQTDM SEQ ID NO: 1306 |
| VSLKAP SEQ ID NO: 1172 | KAFVFP SEQ ID NO: 1167 | EVFTKP SEQ ID NO: 1201 |
| TDMSRK SEQ ID NO: 1307 | MSRKAF SEQ ID NO: 1308 | SRKAFV SEQ ID NO: 1309 |
| VFPKES SEQ ID NO: 1310 | FPKESD SEQ ID NO: 1311 | KESDTS SEQ ID NO: 1312 |
| LSSTRG SEQ ID NO: 1313 | SSTRGY SEQ ID NO: 1314 | STRGYS SEQ ID NO: 1080 |
| KRQDNE SEQ ID NO: 1315 | WSKDIG SEQ ID NO: 1316 | SKDIGY SEQ ID NO: 1317 |
| SIILGQ SEQ ID NO: 1318 | IILGQE SEQ ID NO: 1319 | ILGQEQ SEQ ID NO: 1320 |
| IYLGGP SEQ ID NO: 1321 | YLGGPF SEQ ID NO: 1322 | LGGPFS SEQ ID NO: 1323 |
| ALKYEV SEQ ID NO: 1133 | KYEVQG SEQ ID NO: 1294 | VQGEVF SEQ ID NO: 1324 |
| KPQLWP SEQ ID NO: 1157 | YTELSS SEQ ID NO: 1325 | ILIFWS SEQ ID NO: 1326 |
| LVGDIG SEQ ID NO: 1327 | QEQDSF SEQ ID NO: 1328 | RGYSIF SEQ ID NO: 1329 |
| GAEASI SEQ ID NO: 1330 | QDSFGG SEQ ID NO: 1331 | TIYLGG SEQ ID NO: 1332 |
| EINTIY SEQ ID NO: 1333 | DTSYVS SEQ ID NO: 1334 | AEASII SEQ ID NO: 1335 |
| TSWESA SEQ ID NO: 1336 | SPDEIN SEQ ID NO: 1337 | GGPFSP SEQ ID NO: 1338 |
| YEVQGE SEQ ID NO: 1339 | FVLSPD SEQ ID NO: 1340 | LKKGYT SEQ ID NO: 1341 |
| RKAFVF SEQ ID NO: 1342 | IVEFWV SEQ ID NO: 1343 | ESDTSY SEQ ID NO: 1344 |
| TKPQLW SEQ ID NO: 1345 | EVQGEV SEQ ID NO: 1346 | FVFPK SEQ ID NO: 1059 |
| SDTSYV SEQ ID NO: 1347 | SLKAPL SEQ ID NO: 1222 | LKAPLT SEQ ID NO: 1173 |
| IFSYAT SEQ ID NO: 1348 | SYATKR SEQ ID NO: 1349 | YATKRQ SEQ ID NO: 1350 |
| EFWVDG SEQ ID NO: 1351 | WVDGKP SEQ ID NO: 1352 | VDGKPR SEQ ID NO: 1353 |
| LGQEQD SEQ ID NO: 1354 | GQEQDS SEQ ID NO: 1355 | QSLVGD SEQ ID NO: 1356 |
| SPNVLN SEQ ID NO: 1357 | LNWRA SEQ ID NO: 1127 | LNWRAL SEQ ID NO: 1128 |
| QGEVFT SEQ ID NO: 1358 | GEVFTK SEQ ID NO: 1359 | VFTKPQ SEQ ID NO: 1153 |
| IFWSKD SEQ ID NO: 1181 | VRKSLK SEQ ID NO: 1205 | KKGYTV SEQ ID NO: 1360 |
| FSYATK SEQ ID NO: 1361 | ATKRQD SEQ ID NO: 1362 | FWSKDI SEQ ID NO: 1363 |
| VLNWRA SEQ ID NO: 1249 | NWRAL SEQ ID NO: 1253 | NWRALK SEQ ID NO: 1364 |
| GSQSLV SEQ ID NO: 1365 | DFVLSP SEQ ID NO: 1366 | VLSPDE SEQ ID NO: 1367 |
| LKYEVQ SEQ ID NO: 1134 | TKRQDN SEQ ID NO: 1368 | KGYTVG SEQ ID NO: 1296 |
| GNFEGS SEQ ID NO: 1369 | SLKKGY SEQ ID NO: 1370 | KSLKKG SEQ ID NO: 1371 |
| FVFPKE SEQ ID NO: 1060 | INTIYL SEQ ID NO: 1372 | RALKYE SEQ ID NO: 1373 |
| FYTELS SEQ ID NO: 1374 | WRALKY SEQ ID NO: 1375 | GPFSPN SEQ ID NO: 1376 | or with any of the following sequences at the C-terminal of a peptide:

TABLE 23

C-terminal sequences of protease generated peptide fragments of CRP.

CRP

| | | |
|---|---|---|
| AFVFPK SEQ ID NO: 1033 | KPQLWP SEQ ID NO: 1157 | PDEINT SEQ ID NO: 1377 |
| SPDEIN SEQ ID NO: 1337 | DSFGGN SEQ ID NO: 1378 | VFTKPQ SEQ ID NO: 1153 |
| KESDTS SEQ ID NO: 1312 | SDTSYV SEQ ID NO: 1347 | DTSYVS SEQ ID NO: 1334 |
| LTKPLK SEQ ID NO: 1379 | STRGYS SEQ ID NO: 1080 | YATKRQ SEQ ID NO: 1350 |
| KDIGYS SEQ ID NO: 1380 | DGKPRV SEQ ID NO: 1381 | VDGKPR SEQ ID NO: 1353 |
| GAEASI SEQ ID NO: 1330 | QGEVFT SEQ ID NO: 1358 | NFEGSQ SEQ ID NO: 1382 |
| SPNVLN SEQ ID NO: 1357 | GPFSPN SEQ ID NO: 1376 | RALKYE SEQ ID NO: 1373 |
| ALKYEV SEQ ID NO: 1133 | YEVQGE SEQ ID NO: 1339 | LKYEVQ SEQ ID NO: 1134 |
| KAFVFP SEQ ID NO: 1167 | VSLKAP SEQ ID NO: 1172 | LKAPLT SEQ ID NO 1173 |
| LKKGYT SEQ ID NO: 1341 | LGQEQD SEQ ID NO: 1354 | NVNMWD SEQ ID NO: 1383 |
| PRVRKS SEQ ID NO: 1384 | TVGSEI SEQ ID NO: 1385 | SRKAFV SEQ ID NO: 1309 |
| GYSFTV SEQ ID NO: 1386 | IILGQE SEQ ID NO: 1319 | EGSQSL SEQ ID NO: 1387 |
| INTIYL SEQ ID NO: 1372 | WSKDIG SEQ ID NO: 1316 | EQDSFG SEQ ID NO: 1388 |
| NVLNWR SEQ ID NO: 1389 | ASGIVE SEQ ID NO: 1390 | NTIYLG SEQ ID NO: 1391 |
| VGAEAS SEQ ID NO: 1392 | APLTKP SEQ ID NO: 1393 | FVFPKE SEQ ID NO: 1060 |
| QTDMSR SEQ ID NO: 1394 | TDMSRK SEQ ID NO: 1307 | MSRKAF SEQ ID NO: 1308 |
| PKESDT SEQ ID NO: 1395 | TSYVSL SEQ ID NO: 1396 | ESDTSY SEQ ID NO: 1344 |
| DNEILI SEQ ID NO: 1397 | QDNEIL SEQ ID NO: 1398 | NEILIF SEQ ID NO: 1399 |
| YTVGAE SEQ ID NO: 1400 | TVGAEA SEQ ID NO: 1401 | PFSPNV SEQ ID NO: 1402 |
| FEGSQS SEQ ID NO: 1403 | GNFEGS SEQ ID NO: 1369 | DIGNVN SEQ ID NO: 1404 |
| LNWRA SEQ ID NO: 1127 | LNWRAL SEQ ID NO: 1128 | NWRALK SEQ ID NO: 1364 |
| KYEVQG SEQ ID NO: 1294 | EVFTKP SEQ ID NO: 1201 | VFTKPQ SEQ ID NO: 1153 |
| KRQDNE SEQ ID NO: 1315 | RQDNEI SEQ ID NO: 1405 | IFWSKD SEQ ID NO: 1181 |
| FTKPQL SEQ ID NO: 1406 | VRKSLK SEQ ID NO: 1205 | SYVSLK SEQ ID NO: 1407 |
| SLKAPL SEQ ID NO: 1222 | TKPLKA SEQ ID NO: 1408 | SIFSYA SEQ ID NO: 1409 |
| GSQSLV SEQ ID NO: 1365 | GNVNMW SEQ ID NO: 1410 | SQSLVG SEQ ID NO: 1411 |
| FGGNFE SEQ ID NO: 1412 | GGNFEG SEQ ID NO: 1413 | LVGDIG SEQ ID NO: 1327 |
| VQGEVF SEQ ID NO: 1324 | GKPRVR SEQ ID NO: 1414 | FWSKDI 1363 SEQ ID NO: |
| DMSRKA SEQ ID NO: 1415 | EILIFW SEQ ID NO: 1416 | KKGYTV SEQ ID NO: 1360 |
| FPKESD SEQ ID NO: 1311 | IGYSFT SEQ ID NO: 1417 | |

Elastin

Several candidate proteases may be responsible for the digestion of elastin in fibrotic tissue. We have through a range of in vitro cleavages of pure native proteins determined that the enzymes listed in the following table cleaved elastin at least at the cleavage sites at each end of the following sequences or at the cleavage sites marked '.' or where no '.' is shown, at the ends of the sequences:

TABLE 24

Elastin fragments generated by specific proteases.

| Protease | Sequence between cleavage sites | Nos* |
|---|---|---|
| MMP9 + 12 | GVPGAIPGGVPG SEQ ID NO: 1418 | 028-039 |
| MMP9 + 12 | AIPGGVPGGVFYPGAGLG SEQ ID NO: 1419 | 032-049 |

TABLE 24-continued

Elastin fragments generated by specific proteases.

| Protease | Sequence between cleavage sites | | Nos* |
|---|---|---|---|
| MMP9 + 12 | AIPGGVPGGVFYPGAGLGA | SEQ ID NO: 1420 | 032-050 |
| MMP9 + 12 | GVPGGVFYPGAGLGA | SEQ ID NO: 1421 | 036-050 |
| MMP9 + 12 | GVPGGVFYPGAGLGALG | SEQ ID NO: 1422 | 036-052 |
| MMP9 + 12 | VPGGVFYPGAGLGALGG | SEQ ID NO: 1423 | 037-053 |
| MMP9 + 12 | GVFYPGAGLGALGGGALGPGG | SEQ ID NO: 1424 | 040-060 |
| MMP9 + 12 | VFYPGAGLG | SEQ ID NO: 1425 | 041-049 |
| MMP9 + 12 | VFYPGAGLGA | SEQ ID NO: 1426 | 041-050 |
| MMP9 + 12 | VFYPGAGLGAL | SEQ ID NO: 1427 | 041-051 |
| MMP9 + 12 | VFYPGAGLGALG | SEQ ID NO: 1428 | 041-052 |
| MMP9 + 12 | VFYPGAGLGALGG | SEQ ID NO: 1429 | 041-053 |
| MMP9 + 12 | VFYPGAGLGALGGG | SEQ ID NO: 1430 | 041-054 |
| MMP9 + 12 | VFYPGAGLGALGGGAL | SEQ ID NO: 1431 | 041-056 |
| MMP9 + 12 | VFYPGAGLGALGGGALG | SEQ ID NO: 1432 | 041-057 |
| MMP9 + 12 | VFYPGAGLGALGGGALGPG | SEQ ID NO: 1433 | 041-059 |
| MMP9 + 12 | VFYPGAGLGALGGGALGPGG | SEQ ID NO: 1434 | 041-060 |
| MMP9 + 12 | VFYPGAGLGALGGGALGPGGKPLKPVPGG | SEQ ID NO: 1435 | 041-069 |
| MMP9 + 12 | LGALGGGALGPGGKPLKPVPGG | SEQ ID NO: 1436 | 048-069 |
| MMP9 + 12 | ALGGGALGPGGKPLKPVPGG | SEQ ID NO: 1437 | 050-069 |
| MMP9 + 12 | LGGGALGPGGKPLKPVPG | SEQ ID NO: 1438 | 051-068 |
| MMP9 + 12 | LGGGALGPGGKPLKPVPGG | SEQ ID NO: 1439 | 051-069 |
| MMP9 + 12 | GGALGPGGKPLKPVPGG | SEQ ID NO: 1440 | 053-069 |
| MMP9 + 12 | LGPGGKPLKPVPGG | SEQ ID NO: 1441 | 056-069 |
| MMP9 + 12 | GPGGKPLKPVPGG | SEQ ID NO: 1442 | 057-069 |
| MMP9 + 12 | PGGKPLKPVPGG | SEQ ID NO: 1443 | 058-069 |
| MMP9 + 12 | GKPLKPVPGG | SEQ ID NO: 1444 | 060-069 |
| MMP9 + 12 | PLKPVPGG | SEQ ID NO: 1445 | 062-069 |
| MMP9 + 12 | LKPVPGG | SEQ ID NO: SEQ ID NO: 1446 | 063-069 |
| MMP9 + 12 | GLAGAGLGAGLGAFP | SEQ ID NO: 1447 | 069-083 |
| MMP9 + 12 | GLAGAGLGAGLGAFPA | SEQ ID NO: 1448 | 069-084 |
| MMP9 + 12 | LAGAGLGAGLG | SEQ ID NO: 1449 | 070-080 |
| MMP9 + 12 | LAGAGLGAGLGAFP | SEQ ID NO: 1450 | 070-083 |
| MMP9 + 12 | LAGAGLGAGLGAFPA | SEQ ID NO: 1451 | 070-084 |
| MMP9 + 12 | LAGAGLGAGLGAFPAVT | SEQ ID NO: 1452 | 070-086 |
| MMP9 + 12 | LAGAGLGAGLGAFPAVTFPG | SEQ ID NO: 1453 | 070-089 |
| MMP9 + 12 | LAGAGLGAGLGAFPAVTFPGA | SEQ ID NO: 1454 | 070-090 |
| MMP9 + 12 | LAGAGLGAGLGAFPAVTFPGALVPGG | SEQ ID NO: 1455 | 070-095 |
| MMP9 + 12 | LAGAGLGAGLGAFPAVTFPGALVPGGVA | SEQ ID NO: 1456 | 070-097 |

TABLE 24-continued

Elastin fragments generated by specific proteases.

| Protease | Sequence between cleavage sites | Nos* |
|---|---|---|
| MMP9 + 12 | LAGAGLGAGLGAFPAVTFPGALVPGGVADAAAA SEQ ID NO: 1457 | 070-102 |
| MMP9 + 12 | AGAGLGAGLGAFPAVTFPGALVPGG SEQ ID NO: 1458 | 071-095 |
| MMP9 + 12 | GAGLGAGLGAFPA SEQ ID NO: 1459 | 072-084 |
| MMP9 + 12 | GAGLGAGLGAFPAVTFPGA SEQ ID NO: 1460 | 072-090 |
| MMP9 + 12 | AGLGAGLGAFPA SEQ ID NO: 1461 | 073-084 |
| MMP9 + 12 | GLGAGLGAFPA SEQ ID NO: 1462 | 074-084 |
| MMP9 + 12 | LGAGLGAFPA SEQ ID NO: 1463 | 075-084 |
| MMP9 + 12 | LGAGLGAFPAVTFPGA SEQ ID NO: 1464 | 075-090 |
| MMP9 + 12 | LGAGLGAFPAVTFPGALVPGG SEQ ID NO: 1465 | 075-095 |
| MMP9 + 12 | LGAGLGAFPAVTFPGALVPGGVADAAAA SEQ ID NO: 1466 | 075-102 |
| MMP9 + 12 | AGLGAFPAVTFPG SEQ ID NO: 1467 | 077-089 |
| MMP9 + 12 | LGAFPAVTFPGA SEQ ID NO: 1468 | 079-090 |
| MMP9 + 12 | LGAFPAVTFPGALVPGGVA SEQ ID NO: 1469 | 079-097 |
| MMP9 + 12 | LGAFPAVTFPGALVPGGVADAAAA SEQ ID NO: 1470 | 079-102 |
| MMP9 + 12 | AFPAVTFPGALVPGG SEQ ID NO: 1471 | 081-095 |
| MMP9 + 12 | AVTFPGALVPGG SEQ ID NO: 1472 | 084-095 |
| MMP9 + 12 | AVTFPGALVPGGVADAAAA SEQ ID NO: 1473 | 084-102 |
| MMP9 + 12 | VTFPGALVPGG SEQ ID NO: 1474 | 085-095 |
| MMP9 + 12 | VTFPGALVPGGVADAAAA SEQ ID NO: 1475 | 085-102 |
| MMP9 + 12 | LVPGGVADAAAA SEQ ID NO: 1476 | 091-102 |
| MMP9 + 12 | LVPGGVADAAAAYK SEQ ID NO: 1477 | 091-104 |
| MMP9 + 12 | VADAAAAYK SEQ ID NO: 1478 | 096-104 |
| MMP9 + 12 | KAAKAGA SEQ ID NO: 1479 | 104-110 |
| MMP9 + 12 | LGVSAGAVVPQPGA SEQ ID NO: 1480 | 121-134 |
| MMP9 + 12 | VPGVGLPGVYPGGVLPGAR SEQ ID NO: 1481 | 141-159 |
| MMP9 + 12 | PGVGLPGVYPGGVLPGAR SEQ ID NO: 1482 | 142-159 |
| MMP9 + 12 | GLPGVYPGGVLPGAR SEQ ID NO: 1483 | 145-159 |
| MMP9 + 12 | PGVYPGGVLPGAR SEQ ID NO: 1484 | 147-159 |
| MMP9 + 12 | ARFPGVG SEQ ID NO: 1485 | 158-164 |
| MMP9 + 12 | ARFPGVGVLPG SEQ ID NO: 1486 | 158-168 |
| MMP9 + 12 | RFPGVGVLPGVPTGAG SEQ ID NO: 1487 | 159-174 |
| MMP9 + 12 | FPGVGVLPGVPTG SEQ ID NO: 1488 | 160-172 |
| MMP9 + 12 | FPGVGVLPGVPTGA SEQ ID NO: 1489 | 160-173 |
| MMP9 + 12 | FPGVGVLPGVPTGAGV SEQ ID NO: 1490 | 160-175 |
| MMP9 + 12 | FPGVGVLPGVPTGAGVKPK SEQ ID NO: 1491 | 160-178 |
| MMP9 + 12 | KPKAPGV SEQ ID NO: 1492 | 176-182 |
| MMP9 + 12 | PKAPGV SEQ ID NO: 1493 | 177-182 |

TABLE 24-continued

Elastin fragments generated by specific proteases.

| Protease | Sequence between cleavage sites | Nos* |
|---|---|---|
| MMP9 + 12 | GAFAGIPGVGPFG SEQ ID NO: 1494 | 184-196 |
| MMP9 + 12 | VGPFGGPQPGVPLGYP SEQ ID NO: 1495 | 192-207 |
| MMP9 + 12 | GPQPGVPLGYP SEQ ID NO: 1496 | 197-207 |
| MMP9 + 12 | PQPGVPLGYP SEQ ID NO: 1497 | 198-207 |
| MMP9 + 12 | PGVPLGYP SEQ ID NO: 1498 | 200-207 |
| MMP9 + 12 | GYPIKAPK SEQ ID NO: 1499 | 205-212 |
| MMP9 + 12 | PKLPGGY SEQ ID NO: 1500 | 211-217 |
| MMP9 + 12 | YTTGKLPYGYGPG SEQ ID NO: 1501 | 221-233 |
| MMP9 + 12 | YTTGKLPYGYGPGGVAGAAGK SEQ ID NO: 1502 | 221-241 |
| MMP9 + 12 | TTGKLPYGYG SEQ ID NO: 1503 | 222-231 |
| MMP9 + 12 | TTGKLPYGYGPGGVAGAAGK SEQ ID NO: 1504 | 222-241 |
| MMP9 + 12 | LPYGYGPGGVAGAAGK SEQ ID NO: 1505 | 226-241 |
| MMP9 + 12 | GYGPGGVAGAAGK SEQ ID NO: 1506 | 229-241 |
| MMP9 + 12 | YGPGGVAGAAGK SEQ ID NO: 1507 | 230-241 |
| MMP9 + 12 | AGYPTGTGVGPQAAAAAAAK SEQ ID NO: 1508 | 242-261 |
| MMP9 + 12 | TGVGPQAAAAAAAK SEQ ID NO: 1509 | 248-261 |
| MMP9 + 12 | PQAAAAAAAK SEQ ID NO: 1510 | 252-261 |
| MMP9 + 12 | FGAGAAGVLPGVGGAGVPGVPGAIPGIGG SEQ ID NO: 1511 | 266-294 |
| MMP9 + 12 | FGAGAAGVLPGVGGAGVPGVPGAIPGIGGIAGVGTPAA SEQ ID NO: 1512 | 266-303 |
| MMP9 + 12 | GVLPGVGGAGVPGVPG SEQ ID NO: 1513 | 272-287 |
| MMP9 + 12 | VLPGVGGAGVPGVPGAIPGIGG SEQ ID NO: 1514 | 273-294 |
| MMP9 + 12 | VLPGVGGAGVPGVPGAIPGIGGIAGVGTPA SEQ ID NO: 1515 | 273-302 |
| MMP9 + 12 | VLPGVGGAGVPGVPGAIPGIGGIAGVGTPAA SEQ ID NO: 1516 | 273-303 |
| MMP9 + 12 | GAGVPGVPGAIPG SEQ ID NO: 1517 | 279-291 |
| MMP9 + 12 | GAGVPGVPGAIPGIGGIAGVG SEQ ID NO: 1518 | 279-299 |
| MMP9 + 12 | AGVPGVPGAIPGIG SEQ ID NO: 1519 | 280-293 |
| MMP9 + 12 | AGVPGVPGAIPGIGG SEQ ID NO: 1520 | 280-294 |
| MMP9 + 12 | AGVPGVPGAIPGIGGIAG SEQ ID NO: 1521 | 280-297 |
| MMP9 + 12 | AGVPGVPGAIPGIGGIAGVGTPA SEQ ID NO: 1522 | 280-302 |
| MMP9 + 12 | GVPGVPGAIPGIGG SEQ ID NO: 1523 | 281-294 |
| MMP9 + 12 | GVPGVPGAIPGIGGIA SEQ ID NO: 1524 | 281-296 |
| MMP9 + 12 | GVPGVPGAIPGIGGIAGVG SEQ ID NO: 1525 | 281-299 |
| MMP9 + 12 | VPGVPGAIPGIGG SEQ ID NO: 1526 | 282-294 |
| MMP9 + 12 | GVPGAIPGIGGIAGVGTPA SEQ ID NO: 1527 | 284-302 |
| MMP9 + 12 | VPGAIPGIGGIAGVG SEQ ID NO: 1528 | 285-299 |
| MMP9 + 12 | VPGAIPGIGGIAGVGTPA SEQ ID NO: 1529 | 285-302 |
| MMP9 + 12 | VPGAIPGIGGIAGVGTPAAA SEQ ID NO: 1530 | 285-304 |
| MMP9 + 12 | VPGAIPGIGGIAGVGTPAAAAAAAAAK SEQ ID NO: 1531 | 285-312 |

TABLE 24-continued

Elastin fragments generated by specific proteases.

| Protease | Sequence between cleavage sites | | Nos* |
|---|---|---|---|
| MMP9 + 12 | AIPGIGGIAGVG | SEQ ID NO: 1532 | 288-299 |
| MMP9 + 12 | AIPGIGGIAGVGTPA | SEQ ID NO: 1533 | 288-302 |
| MMP9 + 12 | AIPGIGGIAGVGTPAA | SEQ ID NO: 1534 | 288-303 |
| MMP9 + 12 | AIPGIGGIAGVGTPAAA | SEQ ID NO: 1535 | 288-304 |
| MMP9 + 12 | AIPGIGGIAGVGTPAAAAAA | SEQ ID NO: 1536 | 288-307 |
| MMP9 + 12 | AIPGIGGIAGVGTPAAAAAAAAAAK | SEQ ID NO: 1537 | 288-312 |
| MMP9 + 12 | IPGIGGIAGVGTPAAA | SEQ ID NO: 1538 | 289-304 |
| MMP9 + 12 | IGGIAGVGTPAAAA | SEQ ID NO: 1539 | 292-305 |
| MMP9 + 12 | GIAGVGTPAAAA | SEQ ID NO: 1540 | 294-305 |
| MMP9 + 12 | GIAGVGTPAAAAAAAA | SEQ ID NO: 1541 | 294-309 |
| MMP9 + 12 | GIAGVGTPAAAAAAAAAAK | SEQ ID NO: 1542 | 294-312 |
| MMP9 + 12 | IAGVGTPAAAAAAAA | SEQ ID NO: 1543 | 295-309 |
| MMP9 + 12 | IAGVGTPAAAAAAAAA | SEQ ID NO: 1544 | 295-310 |
| MMP9 + 12 | IAGVGTPAAAAAAAAAAK | SEQ ID NO: 1545 | 295-312 |
| MMP9 + 12 | TPAAAAAAAAAAK | SEQ ID NO: 1546 | 300-312 |
| MMP9 + 12 | PAAAAAAAAAAK | SEQ ID NO: 1547 | 301-312 |
| MMP9 + 12 | AAAAAAAAAAK | SEQ ID NO: 1548 | 302-312 |
| MMP9 + 12 | AAAAAAAAAK | SEQ ID NO: 1549 | 303-312 |
| MMP9 + 12 | AAAAAAAAK | SEQ ID NO: 1550 | 304-312 |
| MMP9 + 12 | AAAAAAAAKA | SEQ ID NO: 1551 | 304-313 |
| MMP9 + 12 | AAAAAAAK | SEQ ID NO: 1552 | 305-312 |
| MMP9 + 12 | LVPGGPGFGPGVVGVPGA | SEQ ID NO: 1553 | 322-339 |
| MMP9 + 12 | GPGFGPGVVGVPG | SEQ ID NO: 1554 | 326-338 |
| MMP9 + 12 | GPGFGPGVVGVPGAGVPGVG | SEQ ID NO: 1555 | 326-345 |
| MMP9 + 12 | GPGFGPGVVGVPGAGVPGVGVPGAGIPVVPG | SEQ ID NO: 1556 | 326-356 |
| MMP9 + 12 | PGFGPGVVGVPG | SEQ ID NO: 1557 | 327-338 |
| MMP9 + 12 | PGFGPGVVGVPGA | SEQ ID NO: 1558 | 327-339 |
| MMP9 + 12 | PGFGPGVVGVPGAG | SEQ ID NO: 1559 | 327-340 |
| MMP9 + 12 | PGVVGVPGAGVPG | SEQ ID NO: 1560 | 331-343 |
| MMP9 + 12 | PGVVGVPGAGVPGVGVPG | SEQ ID NO: 1561 | 331-348 |
| MMP9 + 12 | PGVVGVPGAGVPGVGVPGAGIPVVPGA | SEQ ID NO: 1562 | 331-357 |
| MMP9 + 12 | VVGVPGAGVPGVGVPGA | SEQ ID NO: 1563 | 333-349 |
| MMP9 + 12 | VGVPGAGVPGVGVPGAGIPVVPGAGIPGAAVPGVVSPEA SEQ ID NO: 1564 | | 334-372 |
| MMP9 + 12 | AGVPGVGVPGAGIPVVPG | SEQ ID NO: 1565 | 339-356 |
| MMP9 + 12 | GVPGVGVPGAGIPVVPG | SEQ ID NO: 1566 | 340-356 |
| MMP9 + 12 | GVPGVGVPGAGIPVVPGA | SEQ ID NO: 1567 | 340-357 |
| MMP9 + 12 | VPGVGVPGAGIPVVPG | SEQ ID NO: 1568 | 341-356 |

TABLE 24-continued

Elastin fragments generated by specific proteases.

| Protease | Sequence between cleavage sites | Nos* |
|---|---|---|
| MMP9 + 12 | VGVPGAGIPVVPG SEQ ID NO: 1569 | 344-356 |
| MMP9 + 12 | VGVPGAGIPVVPGAGIPG SEQ ID NO: 1570 | 344-361 |
| MMP9 + 12 | VPGAGIPVVPG SEQ ID NO: 1571 | 346-356 |
| MMP9 + 12 | AGIPVVPGAGIPG SEQ ID NO: 1572 | 349-361 |
| MMP9 + 12 | AGIPVVPGAGIPGAAVPGVVSPEAAAK SEQ ID NO: 1573 | 349-375 |
| MMP9 + 12 | GIPVVPGAGIPG SEQ ID NO: 1574 | 350-361 |
| MMP9 + 12 | IPGAAVPGVVSPEAAAK SEQ ID NO: 1575 | 359-375 |
| MMP9 + 12 | GAAVPGVVSPEAAAK SEQ ID NO: 1576 | 361-375 |
| MMP9 + 12 | AVPGVVSPEAAAK SEQ ID NO: 1577 | 363-375 |
| MMP9 + 12 | VPGVVSPEAAAK SEQ ID NO: 1578 | 364-375 |
| MMP9 + 12 | YGARPGVG SEQ ID NO: 1579 | 383-390 |
| MMP9 + 12 | YGARPGVGVG SEQ ID NO: 1580 | 383-392 |
| MMP9 + 12 | YGARPGVGVGGIPT SEQ ID NO: 1581 | 383-396 |
| MMP9 + 12 | YGARPGVGVGGIPTY SEQ ID NO: 1582 | 383-397 |
| MMP9 + 12 | YGARPGVGVGGIPTYG SEQ ID NO: 1583 | 383-398 |
| MMP9 + 12 | YGARPGVGVGGIPTYGVG SEQ ID NO: 1584 | 383-400 |
| MMP9 + 12 | YGARPGVGVGGIPTYGVGA SEQ ID NO: 1585 | 383-401 |
| MMP9 + 12 | YGARPGVGVGGIPTYGVGAG SEQ ID NO: 1586 | 383-402 |
| MMP9 + 12 | GARPGVGV SEQ ID NO: 1587 | 384-391 |
| MMP9 + 12 | GARPGVGVGG SEQ ID NO: 1588 | 384-393 |
| MMP9 + 12 | GARPGVGVGGIP SEQ ID NO: 1589 | 384-395 |
| MMP9 + 12 | GARPGVGVGGIPTY SEQ ID NO: 1590 | 384-397 |
| MMP9 + 12 | GARPGVGVGGIPTYGV SEQ ID NO: 1591 | 384-399 |
| MMP9 + 12 | GARPGVGVGGIPTYGVG SEQ ID NO: 1592 | 384-400 |
| MMP9 + 12 | GARPGVGVGGIPTYGVGAGGF SEQ ID NO: 1593 | 384-404 |
| MMP9 + 12 | GARPGVGVGGIPTYGVGAGGFPGF SEQ ID NO: 1594 | 384-407 |
| MMP9 + 12 | GARPGVGVGGIPTYGVGAGGFPGFG SEQ ID NO: 1595 | 384-408 |
| MMP9 + 12 | GARPGVGVGGIPTYGVGAGGFPGFGVGVG SEQ ID NO: 1596 | 384-412 |
| MMP9 + 12 | ARPGVGVGG SEQ ID NO: 1597 | 385-393 |
| MMP9 + 12 | ARPGVGVGGIP SEQ ID NO: 1598 | 385-395 |
| MMP9 + 12 | ARPGVGVGGIPTY SEQ ID NO: 1599 | 385-397 |
| MMP9 + 12 | ARPGVGVGGIPTYGVA SEQ ID NO: 1600 | 385-401 |
| MMP9 + 12 | ARPGVGVGGIPTYGVAGG SEQ ID NO: 1601 | 385-403 |
| MMP9 + 12 | ARPGVGVGGIPTYGVAGGFPG SEQ ID NO: 1602 | 385-406 |
| MMP9 + 12 | ARPGVGVGGIPTYGVAGGFPGF SEQ ID NO: 1603 | 385-407 |
| MMP9 + 12 | RPGVGVG SEQ ID NO: 1604 | 386-392 |
| MMP9 + 12 | RPGVGVGG SEQ ID NO: 1605 | 386-393 |
| MMP9 + 12 | PGVGVGGIPTY SEQ ID NO: 1606 | 387-397 |

TABLE 24-continued

Elastin fragments generated by specific proteases.

| Protease | Sequence between cleavage sites | Nos* |
|---|---|---|
| MMP9 + 12 | PGVGVGGIPTYG SEQ ID NO: 1607 | 387-398 |
| MMP9 + 12 | PGVGVGGIPTYGVGAG SEQ ID NO: 1608 | 387-412 |
| MMP9 + 12 | VGGIPTYGVGAG SEQ ID NO: 1609 | 391-402 |
| MMP9 + 12 | GVGAGGFPGFGVGVGGIPGVA SEQ ID NO: 1610 | 398-418 |
| MMP9 + 12 | VGAGGFPGFGVGVG SEQ ID NO: 1611 | 399-412 |
| MMP9 + 12 | VGVGGIPGVAGVPSVGGVPGVGGVPGVGISPEA SEQ ID NO: 1612 | 409-441 |
| MMP9 + 12 | VAGVPSVGGVPGVGGVPG SEQ ID NO: 1613 | 417-434 |
| MMP9 + 12 | VAGVPSVGGVPGVGGVPGVGISPEA SEQ ID NO: 1614 | 417-441 |
| MMP9 + 12 | SVGGVPGVGGVPGVGISPEA SEQ ID NO: 1615 | 422-441 |
| MMP9 + 12 | VGGVPGVGGVPGVGISPEA SEQ ID NO: 1616 | 423-441 |
| MMP9 + 12 | GVPGVGGVPGVGIS SEQ ID NO: 1617 | 425-438 |
| MMP9 + 12 | GVPGVGGVPGVGISPEA SEQ ID NO: 1618 | 425-441 |
| MMP9 + 12 | GVPGVGGVPGVGISPEAQA SEQ ID NO: 1619 | 425-443 |
| MMP9 + 12 | GVPGVGISPEAQAAAAAK SEQ ID NO: 1620 | 431-448 |
| MMP9 + 12 | GVGTPAAAAAK SEQ ID NO: 1621 | 482-492 |
| MMP9 + 12 | TPAAAAAK SEQ ID NO: 1622 | 485-492 |
| MMP9 + 12 | FGLVPGVGVAPGVG SEQ ID NO: 1623 | 500-513 |
| MMP9 + 12 | FGLVPGVGVAPGVGVAPG SEQ ID NO: 1624 | 500-517 |
| MMP9 + 12 | FGLVPGVGVAPGVGVAPGVGVAPG SEQ ID NO: 1625 | 500-523 |
| MMP9 + 12 | FGLVPGVGVAPGVGVAPGVGVAPGVG SEQ ID NO: 1626 | 500-525 |
| MMP9 + 12 | FGLVPGVGVAPGVGVAPGVGVAPGVGLAPG SEQ ID NO: 1627 | 500-529 |
| MMP9 + 12 | FGLVPGVGVAPGVGVAPGVGVAPGVGLAPGVGVAPG SEQ ID NO: 1628 | 500-535 |
| MMP9 + 12 | FGLVPGVGVAPGVGVAPGVGVAPGVGLAPGVGVAPGV SEQ ID NO: 1629 | 500-536 |
| MMP9 + 12 | FGLVPGVGVAPGVGVAPGVGVAPGVGLAPGVGVAPGVGVAPG SEQ ID NO: 1630 | 500-541 |
| MMP9 + 12 | GLVPGVGVAPG SEQ ID NO: 1631 | 501-511 |
| MMP9 + 12 | GLVPGVGVAPGV SEQ ID NO: 1632 | 501-512 |
| MMP9 + 12 | GLVPGVGVAPGVGVA SEQ ID NO: 1633 | 501-515 |
| MMP9 + 12 | GLVPGVGVAPGVGVAP SEQ ID NO: 1634 | 501-516 |
| MMP9 + 12 | GLVPGVGVAPGVGVAPG SEQ ID NO: 1635 | 501-517 |
| MMP9 + 12 | GLVPGVGVAPGVGVAPGVG SEQ ID NO: 1636 | 501-519 |
| MMP9 + 12 | GLVPGVGVAPGVGVAPGVGVAPG SEQ ID NO: 1637 | 501-523 |
| MMP9 + 12 | GLVPGVGVAPGVGVAPGVGVAPGVGL SEQ ID NO: 1638 | 501-524 |
| MMP9 + 12 | GLVPGVGVAPGVGVAPGVGVAPGVGLA SEQ ID NO: 1639 | 501-525 |
| MMP9 + 12 | GLVPGVGVAPGVGVAPGVGVAPGVGLAPG SEQ ID NO: 1640 | 501-527 |
| MMP9 + 12 | GLVPGVGVAPGVGVAPGVGVAPGVGLAPGVG SEQ ID NO: 1641 | 501-529 |
| MMP9 + 12 | GLVPGVGVAPGVGVAPGVGVAPGVGLAPGVGVA SEQ ID NO: 1642 | 501-531 |

TABLE 24-continued

Elastin fragments generated by specific proteases.

| Protease | Sequence between cleavage sites | Nos* |
|---|---|---|
| MMP9 + 12 | GLVPGVGVAPGVGVAPGVGVAPGVGLAPGVGVAPG SEQ ID NO: 1643 | 501-533 |
| MMP9 + 12 | LVPGVGVAPGVG SEQ ID NO: 1644 | 502-513 |
| MMP9 + 12 | LVPGVGVAPGVGVAPG SEQ ID NO: 1645 | 502-517 |
| MMP9 + 12 | LVPGVGVAPGVGVAPGVG SEQ ID NO: 1646 | 502-519 |
| MMP9 + 12 | LVPGVGVAPGVGVAPGVGVAPGVG SEQ ID NO: 1647 | 502-525 |
| MMP9 + 12 | LVPGVGVAPGVGVAPGVGVAPGVGLAPGVGVAPGVG SEQ ID NO: 1648 | 502-537 |
| MMP9 + 12 | PGVGVAPGVGVAPG SEQ ID NO: 1649 | 504-517 |
| MMP9 + 12 | VGVAPGVGVAPGVGV SEQ ID NO: 1650 | 506-520 |
| MMP9 + 12 | VGVAPGVGVAPGVGVAPGVG SEQ ID NO: 1651 | 506-525 |
| MMP9 + 12 | VGVAPGVGVAPGVGVAPGVGLAPGVGVAPG SEQ ID NO: 1652 | 506-535 |
| MMP9 + 12 | VAPGVGVAPGVGVAPG SEQ ID NO: 1653 | 508-523 |
| MMP9 + 12 | VAPGVGVAPGVGVAPGVG SEQ ID NO: 1654 | 508-525 |
| MMP9 + 12 | VAPGVGVAPGVGVAPGVGLAPGVG SEQ ID NO: 1655 | 508-531 |
| MMP9 + 12 | VAPGVGVAPGVGVAPGVGLAPGVGVAPG SEQ ID NO: 1656 | 508-535 |
| MMP9 + 12 | VGVAPGVGVAPGVGLA SEQ ID NO: 1657 | 512-527 |
| MMP9 + 12 | VGVAPGVGVAPGVGLAPGVGVAPG SEQ ID NO: 1658 | 512-535 |
| MMP9 + 12 | VGVAPGVGVAPGVGLAPGVGVAPGVGVAPGVGVAPGIGPGG SEQ ID NO: 1659 | 512-552 |
| MMP9 + 12 | VAPGVGVAPGVGLAPGVGVAPGVG SEQ ID NO: 1660 | 514-537 |
| MMP9 + 12 | VAPGVGVAPGVGLAPGVGVAPGVGVA SEQ ID NO: 1661 | 514-539 |
| MMP9 + 12 | VAPGVGVAPGVGLAPGVGVAPGVGVAPG SEQ ID NO: 1662 | 514-541 |
| MMP9 + 12 | VAPGVGVAPGVGLAPGVGVAPGVGVAPGVGVAPGIGP SEQ ID NO: 1663 | 514-550 |
| MMP9 + 12 | VAPGVGVAPGVGLAPGVGVAPGVGVAPGVGVAPGIGPGG SEQ ID NO: 1664 | 514-552 |
| MMP9 + 12 | PGVGVAPGVGLAPG SEQ ID NO: 1665 | 516-529 |
| MMP9 + 12 | PGVGVAPGVGLAPGVGVAP SEQ ID NO: 1666 | 516-534 |
| MMP9 + 12 | PGVGVAPGVGLAPGVGVAPGVG SEQ ID NO: 1667 | 516-537 |
| MMP9 + 12 | VGVAPGVGLAPGVGVA SEQ ID NO: 1668 | 518-533 |
| MMP9 + 12 | VGVAPGVGLAPGVGVAP SEQ ID NO: 1669 | 518-534 |
| MMP9 + 12 | VGVAPGVGLAPGVGVAPGVGVAPG SEQ ID NO: 1670 | 518-541 |
| MMP9 + 12 | VGVAPGVGLAPGVGVAPGVGVAPGVG SEQ ID NO: 1671 | 518-543 |
| MMP9 + 12 | VGVAPGVGLAPGVGVAPGVGVAPGVGVAPG SEQ ID NO: 1672 | 518-547 |
| MMP9 + 12 | VGVAPGVGLAPGVGVAPGVGVAPGVGVAPGIGPGG SEQ ID NO: 1673 | 518-552 |
| MMP9 + 12 | GVAPGVGLAPGVGVAPGVGVAPGVGVAPGIGPGG SEQ ID NO: 1674 | 519-552 |
| MMP9 + 12 | VAPGVGLAPGVGVA SEQ ID NO: 1675 | 520-533 |
| MMP9 + 12 | VAPGVGLAPGVGVAPG SEQ ID NO: 1676 | 520-535 |
| MMP9 + 12 | VAPGVGLAPGVGVAPGVG SEQ ID NO: 1677 | 520-537 |

TABLE 24-continued

Elastin fragments generated by specific proteases.

| Protease | Sequence between cleavage sites | Nos* |
|---|---|---|
| MMP9 + 12 | VAPGVGLAPGVGVAPGVGVA SEQ ID NO: 1678 | 520-539 |
| MMP9 + 12 | VAPGVGLAPGVGVAPGVGVAPG SEQ ID NO: 1679 | 520-541 |
| MMP9 + 12 | VAPGVGLAPGVGVAPGVGVAPGVGVA SEQ ID NO: 1680 | 520-545 |
| MMP9 + 12 | VAPGVGLAPGVGVAPGVGVAPGVGVAPGIGPGG SEQ ID NO: 1681 | 520-552 |
| MMP9 + 12 | PGVGLAPGVGVAPG SEQ ID NO: 1682 | 522-535 |
| MMP9 + 12 | GVGLAPGVGVAPGVGVAPG SEQ ID NO: 1683 | 523-541 |
| MMP9 + 12 | VGLAPGVGVAPGVG SEQ ID NO: 1684 | 524-537 |
| MMP9 + 12 | VGLAPGVGVAPGVGVAPG SEQ ID NO: 1685 | 524-541 |
| MMP9 + 12 | VGLAPGVGVAPGVGVAPGVGVAPGIG SEQ ID NO: 1686 | 524-549 |
| MMP9 + 12 | VGLAPGVGVAPGVGVAPGVGVAPGIGPGG SEQ ID NO: 1687 | 524-552 |
| MMP9 + 12 | VGLAPGVGVAPGVGVAPGVGVAPGIGPG SEQ ID NO: 1688 | 524-553 |
| MMP9 + 12 | VGLAPGVGVAPGVGVAPGVGVAPGIGPGGVAAA SEQ ID NO: 1689 | 524-556 |
| MMP9 + 12 | LAPGVGVAPGVGVAPGVG SEQ ID NO: 1690 | 526-543 |
| MMP9 + 12 | LAPGVGVAPGVGVAPGVGVA SEQ ID NO: 1691 | 526-545 |
| MMP9 + 12 | LAPGVGVAPGVGVAPGVGVAPGIGP SEQ ID NO: 1692 | 526-550 |
| MMP9 + 12 | LAPGVGVAPGVGVAPGVGVAPGIGPGG SEQ ID NO: 1693 | 526-552 |
| MMP9 + 12 | GVGVAPGVGVAPGVGVAPGIGPGG SEQ ID NO: 1694 | 529-552 |
| MMP9 + 12 | VGVAPGVGVAPGVGVA SEQ ID NO: 1695 | 530-545 |
| MMP9 + 12 | VGVAPGVGVAPGVGVAPG SEQ ID NO: 1696 | 530-547 |
| MMP9 + 12 | VGVAPGVGVAPGVGVAPGIGPG SEQ ID NO: 1697 | 530-551 |
| MMP9 + 12 | VGVAPGVGVAPGVGVAPGIGPGG SEQ ID NO: 1698 | 530-552 |
| MMP9 + 12 | VGVAPGVGVAPGVGVAPGIGPGGVAAA SEQ ID NO: 1699 | 530-556 |
| MMP9 + 12 | VAPGVGVAPGVGVAP SEQ ID NO: 1700 | 532-546 |
| MMP9 + 12 | VAPGVGVAPGVGVAPGIG SEQ ID NO: 1701 | 532-549 |
| MMP9 + 12 | VAPGVGVAPGVGVAPGIGPGG SEQ ID NO: 1702 | 532-552 |
| MMP9 + 12 | PGVGVAPGVGVAPGIGPG SEQ ID NO: 1703 | 534-551 |
| MMP9 + 12 | PGVGVAPGVGVAPGIGPGG SEQ ID NO: 1704 | 534-552 |
| MMP9 + 12 | VGVAPGVGVAPGIGPGG SEQ ID NO: 1705 | 536-552 |
| MMP9 + 12 | VGVAPGVGVAPGIGPGGVAA SEQ ID NO: 1706 | 536-555 |
| MMP9 + 12 | VAPGVGVAPGIGPG SEQ ID NO: 1707 | 538-551 |
| MMP9 + 12 | PGVGVAPGIGPG SEQ ID NO: 1708 | 540-551 |
| MMP9 + 12 | VGVAPGIGPGGVAA SEQ ID NO: 1709 | 542-555 |
| MMP9 + 12 | PGGVAAAAK SEQ ID NO: 1710 | 550-558 |
| MMP9 + 12 | LRAAAGL SEQ ID NO: 1711 | 569-575 |
| MMP9 + 12 | LRAAAGLG SEQ ID NO: 1712 | 569-576 |
| MMP9 + 12 | LRAAAGLGA SEQ ID NO: 1713 | 569-577 |
| MMP9 + 12 | AAAGLGAGIPGLGVG SEQ ID NO: 1714 | 571-585 |
| MMP9 + 12 | AAAGLGAGIPGLGVGVG SEQ ID NO: 1715 | 571-587 |

TABLE 24-continued

Elastin fragments generated by specific proteases.

| Protease | Sequence between cleavage sites | Nos* |
|---|---|---|
| MMP9 + 12 | LGAGIPGLGVG SEQ ID NO: 1716 | 575-585 |
| MMP9 + 12 | LGAGIPGLGVGVG SEQ ID NO: 1717 | 575-587 |
| MMP9 + 12 | LGAGIPGLGVGVGVPGLGVG SEQ ID NO: 1718 | 575-594 |
| MMP9 + 12 | LGAGIPGLGVGVGVPG SEQ ID NO: 1719 | 575-590 |
| MMP9 + 12 | LGAGIPGLGVGVGVPGLGVGA SEQ ID NO: 1720 | 575-595 |
| MMP9 + 12 | LGAGIPGLGVGVGVPGL SEQ ID NO: 1721 | 575-591 |
| MMP9 + 12 | LGAGIPGLGVGVGVPGLG SEQ ID NO: 1722 | 575-592 |
| MMP9 + 12 | LGAGIPGLGVGVGVPGLGVGAGVPG SEQ ID NO: 1723 | 575-599 |
| MMP9 + 12 | LGAGIPGLGVGVGVPGLGVGAGVPGLG SEQ ID NO: 1724 | 575-601 |
| MMP9 + 12 | LGAGIPGLGVGVGVPGLGVGAGVPGLGVG SEQ ID NO: 1725 | 575-603 |
| MMP9 + 12 | LGAGIPGLGVGVGVPGLGVGAGVPGLGVGAGVPGFG SEQ ID NO: 1726 | 575-610 |
| MMP9 + 12 | GAGIPGLGVGVGVPGLG SEQ ID NO: 1727 | 576-592 |
| MMP9 + 12 | AGIPGLGVGVGVPG SEQ ID NO: 1728 | 577-590 |
| MMP9 + 12 | GIPGLGVGVGVPGLGVGA SEQ ID NO: 1729 | 578-595 |
| MMP9 + 12 | LGVGVGVPGLGVGA SEQ ID NO: 1730 | 582-595 |
| MMP9 + 12 | VGVPGLGVGAGVPG SEQ ID NO: 1731 | 586-599 |
| MMP9 + 12 | VGVPGLGVGAGVPGL SEQ ID NO: 1732 | 586-600 |
| MMP9 + 12 | VGVPGLGVGAGVPGLG SEQ ID NO: 1733 | 586-601 |
| MMP9 + 12 | VGVPGLGVGAGVPGLGVG SEQ ID NO: 1734 | 586-603 |
| MMP9 + 12 | VGVPGLGVGAGVPGLGVGA SEQ ID NO: 1735 | 586-604 |
| MMP9 + 12 | VGAGVPGLGVGAGVPGFG SEQ ID NO: 1736 | 593-610 |
| MMP9 + 12 | PGALAAAK SEQ ID NO: 1737 | 646-653 |
| MMP9 + 12 | AKYGAAVPGVLGGLGA SEQ ID NO: 1738 | 655-670 |
| MMP9 + 12 | YGAAVPGVLGG SEQ ID NO: 1739 | 657-667 |
| MMP9 + 12 | YGAAVPGVLGGLG SEQ ID NO: 1740 | 657-669 |
| MMP9 + 12 | YGAAVPGVLGGLGA SEQ ID NO: 1741 | 657-670 |
| MMP9 + 12 | YGAAVPGVLGGLGALG SEQ ID NO: 1742 | 657-672 |
| MMP9 + 12 | YGAAVPGVLGGLGALGGVGIPGG SEQ ID NO: 1743 | 657-679 |
| MMP9 + 12 | YGAAVPGVLGGLGALGGVGIPGGVVGAGPAA SEQ ID NO: 1744 | 657-687 |
| MMP9 + 12 | GAAVPGVLGGLG SEQ ID NO: 1745 | 658-669 |
| MMP9 + 12 | GAAVPGVLGGLGALGGVGIPGG SEQ ID NO: 1746 | 658-679 |
| MMP9 + 12 | AVPGVLGGLGA SEQ ID NO: 1747 | 660-670 |
| MMP9 + 12 | AVPGVLGGLGALGGVGIPGG SEQ ID NO: 1748 | 660-679 |
| MMP9 + 12 | VLGGLGALGGVGIPGG SEQ ID NO: 1749 | 664-679 |
| MMP9 + 12 | GGLGALGGVGIPGGVVGAGPA SEQ ID NO: 1750 | 666-686 |
| MMP9 + 12 | GGLGALGGVGIPGGVVGAGPAAA SEQ ID NO: 1751 | 666-688 |
| MMP9 + 12 | LGALGGVGIPGG SEQ ID NO: 1752 | 668-379 |

TABLE 24-continued

Elastin fragments generated by specific proteases.

| Protease | Sequence between cleavage sites | Nos* |
|---|---|---|
| MMP9 + 12 | LGALGGVGIPGGVVGAGPA SEQ ID NO: 1753 | 668-686 |
| MMP9 + 12 | LGALGGVGIPGGVVGAGPAA SEQ ID NO: 1754 | 668-687 |
| MMP9 + 12 | LGALGGVGIPGGVVGAGPAAA SEQ ID NO: 1755 | 668-688 |
| MMP9 + 12 | LGALGGVGIPGGVVGAGPAAAA SEQ ID NO: 1756 | 668-689 |
| MMP9 + 12 | ALGGVGIPGGVVGAGPAA SEQ ID NO: 1757 | 670-687 |
| MMP9 + 12 | ALGGVGIPGGVVGAGPAAA SEQ ID NO: 1758 | 670-688 |
| MMP9 + 12 | LGGVGIPGGV SEQ ID NO: 1759 | 671-680 |
| MMP9 + 12 | LGGVGIPGGVVGAGPA SEQ ID NO: 1760 | 671-686 |
| MMP9 + 12 | LGGVGIPGGVVGAGPAAA SEQ ID NO: 1761 | 671-688 |
| MMP9 + 12 | LGGVGIPGGVVGAGPAAAAA SEQ ID NO: 1762 | 671-690 |
| MMP9 + 12 | LGGVGIPGGVVGAGPAAAAAAAK SEQ ID NO: 1763 | 671-693 |
| MMP9 + 12 | GVGIPGGVVGAGPAAAA SEQ ID NO: 1764 | 673-689 |
| MMP9 + 12 | GVGIPGGVVGAGPAAAAAAAK SEQ ID NO: 1765 | 673-693 |
| MMP9 + 12 | VGIPGGVVGAGPAAA SEQ ID NO: 1766 | 674-688 |
| MMP9 + 12 | VGIPGGVVGAGPAAAAAAAK SEQ ID NO: 1767 | 674-693 |
| MMP9 + 12 | IPGGVVGAGPAAAA SEQ ID NO: 1768 | 676-689 |
| MMP9 + 12 | VVGAGPAAAAAAAK SEQ ID NO: 1769 | 680-693 |
| MMP9 + 12 | VGAGPAAAAAAAK SEQ ID NO: 1770 | 681-693 |
| MMP9 + 12 | AGPAAAAAAAK SEQ ID NO: 1771 | 683-693 |
| MMP9 + 12 | GPAAAAAAAK SEQ ID NO: 1772 | 684-693 |
| MMP9 + 12 | PAAAAAAAK SEQ ID NO: 1773 | 685-693 |
| MMP9 + 12 | FGLVGAAGLGGLGVGGLGVPGVGG SEQ ID NO: 1774 | 701-724 |
| MMP9 + 12 | GLVGAAGLGGLG SEQ ID NO: 1775 | 702-713 |
| MMP9 + 12 | GLVGAAGLGGLGVGG SEQ ID NO: 1776 | 702-716 |
| MMP9 + 12 | GLVGAAGLGGLGVGGLGVPGVG SEQ ID NO: 1777 | 702-723 |
| MMP9 + 12 | GLVGAAGLGGLGVGGLGVPGVGG SEQ ID NO: 1778 | 702-724 |
| MMP9 + 12 | LVGAAGLGGLGVG SEQ ID NO: 1779 | 703-715 |
| MMP9 + 12 | LVGAAGLGGLGVGG SEQ ID NO: 1780 | 703-716 |
| MMP9 + 12 | LVGAAGLGGLGVGGL SEQ ID NO: 1781 | 703-717 |
| MMP9 + 12 | LVGAAGLGGLGVGGLGVPGVGGLG SEQ ID NO: 1782 | 703-726 |
| MMP9 + 12 | LVGAAGLGGLGVGGLGVPGVGGLGGIPPAAA SEQ ID NO: 1783 | 703-733 |
| MMP9 + 12 | VGAAGLGGLGVGG SEQ ID NO: 1784 | 704-716 |
| MMP9 + 12 | LGGLGVGGLGVPG SEQ ID NO: 1785 | 709-721 |
| MMP9 + 12 | LGGLGVGGLGVPGVG SEQ ID NO: 1786 | 709-723 |
| MMP9 + 12 | LGGLGVGGLGVPGVGGL SEQ ID NO: 1787 | 709-725 |
| MMP9 + 12 | LGGLGVGGLGVPGVGGLG SEQ ID NO: 1788 | 709-726 |
| MMP9 + 12 | LGVGGLGVPGVGGLG SEQ ID NO: 1789 | 712-726 |
| MMP9 + 12 | GLGVPGVGGLGGIPPAAAAK SEQ ID NO: 1790 | 716-735 |

TABLE 24-continued

Elastin fragments generated by specific proteases.

| Protease | Sequence between cleavage sites | Nos* |
|---|---|---|
| MMP9 + 12 | LGGIPPAAAAK SEQ ID NO: 1791 | 725-735 |
| MMP9 + 12 | LGGVLGGAGQFPL SEQ ID NO: 1792 | 744-756 |
| MMP9 + 12 | LGGVLGGAGQFPLGGVAAR SEQ ID NO: 1793 | 744-762 |
| MMP9 + 12 | LGGVLGGAGQFPLGGVAARPG SEQ ID NO: 1794 | 744-764 |
| MMP9 + 12 | LGGVLGGAGQFPLGGVAARPGFG SEQ ID NO: 1795 | 744-766 |
| MMP9 + 12 | GGVLGGAGQFPLGGVAARPG SEQ ID NO: 1796 | 745-764 |
| MMP9 + 12 | GAGQFPLGGVAAR SEQ ID NO: 1797 | 750-762 |
| MMP9 + 12 | GAGQFPLGGVAARPGFG SEQ ID NO: 1798 | 750-766 |
| MMP9 + 12 | AGQFPLGGVAARPGFG SEQ ID NO: 1799 | 751-766 |
| MMP9 + 12 | FPLGGVAARPG SEQ ID NO: 1800 | 754-764 |
| MMP9 + 12 | PLGGVAAR SEQ ID NO: 1801 | 755-762 |
| MMP9 + 12 | PLGGVAARPG SEQ ID NO: 1802 | 755-764 |
| MMP9 + 12 | PLGGVAARPGFG SEQ ID NO: 1803 | 755-766 |
| MMP9 + 12 | PLGGVAARPGFGL SEQ ID NO: 1804 | 755-767 |
| MMP9 + 12 | PLGGVAARPGFGLSPIFPG SEQ ID NO: 1805 | 755-773 |
| MMP9 + 12 | LGGVAAR SEQ ID NO: 1806 | 756-762 |
| MMP9 + 12 | LGGVAARP SEQ ID NO: 1807 | 756-763 |
| MMP9 + 12 | LGGVAARPG SEQ ID NO: 1808 | 756-764 |
| MMP9 + 12 | LGGVAARPGF SEQ ID NO: 1809 | 756-765 |
| MMP9 + 12 | LGGVAARPGFG SEQ ID NO: 1810 | 756-766 |
| MMP9 + 12 | LGGVAARPGFGL SEQ ID NO: 1811 | 756-767 |
| MMP9 + 12 | LGGVAARPGFGLSP SEQ ID NO: 1812 | 756-769 |
| MMP9 + 12 | LGGVAARPGFGLSPIFPG SEQ ID NO: 1813 | 756-773 |
| MMP9 + 12 | LGGVAARPGFGLSPIFPGG SEQ ID NO: 1814 | 756-774 |
| MMP9 + 12 | LGGVAARPGFGLSPIFPGGA SEQ ID NO: 1815 | 756-775 |
| MMP9 + 12 | GGVAARPGFG SEQ ID NO: 1816 | 757-766 |
| MMP9 + 12 | GGVAARPGFGL SEQ ID NO: 1817 | 757-767 |
| MMP9 + 12 | GGVAARPGFGLSPIFPGGA SEQ ID NO: 1818 | 757-775 |
| MMP9 + 12 | GVAARPGFGLSPIF SEQ ID NO: 1819 | 758-771 |
| MMP9 + 12 | GVAARPGFGLSPIFP SEQ ID NO: 1820 | 758-772 |
| MMP9 + 12 | VAARPGFG SEQ ID NO: 1821 | 759-766 |
| MMP9 + 12 | VAARPGFGLSPIFP SEQ ID NO: 1822 | 759-772 |
| MMP9 + 12 | VAARPGFGLSPIFPG SEQ ID NO: 1823 | 759-773 |
| MMP9 + 12 | RPGFGLSPIFPG SEQ ID NO: 1824 | 762-773 |
| MMP9 + 12 | PGFGLSPIFPGG SEQ ID NO: 1825 | 763-774 |
| MMP9 + 12 | PGFGLSPIFPGGA SEQ ID NO: 1826 | 763-775 |
| ADAMTS-1 | P.GVGLPGVYPGGVLPGAR.F SEQ ID NO: 1827 | 143-159 |
| ADAMTS-1 | G.VGLPGVYPGGVLPGAR.F SEQ ID NO: 1828 | 144-159 |

TABLE 24-continued

Elastin fragments generated by specific proteases.

| Protease | Sequence between cleavage sites | Nos* |
|---|---|---|
| ADAMTS-1 | G.LPGVYPGGVLPGAR.F SEQ ID NO: 1829 | 146-159 |
| ADAMTS-1 | P.GVYPGGVLPGAR.F SEQ ID NO: 1830 | 148-159 |
| ADAMTS-1 | K.AGYPTGTGVGPQAAAAAAAK.A SEQ ID NO: 1831 | 242-261 |
| ADAMTS-1 | G.GPGFGPGVVGVPGAGVPGVGVPGA.G SEQ ID NO: 1832 | 326-349 |
| ADAMTS-1 | G.FGPGVVGVPGAGVPGVGVPG.A SEQ ID NO: 1833 | 329-348 |
| ADAMTS-1 | F.GPGVVGVPGAGVPGVGVPG.A SEQ ID NO: 1834 | 330-348 |
| ADAMTS-1 | G.VPGVGVPGAGIPVVPG.A SEQ ID NO: 1835 | 341-356 |
| ADAMTS-1 | G.ARPGVGVGGIPTYGVG.A SEQ ID NO: 1836 | 385-400 |
| ADAMTS-1 | G.ARPGVGVGGIPTYGVGAGG.F SEQ ID NO: 1837 | 385-403 |
| ADAMTS-1 | A.RPGVGVGGIPTYGVGAG.G SEQ ID NO: 1838 | 386-402 |
| ADAMTS-1 | G.GVPGVGGVPGVGISPEAQAAAA.A SEQ ID NO: 1839 | 425-446 |
| ADAMTS-1 | G.VPGVGISPEAQAAAAAK.A SEQ ID NO: 1840 | 432-448 |
| ADAMTS-1 | G.VGISPEAQAAAAAK.A SEQ ID NO: 1841 | 435-448 |
| ADAMTS-1 | V.PGVGVAPGVGVAPGVGVAPGVGL.A SEQ ID NO: 1842 | 504-526 |
| ADAMTS-1 | G.VAPGVGVAPGVGVAPGVGLAPGVGVAPG.V SEQ ID NO: 1843 | 508-535 |
| ADAMTS-1 | G.VGVAPGVGVAPGVGLAPGVG.V SEQ ID NO: 1844 | 512-531 |
| ADAMTS-1 | G.VGVAPGVGVAPGVGLAPGVGVAPGVG.V SEQ ID NO: 1845 | 512-537 |
| ADAMTS-1 | A.PGVGVAPGVGVAPGVGVAPGIGPG.G SEQ ID NO: 1846 | 528-551 |
| ADAMTS-1 | G.VAPGVGVAPGVGVAPGIGPG.G SEQ ID NO: 1847 | 532-551 |
| ADAMTS-1 | G.AAVPGVLGGLGALGGVGIPG.G SEQ ID NO: 1848 | 659-678 |
| ADAMTS-1 | G.AAGLGGLGVGGLGVPGVGGLG.G SEQ ID NO: 1849 | 706-726 |
| ADAMTS-4 | P.GVGLPGVYPGGVLPGAR.F SEQ ID NO: 1827 | 143-159 |
| ADAMTS-4 | G.LPGVYPGGVLPGAR.F SEQ ID NO: 1829 | 146-159 |
| ADAMTS-4 | K.AGYPTGTGVGPQAAAAAAAK.A SEQ ID NO: 1831 | 242-261 |
| ADAMTS-4 | G.GAGVPGVPGAIPGIGGIAGVG.T SEQ ID NO: 1850 | 279-299 |
| ADAMTS-4 | G.AGVPGVPGAIPGIGGIAGVG.T SEQ ID NO: 1851 | 280-299 |
| ADAMTS-4 | A.GVGTPAAAAAAAAAAK.A SEQ ID NO: 1852 | 297-312 |
| ADAMTS-4 | G.VGTPAAAAAAAAAAK.A SEQ ID NO: 1853 | 298-312 |
| ADAMTS-4 | G.GPGFGPGVVGVPGAGVPGVGVPG.A SEQ ID NO: 1854 | 326-348 |
| ADAMTS-4 | G.ARPGVGVGGIPTYGVGA.G SEQ ID NO: 1855 | 385-401 |
| ADAMTS-4 | A.RPGVGVGGIPTYGVGAG.G SEQ ID NO: 1838 | 386-402 |
| ADAMTS-4 | A.RPGVGVGGIPTYGVGAGG.F SEQ ID NO: 1856 | 386-403 |
| ADAMTS-4 | G.VGISPEAQAAAAAK.A SEQ ID NO: 1841 | 435-448 |
| ADAMTS-4 | G.VGVAPGVGVAPGVGVAPGVGLAPGVG.V SEQ ID NO: 1857 | 506-531 |
| ADAMTS-4 | A.PGVGVAPGVGLAPGVGVAPGVGVA.P SEQ ID NO: 1858 | 516-539 |
| ADAMTS-4 | G.VGVAPGVGLAPGVGVAPGVG.V SEQ ID NO: 1859 | 518-537 |
| ADAMTS-4 | L.APGVGVAPGVGVAPGVGVAPGIGPG.G SEQ ID NO: 1860 | 527-551 |

TABLE 24-continued

Elastin fragments generated by specific proteases.

| Protease | Sequence between cleavage sites | Nos* |
|---|---|---|
| ADAMTS-4 | Y.GAAVPGVLGGLGALGGVGIPG.G SEQ ID NO: 1861 | 658-678 |
| ADAMTS-4 | G.AAVPGVLGGLGALGGVGIPG.G SEQ ID NO: 1848 | 659-678 |
| ADAMTS-4 | G.GAGQFPLGGVAARPGFGL.S SEQ ID NO: 1862 | 750-767 |
| ADAMTS-8 | L.VPGGVADAAAAYK.A SEQ ID NO: 1863 | 092-104 |
| ADAMTS-8 | G.VGLPGVYPGGVLPGAR.F SEQ ID NO: 1828 | 144-159 |
| ADAMTS-8 | G.LPGVYPGGVLPGAR.F SEQ ID NO: 1829 | 146-159 |
| ADAMTS-8 | P.GVYPGGVLPGAR.F SEQ ID NO: 1830 | 148-159 |
| ADAMTS-8 | V.YPGGVLPGAR.F SEQ ID NO: 1864 | 150-159 |
| ADAMTS-8 | F.GPGVVGVPGAGVPGVGVPG.A SEQ ID NO: 1834 | 330-348 |
| ADAMTS-8 | G.ARPGVGVGGIPTYGVGA.G SEQ ID NO: 1855 | 385-401 |
| ADAMTS-8 | V.APGVGVAPGVGVAPGVGLAPGVGV.A SEQ ID NO: 1865 | 509-532 |
| ADAMTS-8 | L.APGVGVAPGVGVAPGVGV.A SEQ ID NO: 1866 | 527-544 |
| ADAMTS-8 | L.APGVGVAPGVGVAPGVGVAPG.I SEQ ID NO: 1867 | 527-547 |
| ADAMTS-8 | L.APGVGVAPGVGVAPGVGVAPGIG.P SEQ ID NO: 1868 | 527-549 |
| ADAMTS-8 | L.APGVGVAPGVGVAPGVGVAPGIGP.G SEQ ID NO: 1869 | 527-550 |
| ADAMTS-8 | L.APGVGVAPGVGVAPGVGVAPGIGPG.G SEQ ID NO: 1860 | 527-551 |
| ADAMTS-8 | L.APGVGVAPGVGVAPGVGVAPGIGPGGVAA.A SEQ ID NO: 1870 | 527-555 |
| ADAMTS-8 | G.VGVAPGVGVAPGVGVAPGIGPG.G SEQ ID NO: 1871 | 530-551 |
| ADAMTS-8 | G.VAPGVGVAPGVGVAPGIGPG.G SEQ ID NO: 1847 | 532-551 |
| ADAMTS-8 | G.AAVPGVLGGLGALGGVGIPG.G SEQ ID NO: 1848 | 659-678 |
| ADAMTS-8 | G.AAVPGVLGGLGALGGVGIPGG.V SEQ ID NO: 1872 | 659-679 |
| ADAMTS-8 | A.AVPGVLGGLGALGGVGIPG.G SEQ ID NO: 1873 | 660-678 |
| ADAMTS-8 | A.VPGVLGGLGALGGVGIPGG.V SEQ ID NO: 1874 | 661-679 |
| ADAMTS-8 | A.GQFPLGGVAARPGFGL.S SEQ ID NO: 1875 | 752-767 |
| Cat K | G.ALVPGGVADAAAAYK.A SEQ ID NO: 1876 | 090-104 |
| Cat K | G.LPYTTGKLPYGYGPG.G SEQ ID NO: 1877 | 219-233 |
| Cat K | A.AAAAAKAAAKFGA.G SEQ ID NO: 1878 | 255-268 |
| Cat K | A.GVGTPAAAAAAAAAK.A SEQ ID NO: 1852 | 297-312 |
| Cat K | A.AAAAAAAAKAAKYGA.A SEQ ID NO: 1879 | 303-318 |
| Cat K | G.FGPGVVGVPGAGVPGVGVPG.A SEQ ID NO: 1833 | 329-348 |
| Cat K | G.VGISPEAQAAAAAK.A SEQ ID NO: 1841 | 435-448 |
| Cat K | G.VAPGVGVAPGVGVAPGVGLAPGVG.V SEQ ID NO: 1880 | 508-531 |
| Cat K | G.VGVAPGVGVAPGVGVAPGIGPG.G SEQ ID NO: 1871 | 530-551 |
| Cat K | G.VAPGVGVAPGVGVAPGIGPG.G SEQ ID NO: 1847 | 532-551 |
| Cat S | T.FPGALVPGGVADAAAAYK.A SEQ ID NO: 1881 | 087-104 |
| Cat S | G.VGLPGVYPGGVLPGAR.F SEQ ID NO: 1828 | 144-159 |
| Cat S | G.LPGVYPGGVLPGARFPGVG.V SEQ ID NO: 1882 | 146-164 |
| Cat S | G.YPTGTGVGPQAAAAAAAK.A SEQ ID NO: 1883 | 244-261 |

TABLE 24-continued

Elastin fragments generated by specific proteases.

| Protease | Sequence between cleavage sites | Nos* |
|---|---|---|
| Cat S | G.GAGVPGVPGAIPGIGGIAGVG.T SEQ ID NO: 1850 | 279-299 |
| Cat S | G.TPAAAAAAAAAAKAAK.Y SEQ ID NO: 1884 | 300-315 |
| Cat S | G.VPGAGVPGVGVPGAGIPVVP.G SEQ ID NO: 1885 | 336-355 |
| Cat S | G.VPGAGVPGVGVPGAGIPVVPGAGIPG.A SEQ ID NO: 1886 | 336-361 |
| Cat S | G.ISPEAQAAAAAKAAK.Y SEQ ID NO: 1887 | 437-451 |
| Cat S | V.PGVGVAPGVGVAPGVGVA.P SEQ ID NO: 1888 | 504-521 |
| Cat S | G.VAPGVGVAPGVGVAPGIGPGGVA.A SEQ ID NO: 1889 | 532-554 |
| Cat S | G.IPGGVVGAGPAAAAAAAK.A SEQ ID NO: 1890 | 676-693 |
| MMP1 | G.GVLPGARFPGVGVLPGVPTGA.G SEQ ID NO: 1891 | 153-173 |
| MMP1 | G.GVPGVGGVPGVGISPEA.Q SEQ ID NO: 1892 | 425-441 |
| MMP1 | V.PGVGVAPGVGVAPGVGVA.P SEQ ID NO: 1888 | 504-521 |
| MMP1 | G.VGVAPGVGVAPGVGVAPGVG.L SEQ ID NO: 1893 | 506-525 |
| MMP1 | G.VAPGVGVAPGVGVAPGIGPG.G SEQ ID NO: 1847 | 532-551 |
| MMP1 | A.AVPGVLGGLGALGGVGIPG.G SEQ ID NO: 1873 | 660-678 |
| MMP1 | | |
| MMP3 | G.ALVPGGVADAAAAYK.A SEQ ID NO: 1876 | 090-104 |
| MMP3 | G.YPTGTGVGPQAAAAAAAK.A SEQ ID NO: 1883 | 244-261 |
| MMP3 | G.VPGVPGAIPGIGGIAGVG.T SEQ ID NO: 1894 | 282-299 |
| MMP3 | F.GPGVVGVPGAGVPGVGVPGA.G SEQ ID NO: 1895 | 330-349 |
| MMP3 | G.VGISPEAQAAAAAK.A SEQ ID NO: 1841 | 435-448 |
| MMP3 | G.VGVAPGVGVAPGVGLAPGVG.V SEQ ID NO: 1844 | 512-531 |
| MMP3 | G.VAPGVGVAPGVGVAPGIGPG.G SEQ ID NO: 1847 | 532-551 |
| MMP8 | P.GVYPGGVLPGAR.F SEQ ID NO: 1830 | 148-159 |
| MMP8 | K.AGYPTGTGVGPQAAAAAAAK.A SEQ ID NO: 1831 | 242-261 |
| MMP8 | G.VPGVPGAIPGIGGIAGVG.T SEQ ID NO: 1894 | 282-299 |
| MMP8 | F.GPGVVGVPGAGVPGVGVPG.A SEQ ID NO: 1834 | 330-348 |
| MMP8 | G.VPGVGVPGAGIPVVPGA.G SEQ ID NO: 1896 | 341-357 |
| MMP8 | G.ARPGVGVGGIPTYGVG.A SEQ ID NO: 1836 | 385-400 |
| MMP8 | A.RPGVGVGGIPTYGVGAG.G SEQ ID NO: 1838 | 386-402 |
| MMP8 | G.VGVAPGVGVAPGVGVAP.G SEQ ID NO: 1897 | 506-522 |
| MMP8 | G.VGVAPGVGVAPGVGLAPGVG.V SEQ ID NO: 1844 | 512-531 |
| MMP8 | G.VGVAPGVGVAPGVGVAP.G SEQ ID NO: 1897 | 530-546 |
| MMP8 | G.IPGGVVGAGPAAAAAAAK.A SEQ ID NO: 1890 | 676-693 |

*Aminoacid residue numbers in the human elastin sequence

Accordingly, in a method of the invention, said peptide fragments preferably comprise a neo-epitope formed by cleavage of elastin by a protease at an N- or C-terminal site, or where indicated a site marked by the sign in any one of the partial sequences of elastin in Table 24.

The immunological binding partner may be one specifically reactive with a C-terminal or N-terminal neo-epitope formed by cleavage of elastin.

Suitable immunological binding partners may therefore be specifically reactive with any of the following sequences at the N terminal of a peptide:

TABLE 25

N-terminal sequences of protease generated peptide fragments of elastin.

| | | | | | |
|---|---|---|---|---|---|
| GVPGAI | SEQ ID NO: 1898 | AIPGGV | SEQ ID NO: 1899 | GVPGGV | SEQ ID NO: 1900 |
| ALGGGA | SEQ ID NO: 1901 | LGGGAL | SEQ ID NO: 1902 | GGALGP | SEQ ID NO: 1903 |
| PLKPVP | SEQ ID NO: 1904 | LKPVPG | SEQ ID NO: 1905 | GLAGAG | SEQ ID NO: 1906 |
| GLGAGL | SEQ ID NO: 1907 | LGAGLG | SEQ ID NO: 1908 | AGLGAF | SEQ ID NO: 1909 |
| LVPGGV | SEQ ID NO: 1910 | VADAAA | SEQ ID NO: 1911 | KAAKAG | SEQ ID NO: 1912 |
| PVGYPG | SEQ ID NO: 1913 | ARFPGV | SEQ ID NO: 1914 | RFPGVG | SEQ ID NO: 1915 |
| VGPFGG | SEQ ID NO: 1916 | GPQPGV | SEQ ID NO: 1917 | PQPGVP | SEQ ID NO: 1918 |
| TTGKLP | SEQ ID NO: 1919 | LPYGYG | SEQ ID NO: 1920 | GYGPGG | SEQ ID NO: 1921 |
| FGAGAA | SEQ ID NO: 1922 | GVLPGV | SEQ ID NO: 1923 | VLPGVG | SEQ ID NO: 1924 |
| AGIPGL | SEQ ID NO: 1925 | VPGAIP | SEQ ID NO: 1926 | AIPGIG | SEQ ID NO: 1927 |
| TPAAAA | SEQ ID NO: 1928 | PAAAAA | SEQ ID NO: 1929 | AAAAAA | SEQ ID NO: 1930 |
| VGVPGA | SEQ ID NO: 1931 | AVGPGV | SEQ ID NO: 1932 | GVPGVG | SEQ ID NO: 1933 |
| GIPVVP | SEQ ID NO: 1934 | IPGAAV | SEQ ID NO: 1935 | GAAVPG | SEQ ID NO: 1936 |
| ARPGVG | SEQ ID NO: 1937 | RPGVGV | SEQ ID NO: 1938 | VGGIPT | SEQ ID NO: 1939 |
| SVGGVP | SEQ ID NO: 1940 | VGGVPG | SEQ ID NO: 1941 | GVGTPA | SEQ ID NO: 1942 |
| VGVAPG | SEQ ID NO: 1943 | VAPGVG | SEQ ID NO: 1944 | GVAPGV | SEQ ID NO: 1945 |
| GVPVAP | SEQ ID NO: 1946 | GAGIPG | SEQ ID NO: 1947 | PGGVAA | SEQ ID NO: 1948 |
| LGAGIP | SEQ ID NO: 1949 | PGFGPG | SEQ ID NO: 1950 | PGVVGV | SEQ ID NO: 1951 |
| PGALAA | SEQ ID NO: 1952 | AKYGAA | SEQ ID NO: 1953 | YGAAVP | SEQ ID NO: 1954 |
| ALGGVG | SEQ ID NO: 1955 | LGGVGI | SEQ ID NO: 1956 | GVGIPG | SEQ ID NO: 1957 |
| AGPAAA | SEQ ID NO: 1958 | GPAAAA | SEQ ID NO: 1959 | FGLVGA | SEQ ID NO: 1960 |
| GLGVPG | SEQ ID NO: 1961 | LGGIPP | SEQ ID NO: 1962 | LGGVLG | SEQ ID NO: 1963 |
| PLGGVA | SEQ ID NO: 1964 | LGGVAA | SEQ ID NO: 1965 | GGVAAR | SEQ ID NO: 1966 |
| GVGLPG | SEQ ID NO: 1967 | VGLPGV | SEQ ID NO: 1968 | LPGVYP | SEQ ID NO: 1969 |
| VPGVPV | SEQ ID NO: 1970 | VPGVGI | SEQ ID NO: 1971 | VGISPE | SEQ ID NO: 1972 |
| APGVGV | SEQ ID NO: 1973 | VPGGVA | SEQ ID NO: 1974 | YPGGVL | SEQ ID NO: 1975 |
| GPGFGP | SEQ ID NO: 1976 | YPTGTG | SEQ ID NO: 1977 | VPGAGV | SEQ ID NO: 1978 |
| VPGGVF | SEQ ID NO: 1979 | GVFYPG | SEQ ID NO: 1980 | VFYPGA | SEQ ID NO: 1981 |
| LGPGGK | SEQ ID NO: 1982 | GPGGKP | SEQ ID NO: 1983 | PGGKPL | SEQ ID NO: 1984 |
| LAGAGL | SEQ ID NO: 1985 | AGAGLG | SEQ ID NO: 1986 | GAGLGA | SEQ ID NO: 1987 |
| LGAFPA | SEQ ID NO: 1988 | AFPAVT | SEQ ID NO: 1989 | AVTFPG | SEQ ID NO: 1990 |
| LGVSAG | SEQ ID NO: 1991 | VPGVGL | SEQ ID NO: 1992 | PGVGLP | SEQ ID NO: 1993 |
| FPGVGV | SEQ ID NO: 1994 | KPGAPG | SEQ ID NO: 1995 | PKAPGV | SEQ ID NO: 1493 |
| PGVPLG | SEQ ID NO: 1996 | GYPIKA | SEQ ID NO: 1997 | PKLPGG | SEQ ID NO: 1998 |
| YGPGGV | SEQ ID NO: 1999 | AGYPTG | SEQ ID NO: 2000 | TGVGPQ | SEQ ID NO: 2001 |
| GAGVPG | SEQ ID NO: 2002 | AGVPGV | SEQ ID NO: 2003 | GVPGVP | SEQ ID NO: 2004 |
| IPGIGG | SEQ ID NO: 2005 | IGGIAG | SEQ ID NO: 2006 | GIAGVG | SEQ ID NO: 2007 |
| VPGVGV | SEQ ID NO: 2008 | VPVGVA | SEQ ID NO: 2009 | VPGAGI | SEQ ID NO: 2010 |
| AVPGVV | SEQ ID NO: 2011 | VPGVVS | SEQ ID NO: 2012 | YGARPG | SEQ ID NO: 2013 |

TABLE 25-continued

N-terminal sequences of protease generated peptide fragments of elastin.

| | | |
|---|---|---|
| GVGAGG SEQ ID NO: 2014 | VGAGGF SEQ ID NO: 2015 | VGVGGI SEQ ID NO: 2016 |
| FGLVPG SEQ ID NO: 2017 | GLVPGV SEQ ID NO: 2018 | LVPGVG SEQ ID NO: 2019 |
| PGVGLA SEQ ID NO: 2020 | GVGLAP SEQ ID NO: 2021 | VGLAPG SEQ ID NO: 2022 |
| LRAAAG SEQ ID NO: 2023 | LVGAAG SEQ ID NO: 2024 | LVPGGP SEQ ID NO: 2025 |
| GIPGLG SEQ ID NO: 2026 | LGVGVG SEQ ID NO: 2027 | VGVPGL SEQ ID NO: 2028 |
| AAAGLG SEQ ID NO: 2029 | AVPGVL SEQ ID NO: 2030 | VLGGLG SEQ ID NO: 2031 |
| VGIPGG SEQ ID NO: 2032 | IPGGVV SEQ ID NO: 2033 | VVGAGP SEQ ID NO: 2034 |
| GLVGAA SEQ ID NO: 2035 | VGAAGL SEQ ID NO: 2036 | LGGLGV SEQ ID NO: 2037 |
| GGVLGG SEQ ID NO: 2038 | GAGQFP SEQ ID NO: 2039 | AFQFPL SEQ ID NO: 2040 |
| GVAARP SEQ ID NO: 2041 | VAARPG SEQ ID NO: 2042 | RPGFGL SEQ ID NO: 2043 |
| GVYPGG SEQ ID NO: 2044 | LPYTTG SEQ ID NO: 2045 | FGPGVV SEQ ID NO: 2046 |
| AAVPGV SEQ ID NO: 2047 | AAGLGG SEQ ID NO: 2048 | FPGALV SEQ ID NO: 2049 |
| VPGVLG SEQ ID NO: 2050 | GQFPLG SEQ ID NO: 2051 | ALVPGG SEQ ID NO: 2052 |
| ISPEAQ SEQ ID NO: 2053 | GVLPGA SEQ ID NO: 2054 | VGAGVP SEQ ID NO: 2055 |
| LGALGG SEQ ID NO: 2056 | VPGVPG SEQ ID NO: 2057 | GGLGAL SEQ ID NO: 2058 |
| GKPLKP SEQ ID NO: 2059 | IAGVGT SEQ ID NO: 2060 | VGAGPA SEQ ID NO: 2061 |
| AGLGAG SEQ ID NO: 2062 | VVGVPG SEQ ID NO: 2063 | LGVGGL SEQ ID NO: 2064 |
| VTFPGA SEQ ID NO: 2065 | AGIPVV SEQ ID NO: 2066 | FPLGGV SEQ ID NO: 2067 |
| GLPGVY SEQ ID NO: 2068 | GARPGV SEQ ID NO: 2069 | PGFGLS SEQ ID NO: 2070 |
| GAFAGI SEQ ID NO: 2071 | VAGVPS SEQ ID NO: 2072 | GPGVVG SEQ ID NO: 2073 |
| YTTGKL SEQ ID NO: 2074 | PGVGVA SEQ ID NO: 2075 | VGTPAA SEQ ID NO: 2076 |
| PQAAAA SEQ ID NO: 2077 | LAPGVG SEQ ID NO: 2078 | | or with any of the following sequences at the C-terminal of a peptide:

TABLE 26

C-terminal sequences of protease generated peptide fragments of Elastin.
Elastin

| | | |
|---|---|---|
| PGGVPG SEQ ID NO: 2079 | PGAGLG SEQ ID NO: 2080 | GAGLGA SEQ ID NO: 1987 |
| GALGGG SEQ ID NO: 2081 | LGGGAL SEQ ID NO: 1902 | GGGALG SEQ ID NO: 2082 |
| GLGAFP SEQ ID NO: 2083 | LGAFPA SEQ ID NO: 1988 | LGAGLG SEQ ID NO: 1908 |
| VPGGVA SEQ ID NO: 1974 | ADAAAA SEQ ID NO: 2084 | PGVLGG SEQ ID NO: 2085 |
| RFPGVG SEQ ID NO: 1915 | VGVLPG SEQ ID NO: 2086 | VPTGAG SEQ ID NO: 2087 |
| PKAPGV SEQ ID NO: 1493 | GVGPFG SEQ ID NO: 2088 | VPLGYP SEQ ID NO: 2089 |
| LPYGYG SEQ ID NO: 1920 | AAAAAK SEQ ID NO: 2090 | IPGIGG SEQ ID NO: 2005 |
| GIAGVG SEQ ID NO: 2007 | AIPGIG SEQ ID NO: 1927 | IGGIAG SEQ ID NO: 2006 |
| AAAKA SEQ ID NO: 2091 | VVGVPG SEQ ID NO: 2063 | GVPGVG SEQ ID NO: 1933 |
| GVGVPG SEQ ID NO: 2092 | PVVPGA SEQ ID NO: 2093 | VVSPEA SEQ ID NO: 2094 |

TABLE 26-continued

C-terminal sequences of protease generated peptide fragments of Elastin.
Elastin

| | | | | | |
|---|---|---|---|---|---|
| VGGIPT | SEQ ID NO: 1939 | GGIPTY | SEQ ID NO: 2095 | GIPTYG | SEQ ID NO: 2096 |
| GVGVGG | SEQ ID NO: 2097 | GVGGIP | SEQ ID NO: 2098 | VGVPGL | SEQ ID NO: 2028 |
| GFPGFG | SEQ ID NO: 2099 | FGVGVG | SEQ ID NO: 2100 | GVGAGG | SEQ ID NO: 2014 |
| PGVGIS | SEQ ID NO: 2101 | SPEAQA | SEQ ID NO: 2102 | VAPGVG | SEQ ID NO: 1944 |
| PGVGVA | SEQ ID NO: 2075 | GVGVAP | SEQ ID NO: 2103 | APGVGL | SEQ ID NO: 2104 |
| GIGPGG | SEQ ID NO: 2105 | APGIGP | SEQ ID NO: 2106 | VAPGIG | SEQ ID NO: 2107 |
| RAAAGL | SEQ ID NO: 2108 | AAAGLG | SEQ ID NO: 2029 | AAGLGA | SEQ ID NO: 2109 |
| GVPGLG | SEQ ID NO: 2110 | GVPGFG | SEQ ID NO: 2111 | AGVPGL | SEQ ID NO: 2112 |
| VLGGLG | SEQ ID NO: 2031 | VGIPGG | SEQ ID NO: 2032 | GAGPAA | SEQ ID NO: 2113 |
| PAAAAA | SEQ ID NO: 1929 | VPGVGG | SEQ ID NO: 2114 | GLGGLG | SEQ ID NO: 2115 |
| GLGVPG | SEQ ID NO: 1961 | PGVGGL | SEQ ID NO: 2116 | PAAAAK | SEQ ID NO: 2117 |
| RPGFGL | SEQ ID NO: 2043 | GVAARP | SEQ ID NO: 2041 | AARPGF | SEQ ID NO: 2118 |
| LSPIFP | SEQ ID NO: 2119 | AQAAAA | SEQ ID NO: 2120 | GPGIPG | SEQ ID NO: 2121 |
| GPGGVA | SEQ ID NO: 2122 | TPAAAA | SEQ ID NO: 1928 | PGGVAA | SEQ ID NO: 1948 |
| GLGALG | SEQ ID NO: 2123 | LGALGG | SEQ ID NO: 2056 | ALGPGG | SEQ ID NO: 2124 |
| GALGPG | SEQ ID NO: 2125 | VAPVGV | SEQ ID NO: 2126 | KPVPGG | SEQ ID NO: 2127 |
| AFPAVT | SEQ ID NO: 1989 | AVTFPG | SEQ ID NO: 1990 | VTFPGA | SEQ ID NO: 2065 |
| AAAAYK | SEQ ID NO: 2128 | AAKAGA | SEQ ID NO: 2129 | VPQPGA | SEQ ID NO: 2130 |
| PGVPTG | SEQ ID NO: 2131 | GVPTGA | SEQ ID NO: 2132 | AGVKPK | SEQ ID NO: 2133 |
| PIKAPK | SEQ ID NO: 2134 | KLPGGY | SEQ ID NO: 2135 | YGYGPG | SEQ ID NO: 2136 |
| VGTPAA | SEQ ID NO: 2076 | VPGVPG | SEQ ID NO: 2057 | GVGTPA | SEQ ID NO: 1942 |
| GIGGIA | SEQ ID NO: 2137 | GTPAAA | SEQ ID NO: 2138 | AAAAAA | SEQ ID NO: 1930 |
| IPVVPG | SEQ ID NO: 2139 | VGVPGA | SEQ ID NO: 1931 | GVPGAG | SEQ ID NO: 2140 |
| GAGIPG | SEQ ID NO: 1947 | PEAAAK | SEQ ID NO: 2141 | ARPGVG | SEQ ID NO: 1937 |
| PTYGVG | SEQ ID NO: 2142 | TYGVGA | SEQ ID NO: 2143 | YGVGAG | SEQ ID NO: 2144 |
| IPTYGV | SEQ ID NO: 2145 | PGAIPG | SEQ ID NO: 2146 | VGAGGF | SEQ ID NO: 2015 |
| AGGFPG | SEQ ID NO: 2147 | GIPGVA | SEQ ID NO: 2148 | GISPEA | SEQ ID NO: 2149 |
| VGVAPG | SEQ ID NO: 1943 | VGLAPG | SEQ ID NO: 2022 | VPGAPG | SEQ ID NO: 2150 |
| PGVGLA | SEQ ID NO: 2020 | LAPGVG | SEQ ID NO: 2078 | APGVGV | SEQ ID NO: 1973 |
| GVAPGV | SEQ ID NO: 1945 | GGVAAA | SEQ ID NO: 2151 | PGIGPG | SEQ ID NO: 2152 |
| GLGVGG | SEQ ID NO: 2153 | PGLGVG | SEQ ID NO: 2154 | LGVGVG | SEQ ID NO: 2027 |
| GLGVGA | SEQ ID NO: 2155 | ALAAAK | SEQ ID NO: 2156 | LGGLGA | SEQ ID NO: 2157 |
| VGAGPA | SEQ ID NO: 2061 | AGPAAA | SEQ ID NO: 1958 | GPAAAA | SEQ ID NO: 1959 |
| GGLGVG | SEQ ID NO: 2158 | LGVGGL | SEQ ID NO: 2064 | GVGGLG | SEQ ID NO: 2159 |
| AGQFPL | SEQ ID NO: 2160 | GGVAAR | SEQ ID NO: 1966 | VAARPG | SEQ ID NO: 2042 |
| GFGLSP | SEQ ID NO: 2161 | PIFPGG | SEQ ID NO: 2162 | IFPGGA | SEQ ID NO: 2163 |
| AAKFGA | SEQ ID NO: 2164 | AAKYGA | SEQ ID NO: 2165 | AAKAAK | SEQ ID NO: 2166 |
| AGLGAL | SEQ ID NO: 2167 | GAGVPG | SEQ ID NO: 2002 | GIPGGV | SEQ ID NO: 2168 |

TABLE 26-continued

C-terminal sequences of protease generated peptide fragments of Elastin.
Elastin

| | | | | | |
|---|---|---|---|---|---|
| LKPVPG | SEQ ID NO: 1905 | PGVGVG | SEQ ID NO: 2169 | IPPAAA | SEQ ID NO: 2170 |
| ALVPGG | SEQ ID NO: 2052 | RPGVGV | SEQ ID NO: 1938 | ARPGFG | SEQ ID NO: 2171 |
| VLPGAR | SEQ ID NO: 2172 | GGFPGF | SEQ ID NO: 2173 | GLSPIF | SEQ ID NO: 2174 |
| PTGAGV | SEQ ID NO: 2175 | VGGVPG | SEQ ID NO: 1941 | GIPVVP | SEQ ID NO: 1934 |
| AGAAGK | SEQ ID NO: 2176 | | | | |

Vimentin

Several candidate proteases may be responsible for the digestion of vimentin in fibrotic tissue We have through a range of in vitro cleavages of pure native proteins determined that the enzymes listed in the following table cleaved vimentin at least at the cleavage sites at each end of the following sequences or at the cleavage sites marked '.' or where no '.' is shown, at the ends of the sequences:

TABLE 27

Vimentin fragments generated by specific proteases.

| Protease | Sequence between cleavage sites | Aminoacid residue numbers* |
|---|---|---|
| MMP2, MMP8, Trypsin | RLRSSVPGVR. SEQ ID NO: 2177 | 69-78 |
| MMP2, MMP8, Trypsin | RLRSSVPGVL. SEQ ID NO: 2178 | 69-78 |
| MMP2, MMP8, Trypsin | .LLQDSVDFSL SEQ ID NO: 2179 | 79-89 |
| MMP2, MMP8, Trypsin | .FADLSEAANR SEQ ID NO: 2180 | 295-304 |
| MMP2 | .ISLPLPTFSS SEQ ID NO: 2181 | 410-420 |

*in the human vimentin sequence

Accordingly, in a method of the invention, said peptide fragments preferably comprise a neo-epitope formed by cleavage of vimentin by a protease at an N- or C-terminal site, or where indicated a site marked by the sign in any one of the partial sequences of vimentin in Table 24. The immunological binding partner may be one specifically reactive with a C-terminal or N-terminal neo-epitope formed by cleavage of vimentin. Suitable immunological binding partners may therefore be specifically reactive with any of the following sequences at the N terminal of a peptide:

TABLE 28

N-terminal sequences of protease generated peptide fragments of vimentin.
Vimentin

| | | |
|---|---|---|
| LLQDSV SEQ ID NO: 2182 | FADLSE SEQ ID NO: 2183 | ISLPLP SEQ ID NO: 2184 | or with any of the following sequences at the C-terminal of a peptide:

TABLE 29

C-terminal sequences of protease generated peptide fragments of vimentin.
Vimentin

| | |
|---|---|
| SVPGVR SEQ ID NO: 2185 | SVPGVL SEQ ID NO: 2186 |

Further cleavage sites defining neo-epitopes that may be assayed in a similar manner can be identified by exposing collagens, elastin, CRP and proteoglycans or other fibrotic tissue proteins to any of the enzymes described herein and isolating and sequencing peptides thereby produced. Furthermore, assays may be based on the neo-epitopes generated adjacent the illustrated cleavage sites, i.e. in the C-terminal sequences that lead up to the N-terminal epitopes given above and the N-terminal sequences that connect to the C-terminal epitopes described.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be (1) a synthetic peptide derived from the sequence of collagen type I, III, IV, V, or VI, or from CRP, or from any of the proteoglycans versican, lumican, perlecan, decorin and biglycan peptide, or a competition agent derived from (2) a purified native collagen type I, III, IV, V, or VI, or CRP, or any of the proteoglycans neurocan, brevican, fibromodulin, serglycins, syndecan, betaglycan, versican, lumican, perlecan, decorin and biglycan cleaved by proteases to reveal said neo-epitope.

One suitable method could be a competition immunoassay using monoclonal antibodies or antibody binding fragments binding to neo-epitopes of collagen type I, III, IV, V, VI, CRP, vimentin, or any of the proteoglycans neurocan, brevican, fibromodulin, serglycins, syndecan, betaglycan, versican, lumican, decorin, perlecan and biglycan fragments or neo-epitopes on peptide fragments from other proteins derived from fibrotic tissue. Appropriately selected synthetic peptides coated onto the solid surface of a microtitre plate could compete with the sample for binding to the monoclonal antibodies or binding fragments. Alternatively, purified, native collagen type I, III, IV, V, VI, CRP, neurocan, brevican, fibromodulin, serglycins, syndecan, betaglycan, versican, lumican, decorin, perlecan and biglycan fragments carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin.

The sample may be a sample of serum, blood, plasma or other, e.g. fibrotic tissue biopsy.

Assays may be conducted as sandwich assays using a first immunological binding partner specifically reactive with a said neo-epitope and a second immunological binding partner reactive with the relevant protein to which the neo-epitope belongs. Optionally, said second immunological binding partner is directed to a second neo-epitope of the same protein.

In certain preferred methods the method further comprises comparing the determined level of said binding of said peptide fragments with values characteristic of (a) comparable healthy individuals and/or (b) a pathological fibrotic condition and optionally associating a higher level of the measured peptide (normally indicated by a higher level of binding) with a more severe degree of a said condition.

An aspect of the present invention relates to the development of monoclonal antibodies recognising neo-epitopes as described above, especially for collagen types I and IV. This can be achieved by immunising mice with synthetic peptides originating from the amino acid sequence of collagen type I, III, IV, V, VI, CRP, vimentin, neurocan, brevican, fibromodulin, serglycins, syndecan, betaglycan, versican, lumican, decorin, perlecan and biglycan molecules (including the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-prolongated form of the immunising peptide (for a C-terminal neo-epitope) or an N-terminal prolongated form of the immunising peptide (for an N-terminal neo-epitope). Antibodies for neo-epitopes may also be evaluated to establish a lack of binding capacity to native collagen type I, III, IV, V, VI, CRP, vimentin, neurocan, brevican, fibromodulin, serglycins, syndecan, betaglycan, versican, lumican, decorin, pelecan and biglycan. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of collagen type I, III, IV, V, VI, CRP, vimentin, neurocan, brevican, fibromodulin, serglycins, syndecan, betaglycan, versican, lumican, decorin, perlecan and biglycan by a protease at an end-site in any one of the partial sequences of collagen type I, III, IV, V, VI, CRP, vimentin, neurocan, brevican, fibromodulin, serglycins, syndecan, betaglycan, versican, lumican, decorin, perlecan and biglycan set out above, and may be for instance a monoclonal antibody or a binding fragment thereof.

The invention includes a cell line producing a monoclonal antibody against a C-terminal or N-terminal neo-epitope formed by cleavage of collagen type I, III, IV, V, VI, CRP, vimentin, neurocan, brevican, fibromodulin, serglycins, syndecan, betaglycan, versican, lumican, decorin, perlecan and biglycan at the end-sites of sequences in any one of the partial sequences of collagen type I, III, IV, V, VI, CRP, neurocan, brevican, fibromodulin, serglycins, syndecan, betaglycan, versican, lumican, decorin, perlecan and biglycan set out above.

The invention further provides a peptide comprising a C-terminal or N-terminal neo-epitope formed by cleavage of collagen type I, III, IV, V, VI, CRP, vimentin, neurocan, brevican, fibromodulin, serglycins, syndecan, betaglycan, versican, lumican, decorin, perlecan and biglycan in any one of the partial sequences of these proteins set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of collagen type I, III, IV, V, VI, CRP, vimentin, neurocan, brevican, fibromodulin, serglycins, syndecan, betaglycan, versican, lumican, decorin, perlecan and biglycan in any one of the partial sequences of collagen type I, III, IV, V, VI, CRP, vimentin, neurocan, brevican, fibromodulin, serglycins, syndecan, betaglycan, versican, lumican, decorin, perlecan and biglycan set out above.

The invention further comprises a vector comprising a nucleic acid sequence comprising an expression signal and a coding sequence which codes for the expression of a peptide comprising a C-terminal or N-terminal neo-epitope formed by cleavage of collagen type I, III, IV, V, VI, CRP, vimentin, versican, lumican, decorin, perlecan and biglycan in any one of the partial sequences of collagen type I, III, IV, V, VI, CRP, vimentin, neurocan, brevican, fibromodulin, serglycins, syndecan, betaglycan, versican, lumican, decorin, perlecan and biglycan set out above and further includes a host cell transformed with such a vector and expressing a said peptide.

Yet another aspect of the invention relates to kits, which can be used conveniently for carrying out the methods described above. Such kits may include (1) a microtitre plate coated with synthetic peptide; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native collagen type I, III, IV, V, VI, CRP, vimentin, versican, lumican, decorin, perlecan and biglycan fragments; (2) a monoclonal antibody recognising a neo-epitope on collagen type I, III, IV, V, VI, CRP, vimentin, neurocan, brevican, fibromodulin, serglycins, syndecan, betaglycan, versican, lumican, decorin, perlecan and biglycan fragments and reactive with said purified collagen type I, III, IV, V, VI, CRP, vimentin, neurocan, brevican, fibromodulin, serglycins, syndecan, betaglycan, versican, lumican, decorin, perlecan, and biglycan fragments; and (3) a labelled anti-mouse IgG immunoglobulin. Alternatively, such kits may include (1) a microtitre plate coated with streptavidin; (2) a synthetic peptide linked to biotin; (3) a monoclonal antibody recognising a neo-epitope on collagen type I, III, IV, V, VI, CRP, vimentin, neurocan, brevican, fibromodulin, serglycins, syndecan, betaglycan, versican, lumican, decorin, perlecan and biglycan fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin; (3) a monoclonal antibody recognising a neo-epitope on collagen type I, III, IV, V, VI, CRP, vimentin, neurocan, brevican, fibromodulin, serglycins, syndecan, betaglycan, versican, lumican, decorin, perlecan and biglycan fragments (and reactive with said synthetic peptide) and conjugated to horseradish peroxidase.

Thus, the invention includes an immunoassay kit comprising an immunological binding partner as described herein, especially in respect of collagens types I and IV, and a competition agent which binds said immunological binding partner, and optionally one or more of a wash reagent, a buffer, a stopping reagent, an enzyme label, an enzyme label substrate, calibration standards, an anti-mouse antibody and instructions.

The assays described herein are useful in the diagnosis of fibrosis in patients. In addition, the tests are useful for the assessment of disease progression, and the monitoring of response to therapy. The immunological binding partners of the invention may also be used in immunostaining to show the presence or location of collagen type I, III, IV, V, VI, CRP, vimentin, neurocan, brevican, fibromodulin, serglycins, syndecan, betaglycan, versican, lumican, decorin, perlecan and biglycan cleavage products.

EXEMPLIFICATION

Example 1

Collagen Type III Degraded with MMP-9

Method

Cleavage: Collagen type III isolated from human placenta was dissolved in 10 mM acetic acid (1 mg/ml). The protein solution was then passed through a filter (Microcon Ultracel YM-10) to remove fragment contaminations. MMP-9 was preactivated with 4-aminophenylmercuric acetate (APMA, Sigma) at 37° C. for 3 hours. After activations, collagen type III and MMP-9 were mixed 100:1 and incubated shaking for 3 days at 37° C.

The solution was analyzed by liquid chromatography/mass spectrometry (LC/MS) and the fragments were identified by performing Mascot Search. The peptide sequences were selected by homology search, ensuring no cross-reactivity to other or related proteins, as well as interspecies cross-reactivity.

Antibody design: The peptide sequences were synthesized and conjugated to ovalbumin (OVA). Mice were immunized ever 2-3 weeks, up to five. Antibody titers were checked by screening peptides, both selection and de-selection. When sufficient antibody titers were achieved, positive mice were selected for fusion, euthanized, and the spleen was disintegrated and B-cells were removed for fusion with myeloma cells. Selections of antibody producing cells were done by culturing and re-seeding the surviving chimera cells in single cell clones. Clones are selected by selection and de-selection peptides followed by native reactivity testing (FIG. 1), as neoepitopes are generated by synthetic small peptide sequences, which may not reflect the native proteins. An IgG subtype clone is selected for antibody production. Antibody purification is done by protein-G column.

Assay development: Optimal antibody concentrations are determined by checker-board analysis, with dilutions of antibody coating and screening peptide, in competitions ELISA. The different determination for the collagen degraded by MMP-9 (CO3) assay is shown in Table 30.

TABLE 30

| Limit of Detection, Avarage Inter- and Intraassay variation of the CO3 assay. ||
| --- | --- |
| Limit of Detection | 0.5 ng/ml |
| Average Interassay variation | 3.71% |
| Average Intraassay variation | 5.48% |

Example 2

CO3 in Biological Relevant Samples

CO3 Levels in Bile Duct Ligated Rats Compared to Sham Operated Rats.

Method: Forty female Sprague-Dawley rats (6 months old) were housed at the animal research facilities at Nordic Bioscience. The experiments were approved by the Experimental Animal Committee of the Danish Ministry of Justice, and were performed according to the European Standard for Good Clinical Practice (2008/561-1450). The rats were housed in standard type III-H cages at 18-22° C. with bedding and nest material (Altromin 1324; Altromin, Lage, Germany) and purified water (Milli-Q system; Millipore, Glostrup, Denmark) ad libitum. Rats were kept under conditions of a 12-hour light/dark cycle.

Liver fibrosis was induced by common BDL. In short: The rat was anaesthetized, the bile duct found, two ligations were performed around the bile duct followed by dissection between the ligations, the abdomen was closed. In sham operated rats, the abdomen was closed without bile duct ligation. The rats were divided into 2 groups: Group 1(10 BDL and 10 sham operated rats) were sacrificed after 2 weeks, and Group 2 (9 BDL and 10 sham operated rats) were sacrificed after 4 weeks. On completion of the study period (2, or 4 weeks), after at least 14 hours fasting, all surviving animals were asphyxiated by $CO_2$ and sacrificed by exsanguinations.

Blood samples were taken from the retro-orbital sinus of at least 14 hours fasting rats under light $CO_2/O_2$ anaesthesia at baseline and at termination. The blood were collected and left 30 minutes at room temperature to cloth, followed by centrifugation at 1500 g for 10 minutes. All clot-free liquid were transferred to new tubes and centrifuged again at 1500 g for 10 minutes. The serum were then transferred to clean tubes and stored at −80° C.

CO3 were measured in ×5 diluted serum samples from the rats. Sham and BDL levels were compared by Mann-Whitneys two-tailed nonparametric test ($\alpha=0.05$) of statistical significance assuming normal distribution.

Figure 2A:
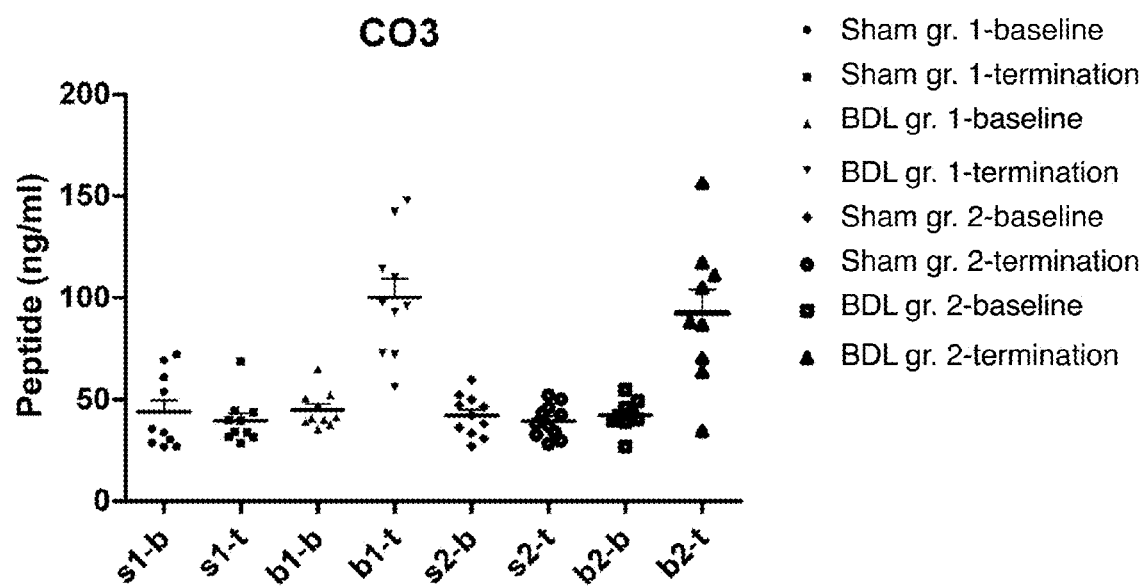
FIGS. 2A-2B show a graph showing CO3 serum levels in sham operated (s) and bile duct ligated rats at baseline (b) and at termination (t) (FIG. 2A) and the corresponding delta-values of CO3 in rat serum: Termination levels–Baseline levels (FIG. 2B).
Figure 2B:
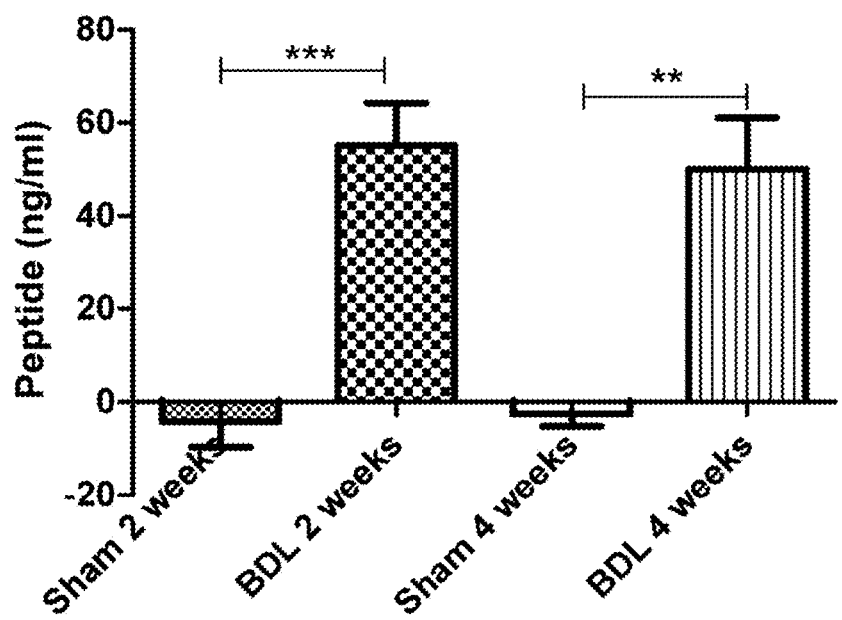

CO3 levels increased significantly in the BDL groups compared to the Sham-operated animals. The results are shown in FIGS. 2A and 2B.

Example 3

CO3 in Different Fibrotic Diseases (Human Serum)

Figure 3:
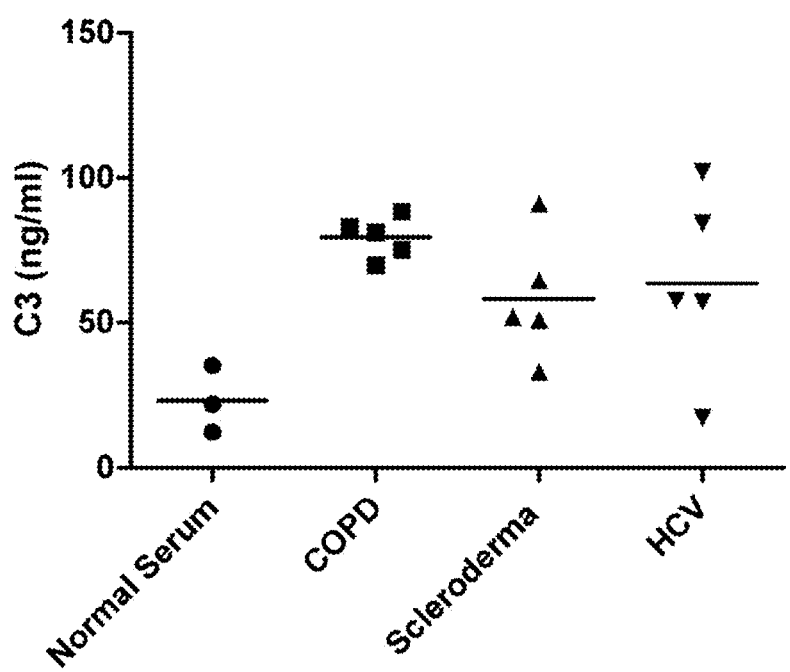
FIG. 3 shows a graph showing CO3 levels in different human serum samples. Normal serum: from healthy individuals. COPD: Chronic Obstructed Pulmonary Disease (leading to lung fibrosis). Scleroderma (leading to skin and lung fibrosis). HCV: Hepatitis virus C (leading to liver fibrosis)

CO3 levels were measured in serum from human with three different fibrotic diseases: Chronic obstructed pulmonary disease (COPD), Scleroderma, and Hepatitis virus C (HCV). The serum samples were retrieved from Sera Laboratories International Ltd (SLI Ltd), UK. CO3 levels were increased in the three different fibrotic diseases (FIG. 3).

Example 4

Antibody Development—Detection of Marker CO3-610C

Type III collagen (Abcam, Cambridge, UK) was degraded in vitro by activated MMP-9 (Merck KGaA, Darmstadt, Germany) for 2 days. Degradation fragments were sequenced by LS-MS/MS and identified by MASCOT search. A specific peptide sequence $^{610}$KNGETGPQ (SEQ ID NO: 2251) was selected for antibody production. The N-terminal of this sequence is residue 610 of human collagen type III. The synthetic peptide was conjugated to ovalbumin prior to subcutaneous immunization of 4-6 week old Balb/C mice with about 200 µL emulsified antigen and 50 µg CO3-610C (KNGETGPQGPGGC-OVA), KNGETGPQGPGGC being SEQ ID NO: 2252. Consecutive immunizations were performed at two week intervals until stable sera titer levels were reached in Freund's incomplete adjuvant. The mice were bled from the second immunization on. At each bleeding, the serum titer was measured and the mouse with highest anti-serum titer was selected for fusion. After the fourth immunization, this mouse was rested for one month and then boosted intravenously with 50 µg CO3-610C in 100 µL 0.9% sodium chloride solution three days before isolation of the spleen for cell fusion.

Monoclonal antibody producing clones were selected using a) immunogenic peptide: KNGETGPQGP-GGC-Ovalbumine (OVA) (807678), b) screening peptide KNGETGPQGP-PG-K-Biotin (807971), KNGETGPQGP-PG-K being SEQ ID NO: 2253 c) de-selection peptides KDGETGAAGPPGK-Biotin (118318) representing a type II collagen alpha 1 chain (SEQ ID NO: 2254), KDGEAGAQGP-PGK-Biotin representing a type I collagen alpha 1 chain degradation product, purchased from the Chinese Peptide Company, Beijing, China (SEQ ID NO: 2255). The ELISA coat plate was obtained from NUNC (Thermofisher, Copenhagen, Denmark). Peptide conjugation reagents and buffers were produced by Pierce (Thermofisher, Copenhagen, Denmark).

Buffer used for dissolving the coating peptide was composed of the following: 40 mM $Na_2HPO_4$, 12 $H_2O$, 7 mM $KH_2PO_4$, 137 mM NaCl, 2.7 mM KCl, 25 mM EDTA, 0.1% Tween 20, 1% BSA, 10% sorbitol, pH 7. For a serum assay, buffer containing the following chemicals was used: 8 mM $Na_2HPO_4$, 12 $H_2O$, 1.5 mM $KH_2PO_4$, 13.7 mM NaCl, 2.7 mM KCl, 0.1% Tween 20, 1% BSA, 0.003% phenol red, pH 7.4. A different buffer used for a urine assay contained 400 mM TRIZMA, 0.05% Tween 20, 0.1% BSA, 0.36% Bronidox L5, pH 8.0. For both serum and urine assays we used a washing buffer composed of 25 mM TRIZMA, 50 mM NaCl, 0.036% Bronidox L5, 0.1% Tween 20, and reaction-stopping buffer composed of 0.1% $H_2SO_4$. ELISA-plates used for the assay development were Streptavidin-coated from Roche (Hvidovre, Denmark) cat.: 11940279. All ELISA plates were analyzed with the ELISA reader from Molecular Devices, SpectraMax M, (CA. USA).

In preliminary experiments, we optimized the reagents, their concentrations and the incubation periods by performing several checkerboard analyses. A 96-well ELISA plate coated with streptavidin was further coated with 5 ng/ml of the synthetic peptide KNGETGPQGP-Biotinylated dissolved in PBS-TBE buffer at 20° C. for 30 minutes by constant shaking at 300 rpm (KNGETGPQGP being SEQ ID NO: 2256). After washing with washing buffer, 20 µL of sample was added, followed by 100 µl of peroxidase conjugated anti-human mAb-NB51-32 CO3-610C solution (23 pg/ml in incubation buffer). The plate was incubated for 1 hour at 20° C. during which time it was shaken at 300 rpm. This was followed by washing and finally, 100 µl tetramethylbenzinidine (TMB) (Kem-En-Tec cat.438OH) was dispensed and the plate incubated for 15 minutes in darkness and shaken at 300 rpm. In order to cease the reaction, 100 µl of stopping solution was added and the plate analyzed in the ELISA reader at 450 nm with 650 nm as reference.

A standard curve was performed by serial dilution of biotinylated-NB51-32 CO3-610C for a serum assay, and biotinylated-NB51-134 CO3-610C for a urine assay. Standard concentrations were 0, 0.33, 1, 3, 9, 27, 81 and 162 ng/ml. We designate fragments detected using the immunoassays so obtained as CO3-610C as the amino acid K at the N-terminal of the sequence KNGETGPQGP is amino acid 610 of the human collagen III sequence.

Example 5

Comparison of CO3-610C and Other Biomarkers in Induced Liver Fibrosis in Rats
Animals 40 female Sprague-Dawley rats aged 6 months were housed at the animal research facilities at Nordic Bioscience, Copenhagen, Denmark. The experiments were approved by the Experimental Animal Committee of the Danish Ministry of Justice and were performed according to the European Standard for Good Clinical Practice (2008/561-1450). The rats were housed in standard type 111-H cages at 18-22° C. with bedding and nest material (Altromin 1324; Altromin, Lage, Germany) and water ad libitum. Rats were kept under conditions of a 12-hour light/dark cycle.
Study Design In 20 rats, liver fibrosis was induced by common BDL. The surgical procedure was performed under sterile conditions. The rat was anaesthetized, the bile duct localized and ligated in two places followed by dissection between the ligations, and the abdomen was closed. The other 20 rats were subjected to a sham operation, in which the abdomen was closed without bile duct ligation. The rats were then divided into 2 groups: Group 1 (10 BDL rats and 10 sham-operated rats) was sacrificed after 2 weeks and Group 2 (10 BDL and 10 sham-operated rats) was sacrificed after 4 weeks. On completion of the study period (2 or 4 weeks), after at least 14 hours fasting, all surviving animals were asphyxiated by $CO_2$ and sacrificed by exsanguinations.
Blood Sampling Blood samples were taken from the retro-orbital sinus of rats after at least 14 hours fasting, under light $CO_2/O_2$ anaesthesia, at baseline and at termination. Blood was left 30 minutes at room temperature to clot, followed by centrifugation at 1500 g for 10 minutes. All clot-free liquid was transferred to fresh tubes and centrifuged again at 1500 g for 10 minutes. The serum was then transferred to clean tubes and stored at −80° C.
Tissue Handling After the rats were put down, their livers were carefully dissected, weighed, fixed in 4% formaldehyde for a minimum of 24 hours, cut into appropriate slices and embedded in paraffin. Sections 5 µm thick were cut, mounted on glass slides and stained with Sirius Red. The liver sections were evaluated histologically by assessment of the architecture, presence of inflammation, proliferation of bile ducts and fibrosis. The de novo bile duct formation in the parenchyma was evaluated semi-quantitatively using the following scoring system: normal=0, mild changes (⅓ or less of the lobule affected)=1, moderate changes (between ⅓ and ⅔ of the lobule affected)=2, and severe changes (⅔ or more of the lobule affected)=3. Digital photographs were captured using an Olympus BX60 microscope with ×40 and ×100 magnification and an Olympus 5050-zoom digital camera (Olympus, Tokyo, Japan).

Determination of Total Collagen and Serum CTX-II

The total collagen concentration was assayed using the commercial QuickZyme Collagen Assay (QuickZyme Bioscience, Leiden, The Netherlands). The concentration of CTX-II was assayed using the commercial Rat CTX-II kit (IDS Nordic, Herlev, Denmark). All samples were assayed in duplicate.

Type III Collagen mRNA Quantification

The number of transcripts of type III collagen (Col3a1) in liver tissue samples was determined by quantitative realtime polymerase chain reaction (RT-PCR) using fluorescent reporter probes. The number of Col3a1 copies in the sample was extrapolated from a standard curve obtained using Col3a1 plasmid cDNA Image Clone 7097081 (Geneservice, Cambridge, UK) as dilution standard. Amounts of Col3a1 were normalized with those of housekeeping gene hypoxanthine phosphoribosyltransferase 1 (Hprt1). Primers and probes for Col3a1 and Hprt1 mRNAs were designed using NCBI Reference Sequences NM_032085.1 and NM_012583.2 as templates, respectively (TIB Molbiol GmbH, Berlin, Gemany). Total RNA was extracted from frozen liver samples using Absolutely RNA Miniprep kit (Stratagene, La Jolla, Calif., USA) following the manufacturer's instructions and its quality assessed in RNA Nano chips using a 2100 Bioanalyzer instrument (Agilent Technologies, Santa Clara, Calif., USA). Immediately after RNA isolation, complementary DNA (cDNA) was synthesised with Transcriptor First Strand cDNA Synthesis kit (Roche, Basel, Switzerland) using 1 μg of RNA as the template. For each sample tested, a cDNA synthesis negative control, omitting reverse transcriptase enzyme from the reaction mix, was included. Separate PCR reactions for Col3a1 and Hprt1 were performed in a 20 μL format using the Lightcycler Faststart DNA Master Plus Hybprobe kit (Roche) according to the manufacturer's instructions. Real time fluorescence data was collected in a Lightcycler 2.0 instrument (Roche).

Extractions

Tissue was pulverized in excess of liquid nitrogen in a steel mortar. Samples were then transferred into a 1.5 ml eppendorf tube and left shaking overnight at 4° C. in 0.5M Acetic Acid solution containing protease inhibitor cocktail (Roche). The samples were then sonicated with ultrasounds using 5 pulses at 60% amplitude (U50 control, IKA Labortechnik) and left for an additional 2 hours at 4° C. after which they were centrifuged for 5 minutes at 13,000 rpm. Supernatant was carefully removed, transferred in a new eppendorf and stored at −80° C.

Densitometry

Densitometry measurements were performed using UN-SCAN-IT Version 6.1 from Silk Scientific (give city, country).

Histology Image Analysis

Histology sections stained with Sirius Red were analyzed using Visiopharm software Version 3.2.8.0 (give city, country). Images were acquired using Pixelink PL-A623C microscope digital camera.

SDS PAGE and Western Blots

20 μg of tissue extract was mixed with loading buffer (Invitrogen LDS 4x, NP0007) containing the reducing agent (NuPAGE, NP0004 from Invitrogen). Samples were then loaded into 4-12% Bis-Tris gradient gel (NP0332BOX from Invitrogen) and run for 52 minutes at 200V. Proteins were then transferred onto a nitrocellulose membrane using the i-Blot transfer system (Invitrogen), blocked with 5% milk in TTBS overnight at 4 degrees. Beta Actin antibody (AbCam ab8229, give company, city country?) was used as a loading control.

Statistical Analysis

Mean values and standard error of the mean (SEM) were calculated using GraphPad Prism (GraphPad Software, Inc., San Diego, Calif., USA) and compared by Student's two-tailed paired t-test ($\alpha$=0.05) of statistical significance assuming normal distribution, or by Mann-Whitney two-tailed non-parametric test ($\alpha$=0.05). The coefficient of correlation ($R^2$) and the corresponding p-value was determined by linear regression.

Results

Figure 4A:
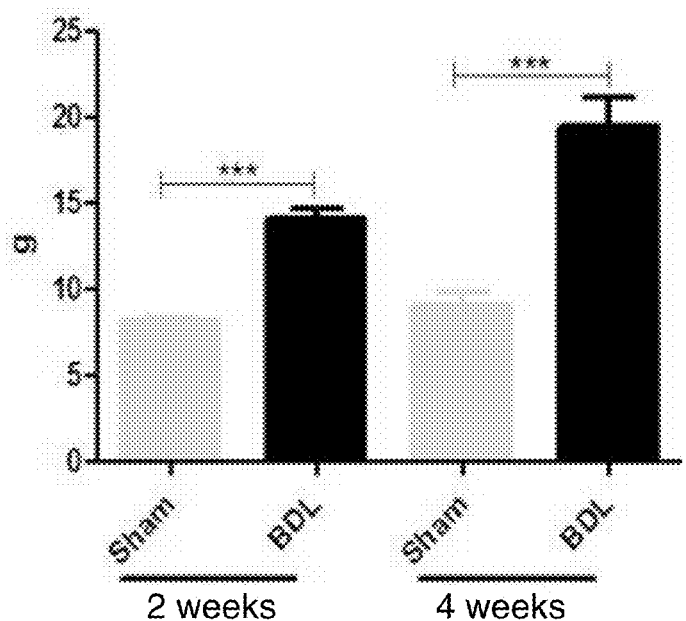
FIGS. 4A-4C show liver weights (FIG. 4A) and liver scores (FIG. 4B) and Sirius Red photomicrographs showing the hepatic structure in sham-operated rats, and in BDL rats 2 and 4 weeks post-surgery determined in Example 5.
Figure 4B:
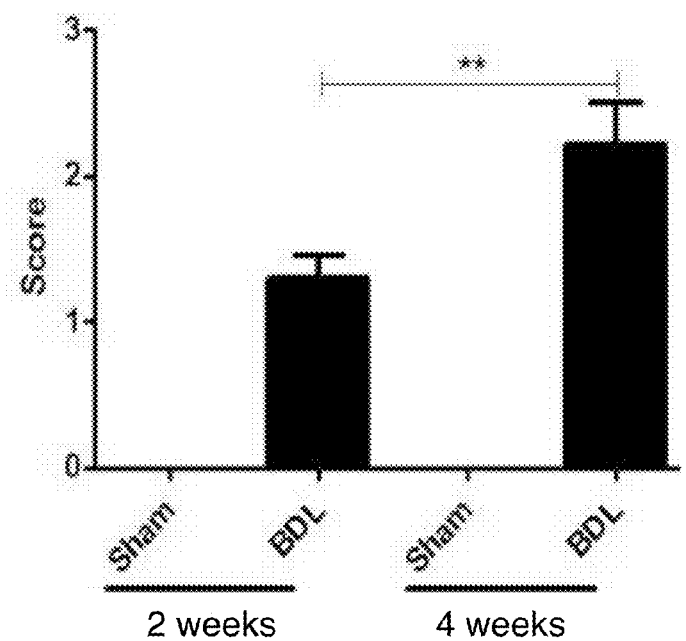

Liver Appearance:

At the time of sacrifice, livers of control animals showed normal gross morphology while livers of BDL animals were enlarged. The liver weights were significantly increased in BDL rats compared to the sham-operated controls (mean weights at sacrifice: 2 weeks post-surgery, sham 8.1 g; BDL 14.1 g; 4 weeks post-surgery, sham 9.0 g; BDL 19.4 g) (FIG. 4A). Semi-quantitative scoring of liver sections using the 0-3 scale showed significantly more structural changes of the liver at 4 weeks compared with 2 weeks (FIG. 4B). FIG. 4A shows liver weight in bile duct ligation (BDL)- or sham-operated rats. Data are shown as mean+SEM.[*, P<0.0001. FIG. 4B shows scoring of the structural changes in the liver of each group. Data are shown as mean+SEM. , P=0.0094. Panel C shows Sirius Red photomicrographs showing the hepatic structure in sham-operated rats, and in BDL rats 2 and 4 weeks post-surgery. The hepatic structure around the portal tract is clearly disrupted in BDL rats compared with the sham-operated rats. Collagens are highlighted in red. Original magnification was ×40.

Figure 4C:
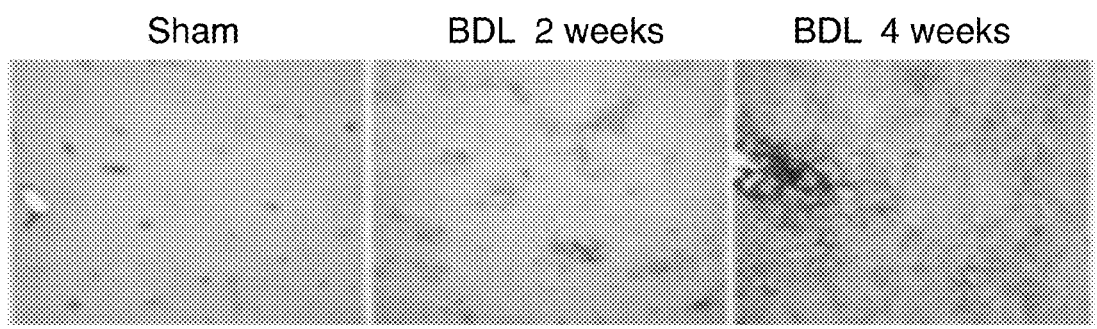

Under histological examination, the livers of sham-operated animals showed no sign of fibrosis and were microscopically normal (FIG. 4C). In the BDL livers, a marked ductal proliferation was observed. In the 2-week post-surgery group, the proliferation was located around the portal tract while in the 4-week group the proliferation had spread (FIG. 4C). Collagen deposition was found around the ductular structures. Inflammation was minimal and confined to the portal tracts. No signs of cholestasis were seen, whether intracellular cholestasis, bile plugs, bile infarctions or hepatocytic rosette formation.

Changes in CO3-610C Levels:

FIG. 5 shows in panel A MMP-9 mediated CO3 degradation serum levels in bile duct ligated (BDL)- or sham-operated rats. Data are shown as mean+standard error of mean. 2 weeks post-surgery * P<0.0001 and 4 weeks post-surgery  P=0.0014. In panel B are shown CO3-610C delta values (termination-baseline paired), 2 weeks post-surgery P<0.0001 and 4 weeks post-surgery P=0.0016. In panel C are shown CTX-II levels in BDL- or sham-operated rats. Data are shown as mean+standard error of mean.

Figure 5A:
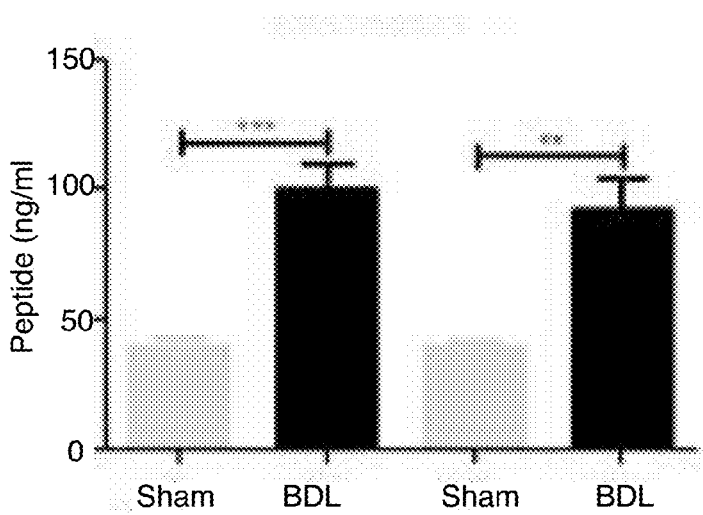
FIGS. 5A-5C show levels of MMP-9 cleavage fragments of Type III collagen measured according to the invention in Example 5.
Figure 5B:
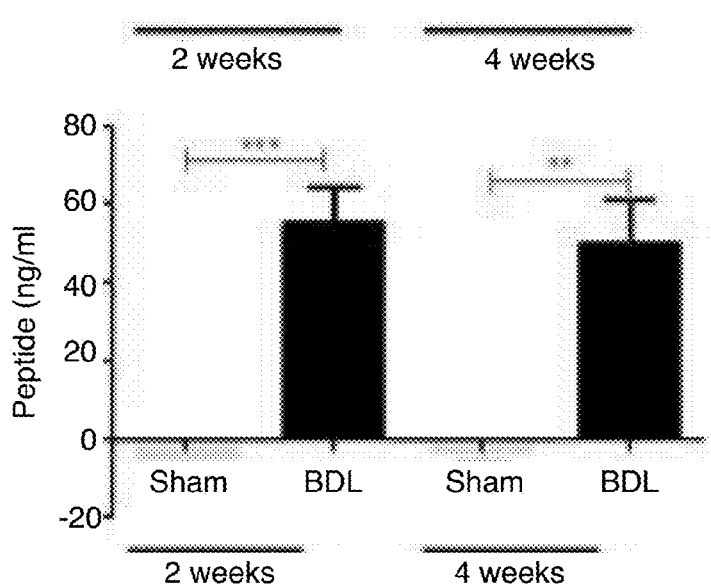
Figure 5C:
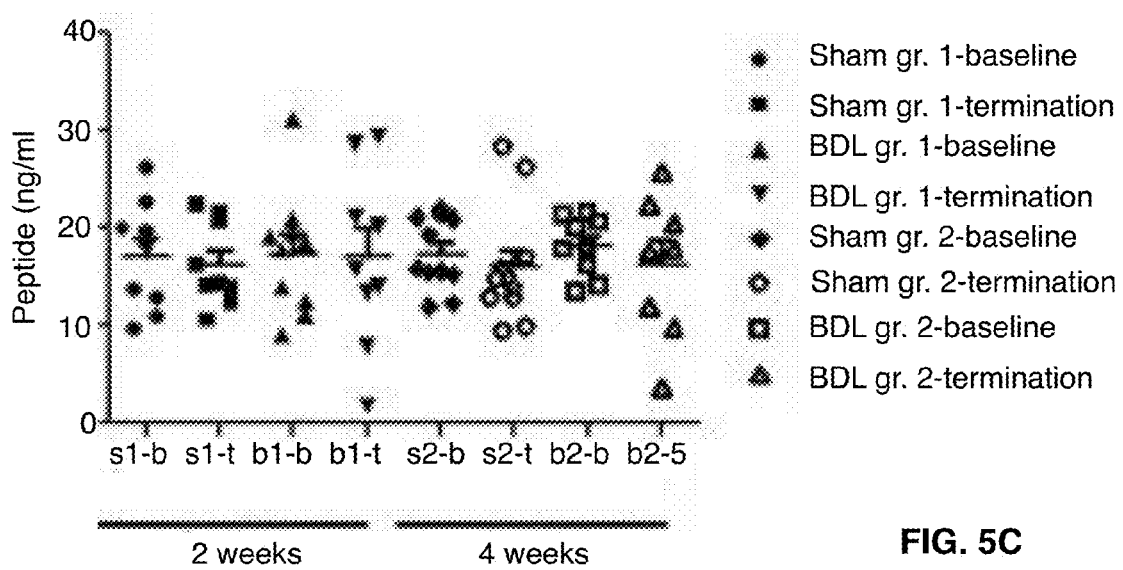

In the BDL groups CO3-610C levels increased significantly compared to sham groups (mean values: 2 weeks, post-surgery sham 39.7 ng/ml, BDL 100.3 ng/ml; average increase between the groups was 153%; 4 weeks post-surgery, sham 39.7, BDL 92.6 ng/ml, average increase between the groups was 133%) (FIGS. 5A-5B). There were no changes in the sham groups. CTX-II levels indicating collagen type II degradation did not change in the sham or BDL groups (FIG. 5C).

Figure 6:
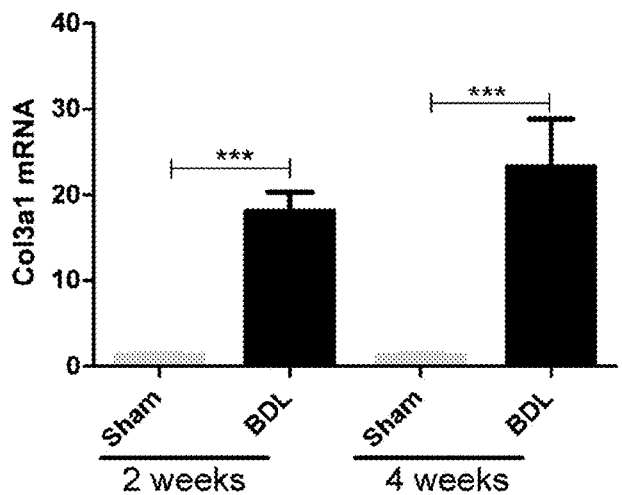
FIG. 6 shows levels of Type III collagen gene expression in BDL or sham-operated rats determined in Example 5.

Type III Collagen Gene Expression:

FIG. 6 shows Type III collagen gene expression in BDL or sham-operated rats. Data are shown as mean+standard of mean; 2 weeks post-surgery P<0.0001 and 4 weeks post-surgery P=0.0006

Type III collagen a1 chain mRNA increased significantly in both BDL groups compared with sham-operated rats.

Western Blot and Densitometry: FIG. 7 shows changes in the expression of CO3-610C in the liver of rats in BDL- and sham-operated groups assessed by A) Western blot 2 and 4 weeks post-surgery and B) Bands from western blot quantified by densitometry.

Figure 7A:
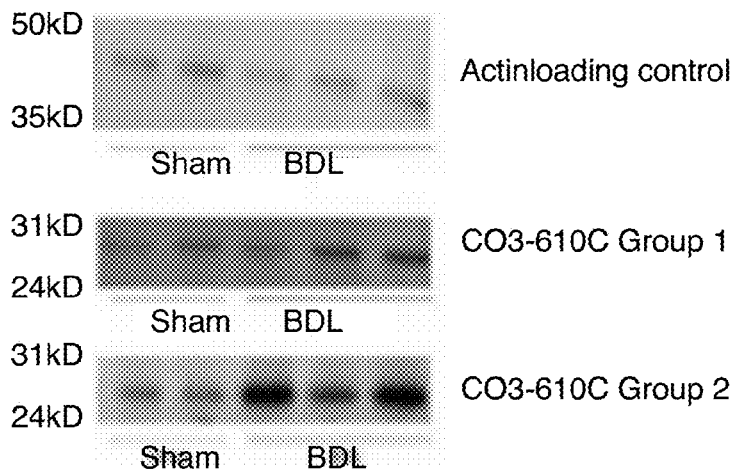
FIGS. 7A-7B show changes of expression levels of the MMP-9 cleavage fragment of Type III collagen reactive with the antibody used in Example 5 as determined by Western blot.
Figure 7B:
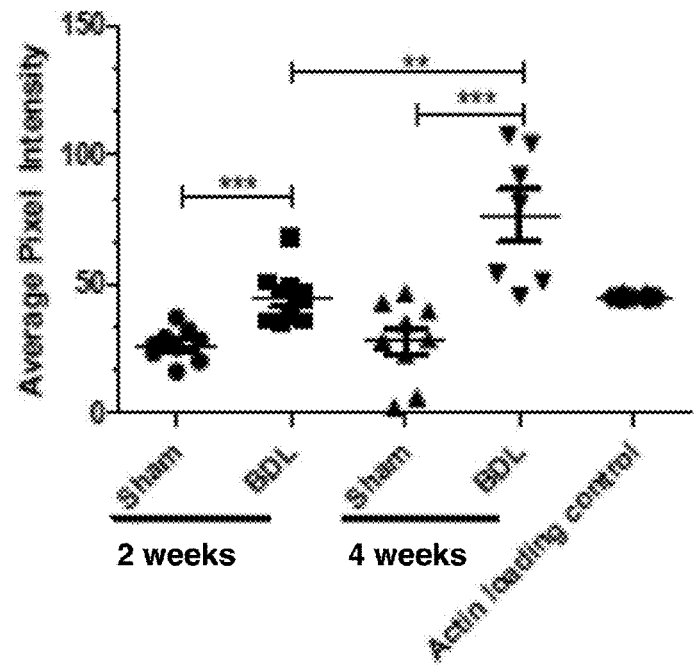

Western blot analysis showed very low levels of CO3-610C in sham-operated rats (FIG. 7A). At and after 2 weeks post-surgery CO3-610C levels prominently increased (FIG. 7A). Results were quantified by densitometry analysis (FIG. 7B).

Figure 8A:
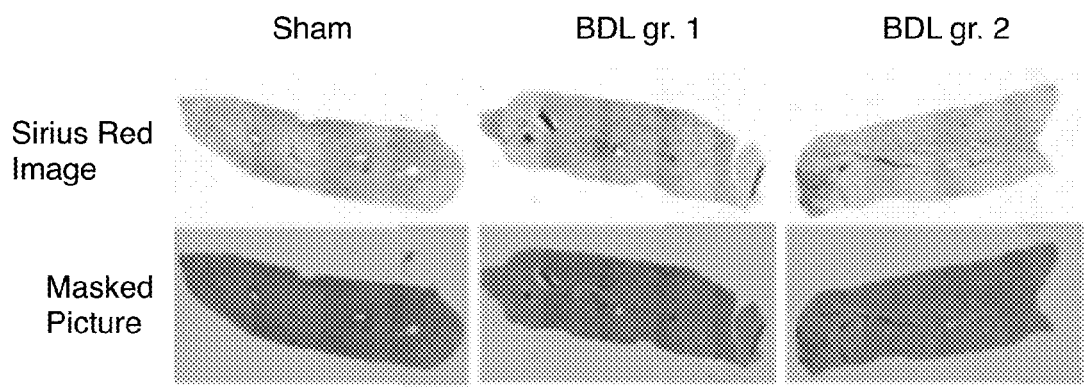
FIGS. 8A-8B show the results of histology staining of liver sections obtained in Example 5.
Figure 8B:
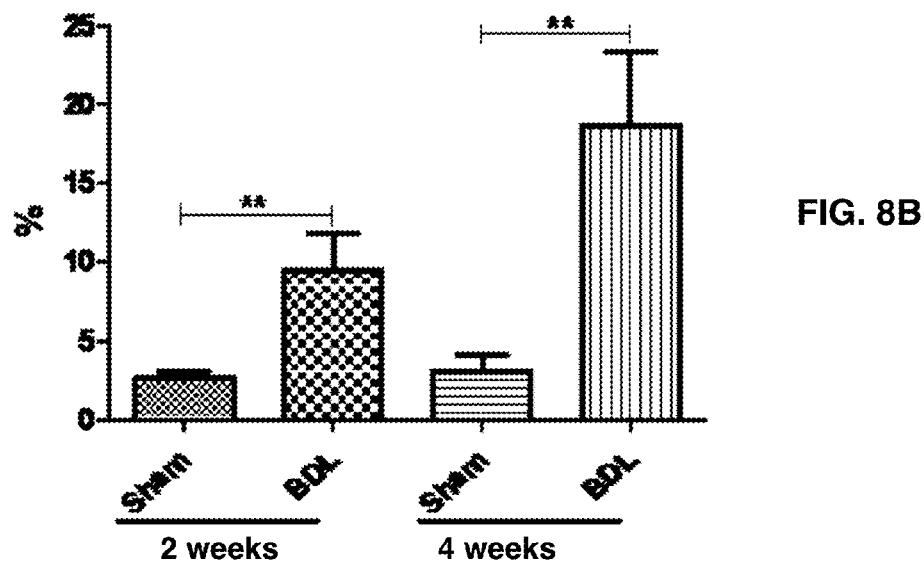

Histology Image Analysis:

FIG. 8A shows in the top row histology sections from BDL- or sham-operated rats stained with Sirius Red. The bottom row shows masked histology sections for quantifying total collagen content (red colour) in the liver. FIG. 8B shows total collagen quantified by Visiopharm software—2 weeks post-surgery P=0.0081; 4 weeks post-surgery P=0.0047. Histology sections stained with Sirius Red and enhanced using Visiopharm software showed increasing collagen content over time in BDL-operated rats. (FIG. 8A). The red color in the mask representing collagen was quantified using the same software (FIG. 8B) and confirmed a significant increase in total collagen content in BDL-operated rats compared with sham-operated rats (2 weeks post-surgery P=0.0081; 4 weeks post-surgery P=0.0047).

Figure 9A:
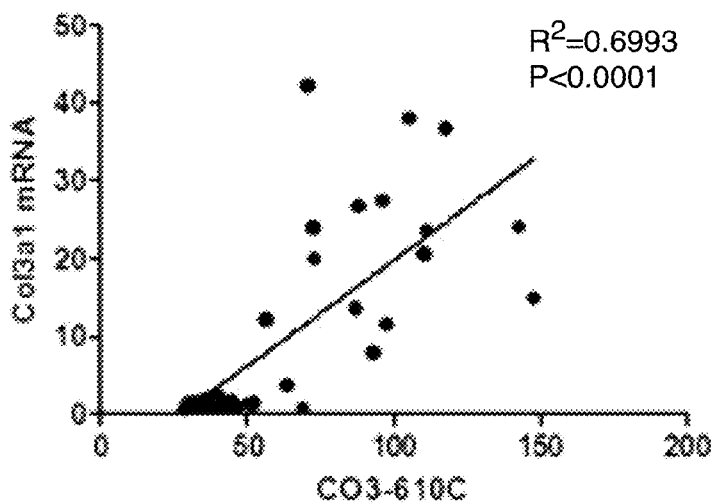
FIGS. 9A-9C shows correlations between measurements of fragments of Type III collagen according to the invention with other liver biomarkers as determined in Example 5.
Figure 9B:
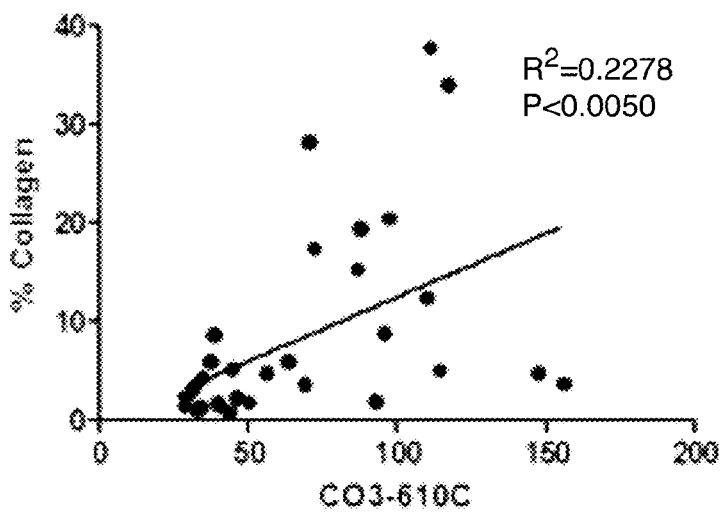
Figure 9C:
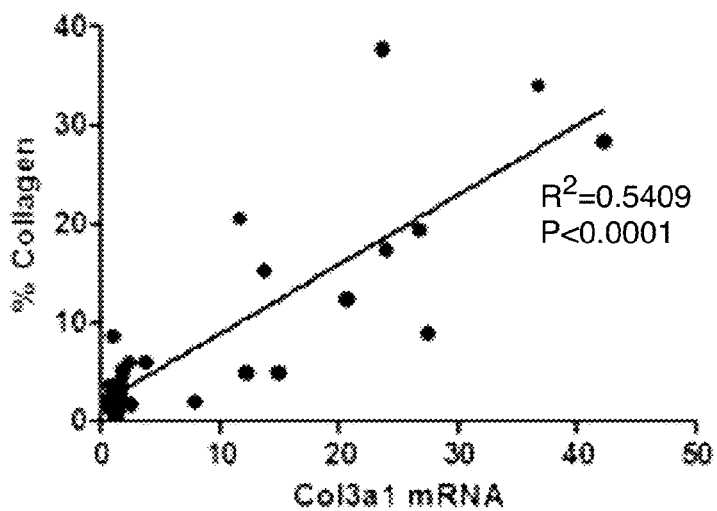

Correlation: FIG. 9A shows a correlation of Col3a1 to CO3-610C was found with $R^2=0.6993$, $P<0.0001$. In FIG. 9B, a correlation of CO3-610C to % collagen was found with $R^2=0.2278$ and $P=0.0050$. In panel C a correlation of Col3a1 to % collagen was found with $R^2=0.5409$, $P<0.0001$. Correlations were found of the following: Col3a1 mRNA to CO3-610C with $R^2=0.6993$ and $P<0.0001$ (FIG. 9A), and CO3-610C to % collagen quantified by visiopharm with $R^2=0.2278$ and $P=0.0050$ (FIG. 9B), and Col3a1 mRNA to % collagen quantified by visiopharm with $R^2=0.5409$ and $P<0.0001$ (FIG. 9C).

ECM remodelling is an integrated process of tissue development, maintenance and pathogenesis. Proteolytic activity is essential in this process for cell migration, removal of damaged tissue, and sequestering of new proteins, for the correct and optimal tissue orientation and quality (108:109). The specific matrix degradation products, neo-epitopes, may be important for the identification of new biochemical markers of liver fibrosis matrix turnover and understanding fibrosis pathogenesis. At present there are no available measuring techniques, nor biochemical markers, that allow for assessment of ECM remodeling in the pathogenesis of fibrosis.

In this example, to investigate the CO3-610C marker under in vivo situations, 6 months BDL rats were chosen, as they previously have been shown to have a lower collagen remodelling compared to younger rats. The rats are skeletally mature, and the growth plate is almost dormant, thereby contributing to a much lower extent to the overall collagen turnover. This influences the sensitivity and specificity for biomarker. These rats clearly presented with hepatic fibrosis, as evaluated by both quantitative histological analysis, and enlargement with increased weight, thus the model was an appropriate one to look for evidence of ECM remodeling, in particular for evidence of collagen type III in serum.

The present data clearly demonstrate the neo-epitope CO3-610C from MMP-9 mediated collagen type III degradation is a diagnostic biochemical marker for liver fibrosis with an average increases in serum of up to 153% from sham to BDL-operated rats.

To further investigate the biological rationale for the increased CO3-610C marker, we did protein extractions from healthy and diseased livers. By western blotting, we identified a predominant band, suggesting this to be an abundant protein fragment in diseased but not healthy livers. This provides evidence for the pathological accuracy of this novel marker.

To further investigate the pathological turnover representation of the liver, we measured type III collagen mRNA. We found an increase of mRNA in the BDL rats compared to those undergoing the sham operation, which correlates with previous findings. These data strongly suggest that liver fibrosis is not only an accumulation of ECM proteins, but also an accelerated turnover situation, in which both tissue formation and tissue degradation both are highly up regulated. Tissue formation outstrips tissue degradation, leading to an accumulation of scar tissue over time. Previous investigators have used other matrix turnover proteins to assess liver fibrosis, one being the type III collagen formation marker N-terminal type III pro-collagen. This marker represents collagen type III formation and has shown to be increased in liver fibrosis in previous studies.

To further understand and the dynamics of the biochemical makers CO3-610C, we did a range of correlations. Most importantly, there was a significant correlation of CO3-610C to the extent of fibrosis measured in the liver by quantitative histology. The level of liver fibrosis was correlated to the expression levels of the mRNA of collagen type III. Finally, the CO3-610C correlated to mRNA of collagen type III in the liver. Taken together, there was a significant correlation of the pathological processes in the liver with the levels of the systemic biochemical markers CO3-610C. In addition the tissue extractions provided evidence that the circulation levels were locally produced.

Example 6

ELISA on Human Serum Samples

Figure 10:
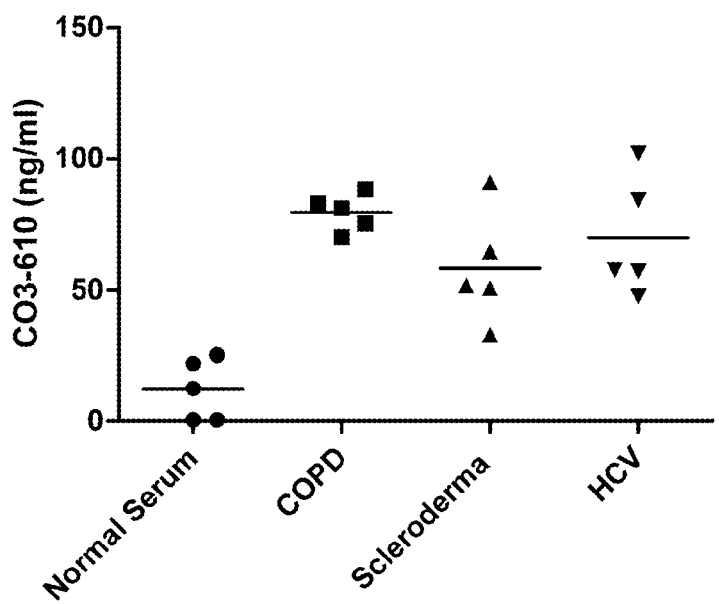
FIG. 10 shows results obtained on human serum samples in Example 6.
Figure 11:
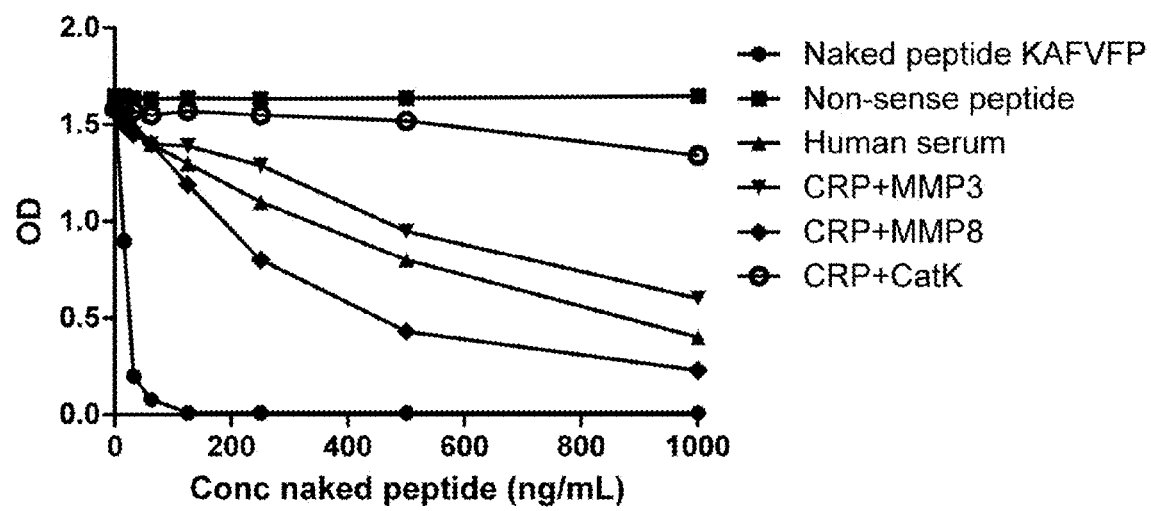
FIG. 11 shows results obtained in testing the reactivity of a monoclonal antibody recognising an N-terminal neo-epitope from CRP.

Human serum samples were obtained from patients with Chronic Obstructive Pulmonary Disease (COPD) (n=5), scleroderma (n=5), chronic hepatitis C virus infection (n=5), and healthy controls (n=5). The serum samples were tested in the CO3-610 ELISA (see Example 4 above) to determine the concentration of CO3-610 fragments. Results are shown in FIG. 10. While serum samples from the healthy subjects had concentration of CO3-610 fragments below 30 ng/ml, the diseased subjects were found to have elevated levels in circulation suggesting massive tissue remodelling in the affected fibrotic tissues.

Example 7

Reactivity of Clone nb94

Mice were immunized with synthetic peptide KAFVFP (SEQ ID NO: 1167) conjugated to ovalbumin (KAFVFP-KESD-GGC-OVA (SEQ ID NO1049)), spleen cells were used for fusion, and monoclonal antibodies tested for reactivity to biotinylated KAFVFP (SEQ ID NO: 1167), i.e. (KAFVFPKESD-biotin (SEQ ID NO: 1049)) immobilized in wells of microtitre plates precoated with streptavidin. Antibodies binding to biotinylated KAFVFPKESD(SEQ ID NO: 1049), which could be inhibited by co-incubation with KAFVFPKESD (SEQ ID NO1049) but not the elongated peptide RKAFVFPKESD (SEQ ID NO: 1166), were selected for further characterization. The preferred monoclonal antibody was designated NB94-37-1A7.

Using a competition ELISA, essentially as described above with biotinylated KAFVFPKESD (SEQ ID NO: 1049) (used at 0.15 ng/ml) immobilized in the wells of streptavidin-coated microtitre plates, an incubation step (90 minutes at 20° C.) with sample and monoclonal antibody NB94-37-1A7 followed by a washing step, and then addition of peroxidase-conjugated anti-mouse immunoglobulins. For competition the following material was used in 2-fold dilutions; (1) the synthetic KAFVFP (SEQ ID NO: 1167) peptide; (2) a nonsense peptide (KNEGTG) unrelated to CRP; (3) a pool of human serum samples; (4) CRP proteolytically cleaved with MMP3 for 7 days, subsequently stopped by addition of EDTA to block protease activity, and stored at −80° C. until testing; (5) same as (4) but using MMP8 instead of MMP3; (6) same as (4) except using Cathepsin K (for 2 days) instead of MMP3 (and E64 as inhibitor to block Cathepsin K activity).

The data demonstrate that monoclonal antibody NB94-37-1A7 binds strongly to the synthetic peptide KAFVFP-KESD (SEQ ID NO1049), and with CPR cleaved with MMP3 and MMP8. Cleavage of CRP with Cathepsin K release less analyte recognized by monoclonal antibody NB94-37-1A7. Finally, the data shows that the antibody binds to peptide fragments in human serum confirming the presence of this sequence in circulating peptide fragments.

Example 8

CO3 in Biological Relevant Samples: CO3 Levels in Carbon Tetrachloride (CCl4)-Induced Cirrhosis in Rats Animals and Induction of Cirrhosis:

This study included 52 male Wistar rats with fibrosis or cirrhosis and 35 male Wistar control rats. To cause them to develop fibrosis or cirrhosis three-month old animals were included in an induction program with carbon tetrachloride (CCl4) and Phenobarbital treatment. $CCl_4$ was administered by inhalation twice weekly and phenobarbital (0.3 g/l) added to the drinking water. Animals were allowed free access to water and food throughout the study.

Fibrosis Quantification:

Liver sections (4 μm) were stained in 0.1% Sirius red F3B (Sigma-Aldrich, St. Louis, Mo.) in saturated picric acid (Sigma-Aldrich). Relative fibrosis area (expressed as a percentage of total liver area) was assessed by analyzing 36 fields of Sirius red-stained liver sections per animal. Each field was acquired at 10× magnification [E600 microscope (Nikon) and RT-Slider SPOT digital camera (Diagnostic Instruments, Inc., Sterling Heights, Mich.). Results were analyzed using a computerized Bioquant Life Science morphometry system. To evaluate the relative fibrosis area, the measured collagen area was divided by the net field area and then multiplied by 100. Subtraction of vascular luminal area from the total field area yielded the final calculation of the net fibrosis area. From each animal analyzed, the amount of fibrosis as percentage was measured and the average value presented.

Classification of Groups According to their Fibrosis/Cirrhosis Stage:

Animals were classified into 4 different stages of fibrosis and cirrhosis (Group A: moderate fibrosis, group B: advanced fibrosis, Group C: moderate cirrhosis, and Group D: advanced cirrhosis) that were determined by the percentage of Sirius red positive liver area (Group A: <5%, Group B: 5 to 10%, Group C: 10 to 15% and Group D: >15%). For this purpose, control and fibrotic/cirrhotic rats were studied considering four different time points during the CCl4 treatment: 8, 12, 16 and 20 weeks after starting the cirrhosis induction program.

Hyaluronic Acid Measurement:

Serum hyaluronan was measured using a sandwich ELISA kit (R&D Systems Inc., Minneapolis, Minn., USA).

Statistics:

Statistical analysis of results was performed by unpaired Student's t tests when appropriate. Data were expressed as mean±S.E.M. and they were considered significant at a p level of 0.05 or less.

Study design: Animals included in this protocol were randomly assigned to one of the following groups: A/eight weeks of $CCl_4$ treatment, B/twelve weeks of $CCl_4$ treatment, C/sixteen weeks of $CCl_4$ treatment and D/twenty weeks of $CCl_4$ treatment. In parallel, four control groups were studied at the same time points. Thirteen fibrotic rats and seven control rats were included in each group. At the end of the study, rats were placed in standard metabolic cages (Tecniplast Deutschland, Hohenpeissenberg, Germany) during an adaptation period of 3 days before proceeding with the twenty-four-hour urine collection. Urinary volumes were determined gravimetrically. During the adaptation period, rats were allowed to get free access to tap water and food. Then, 24-hour urine samples were centrifuged for 5 min at 2,500 rpm and aliquoted into ten polypropylene tubes (400 μL each). Urine samples were stored at −80° C. for subsequent analysis.

At scheduled necropsies, rats were weighed, anesthetized with pentobarbital (50 mg/kl) and decapitated. Blood were collected and allowed to stand at room temperature for 20 min to allow clotting and then centrifuged for 10 min at 2500 rpm. Serum were collected in polypropylene tubes aliquots (400 μl each) and transferred via dry ice to a −80° C. freezer. Collection of baseline blood samples at the beginning of the $CCl_4$ treatment was not considered in order to avoid additional intervention that may increase the risk of infection and/or introduce modifications in the experimental model that may compromise the evolution of the induced pathophysiological process. For histology and Sirius red staining, half of the left lobe of the liver was placed in 10% neutral buffered formalin for 16 hours, embedded in paraffin and sectioned into 4-μm-thick slices. After liver fibrosis quantification, the unused paraffin block material was preserved for biomarker quantification. The other half of the left lobe was flash-frozen in liquid nitrogen and stored for Western blot, RT-PCR or immunohistochemical analysis. Measurements of liver fibrotic area, serum and urine osmolality, $Na^+$ and $K^+$, albumin, creatinine, alanine amino-transferase and lactate dehydrogenase were made according to the Material and Methods section.

Results:

Histological Validation of the Model:

Liver collagen was quantified in all study animals by Sirius red staining of liver slices. The final data for each animal was taken as the average of red staining observed in 36 consecutive microscope fields (FIG. 12).

Figure 12:
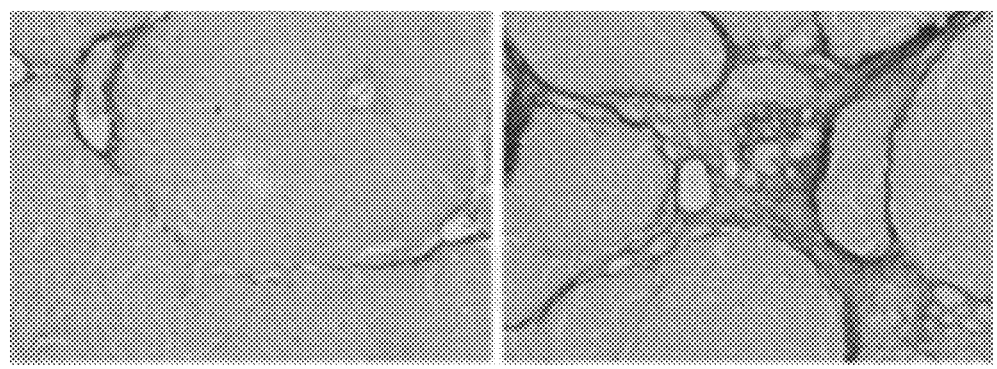
FIG. 12 shows collagen accumulation in rat liver measured in Example 8.

FIG. 12 shows representative pictures from two sets of 36 images used to quantify collagen accumulation in liver in rat #1 (left) and rat #43 (right) treated with carbon tetrachloride for eight and twenty weeks respectively.

The serum CO3 marker shows statistically significant increases in both fibrotic and cirrhotic rats compared to control rats. Animals were classified according to a fully automated syrius red staining of the liver procedure used to quantify fibrosis (FIGS. 13-14).

Figure 13:
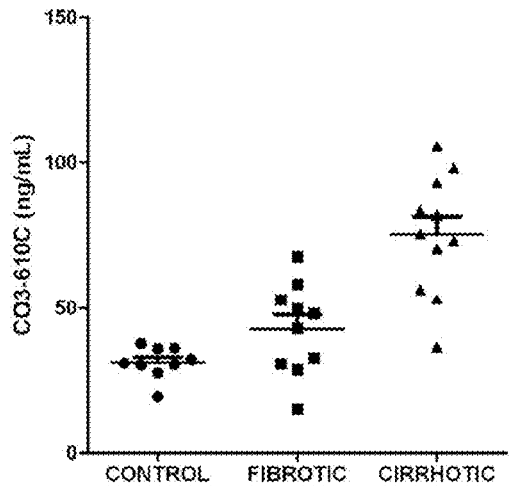
FIG. 13 shows immunoassay results obtained in Example 8.

FIG. 13 shows serum CO3 levels in CCl$_4$ inhalation and control rats as performed in Hospital Clinic (Barcelona). Each point represents one animal. Rats were classified according a computerized image analysis method of syrius red staining of the liver used to quantify fibrosis.

Figure 14:
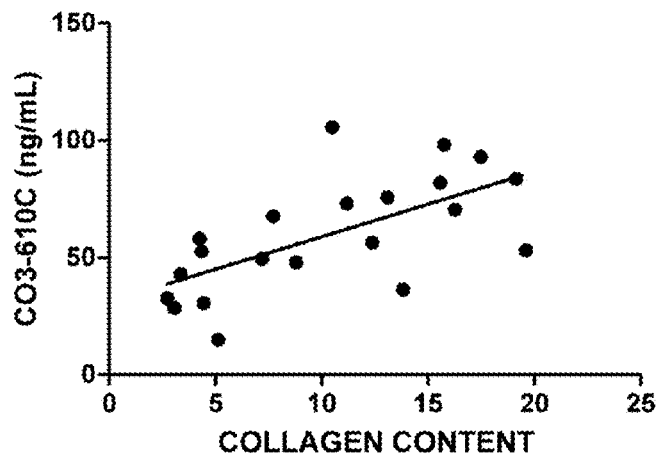
FIG. 14 shows the correlation of the immunoassay results of FIG. 13 with liver collagen content.

When quantitative values of serum CO3 and syrius red staining of the liver were studied in each individual animal, we found a statistically significant correlation between the two variables (R2=0.4087; n=21) (FIG. 14).

Figure 15:
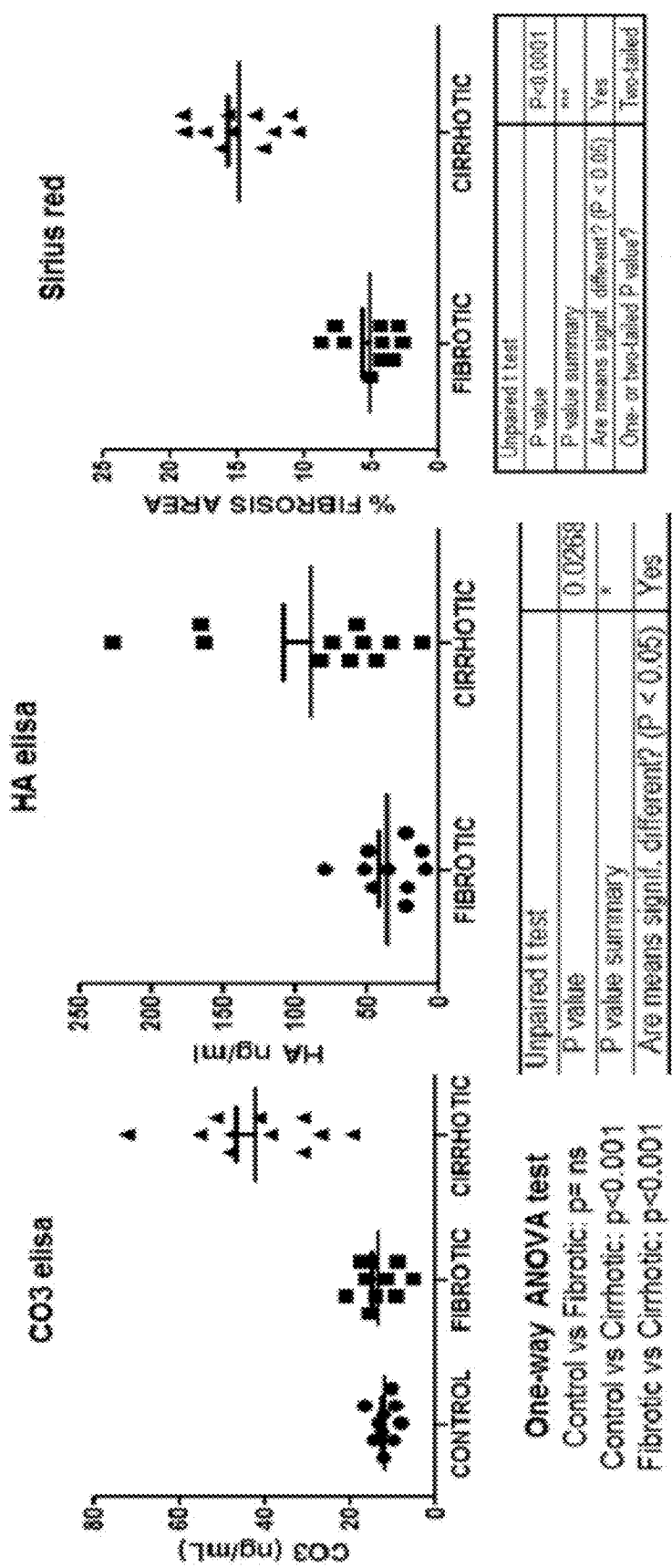
FIG. 15 shows a comparison of the results of an immunoassay according to the invention with measurements of hyaluronic acid and of Sirius red staining in Example 8.
Figure 16A:
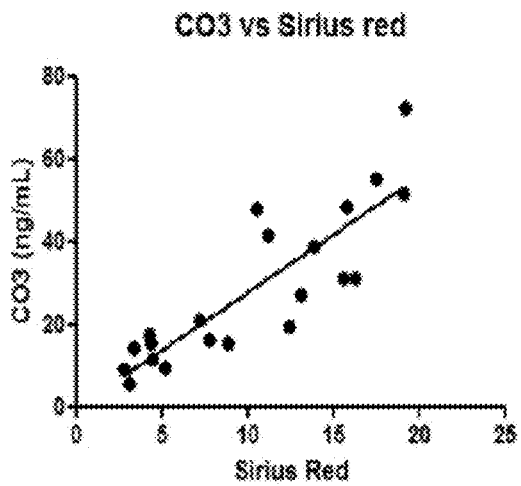
FIGS. 16A-16B show the correlation of results from the immunoassay according to the invention with Sirius red staining (FIG. 16A) and the correlation between hyaluronic acid levels and Sirius red staining (FIG. 16B).
Figure 16B:
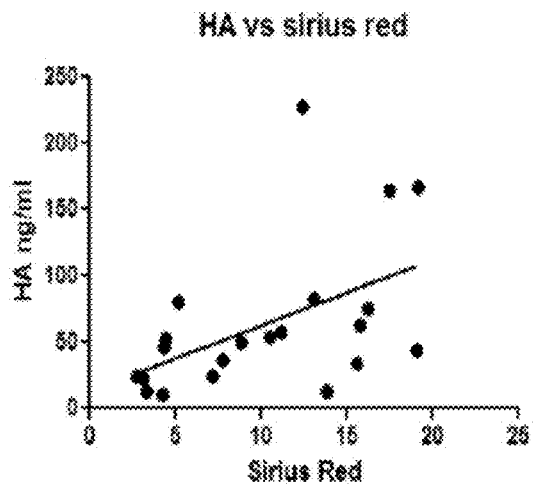
Figure 17:
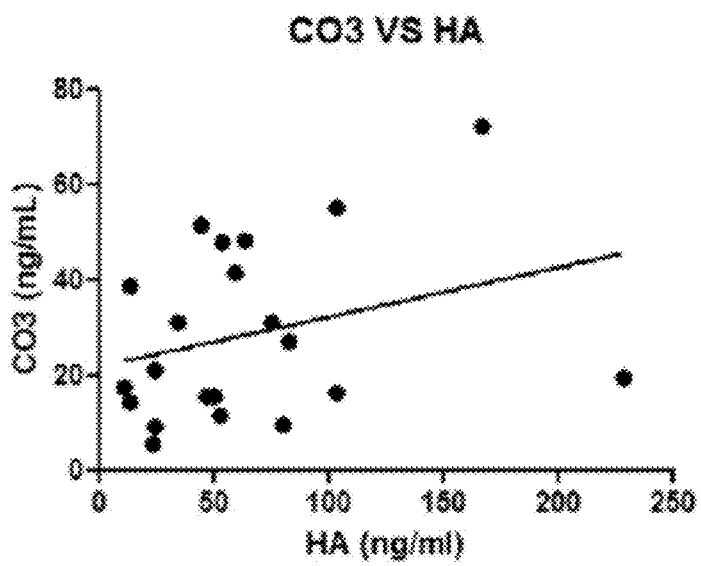
FIG. 17 shows the lack of correlation between the results of the immunoassay of the invention and hyaluronic acid levels.

We have compared the levels of CO3-610C with the serological benchmark of liver fibrosis hyaluronic acid (HA). HA levels were quantified with a commercial ELISA kit and results show significant elevations of this ECM component in cirrhotic rats vs. fibrotic animals (FIGS. 15, 16A-16B). The correlation of CO3 to Sirius red outperformed that of HA. More than seventy percent of the variation in liver fibrosis histological quantification can be explained by the serological measurement of CO3. The remaining thirty percent is due to unknown variables or inherent variability. Instead only 25% of liver fibrosis can be explained by measuring hyaluronic acid (FIG. 15). As expected from the previous result no correlation could be found between CO3 and hyaluronic acid suggesting that they are the result of two independent pathophysiological processes in the development of liver fibrosis (FIG. 17).

Example 9

Bleomycin Induced Skin Fibrosis in Mice

Mice were treated by application to the skin of PBS or bleomycin. Increasing levels in urine of the MMP-9 mediated collagen III (CO3) degradation fragment CO3-610 were associated with skin fibrosis progression in mice.

Figure 18A:
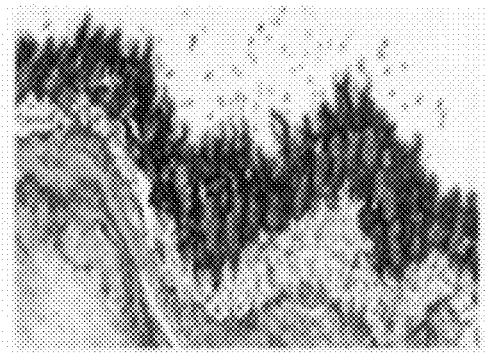
FIGS. 18A-18D show skin sections and skin thickness measurements described in Example 9.
Figure 18B:
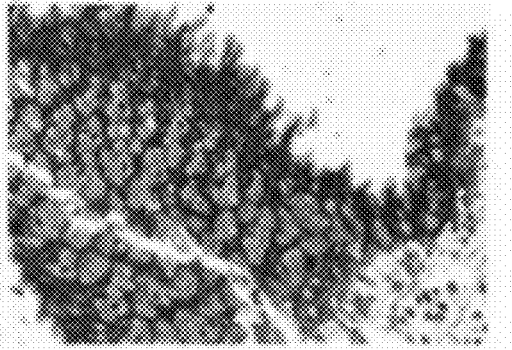
Figure 18C:
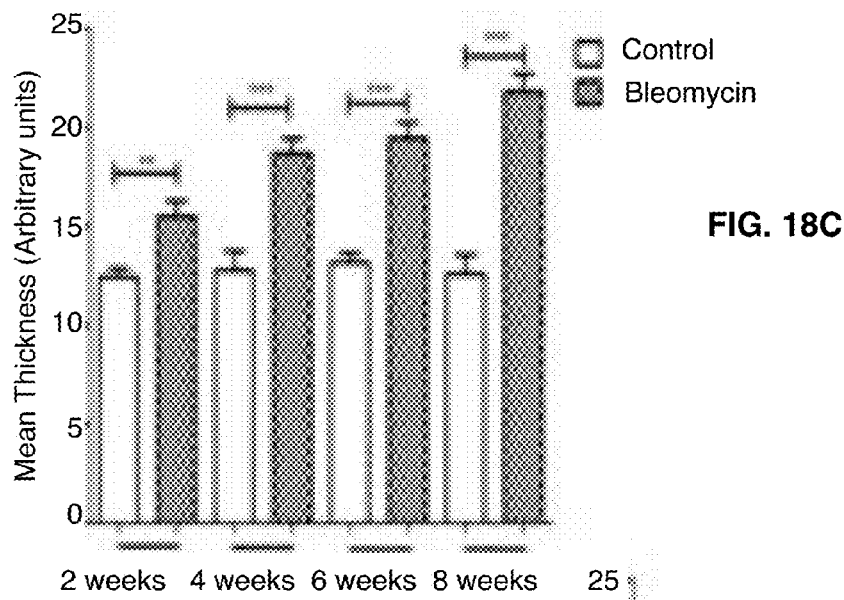
Figure 18D:
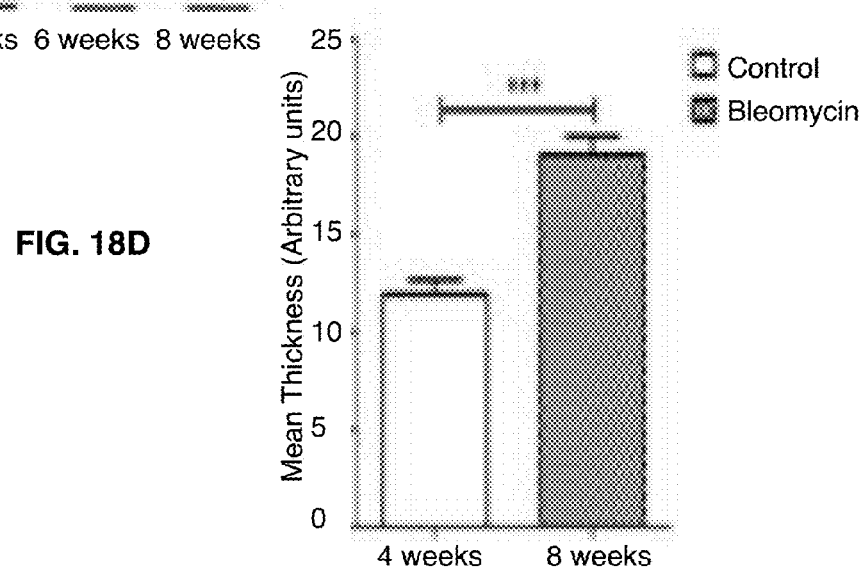

FIGS. 18A-18B shows a skin section from a PBS treated mouse at 8 weeks of treatment (FIG. 18A) and a skin section from Bleomycin treated mouse at 8 weeks of treatment (FIG. 18B). Skin thickness increase between PBS (n=7/time point) and Bleomycin (n=13/time point) treated mice for 2 weeks (P=0.0029), 4 weeks (P=0.0004), 6 weeks (P<0.0001) and 8 weeks (P<0.0001) is plotted in FIGS. 18C-18D. Overall skin thickness increase between PBS (n=28) and Bleomycin (n=52) treated mice for the duration of the study (P<0.0001). Skin width was calculated by Visiopharm software as an overall number per skin section instead of sampling pictures.

Figure 19:
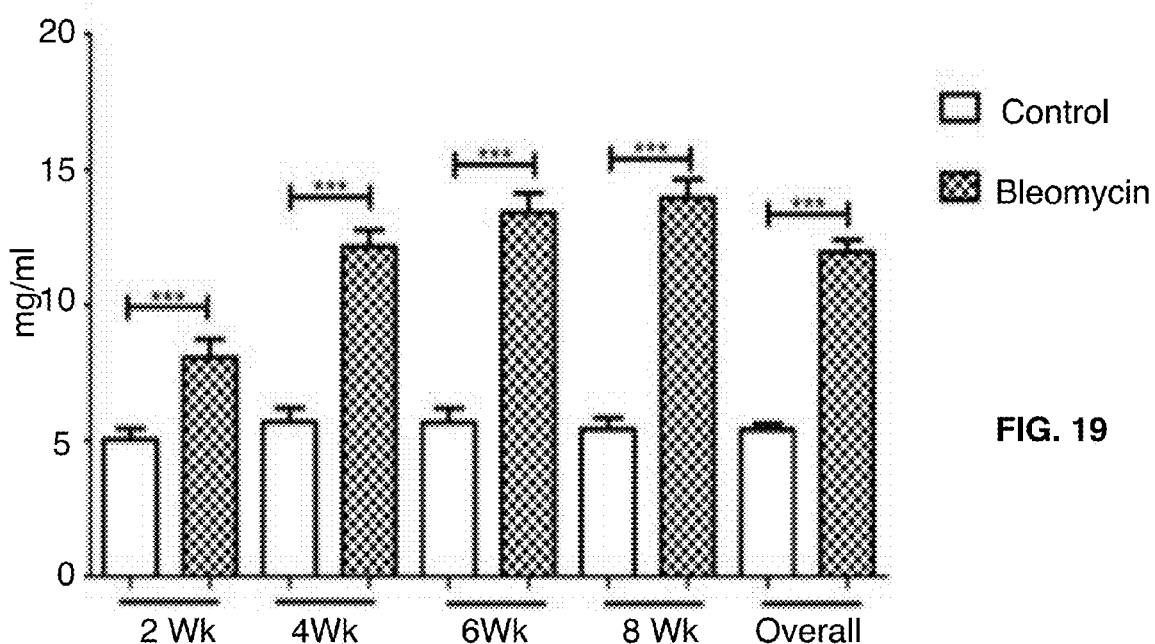
FIG. 19 shows results from an immunoassay according to the invention in Example 9.

FIG. 19 shows CO3-610 urine assay results which demonstrate a significant increase throughout the time points of the study. The figure shows result per time point (n=7 PBS, n=13 Bleomycin treated per termination point) and collective CO3-610 levels for all time points (n=28 PBS and n=52 Bleomycin treated mice). 2 weeks P=0.0008, 4 weeks P<0.0001, 6 weeks P<0.0001, 8 weeks P<0.0001 and overall P<0.0001.

Figure 20A:
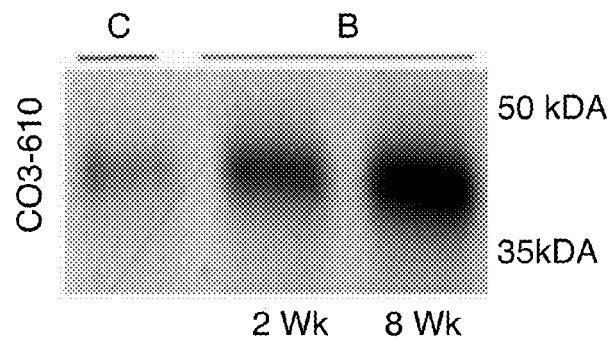
FIGS. 20A-20B shows Western Blot images obtained in Example 9 (FIG. 20A) and the corresponding immunoassay results (FIG. 20B).
Figure 20B:
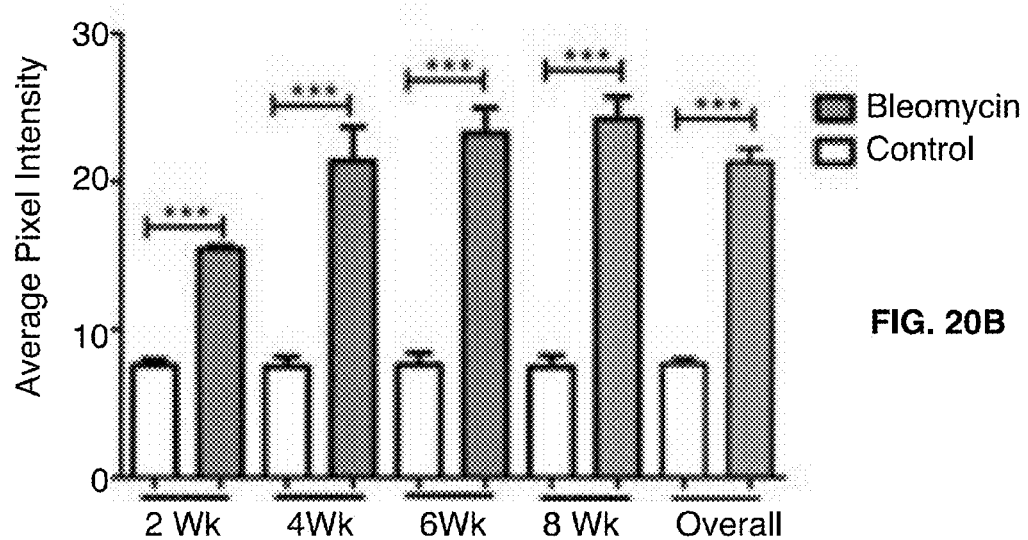

FIGS. 20A-20B shows a CO3-610 Western blots image with control C and Bleomycin B after 2 and 8 weeks treatment (FIG. 20A). CO3-610 densitometry measurements for all time points (n=7 PBS and n=13 Bleomycin treated per termination point) and collective CO3-610 levels (n=28 PBS and n=52 Bleomycin treated mice) are shown in FIG. 20B, demonstrating a statistically significant increase of CO3-610 levels (P<0.0001).

Figure 21:
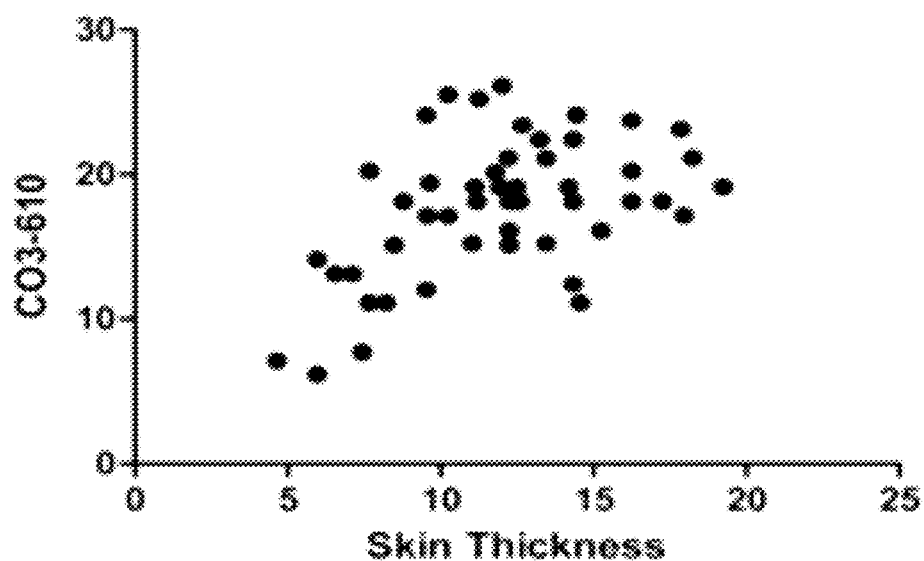
FIG. 21 shows a correlation between immunoassay results and skin thickness measurements.

As seen in FIG. 21, CO3-610 levels in urine assay were found to be correlated with skin thickness progression, and therefore total collagen deposition r=0.4883, R2=0.2384.

Figure 22:
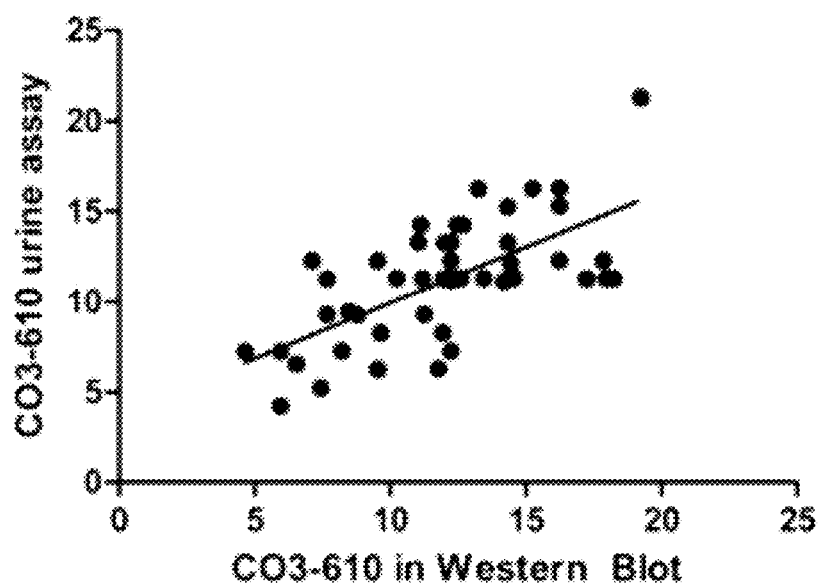
FIG. 22 shows a correlation between urine immunoassay results and Western blot measurements described in Example 9.

As seen in FIG. 22, statistically significant correlation was found (r=0.6528, P<0.0001) between results from the CO3-610 ELISA urine assay and Western blot densitometry measurements.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCE LIST

1. World Health Organization. Reducing Risks, Promoting Healthy Life. Reducing Risks, Promoting Healthy Life, Geneva: WHO, 2002:1-230.
2. Wynn T A. Cellular and molecular mechanisms of fibrosis. J Pathol 2008; 214:199-210.
3. Friedman S L. Mechanisms of disease: Mechanisms of hepatic fibrosis and therapeutic implications. Nat Clin Pract Gastroenterol Hepatol 2004; 1:98-105.
4. Tomasek J J, Gabbiani G, Hinz B, Chaponnier C, Brown R A. Myofibroblasts and mechano-regulation of connective tissue remodelling. Nat Rev Mol Cell Biol 2002; 3:349-363.
5. Wynn T A. Common and unique mechanisms regulate fibrosis in various fibroproliferative diseases. J Clin Invest 2007; 117:524-529.
6. Marcellin P, Asselah T, Boyer N. Fibrosis and disease progression in hepatitis C. Hepatology 2002; 36:S47-S56.
7. Gagliano N, Arosio B, Grizzi F, Masson S, Tagliabue J, Dioguardi N, Vergani C, Annoni G. Reduced collagenolytic activity of matrix metalloproteinases and development of liver fibrosis in the aging rat. Mech Ageing Dev 2002; 123:413-425.
8. Laurent G J. Dynamic state of collagen: pathways of collagen degradation in vivo and their possible role in regulation of collagen mass. Am J Physiol 1987; 252:C1-C9.
9. Mays P K, McAnulty R J, Campa J S, Laurent G J. Age-related changes in collagen synthesis and degradation in rat tissues. Importance of degradation of newly synthesized collagen in regulating collagen production. Biochem J 1991; 276 (Pt 2):307-313.
10. Garrone R, Lethias C, Le Guellec D. Distribution of minor collagens during skin development. Microsc Res Tech 1997; 38:407-412.
11. Gelse K, Poschl E, Aigner T. Collagens—structure, function, and biosynthesis. Adv Drug Deliv Rev 2003; 55:1531-1546.
12. Phan S H, Thrall R S. Pulmonary Fibrosis. Lung Biology in Health and Disease. 80 ed. New York: Marcel Dekker, Inc., 1995.

13. Martinez-Hernandez A, Amenta P S. The hepatic extracellular matrix. II. Ontogenesis, regeneration and cirrhosis. Virchows Arch A Pathol Anat Histopathol 1993; 423:77-84.

14. Gilliam A C. Scleroderma. Curr Dir Autoimmun 2008; 10:258-279.

15. Gressner A M, Weiskirchen R. Modern pathogenetic concepts of liver fibrosis suggest stellate cells and TGF-beta as major players and therapeutic targets. J Cell Mol Med 2006; 10:76-99.

16. Heinegard D, Oldberg A. Structure and biology of cartilage and bone matrix noncollagenous macromolecules. FASEB J 1989; 3:2042-2051.

17. Svensson L, Oldberg A, Heinegard D. Collagen binding proteins. Osteoarthritis and Cartilage 2001; 9:S23-S28.

18. Kiani C, Chen L, Wu Y J, Yee A J, Yang B B. Structure and function of aggrecan. Cell Res 2002; 12:19-32.

19. Krusius T, Gehlsen K R, Ruoslahti E. A fibroblast chondroitin sulfate proteoglycan core protein contains lectin-like and growth factor-like sequences. J Biol Chem 1987; 262:13120-13125.

20. Yang B L, Zhang Y, Cao L, Yang B B. Cell adhesion and proliferation mediated through the G1 domain of versican. J Cell Biochem 1999; 72:210-220.

21. Rauch U, Karthikeyan L, Maurel P, Margolis R U, Margolis R K. Cloning and primary structure of neurocan, a developmentally regulated, aggregating chondroitin sulfate proteoglycan of brain. J Biol Chem 1992; 267:19536-19547.

22. Yamada H, Watanabe K, Shimonaka M, Yamaguchi Y. Molecular cloning of brevican, a novel brain proteoglycan of the aggrecan/versican family. J Biol Chem 1994; 269:10119-10126.

23. Blochberger T C, Cornuet P K, Hassell J R. Isolation and partial characterization of lumican and decorin from adult chicken corneas. A keratan sulfate-containing isoform of decorin is developmentally regulated. J Biol Chem 1992; 267:20613-20619.

24. Fisher L W, Termine J D, Young M F. Deduced protein sequence of bone small proteoglycan I (biglycan) shows homology with proteoglycan II (decorin) and several non-connective tissue proteins in a variety of species. J Biol Chem 1989; 264:4571-4576.

25. Toyama-Sorimachi N, Sorimachi H, Tobita Y, Kitamura F, Yagita H, Suzuki K, Miyasaka M. A novel ligand for CD44 is serglycin, a hematopoietic cell lineage-specific proteoglycan. Possible involvement in lymphoid cell adherence and activation. J Biol Chem 1995; 270:7437-7444.

26. Bartlett A H, Hayashida K, Park P W. Molecular and cellular mechanisms of syndecans in tissue injury and inflammation. Mol Cells 2007; 24:153-166.

27. Lopez-Casillas F, Wrana J L, Massague J. Betaglycan presents ligand to the TGF beta signaling receptor. Cell 1993; 73:1435-1444.

28. Olsen B R. Life without perlecan has its problems. J Cell Biol 1999; 147:909-912.

29. Gabay C, Kushner I. Acute-phase proteins and other systemic responses to inflammation. N Engl J Med 1999; 340:448-454.

30. Benyon R C, Arthur M J. Extracellular matrix degradation and the role of hepatic stellate cells. Semin Liver Dis 2001; 21:373-384.

31. Guo J, Friedman S L. Hepatic fibrogenesis. Semin Liver Dis 2007; 27:413-426.

32. Iredale J P, Benyon R C, Arthur M J, Ferris W F, Alcolado R, Winwood P J, Clark N, Murphy G. Tissue inhibitor of metalloproteinase-1 messenger RNA expression is enhanced relative to interstitial collagenase messenger RNA in experimental liver injury and fibrosis. Hepatology 1996; 24:176-184.

33. Lee K N, Jackson K W, Christiansen V J, Lee C S, Chun J G, McKee P A. Antiplasmin-cleaving enzyme is a soluble form of fibroblast activation protein. Blood 2006; 107:1397-1404.

34. Acharya P S, Zukas A, Chandan V, Katzenstein A L, Pure E. Fibroblast activation protein: a serine protease expressed at the remodeling interface in idiopathic pulmonary fibrosis. Hum Pathol 2006; 37:352-360.

35. Levy M T, McCaughan G W, Marinos G, Gorrell M D. Intrahepatic expression of the hepatic stellate cell marker fibroblast activation protein correlates with the degree of fibrosis in hepatitis C virus infection. Liver 2002; 22:93-101.

36. Meyer O. Prognostic markers for systemic sclerosis. Joint Bone Spine 2006; 73:490-494.

37. Hummers L K. Microvascular damage in systemic sclerosis: detection and monitoring with biomarkers. Curr Rheumatol Rep 2006; 8:131-137.

38. McHugh N J, Distler O, Giacomelli R, Riemekasten G. Non organ based laboratory markers in systemic sclerosis. Clin Exp Rheumatol 2003; 21:S32-S38.

39. Muller-Quernheim J. Serum markers for the staging of disease activity of sarcoidosis and other interstitial lung diseases of unknown etiology. Sarcoidosis Vasc Diffuse Lung Dis 1998; 15:22-37.

40. Gressner O A, Weiskirchen R, Gressner A M. Biomarkers of liver fibrosis: clinical translation of molecular pathogenesis or based on liver-dependent malfunction tests. Clin Chinn Acta 2007; 381:107-113.

41. Gressner O A, Weiskirchen R, Gressner A M. Biomarkers of hepatic fibrosis, fibrogenesis and genetic predisposition pending between fiction and reality. J Cell Mol Med 2007; 11:1031-1051.

42. Mariat C. [Diagnosis and follow-up of chronic kidney graft dysfunction: from DFG to new biomarkers]. Nephrol Ther 2008; 4 Suppl 3:S204-S207.

43. Yoneda M, Mawatari H, Fujita K, Iida H, Yonemitsu K, Kato S, Takahashi H, Kirikoshi H, Inamori M, Nozaki Y, Abe Y, Kubota K, Saito S, Iwasaki T, Terauchi Y, Togo S, Maeyama S, Nakajima A. High-sensitivity C-reactive protein is an independent clinical feature of nonalcoholic steatohepatitis (NASH) and also of the severity of fibrosis in NASH. J Gastroenterol 2007; 42:573-582.

44. Wong V S, Hughes V, Trull A, Wight D G, Petrik J, Alexander G J. Serum hyaluronic acid is a useful marker of liver fibrosis in chronic hepatitis C virus infection. J Viral Hepat 1998; 5:187-192.

45. Parise E R, Oliveira A C, Figueiredo-Mendes C, Lanzoni V, Martins J, Nader H, Ferraz M L. Noninvasive serum markers in the diagnosis of structural liver damage in chronic hepatitis C virus infection. Liver Int 2006; 26:1095-1099.

46. McHutchison J G, Blatt L M, de Medina M, Craig J R, Conrad A, Schiff E R, Tong M J. Measurement of serum hyaluronic acid in patients with chronic hepatitis C and its relationship to liver histology. Consensus Interferon Study Group. J Gastroenterol Hepatol 2000; 15:945-951.

47. Camacho V R, Silveira T R, Oliveira J R, Barros S G, Cerski C T. Relationship between serum concetrations of type III procollagen, hyaluronic acid and histopathological findings in the liver of HCV-positive blood donors. Arq Gastroenterol 2007; 44:118-122.

48. Lorenzo-Zuniga V, Bartoli R, Masnou H, Montoliu S, Morillas R M, Planas R. Serum concentrations of insulinlike growth factor-I (igf-I) as a marker of liver fibrosis in patients with chronic hepatitis C. Dig Dis Sci 2007; 52:3245-3250.

49. Manolakopoulos S, Bethanis S, Liapi C, Stripeli F, Sklavos P, Margeli A, Christidou A, Katsanika A, Vogiatzakis E, Tzourmakliotis D, Theocharis S. An assessment of serum leptin levels in patients with chronic viral hepatitis: a prospective study. BMC Gastroenterol 2007; 7:17.

50. Camacho V R, Silveira T R, Oliveira J R, Barros S G, Cerski C T. Relationship between serum concetrations of type III procollagen, hyluronic acid and histopathological findings in the liver of HCV-positive blood donors. Arq Gastroenterol 2007; 44:118-122.

51. Leroy V, Hilleret M N, Sturm N, Trocme C, Renversez J C, Faure P, Morel F, Zarski J P. Prospective comparison of six non-invasive scores for the diagnosis of liver fibrosis in chronic hepatitis C. J Hepatol 2007; 46:775-782.

52. Trocme C, Leroy V, Sturm N, Hilleret M N, Bottari S, Morel F, Zarski J P. Longitudinal evaluation of a fibrosis index combining MMP-1 and PIIINP compared with MMP-9, TIMP-1 and hyaluronic acid in patients with chronic hepatitis C treated by interferon-alpha and ribavirin. J Viral Hepat 2006; 13:643-651.

53. Zheng M, Cai W M, Weng H L, Liu R H. ROC curves in evaluation of serum fibrosis indices for hepatic fibrosis. World J Gastroenterol 2002; 8:1073-1076.

54. Lebensztejn D M, Sobaniec-Lotowska M E, Bauer M, Kaczmarski M, Voelker M, Schuppan D. Serum fibrosis markers as predictors of an antifibrotic effect of interferon alfa in children with chronic hepatitis B. Eur J Gastroenterol Hepatol 2005; 17:843-848.

55. Lebensztejn D M, Sobaniec-Lotowska M E, Kaczmarski M, Voelker M, Schuppan D. Matrix-derived serum markers in monitoring liver fibrosis in children with chronic hepatitis B treated with interferon alpha. World J Gastroenterol 2006; 12:3338-3343.

56. Tsochatzis E, Papatheodoridis G V, Hadziyannis E, Georgiou A, Kafiri G, Tiniakos D G, Manesis E K, Archimandritis A J. Serum adipokine levels in chronic liver diseases: association of resistin levels with fibrosis severity. Scand J Gastroenterol 2008; 43:1128-1136.

57. Patel K, Gordon S C, Jacobson I, Hezode C, Oh E, Smith K M, Pawlotsky J M, McHutchison J G. Evaluation of a panel of non-invasive serum markers to differentiate mild from moderate-to-advanced liver fibrosis in chronic hepatitis C patients. J Hepatol 2004; 41:935-942.

58. Lieber C S, Weiss D G, Paronetto F. Value of fibrosis markers for staging liver fibrosis in patients with precirrhotic alcoholic liver disease. Alcohol Clin Exp Res 2008; 32:1031-1039.

59. Forns X, Ampurdanes S, Llovet J M, Aponte J, Quinto L, Martinez-Bauer E, Bruguera M, Sanchez-Tapias J M, Rodes J. Identification of chronic hepatitis C patients without hepatic fibrosis by a simple predictive model. Hepatology 2002; 36:986-992.

60. Bourliere M, Penaranda G, Renou C, Botta-Fridlund D, Tran A, Portal I, Lecomte L, Castellani P, Rosenthal-Allieri M A, Gerolami R, Ouzan D, Deydier R, Degott C, Halfon P. Validation and comparison of indexes for fibrosis and cirrhosis prediction in chronic hepatitis C patients: proposal for a pragmatic approach classification without liver biopsies. J Viral Hepat 2006; 13:659-670.

61. Cacoub P, Carrat F, Bedossa P, Lambert J, Penaranda G, Perronne C, Pol S, Halfon P. Comparison of non-invasive liver fibrosis biomarkers in HIV/HCV co-infected patients: the fibrovic study—ANRS HC02. J Hepatol 2008; 48:765-773.

62. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.

63. Grigorescu M, Rusu M, Neculoiu D, Radu C, Serban A, Catanas M, Grigorescu M D. The FibroTest value in discriminating between insignificant and significant fibrosis in chronic hepatitis C patients. The Romanian experience. J Gastrointestin Liver Dis 2007; 16:31-37.

64. Halfon P, Bacq Y, De M A, Penaranda G, Bourliere M, Ouzan D, Tran A, Botta D, Renou C, Brechot M C, Degott C, Paradis V. Comparison of test performance profile for blood tests of liver fibrosis in chronic hepatitis C. J Hepatol 2007; 46:395-402.

65. Halfon P, Bourliere M, Deydier R, Botta-Fridlund D, Renou C, Tran A, Portal I, Allemand I, Bertrand J J, Rosenthal-Allieri A, Rotily M, Sattonet C, Benderitter T, Saint Paul M C, Bonnot H P, Penaranda G, Degott C, Masseyeff M F, Ouzan D. Independent prospective multicenter validation of biochemical markers (fibrotest-actitest) for the prediction of liver fibrosis and activity in patients with chronic hepatitis C: the fibropaca study. Am J Gastroenterol 2006; 101:547-555.

66. Leroy V, Halfon P, Bacq Y, Boursier J, Rousselet M C, Bourliere M, De M A, Sturm N, Hunault G, Penaranda G, Brechot M C, Trocme C, Cales P. Diagnostic accuracy, reproducibility and robustness of fibrosis blood tests in chronic hepatitis C: a meta-analysis with individual data. Clin Biochem 2008; 41:1368-1376.

67. Ratziu V, Massard J, Charlotte F, Messous D, Imbert-Bismut F, Bonyhay L, Tahiri M, Munteanu M, Thabut D, Cadranel J F, Le B B, de L, V, Poynard T. Diagnostic value of biochemical markers (FibroTest-FibroSURE) for the prediction of liver fibrosis in patients with non-alcoholic fatty liver disease. BMC Gastroenterol 2006; 6:6.

68. Poynard T, Imbert-Bismut F, Ratziu V, Chevret S, Jardel C, Moussalli J, Messous D, Degos F. Biochemical markers of liver fibrosis in patients infected by hepatitis C virus: longitudinal validation in a randomized trial. J Viral Hepat 2002; 9:128-133.

69. Poynard T, Munteanu M, Imbert-Bismut F, Charlotte F, Thabut D, Le C S, Messous D, Thibault V, Benhamou Y, Moussalli J, Ratziu V. Prospective analysis of discordant results between biochemical markers and biopsy in patients with chronic hepatitis C. Clin Chem 2004; 50:1344-1355.

70. Poynard T, Morra R, Halfon P, Castera L, Ratziu V, Imbert-Bismut F, Naveau S, Thabut D, Lebrec D, Zoulim F, Bourliere M, Cacoub P, Messous D, Munteanu M, de L, V. Meta-analyses of FibroTest diagnostic value in chronic liver disease. BMC Gastroenterol 2007; 7:40.

71. Ngo Y, Munteanu M, Messous D, Charlotte F, Imbert-Bismut F, Thabut D, Lebray P, Thibault V, Benhamou Y, Moussalli J, Ratziu V, Poynard T. A prospective analysis of the prognostic value of biomarkers (FibroTest) in patients with chronic hepatitis C. Clin Chem 2006; 52:1887-1896.

72. Naveau S, Raynard B, Ratziu V, Abella A, Imbert-Bismut F, Messous D, Beuzen F, Capron F, Thabut D, Munteanu M, Chaput J C, Poynard T. Biomarkers for the prediction of liver fibrosis in patients with chronic alcoholic liver disease. Clin Gastroenterol Hepatol 2005; 3:167-174.

73. Myers R P, Tainturier M H, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003; 39:222-230.

74. Jacqueminet S, Lebray P, Morra R, Munteanu M, Devers L, Messous D, Bernard M, Hartemann-Heurtier A, Imbert-Bismut F, Ratziu V, Grimaldi A, Poynard T. Screening for liver fibrosis by using a noninvasive biomarker in patients with diabetes. Clin Gastroenterol Hepatol 2008; 6:828-831.

75. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.

76. Poynard T, Zoulim F, Ratziu V, Degos F, Imbert-Bismut F, Deny P, Landais P, El H A, Slama A, Blin P, Thibault V, Parvaz P, Munteanu M, Trepo C. Longitudinal assessment of histology surrogate markers (FibroTest-ActiTest) during lamivudine therapy in patients with chronic hepatitis B infection. Am J Gastroenterol 2005; 100:1970-1980.

77. Poynard T, Munteanu M, Imbert-Bismut F, Charlotte F, Thabut D, Le C S, Messous D, Thibault V, Benhamou Y, Moussalli J, Ratziu V. Prospective analysis of discordant results between biochemical markers and biopsy in patients with chronic hepatitis C. Clin Chem 2004; 50:1344-1355.

78. Myers R P, Tainturier M H, Ratziu V, Piton A, Thibault V, Imbert-Bismut F, Messous D, Charlotte F, Di M, V, Benhamou Y, Poynard T. Prediction of liver histological lesions with biochemical markers in patients with chronic hepatitis B. J Hepatol 2003; 39:222-230.

79. Carvalho-Filho R J, Schiavon L L, Narciso-Schiavon J L, Sampaio J P, Lanzoni V P, Ferraz M L, Silva A E. Optimized cutoffs improve performance of the aspartate aminotransferase to platelet ratio index for predicting significant liver fibrosis in human immunodeficiency virus/hepatitis C virus co-infection. Liver Int 2008; 28:486-493.

80. Al-Mohri H, Cooper C, Murphy T, Klein M B. Validation of a simple model for predicting liver fibrosis in HIV/hepatitis C virus-coinfected patients. HIV Med 2005; 6:375-378.

81. Cales P, Laine F, Boursier J, Deugnier Y, Moal V, Oberti F, Hunault G, Rousselet M C, Hubert I, Laafi J, Ducluzeaux P H, Lunel F. Comparison of blood tests for liver fibrosis specific or not to NAFLD. J Hepatol 2008.

82. Paggi S, Colli A, Fraquelli M, Vigano M, Del P P, Facciotto C, Colombo M, Ronchi G, Conte D. A non-invasive algorithm accurately predicts advanced fibrosis in hepatitis C: a comparison using histology with internal-external validation. J Hepatol 2008; 49:564-571.

83. Trang T, Petersen J R, Snyder N. Non-invasive markers of hepatic fibrosis in patients co-infected with HCV and HIV: comparison of the APRI and FIB-4 index. Clin Chim Acta 2008; 397:51-54.

84. Snyder N, Gajula L, Xiao S Y, Grady J, Luxon B, Lau D T, Soloway R, Petersen J. APRI: an easy and validated predictor of hepatic fibrosis in chronic hepatitis C. J Clin Gastroenterol 2006; 40:535-542.

85. Snyder N, Nguyen A, Gajula L, Soloway R, Xiao S Y, Lau D T, Petersen J. The APRI may be enhanced by the use of the FIBROSpect II in the estimation of fibrosis in chronic hepatitis C. Clin Chim Acta 2007; 381:119-123.

86. Hongbo L, Xiaohui L, Hong K, Wei W, Yong Z. Assessing routine and serum markers of liver fibrosis in CHB patients using parallel and serial interpretation. Clin Biochem 2007; 40:562-566.

87. Nunes D, Fleming C, Offner G, O'Brien M, Tumilty S, Fix O, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.

88. Adams L A, Bulsara M, Rossi E, DeBoer B, Speers D, George J, Kench J, Farrell G, McCaughan G W, Jeffrey G P. Hepascore: an accurate validated predictor of liver fibrosis in chronic hepatitis C infection. Clin Chem 2005; 51:1867-1873.

89. Koda M, Matunaga Y, Kawakami M, Kishimoto Y, Suou T, Murawaki Y. FibroIndex, a practical index for predicting significant fibrosis in patients with chronic hepatitis C. Hepatology 2007; 45:297-306.

90. Metwally M A, Zein C O, Zein N N. Predictors and noninvasive identification of severe liver fibrosis in patients with chronic hepatitis C. Dig Dis Sci 2007; 52:582-588.

91. Mohamadnejad M, Montazeri G, Fazlollahi A, Zamani F, Nasiri J, Nobakht H, Forouzanfar M H, Abedian S, Tavangar S M, Mohamadkhani A, Ghoujeghi F, Estakhri A, Nouri N, Farzadi Z, Najjari A, Malekzadeh R. Noninvasive markers of liver fibrosis and inflammation in chronic hepatitis B-virus related liver disease. Am J Gastroenterol 2006; 101:2537-2545.

92. Zaman A, Rosen H R, Ingram K, Corless C L, Oh E, Smith K. Assessment of FIBROSpect II to detect hepatic fibrosis in chronic hepatitis C patients. Am J Med 2007; 120:280-14.

93. Patel K, Nelson D R, Rockey D C, Afdhal N H, Smith K M, Oh E, Hettinger K, Vallee M, Dev A, Smith-Riggs M, McHutchison J G. Correlation of FIBROSpect II with histologic and morphometric evaluation of liver fibrosis in chronic hepatitis C. Clin Gastroenterol Hepatol 2008; 6:242-247.

94. Sebastiani G, Vario A, Guido M, Noventa F, Plebani M, Pistis R, Ferrari A, Alberti A. Stepwise combination algorithms of non-invasive markers to diagnose significant fibrosis in chronic hepatitis C. J Hepatol 2006; 44:686-693.

95. Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-1075.

96. Nunes D, Fleming C, Offner G, O'Brien M, Tumilty S, Fix 0, Heeren T, Koziel M, Graham C, Craven D E, Stuver S, Horsburgh C R, Jr. HIV infection does not affect the performance of noninvasive markers of fibrosis for the diagnosis of hepatitis C virus-related liver disease. J Acquir Immune Defic Syndr 2005; 40:538-544.

97. Castera L, Vergniol J, Foucher J, Le B B, Chanteloup E, Haaser M, Darriet M, Couzigou P, de L, V. Prospective comparison of transient elastography, Fibrotest, APRI, and liver biopsy for the assessment of fibrosis in chronic hepatitis C. Gastroenterology 2005; 128:343-350.

98. Guanabens N, Pares A, Alvarez L, Martinez de Osaba M J, Monegal A, Penis P, Ballesta A M, Rodes J. Collagen-related markers of bone turnover reflect the severity of liver fibrosis in patients with primary biliary cirrhosis. J Bone Miner Res 1998; 13:731-738.

99. Moller S, Hansen M, Hillingso J, Jensen J E, Henriksen J H. Elevated carboxy terminal cross linked telopeptide of type I collagen in alcoholic cirrhosis: relation to liver and kidney function and bone metabolism. Gut 1999; 44:417-423.

100. Rosen H N, Parker R A, Greenspan S L, Iloputaife I D, Bookman L, Chapin D, Perlmutter I, Kessel B, Qvist P, Rosenblatt M. Evaluation of ability of biochemical markers of bone turnover to predict a response to increased doses of HRT. Calcif Tissue Int 2004; 74:415-423.

101. Lein M, Wirth M, Miller K, Eickenberg H U, Weissbach L, Schmidt K, Haus U, Stephan C, Meissner S, Loening S A, Jung K. Serial Markers of Bone Turnover in Men with Metastatic Prostate Cancer Treated with Zoledronic Acid for Detection of Bone Metastases Progression. Eur Urol 2007.

102. Attallah A M, Toson E A, Shiha G E, Omran M M, bdel-Aziz M M, E I-Dosoky I. Evaluation of serum procollagen aminoterminal propeptide III, laminin, and hydroxyproline as predictors of severe fibrosis in patients with chronic hepatitis C. J Immunoassay Immunochem 2007; 28:199-211.

103. Ulrich D, Noah E M, von H D, Pallua N. TIMP-1, MMP-2, MMP-9, and PIIINP as serum markers for skin fibrosis in patients following severe burn trauma. Plast Reconstr Surg 2003; 111:1423-1431.

104. Farkkila M, Rautiainen H, Karkkainen P, Karvonen A L, Nurmi H, Niemela O. Serological markers for monitoring disease progression in noncirrhotic primary biliary cirrhosis on ursodeoxycholic acid therapy. Liver Int 2008; 28:787-797.

105. Guechot J, Poupon R E, Giral P, Balkau B, Giboudeau J, Poupon R. Relationship between procollagen III aminoterminal propeptide and hyaluronan serum levels and histological fibrosis in primary biliary cirrhosis and chronic viral hepatitis C. J Hepatol 1994; 20:388-393.

106. Klappacher G, Franzen P, Haab D, Mehrabi M, Binder M, Plesch K, Pacher R, Grimm M, Pribill I, Eichler H G. Measuring extracellular matrix turnover in the serum of patients with idiopathic or ischemic dilated cardiomyopathy and impact on diagnosis and prognosis. Am J Cardiol 1995; 75:913-918.

107. Imbert-Bismut F, Ratziu V, Pieroni L, Charlotte F, Benhamou Y, Poynard T. Biochemical markers of liver fibrosis in patients with hepatitis C virus infection: a prospective study. Lancet 2001; 357:1069-1075.

108. Suzuki, K., Enghild, J. J., Morodomi, T., Salvesen, G., and Nagase, H. 1990. Mechanisms of activation of tissue procollagenase by matrix metalloproteinase 3 (stromelysin). Biochemistry 29:10261-10270.

109. Lijnen, H. R. 2001. Plasmin and matrix metalloproteinases in vascular remodeling. Thromb. Haemost. 86:324-333.

Those skilled in the art will recognize, or be able to ascertain using no more than routine experimentation, many equivalents the specific embodiments of the invention described herein. Such equivalents are intended to be encompassed by this invention and the following claims.

---

What is claimed is:

1. A method of diagnosis or of quantitation of fibrosis comprising:

obtaining a patient biofluid sample, conducting an immunoassay to measure fragments of collagen type III having an N- or C-terminal neo epitope formed by cleavage of intact collagen type III by MMP1, MMP2, MMP3, MMP8, MMP9, MMP13, CathepsinK, CathepsinS, ADAMTS1, ADAMTS4, ADAMTS5, or ADAMTS8, said fragments being naturally present in said sample, and associating an elevation of said measure in said patient above a normal level with the presence or extent of fibrosis, wherein said immunoassay is conducted by a method comprising:

contacting the fragments of collagen type III having said N- or C-terminal neo epitope that are naturally present in said sample with an immunological binding partner specifically reactive with the N- or C-terminal neo-epitope but not reactive with intact collagen type III, and measuring the extent of binding of peptide fragments to said immunological binding partner to measure therein protein fragments comprising said neo-epitope, wherein said immunological binding partner specifically binds to an N-terminal neo epitope amino acid sequence formed by cleavage of collagen type III by MMP1, MMP2, MMP3, MMP8, MMP9, MMP13, CathepsinK, CathepsinS, ADAMTS1, ADAMTS4, ADAMTS5, or ADAMTS8, said N-terminal amino acid sequence selected from the group consisting of:

| Collagen type III |
|---|
| GIPGAP . . . SEQ ID NO: 372 |
| IAGITG . . . SEQ ID NO: 375 |
| KGDAGQ . . . SEQ ID NO: 381 |
| GKSGDR . . . SEQ ID NO: 383 |

Collagen type III

| | |
|---|---|
| DGTSGH | SEQ ID NO: 135 |
| GPPGVA | SEQ ID NO: 158 |
| GARGLA | SEQ ID NO: 111 |
| KGESGK | SEQ ID NO: 374 |
| QPGVMG | SEQ ID NO: 144 |
| GPPGPT | SEQ ID NO: 391 |
| GLPGPP | SEQ ID NO: 394 |
| GINGSP | SEQ ID NO: 397 |
| LMGARG | SEQ ID NO: 400 |
| DKGEPG | SEQ ID NO: 403 |
| PGMKGH | SEQ ID NO: 406 |
| FPGMKG | SEQ ID NO: 409 |
| GQPGDK | SEQ ID NO: 412 |
| GSDGQP | SEQ ID NO: 405 |
| GFPGAP | SEQ ID NO: 420 |
| PGPQGH | SEQ ID NO: 426 |
| PGPPGI | SEQ ID NO: 432 |
| GPPGSN | SEQ ID NO: 423 |
| PQGLQG | SEQ ID NO: 440 |
| GAPGFR | SEQ ID NO: 435 |
| GAPGPQ | SEQ ID NO: 445 |
| GPTGPI | SEQ ID NO: 448 |
| KGSPGA | SEQ ID NO: 444 |
| GSRGAP | SEQ ID NO: 462 |
| NTGAPG | SEQ ID NO: 437 |
| HAGAQG | SEQ ID NO: 434 |
| PGPQGP | SEQ ID NO: 453 |
| AGQPGE | SEQ ID NO: 454 |
| VKGERG | SEQ ID NO: 159 |
| GPPGAP | SEQ ID NO: 461 |
| GSPGAQ | SEQ ID NO: 464 |
| PGAPGL | SEQ ID NO: 467 |
| ESCPTG | SEQ ID NO: 433 |
| GPAGIP | SEQ ID NO: 441 |
| GDPGPP | SEQ ID NO: 373 |
| IKGHRG | SEQ ID NO: 376 |
| ITGARG | SEQ ID NO: 379 |
| LQGLPG | SEQ ID NO: 384 |
| IGSPGP | SEQ ID NO: |
| AGPPGM | SEQ ID NO: 145 |
| GAPGEK | SEQ ID NO: 141 |
| GLSGER | SEQ ID NO: 387 |
| IPGAPG | SEQ ID NO: 117 |
| INGSPG | SEQ ID NO: 392 |
| KNGETG | SEQ ID NO: 395 |
| PGENGK | SEQ ID NO: 398 |
| GKDGES | SEQ ID NO: 418 |
| GHAGAQ | SEQ ID NO: 404 |
| FPGARG | SEQ ID NO: 407 |
| PGDKGE | SEQ ID NO: 410 |
| GPPGEN | SEQ ID NO: 413 |
| PGVPGA | SEQ ID NO: 416 |
| GPPGPP | SEQ ID NO: 100 |
| GAAGEP | SEQ ID NO: 421 |
| PGFPGM | SEQ ID NO: 427 |
| GITGAR | SEQ ID NO: 430 |
| RPGLPG | SEQ ID NO: 436 |
| GPPGVA | SEQ ID NO: 158 |
| PGFRGP | SEQ ID NO: 443 |
| GFPGNP | SEQ ID NO: 446 |
| GDAGQP | SEQ ID NO: 449 |
| GSPGER | SEQ ID NO: 439 |
| TGARGL | SEQ ID NO: 378 |
| VGGLAG | SEQ ID NO: 155 |
| PGAPGG | SEQ ID NO: 455 |
| AGQQGA | SEQ ID NO: 457 |
| GLAGPP | SEQ ID NO: 388 |
| GGAGEP | SEQ ID NO: 463 |
| SPGAQG | SEQ ID NO: 465 |
| IKGPAG | SEQ ID NO: 169 |
| GIPGQP | SEQ ID NO: 468 |
| DAGAPG | SEQ ID NO: 469 |
| LAGPPG | SEQ ID NO: 89 |
| RGLAGP | SEQ ID NO: 377 |
| VKGESG | SEQ ID NO: 380 |
| LRGGAG | SEQ ID NO: 382 |
| AIGSPG | SEQ ID NO: 143 |

| Collagen type III | |
|---|---|
| LSGERG | SEQ ID NO: 176 |
| PQGPPG | SEQ ID NO: 389 |
| YQGPPG | SEQ ID NO: 401 |
| FRGPAG | SEQ ID NO: 137 |
| GPPGEP | SEQ ID NO: 393 |
| LPGIAG | SEQ ID NO: 396 |
| QQGAIG | SEQ ID NO: 390 |
| GERGAP | SEQ ID NO: 402 |
| GFPGAR | SEQ ID NO: 408 |
| GDKGET | SEQ ID NO: 411 |
| AAGFPG | SEQ ID NO: 417 |
| GARGND | SEQ ID NO: 419 |
| GGAGPP | SEQ ID NO: 425 |
| GARGPP | SEQ ID NO: 422 |
| GSPGGP | SEQ ID NO: 428 |
| GIAGIT | SEQ ID NO: 431 |
| GAPGPM | SEQ ID NO: 438 |
| SGDRGE | SEQ ID NO: 429 |
| GPVGPS | SEQ ID NO: 447 |
| GPPGIN | SEQ ID NO: 470 |
| NGEKGE | SEQ ID NO: 450 |
| AIGPSG | SEQ ID NO: 368 |
| ERGLPG | SEQ ID NO: 385 |
| VAGPPG | SEQ ID NO: 452 |
| GIPGFP | SEQ ID NO: 414 |
| PGPPGP | SEQ ID NO: 458 |
| GRNGEK | SEQ ID NO: 460 |
| SPGGKG | SEQ ID NO: 459 |
| PGVSGP | SEQ ID NO: 466 |
| PGAPGQ | SEQ ID NO: 456 |
| SRGAPG | SEQ ID NO: 451 |
| GPKGDA | SEQ ID NO: 424 | or wherein said immunological binding partner specifically binds to a C-terminal neo epitope amino acid sequence formed by cleavage of collagen type III by MMP1, MMP2, MMP3, MMP8, MMP9, MMP13, CathepsinK, CathepsinS, ADAMTS1, ADAMTS4, ADAMTS5, or ADAMTS8, wherein said C-terminal amino acid sequence is selected from the group consisting of:

| Collagen type III | |
|---|---|
| . . . GPPGPA | SEQ ID NO: 94 |
| . . . GMPGPR | SEQ ID NO: 473 |
| . . . ERGAAG | SEQ ID NO: 476 |
| . . . ERGPPG | SEQ ID NO: 147 |
| . . . GLPGLA | SEQ ID NO: 486 |
| . . . GLAGTA | SEQ ID NO: 488 |
| . . . LAGPPG | SEQ ID NO: 89 |
| . . . IPGFPG | SEQ ID NO: 492 |
| . . . FPGPKG | SEQ ID NO: 491 |
| . . . GPPGIC | SEQ ID NO: 2187 |
| . . . PGPQGL | SEQ ID NO: 497 |
| . . . SPGPKG | SEQ ID NO: 499 |
| . . . LPGPPG | SEQ ID NO: 72 |
| . . . GHRGFD | SEQ ID NO: 503 |
| . . . GLPGIA | SEQ ID NO: 507 |
| . . . GLPGPP | SEQ ID NO: 394 |
| . . . TGARGL | SEQ ID NO: 378 |
| . . . PQGLPG | SEQ ID NO: 508 |
| . . . GTPGLQ | SEQ ID NO: 521 |
| . . . GMKGHR | SEQ ID NO: 531 |
| . . . EMGPAG | SEQ ID NO: 534 |
| . . . GVKGER | SEQ ID NO: 538 |
| . . . GPPGPR | SEQ ID NO: 544 |
| . . . AGPRGA | SEQ ID NO: 547 |
| . . . GRNGDP | SEQ ID NO: 171 |
| . . . AGIPGF | SEQ ID NO: 496 |
| . . . PPGPQG | SEQ ID NO: 103 |
| . . . IPGAPG | SEQ ID NO: 117 |
| . . . TSGHPG | SEQ ID NO: 518 |
| . . . PSGPPG | SEQ ID NO: 483 |
| . . . PPGPAG | SEQ ID NO: 52 |
| . . . FPGMKG | SEQ ID NO: 409 |
| . . . EKGPAG | SEQ ID NO: 515 |
| . . . MPGPRG | SEQ ID NO: 523 |
| . . . GIPGAP | SEQ ID NO: 372 |
| . . . NGDPGI | SEQ ID NO: 471 |
| . . . SPGPAG | SEQ ID NO: 474 |
| . . . PGPLGI | SEQ ID NO: 477 |
| . . . PGPPGT | SEQ ID NO: 479 |
| . . . APGLRG | SEQ ID NO: 481 |
| . . . GSPGPA | SEQ ID NO: 484 |
| . . . PGLMGA | SEQ ID NO: 489 |
| . . . GPPGPQ | SEQ ID NO: 490 |
| . . . GPAGIP | SEQ ID NO: 441 |
| . . . PPGPPG | SEQ ID NO: 119 |
| . . . GAPGLM | SEQ ID NO: 498 |
| . . . LPGAAG | SEQ ID NO: 2188 |
| . . . GPPGIN | SEQ ID NO: 470 |
| . . . PGLPGI | SEQ ID NO: 504 |
| . . . PGPKGD | SEQ ID NO: 506 |
| . . . GANGLP | SEQ ID NO: 510 |
| . . . GPPGIK | SEQ ID NO: 512 |
| . . . GAPGLR | SEQ ID NO: 509 |
| . . . GEVGPA | SEQ ID NO: 514 |
| . . . GKPGAN | SEQ ID NO: 537 |
| . . . PGAAGF | SEQ ID NO: 539 |
| . . . GDAGAP | SEQ ID NO: 542 |
| . . . GPAGPR | SEQ ID NO: 545 |
| . . . GGKGER | SEQ ID NO: 548 |
| . . . GPAGAN | SEQ ID NO: 550 |
| . . . VKGESG | SEQ ID NO: 380 |
| . . . TGPRGP | SEQ ID NO: 177 |
| . . . EPGPRG | SEQ ID NO: 516 |
| . . . GAPGPA | SEQ ID NO: 519 |
| . . . GTSGHP | SEQ ID NO: 522 |
| . . . GAPGLK | SEQ ID NO: 525 |
| . . . GEPGPR | SEQ ID NO: 500 |
| . . . PGPKGN | SEQ ID NO: 527 |
| . . . PPGAPG | SEQ ID NO: 517 |
| . . . TPGLQG | SEQ ID NO: 520 |
| . . . SPGPQG | SEQ ID NO: 472 |
| . . . PGPQGV | SEQ ID NO: 475 |
| . . . AAGTPG | SEQ ID NO: 478 |
| . . . GNRGER | SEQ ID NO: 480 |
| . . . HPGSPG | SEQ ID NO: 482 |
| . . . GPAGPP | SEQ ID NO: 485 |
| . . . QGPPGP | SEQ ID NO: 487 |
| . . . GFPGMK | SEQ ID NO: 493 |
| . . . FPGAPG | SEQ ID NO: 494 |

| Collagen type III | | |
|---|---|---|
| . . . FPGARG | SEQ ID NO: | 407 |
| . . . GAIGPS | SEQ ID NO: | 495 |
| . . . APGPLG | SEQ ID NO: | 2189 |
| . . . IPGQPG | SEQ ID NO: | 501 |
| . . . GAAGIK | SEQ ID NO: | 505 |
| . . . GPPGVA | SEQ ID NO: | 158 |
| . . . GPPGPS | SEQ ID NO: | 511 |
| . . . TAGFPG | SEQ ID NO: | 513 |
| . . . GPQGVK | SEQ ID NO: | 524 |
| . . . QPGPPG | SEQ ID NO: | 536 |
| . . . PGANGL | SEQ ID NO: | 529 |
| . . . GPAGER | SEQ ID NO: | 543 |
| . . . RGFDGR | SEQ ID NO: | 546 |
| . . . APGLMG | SEQ ID NO: | 549 |
| . . . PQGVKG | SEQ ID NO: | 541 |
| . . . TGERGA | SEQ ID NO: | 540 |
| . . . GSPGYQ | SEQ ID NO: | 526 |
| . . . GAAGAR | SEQ ID NO: | 528 |
| . . . TGAPGS | SEQ ID NO: | 502 |
| . . . GTGGPP | SEQ ID NO: | 530 |
| . . . GITGAR | SEQ ID NO: | 430 |
| . . . GIAGPR | SEQ ID NO: | 535 |
| . . . GLSGER | SEQ ID NO: | 387 |
| . . . EGGPPG | SEQ ID NO: | 532 |
| . . . GFPGAR | SEQ ID NO: | 408. |

2. A method as claimed in claim 1, wherein said immunological binding partner specifically binds fragments of collagen type III comprising an N-terminal sequence KNGETG (SEQ ID NO: 395).

3. A method as claimed in claim 1, wherein said immunological binding partner specifically binds to N-terminal sequence KNGETGPQ . . . (SEQ ID NO: 2251).

4. A method as claimed in claim 1, wherein said immunological binding partner specifically binds to N-terminal sequence GAPGFR . . . (SEQ ID NO: 435).

5. A method as claimed in claim 1, wherein said immunological binding partner is a polyclonal antibody or a monoclonal antibody.

* * * * *

SEQUENCE LISTING

```
<160> NUMBER OF SEQ ID NOS: 2256

<210> SEQ ID NO 1
<211> LENGTH: 10
<212> TYPE: PRT
<213> ORGANISM: Homo sapiens

<400> SEQUENCE: 1

Pro Gly Ile Pro Gly Arg Asn Gly Asp Pro
1               5                   10

<210> SEQ ID NO 2
<211> LENGTH: 10
<212> TYPE: PRT
<213> ORGANISM: Homo sapiens

<400> SEQUENCE: 2

Glu Ser Cys Pro Thr Gly Pro Gln Asn Tyr
1               5                   10

<210> SEQ ID NO 3
<211> LENGTH: 10
<212> TYPE: PRT
<213> ORGANISM: Homo sapiens

<400> SEQUENCE: 3

Pro Lys Gly Asp Thr Gly Pro Arg Gly Pro
1               5                   10

<210> SEQ ID NO 4
<211> LENGTH: 25
<212> TYPE: PRT
<213> ORGANISM: Homo sapiens
<220> FEATURE:
<221> NAME/KEY: MOD_RES
<222> LOCATION: (16)..(17)
<223> OTHER INFORMATION: proline or hydroxyproline
<220> FEATURE:
<221> NAME/KEY: MOD_RES
<222> LOCATION: (20)..(20)
<223> OTHER INFORMATION: proline or hydroxyproline
```

```
<400> SEQUENCE: 4

Val Pro Gly Pro Met Gly Pro Ser Gly Pro Arg Gly Leu Pro Gly Xaa
1               5                   10                  15

Xaa Gly Ala Xaa Gly Pro Gln Gly Phe
            20                  25

<210> SEQ ID NO 5
<211> LENGTH: 26
<212> TYPE: PRT
<213> ORGANISM: Homo sapiens
<220> FEATURE:
<221> NAME/KEY: MOD_RES
<222> LOCATION: (17)..(18)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline

<400> SEQUENCE: 5

Ser Val Pro Gly Pro Met Gly Pro Ser Gly Pro Arg Gly Leu Pro Gly
1               5                   10                  15

Xaa Xaa Gly Ala Xaa Gly Pro Gln Gly Phe
            20                  25

<210> SEQ ID NO 6
<211> LENGTH: 28
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: methionine or oxidised methionine
<220> FEATURE:
<221> NAME/KEY: MOD_RES
<222> LOCATION: (19)..(20)
<223> OTHER INFORMATION: proline or hydroxyproline
<220> FEATURE:
<221> NAME/KEY: MOD_RES
<222> LOCATION: (23)..(23)
<223> OTHER INFORMATION: proline or hydroxyproline

<400> SEQUENCE: 6

Gly Ile Ser Val Pro Gly Pro Xaa Gly Pro Ser Gly Pro Arg Gly Leu
1               5                   10                  15

Pro Gly Xaa Xaa Gly Ala Xaa Gly Pro Gln Gly Phe
            20                  25

<210> SEQ ID NO 7
<211> LENGTH: 29
<212> TYPE: PRT
<213> ORGANISM: Homo sapiens
<220> FEATURE:
<221> NAME/KEY: MOD_RES
<222> LOCATION: (23)..(24)
<223> OTHER INFORMATION: proline or hydroxy proline
<220> FEATURE:
<221> NAME/KEY: MOD_RES
<222> LOCATION: (26)..(26)
<223> OTHER INFORMATION: proline or hydroxy proline

<400> SEQUENCE: 7

Gly Phe Gln Gly Pro Pro Gly Glu Pro Gly Glu Pro Gly Ala Ser Gly
1               5                   10                  15

Pro Met Gly Pro Arg Gly Xaa Xaa Gly Xaa Pro Gly Lys
            20                  25
```

```
<210> SEQ ID NO 8
<211> LENGTH: 25
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: methionine or oxidised methionine
<220> FEATURE:
<221> NAME/KEY: MOD_RES
<222> LOCATION: (17)..(17)
<223> OTHER INFORMATION: proline or hydroxyproline
<220> FEATURE:
<221> NAME/KEY: MOD_RES
<222> LOCATION: (20)..(20)
<223> OTHER INFORMATION: proline or hydroxyproline

<400> SEQUENCE: 8

Val Pro Gly Pro Xaa Gly Pro Ser Gly Pro Arg Gly Leu Pro Gly Pro
1               5                   10                  15

Xaa Gly Ala Xaa Gly Pro Gln Gly Phe
            20                  25

<210> SEQ ID NO 9
<211> LENGTH: 37
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: lysine or hydroxylysine
<220> FEATURE:
<221> NAME/KEY: MOD_RES
<222> LOCATION: (23)..(23)
<223> OTHER INFORMATION: proline or hydroxyproline
<220> FEATURE:
<221> NAME/KEY: MOD_RES
<222> LOCATION: (29)..(29)
<223> OTHER INFORMATION: proline or hydroxyproline

<400> SEQUENCE: 9

Phe Ser Gly Leu Asp Gly Ala Lys Gly Asp Ala Gly Pro Ala Gly Pro
1               5                   10                  15

Xaa Gly Glu Pro Gly Ser Xaa Gly Glu Asn Gly Ala Xaa Gly Gln Met
            20                  25                  30

Gly Pro Arg Gly Leu
        35

<210> SEQ ID NO 10
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 10

Gly Leu Xaa Gly Glu Arg Gly Arg Xaa Gly Ala Xaa Gly Pro Ala Gly
1               5                   10                  15

Ala
```

<210> SEQ ID NO 11
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (20)..(20)
<223> OTHER INFORMATION: proline or hydroxyproline

<400> SEQUENCE: 11

Gly Leu Thr Gly Ser Xaa Gly Ser Xaa Gly Pro Asp Gly Lys Thr Gly
1               5                   10                  15

Pro Pro Gly Xaa Ala Gly Gln
            20

<210> SEQ ID NO 12
<211> LENGTH: 31
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline
<220> FEATURE:
<221> NAME/KEY: MOD_RES
<222> LOCATION: (20)..(20)
<223> OTHER INFORMATION: proline or hydroxyproline
<220> FEATURE:
<221> NAME/KEY: MOD_RES
<222> LOCATION: (26)..(26)
<223> OTHER INFORMATION: proline or hydroxyproline

<400> SEQUENCE: 12

Glu Arg Gly Ser Xaa Gly Pro Ala Gly Pro Lys Gly Ser Xaa Gly Glu
1               5                   10                  15

Ala Gly Arg Xaa Gly Glu Ala Gly Leu Xaa Gly Ala Lys Gly Leu
            20                  25                  30

<210> SEQ ID NO 13
<211> LENGTH: 32
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (8)..(8)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline
<220> FEATURE:
<221> NAME/KEY: MOD_RES
<222> LOCATION: (27)..(27)
<223> OTHER INFORMATION: proline or hydroxyproline
<220> FEATURE:

```
<221> NAME/KEY: MOD_RES
<222> LOCATION: (31)..(31)
<223> OTHER INFORMATION: proline or hydroxyproline

<400> SEQUENCE: 13

Gly Glu Arg Gly Ser Xaa Gly Xaa Ala Gly Pro Lys Gly Ser Pro Gly
1               5                   10                  15

Glu Ala Gly Arg Xaa Gly Glu Ala Gly Leu Xaa Gly Ala Lys Gly Leu
            20                  25                  30

<210> SEQ ID NO 14
<211> LENGTH: 23
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (20)..(20)
<223> OTHER INFORMATION: proline or hydroxyproline

<400> SEQUENCE: 14

Gly Leu Thr Gly Ser Xaa Gly Ser Xaa Gly Pro Asp Gly Lys Thr Gly
1               5                   10                  15

Pro Pro Gly Xaa Ala Gly Gln
            20

<210> SEQ ID NO 15
<211> LENGTH: 35
<212> TYPE: PRT
<213> ORGANISM: Homo sapiens

<400> SEQUENCE: 15

Gly Leu Thr Gly Ser Pro Gly Ser Pro Gly Pro Asp Gly Lys Thr Gly
1               5                   10                  15

Pro Pro Gly Pro Ala Gly Gln Asp Gly Arg Pro Gly Pro Pro Gly Pro
            20                  25                  30

Pro Gly Ala
        35

<210> SEQ ID NO 16
<211> LENGTH: 38
<212> TYPE: PRT
<213> ORGANISM: Homo sapiens

<400> SEQUENCE: 16

Gly Leu Thr Gly Ser Pro Gly Ser Pro Gly Pro Asp Gly Lys Thr Gly
1               5                   10                  15

Pro Pro Gly Pro Ala Gly Gln Asp Gly Arg Pro Gly Pro Pro Gly Pro
            20                  25                  30

Pro Gly Ala Arg Gly Gln
        35

<210> SEQ ID NO 17
<211> LENGTH: 17
<212> TYPE: PRT
<213> ORGANISM: Homo sapiens

<400> SEQUENCE: 17
```

```
Gly Gln Asp Gly Arg Pro Gly Pro Pro Gly Pro Pro Gly Ala Arg Gly
1               5                   10                  15

Gln

<210> SEQ ID NO 18
<211> LENGTH: 38
<212> TYPE: PRT
<213> ORGANISM: Homo sapiens

<400> SEQUENCE: 18

Gly Leu Thr Gly Ser Pro Gly Ser Pro Gly Pro Asp Gly Lys Thr Gly
1               5                   10                  15

Pro Pro Gly Pro Ala Gly Gln Asp Gly Arg Pro Gly Pro Pro Gly Pro
            20                  25                  30

Pro Gly Ala Arg Gly Gln
        35

<210> SEQ ID NO 19
<211> LENGTH: 33
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (30)..(30)
<223> OTHER INFORMATION: proline or hydroxyproline

<400> SEQUENCE: 19

Gly Lys Asp Gly Glu Ala Gly Ala Gln Gly Pro Xaa Gly Pro Ala Gly
1               5                   10                  15

Pro Ala Gly Glu Arg Gly Glu Gln Gly Pro Ala Gly Ser Xaa Gly Phe
            20                  25                  30

Gln

<210> SEQ ID NO 20
<211> LENGTH: 15
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline

<400> SEQUENCE: 20

Gly Glu Arg Gly Glu Gln Gly Pro Ala Gly Ser Xaa Gly Phe Gln
1               5                   10                  15

<210> SEQ ID NO 21
<211> LENGTH: 47
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (7)..(7)
<223> OTHER INFORMATION: proline or hydroxyproline
<220> FEATURE:
<221> NAME/KEY: MOD_RES
<222> LOCATION: (40)..(40)
<223> OTHER INFORMATION: proline or hydroxyproline
```

-continued

```
<220> FEATURE:
<221> NAME/KEY: MOD_RES
<222> LOCATION: (44)..(44)
<223> OTHER INFORMATION: proline or hydroxyproline

<400> SEQUENCE: 21

Glu Arg Gly Val Xaa Gly Xaa Pro Gly Ala Val Gly Pro Ala Gly Lys
1               5                   10                  15

Asp Gly Glu Ala Gly Ala Gln Gly Pro Pro Gly Pro Ala Gly Pro Ala
            20                  25                  30

Gly Glu Arg Gly Glu Gln Gly Xaa Ala Gly Ser Xaa Gly Phe Gln
        35                  40                  45

<210> SEQ ID NO 22
<211> LENGTH: 10
<212> TYPE: PRT
<213> ORGANISM: Homo sapiens

<400> SEQUENCE: 22

Pro Lys Gly Asp Thr Gly Pro Arg Gly Pro
1               5                   10

<210> SEQ ID NO 23
<211> LENGTH: 6
<212> TYPE: PRT
<213> ORGANISM: Homo sapiens

<400> SEQUENCE: 23

Ile Ser Val Pro Gly Pro
1               5

<210> SEQ ID NO 24
<211> LENGTH: 6
<212> TYPE: PRT
<213> ORGANISM: Homo sapiens

<400> SEQUENCE: 24

Val Pro Gly Pro Met Gly
1               5

<210> SEQ ID NO 25
<211> LENGTH: 6
<212> TYPE: PRT
<213> ORGANISM: Homo sapiens

<400> SEQUENCE: 25

Pro Gly Pro Met Gly Pro
1               5

<210> SEQ ID NO 26
<211> LENGTH: 6
<212> TYPE: PRT
<213> ORGANISM: Homo sapiens

<400> SEQUENCE: 26

Leu Pro Gly Pro Gly Gly
1               5

<210> SEQ ID NO 27
<211> LENGTH: 6
<212> TYPE: PRT
<213> ORGANISM: Homo sapiens

<400> SEQUENCE: 27
```

Phe Gln Gly Pro Pro Gly
1               5

<210> SEQ ID NO 28
<211> LENGTH: 6
<212> TYPE: PRT
<213> ORGANISM: Homo sapiens

<400> SEQUENCE: 28

Lys Asn Gly Asp Asp Gly
1               5

<210> SEQ ID NO 29
<211> LENGTH: 6
<212> TYPE: PRT
<213> ORGANISM: Homo sapiens

<400> SEQUENCE: 29

Ala Arg Gly Leu Pro Gly
1               5

<210> SEQ ID NO 30
<211> LENGTH: 6
<212> TYPE: PRT
<213> ORGANISM: Homo sapiens

<400> SEQUENCE: 30

Ser Gly Leu Asp Gly Ala
1               5

<210> SEQ ID NO 31
<211> LENGTH: 6
<212> TYPE: PRT
<213> ORGANISM: Homo sapiens

<400> SEQUENCE: 31

Leu Asp Gly Ala Lys Gly
1               5

<210> SEQ ID NO 32
<211> LENGTH: 6
<212> TYPE: PRT
<213> ORGANISM: Homo sapiens

<400> SEQUENCE: 32

Leu Pro Gly Glu Arg Gly
1               5

<210> SEQ ID NO 33
<211> LENGTH: 6
<212> TYPE: PRT
<213> ORGANISM: Homo sapiens

<400> SEQUENCE: 33

Val Arg Gly Glu Pro Gly
1               5

<210> SEQ ID NO 34
<211> LENGTH: 6
<212> TYPE: PRT
<213> ORGANISM: Homo sapiens

<400> SEQUENCE: 34

Pro Gly Ala Lys Gly Ala
1               5

<210> SEQ ID NO 35
<211> LENGTH: 6
<212> TYPE: PRT
<213> ORGANISM: Homo sapiens

<400> SEQUENCE: 35

Gly Gly Pro Pro Gly Pro
1               5

<210> SEQ ID NO 36
<211> LENGTH: 6
<212> TYPE: PRT
<213> ORGANISM: Homo sapiens

<400> SEQUENCE: 36

Asn Ser Gly Glu Pro Gly
1               5

<210> SEQ ID NO 37
<211> LENGTH: 6
<212> TYPE: PRT
<213> ORGANISM: Homo sapiens

<400> SEQUENCE: 37

Asp Gly Val Ala Gly Pro
1               5

<210> SEQ ID NO 38
<211> LENGTH: 6
<212> TYPE: PRT
<213> ORGANISM: Homo sapiens

<400> SEQUENCE: 38

Glu Arg Gly Ser Pro Gly
1               5

<210> SEQ ID NO 39
<211> LENGTH: 6
<212> TYPE: PRT
<213> ORGANISM: Homo sapiens

<400> SEQUENCE: 39

Leu Thr Gly Ser Pro Gly
1               5

<210> SEQ ID NO 40
<211> LENGTH: 6
<212> TYPE: PRT
<213> ORGANISM: Homo sapiens

<400> SEQUENCE: 40

Gln Asp Gly Arg Pro Gly
1               5

<210> SEQ ID NO 41
<211> LENGTH: 6
<212> TYPE: PRT
<213> ORGANISM: Homo sapiens

<400> SEQUENCE: 41

Arg Gly Val Pro Gly Pro
1               5

```
<210> SEQ ID NO 42
<211> LENGTH: 6
<212> TYPE: PRT
<213> ORGANISM: Homo sapiens

<400> SEQUENCE: 42

Val Gly Pro Ala Gly Lys
1               5

<210> SEQ ID NO 43
<211> LENGTH: 6
<212> TYPE: PRT
<213> ORGANISM: Homo sapiens

<400> SEQUENCE: 43

Glu Arg Gly Glu Gln Gly
1               5

<210> SEQ ID NO 44
<211> LENGTH: 6
<212> TYPE: PRT
<213> ORGANISM: Homo sapiens

<400> SEQUENCE: 44

Arg Gly Glu Gln Gly Pro
1               5

<210> SEQ ID NO 45
<211> LENGTH: 6
<212> TYPE: PRT
<213> ORGANISM: Homo sapiens

<400> SEQUENCE: 45

Pro Gly Glu Arg Gly Val
1               5

<210> SEQ ID NO 46
<211> LENGTH: 6
<212> TYPE: PRT
<213> ORGANISM: Homo sapiens

<400> SEQUENCE: 46

Ala Asn Gly Ala Pro Gly
1               5

<210> SEQ ID NO 47
<211> LENGTH: 6
<212> TYPE: PRT
<213> ORGANISM: Homo sapiens

<400> SEQUENCE: 47

Ala Arg Gly Ala Pro Gly
1               5

<210> SEQ ID NO 48
<211> LENGTH: 6
<212> TYPE: PRT
<213> ORGANISM: Homo sapiens

<400> SEQUENCE: 48

Pro Gly Asp Arg Gly Glu
1               5

<210> SEQ ID NO 49
<211> LENGTH: 6
```

```
<212> TYPE: PRT
<213> ORGANISM: Homo sapiens

<400> SEQUENCE: 49

Ala Lys Gly Asp Ala Gly
1               5

<210> SEQ ID NO 50
<211> LENGTH: 6
<212> TYPE: PRT
<213> ORGANISM: Homo sapiens

<400> SEQUENCE: 50

Pro Ile Gly Asn Val Gly
1               5

<210> SEQ ID NO 51
<211> LENGTH: 6
<212> TYPE: PRT
<213> ORGANISM: Homo sapiens

<400> SEQUENCE: 51

Ala Ala Gly Arg Val Gly
1               5

<210> SEQ ID NO 52
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (4)..(4)
<223> OTHER INFORMATION: proline or hydroxyproline

<400> SEQUENCE: 52

Pro Xaa Gly Xaa Ala Gly
1               5

<210> SEQ ID NO 53
<211> LENGTH: 6
<212> TYPE: PRT
<213> ORGANISM: Homo sapiens

<400> SEQUENCE: 53

Gly Ala Asp Gly Pro Ala
1               5

<210> SEQ ID NO 54
<211> LENGTH: 6
<212> TYPE: PRT
<213> ORGANISM: Homo sapiens

<400> SEQUENCE: 54

Gly Pro Gln Gly Ile Ala
1               5

<210> SEQ ID NO 55
<211> LENGTH: 6
<212> TYPE: PRT
<213> ORGANISM: Homo sapiens

<400> SEQUENCE: 55
```

Gly Gln Arg Gly Val Val
1               5

<210> SEQ ID NO 56
<211> LENGTH: 6
<212> TYPE: PRT
<213> ORGANISM: Homo sapiens

<400> SEQUENCE: 56

Gln Arg Gly Val Val Gly
1               5

<210> SEQ ID NO 57
<211> LENGTH: 6
<212> TYPE: PRT
<213> ORGANISM: Homo sapiens

<400> SEQUENCE: 57

Gly Leu Pro Gly Gln Arg
1               5

<210> SEQ ID NO 58
<211> LENGTH: 6
<212> TYPE: PRT
<213> ORGANISM: Homo sapiens

<400> SEQUENCE: 58

Pro Gly Leu Pro Gly Pro
1               5

<210> SEQ ID NO 59
<211> LENGTH: 6
<212> TYPE: PRT
<213> ORGANISM: Homo sapiens

<400> SEQUENCE: 59

Pro Met Gly Pro Pro Gly
1               5

<210> SEQ ID NO 60
<211> LENGTH: 6
<212> TYPE: PRT
<213> ORGANISM: Homo sapiens

<400> SEQUENCE: 60

Met Gly Pro Pro Gly Leu
1               5

<210> SEQ ID NO 61
<211> LENGTH: 6
<212> TYPE: PRT
<213> ORGANISM: Homo sapiens

<400> SEQUENCE: 61

Asp Lys Gly Glu Thr Gly
1               5

<210> SEQ ID NO 62
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

```
<400> SEQUENCE: 62

Leu Gln Gly Pro Xaa Gly
1               5

<210> SEQ ID NO 63
<211> LENGTH: 6
<212> TYPE: PRT
<213> ORGANISM: Homo sapiens

<400> SEQUENCE: 63

Ser Ala Gly Ala Pro Gly
1               5

<210> SEQ ID NO 64
<211> LENGTH: 6
<212> TYPE: PRT
<213> ORGANISM: Homo sapiens

<400> SEQUENCE: 64

Arg Thr Gly Asp Ala Gly
1               5

<210> SEQ ID NO 65
<211> LENGTH: 5
<212> TYPE: PRT
<213> ORGANISM: Homo sapiens

<400> SEQUENCE: 65

Phe Asp Phe Ser Phe
1               5

<210> SEQ ID NO 66
<211> LENGTH: 5
<212> TYPE: PRT
<213> ORGANISM: Homo sapiens

<400> SEQUENCE: 66

Phe Asp Phe Ser Phe
1               5

<210> SEQ ID NO 67
<211> LENGTH: 6
<212> TYPE: PRT
<213> ORGANISM: Homo sapiens

<400> SEQUENCE: 67

Ala Thr Gly Ala Ala Gly
1               5

<210> SEQ ID NO 68
<211> LENGTH: 6
<212> TYPE: PRT
<213> ORGANISM: Homo sapiens

<400> SEQUENCE: 68

Ala Lys Gly Glu Ala Gly
1               5

<210> SEQ ID NO 69
<211> LENGTH: 6
<212> TYPE: PRT
<213> ORGANISM: Homo sapiens

<400> SEQUENCE: 69
```

Gly Ile Ala Gly Ala Pro
1               5

<210> SEQ ID NO 70
<211> LENGTH: 6
<212> TYPE: PRT
<213> ORGANISM: Homo sapiens

<400> SEQUENCE: 70

Ile Ala Gly Ala Pro Gly
1               5

<210> SEQ ID NO 71
<211> LENGTH: 6
<212> TYPE: PRT
<213> ORGANISM: Homo sapiens

<400> SEQUENCE: 71

Val Gln Gly Pro Pro Gly
1               5

<210> SEQ ID NO 72
<211> LENGTH: 6
<212> TYPE: PRT
<213> ORGANISM: Homo sapiens
<220> FEATURE:
<221> NAME/KEY: MOD_RES
<222> LOCATION: (4)..(5)
<223> OTHER INFORMATION: proline or hydroxproline

<400> SEQUENCE: 72

Leu Pro Gly Xaa Xaa Gly
1               5

<210> SEQ ID NO 73
<211> LENGTH: 6
<212> TYPE: PRT
<213> ORGANISM: Homo sapiens

<400> SEQUENCE: 73

Ala Gly Pro Lys Gly Ser
1               5

<210> SEQ ID NO 74
<211> LENGTH: 6
<212> TYPE: PRT
<213> ORGANISM: Homo sapiens

<400> SEQUENCE: 74

Arg Gly Ser Pro Gly Pro
1               5

<210> SEQ ID NO 75
<211> LENGTH: 6
<212> TYPE: PRT
<213> ORGANISM: Homo sapiens

<400> SEQUENCE: 75

Phe Ala Gly Pro Pro Gly
1               5

<210> SEQ ID NO 76
<211> LENGTH: 6
<212> TYPE: PRT
<213> ORGANISM: Homo sapiens

```
<400> SEQUENCE: 76

Gln Ala Gly Val Met Gly
1               5

<210> SEQ ID NO 77
<211> LENGTH: 6
<212> TYPE: PRT
<213> ORGANISM: Homo sapiens

<400> SEQUENCE: 77

Ala Arg Gly Gln Ala Gly
1               5

<210> SEQ ID NO 78
<211> LENGTH: 6
<212> TYPE: PRT
<213> ORGANISM: Homo sapiens

<400> SEQUENCE: 78

Asn Val Gly Ala Pro Gly
1               5

<210> SEQ ID NO 79
<211> LENGTH: 6
<212> TYPE: PRT
<213> ORGANISM: Homo sapiens

<400> SEQUENCE: 79

Pro Ala Gly Glu Arg Gly
1               5

<210> SEQ ID NO 80
<211> LENGTH: 6
<212> TYPE: PRT
<213> ORGANISM: Homo sapiens

<400> SEQUENCE: 80

Lys Asp Gly Glu Ala Gly
1               5

<210> SEQ ID NO 81
<211> LENGTH: 6
<212> TYPE: PRT
<213> ORGANISM: Homo sapiens

<400> SEQUENCE: 81

Gly Glu Val Gly Pro Pro
1               5

<210> SEQ ID NO 82
<211> LENGTH: 6
<212> TYPE: PRT
<213> ORGANISM: Homo sapiens

<400> SEQUENCE: 82

Ala Arg Gly Glu Arg Gly
1               5

<210> SEQ ID NO 83
<211> LENGTH: 6
<212> TYPE: PRT
<213> ORGANISM: Homo sapiens

<400> SEQUENCE: 83
```

Gln Gly Leu Pro Gly Pro
1               5

<210> SEQ ID NO 84
<211> LENGTH: 6
<212> TYPE: PRT
<213> ORGANISM: Homo sapiens

<400> SEQUENCE: 84

Ile Ala Gly Gln Arg Gly
1               5

<210> SEQ ID NO 85
<211> LENGTH: 6
<212> TYPE: PRT
<213> ORGANISM: Homo sapiens

<400> SEQUENCE: 85

Leu Thr Gly Pro Ile Gly
1               5

<210> SEQ ID NO 86
<211> LENGTH: 6
<212> TYPE: PRT
<213> ORGANISM: Homo sapiens

<400> SEQUENCE: 86

Ala Gly Leu Pro Gly Pro
1               5

<210> SEQ ID NO 87
<211> LENGTH: 6
<212> TYPE: PRT
<213> ORGANISM: Homo sapiens

<400> SEQUENCE: 87

Arg Gly Val Val Gly Leu
1               5

<210> SEQ ID NO 88
<211> LENGTH: 6
<212> TYPE: PRT
<213> ORGANISM: Homo sapiens

<400> SEQUENCE: 88

Ala Gly Pro Pro Gly Ala
1               5

<210> SEQ ID NO 89
<211> LENGTH: 6
<212> TYPE: PRT
<213> ORGANISM: Homo sapiens

<400> SEQUENCE: 89

Leu Ala Gly Pro Pro Gly
1               5

<210> SEQ ID NO 90
<211> LENGTH: 6
<212> TYPE: PRT
<213> ORGANISM: Homo sapiens

<400> SEQUENCE: 90

Glu Pro Gly Lys Gln Gly
1               5

<210> SEQ ID NO 91
<211> LENGTH: 6
<212> TYPE: PRT
<213> ORGANISM: Homo sapiens

<400> SEQUENCE: 91

Ala Thr Gly Phe Pro Gly
1               5

<210> SEQ ID NO 92
<211> LENGTH: 6
<212> TYPE: PRT
<213> ORGANISM: Homo sapiens

<400> SEQUENCE: 92

Pro Ser Gly Ala Ser Gly
1               5

<210> SEQ ID NO 93
<211> LENGTH: 6
<212> TYPE: PRT
<213> ORGANISM: Homo sapiens

<400> SEQUENCE: 93

Gly Lys Gln Gly Pro Ser
1               5

<210> SEQ ID NO 94
<211> LENGTH: 6
<212> TYPE: PRT
<213> ORGANISM: Homo sapiens

<400> SEQUENCE: 94

Gly Pro Pro Gly Pro Ala
1               5

<210> SEQ ID NO 95
<211> LENGTH: 6
<212> TYPE: PRT
<213> ORGANISM: Homo sapiens

<400> SEQUENCE: 95

Ala Gly Gln Arg Gly Val
1               5

<210> SEQ ID NO 96
<211> LENGTH: 6
<212> TYPE: PRT
<213> ORGANISM: Homo sapiens

<400> SEQUENCE: 96

Ala Arg Gly Pro Ala Gly
1               5

<210> SEQ ID NO 97
<211> LENGTH: 6
<212> TYPE: PRT
<213> ORGANISM: Homo sapiens

<400> SEQUENCE: 97

Ala Ser Gly Pro Ala Gly
1               5

```
<210> SEQ ID NO 98
<211> LENGTH: 6
<212> TYPE: PRT
<213> ORGANISM: Homo sapiens

<400> SEQUENCE: 98

Val Val Gly Leu Pro Gly
1               5

<210> SEQ ID NO 99
<211> LENGTH: 6
<212> TYPE: PRT
<213> ORGANISM: Homo sapiens

<400> SEQUENCE: 99

Val Gly Pro Pro Gly Pro
1               5

<210> SEQ ID NO 100
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline

<400> SEQUENCE: 100

Gly Xaa Pro Gly Xaa Xaa
1               5

<210> SEQ ID NO 101
<211> LENGTH: 6
<212> TYPE: PRT
<213> ORGANISM: Homo sapiens

<400> SEQUENCE: 101

Gln Leu Ser Tyr Gly Tyr
1               5

<210> SEQ ID NO 102
<211> LENGTH: 6
<212> TYPE: PRT
<213> ORGANISM: Homo sapiens

<400> SEQUENCE: 102

Glu Lys Ser Thr Gly Gly
1               5

<210> SEQ ID NO 103
<211> LENGTH: 6
<212> TYPE: PRT
<213> ORGANISM: Homo sapiens

<400> SEQUENCE: 103

Pro Pro Gly Pro Gln Gly
1               5

<210> SEQ ID NO 104
```

```
<211> LENGTH: 6
<212> TYPE: PRT
<213> ORGANISM: Homo sapiens

<400> SEQUENCE: 104

Lys Gly His Arg Gly Phe
1               5

<210> SEQ ID NO 105
<211> LENGTH: 6
<212> TYPE: PRT
<213> ORGANISM: Homo sapiens

<400> SEQUENCE: 105

Pro Ser Gly Pro Arg Gly
1               5

<210> SEQ ID NO 106
<211> LENGTH: 6
<212> TYPE: PRT
<213> ORGANISM: Homo sapiens

<400> SEQUENCE: 106

Ala Pro Gly Pro Gln Gly
1               5

<210> SEQ ID NO 107
<211> LENGTH: 6
<212> TYPE: PRT
<213> ORGANISM: Homo sapiens

<400> SEQUENCE: 107

Ala Pro Gly Pro Ala Gly
1               5

<210> SEQ ID NO 108
<211> LENGTH: 6
<212> TYPE: PRT
<213> ORGANISM: Homo sapiens

<400> SEQUENCE: 108

Phe Pro Gly Ala Val Gly
1               5

<210> SEQ ID NO 109
<211> LENGTH: 6
<212> TYPE: PRT
<213> ORGANISM: Homo sapiens

<400> SEQUENCE: 109

Ser Glu Gly Pro Gln Gly
1               5

<210> SEQ ID NO 110
<211> LENGTH: 6
<212> TYPE: PRT
<213> ORGANISM: Homo sapiens

<400> SEQUENCE: 110

Gly Ala Asn Gly Ala Pro
1               5

<210> SEQ ID NO 111
<211> LENGTH: 6
<212> TYPE: PRT
```

```
<213> ORGANISM: Homo sapiens

<400> SEQUENCE: 111

Gly Ala Arg Gly Leu Ala
1               5

<210> SEQ ID NO 112
<211> LENGTH: 6
<212> TYPE: PRT
<213> ORGANISM: Homo sapiens

<400> SEQUENCE: 112

Ser Gly Pro Gln Gly Pro
1               5

<210> SEQ ID NO 113
<211> LENGTH: 6
<212> TYPE: PRT
<213> ORGANISM: Homo sapiens

<400> SEQUENCE: 113

Glu Pro Gly Pro Val Gly
1               5

<210> SEQ ID NO 114
<211> LENGTH: 6
<212> TYPE: PRT
<213> ORGANISM: Homo sapiens

<400> SEQUENCE: 114

Glu Pro Gly Pro Thr Gly
1               5

<210> SEQ ID NO 115
<211> LENGTH: 6
<212> TYPE: PRT
<213> ORGANISM: Homo sapiens

<400> SEQUENCE: 115

Arg Gly Phe Pro Gly Ala
1               5

<210> SEQ ID NO 116
<211> LENGTH: 6
<212> TYPE: PRT
<213> ORGANISM: Homo sapiens

<400> SEQUENCE: 116

Lys Gly Pro Ala Gly Glu
1               5

<210> SEQ ID NO 117
<211> LENGTH: 6
<212> TYPE: PRT
<213> ORGANISM: Homo sapiens

<400> SEQUENCE: 117

Ile Pro Gly Ala Pro Gly
1               5

<210> SEQ ID NO 118
<211> LENGTH: 6
<212> TYPE: PRT
<213> ORGANISM: Homo sapiens
```

```
<400> SEQUENCE: 118

Leu Pro Gly Ala Lys Gly
1               5

<210> SEQ ID NO 119
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: proline or hydroxyproline
<220> FEATURE:
<221> NAME/KEY: MOD_RES
<222> LOCATION: (4)..(5)
<223> OTHER INFORMATION: proline or hydroxyproline

<400> SEQUENCE: 119

Xaa Xaa Gly Xaa Xaa Gly
1               5

<210> SEQ ID NO 120
<211> LENGTH: 6
<212> TYPE: PRT
<213> ORGANISM: Homo sapiens

<400> SEQUENCE: 120

Pro Pro Gly Ala Arg Gly
1               5

<210> SEQ ID NO 121
<211> LENGTH: 6
<212> TYPE: PRT
<213> ORGANISM: Homo sapiens

<400> SEQUENCE: 121

Pro Gly Lys Ala Gly Glu
1               5

<210> SEQ ID NO 122
<211> LENGTH: 6
<212> TYPE: PRT
<213> ORGANISM: Homo sapiens

<400> SEQUENCE: 122

Ala Val Gly Pro Ala Gly
1               5

<210> SEQ ID NO 123
<211> LENGTH: 6
<212> TYPE: PRT
<213> ORGANISM: Homo sapiens

<400> SEQUENCE: 123

Pro Ala Gly Pro Ala Gly
1               5

<210> SEQ ID NO 124
<211> LENGTH: 6
<212> TYPE: PRT
<213> ORGANISM: Homo sapiens

<400> SEQUENCE: 124

Ala Gly Pro Ala Gly Glu
1               5
```

<210> SEQ ID NO 125
<211> LENGTH: 6
<212> TYPE: PRT
<213> ORGANISM: Homo sapiens

<400> SEQUENCE: 125

Ala Pro Gly Pro Asp Gly
1               5

<210> SEQ ID NO 126
<211> LENGTH: 6
<212> TYPE: PRT
<213> ORGANISM: Homo sapiens

<400> SEQUENCE: 126

Arg Gly Glu Arg Gly Phe
1               5

<210> SEQ ID NO 127
<211> LENGTH: 6
<212> TYPE: PRT
<213> ORGANISM: Homo sapiens

<400> SEQUENCE: 127

Pro Ala Gly Pro Arg Gly
1               5

<210> SEQ ID NO 128
<211> LENGTH: 6
<212> TYPE: PRT
<213> ORGANISM: Homo sapiens

<400> SEQUENCE: 128

Lys Asp Gly Val Arg Gly
1               5

<210> SEQ ID NO 129
<211> LENGTH: 6
<212> TYPE: PRT
<213> ORGANISM: Homo sapiens

<400> SEQUENCE: 129

Pro Ala Gly Pro Thr Gly
1               5

<210> SEQ ID NO 130
<211> LENGTH: 6
<212> TYPE: PRT
<213> ORGANISM: Homo sapiens

<400> SEQUENCE: 130

Thr Gly Ala Arg Gly Ala
1               5

<210> SEQ ID NO 131
<211> LENGTH: 6
<212> TYPE: PRT
<213> ORGANISM: Homo sapiens

<400> SEQUENCE: 131

Pro Gly Pro Ala Gly Phe
1               5

<210> SEQ ID NO 132

```
<211> LENGTH: 6
<212> TYPE: PRT
<213> ORGANISM: Homo sapiens

<400> SEQUENCE: 132

Glu Pro Gly Asp Ala Gly
1               5

<210> SEQ ID NO 133
<211> LENGTH: 6
<212> TYPE: PRT
<213> ORGANISM: Homo sapiens

<400> SEQUENCE: 133

Pro Ala Gly Pro Pro Gly
1               5

<210> SEQ ID NO 134
<211> LENGTH: 6
<212> TYPE: PRT
<213> ORGANISM: Homo sapiens

<400> SEQUENCE: 134

Ser Ala Gly Pro Pro Gly
1               5

<210> SEQ ID NO 135
<211> LENGTH: 6
<212> TYPE: PRT
<213> ORGANISM: Homo sapiens

<400> SEQUENCE: 135

Asp Gly Thr Ser Gly His
1               5

<210> SEQ ID NO 136
<211> LENGTH: 6
<212> TYPE: PRT
<213> ORGANISM: Homo sapiens

<400> SEQUENCE: 136

Asn Ala Gly Pro Pro Gly
1               5

<210> SEQ ID NO 137
<211> LENGTH: 6
<212> TYPE: PRT
<213> ORGANISM: Homo sapiens

<400> SEQUENCE: 137

Phe Arg Gly Pro Ala Gly
1               5

<210> SEQ ID NO 138
<211> LENGTH: 6
<212> TYPE: PRT
<213> ORGANISM: Homo sapiens

<400> SEQUENCE: 138

Gly Glu Lys Gly Ser Pro
1               5

<210> SEQ ID NO 139
<211> LENGTH: 6
<212> TYPE: PRT
```

```
<213> ORGANISM: Homo sapiens

<400> SEQUENCE: 139

Gly Ala Pro Gly Thr Pro
1               5

<210> SEQ ID NO 140
<211> LENGTH: 6
<212> TYPE: PRT
<213> ORGANISM: Homo sapiens

<400> SEQUENCE: 140

Pro Gly Pro Gln Gly Ile
1               5

<210> SEQ ID NO 141
<211> LENGTH: 6
<212> TYPE: PRT
<213> ORGANISM: Homo sapiens

<400> SEQUENCE: 141

Gly Ala Pro Gly Glu Lys
1               5

<210> SEQ ID NO 142
<211> LENGTH: 6
<212> TYPE: PRT
<213> ORGANISM: Homo sapiens

<400> SEQUENCE: 142

Pro Gln Gly Ile Ala Gly
1               5

<210> SEQ ID NO 143
<211> LENGTH: 6
<212> TYPE: PRT
<213> ORGANISM: Homo sapiens

<400> SEQUENCE: 143

Ala Ile Gly Ser Pro Gly
1               5

<210> SEQ ID NO 144
<211> LENGTH: 6
<212> TYPE: PRT
<213> ORGANISM: Homo sapiens

<400> SEQUENCE: 144

Gln Pro Gly Val Met Gly
1               5

<210> SEQ ID NO 145
<211> LENGTH: 6
<212> TYPE: PRT
<213> ORGANISM: Homo sapiens

<400> SEQUENCE: 145

Ala Gly Pro Pro Gly Met
1               5

<210> SEQ ID NO 146
<211> LENGTH: 6
<212> TYPE: PRT
<213> ORGANISM: Homo sapiens
```

```
<400> SEQUENCE: 146

Gly Pro Ser Gly Glu Pro
1               5

<210> SEQ ID NO 147
<211> LENGTH: 6
<212> TYPE: PRT
<213> ORGANISM: Homo sapiens

<400> SEQUENCE: 147

Glu Arg Gly Pro Pro Gly
1               5

<210> SEQ ID NO 148
<211> LENGTH: 6
<212> TYPE: PRT
<213> ORGANISM: Homo sapiens

<400> SEQUENCE: 148

Arg Gly Pro Pro Gly Pro
1               5

<210> SEQ ID NO 149
<211> LENGTH: 6
<212> TYPE: PRT
<213> ORGANISM: Homo sapiens

<400> SEQUENCE: 149

Pro Val Gly Pro Val Gly
1               5

<210> SEQ ID NO 150
<211> LENGTH: 6
<212> TYPE: PRT
<213> ORGANISM: Homo sapiens

<400> SEQUENCE: 150

Pro Gln Gly Pro Arg Gly
1               5

<210> SEQ ID NO 151
<211> LENGTH: 6
<212> TYPE: PRT
<213> ORGANISM: Homo sapiens

<400> SEQUENCE: 151

His Arg Gly Phe Ser Gly
1               5

<210> SEQ ID NO 152
<211> LENGTH: 6
<212> TYPE: PRT
<213> ORGANISM: Homo sapiens

<400> SEQUENCE: 152

Glu Gln Gly Pro Ser Gly
1               5

<210> SEQ ID NO 153
<211> LENGTH: 6
<212> TYPE: PRT
<213> ORGANISM: Homo sapiens

<400> SEQUENCE: 153
```

```
Pro Arg Gly Pro Pro Gly
1               5

<210> SEQ ID NO 154
<211> LENGTH: 6
<212> TYPE: PRT
<213> ORGANISM: Homo sapiens

<400> SEQUENCE: 154

Pro Pro Gly Pro Arg Gly
1               5

<210> SEQ ID NO 155
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Hydroxyproline
<220> FEATURE:
<221> NAME/KEY: MOD_RES
<222> LOCATION: (5)..(6)
<223> OTHER INFORMATION: Hydroxyproline

<400> SEQUENCE: 155

Val Gly Gly Leu Ala Gly
1               5

<210> SEQ ID NO 156
<211> LENGTH: 6
<212> TYPE: PRT
<213> ORGANISM: Homo sapiens

<400> SEQUENCE: 156

Gly Pro Pro Ser Ala Gly
1               5

<210> SEQ ID NO 157
<211> LENGTH: 6
<212> TYPE: PRT
<213> ORGANISM: Homo sapiens

<400> SEQUENCE: 157

Pro Pro Ser Ala Gly Phe
1               5

<210> SEQ ID NO 158

<400> SEQUENCE: 158

000

<210> SEQ ID NO 159
<211> LENGTH: 6
<212> TYPE: PRT
<213> ORGANISM: Homo sapiens

<400> SEQUENCE: 159

Val Lys Gly Glu Arg Gly
1               5

<210> SEQ ID NO 160
<211> LENGTH: 6
<212> TYPE: PRT
<213> ORGANISM: Homo sapiens
```

```
<400> SEQUENCE: 160

Thr Pro Gly Pro Gln Gly
1               5

<210> SEQ ID NO 161
<211> LENGTH: 6
<212> TYPE: PRT
<213> ORGANISM: Homo sapiens

<400> SEQUENCE: 161

Gln Met Gly Pro Arg Gly
1               5

<210> SEQ ID NO 162
<211> LENGTH: 6
<212> TYPE: PRT
<213> ORGANISM: Homo sapiens

<400> SEQUENCE: 162

Pro Gly Pro Pro Gly Ala
1               5

<210> SEQ ID NO 163
<211> LENGTH: 6
<212> TYPE: PRT
<213> ORGANISM: Homo sapiens

<400> SEQUENCE: 163

Gln Gly Ile Ala Gly Gln
1               5

<210> SEQ ID NO 164
<211> LENGTH: 6
<212> TYPE: PRT
<213> ORGANISM: Homo sapiens

<400> SEQUENCE: 164

Pro Gly Ala Asp Gly Gln
1               5

<210> SEQ ID NO 165
<211> LENGTH: 6
<212> TYPE: PRT
<213> ORGANISM: Homo sapiens

<400> SEQUENCE: 165

Ala Gly Ser Pro Gly Phe
1               5

<210> SEQ ID NO 166
<211> LENGTH: 6
<212> TYPE: PRT
<213> ORGANISM: Homo sapiens

<400> SEQUENCE: 166

Leu Pro Gly Pro Ser Gly
1               5

<210> SEQ ID NO 167
<211> LENGTH: 6
<212> TYPE: PRT
<213> ORGANISM: Homo sapiens

<400> SEQUENCE: 167
```

```
Pro Pro Gly Pro Lys Gly
1               5

<210> SEQ ID NO 168
<211> LENGTH: 6
<212> TYPE: PRT
<213> ORGANISM: Homo sapiens

<400> SEQUENCE: 168

Pro Gly Glu Arg Gly Ala
1               5

<210> SEQ ID NO 169
<211> LENGTH: 6
<212> TYPE: PRT
<213> ORGANISM: Homo sapiens

<400> SEQUENCE: 169

Ile Lys Gly Pro Ala Gly
1               5

<210> SEQ ID NO 170
<211> LENGTH: 6
<212> TYPE: PRT
<213> ORGANISM: Homo sapiens

<400> SEQUENCE: 170

Pro Lys Gly Pro Ala Gly
1               5

<210> SEQ ID NO 171
<211> LENGTH: 6
<212> TYPE: PRT
<213> ORGANISM: Homo sapiens

<400> SEQUENCE: 171

Gly Arg Asn Gly Asp Pro
1               5

<210> SEQ ID NO 172
<211> LENGTH: 6
<212> TYPE: PRT
<213> ORGANISM: Homo sapiens

<400> SEQUENCE: 172

Ser Pro Gly Glu Gln Gly
1               5

<210> SEQ ID NO 173
<211> LENGTH: 6
<212> TYPE: PRT
<213> ORGANISM: Homo sapiens

<400> SEQUENCE: 173

Gly Pro Ala Gly Arg Pro
1               5

<210> SEQ ID NO 174
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
```

```
<400> SEQUENCE: 174

Pro Xaa Gly Pro Ile Gly
1               5

<210> SEQ ID NO 175
<211> LENGTH: 6
<212> TYPE: PRT
<213> ORGANISM: Homo sapiens

<400> SEQUENCE: 175

Thr Gly Asp Ala Gly Pro
1               5

<210> SEQ ID NO 176
<211> LENGTH: 6
<212> TYPE: PRT
<213> ORGANISM: Homo sapiens

<400> SEQUENCE: 176

Leu Ser Gly Glu Arg Gly
1               5

<210> SEQ ID NO 177
<211> LENGTH: 6
<212> TYPE: PRT
<213> ORGANISM: Homo sapiens

<400> SEQUENCE: 177

Thr Gly Pro Arg Gly Pro
1               5

<210> SEQ ID NO 178
<211> LENGTH: 20
<212> TYPE: PRT
<213> ORGANISM: Homo sapiens

<400> SEQUENCE: 178

Ala Gly Ile Pro Gly Ala Pro Gly Leu Met Gly Ala Arg Gly Pro Pro
1               5                   10                  15

Gly Pro Ala Gly
            20

<210> SEQ ID NO 179
<211> LENGTH: 19
<212> TYPE: PRT
<213> ORGANISM: Homo sapiens

<400> SEQUENCE: 179

Lys Gly Asp Pro Gly Pro Pro Gly Ile Pro Gly Arg Asn Gly Asp Pro
1               5                   10                  15

Gly Ile Pro

<210> SEQ ID NO 180
<211> LENGTH: 20
<212> TYPE: PRT
<213> ORGANISM: Homo sapiens

<400> SEQUENCE: 180

Gly Leu Ala Gly Pro Pro Gly Met Pro Gly Pro Arg Gly Ser Pro Gly
1               5                   10                  15

Pro Gln Gly Val
            20
```

<210> SEQ ID NO 181
<211> LENGTH: 21
<212> TYPE: PRT
<213> ORGANISM: Homo sapiens

<400> SEQUENCE: 181

Gly Glu Arg Gly Leu Pro Gly Pro Pro Gly Ile Lys Gly Pro Ala Gly
1               5                   10                  15

Ile Pro Gly Phe Pro
            20

<210> SEQ ID NO 182
<211> LENGTH: 22
<212> TYPE: PRT
<213> ORGANISM: Homo sapiens

<400> SEQUENCE: 182

Gly Ile Ala Gly Ile Thr Gly Ala Arg Gly Leu Ala Gly Pro Pro Gly
1               5                   10                  15

Met Pro Gly Pro Arg Gly
            20

<210> SEQ ID NO 183
<211> LENGTH: 23
<212> TYPE: PRT
<213> ORGANISM: Homo sapiens

<400> SEQUENCE: 183

Gly Ile Lys Gly His Arg Gly Phe Pro Gly Asn Pro Gly Ala Pro Gly
1               5                   10                  15

Ser Pro Gly Pro Ala Gly Gln
            20

<210> SEQ ID NO 184
<211> LENGTH: 23
<212> TYPE: PRT
<213> ORGANISM: Homo sapiens

<400> SEQUENCE: 184

Ala Arg Gly Leu Ala Gly Pro Pro Gly Met Pro Gly Pro Arg Gly Ser
1               5                   10                  15

Pro Gly Pro Gln Gly Val Lys
            20

<210> SEQ ID NO 185
<211> LENGTH: 25
<212> TYPE: PRT
<213> ORGANISM: Homo sapiens

<400> SEQUENCE: 185

Ile Thr Gly Ala Arg Gly Leu Ala Gly Pro Pro Gly Met Pro Gly Pro
1               5                   10                  15

Arg Gly Ser Pro Gly Pro Gln Gly Val
            20                  25

<210> SEQ ID NO 186
<211> LENGTH: 26
<212> TYPE: PRT
<213> ORGANISM: Homo sapiens

<400> SEQUENCE: 186

Ile Thr Gly Ala Arg Gly Leu Ala Gly Pro Pro Gly Met Pro Gly Pro

```
                1               5                  10                 15
Arg Gly Ser Pro Gly Pro Gln Gly Val Lys
                20                 25

<210> SEQ ID NO 187
<211> LENGTH: 26
<212> TYPE: PRT
<213> ORGANISM: Homo sapiens

<400> SEQUENCE: 187

Gly Ile Thr Gly Ala Arg Gly Leu Ala Gly Pro Pro Gly Met Pro Gly
1               5                  10                 15

Pro Arg Gly Ser Pro Gly Pro Gln Gly Val
                20                 25

<210> SEQ ID NO 188
<211> LENGTH: 26
<212> TYPE: PRT
<213> ORGANISM: Homo sapiens

<400> SEQUENCE: 188

Gly Val Lys Gly Glu Ser Gly Lys Pro Gly Ala Asn Gly Leu Ser Gly
1               5                  10                 15

Glu Arg Gly Pro Pro Gly Pro Gln Gly Leu
                20                 25

<210> SEQ ID NO 189
<211> LENGTH: 26
<212> TYPE: PRT
<213> ORGANISM: Homo sapiens

<400> SEQUENCE: 189

Gly Ser Arg Gly Ala Pro Gly Pro Gln Gly Pro Arg Gly Asp Lys Gly
1               5                  10                 15

Glu Thr Gly Glu Arg Gly Ala Ala Gly Ile
                20                 25

<210> SEQ ID NO 190
<211> LENGTH: 28
<212> TYPE: PRT
<213> ORGANISM: Homo sapiens

<400> SEQUENCE: 190

Pro Lys Gly Asp Ala Gly Gln Pro Gly Glu Lys Gly Ser Pro Gly Ala
1               5                  10                 15

Gln Gly Pro Pro Gly Ala Pro Gly Pro Leu Gly Ile
                20                 25

<210> SEQ ID NO 191
<211> LENGTH: 27
<212> TYPE: PRT
<213> ORGANISM: Homo sapiens

<400> SEQUENCE: 191

Gly Ile Thr Gly Ala Arg Gly Leu Ala Gly Pro Pro Gly Met Pro Gly
1               5                  10                 15

Pro Arg Gly Ser Pro Gly Pro Gln Gly Val Lys
                20                 25

<210> SEQ ID NO 192
<211> LENGTH: 32
<212> TYPE: PRT
```

```
<213> ORGANISM: Homo sapiens

<400> SEQUENCE: 192

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala Ala Gly Thr Pro Gly Leu
            20                  25                  30

<210> SEQ ID NO 193
<211> LENGTH: 35
<212> TYPE: PRT
<213> ORGANISM: Homo sapiens

<400> SEQUENCE: 193

Gly His Ala Gly Ala Gln Gly Pro Pro Gly Pro Pro Gly Ile Asn Gly
1               5                   10                  15

Ser Pro Gly Gly Lys Gly Glu Met Gly Pro Ala Gly Ile Pro Gly Ala
            20                  25                  30

Pro Gly Leu
        35

<210> SEQ ID NO 194
<211> LENGTH: 48
<212> TYPE: PRT
<213> ORGANISM: Homo sapiens

<400> SEQUENCE: 194

Ala Gly Lys Ser Gly Asp Arg Gly Glu Ser Gly Pro Ala Gly Pro Ala
1               5                   10                  15

Gly Ala Pro Gly Pro Ala Gly Ser Arg Gly Ala Pro Gly Pro Gln Gly
            20                  25                  30

Pro Arg Gly Asp Lys Gly Glu Thr Gly Glu Arg Gly Ala Ala Gly Ile
        35                  40                  45

<210> SEQ ID NO 195
<211> LENGTH: 50
<212> TYPE: PRT
<213> ORGANISM: Homo sapiens

<400> SEQUENCE: 195

Gly Leu Gln Gly Leu Pro Gly Thr Gly Gly Pro Pro Gly Glu Asn Gly
1               5                   10                  15

Lys Pro Gly Glu Pro Gly Pro Lys Gly Asp Ala Gly Ala Pro Gly Ala
            20                  25                  30

Pro Gly Gly Lys Gly Asp Ala Gly Ala Pro Gly Glu Arg Gly Pro Pro
        35                  40                  45

Gly Leu
    50

<210> SEQ ID NO 196
<211> LENGTH: 21
<212> TYPE: PRT
<213> ORGANISM: Homo sapiens

<400> SEQUENCE: 196

Gly Glu Arg Gly Leu Pro Gly Pro Gly Ile Lys Gly Pro Ala Gly
1               5                   10                  15

Ile Pro Gly Phe Pro
            20
```

-continued

```
<210> SEQ ID NO 197
<211> LENGTH: 24
<212> TYPE: PRT
<213> ORGANISM: Homo sapiens

<400> SEQUENCE: 197

Ala Val Gly Gly Leu Ala Gly Tyr Pro Gly Pro Ala Gly Pro Pro Gly
1               5                   10                  15

Pro Pro Gly Pro Pro Gly Thr Ser
            20

<210> SEQ ID NO 198
<211> LENGTH: 24
<212> TYPE: PRT
<213> ORGANISM: Homo sapiens

<400> SEQUENCE: 198

Lys Asp Gly Thr Ser Gly His Pro Gly Pro Ile Gly Pro Pro Gly Pro
1               5                   10                  15

Arg Gly Asn Arg Gly Glu Arg Gly
            20

<210> SEQ ID NO 199
<211> LENGTH: 29
<212> TYPE: PRT
<213> ORGANISM: Homo sapiens

<400> SEQUENCE: 199

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser
            20                  25

<210> SEQ ID NO 200
<211> LENGTH: 29
<212> TYPE: PRT
<213> ORGANISM: Homo sapiens

<400> SEQUENCE: 200

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 201
<211> LENGTH: 31
<212> TYPE: PRT
<213> ORGANISM: Homo sapiens

<400> SEQUENCE: 201

Ala Pro Gly Ala Pro Gly Gly Lys Gly Asp Ala Gly Ala Pro Gly Glu
1               5                   10                  15

Arg Gly Pro Pro Gly Leu Ala Gly Ala Pro Gly Leu Arg Gly Gly
            20                  25                  30

<210> SEQ ID NO 202
<211> LENGTH: 32
<212> TYPE: PRT
<213> ORGANISM: Homo sapiens

<400> SEQUENCE: 202

Ala Val Gly Gly Leu Ala Gly Tyr Pro Gly Pro Ala Gly Pro Pro Gly
1               5                   10                  15
```

```
Pro Pro Gly Pro Pro Gly Thr Ser Gly His Pro Gly Ser Pro Gly Ser
            20                  25                  30

<210> SEQ ID NO 203
<211> LENGTH: 22
<212> TYPE: PRT
<213> ORGANISM: Homo sapiens

<400> SEQUENCE: 203

Ala Ile Gly Ser Pro Gly Pro Ala Gly Pro Arg Gly Pro Val Gly Pro
1               5                   10                  15

Ser Gly Pro Pro Gly Lys
            20

<210> SEQ ID NO 204
<211> LENGTH: 23
<212> TYPE: PRT
<213> ORGANISM: Homo sapiens

<400> SEQUENCE: 204

Gly Ala Ile Gly Ser Pro Gly Pro Ala Gly Pro Arg Gly Pro Val Gly
1               5                   10                  15

Pro Ser Gly Pro Pro Gly Lys
            20

<210> SEQ ID NO 205
<211> LENGTH: 15
<212> TYPE: PRT
<213> ORGANISM: Homo sapiens

<400> SEQUENCE: 205

Pro Ala Gly Gln Gln Gly Ala Ile Gly Ser Pro Gly Pro Ala Gly
1               5                   10                  15

<210> SEQ ID NO 206
<211> LENGTH: 20
<212> TYPE: PRT
<213> ORGANISM: Homo sapiens

<400> SEQUENCE: 206

Gly Gly Pro Pro Gly Val Ala Gly Pro Gly Gly Ser Gly Pro Ala
1               5                   10                  15

Gly Pro Pro Gly
            20

<210> SEQ ID NO 207
<211> LENGTH: 19
<212> TYPE: PRT
<213> ORGANISM: Homo sapiens

<400> SEQUENCE: 207

Leu Ala Gly Pro Pro Gly Met Pro Gly Pro Arg Gly Ser Pro Gly Pro
1               5                   10                  15

Gln Gly Val

<210> SEQ ID NO 208
<211> LENGTH: 19
<212> TYPE: PRT
<213> ORGANISM: Homo sapiens

<400> SEQUENCE: 208

Gly Leu Ser Gly Glu Arg Gly Pro Pro Gly Pro Gln Gly Leu Pro Gly
```

-continued

```
1               5                   10                  15

Leu Ala Gly

<210> SEQ ID NO 209
<211> LENGTH: 21
<212> TYPE: PRT
<213> ORGANISM: Homo sapiens

<400> SEQUENCE: 209

Arg Gly Leu Ala Gly Pro Pro Gly Met Pro Gly Pro Arg Gly Ser Pro
1               5                   10                  15

Gly Pro Gln Gly Val
            20

<210> SEQ ID NO 210
<211> LENGTH: 21
<212> TYPE: PRT
<213> ORGANISM: Homo sapiens

<400> SEQUENCE: 210

Gly Leu Ala Gly Pro Pro Gly Met Pro Gly Pro Arg Gly Ser Pro Gly
1               5                   10                  15

Pro Gln Gly Val Lys
            20

<210> SEQ ID NO 211
<211> LENGTH: 22
<212> TYPE: PRT
<213> ORGANISM: Homo sapiens

<400> SEQUENCE: 211

Arg Gly Leu Ala Gly Pro Pro Gly Met Pro Gly Pro Arg Gly Ser Pro
1               5                   10                  15

Gly Pro Gln Gly Val Lys
            20

<210> SEQ ID NO 212
<211> LENGTH: 21
<212> TYPE: PRT
<213> ORGANISM: Homo sapiens

<400> SEQUENCE: 212

Gly Pro Gln Gly Pro Pro Gly Lys Asn Gly Glu Thr Gly Pro Gln Gly
1               5                   10                  15

Pro Pro Gly Pro Thr
            20

<210> SEQ ID NO 213
<211> LENGTH: 22
<212> TYPE: PRT
<213> ORGANISM: Homo sapiens

<400> SEQUENCE: 213

Gly Val Lys Gly Glu Arg Gly Ser Pro Gly Gly Pro Gly Ala Ala Gly
1               5                   10                  15

Phe Pro Gly Ala Arg Gly
            20

<210> SEQ ID NO 214
<211> LENGTH: 22
<212> TYPE: PRT
<213> ORGANISM: Homo sapiens
```

<400> SEQUENCE: 214

Ala Arg Gly Leu Ala Gly Pro Pro Gly Met Pro Gly Pro Arg Gly Ser
1               5                   10                  15

Pro Gly Pro Gln Gly Val
            20

<210> SEQ ID NO 215
<211> LENGTH: 23
<212> TYPE: PRT
<213> ORGANISM: Homo sapiens

<400> SEQUENCE: 215

Asn Gly Leu Ser Gly Glu Arg Gly Pro Pro Gly Pro Gln Gly Leu Pro
1               5                   10                  15

Gly Leu Ala Gly Thr Ala Gly
            20

<210> SEQ ID NO 216
<211> LENGTH: 24
<212> TYPE: PRT
<213> ORGANISM: Homo sapiens

<400> SEQUENCE: 216

Ala Val Gly Gly Leu Ala Gly Tyr Pro Gly Pro Ala Gly Pro Pro Gly
1               5                   10                  15

Pro Pro Gly Pro Pro Gly Thr Ser
            20

<210> SEQ ID NO 217
<211> LENGTH: 24
<212> TYPE: PRT
<213> ORGANISM: Homo sapiens

<400> SEQUENCE: 217

Gly Ser Pro Gly Gly Lys Gly Glu Met Gly Pro Ala Gly Ile Pro Gly
1               5                   10                  15

Ala Pro Gly Leu Met Gly Ala Arg
            20

<210> SEQ ID NO 218
<211> LENGTH: 24
<212> TYPE: PRT
<213> ORGANISM: Homo sapiens

<400> SEQUENCE: 218

Thr Gly Ala Arg Gly Leu Ala Gly Pro Pro Gly Met Pro Gly Pro Arg
1               5                   10                  15

Gly Ser Pro Gly Pro Gln Gly Val
            20

<210> SEQ ID NO 219
<211> LENGTH: 25
<212> TYPE: PRT
<213> ORGANISM: Homo sapiens

<400> SEQUENCE: 219

Val Lys Gly Glu Ser Gly Lys Pro Gly Ala Asn Gly Leu Ser Gly Glu
1               5                   10                  15

Arg Gly Pro Pro Gly Pro Gln Gly Leu
            20                  25

-continued

<210> SEQ ID NO 220
<211> LENGTH: 53
<212> TYPE: PRT
<213> ORGANISM: Homo sapiens

<400> SEQUENCE: 220

Gly Val Lys Gly Glu Arg Gly Ser Pro Gly Pro Gly Ala Ala Gly
1               5                   10                  15

Phe Pro Gly Ala Arg Gly Leu Pro Gly Pro Gly Ser Asn Gly Asn
                20                  25                  30

Pro Gly Pro Pro Gly Pro Ser Gly Ser Pro Gly Lys Asp Gly Pro Pro
        35                  40                  45

Gly Pro Ala Gly Asn
        50

<210> SEQ ID NO 221
<211> LENGTH: 32
<212> TYPE: PRT
<213> ORGANISM: Homo sapiens

<400> SEQUENCE: 221

Gly Ser Pro Gly Ala Gln Gly Pro Pro Gly Ala Pro Gly Pro Leu Gly
1               5                   10                  15

Ile Ala Gly Ile Thr Gly Ala Arg Gly Leu Ala Gly Pro Pro Gly Met
                20                  25                  30

<210> SEQ ID NO 222
<211> LENGTH: 32
<212> TYPE: PRT
<213> ORGANISM: Homo sapiens

<400> SEQUENCE: 222

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
                20                  25                  30

<210> SEQ ID NO 223
<211> LENGTH: 32
<212> TYPE: PRT
<213> ORGANISM: Homo sapiens

<400> SEQUENCE: 223

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
                20                  25                  30

<210> SEQ ID NO 224
<211> LENGTH: 29
<212> TYPE: PRT
<213> ORGANISM: Homo sapiens

<400> SEQUENCE: 224

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
                20                  25

<210> SEQ ID NO 225
<211> LENGTH: 14

```
<212> TYPE: PRT
<213> ORGANISM: Homo sapiens

<400> SEQUENCE: 225

Gly Ile Lys Gly Pro Ala Gly Ile Pro Gly Phe Pro Gly Met
1               5                   10

<210> SEQ ID NO 226
<211> LENGTH: 14
<212> TYPE: PRT
<213> ORGANISM: Homo sapiens

<400> SEQUENCE: 226

Gly Gln Pro Gly Val Met Gly Phe Pro Gly Pro Lys Gly Asn
1               5                   10

<210> SEQ ID NO 227
<211> LENGTH: 16
<212> TYPE: PRT
<213> ORGANISM: Homo sapiens

<400> SEQUENCE: 227

Gly Ile Lys Gly Pro Ala Gly Ile Pro Gly Phe Pro Gly Met Lys Gly
1               5                   10                  15

<210> SEQ ID NO 228
<211> LENGTH: 17
<212> TYPE: PRT
<213> ORGANISM: Homo sapiens

<400> SEQUENCE: 228

Gly Ile Lys Gly Pro Ala Gly Ile Pro Gly Phe Pro Gly Met Lys Gly
1               5                   10                  15

His

<210> SEQ ID NO 229
<211> LENGTH: 19
<212> TYPE: PRT
<213> ORGANISM: Homo sapiens

<400> SEQUENCE: 229

Ile Pro Gly Ala Pro Gly Leu Met Gly Ala Arg Gly Pro Pro Gly Pro
1               5                   10                  15

Ala Gly Ala

<210> SEQ ID NO 230
<211> LENGTH: 19
<212> TYPE: PRT
<213> ORGANISM: Homo sapiens

<400> SEQUENCE: 230

Gly Glu Arg Gly Leu Pro Gly Pro Gly Ile Lys Gly Pro Ala Gly Ile
1               5                   10                  15

Ile Pro Gly

<210> SEQ ID NO 231
<211> LENGTH: 20
<212> TYPE: PRT
<213> ORGANISM: Homo sapiens

<400> SEQUENCE: 231

Gly Ile Pro Gly Ala Pro Gly Leu Met Gly Ala Arg Gly Pro Pro Gly
1               5                   10                  15
```

Pro Ala Gly Ala
        20

<210> SEQ ID NO 232
<211> LENGTH: 20
<212> TYPE: PRT
<213> ORGANISM: Homo sapiens

<400> SEQUENCE: 232

Gly Phe Arg Gly Pro Ala Gly Pro Asn Gly Ile Pro Gly Glu Lys Gly
1               5                   10                  15

Pro Ala Gly Glu
        20

<210> SEQ ID NO 233
<211> LENGTH: 20
<212> TYPE: PRT
<213> ORGANISM: Homo sapiens

<400> SEQUENCE: 233

Pro Gly Ile Pro Gly Gln Pro Gly Ser Pro Gly Ser Pro Gly Pro Pro
1               5                   10                  15

Gly Ile Cys Glu
        20

<210> SEQ ID NO 234
<211> LENGTH: 21
<212> TYPE: PRT
<213> ORGANISM: Homo sapiens

<400> SEQUENCE: 234

Gly Glu Arg Gly Leu Pro Gly Pro Gly Ile Lys Gly Pro Ala Gly
1               5                   10                  15

Ile Pro Gly Phe Pro
        20

<210> SEQ ID NO 235
<211> LENGTH: 23
<212> TYPE: PRT
<213> ORGANISM: Homo sapiens

<400> SEQUENCE: 235

Ala Val Gly Gly Leu Ala Gly Tyr Pro Gly Pro Ala Gly Pro Pro Gly
1               5                   10                  15

Pro Pro Gly Pro Pro Gly Thr
        20

<210> SEQ ID NO 236
<211> LENGTH: 23
<212> TYPE: PRT
<213> ORGANISM: Homo sapiens

<400> SEQUENCE: 236

Gly Val Lys Gly Glu Arg Gly Ser Pro Gly Gly Pro Gly Ala Ala Gly
1               5                   10                  15

Phe Pro Gly Ala Arg Gly Leu
        20

<210> SEQ ID NO 237
<211> LENGTH: 26
<212> TYPE: PRT
<213> ORGANISM: Homo sapiens

```
<400> SEQUENCE: 237

Gly Asp Ala Gly Ala Pro Gly Ala Pro Gly Lys Gly Asp Ala Gly
1               5                   10                  15

Ala Pro Gly Glu Arg Gly Pro Pro Gly Leu
            20                  25

<210> SEQ ID NO 238
<211> LENGTH: 25
<212> TYPE: PRT
<213> ORGANISM: Homo sapiens

<400> SEQUENCE: 238

Gln Gly Pro Pro Gly Pro Thr Gly Pro Gly Gly Asp Lys Gly Asp Thr
1               5                   10                  15

Gly Pro Pro Gly Pro Gln Gly Leu Gln
            20                  25

<210> SEQ ID NO 239
<211> LENGTH: 25
<212> TYPE: PRT
<213> ORGANISM: Homo sapiens

<400> SEQUENCE: 239

Gly Ile Asn Gly Ser Pro Gly Gly Lys Gly Glu Met Gly Pro Ala Gly
1               5                   10                  15

Ile Pro Gly Ala Pro Gly Leu Met Gly
            20                  25

<210> SEQ ID NO 240
<211> LENGTH: 26
<212> TYPE: PRT
<213> ORGANISM: Homo sapiens

<400> SEQUENCE: 240

Gln Gly Pro Pro Gly Glu Pro Gly Gln Ala Gly Pro Ser Gly Pro Pro
1               5                   10                  15

Gly Pro Pro Gly Ala Ile Gly Pro Ser Gly
            20                  25

<210> SEQ ID NO 241
<211> LENGTH: 26
<212> TYPE: PRT
<213> ORGANISM: Homo sapiens

<400> SEQUENCE: 241

Pro Gly Pro Pro Gly Ile Asn Gly Ser Pro Gly Gly Lys Gly Glu Met
1               5                   10                  15

Gly Pro Ala Gly Ile Pro Gly Ala Pro Gly
            20                  25

<210> SEQ ID NO 242
<211> LENGTH: 33
<212> TYPE: PRT
<213> ORGANISM: Homo sapiens

<400> SEQUENCE: 242

Arg Gly Leu Pro Gly Pro Pro Gly Ser Asn Gly Asn Pro Gly Pro Pro
1               5                   10                  15

Gly Pro Ser Gly Ser Pro Gly Lys Asp Gly Pro Pro Gly Pro Ala Gly
            20                  25                  30
```

Asn

<210> SEQ ID NO 243
<211> LENGTH: 32
<212> TYPE: PRT
<213> ORGANISM: Homo sapiens

<400> SEQUENCE: 243

Gly Lys Asn Gly Glu Thr Gly Pro Gln Gly Pro Pro Gly Pro Thr Gly
1               5                   10                  15

Pro Gly Gly Asp Lys Gly Asp Thr Gly Pro Pro Gly Pro Gln Gly Leu
            20                  25                  30

<210> SEQ ID NO 244
<211> LENGTH: 32
<212> TYPE: PRT
<213> ORGANISM: Homo sapiens

<400> SEQUENCE: 244

Gly Leu Pro Gly Ile Ala Gly Pro Arg Gly Ser Pro Gly Glu Arg Gly
1               5                   10                  15

Glu Thr Gly Pro Pro Gly Pro Ala Gly Phe Pro Gly Ala Pro Gly Gln
            20                  25                  30

<210> SEQ ID NO 245
<211> LENGTH: 35
<212> TYPE: PRT
<213> ORGANISM: Homo sapiens

<400> SEQUENCE: 245

Gly Ile Asn Gly Ser Pro Gly Gly Lys Gly Glu Met Gly Pro Ala Gly
1               5                   10                  15

Ile Pro Gly Ala Pro Gly Leu Met Gly Ala Arg Gly Pro Pro Gly Pro
            20                  25                  30

Ala Gly Ala
        35

<210> SEQ ID NO 246
<211> LENGTH: 36
<212> TYPE: PRT
<213> ORGANISM: Homo sapiens

<400> SEQUENCE: 246

Pro Gly Ile Asn Gly Ser Pro Gly Gly Lys Gly Glu Met Gly Pro Ala
1               5                   10                  15

Gly Ile Pro Gly Ala Pro Gly Leu Met Gly Ala Arg Gly Pro Pro Gly
            20                  25                  30

Pro Ala Gly Ala
        35

<210> SEQ ID NO 247
<211> LENGTH: 40
<212> TYPE: PRT
<213> ORGANISM: Homo sapiens

<400> SEQUENCE: 247

Pro Pro Gly Glu Asn Gly Lys Pro Gly Glu Pro Gly Pro Lys Gly Asp
1               5                   10                  15

Ala Gly Ala Pro Gly Ala Pro Gly Gly Lys Gly Asp Ala Gly Ala Pro
            20                  25                  30

Gly Glu Arg Gly Pro Pro Gly Leu

```
                35                  40

<210> SEQ ID NO 248
<211> LENGTH: 38
<212> TYPE: PRT
<213> ORGANISM: Homo sapiens

<400> SEQUENCE: 248

Gly Leu Lys Gly Glu Asn Gly Leu Pro Gly Glu Asn Gly Ala Pro Gly
1               5                   10                  15

Pro Met Gly Pro Arg Gly Ala Pro Gly Glu Arg Gly Arg Pro Gly Leu
                20                  25                  30

Pro Gly Ala Ala Gly Ala
            35

<210> SEQ ID NO 249
<211> LENGTH: 41
<212> TYPE: PRT
<213> ORGANISM: Homo sapiens

<400> SEQUENCE: 249

Gly Asn Thr Gly Ala Pro Gly Ser Pro Gly Val Ser Gly Pro Lys Gly
1               5                   10                  15

Asp Ala Gly Gln Pro Gly Glu Lys Gly Ser Pro Gly Ala Gln Gly Pro
                20                  25                  30

Pro Gly Ala Pro Gly Pro Leu Gly Ile
            35                  40

<210> SEQ ID NO 250
<211> LENGTH: 41
<212> TYPE: PRT
<213> ORGANISM: Homo sapiens

<400> SEQUENCE: 250

Gly Leu Met Gly Ala Arg Gly Pro Pro Gly Pro Ala Gly Ala Asn Gly
1               5                   10                  15

Ala Pro Gly Leu Arg Gly Gly Ala Gly Glu Pro Gly Lys Asn Gly Ala
                20                  25                  30

Lys Gly Glu Pro Gly Pro Arg Gly Glu
            35                  40

<210> SEQ ID NO 251
<211> LENGTH: 50
<212> TYPE: PRT
<213> ORGANISM: Homo sapiens

<400> SEQUENCE: 251

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala Ala Gly Thr Pro Gly Leu
                20                  25                  30

Gln Gly Met Pro Gly Glu Arg Gly Gly Leu Gly Ser Pro Gly Pro Lys
            35                  40                  45

Gly Asp
    50

<210> SEQ ID NO 252
<211> LENGTH: 26
<212> TYPE: PRT
<213> ORGANISM: Homo sapiens
```

<400> SEQUENCE: 252

Gly Gln Gln Gly Ala Ile Gly Ser Pro Gly Pro Ala Gly Pro Arg Gly
1               5                   10                  15

Pro Val Gly Pro Ser Gly Pro Pro Gly Lys
            20                  25

<210> SEQ ID NO 253
<211> LENGTH: 24
<212> TYPE: PRT
<213> ORGANISM: Homo sapiens

<400> SEQUENCE: 253

Lys Gly Asp Pro Gly Pro Pro Gly Ile Pro Gly Arg Asn Gly Asp Pro
1               5                   10                  15

Gly Ile Pro Gly Gln Pro Gly Ser
            20

<210> SEQ ID NO 254
<211> LENGTH: 26
<212> TYPE: PRT
<213> ORGANISM: Homo sapiens

<400> SEQUENCE: 254

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala
            20                  25

<210> SEQ ID NO 255
<211> LENGTH: 32
<212> TYPE: PRT
<213> ORGANISM: Homo sapiens

<400> SEQUENCE: 255

Gly Lys Asn Gly Glu Thr Gly Pro Gln Gly Pro Pro Gly Pro Thr Gly
1               5                   10                  15

Pro Gly Gly Asp Lys Gly Asp Thr Gly Pro Pro Gly Pro Gln Gly Leu
            20                  25                  30

<210> SEQ ID NO 256
<211> LENGTH: 23
<212> TYPE: PRT
<213> ORGANISM: Homo sapiens

<400> SEQUENCE: 256

Gly Tyr Gln Gly Pro Pro Gly Glu Pro Gly Gln Ala Gly Pro Ser Gly
1               5                   10                  15

Pro Pro Gly Pro Pro Gly Ala
            20

<210> SEQ ID NO 257
<211> LENGTH: 20
<212> TYPE: PRT
<213> ORGANISM: Homo sapiens

<400> SEQUENCE: 257

Gly Val Ala Gly Pro Pro Gly Ser Gly Pro Ala Gly Pro Pro Gly Gly
1               5                   10                  15

Pro Gln Gly Val
            20

```
<210> SEQ ID NO 258
<211> LENGTH: 35
<212> TYPE: PRT
<213> ORGANISM: Homo sapiens

<400> SEQUENCE: 258

Gly Asp Lys Gly Glu Pro Gly Gly Pro Gly Ala Asp Gly Val Pro Gly
1               5                   10                  15

Lys Asp Gly Pro Arg Gly Pro Thr Gly Pro Ile Gly Pro Pro Gly Pro
            20                  25                  30

Ala Gly Gln
        35

<210> SEQ ID NO 259
<211> LENGTH: 17
<212> TYPE: PRT
<213> ORGANISM: Homo sapiens

<400> SEQUENCE: 259

Gln Gly His Ala Gly Ala Gln Gly Pro Pro Gly Pro Pro Gly Ile Asn
1               5                   10                  15

Gly

<210> SEQ ID NO 260
<211> LENGTH: 11
<212> TYPE: PRT
<213> ORGANISM: Homo sapiens

<400> SEQUENCE: 260

Ala Gly Glu Arg Gly Ala Pro Gly Pro Ala Gly
1               5                   10

<210> SEQ ID NO 261
<211> LENGTH: 11
<212> TYPE: PRT
<213> ORGANISM: Homo sapiens

<400> SEQUENCE: 261

Ala Gly Ile Pro Gly Phe Pro Gly Met Lys Gly
1               5                   10

<210> SEQ ID NO 262
<211> LENGTH: 12
<212> TYPE: PRT
<213> ORGANISM: Homo sapiens

<400> SEQUENCE: 262

Phe Pro Gly Met Lys Gly His Arg Gly Phe Asp Gly
1               5                   10

<210> SEQ ID NO 263
<211> LENGTH: 14
<212> TYPE: PRT
<213> ORGANISM: Homo sapiens

<400> SEQUENCE: 263

Gly Phe Pro Gly Ala Arg Gly Leu Pro Gly Pro Pro Gly Ser
1               5                   10

<210> SEQ ID NO 264
<211> LENGTH: 15
<212> TYPE: PRT
<213> ORGANISM: Homo sapiens
```

<400> SEQUENCE: 264

Ala Gly Phe Pro Gly Ala Arg Gly Leu Pro Gly Pro Pro Gly Ser
1               5                   10                  15

<210> SEQ ID NO 265
<211> LENGTH: 15
<212> TYPE: PRT
<213> ORGANISM: Homo sapiens

<400> SEQUENCE: 265

Pro Pro Gly Pro Pro Gly Pro Pro Gly Thr Ser Gly His Pro Gly
1               5                   10                  15

<210> SEQ ID NO 266
<211> LENGTH: 13
<212> TYPE: PRT
<213> ORGANISM: Homo sapiens

<400> SEQUENCE: 266

Gly Phe Pro Gly Met Lys Gly His Arg Gly Phe Asp Gly
1               5                   10

<210> SEQ ID NO 267
<211> LENGTH: 17
<212> TYPE: PRT
<213> ORGANISM: Homo sapiens

<400> SEQUENCE: 267

Gln Pro Gly Asp Lys Gly Glu Gly Gly Ala Pro Gly Leu Pro Gly Ile
1               5                   10                  15

Ala

<210> SEQ ID NO 268
<211> LENGTH: 17
<212> TYPE: PRT
<213> ORGANISM: Homo sapiens

<400> SEQUENCE: 268

Arg Gly Asp Lys Gly Glu Thr Gly Glu Arg Gly Ala Ala Gly Ile Lys
1               5                   10                  15

Gly

<210> SEQ ID NO 269
<211> LENGTH: 17
<212> TYPE: PRT
<213> ORGANISM: Homo sapiens

<400> SEQUENCE: 269

Asp Gly Arg Asn Gly Glu Lys Gly Glu Thr Gly Ala Pro Gly Leu Lys
1               5                   10                  15

Gly

<210> SEQ ID NO 270
<211> LENGTH: 20
<212> TYPE: PRT
<213> ORGANISM: Homo sapiens

<400> SEQUENCE: 270

Ala Gly Gln Pro Gly Asp Lys Gly Glu Gly Gly Ala Pro Gly Leu Pro
1               5                   10                  15

Gly Ile Ala Gly
            20

<210> SEQ ID NO 271
<211> LENGTH: 19
<212> TYPE: PRT
<213> ORGANISM: Homo sapiens

<400> SEQUENCE: 271

Gly Gly Pro Pro Gly Glu Asn Gly Lys Pro Gly Glu Pro Gly Pro Lys
1               5                   10                  15

Gly Asp Ala

<210> SEQ ID NO 272
<211> LENGTH: 17
<212> TYPE: PRT
<213> ORGANISM: Homo sapiens

<400> SEQUENCE: 272

Ala Gly Ile Pro Gly Phe Pro Gly Met Lys Gly His Arg Gly Phe Asp
1               5                   10                  15

Gly

<210> SEQ ID NO 273
<211> LENGTH: 20
<212> TYPE: PRT
<213> ORGANISM: Homo sapiens

<400> SEQUENCE: 273

Arg Gly Gly Ala Gly Glu Pro Gly Lys Asn Gly Ala Lys Gly Glu Pro
1               5                   10                  15

Gly Pro Arg Gly
            20

<210> SEQ ID NO 274
<211> LENGTH: 26
<212> TYPE: PRT
<213> ORGANISM: Homo sapiens

<400> SEQUENCE: 274

Lys Gly Glu Arg Gly Ser Pro Gly Gly Pro Gly Ala Ala Gly Phe Pro
1               5                   10                  15

Gly Ala Arg Gly Leu Pro Gly Pro Pro Gly
            20                  25

<210> SEQ ID NO 275
<211> LENGTH: 27
<212> TYPE: PRT
<213> ORGANISM: Homo sapiens

<400> SEQUENCE: 275

Ile Pro Gly Val Pro Gly Ala Lys Gly Glu Asp Gly Lys Asp Gly Ser
1               5                   10                  15

Pro Gly Glu Pro Gly Ala Asn Gly Leu Pro Gly
            20                  25

<210> SEQ ID NO 276
<211> LENGTH: 28
<212> TYPE: PRT
<213> ORGANISM: Homo sapiens

<400> SEQUENCE: 276

Gly Ala Ala Gly Phe Pro Gly Ala Arg Gly Leu Pro Gly Pro Pro Gly
1               5                   10                  15

```
Ser Asn Gly Asn Pro Gly Pro Pro Gly Pro Ser Gly
            20                  25

<210> SEQ ID NO 277
<211> LENGTH: 26
<212> TYPE: PRT
<213> ORGANISM: Homo sapiens

<400> SEQUENCE: 277

Arg Pro Gly Pro Pro Gly Pro Ser Gly Pro Arg Gly Gln Pro Gly Val
1               5                   10                  15

Met Gly Phe Pro Gly Pro Lys Gly Asn Asp
            20                  25

<210> SEQ ID NO 278
<211> LENGTH: 29
<212> TYPE: PRT
<213> ORGANISM: Homo sapiens

<400> SEQUENCE: 278

Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly
            20                  25

<210> SEQ ID NO 279
<211> LENGTH: 26
<212> TYPE: PRT
<213> ORGANISM: Homo sapiens

<400> SEQUENCE: 279

Ala Gly Lys Asp Gly Glu Ser Gly Arg Pro Gly Arg Pro Gly Glu Arg
1               5                   10                  15

Gly Leu Pro Gly Pro Pro Gly Ile Lys Gly
            20                  25

<210> SEQ ID NO 280
<211> LENGTH: 30
<212> TYPE: PRT
<213> ORGANISM: Homo sapiens

<400> SEQUENCE: 280

Ala Gly Ala Arg Gly Asn Asp Gly Ala Arg Gly Ser Asp Gly Gln Pro
1               5                   10                  15

Gly Pro Pro Gly Pro Pro Gly Thr Ala Gly Phe Pro Gly Ser
            20                  25                  30

<210> SEQ ID NO 281
<211> LENGTH: 31
<212> TYPE: PRT
<213> ORGANISM: Homo sapiens

<400> SEQUENCE: 281

Ser Pro Gly Val Ser Gly Pro Lys Gly Asp Ala Gly Gln Pro Gly Glu
1               5                   10                  15

Lys Gly Ser Pro Gly Ala Gln Gly Pro Pro Gly Ala Pro Gly Pro
            20                  25                  30

<210> SEQ ID NO 282
<211> LENGTH: 32
<212> TYPE: PRT
<213> ORGANISM: Homo sapiens
```

<400> SEQUENCE: 282

Arg Gly Ser Asp Gly Gln Pro Gly Pro Pro Gly Thr Ala
1               5                   10                  15

Gly Phe Pro Gly Ser Pro Gly Ala Lys Gly Glu Val Gly Pro Ala Gly
            20                  25                  30

<210> SEQ ID NO 283
<211> LENGTH: 32
<212> TYPE: PRT
<213> ORGANISM: Homo sapiens

<400> SEQUENCE: 283

Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly Leu Met Gly
            20                  25                  30

<210> SEQ ID NO 284
<211> LENGTH: 33
<212> TYPE: PRT
<213> ORGANISM: Homo sapiens

<400> SEQUENCE: 284

Ala Gly Pro Pro Gly Pro Pro Gly Pro Pro Gly Thr Ser Gly His Pro
1               5                   10                  15

Gly Ser Pro Gly Ser Pro Gly Tyr Gln Gly Pro Pro Gly Glu Pro Gly
            20                  25                  30

Gln

<210> SEQ ID NO 285
<211> LENGTH: 33
<212> TYPE: PRT
<213> ORGANISM: Homo sapiens

<400> SEQUENCE: 285

Phe Pro Gly Ala Pro Gly Gln Asn Gly Glu Pro Gly Gly Lys Gly Glu
1               5                   10                  15

Arg Gly Ala Pro Gly Glu Lys Gly Glu Gly Gly Pro Pro Gly Val Ala
            20                  25                  30

Gly

<210> SEQ ID NO 286
<211> LENGTH: 33
<212> TYPE: PRT
<213> ORGANISM: Homo sapiens

<400> SEQUENCE: 286

Ala Gly Phe Pro Gly Ala Pro Gly Gln Asn Gly Glu Pro Gly Gly Lys
1               5                   10                  15

Gly Glu Arg Gly Ala Pro Gly Glu Lys Gly Glu Gly Gly Pro Pro Gly
            20                  25                  30

Val

<210> SEQ ID NO 287
<211> LENGTH: 41
<212> TYPE: PRT
<213> ORGANISM: Homo sapiens

<400> SEQUENCE: 287

```
Ala Gly Ala Arg Gly Asn Asp Gly Ala Arg Gly Ser Asp Gly Gln Pro
1               5                   10                  15

Gly Pro Pro Gly Pro Pro Gly Thr Ala Gly Phe Pro Gly Ser Pro Gly
            20                  25                  30

Ala Lys Gly Glu Val Gly Pro Ala Gly
        35                  40

<210> SEQ ID NO 288
<211> LENGTH: 53
<212> TYPE: PRT
<213> ORGANISM: Homo sapiens

<400> SEQUENCE: 288

Arg Gly Ala Ala Gly Glu Pro Gly Arg Asp Gly Val Pro Gly Gly Pro
1               5                   10                  15

Gly Met Arg Gly Met Pro Gly Ser Pro Gly Gly Pro Gly Ser Asp Gly
            20                  25                  30

Lys Pro Gly Pro Pro Gly Ser Gln Gly Glu Ser Gly Arg Pro Gly Pro
        35                  40                  45

Pro Gly Pro Ser Gly
    50

<210> SEQ ID NO 289
<211> LENGTH: 12
<212> TYPE: PRT
<213> ORGANISM: Homo sapiens

<400> SEQUENCE: 289

Gly Ile Ala Gly Ile Thr Gly Ala Arg Gly Leu Ala
1               5                   10

<210> SEQ ID NO 290
<211> LENGTH: 18
<212> TYPE: PRT
<213> ORGANISM: Homo sapiens

<400> SEQUENCE: 290

Ala Gly Pro Pro Gly Pro Pro Gly Ala Ala Gly Thr Pro Gly Leu Gln
1               5                   10                  15

Gly Met

<210> SEQ ID NO 291
<211> LENGTH: 18
<212> TYPE: PRT
<213> ORGANISM: Homo sapiens

<400> SEQUENCE: 291

Asn Gly Leu Ser Gly Glu Arg Gly Pro Pro Gly Pro Gln Gly Leu Pro
1               5                   10                  15

Gly Leu

<210> SEQ ID NO 292
<211> LENGTH: 20
<212> TYPE: PRT
<213> ORGANISM: Homo sapiens

<400> SEQUENCE: 292

Met Gly Ala Arg Gly Pro Pro Gly Pro Ala Gly Ala Asn Gly Ala Pro
1               5                   10                  15

Gly Leu Arg Gly
            20
```

<210> SEQ ID NO 293
<211> LENGTH: 20
<212> TYPE: PRT
<213> ORGANISM: Homo sapiens

<400> SEQUENCE: 293

Asn Gly Leu Ser Gly Glu Arg Gly Pro Pro Gly Pro Gln Gly Leu Pro
1               5                   10                  15

Gly Leu Ala Gly
            20

<210> SEQ ID NO 294
<211> LENGTH: 23
<212> TYPE: PRT
<213> ORGANISM: Homo sapiens

<400> SEQUENCE: 294

Gly Ile Ala Gly Ile Thr Gly Ala Arg Gly Leu Ala Gly Pro Pro Gly
1               5                   10                  15

Met Pro Gly Pro Arg Gly Ser
            20

<210> SEQ ID NO 295
<211> LENGTH: 29
<212> TYPE: PRT
<213> ORGANISM: Homo sapiens

<400> SEQUENCE: 295

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 296
<211> LENGTH: 32
<212> TYPE: PRT
<213> ORGANISM: Homo sapiens

<400> SEQUENCE: 296

Arg Gly Gly Ala Gly Pro Pro Gly Pro Glu Gly Gly Lys Gly Ala Ala
1               5                   10                  15

Gly Pro Pro Gly Pro Pro Gly Ala Ala Gly Thr Pro Gly Leu Gln Gly
            20                  25                  30

<210> SEQ ID NO 297
<211> LENGTH: 30
<212> TYPE: PRT
<213> ORGANISM: Homo sapiens

<400> SEQUENCE: 297

Ser Gly Pro Lys Gly Asp Ala Gly Gln Pro Gly Glu Lys Gly Ser Pro
1               5                   10                  15

Gly Ala Gln Gly Pro Pro Gly Ala Pro Gly Pro Leu Gly Ile
            20                  25                  30

<210> SEQ ID NO 298
<211> LENGTH: 31
<212> TYPE: PRT
<213> ORGANISM: Homo sapiens

<400> SEQUENCE: 298

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val Lys Gly
            20                  25                  30

<210> SEQ ID NO 299
<211> LENGTH: 30
<212> TYPE: PRT
<213> ORGANISM: Homo sapiens

<400> SEQUENCE: 299

Ser Gly Pro Lys Gly Asp Ala Gly Gln Pro Gly Glu Lys Gly Ser Pro
1               5                   10                  15

Gly Ala Gln Gly Pro Pro Gly Ala Pro Gly Pro Leu Gly Ile
            20                  25                  30

<210> SEQ ID NO 300
<211> LENGTH: 31
<212> TYPE: PRT
<213> ORGANISM: Homo sapiens

<400> SEQUENCE: 300

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val Lys Gly
            20                  25                  30

<210> SEQ ID NO 301
<211> LENGTH: 37
<212> TYPE: PRT
<213> ORGANISM: Homo sapiens

<400> SEQUENCE: 301

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser Pro Gly Ser
            20                  25                  30

Pro Gly Tyr Gln Gly
        35

<210> SEQ ID NO 302
<211> LENGTH: 40
<212> TYPE: PRT
<213> ORGANISM: Homo sapiens

<400> SEQUENCE: 302

Glu Pro Gly Pro Gln Gly His Ala Gly Ala Gln Gly Pro Pro Gly Pro
1               5                   10                  15

Pro Gly Ile Asn Gly Ser Pro Gly Gly Lys Gly Glu Met Gly Pro Ala
            20                  25                  30

Gly Ile Pro Gly Ala Pro Gly Leu
        35                  40

<210> SEQ ID NO 303
<211> LENGTH: 12
<212> TYPE: PRT
<213> ORGANISM: Homo sapiens

<400> SEQUENCE: 303

Ile Pro Gly Phe Pro Gly Met Lys Gly His Arg Gly
1               5                   10

<210> SEQ ID NO 304
<211> LENGTH: 17
<212> TYPE: PRT
<213> ORGANISM: Homo sapiens

<400> SEQUENCE: 304

Arg Gly Ser Pro Gly Gly Pro Gly Ala Ala Gly Phe Pro Gly Ala Arg
1               5                   10                  15
Gly

<210> SEQ ID NO 305
<211> LENGTH: 17
<212> TYPE: PRT
<213> ORGANISM: Homo sapiens

<400> SEQUENCE: 305

Lys Gly Pro Ala Gly Ile Pro Gly Phe Pro Gly Met Lys Gly His Arg
1               5                   10                  15
Gly

<210> SEQ ID NO 306
<211> LENGTH: 20
<212> TYPE: PRT
<213> ORGANISM: Homo sapiens

<400> SEQUENCE: 306

Arg Gly Leu Ala Gly Pro Pro Gly Met Pro Gly Pro Arg Gly Ser Pro
1               5                   10                  15
Gly Pro Gln Gly
            20

<210> SEQ ID NO 307
<211> LENGTH: 20
<212> TYPE: PRT
<213> ORGANISM: Homo sapiens

<400> SEQUENCE: 307

Ala Gly Ile Thr Gly Ala Arg Gly Leu Ala Gly Pro Pro Gly Met Pro
1               5                   10                  15
Gly Pro Arg Gly
            20

<210> SEQ ID NO 308
<211> LENGTH: 23
<212> TYPE: PRT
<213> ORGANISM: Homo sapiens

<400> SEQUENCE: 308

Leu Gly Ile Ala Gly Ile Thr Gly Ala Arg Gly Leu Ala Gly Pro Pro
1               5                   10                  15
Gly Met Pro Gly Pro Arg Gly
            20

<210> SEQ ID NO 309
<211> LENGTH: 23
<212> TYPE: PRT
<213> ORGANISM: Homo sapiens

<400> SEQUENCE: 309

Thr Gly Ala Arg Gly Leu Ala Gly Pro Pro Gly Met Pro Gly Pro Arg
1               5                   10                  15

```
Gly Ser Pro Gly Pro Gln Gly
        20

<210> SEQ ID NO 310
<211> LENGTH: 24
<212> TYPE: PRT
<213> ORGANISM: Homo sapiens

<400> SEQUENCE: 310

Gln Gly Pro Pro Gly Pro Pro Gly Ile Asn Gly Ser Pro Gly Gly Lys
1               5                   10                  15

Gly Glu Met Gly Pro Ala Gly Ile
        20

<210> SEQ ID NO 311
<211> LENGTH: 24
<212> TYPE: PRT
<213> ORGANISM: Homo sapiens

<400> SEQUENCE: 311

Leu Pro Gly Pro Pro Gly Ile Lys Gly Pro Ala Gly Ile Pro Gly Phe
1               5                   10                  15

Pro Gly Met Lys Gly His Arg Gly
        20

<210> SEQ ID NO 312
<211> LENGTH: 26
<212> TYPE: PRT
<213> ORGANISM: Homo sapiens

<400> SEQUENCE: 312

Ala Gly Ile Thr Gly Ala Arg Gly Leu Ala Gly Pro Pro Gly Met Pro
1               5                   10                  15

Gly Pro Arg Gly Ser Pro Gly Pro Gln Gly
        20                  25

<210> SEQ ID NO 313
<211> LENGTH: 26
<212> TYPE: PRT
<213> ORGANISM: Homo sapiens

<400> SEQUENCE: 313

Thr Gly Ala Arg Gly Leu Ala Gly Pro Pro Gly Met Pro Gly Pro Arg
1               5                   10                  15

Gly Ser Pro Gly Pro Gln Gly Val Lys Gly
        20                  25

<210> SEQ ID NO 314
<211> LENGTH: 26
<212> TYPE: PRT
<213> ORGANISM: Homo sapiens

<400> SEQUENCE: 314

Arg Gly Leu Pro Gly Pro Pro Gly Ile Lys Gly Pro Ala Gly Ile Pro
1               5                   10                  15

Gly Phe Pro Gly Met Lys Gly His Arg Gly
        20                  25

<210> SEQ ID NO 315
<211> LENGTH: 29
<212> TYPE: PRT
<213> ORGANISM: Homo sapiens
```

```
<400> SEQUENCE: 315

Gly Arg Pro Gly Leu Pro Gly Ala Ala Gly Ala Arg Gly Asn Asp Gly
1               5                   10                  15

Ala Arg Gly Ser Asp Gly Gln Pro Gly Pro Pro Gly Pro
            20                  25

<210> SEQ ID NO 316
<211> LENGTH: 29
<212> TYPE: PRT
<213> ORGANISM: Homo sapiens

<400> SEQUENCE: 316

Asn Gly Ala Pro Gly Pro Met Gly Pro Arg Gly Ala Pro Gly Glu Arg
1               5                   10                  15

Gly Arg Pro Gly Leu Pro Gly Ala Ala Gly Ala Arg Gly
            20                  25

<210> SEQ ID NO 317
<211> LENGTH: 29
<212> TYPE: PRT
<213> ORGANISM: Homo sapiens

<400> SEQUENCE: 317

Ala Gly Ser Arg Gly Ala Pro Gly Pro Gln Gly Pro Arg Gly Asp Lys
1               5                   10                  15

Gly Glu Thr Gly Glu Arg Gly Ala Ala Gly Ile Lys Gly
            20                  25

<210> SEQ ID NO 318
<211> LENGTH: 32
<212> TYPE: PRT
<213> ORGANISM: Homo sapiens

<400> SEQUENCE: 318

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

<210> SEQ ID NO 319
<211> LENGTH: 34
<212> TYPE: PRT
<213> ORGANISM: Homo sapiens

<400> SEQUENCE: 319

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

Leu Ser

<210> SEQ ID NO 320
<211> LENGTH: 37
<212> TYPE: PRT
<213> ORGANISM: Homo sapiens

<400> SEQUENCE: 320

Pro Gly Pro Pro Gly Ser Asn Gly Asn Pro Gly Pro Pro Gly Pro Ser
1               5                   10                  15

Gly Ser Pro Gly Lys Asp Gly Pro Pro Gly Pro Ala Gly Asn Thr Gly
            20                  25                  30
```

```
Ala Pro Gly Ser Pro
        35

<210> SEQ ID NO 321
<211> LENGTH: 35
<212> TYPE: PRT
<213> ORGANISM: Homo sapiens

<400> SEQUENCE: 321

Thr Gly Ala Arg Gly Leu Ala Gly Pro Pro Gly Met Pro Gly Pro Arg
1               5                   10                  15

Gly Ser Pro Gly Pro Gln Gly Val Lys Gly Glu Ser Gly Lys Pro Gly
            20                  25                  30

Ala Asn Gly
        35

<210> SEQ ID NO 322
<211> LENGTH: 38
<212> TYPE: PRT
<213> ORGANISM: Homo sapiens

<400> SEQUENCE: 322

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly
        35

<210> SEQ ID NO 323
<211> LENGTH: 40
<212> TYPE: PRT
<213> ORGANISM: Homo sapiens

<400> SEQUENCE: 323

Gly Gly Pro Pro Gly Val Ala Gly Pro Pro Gly Gly Ser Gly Pro Ala
1               5                   10                  15

Gly Pro Pro Gly Pro Gln Gly Val Lys Gly Glu Arg Gly Ser Pro Gly
            20                  25                  30

Gly Pro Gly Ala Ala Gly Phe Pro
        35                  40

<210> SEQ ID NO 324
<211> LENGTH: 48
<212> TYPE: PRT
<213> ORGANISM: Homo sapiens

<400> SEQUENCE: 324

Lys Ser Gly Asp Arg Gly Glu Ser Gly Pro Ala Gly Pro Ala Gly Ala
1               5                   10                  15

Pro Gly Pro Ala Gly Ser Arg Gly Ala Pro Gly Pro Gln Gly Pro Arg
            20                  25                  30

Gly Asp Lys Gly Glu Thr Gly Glu Arg Gly Ala Ala Gly Ile Lys Gly
        35                  40                  45

<210> SEQ ID NO 325
<211> LENGTH: 12
<212> TYPE: PRT
<213> ORGANISM: Homo sapiens

<400> SEQUENCE: 325
```

```
Ile Pro Gly Phe Pro Gly Met Lys Gly His Arg Gly
1               5                   10
```

<210> SEQ ID NO 326
<211> LENGTH: 14
<212> TYPE: PRT
<213> ORGANISM: Homo sapiens

<400> SEQUENCE: 326

```
Arg Gly Leu Ala Gly Pro Pro Gly Met Pro Gly Pro Arg Gly
1               5                   10
```

<210> SEQ ID NO 327
<211> LENGTH: 16
<212> TYPE: PRT
<213> ORGANISM: Homo sapiens

<400> SEQUENCE: 327

```
Gly Pro Gln Gly Leu Gln Gly Leu Pro Gly Thr Gly Gly Pro Pro Gly
1               5                   10                  15
```

<210> SEQ ID NO 328
<211> LENGTH: 17
<212> TYPE: PRT
<213> ORGANISM: Homo sapiens

<400> SEQUENCE: 328

```
Lys Gly Pro Ala Gly Ile Pro Gly Phe Pro Gly Met Lys Gly His Arg
1               5                   10                  15

Gly
```

<210> SEQ ID NO 329
<211> LENGTH: 21
<212> TYPE: PRT
<213> ORGANISM: Homo sapiens

<400> SEQUENCE: 329

```
Arg Gly Leu Ala Gly Pro Pro Gly Met Pro Gly Pro Arg Gly Ser Pro
1               5                   10                  15

Gly Pro Gln Gly Val
                20
```

<210> SEQ ID NO 330
<211> LENGTH: 23
<212> TYPE: PRT
<213> ORGANISM: Homo sapiens

<400> SEQUENCE: 330

```
Gly Gly Pro Pro Gly Glu Asn Gly Lys Pro Gly Glu Pro Gly Pro Lys
1               5                   10                  15

Gly Asp Ala Gly Ala Pro Gly
                20
```

<210> SEQ ID NO 331
<211> LENGTH: 24
<212> TYPE: PRT
<213> ORGANISM: Homo sapiens

<400> SEQUENCE: 331

```
Ala Pro Gly Phe Arg Gly Pro Ala Gly Pro Asn Gly Ile Pro Gly Glu
1               5                   10                  15

Lys Gly Pro Ala Gly Glu Arg Gly
```

```
                        20

<210> SEQ ID NO 332
<211> LENGTH: 27
<212> TYPE: PRT
<213> ORGANISM: Homo sapiens

<400> SEQUENCE: 332

Glu Lys Gly Ser Pro Gly Ala Gln Gly Pro Pro Gly Ala Pro Gly Pro
1               5                   10                  15

Leu Gly Ile Ala Gly Ile Thr Gly Ala Arg Gly
            20                  25

<210> SEQ ID NO 333
<211> LENGTH: 24
<212> TYPE: PRT
<213> ORGANISM: Homo sapiens

<400> SEQUENCE: 333

Leu Pro Gly Pro Pro Gly Ile Lys Gly Pro Ala Gly Ile Pro Gly Phe
1               5                   10                  15

Pro Gly Met Lys Gly His Arg Gly
            20

<210> SEQ ID NO 334
<211> LENGTH: 26
<212> TYPE: PRT
<213> ORGANISM: Homo sapiens

<400> SEQUENCE: 334

Arg Gly Ala Pro Gly Phe Arg Gly Pro Ala Gly Pro Asn Gly Ile Pro
1               5                   10                  15

Gly Glu Lys Gly Pro Ala Gly Glu Arg Gly
            20                  25

<210> SEQ ID NO 335
<211> LENGTH: 26
<212> TYPE: PRT
<213> ORGANISM: Homo sapiens

<400> SEQUENCE: 335

Arg Gly Leu Pro Gly Pro Pro Gly Ile Lys Gly Pro Ala Gly Ile Pro
1               5                   10                  15

Gly Phe Pro Gly Met Lys Gly His Arg Gly
            20                  25

<210> SEQ ID NO 336
<211> LENGTH: 29
<212> TYPE: PRT
<213> ORGANISM: Homo sapiens

<400> SEQUENCE: 336

Arg Gly Pro Val Gly Pro Ser Gly Pro Pro Gly Lys Asp Gly Thr Ser
1               5                   10                  15

Gly His Pro Gly Pro Ile Gly Pro Pro Gly Pro Arg Gly
            20                  25

<210> SEQ ID NO 337
<211> LENGTH: 27
<212> TYPE: PRT
<213> ORGANISM: Homo sapiens

<400> SEQUENCE: 337
```

Ala Pro Gly Pro Gln Gly Pro Arg Gly Asp Lys Gly Glu Thr Gly Glu
1               5                   10                  15

Arg Gly Ala Ala Gly Ile Lys Gly His Arg Gly
            20                  25

<210> SEQ ID NO 338
<211> LENGTH: 29
<212> TYPE: PRT
<213> ORGANISM: Homo sapiens

<400> SEQUENCE: 338

Arg Gly Ala Pro Gly Pro Gln Gly Pro Arg Gly Asp Lys Gly Glu Thr
1               5                   10                  15

Gly Glu Arg Gly Ala Ala Gly Ile Lys Gly His Arg Gly
            20                  25

<210> SEQ ID NO 339
<211> LENGTH: 32
<212> TYPE: PRT
<213> ORGANISM: Homo sapiens

<400> SEQUENCE: 339

Arg Gly Phe Pro Gly Asn Pro Gly Ala Pro Gly Ser Pro Gly Pro Ala
1               5                   10                  15

Gly Gln Gln Gly Ala Ile Gly Ser Pro Gly Pro Ala Gly Pro Arg Gly
            20                  25                  30

<210> SEQ ID NO 340
<211> LENGTH: 29
<212> TYPE: PRT
<213> ORGANISM: Homo sapiens

<400> SEQUENCE: 340

Leu Pro Gly Pro Pro Gly Ile Lys Gly Pro Ala Gly Ile Pro Gly Phe
1               5                   10                  15

Pro Gly Met Lys Gly His Arg Gly Phe Asp Gly Arg Asn
            20                  25

<210> SEQ ID NO 341
<211> LENGTH: 33
<212> TYPE: PRT
<213> ORGANISM: Homo sapiens

<400> SEQUENCE: 341

Asp Ala Gly Gln Pro Gly Glu Lys Gly Ser Pro Gly Ala Gln Gly Pro
1               5                   10                  15

Pro Gly Ala Pro Gly Pro Leu Gly Ile Ala Gly Ile Thr Gly Ala Arg
            20                  25                  30

Gly

<210> SEQ ID NO 342
<211> LENGTH: 35
<212> TYPE: PRT
<213> ORGANISM: Homo sapiens

<400> SEQUENCE: 342

Arg Gly Pro Thr Gly Pro Ile Gly Pro Pro Gly Pro Ala Gly Gln Pro
1               5                   10                  15

Gly Asp Lys Gly Glu Gly Gly Ala Pro Gly Leu Pro Gly Ile Ala Gly
            20                  25                  30

Pro Arg Gly
        35

<210> SEQ ID NO 343
<211> LENGTH: 35
<212> TYPE: PRT
<213> ORGANISM: Homo sapiens

<400> SEQUENCE: 343

Lys Gly Asp Ala Gly Gln Pro Gly Glu Lys Gly Ser Pro Gly Ala Gln
1               5                   10                  15

Gly Pro Pro Gly Ala Pro Gly Pro Leu Gly Ile Ala Gly Ile Thr Gly
            20                  25                  30

Ala Arg Gly
        35

<210> SEQ ID NO 344
<211> LENGTH: 33
<212> TYPE: PRT
<213> ORGANISM: Homo sapiens

<400> SEQUENCE: 344

Arg Asn Gly Glu Lys Gly Glu Thr Gly Ala Pro Gly Leu Lys Gly Glu
1               5                   10                  15

Asn Gly Leu Pro Gly Glu Asn Gly Ala Pro Gly Pro Met Gly Pro Arg
            20                  25                  30

Gly

<210> SEQ ID NO 345
<211> LENGTH: 35
<212> TYPE: PRT
<213> ORGANISM: Homo sapiens

<400> SEQUENCE: 345

Ala Pro Gly Phe Arg Gly Pro Ala Gly Pro Asn Gly Ile Pro Gly Glu
1               5                   10                  15

Lys Gly Pro Ala Gly Glu Arg Gly Ala Pro Gly Pro Ala Gly Pro Arg
            20                  25                  30

Gly Ala Ala
        35

<210> SEQ ID NO 346
<211> LENGTH: 35
<212> TYPE: PRT
<213> ORGANISM: Homo sapiens

<400> SEQUENCE: 346

Arg Gly Ala Pro Gly Phe Arg Gly Pro Ala Gly Pro Asn Gly Ile Pro
1               5                   10                  15

Gly Glu Lys Gly Pro Ala Gly Glu Arg Gly Ala Pro Gly Pro Ala Gly
            20                  25                  30

Pro Arg Gly
        35

<210> SEQ ID NO 347
<211> LENGTH: 35
<212> TYPE: PRT
<213> ORGANISM: Homo sapiens

<400> SEQUENCE: 347

Arg Gly Ser Pro Gly Glu Arg Gly Glu Thr Gly Pro Pro Gly Pro Ala

-continued

```
                1               5                  10                  15
Gly Phe Pro Gly Ala Pro Gly Gln Asn Gly Glu Pro Gly Gly Lys Gly
                20                  25                  30
Glu Arg Gly
        35

<210> SEQ ID NO 348
<211> LENGTH: 38
<212> TYPE: PRT
<213> ORGANISM: Homo sapiens

<400> SEQUENCE: 348

Gly His Ala Gly Ala Gln Gly Pro Pro Gly Pro Pro Gly Ile Asn Gly
1               5                  10                  15

Ser Pro Gly Gly Lys Gly Glu Met Gly Pro Ala Gly Ile Pro Gly Ala
                20                  25                  30

Pro Gly Leu Met Gly Ala
        35

<210> SEQ ID NO 349
<211> LENGTH: 38
<212> TYPE: PRT
<213> ORGANISM: Homo sapiens

<400> SEQUENCE: 349

Arg Gly Leu Ala Gly Pro Pro Gly Met Pro Gly Pro Arg Gly Ser Pro
1               5                  10                  15

Gly Pro Gln Gly Val Lys Gly Glu Ser Gly Lys Pro Gly Ala Asn Gly
                20                  25                  30

Leu Ser Gly Glu Arg Gly
        35

<210> SEQ ID NO 350
<211> LENGTH: 13
<212> TYPE: PRT
<213> ORGANISM: Homo sapiens

<400> SEQUENCE: 350

Leu Gly Ile Ala Gly Ile Thr Gly Ala Arg Gly Leu Ala
1               5                  10

<210> SEQ ID NO 351
<211> LENGTH: 12
<212> TYPE: PRT
<213> ORGANISM: Homo sapiens

<400> SEQUENCE: 351

Ile Pro Gly Phe Pro Gly Met Lys Gly His Arg Gly
1               5                  10

<210> SEQ ID NO 352
<211> LENGTH: 14
<212> TYPE: PRT
<213> ORGANISM: Homo sapiens

<400> SEQUENCE: 352

Arg Gly Leu Ala Gly Pro Pro Gly Met Pro Gly Pro Arg Gly
1               5                  10

<210> SEQ ID NO 353
<211> LENGTH: 20
<212> TYPE: PRT
```

```
<213> ORGANISM: Homo sapiens

<400> SEQUENCE: 353

Gln Gly Pro Pro Gly Ala Pro Gly Leu Gly Ile Ala Gly Ile Thr
1               5                   10                  15

Gly Ala Arg Gly
            20

<210> SEQ ID NO 354
<211> LENGTH: 20
<212> TYPE: PRT
<213> ORGANISM: Homo sapiens

<400> SEQUENCE: 354

Ala Gly Ile Thr Gly Ala Arg Gly Leu Ala Gly Pro Pro Gly Met Pro
1               5                   10                  15

Gly Pro Arg Gly
            20

<210> SEQ ID NO 355
<211> LENGTH: 23
<212> TYPE: PRT
<213> ORGANISM: Homo sapiens

<400> SEQUENCE: 355

Ala Gly Ile Pro Gly Ala Pro Gly Leu Met Gly Ala Arg Gly Pro Pro
1               5                   10                  15

Gly Pro Ala Gly Ala Asn Gly
            20

<210> SEQ ID NO 356
<211> LENGTH: 24
<212> TYPE: PRT
<213> ORGANISM: Homo sapiens

<400> SEQUENCE: 356

Arg Gly Leu Ala Gly Pro Pro Gly Met Pro Gly Pro Arg Gly Ser Pro
1               5                   10                  15

Gly Pro Gln Gly Val Lys Gly Glu
            20

<210> SEQ ID NO 357
<211> LENGTH: 26
<212> TYPE: PRT
<213> ORGANISM: Homo sapiens

<400> SEQUENCE: 357

Lys Gly Ser Pro Gly Ala Gln Gly Pro Pro Gly Ala Pro Gly Pro Leu
1               5                   10                  15

Gly Ile Ala Gly Ile Thr Gly Ala Arg Gly
            20                  25

<210> SEQ ID NO 358
<211> LENGTH: 24
<212> TYPE: PRT
<213> ORGANISM: Homo sapiens

<400> SEQUENCE: 358

Leu Pro Gly Pro Pro Gly Ile Lys Gly Pro Ala Gly Ile Pro Gly Phe
1               5                   10                  15

Pro Gly Met Lys Gly His Arg Gly
            20
```

<210> SEQ ID NO 359
<211> LENGTH: 24
<212> TYPE: PRT
<213> ORGANISM: Homo sapiens

<400> SEQUENCE: 359

Lys Asp Gly Thr Ser Gly His Pro Gly Pro Ile Gly Pro Pro Gly Pro
1               5                   10                  15

Arg Gly Asn Arg Gly Glu Arg Gly
            20

<210> SEQ ID NO 360
<211> LENGTH: 26
<212> TYPE: PRT
<213> ORGANISM: Homo sapiens

<400> SEQUENCE: 360

Ala Gly Ile Thr Gly Ala Arg Gly Leu Ala Gly Pro Pro Gly Met Pro
1               5                   10                  15

Gly Pro Arg Gly Ser Pro Gly Pro Gln Gly
            20                  25

<210> SEQ ID NO 361
<211> LENGTH: 27
<212> TYPE: PRT
<213> ORGANISM: Homo sapiens

<400> SEQUENCE: 361

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys
            20                  25

<210> SEQ ID NO 362
<211> LENGTH: 32
<212> TYPE: PRT
<213> ORGANISM: Homo sapiens

<400> SEQUENCE: 362

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

<210> SEQ ID NO 363
<211> LENGTH: 34
<212> TYPE: PRT
<213> ORGANISM: Homo sapiens

<400> SEQUENCE: 363

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

Leu Ser

<210> SEQ ID NO 364
<211> LENGTH: 37
<212> TYPE: PRT
<213> ORGANISM: Homo sapiens

<400> SEQUENCE: 364

Pro Gly Pro Gly Ser Asn Gly Asn Pro Gly Pro Gly Pro Gly Pro Ser
1               5                   10                  15
Gly Ser Pro Gly Lys Asp Gly Pro Gly Pro Ala Gly Asn Thr Gly
            20                  25                  30
Ala Pro Gly Ser Pro
            35

<210> SEQ ID NO 365
<211> LENGTH: 38
<212> TYPE: PRT
<213> ORGANISM: Homo sapiens

<400> SEQUENCE: 365

Arg Gly Ala Pro Gly Glu Lys Gly Glu Gly Gly Pro Pro Gly Val Ala
1               5                   10                  15
Gly Pro Pro Gly Gly Ser Gly Pro Ala Gly Pro Pro Gly Pro Gln Gly
            20                  25                  30
Val Lys Gly Glu Arg Gly
            35

<210> SEQ ID NO 366
<211> LENGTH: 44
<212> TYPE: PRT
<213> ORGANISM: Homo sapiens

<400> SEQUENCE: 366

Lys Ser Gly Asp Arg Gly Glu Ser Gly Pro Ala Gly Pro Ala Gly Ala
1               5                   10                  15
Pro Gly Pro Ala Gly Ser Arg Gly Ala Pro Gly Pro Gln Gly Pro Arg
            20                  25                  30
Gly Asp Lys Gly Glu Thr Gly Glu Arg Gly Ala Ala
            35                  40

<210> SEQ ID NO 367
<211> LENGTH: 53
<212> TYPE: PRT
<213> ORGANISM: Homo sapiens

<400> SEQUENCE: 367

Arg Gly Ala Pro Gly Glu Lys Gly Glu Gly Gly Pro Pro Gly Val Ala
1               5                   10                  15
Gly Pro Pro Gly Gly Ser Gly Pro Ala Gly Pro Pro Gly Pro Gln Gly
            20                  25                  30
Val Lys Gly Glu Arg Gly Ser Pro Gly Gly Pro Gly Ala Ala Gly Phe
            35                  40                  45
Pro Gly Ala Arg Gly
            50

<210> SEQ ID NO 368
<211> LENGTH: 6
<212> TYPE: PRT
<213> ORGANISM: Homo sapiens

<400> SEQUENCE: 368

Ala Ile Gly Pro Ser Gly
1               5

<210> SEQ ID NO 369
<211> LENGTH: 10

```
<212> TYPE: PRT
<213> ORGANISM: Homo sapiens

<400> SEQUENCE: 369

Pro Gly Ile Pro Gly Arg Asn Gly Asp Pro
1               5                   10

<210> SEQ ID NO 370
<211> LENGTH: 10
<212> TYPE: PRT
<213> ORGANISM: Homo sapiens

<400> SEQUENCE: 370

Glu Ser Cys Pro Thr Gly Pro Gln Asn Tyr
1               5                   10

<210> SEQ ID NO 371
<211> LENGTH: 10
<212> TYPE: PRT
<213> ORGANISM: Homo sapiens

<400> SEQUENCE: 371

Pro Lys Gly Asp Thr Gly Pro Arg Gly Pro
1               5                   10

<210> SEQ ID NO 372
<211> LENGTH: 6
<212> TYPE: PRT
<213> ORGANISM: Homo sapiens

<400> SEQUENCE: 372

Gly Ile Pro Gly Ala Pro
1               5

<210> SEQ ID NO 373
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (5)..(6)
<223> OTHER INFORMATION: proline or hydroxyproline

<400> SEQUENCE: 373

Gly Asp Xaa Gly Xaa Xaa
1               5

<210> SEQ ID NO 374
<211> LENGTH: 6
<212> TYPE: PRT
<213> ORGANISM: Homo sapiens

<400> SEQUENCE: 374

Lys Gly Glu Ser Gly Lys
1               5

<210> SEQ ID NO 375
<211> LENGTH: 6
<212> TYPE: PRT
<213> ORGANISM: Homo sapiens

<400> SEQUENCE: 375
```

Ile Ala Gly Ile Thr Gly
1               5

<210> SEQ ID NO 376
<211> LENGTH: 6
<212> TYPE: PRT
<213> ORGANISM: Homo sapiens

<400> SEQUENCE: 376

Ile Lys Gly His Arg Gly
1               5

<210> SEQ ID NO 377
<211> LENGTH: 6
<212> TYPE: PRT
<213> ORGANISM: Homo sapiens

<400> SEQUENCE: 377

Arg Gly Leu Ala Gly Pro
1               5

<210> SEQ ID NO 378
<211> LENGTH: 6
<212> TYPE: PRT
<213> ORGANISM: Homo sapiens

<400> SEQUENCE: 378

Thr Gly Ala Arg Gly Leu
1               5

<210> SEQ ID NO 379
<211> LENGTH: 6
<212> TYPE: PRT
<213> ORGANISM: Homo sapiens

<400> SEQUENCE: 379

Ile Thr Gly Ala Arg Gly
1               5

<210> SEQ ID NO 380
<211> LENGTH: 6
<212> TYPE: PRT
<213> ORGANISM: Homo sapiens

<400> SEQUENCE: 380

Val Lys Gly Glu Ser Gly
1               5

<210> SEQ ID NO 381
<211> LENGTH: 6
<212> TYPE: PRT
<213> ORGANISM: Homo sapiens

<400> SEQUENCE: 381

Lys Gly Asp Ala Gly Gln
1               5

<210> SEQ ID NO 382
<211> LENGTH: 6
<212> TYPE: PRT
<213> ORGANISM: Homo sapiens

<400> SEQUENCE: 382

Leu Arg Gly Gly Ala Gly
1               5

<210> SEQ ID NO 383
<211> LENGTH: 6
<212> TYPE: PRT
<213> ORGANISM: Homo sapiens

<400> SEQUENCE: 383

Gly Lys Ser Gly Asp Arg
1               5

<210> SEQ ID NO 384
<211> LENGTH: 6
<212> TYPE: PRT
<213> ORGANISM: Homo sapiens

<400> SEQUENCE: 384

Leu Gln Gly Leu Pro Gly
1               5

<210> SEQ ID NO 385
<211> LENGTH: 6
<212> TYPE: PRT
<213> ORGANISM: Homo sapiens

<400> SEQUENCE: 385

Glu Arg Gly Leu Pro Gly
1               5

<210> SEQ ID NO 386
<211> LENGTH: 6
<212> TYPE: PRT
<213> ORGANISM: Homo sapiens

<400> SEQUENCE: 386

Ile Gly Ser Pro Gly Pro
1               5

<210> SEQ ID NO 387
<211> LENGTH: 6
<212> TYPE: PRT
<213> ORGANISM: Homo sapiens

<400> SEQUENCE: 387

Gly Leu Ser Gly Glu Arg
1               5

<210> SEQ ID NO 388
<211> LENGTH: 6
<212> TYPE: PRT
<213> ORGANISM: Homo sapiens

<400> SEQUENCE: 388

Gly Leu Ala Gly Pro Pro
1               5

<210> SEQ ID NO 389
<211> LENGTH: 6
<212> TYPE: PRT
<213> ORGANISM: Homo sapiens

<400> SEQUENCE: 389

Pro Gln Gly Pro Pro Gly
1               5

```
<210> SEQ ID NO 390
<211> LENGTH: 6
<212> TYPE: PRT
<213> ORGANISM: Homo sapiens

<400> SEQUENCE: 390

Gln Gln Gly Ala Ile Gly
1               5

<210> SEQ ID NO 391
<211> LENGTH: 6
<212> TYPE: PRT
<213> ORGANISM: Homo sapiens

<400> SEQUENCE: 391

Gly Pro Pro Gly Pro Thr
1               5

<210> SEQ ID NO 392
<211> LENGTH: 6
<212> TYPE: PRT
<213> ORGANISM: Homo sapiens

<400> SEQUENCE: 392

Ile Asn Gly Ser Pro Gly
1               5

<210> SEQ ID NO 393
<211> LENGTH: 6
<212> TYPE: PRT
<213> ORGANISM: Homo sapiens

<400> SEQUENCE: 393

Gly Pro Pro Gly Glu Pro
1               5

<210> SEQ ID NO 394
<211> LENGTH: 6
<212> TYPE: PRT
<213> ORGANISM: Homo sapiens

<400> SEQUENCE: 394

Gly Leu Pro Gly Pro Pro
1               5

<210> SEQ ID NO 395
<211> LENGTH: 6
<212> TYPE: PRT
<213> ORGANISM: Homo sapiens

<400> SEQUENCE: 395

Lys Asn Gly Glu Thr Gly
1               5

<210> SEQ ID NO 396
<211> LENGTH: 6
<212> TYPE: PRT
<213> ORGANISM: Homo sapiens

<400> SEQUENCE: 396

Leu Pro Gly Ile Ala Gly
1               5

<210> SEQ ID NO 397
<211> LENGTH: 6
```

```
<212> TYPE: PRT
<213> ORGANISM: Homo sapiens

<400> SEQUENCE: 397

Gly Ile Asn Gly Ser Pro
1               5

<210> SEQ ID NO 398
<211> LENGTH: 6
<212> TYPE: PRT
<213> ORGANISM: Homo sapiens

<400> SEQUENCE: 398

Gly Ile Asn Gly Ser Pro
1               5

<210> SEQ ID NO 399
<211> LENGTH: 6
<212> TYPE: PRT
<213> ORGANISM: Homo sapiens

<400> SEQUENCE: 399

Leu Lys Gly Glu Asn Gly
1               5

<210> SEQ ID NO 400
<211> LENGTH: 6
<212> TYPE: PRT
<213> ORGANISM: Homo sapiens

<400> SEQUENCE: 400

Leu Met Gly Ala Arg Gly
1               5

<210> SEQ ID NO 401
<211> LENGTH: 6
<212> TYPE: PRT
<213> ORGANISM: Homo sapiens

<400> SEQUENCE: 401

Tyr Gln Gly Pro Pro Gly
1               5

<210> SEQ ID NO 402
<211> LENGTH: 6
<212> TYPE: PRT
<213> ORGANISM: Homo sapiens

<400> SEQUENCE: 402

Gly Glu Arg Gly Ala Pro
1               5

<210> SEQ ID NO 403
<211> LENGTH: 6
<212> TYPE: PRT
<213> ORGANISM: Homo sapiens

<400> SEQUENCE: 403

Asp Lys Gly Glu Pro Gly
1               5

<210> SEQ ID NO 404
<211> LENGTH: 6
<212> TYPE: PRT
<213> ORGANISM: Homo sapiens
```

<400> SEQUENCE: 404

Gly His Ala Gly Ala Gln
1               5

<210> SEQ ID NO 405
<211> LENGTH: 6
<212> TYPE: PRT
<213> ORGANISM: Homo sapiens

<400> SEQUENCE: 405

Gly Ser Asp Gly Gln Pro
1               5

<210> SEQ ID NO 406
<211> LENGTH: 6
<212> TYPE: PRT
<213> ORGANISM: Homo sapiens

<400> SEQUENCE: 406

Pro Gly Met Lys Gly His
1               5

<210> SEQ ID NO 407
<211> LENGTH: 6
<212> TYPE: PRT
<213> ORGANISM: Homo sapiens

<400> SEQUENCE: 407

Phe Pro Gly Ala Arg Gly
1               5

<210> SEQ ID NO 408
<211> LENGTH: 6
<212> TYPE: PRT
<213> ORGANISM: Homo sapiens

<400> SEQUENCE: 408

Gly Phe Pro Gly Ala Arg
1               5

<210> SEQ ID NO 409
<211> LENGTH: 6
<212> TYPE: PRT
<213> ORGANISM: Homo sapiens

<400> SEQUENCE: 409

Phe Pro Gly Met Lys Gly
1               5

<210> SEQ ID NO 410
<211> LENGTH: 6
<212> TYPE: PRT
<213> ORGANISM: Homo sapiens

<400> SEQUENCE: 410

Pro Gly Asp Lys Gly Glu
1               5

<210> SEQ ID NO 411
<211> LENGTH: 6
<212> TYPE: PRT
<213> ORGANISM: Homo sapiens

<400> SEQUENCE: 411

```
Gly Asp Lys Gly Glu Thr
1               5

<210> SEQ ID NO 412
<211> LENGTH: 6
<212> TYPE: PRT
<213> ORGANISM: Homo sapiens

<400> SEQUENCE: 412

Gly Gln Pro Gly Asp Lys
1               5

<210> SEQ ID NO 413
<211> LENGTH: 6
<212> TYPE: PRT
<213> ORGANISM: Homo sapiens

<400> SEQUENCE: 413

Gly Pro Pro Gly Glu Asn
1               5

<210> SEQ ID NO 414
<211> LENGTH: 6
<212> TYPE: PRT
<213> ORGANISM: Homo sapiens

<400> SEQUENCE: 414

Gly Ile Pro Gly Phe Pro
1               5

<210> SEQ ID NO 415
<211> LENGTH: 6
<212> TYPE: PRT
<213> ORGANISM: Homo sapiens

<400> SEQUENCE: 415

Gly Glu Arg Gly Ser Pro
1               5

<210> SEQ ID NO 416
<211> LENGTH: 6
<212> TYPE: PRT
<213> ORGANISM: Homo sapiens

<400> SEQUENCE: 416

Pro Gly Val Pro Gly Ala
1               5

<210> SEQ ID NO 417
<211> LENGTH: 6
<212> TYPE: PRT
<213> ORGANISM: Homo sapiens

<400> SEQUENCE: 417

Ala Ala Gly Phe Pro Gly
1               5

<210> SEQ ID NO 418
<211> LENGTH: 6
<212> TYPE: PRT
<213> ORGANISM: Homo sapiens

<400> SEQUENCE: 418

Gly Lys Asp Gly Glu Ser
```

```
1               5

<210> SEQ ID NO 419
<211> LENGTH: 6
<212> TYPE: PRT
<213> ORGANISM: Homo sapiens

<400> SEQUENCE: 419

Gly Ala Arg Gly Asn Asp
1               5

<210> SEQ ID NO 420
<211> LENGTH: 6
<212> TYPE: PRT
<213> ORGANISM: Homo sapiens

<400> SEQUENCE: 420

Gly Phe Pro Gly Ala Pro
1               5

<210> SEQ ID NO 421
<211> LENGTH: 6
<212> TYPE: PRT
<213> ORGANISM: Homo sapiens

<400> SEQUENCE: 421

Gly Ala Ala Gly Glu Pro
1               5

<210> SEQ ID NO 422
<211> LENGTH: 6
<212> TYPE: PRT
<213> ORGANISM: Homo sapiens

<400> SEQUENCE: 422

Gly Ala Arg Gly Pro Pro
1               5

<210> SEQ ID NO 423
<211> LENGTH: 6
<212> TYPE: PRT
<213> ORGANISM: Homo sapiens

<400> SEQUENCE: 423

Gly Pro Pro Gly Ser Asn
1               5

<210> SEQ ID NO 424
<211> LENGTH: 6
<212> TYPE: PRT
<213> ORGANISM: Homo sapiens

<400> SEQUENCE: 424

Gly Pro Lys Gly Asp Ala
1               5

<210> SEQ ID NO 425
<211> LENGTH: 6
<212> TYPE: PRT
<213> ORGANISM: Homo sapiens

<400> SEQUENCE: 425

Gly Gly Ala Gly Pro Pro
1               5
```

<210> SEQ ID NO 426
<211> LENGTH: 6
<212> TYPE: PRT
<213> ORGANISM: Homo sapiens

<400> SEQUENCE: 426

Pro Gly Pro Gln Gly His
1               5

<210> SEQ ID NO 427
<211> LENGTH: 6
<212> TYPE: PRT
<213> ORGANISM: Homo sapiens

<400> SEQUENCE: 427

Pro Gly Phe Pro Gly Met
1               5

<210> SEQ ID NO 428
<211> LENGTH: 6
<212> TYPE: PRT
<213> ORGANISM: Homo sapiens

<400> SEQUENCE: 428

Gly Ser Pro Gly Gly Pro
1               5

<210> SEQ ID NO 429
<211> LENGTH: 6
<212> TYPE: PRT
<213> ORGANISM: Homo sapiens

<400> SEQUENCE: 429

Ser Gly Asp Arg Gly Glu
1               5

<210> SEQ ID NO 430
<211> LENGTH: 6
<212> TYPE: PRT
<213> ORGANISM: Homo sapiens

<400> SEQUENCE: 430

Gly Ile Thr Gly Ala Arg
1               5

<210> SEQ ID NO 431
<211> LENGTH: 6
<212> TYPE: PRT
<213> ORGANISM: Homo sapiens

<400> SEQUENCE: 431

Gly Ile Ala Gly Ile Thr
1               5

<210> SEQ ID NO 432
<211> LENGTH: 6
<212> TYPE: PRT
<213> ORGANISM: Homo sapiens

<400> SEQUENCE: 432

Pro Gly Pro Pro Gly Ile
1               5

<210> SEQ ID NO 433

```
<211> LENGTH: 6
<212> TYPE: PRT
<213> ORGANISM: Homo sapiens

<400> SEQUENCE: 433

Glu Ser Cys Pro Thr Gly
1               5

<210> SEQ ID NO 434
<211> LENGTH: 6
<212> TYPE: PRT
<213> ORGANISM: Homo sapiens

<400> SEQUENCE: 434

His Ala Gly Ala Gln Gly
1               5

<210> SEQ ID NO 435
<211> LENGTH: 6
<212> TYPE: PRT
<213> ORGANISM: Homo sapiens

<400> SEQUENCE: 435

Gly Ala Pro Gly Phe Arg
1               5

<210> SEQ ID NO 436
<211> LENGTH: 6
<212> TYPE: PRT
<213> ORGANISM: Homo sapiens

<400> SEQUENCE: 436

Arg Pro Gly Leu Pro Gly
1               5

<210> SEQ ID NO 437
<211> LENGTH: 6
<212> TYPE: PRT
<213> ORGANISM: Homo sapiens

<400> SEQUENCE: 437

Asn Thr Gly Ala Pro Gly
1               5

<210> SEQ ID NO 438
<211> LENGTH: 6
<212> TYPE: PRT
<213> ORGANISM: Homo sapiens

<400> SEQUENCE: 438

Gly Ala Pro Gly Pro Met
1               5

<210> SEQ ID NO 439
<211> LENGTH: 6
<212> TYPE: PRT
<213> ORGANISM: Homo sapiens

<400> SEQUENCE: 439

Gly Ser Pro Gly Glu Arg
1               5

<210> SEQ ID NO 440
<211> LENGTH: 6
<212> TYPE: PRT
```

<213> ORGANISM: Homo sapiens

<400> SEQUENCE: 440

Pro Gln Gly Leu Gln Gly
1               5

<210> SEQ ID NO 441
<211> LENGTH: 6
<212> TYPE: PRT
<213> ORGANISM: Homo sapiens

<400> SEQUENCE: 441

Gly Pro Ala Gly Ile Pro
1               5

<210> SEQ ID NO 442
<211> LENGTH: 6
<212> TYPE: PRT
<213> ORGANISM: Homo sapiens

<400> SEQUENCE: 442

Asp Arg Gly Pro Gln Gly
1               5

<210> SEQ ID NO 443
<211> LENGTH: 6
<212> TYPE: PRT
<213> ORGANISM: Homo sapiens

<400> SEQUENCE: 443

Pro Gly Phe Arg Gly Pro
1               5

<210> SEQ ID NO 444
<211> LENGTH: 6
<212> TYPE: PRT
<213> ORGANISM: Homo sapiens

<400> SEQUENCE: 444

Lys Gly Ser Pro Gly Ala
1               5

<210> SEQ ID NO 445
<211> LENGTH: 6
<212> TYPE: PRT
<213> ORGANISM: Homo sapiens

<400> SEQUENCE: 445

Gly Ala Pro Gly Pro Gln
1               5

<210> SEQ ID NO 446
<211> LENGTH: 6
<212> TYPE: PRT
<213> ORGANISM: Homo sapiens

<400> SEQUENCE: 446

Gly Phe Pro Gly Asn Pro
1               5

<210> SEQ ID NO 447
<211> LENGTH: 6
<212> TYPE: PRT
<213> ORGANISM: Homo sapiens

<400> SEQUENCE: 447

Gly Pro Val Gly Pro Ser
1               5

<210> SEQ ID NO 448
<211> LENGTH: 6
<212> TYPE: PRT
<213> ORGANISM: Homo sapiens

<400> SEQUENCE: 448

Gly Pro Thr Gly Pro Ile
1               5

<210> SEQ ID NO 449
<211> LENGTH: 6
<212> TYPE: PRT
<213> ORGANISM: Homo sapiens

<400> SEQUENCE: 449

Gly Asp Ala Gly Gln Pro
1               5

<210> SEQ ID NO 450
<211> LENGTH: 6
<212> TYPE: PRT
<213> ORGANISM: Homo sapiens

<400> SEQUENCE: 450

Asn Gly Glu Lys Gly Glu
1               5

<210> SEQ ID NO 451
<211> LENGTH: 6
<212> TYPE: PRT
<213> ORGANISM: Homo sapiens

<400> SEQUENCE: 451

Ser Arg Gly Ala Pro Gly
1               5

<210> SEQ ID NO 452
<211> LENGTH: 6
<212> TYPE: PRT
<213> ORGANISM: Homo sapiens

<400> SEQUENCE: 452

Val Ala Gly Pro Pro Gly
1               5

<210> SEQ ID NO 453
<211> LENGTH: 6
<212> TYPE: PRT
<213> ORGANISM: Homo sapiens

<400> SEQUENCE: 453

Pro Gly Pro Gln Gly Pro
1               5

<210> SEQ ID NO 454
<211> LENGTH: 6
<212> TYPE: PRT
<213> ORGANISM: Homo sapiens

<400> SEQUENCE: 454

-continued

Ala Gly Gln Pro Gly Glu
1               5

<210> SEQ ID NO 455
<211> LENGTH: 6
<212> TYPE: PRT
<213> ORGANISM: Homo sapiens

<400> SEQUENCE: 455

Pro Gly Ala Pro Gly Gly
1               5

<210> SEQ ID NO 456
<211> LENGTH: 6
<212> TYPE: PRT
<213> ORGANISM: Homo sapiens

<400> SEQUENCE: 456

Pro Gly Ala Pro Gly Gln
1               5

<210> SEQ ID NO 457
<211> LENGTH: 6
<212> TYPE: PRT
<213> ORGANISM: Homo sapiens

<400> SEQUENCE: 457

Ala Gly Gln Gln Gly Ala
1               5

<210> SEQ ID NO 458
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline

<400> SEQUENCE: 458

Xaa Gly Xaa Pro Gly Xaa
1               5

<210> SEQ ID NO 459
<211> LENGTH: 6
<212> TYPE: PRT
<213> ORGANISM: Homo sapiens

<400> SEQUENCE: 459

Ser Pro Gly Gly Lys Gly
1               5

<210> SEQ ID NO 460
<211> LENGTH: 6
<212> TYPE: PRT
<213> ORGANISM: Homo sapiens

<400> SEQUENCE: 460

Gly Arg Asn Gly Glu Lys

```
1               5

<210> SEQ ID NO 461
<211> LENGTH: 6
<212> TYPE: PRT
<213> ORGANISM: Homo sapiens

<400> SEQUENCE: 461

Gly Pro Pro Gly Ala Pro
1               5

<210> SEQ ID NO 462
<211> LENGTH: 6
<212> TYPE: PRT
<213> ORGANISM: Homo sapiens

<400> SEQUENCE: 462

Gly Ser Arg Gly Ala Pro
1               5

<210> SEQ ID NO 463
<211> LENGTH: 6
<212> TYPE: PRT
<213> ORGANISM: Homo sapiens

<400> SEQUENCE: 463

Gly Gly Ala Gly Glu Pro
1               5

<210> SEQ ID NO 464
<211> LENGTH: 6
<212> TYPE: PRT
<213> ORGANISM: Homo sapiens

<400> SEQUENCE: 464

Gly Ser Pro Gly Ala Gln
1               5

<210> SEQ ID NO 465
<211> LENGTH: 6
<212> TYPE: PRT
<213> ORGANISM: Homo sapiens

<400> SEQUENCE: 465

Ser Pro Gly Ala Gln Gly
1               5

<210> SEQ ID NO 466
<211> LENGTH: 6
<212> TYPE: PRT
<213> ORGANISM: Homo sapiens

<400> SEQUENCE: 466

Pro Gly Val Ser Gly Pro
1               5

<210> SEQ ID NO 467
<211> LENGTH: 6
<212> TYPE: PRT
<213> ORGANISM: Homo sapiens

<400> SEQUENCE: 467

Pro Gly Ala Pro Gly Leu
1               5
```

```
<210> SEQ ID NO 468
<211> LENGTH: 6
<212> TYPE: PRT
<213> ORGANISM: Homo sapiens

<400> SEQUENCE: 468

Gly Ile Pro Gly Gln Pro
1               5

<210> SEQ ID NO 469
<211> LENGTH: 6
<212> TYPE: PRT
<213> ORGANISM: Homo sapiens

<400> SEQUENCE: 469

Asp Ala Gly Ala Pro Gly
1               5

<210> SEQ ID NO 470
<211> LENGTH: 6
<212> TYPE: PRT
<213> ORGANISM: Homo sapiens

<400> SEQUENCE: 470

Gly Pro Pro Gly Ile Asn
1               5

<210> SEQ ID NO 471
<211> LENGTH: 6
<212> TYPE: PRT
<213> ORGANISM: Homo sapiens

<400> SEQUENCE: 471

Asn Gly Asp Pro Gly Ile
1               5

<210> SEQ ID NO 472
<211> LENGTH: 6
<212> TYPE: PRT
<213> ORGANISM: Homo sapiens

<400> SEQUENCE: 472

Ser Pro Gly Pro Gln Gly
1               5

<210> SEQ ID NO 473
<211> LENGTH: 6
<212> TYPE: PRT
<213> ORGANISM: Homo sapiens

<400> SEQUENCE: 473

Gly Met Pro Gly Pro Arg
1               5

<210> SEQ ID NO 474
<211> LENGTH: 6
<212> TYPE: PRT
<213> ORGANISM: Homo sapiens

<400> SEQUENCE: 474

Ser Pro Gly Pro Ala Gly
1               5

<210> SEQ ID NO 475
```

```
<211> LENGTH: 6
<212> TYPE: PRT
<213> ORGANISM: Homo sapiens

<400> SEQUENCE: 475

Pro Gly Pro Gln Gly Val
1               5

<210> SEQ ID NO 476
<211> LENGTH: 6
<212> TYPE: PRT
<213> ORGANISM: Homo sapiens

<400> SEQUENCE: 476

Glu Arg Gly Ala Ala Gly
1               5

<210> SEQ ID NO 477
<211> LENGTH: 6
<212> TYPE: PRT
<213> ORGANISM: Homo sapiens

<400> SEQUENCE: 477

Pro Gly Pro Leu Gly Ile
1               5

<210> SEQ ID NO 478
<211> LENGTH: 6
<212> TYPE: PRT
<213> ORGANISM: Homo sapiens

<400> SEQUENCE: 478

Ala Ala Gly Thr Pro Gly
1               5

<210> SEQ ID NO 479
<211> LENGTH: 6
<212> TYPE: PRT
<213> ORGANISM: Homo sapiens

<400> SEQUENCE: 479

Pro Gly Pro Pro Gly Thr
1               5

<210> SEQ ID NO 480
<211> LENGTH: 6
<212> TYPE: PRT
<213> ORGANISM: Homo sapiens

<400> SEQUENCE: 480

Gly Asn Arg Gly Glu Arg
1               5

<210> SEQ ID NO 481
<211> LENGTH: 6
<212> TYPE: PRT
<213> ORGANISM: Homo sapiens

<400> SEQUENCE: 481

Ala Pro Gly Leu Arg Gly
1               5

<210> SEQ ID NO 482
<211> LENGTH: 6
<212> TYPE: PRT
```

<213> ORGANISM: Homo sapiens

<400> SEQUENCE: 482

His Pro Gly Ser Pro Gly
1               5

<210> SEQ ID NO 483
<211> LENGTH: 6
<212> TYPE: PRT
<213> ORGANISM: Homo sapiens

<400> SEQUENCE: 483

Pro Ser Gly Pro Pro Gly
1               5

<210> SEQ ID NO 484
<211> LENGTH: 6
<212> TYPE: PRT
<213> ORGANISM: Homo sapiens

<400> SEQUENCE: 484

Gly Ser Pro Gly Pro Ala
1               5

<210> SEQ ID NO 485
<211> LENGTH: 6
<212> TYPE: PRT
<213> ORGANISM: Homo sapiens

<400> SEQUENCE: 485

Gly Pro Ala Gly Pro Pro
1               5

<210> SEQ ID NO 486
<211> LENGTH: 6
<212> TYPE: PRT
<213> ORGANISM: Homo sapiens

<400> SEQUENCE: 486

Gly Leu Pro Gly Leu Ala
1               5

<210> SEQ ID NO 487
<211> LENGTH: 6
<212> TYPE: PRT
<213> ORGANISM: Homo sapiens

<400> SEQUENCE: 487

Gln Gly Pro Pro Gly Pro
1               5

<210> SEQ ID NO 488
<211> LENGTH: 6
<212> TYPE: PRT
<213> ORGANISM: Homo sapiens

<400> SEQUENCE: 488

Gly Leu Ala Gly Thr Ala
1               5

<210> SEQ ID NO 489
<211> LENGTH: 6
<212> TYPE: PRT
<213> ORGANISM: Homo sapiens

```
<400> SEQUENCE: 489

Pro Gly Leu Met Gly Ala
1               5

<210> SEQ ID NO 490
<211> LENGTH: 6
<212> TYPE: PRT
<213> ORGANISM: Homo sapiens

<400> SEQUENCE: 490

Gly Pro Pro Gly Pro Gln
1               5

<210> SEQ ID NO 491
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (4)..(4)
<223> OTHER INFORMATION: proline or hydroxyproline

<400> SEQUENCE: 491

Phe Xaa Gly Xaa Lys Gly
1               5

<210> SEQ ID NO 492
<211> LENGTH: 6
<212> TYPE: PRT
<213> ORGANISM: Homo sapiens

<400> SEQUENCE: 492

Ile Pro Gly Phe Pro Gly
1               5

<210> SEQ ID NO 493
<211> LENGTH: 6
<212> TYPE: PRT
<213> ORGANISM: Homo sapiens

<400> SEQUENCE: 493

Gly Phe Pro Gly Met Lys
1               5

<210> SEQ ID NO 494
<211> LENGTH: 6
<212> TYPE: PRT
<213> ORGANISM: Homo sapiens

<400> SEQUENCE: 494

Phe Pro Gly Ala Pro Gly
1               5

<210> SEQ ID NO 495
<211> LENGTH: 6
<212> TYPE: PRT
<213> ORGANISM: Homo sapiens

<400> SEQUENCE: 495

Gly Ala Ile Gly Pro Ser
1               5
```

```
<210> SEQ ID NO 496
<211> LENGTH: 6
<212> TYPE: PRT
<213> ORGANISM: Homo sapiens

<400> SEQUENCE: 496

Ala Gly Ile Pro Gly Phe
1               5

<210> SEQ ID NO 497
<211> LENGTH: 6
<212> TYPE: PRT
<213> ORGANISM: Homo sapiens

<400> SEQUENCE: 497

Pro Gly Pro Gln Gly Leu
1               5

<210> SEQ ID NO 498
<211> LENGTH: 6
<212> TYPE: PRT
<213> ORGANISM: Homo sapiens

<400> SEQUENCE: 498

Gly Ala Pro Gly Leu Met
1               5

<210> SEQ ID NO 499
<211> LENGTH: 6
<212> TYPE: PRT
<213> ORGANISM: Homo sapiens

<400> SEQUENCE: 499

Ser Pro Gly Pro Lys Gly
1               5

<210> SEQ ID NO 500
<211> LENGTH: 6
<212> TYPE: PRT
<213> ORGANISM: Homo sapiens

<400> SEQUENCE: 500

Gly Glu Pro Gly Pro Arg
1               5

<210> SEQ ID NO 501
<211> LENGTH: 6
<212> TYPE: PRT
<213> ORGANISM: Homo sapiens

<400> SEQUENCE: 501

Ile Pro Gly Gln Pro Gly
1               5

<210> SEQ ID NO 502
<211> LENGTH: 6
<212> TYPE: PRT
<213> ORGANISM: Homo sapiens

<400> SEQUENCE: 502

Thr Gly Ala Pro Gly Ser
1               5

<210> SEQ ID NO 503
```

```
<211> LENGTH: 6
<212> TYPE: PRT
<213> ORGANISM: Homo sapiens

<400> SEQUENCE: 503

Gly His Arg Gly Phe Asp
1               5

<210> SEQ ID NO 504
<211> LENGTH: 6
<212> TYPE: PRT
<213> ORGANISM: Homo sapiens

<400> SEQUENCE: 504

Pro Gly Leu Pro Gly Ile
1               5

<210> SEQ ID NO 505
<211> LENGTH: 6
<212> TYPE: PRT
<213> ORGANISM: Homo sapiens

<400> SEQUENCE: 505

Gly Ala Ala Gly Ile Lys
1               5

<210> SEQ ID NO 506
<211> LENGTH: 6
<212> TYPE: PRT
<213> ORGANISM: Homo sapiens

<400> SEQUENCE: 506

Pro Gly Pro Lys Gly Asp
1               5

<210> SEQ ID NO 507
<211> LENGTH: 6
<212> TYPE: PRT
<213> ORGANISM: Homo sapiens

<400> SEQUENCE: 507

Gly Leu Pro Gly Ile Ala
1               5

<210> SEQ ID NO 508
<211> LENGTH: 6
<212> TYPE: PRT
<213> ORGANISM: Homo sapiens

<400> SEQUENCE: 508

Pro Gln Gly Leu Pro Gly
1               5

<210> SEQ ID NO 509
<211> LENGTH: 6
<212> TYPE: PRT
<213> ORGANISM: Homo sapiens

<400> SEQUENCE: 509

Gly Ala Pro Gly Leu Arg
1               5

<210> SEQ ID NO 510
<211> LENGTH: 6
<212> TYPE: PRT
```

<213> ORGANISM: Homo sapiens

<400> SEQUENCE: 510

Gly Ala Asn Gly Leu Pro
1               5

<210> SEQ ID NO 511
<211> LENGTH: 6
<212> TYPE: PRT
<213> ORGANISM: Homo sapiens

<400> SEQUENCE: 511

Gly Pro Pro Gly Pro Ser
1               5

<210> SEQ ID NO 512
<211> LENGTH: 6
<212> TYPE: PRT
<213> ORGANISM: Homo sapiens

<400> SEQUENCE: 512

Gly Pro Pro Gly Ile Lys
1               5

<210> SEQ ID NO 513
<211> LENGTH: 6
<212> TYPE: PRT
<213> ORGANISM: Homo sapiens

<400> SEQUENCE: 513

Thr Ala Gly Phe Pro Gly
1               5

<210> SEQ ID NO 514
<211> LENGTH: 6
<212> TYPE: PRT
<213> ORGANISM: Homo sapiens

<400> SEQUENCE: 514

Gly Glu Val Gly Pro Ala
1               5

<210> SEQ ID NO 515
<211> LENGTH: 6
<212> TYPE: PRT
<213> ORGANISM: Homo sapiens

<400> SEQUENCE: 515

Glu Lys Gly Pro Ala Gly
1               5

<210> SEQ ID NO 516
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 516

Glu Xaa Gly Pro Arg Gly
1               5

<210> SEQ ID NO 517

```
<211> LENGTH: 6
<212> TYPE: PRT
<213> ORGANISM: Homo sapiens

<400> SEQUENCE: 517

Pro Pro Gly Ala Pro Gly
1               5

<210> SEQ ID NO 518
<211> LENGTH: 6
<212> TYPE: PRT
<213> ORGANISM: Homo sapiens

<400> SEQUENCE: 518

Thr Ser Gly His Pro Gly
1               5

<210> SEQ ID NO 519
<211> LENGTH: 6
<212> TYPE: PRT
<213> ORGANISM: Homo sapiens

<400> SEQUENCE: 519

Gly Ala Pro Gly Pro Ala
1               5

<210> SEQ ID NO 520
<211> LENGTH: 6
<212> TYPE: PRT
<213> ORGANISM: Homo sapiens

<400> SEQUENCE: 520

Thr Pro Gly Leu Gln Gly
1               5

<210> SEQ ID NO 521
<211> LENGTH: 6
<212> TYPE: PRT
<213> ORGANISM: Homo sapiens

<400> SEQUENCE: 521

Gly Thr Pro Gly Leu Gln
1               5

<210> SEQ ID NO 522
<211> LENGTH: 6
<212> TYPE: PRT
<213> ORGANISM: Homo sapiens

<400> SEQUENCE: 522

Gly Thr Ser Gly His Pro
1               5

<210> SEQ ID NO 523
<211> LENGTH: 6
<212> TYPE: PRT
<213> ORGANISM: Homo sapiens

<400> SEQUENCE: 523

Met Pro Gly Pro Arg Gly
1               5

<210> SEQ ID NO 524
<211> LENGTH: 6
<212> TYPE: PRT
```

```
<213> ORGANISM: Homo sapiens

<400> SEQUENCE: 524

Gly Pro Gln Gly Val Lys
1               5

<210> SEQ ID NO 525
<211> LENGTH: 6
<212> TYPE: PRT
<213> ORGANISM: Homo sapiens

<400> SEQUENCE: 525

Gly Ala Pro Gly Leu Lys
1               5

<210> SEQ ID NO 526
<211> LENGTH: 6
<212> TYPE: PRT
<213> ORGANISM: Homo sapiens

<400> SEQUENCE: 526

Gly Ser Pro Gly Tyr Gln
1               5

<210> SEQ ID NO 527
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
<222> LOCATION: (4)..(4)
<223> OTHER INFORMATION: lysine or hydroxylysine

<400> SEQUENCE: 527

Xaa Gly Pro Xaa Gly Asn
1               5

<210> SEQ ID NO 528
<211> LENGTH: 6
<212> TYPE: PRT
<213> ORGANISM: Homo sapiens

<400> SEQUENCE: 528

Gly Ala Ala Gly Ala Arg
1               5

<210> SEQ ID NO 529
<211> LENGTH: 6
<212> TYPE: PRT
<213> ORGANISM: Homo sapiens

<400> SEQUENCE: 529

Pro Gly Ala Asn Gly Leu
1               5

<210> SEQ ID NO 530
<211> LENGTH: 6
<212> TYPE: PRT
<213> ORGANISM: Homo sapiens

<400> SEQUENCE: 530

Gly Thr Gly Gly Pro Pro
```

```
<210> SEQ ID NO 531
<211> LENGTH: 6
<212> TYPE: PRT
<213> ORGANISM: Homo sapiens

<400> SEQUENCE: 531

Gly Met Lys Gly His Arg
1               5

<210> SEQ ID NO 532
<211> LENGTH: 6
<212> TYPE: PRT
<213> ORGANISM: Homo sapiens

<400> SEQUENCE: 532

Glu Gly Gly Pro Pro Gly
1               5

<210> SEQ ID NO 533
<211> LENGTH: 6
<212> TYPE: PRT
<213> ORGANISM: Homo sapiens

<400> SEQUENCE: 533

Gly Ser Pro Gly Pro Gln
1               5

<210> SEQ ID NO 534
<211> LENGTH: 6
<212> TYPE: PRT
<213> ORGANISM: Homo sapiens

<400> SEQUENCE: 534

Glu Met Gly Pro Ala Gly
1               5

<210> SEQ ID NO 535
<211> LENGTH: 6
<212> TYPE: PRT
<213> ORGANISM: Homo sapiens

<400> SEQUENCE: 535

Gly Ile Ala Gly Pro Arg
1               5

<210> SEQ ID NO 536
<211> LENGTH: 6
<212> TYPE: PRT
<213> ORGANISM: Homo sapiens

<400> SEQUENCE: 536

Gln Pro Gly Pro Pro Gly
1               5

<210> SEQ ID NO 537
<211> LENGTH: 6
<212> TYPE: PRT
<213> ORGANISM: Homo sapiens

<400> SEQUENCE: 537

Gly Lys Pro Gly Ala Asn
1               5
```

<210> SEQ ID NO 538
<211> LENGTH: 6
<212> TYPE: PRT
<213> ORGANISM: Homo sapiens

<400> SEQUENCE: 538

Gly Val Lys Gly Glu Arg
1               5

<210> SEQ ID NO 539
<211> LENGTH: 6
<212> TYPE: PRT
<213> ORGANISM: Homo sapiens

<400> SEQUENCE: 539

Pro Gly Ala Ala Gly Phe
1               5

<210> SEQ ID NO 540
<211> LENGTH: 6
<212> TYPE: PRT
<213> ORGANISM: Homo sapiens

<400> SEQUENCE: 540

Thr Gly Glu Arg Gly Ala
1               5

<210> SEQ ID NO 541
<211> LENGTH: 6
<212> TYPE: PRT
<213> ORGANISM: Homo sapiens

<400> SEQUENCE: 541

Pro Gln Gly Val Lys Gly
1               5

<210> SEQ ID NO 542
<211> LENGTH: 6
<212> TYPE: PRT
<213> ORGANISM: Homo sapiens

<400> SEQUENCE: 542

Gly Asp Ala Gly Ala Pro
1               5

<210> SEQ ID NO 543
<211> LENGTH: 6
<212> TYPE: PRT
<213> ORGANISM: Homo sapiens

<400> SEQUENCE: 543

Gly Pro Ala Gly Glu Arg
1               5

<210> SEQ ID NO 544
<211> LENGTH: 6
<212> TYPE: PRT
<213> ORGANISM: Homo sapiens

<400> SEQUENCE: 544

Gly Pro Pro Gly Pro Arg
1               5

<210> SEQ ID NO 545

```
<211> LENGTH: 6
<212> TYPE: PRT
<213> ORGANISM: Homo sapiens

<400> SEQUENCE: 545

Gly Pro Ala Gly Pro Arg
1               5

<210> SEQ ID NO 546
<211> LENGTH: 6
<212> TYPE: PRT
<213> ORGANISM: Homo sapiens

<400> SEQUENCE: 546

Arg Gly Phe Asp Gly Arg
1               5

<210> SEQ ID NO 547
<211> LENGTH: 6
<212> TYPE: PRT
<213> ORGANISM: Homo sapiens

<400> SEQUENCE: 547

Ala Gly Pro Arg Gly Ala
1               5

<210> SEQ ID NO 548
<211> LENGTH: 6
<212> TYPE: PRT
<213> ORGANISM: Homo sapiens

<400> SEQUENCE: 548

Gly Gly Lys Gly Glu Arg
1               5

<210> SEQ ID NO 549
<211> LENGTH: 6
<212> TYPE: PRT
<213> ORGANISM: Homo sapiens

<400> SEQUENCE: 549

Ala Pro Gly Leu Met Gly
1               5

<210> SEQ ID NO 550
<211> LENGTH: 6
<212> TYPE: PRT
<213> ORGANISM: Homo sapiens

<400> SEQUENCE: 550

Gly Pro Ala Gly Ala Asn
1               5

<210> SEQ ID NO 551
<211> LENGTH: 12
<212> TYPE: PRT
<213> ORGANISM: Homo sapiens

<400> SEQUENCE: 551

Asp Ile Asp Gly Tyr Arg Gly Pro Pro Gly Pro Gln
1               5                   10

<210> SEQ ID NO 552
<211> LENGTH: 15
<212> TYPE: PRT
```

<213> ORGANISM: Homo sapiens

<400> SEQUENCE: 552

Ser Met Gly Pro Pro Gly Thr Pro Ser Val Asp His Gly Phe Leu
1               5                   10                  15

<210> SEQ ID NO 553
<211> LENGTH: 20
<212> TYPE: PRT
<213> ORGANISM: Homo sapiens

<400> SEQUENCE: 553

Pro Asp Gly Leu Pro Gly Ser Met Gly Pro Pro Gly Thr Pro Ser Val
1               5                   10                  15

Asp His Gly Phe
            20

<210> SEQ ID NO 554
<211> LENGTH: 21
<212> TYPE: PRT
<213> ORGANISM: Homo sapiens

<400> SEQUENCE: 554

Pro Asp Gly Leu Pro Gly Ser Met Gly Pro Pro Gly Thr Pro Ser Val
1               5                   10                  15

Asp His Gly Phe Leu
            20

<210> SEQ ID NO 555
<211> LENGTH: 22
<212> TYPE: PRT
<213> ORGANISM: Homo sapiens

<400> SEQUENCE: 555

Pro Asp Gly Leu Pro Gly Ser Met Gly Pro Pro Gly Thr Pro Ser Val
1               5                   10                  15

Asp His Gly Phe Leu Val
            20

<210> SEQ ID NO 556
<211> LENGTH: 23
<212> TYPE: PRT
<213> ORGANISM: Homo sapiens

<400> SEQUENCE: 556

Pro Ser Gly Arg Asp Gly Leu Pro Gly Pro Gly Ser Pro Gly Pro
1               5                   10                  15

Pro Gly Gln Pro Gly Tyr Thr
            20

<210> SEQ ID NO 557
<211> LENGTH: 25
<212> TYPE: PRT
<213> ORGANISM: Homo sapiens

<400> SEQUENCE: 557

Pro Ser Gly Arg Asp Gly Leu Pro Gly Pro Gly Ser Pro Gly Pro
1               5                   10                  15

Pro Gly Gln Pro Gly Tyr Thr Asn Gly
            20                  25

<210> SEQ ID NO 558

<211> LENGTH: 26
<212> TYPE: PRT
<213> ORGANISM: Homo sapiens

<400> SEQUENCE: 558

Pro Ser Gly Arg Asp Gly Leu Pro Gly Pro Pro Gly Ser Pro Gly Pro
1               5                   10                  15

Pro Gly Gln Pro Gly Tyr Thr Asn Gly Ile
            20                  25

<210> SEQ ID NO 559
<211> LENGTH: 26
<212> TYPE: PRT
<213> ORGANISM: Homo sapiens

<400> SEQUENCE: 559

Ile Pro Gly Ser Lys Gly Glu Gln Gly Phe Met Gly Pro Pro Gly Pro
1               5                   10                  15

Gln Gly Gln Pro Gly Leu Pro Gly Ser Pro
            20                  25

<210> SEQ ID NO 560
<211> LENGTH: 27
<212> TYPE: PRT
<213> ORGANISM: Homo sapiens

<400> SEQUENCE: 560

Pro Arg Gly Phe Pro Gly Pro Gly Pro Asp Gly Leu Pro Gly Ser
1               5                   10                  15

Met Gly Pro Pro Gly Thr Pro Ser Val Asp His
            20                  25

<210> SEQ ID NO 561
<211> LENGTH: 16
<212> TYPE: PRT
<213> ORGANISM: Homo sapiens

<400> SEQUENCE: 561

Glu Pro Gly Pro Pro Gly Leu Pro Gly Ser Val Gly Ser Pro Gly Val
1               5                   10                  15

<210> SEQ ID NO 562
<211> LENGTH: 14
<212> TYPE: PRT
<213> ORGANISM: Homo sapiens

<400> SEQUENCE: 562

Ile Asp Gly Tyr Arg Gly Pro Pro Gly Pro Gln Gly Pro Pro
1               5                   10

<210> SEQ ID NO 563
<211> LENGTH: 19
<212> TYPE: PRT
<213> ORGANISM: Homo sapiens

<400> SEQUENCE: 563

Pro Arg Gly Phe Pro Gly Pro Gly Pro Asp Gly Leu Pro Gly Ser
1               5                   10                  15

Met Gly Pro

<210> SEQ ID NO 564
<211> LENGTH: 20
<212> TYPE: PRT

<213> ORGANISM: Homo sapiens

<400> SEQUENCE: 564

Asp Gly Leu Pro Gly Ser Met Gly Pro Pro Gly Thr Pro Ser Val Asp
1               5                   10                  15

His Gly Phe Leu
            20

<210> SEQ ID NO 565
<211> LENGTH: 21
<212> TYPE: PRT
<213> ORGANISM: Homo sapiens

<400> SEQUENCE: 565

Asp Gly Leu Pro Gly Ser Met Gly Pro Pro Gly Thr Pro Ser Val Asp
1               5                   10                  15

His Gly Phe Leu Val
            20

<210> SEQ ID NO 566
<211> LENGTH: 29
<212> TYPE: PRT
<213> ORGANISM: Homo sapiens

<400> SEQUENCE: 566

Pro Gly Leu Pro Gly Gln Gln Gly Ala Pro Gly Ile Pro Gly Phe Pro
1               5                   10                  15

Gly Ser Lys Gly Glu Met Gly Val Met Gly Thr Pro Gly
            20                  25

<210> SEQ ID NO 567
<211> LENGTH: 31
<212> TYPE: PRT
<213> ORGANISM: Homo sapiens

<400> SEQUENCE: 567

Ile Gly Ile Pro Gly Met Pro Gly Ser Pro Gly Leu Lys Gly Ser Pro
1               5                   10                  15

Gly Ser Val Gly Tyr Pro Gly Ser Pro Gly Leu Pro Gly Glu Lys
            20                  25                  30

<210> SEQ ID NO 568
<211> LENGTH: 37
<212> TYPE: PRT
<213> ORGANISM: Homo sapiens

<400> SEQUENCE: 568

Pro Gly Pro Pro Gly Pro Pro Gly Glu Lys Gly Gln Met Gly Leu Ser
1               5                   10                  15

Phe Gln Gly Pro Lys Gly Asp Lys Gly Asp Gln Gly Val Ser Gly Pro
            20                  25                  30

Pro Gly Val Pro Gly
            35

<210> SEQ ID NO 569
<211> LENGTH: 39
<212> TYPE: PRT
<213> ORGANISM: Homo sapiens

<400> SEQUENCE: 569

Pro Gly Ile Gly Pro Pro Gly Ala Arg Gly Pro Pro Gly Gly Gln Gly
1               5                   10                  15

Pro Pro Gly Leu Ser Gly Pro Pro Gly Ile Lys Gly Glu Lys Gly Phe
            20                  25                  30

Pro Gly Phe Pro Gly Leu Asp
            35

<210> SEQ ID NO 570
<211> LENGTH: 15
<212> TYPE: PRT
<213> ORGANISM: Homo sapiens

<400> SEQUENCE: 570

Glu Pro Gly Leu Pro Gly Ile Pro Gly Val Ser Gly Pro Lys Gly
1               5                   10                  15

<210> SEQ ID NO 571
<211> LENGTH: 19
<212> TYPE: PRT
<213> ORGANISM: Homo sapiens

<400> SEQUENCE: 571

Gly Glu Lys Gly Gln Lys Gly Asp Thr Gly Pro Pro Gly Pro Pro Gly
1               5                   10                  15

Leu Val Ile

<210> SEQ ID NO 572
<211> LENGTH: 38
<212> TYPE: PRT
<213> ORGANISM: Homo sapiens

<400> SEQUENCE: 572

Leu Pro Gly Ile Gly Val Gln Gly Pro Pro Gly Pro Pro Gly Ile Pro
1               5                   10                  15

Gly Pro Ile Gly Gln Pro Gly Leu His Gly Ile Pro Gly Glu Lys Gly
            20                  25                  30

Asp Pro Gly Pro Pro Gly
            35

<210> SEQ ID NO 573
<211> LENGTH: 14
<212> TYPE: PRT
<213> ORGANISM: Homo sapiens

<400> SEQUENCE: 573

Gly Ser Pro Gly Ile Pro Gly His Gln Gly Glu Met Gly Pro
1               5                   10

<210> SEQ ID NO 574
<211> LENGTH: 14
<212> TYPE: PRT
<213> ORGANISM: Homo sapiens

<400> SEQUENCE: 574

Glu Pro Gly Met Gln Gly Glu Pro Gly Pro Gly Pro Pro
1               5                   10

<210> SEQ ID NO 575
<211> LENGTH: 18
<212> TYPE: PRT
<213> ORGANISM: Homo sapiens

<400> SEQUENCE: 575

Gly Pro Pro Gly Arg Leu Gly Ala Pro Gly Thr Pro Gly Leu Pro Gly

```
1               5                   10                  15

Pro Arg

<210> SEQ ID NO 576
<211> LENGTH: 14
<212> TYPE: PRT
<213> ORGANISM: Homo sapiens

<400> SEQUENCE: 576

Pro Pro Gly Pro Lys Gly Phe Pro Gly Ile Pro Gly Pro Pro
1               5                   10

<210> SEQ ID NO 577
<211> LENGTH: 14
<212> TYPE: PRT
<213> ORGANISM: Homo sapiens

<400> SEQUENCE: 577

Ala Lys Gly Gln Pro Gly Leu Pro Gly Phe Pro Gly Thr Pro
1               5                   10

<210> SEQ ID NO 578
<211> LENGTH: 17
<212> TYPE: PRT
<213> ORGANISM: Homo sapiens

<400> SEQUENCE: 578

Asp Arg Gly Pro Pro Gly Pro Pro Gly Ile Arg Gly Pro Gly Pro
1               5                   10                  15

Pro

<210> SEQ ID NO 579
<211> LENGTH: 19
<212> TYPE: PRT
<213> ORGANISM: Homo sapiens

<400> SEQUENCE: 579

Pro Gly Pro Pro Gly Glu Lys Gly Lys Pro Gly Gln Asp Gly Ile Pro
1               5                   10                  15

Gly Pro Ala

<210> SEQ ID NO 580
<211> LENGTH: 26
<212> TYPE: PRT
<213> ORGANISM: Homo sapiens

<400> SEQUENCE: 580

Leu Leu Gly Ser Lys Gly Glu Lys Gly Glu Pro Gly Leu Pro Gly Ile
1               5                   10                  15

Pro Gly Val Ser Gly Pro Lys Gly Tyr Gln
                20                  25

<210> SEQ ID NO 581
<211> LENGTH: 19
<212> TYPE: PRT
<213> ORGANISM: Homo sapiens

<400> SEQUENCE: 581

Asp Gly Leu Pro Gly Ser Met Gly Pro Pro Gly Thr Pro Ser Val Asp
1               5                   10                  15

His Gly Phe
```

<210> SEQ ID NO 582
<211> LENGTH: 22
<212> TYPE: PRT
<213> ORGANISM: Homo sapiens

<400> SEQUENCE: 582

Thr Gly Pro Leu Gly Glu Lys Gly Glu Arg Gly Tyr Pro Gly Thr Pro
1               5                   10                  15

Gly Pro Arg Gly Glu Pro
            20

<210> SEQ ID NO 583
<211> LENGTH: 43
<212> TYPE: PRT
<213> ORGANISM: Homo sapiens

<400> SEQUENCE: 583

Gly Leu Gln Gly Ile Arg Gly Glu Pro Gly Pro Pro Gly Leu Pro Gly
1               5                   10                  15

Ser Val Gly Ser Pro Gly Val Pro Gly Ile Gly Pro Pro Gly Ala Arg
            20                  25                  30

Gly Pro Pro Gly Gly Gln Gly Pro Pro Gly Leu
        35                  40

<210> SEQ ID NO 584
<211> LENGTH: 28
<212> TYPE: PRT
<213> ORGANISM: Homo sapiens

<400> SEQUENCE: 584

Asp Pro Gly Leu Lys Gly Asp Lys Gly Asp Val Gly Leu Pro Gly Lys
1               5                   10                  15

Pro Gly Ser Met Asp Lys Val Asp Met Gly Ser Met
            20                  25

<210> SEQ ID NO 585
<211> LENGTH: 17
<212> TYPE: PRT
<213> ORGANISM: Homo sapiens

<400> SEQUENCE: 585

Leu Pro Gly Pro Met Gly Pro Pro Gly Leu Pro Gly Ile Asp Gly Val
1               5                   10                  15

Lys

<210> SEQ ID NO 586
<211> LENGTH: 28
<212> TYPE: PRT
<213> ORGANISM: Homo sapiens

<400> SEQUENCE: 586

Gly Ile Arg Gly Glu Pro Gly Pro Pro Gly Leu Pro Gly Ser Val Gly
1               5                   10                  15

Ser Pro Gly Val Pro Gly Ile Gly Pro Pro Gly Ala
            20                  25

<210> SEQ ID NO 587
<211> LENGTH: 28
<212> TYPE: PRT
<213> ORGANISM: Homo sapiens

<400> SEQUENCE: 587

```
Gly Phe Pro Gly Pro Gly Pro Asp Gly Leu Pro Gly Ser Met Gly
1               5                   10                  15

Pro Pro Gly Thr Pro Ser Val Asp His Gly Phe Leu
            20                  25
```

<210> SEQ ID NO 588
<211> LENGTH: 31
<212> TYPE: PRT
<213> ORGANISM: Homo sapiens

<400> SEQUENCE: 588

```
Gly Leu Gln Gly Ile Arg Gly Glu Pro Gly Pro Pro Gly Leu Pro Gly
1               5                   10                  15

Ser Val Gly Ser Pro Gly Val Pro Gly Ile Gly Pro Pro Gly Ala
            20                  25                  30
```

<210> SEQ ID NO 589
<211> LENGTH: 40
<212> TYPE: PRT
<213> ORGANISM: Homo sapiens

<400> SEQUENCE: 589

```
Gly Ile Arg Gly Glu Pro Gly Pro Pro Gly Leu Pro Gly Ser Val Gly
1               5                   10                  15

Ser Pro Gly Val Pro Gly Ile Gly Pro Pro Gly Ala Arg Gly Pro Pro
            20                  25                  30

Gly Gly Gln Gly Pro Pro Gly Leu
        35                  40
```

<210> SEQ ID NO 590
<211> LENGTH: 17
<212> TYPE: PRT
<213> ORGANISM: Homo sapiens

<400> SEQUENCE: 590

```
Glu Asp Gly Val Ile Gly Met Met Gly Phe Pro Gly Ala Ile Gly Pro
1               5                   10                  15

Pro
```

<210> SEQ ID NO 591
<211> LENGTH: 34
<212> TYPE: PRT
<213> ORGANISM: Homo sapiens

<400> SEQUENCE: 591

```
Tyr Pro Gly Asn Pro Gly Ile Leu Gly Pro Pro Gly Glu Asp Gly Val
1               5                   10                  15

Ile Gly Met Met Gly Phe Pro Gly Ala Ile Gly Pro Pro Gly Pro Pro
            20                  25                  30

Gly Asn
```

<210> SEQ ID NO 592
<211> LENGTH: 16
<212> TYPE: PRT
<213> ORGANISM: Homo sapiens

<400> SEQUENCE: 592

```
Ile Pro Pro Ser Asp Glu Ile Cys Glu Pro Gly Pro Pro Gly Pro Pro
1               5                   10                  15
```

```
<210> SEQ ID NO 593
<211> LENGTH: 26
<212> TYPE: PRT
<213> ORGANISM: Homo sapiens

<400> SEQUENCE: 593

Leu Pro Gly Leu Pro Gly Pro Lys Gly Glu Pro Gly Leu Pro Gly Tyr
1               5                   10                  15

Pro Gly Asn Pro Gly Ile Lys Gly Ser Val
            20                  25

<210> SEQ ID NO 594
<211> LENGTH: 19
<212> TYPE: PRT
<213> ORGANISM: Homo sapiens

<400> SEQUENCE: 594

Gly Ile Lys Gly Asp Lys Gly Ser Met Gly His Pro Gly Pro Lys Gly
1               5                   10                  15

Pro Pro Gly

<210> SEQ ID NO 595
<211> LENGTH: 22
<212> TYPE: PRT
<213> ORGANISM: Homo sapiens

<400> SEQUENCE: 595

Thr Pro Gly Ser Pro Gly Cys Ala Gly Ser Pro Gly Leu Pro Gly Ser
1               5                   10                  15

Pro Gly Pro Pro Gly Pro
            20

<210> SEQ ID NO 596
<211> LENGTH: 46
<212> TYPE: PRT
<213> ORGANISM: Homo sapiens

<400> SEQUENCE: 596

Pro Gly Ala Pro Gly Pro Gln Gly Leu Pro Gly Pro Pro Gly Phe Pro
1               5                   10                  15

Gly Pro Val Gly Pro Pro Gly Pro Gly Phe Phe Gly Phe Pro Gly
            20                  25                  30

Ala Met Gly Pro Arg Gly Pro Lys Gly His Met Gly Glu Arg
            35                  40                  45

<210> SEQ ID NO 597
<211> LENGTH: 11
<212> TYPE: PRT
<213> ORGANISM: Homo sapiens

<400> SEQUENCE: 597

Gly Leu Pro Gly Phe Ala Gly Asn Pro Gly Pro
1               5                   10

<210> SEQ ID NO 598
<211> LENGTH: 17
<212> TYPE: PRT
<213> ORGANISM: Homo sapiens

<400> SEQUENCE: 598

Gly Ala Glu Gly Leu Pro Gly Ser Pro Gly Phe Pro Gly Pro Gln Gly
1               5                   10                  15
```

Asp

<210> SEQ ID NO 599
<211> LENGTH: 17
<212> TYPE: PRT
<213> ORGANISM: Homo sapiens

<400> SEQUENCE: 599

Met Gly Pro Pro Gly Val Pro Gly Phe Gln Gly Pro Lys Gly Leu Pro
1               5                   10                  15

Gly

<210> SEQ ID NO 600
<211> LENGTH: 17
<212> TYPE: PRT
<213> ORGANISM: Homo sapiens

<400> SEQUENCE: 600

Asp Ile Asp Gly Tyr Arg Gly Pro Pro Gly Pro Gln Gly Pro Pro Gly
1               5                   10                  15

Glu

<210> SEQ ID NO 601
<211> LENGTH: 18
<212> TYPE: PRT
<213> ORGANISM: Homo sapiens

<400> SEQUENCE: 601

Gly Asp Gln Gly Asp Gln Gly Val Pro Gly Ala Lys Gly Leu Pro Gly
1               5                   10                  15

Pro Pro

<210> SEQ ID NO 602
<211> LENGTH: 18
<212> TYPE: PRT
<213> ORGANISM: Homo sapiens

<400> SEQUENCE: 602

Gly Asp Arg Gly Pro Gln Gly Gln Pro Gly Leu Pro Gly Leu Pro Gly
1               5                   10                  15

Pro Met

<210> SEQ ID NO 603
<211> LENGTH: 27
<212> TYPE: PRT
<213> ORGANISM: Homo sapiens

<400> SEQUENCE: 603

Glu Lys Gly Ser Ile Gly Ile Pro Gly Met Pro Gly Ser Pro Gly Leu
1               5                   10                  15

Lys Gly Ser Pro Gly Ser Val Gly Tyr Pro Gly
            20                  25

<210> SEQ ID NO 604
<211> LENGTH: 49
<212> TYPE: PRT
<213> ORGANISM: Homo sapiens

<400> SEQUENCE: 604

Gly Leu Gln Gly Ile Arg Gly Glu Pro Gly Pro Pro Gly Leu Pro Gly
1               5                   10                  15

-continued

Ser Val Gly Ser Pro Gly Val Pro Gly Ile Gly Pro Gly Ala Arg
            20                  25                  30

Gly Pro Pro Gly Gly Gln Gly Pro Pro Gly Leu Ser Gly Pro Pro Gly
        35                  40                  45

Ile

<210> SEQ ID NO 605
<211> LENGTH: 19
<212> TYPE: PRT
<213> ORGANISM: Homo sapiens

<400> SEQUENCE: 605

Pro Gly Pro Pro Gly Leu Met Gly Pro Pro Gly Pro Pro Gly Leu Pro
1               5                   10                  15

Gly Pro Lys

<210> SEQ ID NO 606
<211> LENGTH: 23
<212> TYPE: PRT
<213> ORGANISM: Homo sapiens

<400> SEQUENCE: 606

Gly Glu Arg Gly Ser Pro Gly Ile Pro Gly Ala Pro Gly Pro Ile Gly
1               5                   10                  15

Pro Pro Gly Ser Pro Gly Leu
            20

<210> SEQ ID NO 607
<211> LENGTH: 44
<212> TYPE: PRT
<213> ORGANISM: Homo sapiens

<400> SEQUENCE: 607

Pro Gly Ile Pro Gly Ala Pro Gly Ala Pro Gly Phe Pro Gly Ser Lys
1               5                   10                  15

Gly Glu Pro Gly Asp Ile Leu Thr Phe Pro Gly Met Lys Gly Asp Lys
            20                  25                  30

Gly Glu Leu Gly Ser Pro Gly Ala Pro Gly Leu Pro
        35                  40

<210> SEQ ID NO 608
<211> LENGTH: 18
<212> TYPE: PRT
<213> ORGANISM: Homo sapiens

<400> SEQUENCE: 608

Cys Asp Gly Gly Val Pro Asn Thr Gly Pro Pro Gly Glu Pro Gly Pro
1               5                   10                  15

Pro Gly

<210> SEQ ID NO 609
<211> LENGTH: 6
<212> TYPE: PRT
<213> ORGANISM: Homo sapiens

<400> SEQUENCE: 609

Ile Asp Gly Tyr Arg Gly
1               5

<210> SEQ ID NO 610
<211> LENGTH: 6

```
<212> TYPE: PRT
<213> ORGANISM: Homo sapiens

<400> SEQUENCE: 610

Met Gly Pro Pro Gly Thr
1               5

<210> SEQ ID NO 611
<211> LENGTH: 6
<212> TYPE: PRT
<213> ORGANISM: Homo sapiens

<400> SEQUENCE: 611

Asp Gly Leu Pro Gly Ser
1               5

<210> SEQ ID NO 612
<211> LENGTH: 6
<212> TYPE: PRT
<213> ORGANISM: Homo sapiens

<400> SEQUENCE: 612

Pro Gly Ser Lys Gly Glu
1               5

<210> SEQ ID NO 613
<211> LENGTH: 6
<212> TYPE: PRT
<213> ORGANISM: Homo sapiens

<400> SEQUENCE: 613

Arg Gly Phe Pro Gly Pro
1               5

<210> SEQ ID NO 614
<211> LENGTH: 6
<212> TYPE: PRT
<213> ORGANISM: Homo sapiens

<400> SEQUENCE: 614

Pro Gly Pro Pro Gly Leu
1               5

<210> SEQ ID NO 615
<211> LENGTH: 6
<212> TYPE: PRT
<213> ORGANISM: Homo sapiens

<400> SEQUENCE: 615

Gly Leu Pro Gly Ser Met
1               5

<210> SEQ ID NO 616
<211> LENGTH: 6
<212> TYPE: PRT
<213> ORGANISM: Homo sapiens

<400> SEQUENCE: 616

Gly Leu Pro Gly Gln Gln
1               5

<210> SEQ ID NO 617
<211> LENGTH: 6
<212> TYPE: PRT
<213> ORGANISM: Homo sapiens
```

<400> SEQUENCE: 617

Leu Gly Ser Lys Gly Glu
1               5

<210> SEQ ID NO 618
<211> LENGTH: 6
<212> TYPE: PRT
<213> ORGANISM: Homo sapiens

<400> SEQUENCE: 618

Pro Gly Ile Gly Val Gln
1               5

<210> SEQ ID NO 619
<211> LENGTH: 6
<212> TYPE: PRT
<213> ORGANISM: Homo sapiens

<400> SEQUENCE: 619

Ser Pro Gly Ile Pro Gly
1               5

<210> SEQ ID NO 620
<211> LENGTH: 6
<212> TYPE: PRT
<213> ORGANISM: Homo sapiens

<400> SEQUENCE: 620

Pro Gly Met Gln Gly Glu
1               5

<210> SEQ ID NO 621
<211> LENGTH: 6
<212> TYPE: PRT
<213> ORGANISM: Homo sapiens

<400> SEQUENCE: 621

Pro Gly Pro Lys Gly Phe
1               5

<210> SEQ ID NO 622
<211> LENGTH: 6
<212> TYPE: PRT
<213> ORGANISM: Homo sapiens

<400> SEQUENCE: 622

Lys Gly Gln Pro Gly Leu
1               5

<210> SEQ ID NO 623
<211> LENGTH: 6
<212> TYPE: PRT
<213> ORGANISM: Homo sapiens

<400> SEQUENCE: 623

Pro Pro Ser Asp Glu Ile
1               5

<210> SEQ ID NO 624
<211> LENGTH: 6
<212> TYPE: PRT
<213> ORGANISM: Homo sapiens

<400> SEQUENCE: 624

```
Pro Gly Leu Lys Gly Asp
1               5
```

<210> SEQ ID NO 625
<211> LENGTH: 6
<212> TYPE: PRT
<213> ORGANISM: Homo sapiens

<400> SEQUENCE: 625

```
Gly Pro Leu Gly Glu Lys
1               5
```

<210> SEQ ID NO 626
<211> LENGTH: 6
<212> TYPE: PRT
<213> ORGANISM: Homo sapiens

<400> SEQUENCE: 626

```
Ile Arg Gly Glu Pro Gly
1               5
```

<210> SEQ ID NO 627
<211> LENGTH: 6
<212> TYPE: PRT
<213> ORGANISM: Homo sapiens

<400> SEQUENCE: 627

```
Phe Pro Gly Pro Pro Gly
1               5
```

<210> SEQ ID NO 628
<211> LENGTH: 6
<212> TYPE: PRT
<213> ORGANISM: Homo sapiens

<400> SEQUENCE: 628

```
Leu Gln Gly Ile Arg Gly
1               5
```

<210> SEQ ID NO 629
<211> LENGTH: 6
<212> TYPE: PRT
<213> ORGANISM: Homo sapiens

<400> SEQUENCE: 629

```
Asp Gly Val Ile Gly Met
1               5
```

<210> SEQ ID NO 630
<211> LENGTH: 6
<212> TYPE: PRT
<213> ORGANISM: Homo sapiens

<400> SEQUENCE: 630

```
Pro Gly Asn Pro Gly Ile
1               5
```

<210> SEQ ID NO 631
<211> LENGTH: 6
<212> TYPE: PRT
<213> ORGANISM: Homo sapiens

<400> SEQUENCE: 631

```
Ile Lys Gly Asp Lys Gly
```

```
1               5

<210> SEQ ID NO 632
<211> LENGTH: 6
<212> TYPE: PRT
<213> ORGANISM: Homo sapiens

<400> SEQUENCE: 632

Pro Gly Ser Pro Gly Cys
1               5

<210> SEQ ID NO 633
<211> LENGTH: 6
<212> TYPE: PRT
<213> ORGANISM: Homo sapiens

<400> SEQUENCE: 633

Gly Pro Pro Gly Val Pro
1               5

<210> SEQ ID NO 634
<211> LENGTH: 6
<212> TYPE: PRT
<213> ORGANISM: Homo sapiens

<400> SEQUENCE: 634

Asp Gln Gly Asp Gln Gly
1               5

<210> SEQ ID NO 635
<211> LENGTH: 6
<212> TYPE: PRT
<213> ORGANISM: Homo sapiens

<400> SEQUENCE: 635

Lys Gly Ser Ile Gly Ile
1               5

<210> SEQ ID NO 636
<211> LENGTH: 6
<212> TYPE: PRT
<213> ORGANISM: Homo sapiens

<400> SEQUENCE: 636

Pro Pro Gly Arg Leu Gly
1               5

<210> SEQ ID NO 637
<211> LENGTH: 6
<212> TYPE: PRT
<213> ORGANISM: Homo sapiens

<400> SEQUENCE: 637

Glu Lys Gly Gln Lys Gly
1               5

<210> SEQ ID NO 638
<211> LENGTH: 6
<212> TYPE: PRT
<213> ORGANISM: Homo sapiens

<400> SEQUENCE: 638

Asp Gly Gly Val Pro Asn
1               5
```

<210> SEQ ID NO 639
<211> LENGTH: 6
<212> TYPE: PRT
<213> ORGANISM: Homo sapiens

<400> SEQUENCE: 639

Ser Gly Arg Asp Gly Leu
1               5

<210> SEQ ID NO 640
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Proline or hydroxyproline

<400> SEQUENCE: 640

Gly Xaa Xaa Gly Glu Lys
1               5

<210> SEQ ID NO 641
<211> LENGTH: 6
<212> TYPE: PRT
<213> ORGANISM: Homo sapiens

<400> SEQUENCE: 641

Ala Glu Gly Leu Pro Gly
1               5

<210> SEQ ID NO 642
<211> LENGTH: 6
<212> TYPE: PRT
<213> ORGANISM: Homo sapiens

<400> SEQUENCE: 642

Asp Gly Tyr Arg Gly Pro
1               5

<210> SEQ ID NO 643
<211> LENGTH: 6
<212> TYPE: PRT
<213> ORGANISM: Homo sapiens

<400> SEQUENCE: 643

Gly Pro Pro Gly Leu Met
1               5

<210> SEQ ID NO 644
<211> LENGTH: 6
<212> TYPE: PRT
<213> ORGANISM: Homo sapiens

<400> SEQUENCE: 644

Leu Pro Gly Phe Ala Gly
1               5

<210> SEQ ID NO 645
<211> LENGTH: 6
<212> TYPE: PRT
<213> ORGANISM: Homo sapiens

<400> SEQUENCE: 645

Gly Ile Pro Gly Met Pro

```
1               5

<210> SEQ ID NO 646
<211> LENGTH: 6
<212> TYPE: PRT
<213> ORGANISM: Homo sapiens

<400> SEQUENCE: 646

Ser Val Asp His Gly Phe
1               5

<210> SEQ ID NO 647
<211> LENGTH: 6
<212> TYPE: PRT
<213> ORGANISM: Homo sapiens

<400> SEQUENCE: 647

Pro Ser Val Asp His Gly
1               5

<210> SEQ ID NO 648
<211> LENGTH: 6
<212> TYPE: PRT
<213> ORGANISM: Homo sapiens

<400> SEQUENCE: 648

Val Asp His Gly Phe Leu
1               5

<210> SEQ ID NO 649
<211> LENGTH: 6
<212> TYPE: PRT
<213> ORGANISM: Homo sapiens

<400> SEQUENCE: 649

Pro Gly Gln Pro Gly Tyr
1               5

<210> SEQ ID NO 650
<211> LENGTH: 6
<212> TYPE: PRT
<213> ORGANISM: Homo sapiens

<400> SEQUENCE: 650

Gln Pro Gly Tyr Thr Asn
1               5

<210> SEQ ID NO 651
<211> LENGTH: 6
<212> TYPE: PRT
<213> ORGANISM: Homo sapiens

<400> SEQUENCE: 651

Pro Gly Leu Pro Gly Ser
1               5

<210> SEQ ID NO 652
<211> LENGTH: 6
<212> TYPE: PRT
<213> ORGANISM: Homo sapiens

<400> SEQUENCE: 652

Gly Thr Pro Ser Val Asp
1               5
```

<210> SEQ ID NO 653
<211> LENGTH: 6
<212> TYPE: PRT
<213> ORGANISM: Homo sapiens

<400> SEQUENCE: 653

Ser Val Gly Ser Pro Gly
1               5

<210> SEQ ID NO 654
<211> LENGTH: 6
<212> TYPE: PRT
<213> ORGANISM: Homo sapiens

<400> SEQUENCE: 654

Leu Pro Gly Ser Met Gly
1               5

<210> SEQ ID NO 655
<211> LENGTH: 6
<212> TYPE: PRT
<213> ORGANISM: Homo sapiens

<400> SEQUENCE: 655

Pro Gly Phe Pro Gly Leu
1               5

<210> SEQ ID NO 656
<211> LENGTH: 6
<212> TYPE: PRT
<213> ORGANISM: Homo sapiens

<400> SEQUENCE: 656

Pro Gly Leu Pro Gly Glu
1               5

<210> SEQ ID NO 657
<211> LENGTH: 6
<212> TYPE: PRT
<213> ORGANISM: Homo sapiens

<400> SEQUENCE: 657

His Gln Gly Glu Met Gly
1               5

<210> SEQ ID NO 658
<211> LENGTH: 6
<212> TYPE: PRT
<213> ORGANISM: Homo sapiens

<400> SEQUENCE: 658

Gly Pro Pro Gly Leu Val
1               5

<210> SEQ ID NO 659
<211> LENGTH: 6
<212> TYPE: PRT
<213> ORGANISM: Homo sapiens

<400> SEQUENCE: 659

Pro Gly Ile Pro Gly Pro
1               5

<210> SEQ ID NO 660

```
<211> LENGTH: 6
<212> TYPE: PRT
<213> ORGANISM: Homo sapiens

<400> SEQUENCE: 660

Pro Gly Phe Pro Gly Thr
1               5

<210> SEQ ID NO 661
<211> LENGTH: 6
<212> TYPE: PRT
<213> ORGANISM: Homo sapiens

<400> SEQUENCE: 661

Asp Gly Ile Pro Gly Pro
1               5

<210> SEQ ID NO 662
<211> LENGTH: 6
<212> TYPE: PRT
<213> ORGANISM: Homo sapiens

<400> SEQUENCE: 662

Asp Gly Ile Pro Gly Pro
1               5

<210> SEQ ID NO 663
<211> LENGTH: 6
<212> TYPE: PRT
<213> ORGANISM: Homo sapiens

<400> SEQUENCE: 663

Pro Gly Pro Arg Gly Glu
1               5

<210> SEQ ID NO 664
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Proline or hydroxyproline

<400> SEQUENCE: 664

Gly Gln Gly Pro Xaa Gly
1               5

<210> SEQ ID NO 665
<211> LENGTH: 6
<212> TYPE: PRT
<213> ORGANISM: Homo sapiens

<400> SEQUENCE: 665

Lys Val Asp Met Gly Ser
1               5

<210> SEQ ID NO 666
<211> LENGTH: 6
<212> TYPE: PRT
<213> ORGANISM: Homo sapiens

<400> SEQUENCE: 666

Pro Gly Ile Asp Gly Val
1               5
```

```
<210> SEQ ID NO 667
<211> LENGTH: 6
<212> TYPE: PRT
<213> ORGANISM: Homo sapiens

<400> SEQUENCE: 667

Lys Gly His Met Gly Glu
1               5

<210> SEQ ID NO 668
<211> LENGTH: 6
<212> TYPE: PRT
<213> ORGANISM: Homo sapiens

<400> SEQUENCE: 668

Pro Gly Ala Ile Gly Pro
1               5

<210> SEQ ID NO 669
<211> LENGTH: 6
<212> TYPE: PRT
<213> ORGANISM: Homo sapiens

<400> SEQUENCE: 669

Lys Gly Leu Pro Gly Pro
1               5

<210> SEQ ID NO 670
<211> LENGTH: 6
<212> TYPE: PRT
<213> ORGANISM: Homo sapiens

<400> SEQUENCE: 670

Gly Pro Lys Gly Leu Pro
1               5

<210> SEQ ID NO 671
<211> LENGTH: 6
<212> TYPE: PRT
<213> ORGANISM: Homo sapiens

<400> SEQUENCE: 671

Gly Pro Lys Gly Pro Pro
1               5

<210> SEQ ID NO 672
<211> LENGTH: 6
<212> TYPE: PRT
<213> ORGANISM: Homo sapiens

<400> SEQUENCE: 672

Ser Pro Gly Pro Pro Gly
1               5

<210> SEQ ID NO 673
<211> LENGTH: 6
<212> TYPE: PRT
<213> ORGANISM: Homo sapiens

<400> SEQUENCE: 673

Gly Ser Val Gly Tyr Pro
1               5

<210> SEQ ID NO 674
```

```
<211> LENGTH: 6
<212> TYPE: PRT
<213> ORGANISM: Homo sapiens

<400> SEQUENCE: 674

Pro Pro Gly Ser Pro Gly
1               5

<210> SEQ ID NO 675
<211> LENGTH: 6
<212> TYPE: PRT
<213> ORGANISM: Homo sapiens

<400> SEQUENCE: 675

Gly Glu Pro Gly Pro Pro
1               5

<210> SEQ ID NO 676
<211> LENGTH: 6
<212> TYPE: PRT
<213> ORGANISM: Homo sapiens

<400> SEQUENCE: 676

Ala Gly Asn Pro Gly Pro
1               5

<210> SEQ ID NO 677
<211> LENGTH: 6
<212> TYPE: PRT
<213> ORGANISM: Homo sapiens

<400> SEQUENCE: 677

Pro Gly Ile Lys Gly Ser
1               5

<210> SEQ ID NO 678
<211> LENGTH: 6
<212> TYPE: PRT
<213> ORGANISM: Homo sapiens

<400> SEQUENCE: 678

Pro Gly Tyr Thr Asn Gly
1               5

<210> SEQ ID NO 679
<211> LENGTH: 6
<212> TYPE: PRT
<213> ORGANISM: Homo sapiens

<400> SEQUENCE: 679

Phe Pro Gly Pro Gln Gly
1               5

<210> SEQ ID NO 680
<211> LENGTH: 6
<212> TYPE: PRT
<213> ORGANISM: Homo sapiens

<400> SEQUENCE: 680

Leu Ser Gly Pro Pro Gly
1               5

<210> SEQ ID NO 681
<211> LENGTH: 6
<212> TYPE: PRT
```

<213> ORGANISM: Homo sapiens

<400> SEQUENCE: 681

Gly Val Met Gly Thr Pro
1               5

<210> SEQ ID NO 682
<211> LENGTH: 6
<212> TYPE: PRT
<213> ORGANISM: Homo sapiens

<400> SEQUENCE: 682

Gly Val Ser Gly Pro Lys
1               5

<210> SEQ ID NO 683
<211> LENGTH: 15
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Proline or hydroxyproline
<220> FEATURE:
<221> NAME/KEY: MOD_RES
<222> LOCATION: (6)..(6)
<223> OTHER INFORMATION: Proline or hydroxyproline
<220> FEATURE:
<221> NAME/KEY: MOD_RES
<222> LOCATION: (9)..(9)
<223> OTHER INFORMATION: Proline or hydroxyproline

<400> SEQUENCE: 683

Lys Gly Asp Xaa Gly Xaa Pro Gly Xaa Ile Gly Ser Leu Gly His
1               5                   10                  15

<210> SEQ ID NO 684
<211> LENGTH: 14
<212> TYPE: PRT
<213> ORGANISM: Homo sapiens

<400> SEQUENCE: 684

Gly Leu Arg Gly Ile Pro Gly Pro Val Gly Glu Pro Gly Leu
1               5                   10

<210> SEQ ID NO 685
<211> LENGTH: 17
<212> TYPE: PRT
<213> ORGANISM: Homo sapiens

<400> SEQUENCE: 685

Val Ile Gly Pro Pro Gly Leu Gln Gly Leu Pro Gly Pro Pro Gly Glu
1               5                   10                  15

Lys

<210> SEQ ID NO 686
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Proline or hydroxyproline
<220> FEATURE:
<221> NAME/KEY: MOD_RES
<222> LOCATION: (15)..(15)
<223> OTHER INFORMATION: Proline or hydroxyproline -continued

```
<400> SEQUENCE: 686

Gly Lys Asp Gly Ile Xaa Gly Pro Leu Gly Pro Leu Gly Pro Xaa Gly
1               5                   10                  15
Ala

<210> SEQ ID NO 687
<211> LENGTH: 16
<212> TYPE: PRT
<213> ORGANISM: Homo sapiens

<400> SEQUENCE: 687

Gly Leu Arg Gly Ile Pro Gly Pro Val Gly Glu Pro Gly Leu Leu Gly
1               5                   10                  15

<210> SEQ ID NO 688
<211> LENGTH: 17
<212> TYPE: PRT
<213> ORGANISM: Homo sapiens

<400> SEQUENCE: 688

Gly Val Leu Gly Pro Gln Gly Lys Thr Gly Glu Val Gly Pro Leu Gly
1               5                   10                  15
Glu

<210> SEQ ID NO 689
<211> LENGTH: 18
<212> TYPE: PRT
<213> ORGANISM: Homo sapiens

<400> SEQUENCE: 689

Lys Asp Gly Ile Pro Gly Pro Leu Gly Pro Leu Gly Pro Pro Gly Ala
1               5                   10                  15
Ala Gly

<210> SEQ ID NO 690
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline

<400> SEQUENCE: 690

Gly Glu Asp Gly Glu Arg Gly Ala Glu Gly Pro Xaa Gly Pro Thr Gly
1               5                   10                  15
Gln

<210> SEQ ID NO 691
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Proline or hydroxyproline
<220> FEATURE:
<221> NAME/KEY: MOD_RES
<222> LOCATION: (9)..(9)
<223> OTHER INFORMATION: Proline or hydroxyproline
<220> FEATURE:
<221> NAME/KEY: MOD_RES
<222> LOCATION: (11)..(11)
<223> OTHER INFORMATION: Proline or hydroxyproline
<220> FEATURE:
```

```
<221> NAME/KEY: MOD_RES
<222> LOCATION: (15)..(15)
<223> OTHER INFORMATION: Proline or hydroxyproline

<400> SEQUENCE: 691

Gly Leu Gln Gly Pro Xaa Gly Phe Xaa Gly Xaa Lys Gly Pro Xaa Gly
1               5                   10                  15

His

<210> SEQ ID NO 692
<211> LENGTH: 19
<212> TYPE: PRT
<213> ORGANISM: Homo sapiens

<400> SEQUENCE: 692

Pro Ile Gly Ser Leu Gly His Pro Gly Pro Pro Gly Val Ala Gly Pro
1               5                   10                  15

Leu Gly Gln

<210> SEQ ID NO 693
<211> LENGTH: 16
<212> TYPE: PRT
<213> ORGANISM: Homo sapiens

<400> SEQUENCE: 693

Gly Ile Arg Gly Pro Pro Gly Thr Val Ile Met Met Pro Phe Gln Phe
1               5                   10                  15

<210> SEQ ID NO 694
<211> LENGTH: 19
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (11)..(11)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 694

Gly Gln Met Gly Pro Xaa Gly Pro Leu Gly Xaa Ser Gly Leu Xaa Gly
1               5                   10                  15

Leu Lys Gly

<210> SEQ ID NO 695
<211> LENGTH: 20
<212> TYPE: PRT
<213> ORGANISM: Homo sapiens

<400> SEQUENCE: 695

Gly Leu Leu Gly Ala Pro Gly Gln Met Gly Pro Pro Gly Pro Pro Gly
1               5                   10                  15

Pro Ser Gly Leu
            20

<210> SEQ ID NO 696
<211> LENGTH: 20
<212> TYPE: PRT
<213> ORGANISM: Homo sapiens
```

```
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline

<400> SEQUENCE: 696

Gly Leu Arg Gly Ile Xaa Gly Pro Val Gly Glu Xaa Gly Leu Leu Gly
1               5                   10                  15

Ala Xaa Gly Gln
            20

<210> SEQ ID NO 697
<211> LENGTH: 20
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 697

Gly Leu Leu Gly Pro Arg Gly Ser Xaa Gly Pro Thr Gly Arg Xaa Gly
1               5                   10                  15

Val Thr Gly Ile
            20

<210> SEQ ID NO 698
<211> LENGTH: 17
<212> TYPE: PRT
<213> ORGANISM: Homo sapiens

<400> SEQUENCE: 698

Gly Ile Arg Gly Pro Pro Gly Thr Val Ile Met Met Pro Phe Gln Phe
1               5                   10                  15

Ala

<210> SEQ ID NO 699
<211> LENGTH: 21
<212> TYPE: PRT
<213> ORGANISM: Homo sapiens

<400> SEQUENCE: 699

Gly Lys Asp Gly Ile Pro Gly Pro Leu Gly Pro Leu Gly Pro Pro Gly
1               5                   10                  15

Ala Ala Gly Pro Ser
            20

<210> SEQ ID NO 700
<211> LENGTH: 23
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: proline or hydroxyproline
```

```
<220> FEATURE:
<221> NAME/KEY: MOD_RES
<222> LOCATION: (15)..(15)
<223> OTHER INFORMATION: proline or hydroxyproline

<400> SEQUENCE: 700

Gly Lys Asp Gly Ile Pro Gly Xaa Leu Gly Pro Leu Gly Pro Xaa Gly
1               5                   10                  15

Ala Ala Gly Pro Ser Gly Glu
            20

<210> SEQ ID NO 701
<211> LENGTH: 24
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: lysine or hydroxylysine
<220> FEATURE:
<221> NAME/KEY: MOD_RES
<222> LOCATION: (19)..(19)
<223> OTHER INFORMATION: proline or hydroxyproline

<400> SEQUENCE: 701

Gln Gly Leu Pro Gly Leu Glu Gly Arg Glu Gly Ala Xaa Gly Glu Leu
1               5                   10                  15

Gly Pro Xaa Gly Pro Leu Gly Lys
            20

<210> SEQ ID NO 702
<211> LENGTH: 30
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: lysine or hydroxylysine
<220> FEATURE:
<221> NAME/KEY: MOD_RES
<222> LOCATION: (16)..(16)
<223> OTHER INFORMATION: proline or hydroxyproline
<220> FEATURE:
<221> NAME/KEY: MOD_RES
<222> LOCATION: (24)..(24)
<223> OTHER INFORMATION: proline or hydroxyproline

<400> SEQUENCE: 702

Leu Gly Pro Ile Gly Glu Xaa Gly Lys Ser Gly Lys Thr Gly Gln Xaa
1               5                   10                  15

Gly Leu Glu Gly Glu Arg Gly Xaa Pro Gly Ser Arg Gly Glu
            20                  25                  30

<210> SEQ ID NO 703
<211> LENGTH: 32
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline
<220> FEATURE:
```

```
<221> NAME/KEY: MOD_RES
<222> LOCATION: (21)..(21)
<223> OTHER INFORMATION: methionine or oxidised methionine
<220> FEATURE:
<221> NAME/KEY: MOD_RES
<222> LOCATION: (23)..(23)
<223> OTHER INFORMATION: proline or hydroxyproline

<400> SEQUENCE: 703

Gly Leu Arg Gly Ile Pro Gly Xaa Val Gly Glu Xaa Gly Leu Leu Gly
1               5                   10                  15

Ala Xaa Gly Gln Xaa Gly Xaa Pro Gly Pro Leu Gly Pro Ser Gly Leu
            20                  25                  30

<210> SEQ ID NO 704
<211> LENGTH: 35
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline

<400> SEQUENCE: 704

Gly Ala Asn Gly Ser Xaa Gly Glu Arg Gly Pro Leu Gly Pro Ala Gly
1               5                   10                  15

Gly Ile Gly Leu Xaa Gly Gln Ser Gly Ser Glu Gly Pro Val Gly Pro
            20                  25                  30

Ala Gly Lys
        35

<210> SEQ ID NO 705
<211> LENGTH: 38
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (11)..(12)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline
<220> FEATURE:
<221> NAME/KEY: MOD_RES
<222> LOCATION: (26)..(26)
<223> OTHER INFORMATION: proline or hydroxyproline

<400> SEQUENCE: 705

Gly Leu Ile Gly Thr Xaa Gly Glu Lys Gly Xaa Xaa Gly Asn Xaa Gly
1               5                   10                  15

Ile Xaa Gly Leu Xaa Gly Ser Asp Gly Xaa Leu Gly His Pro Gly His
            20                  25                  30
```

```
Glu Gly Pro Thr Gly Glu
        35

<210> SEQ ID NO 706
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline

<400> SEQUENCE: 706

Gly Leu Xaa Gly Glu Xaa Gly Pro Arg Gly Leu
1               5                   10

<210> SEQ ID NO 707
<211> LENGTH: 12
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: methionine or oxidised methionine

<400> SEQUENCE: 707

Leu Ala Leu Arg Gly Pro Ala Gly Pro Xaa Gly Leu
1               5                   10

<210> SEQ ID NO 708
<211> LENGTH: 13
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: methionine or oxidised methionine

<400> SEQUENCE: 708

Arg Leu Ala Leu Arg Gly Pro Ala Gly Pro Xaa Gly Leu
1               5                   10

<210> SEQ ID NO 709
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 709

Gly Leu Thr Gly Arg Xaa Gly Pro Val Gly Pro Xaa Gly Ser Gly Gly
1               5                   10                  15

Leu

<210> SEQ ID NO 710
<211> LENGTH: 17
<212> TYPE: PRT
<213> ORGANISM: Homo sapiens
<220> FEATURE:
```

```
<221> NAME/KEY: MOD_RES
<222> LOCATION: (6)..(6)
<223> OTHER INFORMATION: lysine or hydroxylysine
<220> FEATURE:
<221> NAME/KEY: MOD_RES
<222> LOCATION: (11)..(12)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline

<400> SEQUENCE: 710

Gly Leu Leu Gly Pro Xaa Gly Pro Pro Gly Xaa Xaa Gly Xaa Pro Gly
1               5                   10                  15

Val

<210> SEQ ID NO 711
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline

<400> SEQUENCE: 711

Gly Ile Xaa Gly Arg Xaa Gly Pro Gln Gly Pro Pro Gly Xaa Ala Gly
1               5                   10                  15

Glu

<210> SEQ ID NO 712
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (13)..(13)
<223> OTHER INFORMATION: proline or hydroxyproline
<220> FEATURE:
<221> NAME/KEY: MOD_RES
<222> LOCATION: (16)..(16)
<223> OTHER INFORMATION: proline or hydroxyproline

<400> SEQUENCE: 712

Pro Gly Xaa Asp Gly Xaa Pro Gly Pro Met Gly Pro Xaa Gly Leu Xaa
1               5                   10                  15

Gly

<210> SEQ ID NO 713
<211> LENGTH: 17
<212> TYPE: PRT
<213> ORGANISM: Homo sapiens
<220> FEATURE:
```

```
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 713

Gly Gln Xaa Gly Pro Ser Gly Ala Asp Gly Glu Xaa Gly Pro Arg Gly
1               5                   10                  15

Gln

<210> SEQ ID NO 714
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 714

Gly Glu Thr Gly Phe Gln Gly Lys Thr Gly Pro Xaa Gly Pro Xaa Gly
1               5                   10                  15

Val

<210> SEQ ID NO 715
<211> LENGTH: 16
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 715

Gly Leu Arg Gly Phe Xaa Gly Asp Arg Gly Leu Xaa Gly Pro Val Gly
1               5                   10                  15

<210> SEQ ID NO 716
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 716

Gly Leu Arg Gly Phe Xaa Gly Asp Arg Gly Leu Xaa Gly Pro Val Gly
1               5                   10                  15

Ala

<210> SEQ ID NO 717
<211> LENGTH: 20
```

```
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 717

Gly Lys Thr Gly Pro Ile Gly Pro Gln Gly Ala Xaa Gly Lys Xaa Gly
1               5                   10                  15

Pro Asp Gly Leu
            20

<210> SEQ ID NO 718
<211> LENGTH: 20
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (17)..(18)
<223> OTHER INFORMATION: proline or hydroxyproline

<400> SEQUENCE: 718

Gly Xaa Xaa Gly Arg Xaa Gly Leu Pro Gly Ala Asp Gly Leu Pro Gly
1               5                   10                  15

Xaa Xaa Gly Thr
            20

<210> SEQ ID NO 719
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: lysine or hydroxylysine
<220> FEATURE:
<221> NAME/KEY: MOD_RES
<222> LOCATION: (12)..(12)
<223> OTHER INFORMATION: proline or hydroxyproline

<400> SEQUENCE: 719

Gly Leu Xaa Gly Asn Glu Gly Pro Pro Gly Pro Xaa Gly Pro Ala Gly
1               5                   10                  15

Ser Pro Gly Glu Arg
            20

<210> SEQ ID NO 720
<211> LENGTH: 20
<212> TYPE: PRT
<213> ORGANISM: Homo sapiens
<220> FEATURE:
<221> NAME/KEY: MOD_RES
<222> LOCATION: (6)..(6)
```

```
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 720

Gly Leu Arg Gly Phe Xaa Gly Asp Arg Gly Leu Xaa Gly Pro Val Gly
1               5                   10                  15

Ala Leu Gly Leu
            20

<210> SEQ ID NO 721
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline

<400> SEQUENCE: 721

Gly Glu Arg Gly His Xaa Gly Pro Xaa Gly Pro Xaa Gly Glu Gln Gly
1               5                   10                  15

Leu Xaa Gly Leu
            20

<210> SEQ ID NO 722
<211> LENGTH: 21
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: proline or hydroxyproline
<220> FEATURE:
<221> NAME/KEY: MOD_RES
<222> LOCATION: (10)..(10)
<223> OTHER INFORMATION: lysine or hydroxylysine
<220> FEATURE:
<221> NAME/KEY: MOD_RES
<222> LOCATION: (16)..(16)
<223> OTHER INFORMATION: proline or hydroxyproline

<400> SEQUENCE: 722

Ile Gly Pro Xaa Gly Glu Gln Gly Glu Xaa Gly Asp Arg Gly Leu Xaa
1               5                   10                  15

Gly Pro Gln Gly Ser
            20

<210> SEQ ID NO 723
<211> LENGTH: 24
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: proline or hydroxyproline
```

```
<220> FEATURE:
<221> NAME/KEY: MOD_RES
<222> LOCATION: (11)..(12)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline

<400> SEQUENCE: 723

Gly Glu Ala Gly His Pro Gly Pro Xaa Gly Xaa Xaa Gly Xaa Pro Gly
1               5                  10                  15

Glu Val Ile Gln Pro Leu Pro Ile
            20

<210> SEQ ID NO 724
<211> LENGTH: 26
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: lysine or hydroxylysine
<220> FEATURE:
<221> NAME/KEY: MOD_RES
<222> LOCATION: (22)..(22)
<223> OTHER INFORMATION: proline or hydroxyproline
<220> FEATURE:
<221> NAME/KEY: MOD_RES
<222> LOCATION: (25)..(25)
<223> OTHER INFORMATION: proline or hydroxyproline

<400> SEQUENCE: 724

Lys Xaa Gly Pro Xaa Gly Asn Ser Gly Gly Asp Gly Pro Ala Gly Pro
1               5                  10                  15

Pro Gly Glu Arg Gly Xaa Asn Gly Xaa Gln
            20                  25

<210> SEQ ID NO 725
<211> LENGTH: 26
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline
<220> FEATURE:
<221> NAME/KEY: MOD_RES
<222> LOCATION: (18)..(18)
<223> OTHER INFORMATION: methionine or oxidised methionine
<220> FEATURE:
<221> NAME/KEY: MOD_RES
<222> LOCATION: (21)..(21)
<223> OTHER INFORMATION: proline or hydroxyproline
<220> FEATURE:
<221> NAME/KEY: MOD_RES
<222> LOCATION: (24)..(24)
<223> OTHER INFORMATION: proline or hydroxyproline

<400> SEQUENCE: 725

Gly Glu Gln Gly Leu Xaa Gly Ser Xaa Gly Pro Asp Gly Pro Pro Gly
1               5                  10                  15

Pro Xaa Gly Pro Xaa Gly Leu Xaa Gly Leu
            20                  25
```

```
                 20                  25

<210> SEQ ID NO 726
<211> LENGTH: 27
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (24)..(24)
<223> OTHER INFORMATION: proline or hydroxyproline

<400> SEQUENCE: 726

Glu Gly Xaa Xaa Gly Glu Lys Gly Gly Gln Gly Xaa Pro Gly Pro Gln
1               5                   10                  15

Gly Pro Ile Gly Tyr Pro Gly Xaa Arg Gly Val
            20                  25

<210> SEQ ID NO 727
<211> LENGTH: 26
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (8)..(8)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline

<400> SEQUENCE: 727

Gly Phe Xaa Gly Xaa Lys Gly Xaa Pro Gly Pro Xaa Gly Lys Asp Gly
1               5                   10                  15

Leu Xaa Gly His Xaa Gly Gln Arg Gly Glu
            20                  25

<210> SEQ ID NO 728
<211> LENGTH: 11
<212> TYPE: PRT
<213> ORGANISM: Homo sapiens

<400> SEQUENCE: 728

Leu Pro Phe Arg Phe Gly Gly Gly Gly Asp Ala
1               5                   10

<210> SEQ ID NO 729
```

```
<211> LENGTH: 11
<212> TYPE: PRT
<213> ORGANISM: Homo sapiens

<400> SEQUENCE: 729

Gly Ser Lys Gly Pro Met Val Ser Ala Gln Glu
1               5                   10

<210> SEQ ID NO 730
<211> LENGTH: 11
<212> TYPE: PRT
<213> ORGANISM: Homo sapiens

<400> SEQUENCE: 730

Gln Glu Ser Gln Ala Gln Ala Ile Leu Gln Gln
1               5                   10

<210> SEQ ID NO 731
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: lysine or hydroxylysine

<400> SEQUENCE: 731

Gly Ala Ile Gly Pro Xaa Gly Glu Xaa Gly Pro Leu Gly Lys
1               5                   10

<210> SEQ ID NO 732
<211> LENGTH: 15
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (13)..(13)
<223> OTHER INFORMATION: proline or hydroxyproline

<400> SEQUENCE: 732

Gly Gly Xaa Asn Gly Asp Pro Gly Pro Leu Gly Pro Xaa Gly Glu
1               5                   10                  15

<210> SEQ ID NO 733
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (4)..(5)
<223> OTHER INFORMATION: proline or hydroxyproline
<220> FEATURE:
<221> NAME/KEY: MOD_RES
<222> LOCATION: (11)..(11)
<223> OTHER INFORMATION: proline or hydroxyproline

<400> SEQUENCE: 733

Pro Xaa Gly Xaa Xaa Gly Glu Gln Gly Leu Xaa Gly Leu Ala
```

<210> SEQ ID NO 734
<211> LENGTH: 17
<212> TYPE: PRT
<213> ORGANISM: Homo sapiens
<220> FEATURE:
<221> NAME/KEY: MOD_RES
<222> LOCATION: (11)..(12)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline

<400> SEQUENCE: 734

Gly Leu Leu Gly Pro Lys Gly Pro Pro Gly Xaa Xaa Gly Xaa Pro Gly
1               5                   10                  15
Val

<210> SEQ ID NO 735
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 735

Gly Gln Gln Gly Asn Xaa Gly Ala Gln Gly Leu Xaa Gly Pro Gln Gly
1               5                   10                  15
Ala

<210> SEQ ID NO 736
<211> LENGTH: 17
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: lysine or hydroxylysine
<220> FEATURE:
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 736

Gly Xaa Glu Gly Xaa Pro Gly Glu Lys Gly Gly Gln Gly Pro Xaa Gly
1               5                   10                  15
Pro

<210> SEQ ID NO 737
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline
<220> FEATURE:

```
<221> NAME/KEY: MOD_RES
<222> LOCATION: (15)..(15)
<223> OTHER INFORMATION: proline or hydroxyproline

<400> SEQUENCE: 737

Gly Glu Thr Gly Phe Gln Gly Lys Thr Gly Pro Xaa Gly Pro Xaa Gly
1               5                   10                  15

Val

<210> SEQ ID NO 738
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: lysine or hydroxylysine
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 738

Gly Glu Xaa Gly His Xaa Gly Leu Ile Gly Leu Ile Gly Pro Xaa Gly
1               5                   10                  15

Glu

<210> SEQ ID NO 739
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 739

Gly Lys Thr Gly Pro Ile Gly Pro Gln Gly Ala Xaa Gly Lys Xaa Gly
1               5                   10                  15

Pro Asp Gly Leu
            20

<210> SEQ ID NO 740
<211> LENGTH: 20
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (12)..(13)
<223> OTHER INFORMATION: proline or hydroxyproline
<220> FEATURE:
<221> NAME/KEY: MOD_RES
<222> LOCATION: (16)..(16)
<223> OTHER INFORMATION: proline or hydroxyproline
```

```
<400> SEQUENCE: 740

Pro Gly Xaa Asp Gly Xaa Pro Gly Pro Met Gly Xaa Xaa Gly Leu Xaa
1               5                   10                  15

Gly Leu Lys Gly
            20

<210> SEQ ID NO 741
<211> LENGTH: 26
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: proline or hydroxyproline
<220> FEATURE:
<221> NAME/KEY: MOD_RES
<222> LOCATION: (17)..(17)
<223> OTHER INFORMATION: proline or hydroxyproline
<220> FEATURE:
<221> NAME/KEY: MOD_RES
<222> LOCATION: (20)..(21)
<223> OTHER INFORMATION: proline or hydroxyproline

<400> SEQUENCE: 741

Gly Glu Arg Gly Pro Asn Gly Pro Gln Gly Pro Thr Gly Phe Xaa Gly
1               5                   10                  15

Xaa Lys Gly Xaa Xaa Gly Pro Pro Gly Lys
            20                  25

<210> SEQ ID NO 742
<211> LENGTH: 26
<212> TYPE: PRT
<213> ORGANISM: Homo sapiens
<220> FEATURE:
<221> NAME/KEY: MOD_RES
<222> LOCATION: (7)..(8)
<223> OTHER INFORMATION: proline or hydroxyproline

<400> SEQUENCE: 742

Leu Ile Gly Leu Ile Gly Xaa Xaa Gly Glu Gln Gly Glu Lys Gly Asp
1               5                   10                  15

Arg Gly Leu Pro Gly Pro Gln Gly Ser Ser
            20                  25

<210> SEQ ID NO 743
<211> LENGTH: 31
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: proline or hydroxyproline
<220> FEATURE:
<221> NAME/KEY: MOD_RES
<222> LOCATION: (6)..(7)
<223> OTHER INFORMATION: proline or hydroxyproline

<400> SEQUENCE: 743

Ile Gly Pro Xaa Gly Xaa Xaa Gly Leu Pro Gly Pro Pro Gly Pro Lys
1               5                   10                  15

Gly Ala Lys Gly Ser Ser Gly Pro Thr Gly Pro Lys Gly Glu Ala
            20                  25                  30

<210> SEQ ID NO 744
<211> LENGTH: 30
<212> TYPE: PRT
```

```
<213> ORGANISM: Homo sapiens
<220> FEATURE:
<221> NAME/KEY: MOD_RES
<222> LOCATION: (4)..(5)
<223> OTHER INFORMATION: proline or hydroxyproline
<220> FEATURE:
<221> NAME/KEY: MOD_RES
<222> LOCATION: (8)..(8)
<223> OTHER INFORMATION: lysine or hydroxylysine
<220> FEATURE:
<221> NAME/KEY: MOD_RES
<222> LOCATION: (14)..(14)
<223> OTHER INFORMATION: proline or hydroxyproline

<400> SEQUENCE: 744

Pro Leu Gly Xaa Xaa Gly Glu Xaa Gly Lys Leu Gly Val Xaa Gly Leu
1               5                   10                  15

Pro Gly Tyr Pro Gly Arg Gln Gly Pro Lys Gly Ser Ile Gly
            20                  25                  30

<210> SEQ ID NO 745
<211> LENGTH: 33
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: proline or hydroxyproline
<220> FEATURE:
<221> NAME/KEY: MOD_RES
<222> LOCATION: (19)..(19)
<223> OTHER INFORMATION: lysine or hydroxylysine
<220> FEATURE:
<221> NAME/KEY: MOD_RES
<222> LOCATION: (25)..(25)
<223> OTHER INFORMATION: proline or hydroxyproline
<220> FEATURE:
<221> NAME/KEY: MOD_RES
<222> LOCATION: (28)..(28)
<223> OTHER INFORMATION: proline or hydroxyproline

<400> SEQUENCE: 745

Gln Gly Pro Lys Gly Ser Ile Gly Phe Pro Gly Phe Xaa Gly Ala Asn
1               5                   10                  15

Gly Glu Xaa Gly Gly Arg Gly Thr Xaa Gly Lys Xaa Gly Pro Arg Gly
            20                  25                  30

Gln

<210> SEQ ID NO 746
<211> LENGTH: 15
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: proline or hydroxyproline

<400> SEQUENCE: 746

Pro Gly Pro Lys Gly Asp Pro Gly Pro Xaa Gly Pro Ile Gly Ser
1               5                   10                  15

<210> SEQ ID NO 747
<211> LENGTH: 14
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
```

```
<221> NAME/KEY: MOD_RES
<222> LOCATION: (5)..(5)
<223> OTHER INFORMATION: proline or hydroxyproline
<220> FEATURE:
<221> NAME/KEY: MOD_RES
<222> LOCATION: (11)..(11)
<223> OTHER INFORMATION: proline or hydroxyproline

<400> SEQUENCE: 747

Ala Xaa Gly Ile Xaa Gly Glu Lys Gly Leu Xaa Gly Leu Gln
1               5                   10

<210> SEQ ID NO 748
<211> LENGTH: 16
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (10)..(10)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (15)..(15)
<223> OTHER INFORMATION: proline or hydroxyproline

<400> SEQUENCE: 748

Gln Gly Xaa Xaa Gly Xaa Lys Gly Asp Xaa Gly Xaa Pro Gly Xaa Ile
1               5                   10                  15

<210> SEQ ID NO 749
<211> LENGTH: 17
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline
<220> FEATURE:
<221> NAME/KEY: MOD_RES
<222> LOCATION: (9)..(9)
<223> OTHER INFORMATION: proline or hydroxyproline

<400> SEQUENCE: 749

Gly Ser Leu Gly His Xaa Gly Pro Xaa Gly Val Ala Gly Pro Leu Gly
1               5                   10                  15

Gln

<210> SEQ ID NO 750
<211> LENGTH: 17
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: proline or hydroxyproline

<400> SEQUENCE: 750

Gly Glu Leu Gly Phe Gln Gly Gln Thr Gly Pro Xaa Gly Pro Ala Gly
1               5                   10                  15
```

Val

```
<210> SEQ ID NO 751
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: lysine or hydroxylysine
<220> FEATURE:
<221> NAME/KEY: MOD_RES
<222> LOCATION: (15)..(15)
<223> OTHER INFORMATION: proline or hydroxyproline

<400> SEQUENCE: 751
```

Gly Glu Xaa Gly His Ile Gly Leu Ile Gly Leu Ile Gly Pro Xaa Gly
1               5                   10                  15

Glu

```
<210> SEQ ID NO 752
<211> LENGTH: 20
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline

<400> SEQUENCE: 752
```

Gly Xaa Val Gly Glu Pro Gly Leu Leu Gly Ala Xaa Gly Gln Met Gly
1               5                   10                  15

Pro Pro Gly Pro
            20

```
<210> SEQ ID NO 753
<211> LENGTH: 26
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: proline or hydroxyproline
<220> FEATURE:
<221> NAME/KEY: MOD_RES
<222> LOCATION: (14)..(14)
<223> OTHER INFORMATION: lysine or hydroxylysine
<220> FEATURE:
<221> NAME/KEY: MOD_RES
<222> LOCATION: (18)..(18)
<223> OTHER INFORMATION: proline or hydroxyproline

<400> SEQUENCE: 753
```

Gly Ser Arg Gly Glu Arg Gly Pro Pro Gly Xaa Thr Gly Xaa Asp Gly
1               5                   10                  15

Ile Xaa Gly Pro Leu Gly Pro Leu Gly Pro
            20                  25

```
<210> SEQ ID NO 754
<211> LENGTH: 26
<212> TYPE: PRT
<213> ORGANISM: Homo sapiens
<220> FEATURE:
<221> NAME/KEY: MOD_RES
```

```
<222> LOCATION: (5)..(5)
<223> OTHER INFORMATION: lysine or hydroxylysine
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline

<400> SEQUENCE: 754

Gly Glu Lys Gly Xaa Ser Gly Lys Thr Gly Gln Xaa Gly Leu Glu Gly
1               5                   10                  15

Glu Arg Gly Pro Xaa Gly Ser Arg Gly Glu
            20                  25

<210> SEQ ID NO 755
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 755

Leu Xaa Gly Glu Xaa Gly Pro Arg Gly Leu
1               5                   10

<210> SEQ ID NO 756
<211> LENGTH: 11
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: methionine or oxidised methionine

<400> SEQUENCE: 756

Ala Leu Arg Gly Pro Ala Gly Pro Xaa Gly Leu
1               5                   10

<210> SEQ ID NO 757
<211> LENGTH: 35
<212> TYPE: PRT
<213> ORGANISM: Homo sapiens
<220> FEATURE:
<221> NAME/KEY: MOD_RES
<222> LOCATION: (8)..(9)
<223> OTHER INFORMATION: proline or hydroxyproline
<220> FEATURE:
<221> NAME/KEY: MOD_RES
<222> LOCATION: (14)..(14)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline
<220> FEATURE:
<221> NAME/KEY: MOD_RES
<222> LOCATION: (21)..(21)
<223> OTHER INFORMATION: proline or hydroxyproline
<220> FEATURE:
<221> NAME/KEY: MOD_RES
<222> LOCATION: (23)..(23)
<223> OTHER INFORMATION: methionine or oxidised methionine
<220> FEATURE:
```

```
<221> NAME/KEY: MOD_RES
<222> LOCATION: (24)..(24)
<223> OTHER INFORMATION: proline or hydroxyproline
<220> FEATURE:
<221> NAME/KEY: MOD_RES
<222> LOCATION: (29)..(30)
<223> OTHER INFORMATION: proline or hydroxyproline
<220> FEATURE:
<221> NAME/KEY: MOD_RES
<222> LOCATION: (33)..(33)
<223> OTHER INFORMATION: proline or hydroxyproline

<400> SEQUENCE: 757
```

Gly Pro Gln Gly Ala Ile Gly Xaa Xaa Gly Glu Lys Gly Xaa Leu Gly
1               5                   10                  15

Lys Xaa Gly Leu Xaa Gly Xaa Xaa Gly Ala Asp Gly Xaa Xaa Gly His
            20                  25                  30

Xaa Gly Lys
        35

```
<210> SEQ ID NO 758
<211> LENGTH: 36
<212> TYPE: PRT
<213> ORGANISM: Homo sapiens
<220> FEATURE:
<221> NAME/KEY: MOD_RES
<222> LOCATION: (15)..(16)
<223> OTHER INFORMATION: proline or hydroxyproline
<220> FEATURE:
<221> NAME/KEY: MOD_RES
<222> LOCATION: (22)..(22)
<223> OTHER INFORMATION: lysine or hydroxylysine
<220> FEATURE:
<221> NAME/KEY: MOD_RES
<222> LOCATION: (25)..(25)
<223> OTHER INFORMATION: proline or hydroxyproline

<400> SEQUENCE: 758
```

Ala Gly Pro Met Gly Leu Thr Gly Arg Pro Gly Pro Val Gly Xaa Xaa
1               5                   10                  15

Gly Ser Gly Gly Leu Xaa Gly Glu Xaa Gly Asp Val Gly Pro Gln Gly
            20                  25                  30

Pro Arg Gly Val
        35

```
<210> SEQ ID NO 759
<211> LENGTH: 35
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: proline or hydroxyproline
<220> FEATURE:
<221> NAME/KEY: MOD_RES
<222> LOCATION: (12)..(12)
<223> OTHER INFORMATION: proline or hydroxyproline
<220> FEATURE:
<221> NAME/KEY: MOD_RES
<222> LOCATION: (18)..(18)
<223> OTHER INFORMATION: proline or hydroxyproline
<220> FEATURE:
<221> NAME/KEY: MOD_RES
<222> LOCATION: (21)..(21)
<223> OTHER INFORMATION: methionine or oxidised methionine
<220> FEATURE:
<221> NAME/KEY: MOD_RES
<222> LOCATION: (23)..(24)
<223> OTHER INFORMATION: proline or hydroxyproline

<400> SEQUENCE: 759
```

Gly Leu Arg Gly Ile Pro Gly Xaa Val Gly Glu Xaa Gly Leu Leu Gly
1               5                   10                  15

Ala Xaa Gly Gln Xaa Gly Xaa Xaa Gly Pro Leu Gly Pro Ser Gly Leu
            20              25                  30

Pro Gly Leu
        35

<210> SEQ ID NO 760
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 760

Leu Arg Gly Ile Xaa Gly
1               5

<210> SEQ ID NO 761
<211> LENGTH: 6
<212> TYPE: PRT
<213> ORGANISM: Homo sapiens

<400> SEQUENCE: 761

Ile Gly Pro Pro Gly Ile
1               5

<210> SEQ ID NO 762
<211> LENGTH: 6
<212> TYPE: PRT
<213> ORGANISM: Homo sapiens

<400> SEQUENCE: 762

Ile Gly Ser Leu Gly His
1               5

<210> SEQ ID NO 763
<211> LENGTH: 6
<212> TYPE: PRT
<213> ORGANISM: Homo sapiens

<400> SEQUENCE: 763

Ile Arg Gly Pro Pro Gly
1               5

<210> SEQ ID NO 764
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 764

Ala Asn Gly Ser Xaa Gly
1               5

<210> SEQ ID NO 765
<211> LENGTH: 6
<212> TYPE: PRT
<213> ORGANISM: Homo sapiens
<220> FEATURE:

```
<221> NAME/KEY: MOD_RES
<222> LOCATION: (5)..(5)
<223> OTHER INFORMATION: proline or hydroxyproline

<400> SEQUENCE: 765

Leu Ile Gly Thr Xaa Gly
1               5

<210> SEQ ID NO 766
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 766

Leu Xaa Gly Glu Xaa Gly
1               5

<210> SEQ ID NO 767
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 767

Ile Xaa Gly Arg Xaa Gly
1               5

<210> SEQ ID NO 768
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 768

Gly Xaa Asp Gly Xaa Pro
1               5

<210> SEQ ID NO 769
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 769

Gln Xaa Gly Pro Ser Gly
```

```
1               5

<210> SEQ ID NO 770
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: lysine or hydroxylysine

<400> SEQUENCE: 770

Leu Xaa Gly Asn Glu Gly
1               5

<210> SEQ ID NO 771
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 771

Glu Arg Gly His Xaa Gly
1               5

<210> SEQ ID NO 772
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline

<400> SEQUENCE: 772

Gly Pro Xaa Gly Glu Gln
1               5

<210> SEQ ID NO 773
<211> LENGTH: 6
<212> TYPE: PRT
<213> ORGANISM: Homo sapiens

<400> SEQUENCE: 773

Pro Phe Arg Phe Gly Gly
1               5

<210> SEQ ID NO 774
<211> LENGTH: 6
<212> TYPE: PRT
<213> ORGANISM: Homo sapiens

<400> SEQUENCE: 774

Glu Ser Gln Ala Gln Ala
1               5

<210> SEQ ID NO 775
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: lysine or hydroxylysine
```

```
<400> SEQUENCE: 775

Leu Leu Gly Pro Xaa Gly
1               5

<210> SEQ ID NO 776
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 776

Gln Gln Gly Asn Xaa Gly
1               5

<210> SEQ ID NO 777
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: lysine or hydroxylysine
<220> FEATURE:
<221> NAME/KEY: MOD_RES
<222> LOCATION: (4)..(4)
<223> OTHER INFORMATION: proline or hydroxyproline

<400> SEQUENCE: 777

Xaa Glu Gly Xaa Pro Gly
1               5

<210> SEQ ID NO 778
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline

<400> SEQUENCE: 778

Ile Gly Leu Ile Gly Xaa
1               5

<210> SEQ ID NO 779
<211> LENGTH: 6
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: proline or hydroxyproline

<400> SEQUENCE: 779

Leu Gly Xaa Xaa Gly Glu
1               5

<210> SEQ ID NO 780
<211> LENGTH: 6
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: proline or hydroxyproline
<220> FEATURE:
```

```
<221> NAME/KEY: MOD_RES
<222> LOCATION: (5)..(5)
<223> OTHER INFORMATION: proline or hydroxyproline

<400> SEQUENCE: 780

Gly Xaa Xaa Gly Xaa Lys
1               5

<210> SEQ ID NO 781
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 781

Ser Leu Gly His Xaa Gly
1               5

<210> SEQ ID NO 782
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 782

Lys Asp Gly Ile Xaa Gly
1               5

<210> SEQ ID NO 783
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 783

Pro Val Gly Glu Pro Gly
1               5

<210> SEQ ID NO 784
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
<222> LOCATION: (4)..(4)
<223> OTHER INFORMATION: proline or hydroxyproline

<400> SEQUENCE: 784

Xaa Gly Glu Xaa Gly Pro
1               5

<210> SEQ ID NO 785
<211> LENGTH: 6
<212> TYPE: PRT
<213> ORGANISM: Homo sapiens
<220> FEATURE:
```

```
<221> NAME/KEY: MOD_RES
<222> LOCATION: (5)..(5)
<223> OTHER INFORMATION: proline or hydroxyproline

<400> SEQUENCE: 785

Leu Leu Gly Ala Xaa Gly
1               5

<210> SEQ ID NO 786
<211> LENGTH: 6
<212> TYPE: PRT
<213> ORGANISM: Homo sapiens

<400> SEQUENCE: 786

Gly Leu Pro Gly Leu Glu
1               5

<210> SEQ ID NO 787
<211> LENGTH: 6
<212> TYPE: PRT
<213> ORGANISM: Homo sapiens

<400> SEQUENCE: 787

Gly Ile Pro Gly Glu Lys
1               5

<210> SEQ ID NO 788
<211> LENGTH: 6
<212> TYPE: PRT
<213> ORGANISM: Homo sapiens

<400> SEQUENCE: 788

Leu Ala Leu Arg Gly Pro
1               5

<210> SEQ ID NO 789
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 789

Leu Thr Gly Arg Xaa Gly
1               5

<210> SEQ ID NO 790
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 790

Leu Arg Gly Phe Xaa Gly
1               5

<210> SEQ ID NO 791
<211> LENGTH: 6
<212> TYPE: PRT
<213> ORGANISM: Homo sapiens

<400> SEQUENCE: 791
```

```
Lys Thr Gly Pro Ile Gly
1               5

<210> SEQ ID NO 792
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 792

Xaa Xaa Gly Arg Xaa Gly
1               5

<210> SEQ ID NO 793
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 793

Glu Gln Gly Leu Xaa Gly
1               5

<210> SEQ ID NO 794
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: proline or hydroxyproline

<400> SEQUENCE: 794

Ala Ile Gly Gly Pro Xaa
1               5

<210> SEQ ID NO 795
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 795

Gly Xaa Asn Gly Asp Pro
1               5

<210> SEQ ID NO 796
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
```

```
<222> LOCATION: (3)..(4)
<223> OTHER INFORMATION: proline or hydroxyproline

<400> SEQUENCE: 796

Xaa Gly Xaa Xaa Gly Glu
1               5

<210> SEQ ID NO 797
<211> LENGTH: 6
<212> TYPE: PRT
<213> ORGANISM: Homo sapiens

<400> SEQUENCE: 797

Leu Leu Gly Pro Arg Gly
1               5

<210> SEQ ID NO 798
<211> LENGTH: 6
<212> TYPE: PRT
<213> ORGANISM: Homo sapiens

<400> SEQUENCE: 798

Glu Arg Gly Pro Asn Gly
1               5

<210> SEQ ID NO 799
<211> LENGTH: 6
<212> TYPE: PRT
<213> ORGANISM: Homo sapiens

<400> SEQUENCE: 799

Gly Pro Lys Gly Asp Pro
1               5

<210> SEQ ID NO 800
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
<222> LOCATION: (4)..(4)
<223> OTHER INFORMATION: proline or hydroxyproline

<400> SEQUENCE: 800

Xaa Gly Ile Xaa Gly Glu
1               5

<210> SEQ ID NO 801
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: lysine or hydroxylysine

<400> SEQUENCE: 801

Glu Xaa Gly His Ile Gly
1               5

<210> SEQ ID NO 802
<211> LENGTH: 6
<212> TYPE: PRT
```

```
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 802

Gln Met Gly Pro Xaa Gly
1               5

<210> SEQ ID NO 803
<211> LENGTH: 6
<212> TYPE: PRT
<213> ORGANISM: Homo sapiens

<400> SEQUENCE: 803

Ser Arg Gly Glu Arg Gly
1               5

<210> SEQ ID NO 804
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: lysine or hydroxylysine

<400> SEQUENCE: 804

Glu Lys Gly Xaa Ser Gly
1               5

<210> SEQ ID NO 805
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: lysine or hydroxylysine

<400> SEQUENCE: 805

Gly Pro Ile Gly Glu Xaa
1               5

<210> SEQ ID NO 806
<211> LENGTH: 6
<212> TYPE: PRT
<213> ORGANISM: Homo sapiens

<400> SEQUENCE: 806

Pro Gln Gly Ala Ile Gly
1               5

<210> SEQ ID NO 807
<211> LENGTH: 6
<212> TYPE: PRT
<213> ORGANISM: Homo sapiens

<400> SEQUENCE: 807

Gly Pro Met Gly Leu Thr
1               5

<210> SEQ ID NO 808
<211> LENGTH: 6
<212> TYPE: PRT
<213> ORGANISM: Homo sapiens
```

```
<400> SEQUENCE: 808

Glu Thr Gly Phe Gln Gly
1               5

<210> SEQ ID NO 809
<211> LENGTH: 6
<212> TYPE: PRT
<213> ORGANISM: Homo sapiens

<400> SEQUENCE: 809

Gly Ser Lys Gly Pro Met
1               5

<210> SEQ ID NO 810
<211> LENGTH: 6
<212> TYPE: PRT
<213> ORGANISM: Homo sapiens

<400> SEQUENCE: 810

Ala Leu Arg Gly Pro Ala
1               5

<210> SEQ ID NO 811
<211> LENGTH: 6
<212> TYPE: PRT
<213> ORGANISM: Homo sapiens

<400> SEQUENCE: 811

Glu Ala Gly His Pro Gly
1               5

<210> SEQ ID NO 812
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: lysine or hydroxylysine
<220> FEATURE:
<221> NAME/KEY: MOD_RES
<222> LOCATION: (5)..(5)
<223> OTHER INFORMATION: proline or hydroxyproline

<400> SEQUENCE: 812

Glu Xaa Gly His Xaa Gly
1               5

<210> SEQ ID NO 813
<211> LENGTH: 5
<212> TYPE: PRT
<213> ORGANISM: Homo sapiens

<400> SEQUENCE: 813

Lys Asp Gly Ile Pro
1               5

<210> SEQ ID NO 814
<211> LENGTH: 6
<212> TYPE: PRT
<213> ORGANISM: Homo sapiens

<400> SEQUENCE: 814

Val Leu Gly Pro Gln Gly
1               5
```

<210> SEQ ID NO 815
<211> LENGTH: 6
<212> TYPE: PRT
<213> ORGANISM: Homo sapiens

<400> SEQUENCE: 815

Glu Asp Gly Glu Arg Gly
1               5

<210> SEQ ID NO 816
<211> LENGTH: 6
<212> TYPE: PRT
<213> ORGANISM: Homo sapiens

<400> SEQUENCE: 816

Gly Pro Lys Gly Ser Ile
1               5

<210> SEQ ID NO 817
<211> LENGTH: 6
<212> TYPE: PRT
<213> ORGANISM: Homo sapiens

<400> SEQUENCE: 817

Glu Leu Gly Phe Gln Gly
1               5

<210> SEQ ID NO 818
<211> LENGTH: 6
<212> TYPE: PRT
<213> ORGANISM: Homo sapiens

<400> SEQUENCE: 818

Leu Arg Gly Pro Ala Gly
1               5

<210> SEQ ID NO 819
<211> LENGTH: 6
<212> TYPE: PRT
<213> ORGANISM: Homo sapiens

<400> SEQUENCE: 819

Pro Ile Gly Ser Leu Gly
1               5

<210> SEQ ID NO 820
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 820

Pro Xaa Gly Pro Thr Gly
1               5

<210> SEQ ID NO 821
<211> LENGTH: 6
<212> TYPE: PRT
<213> ORGANISM: Homo sapiens
<220> FEATURE:
<221> NAME/KEY: MOD_RES
<222> LOCATION: (1)..(1)

```
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 821

Xaa Lys Gly Pro Xaa Gly
1               5

<210> SEQ ID NO 822
<211> LENGTH: 6
<212> TYPE: PRT
<213> ORGANISM: Homo sapiens

<400> SEQUENCE: 822

Val Ala Gly Pro Leu Gly
1               5

<210> SEQ ID NO 823
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 823

Arg Xaa Gly Val Thr Gly
1               5

<210> SEQ ID NO 824
<211> LENGTH: 6
<212> TYPE: PRT
<213> ORGANISM: Homo sapiens

<400> SEQUENCE: 824

Met Met Pro Phe Gln Phe
1               5

<210> SEQ ID NO 825
<211> LENGTH: 6
<212> TYPE: PRT
<213> ORGANISM: Homo sapiens

<400> SEQUENCE: 825

Pro Gly Ala Ala Gly Pro
1               5

<210> SEQ ID NO 826
<211> LENGTH: 6
<212> TYPE: PRT
<213> ORGANISM: Homo sapiens

<400> SEQUENCE: 826

Pro Val Gly Pro Ala Gly
1               5

<210> SEQ ID NO 827
<211> LENGTH: 6
<212> TYPE: PRT
<213> ORGANISM: Homo sapiens

<400> SEQUENCE: 827

His Glu Gly Pro Thr Gly
```

```
1               5

<210> SEQ ID NO 828
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline
<220> FEATURE:
<221> NAME/KEY: MOD_RES
<222> LOCATION: (6)..(6)
<223> OTHER INFORMATION: proline or hydroxyproline

<400> SEQUENCE: 828

Gly Pro Xaa Gly Leu Xaa
1               5

<210> SEQ ID NO 829
<211> LENGTH: 6
<212> TYPE: PRT
<213> ORGANISM: Homo sapiens

<400> SEQUENCE: 829

Ala Gly Ser Pro Gly Glu
1               5

<210> SEQ ID NO 830
<211> LENGTH: 6
<212> TYPE: PRT
<213> ORGANISM: Homo sapiens

<400> SEQUENCE: 830

Pro Val Gly Ala Leu Gly
1               5

<210> SEQ ID NO 831
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: proline or hydroxyproline

<400> SEQUENCE: 831

Tyr Pro Gly Xaa Arg Gly
1               5

<210> SEQ ID NO 832
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 832

His Xaa Gly Gln Arg Gly
1               5

<210> SEQ ID NO 833
<211> LENGTH: 6
<212> TYPE: PRT
<213> ORGANISM: Homo sapiens
```

```
<400> SEQUENCE: 833

Gly Gly Gly Gly Asp Ala
1               5

<210> SEQ ID NO 834
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 834

Leu Ile Gly Pro Xaa Gly
1               5

<210> SEQ ID NO 835
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline

<400> SEQUENCE: 835

Gly Leu Xaa Gly Leu Lys
1               5

<210> SEQ ID NO 836
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: proline or hydroxyproline

<400> SEQUENCE: 836

Lys Gly Leu Xaa Gly Leu
1               5

<210> SEQ ID NO 837
<211> LENGTH: 6
<212> TYPE: PRT
<213> ORGANISM: Homo sapiens

<400> SEQUENCE: 837

Gln Gln Ala Arg Leu Ala
1               5

<210> SEQ ID NO 838
<211> LENGTH: 6
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 838

Xaa Xaa Gly His Xaa Gly
1               5
```

<210> SEQ ID NO 839
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: proline or hydroxyproline

<400> SEQUENCE: 839

Pro Leu Gly Pro Xaa Gly
1               5

<210> SEQ ID NO 840
<211> LENGTH: 6
<212> TYPE: PRT
<213> ORGANISM: Homo sapiens

<400> SEQUENCE: 840

Gly Glu Pro Gly Leu Leu
1               5

<210> SEQ ID NO 841
<211> LENGTH: 6
<212> TYPE: PRT
<213> ORGANISM: Homo sapiens

<400> SEQUENCE: 841

Glu Val Gly Pro Leu Gly
1               5

<210> SEQ ID NO 842
<211> LENGTH: 6
<212> TYPE: PRT
<213> ORGANISM: Homo sapiens

<400> SEQUENCE: 842

Ile Met Met Pro Phe Gln
1               5

<210> SEQ ID NO 843
<211> LENGTH: 6
<212> TYPE: PRT
<213> ORGANISM: Homo sapiens

<400> SEQUENCE: 843

Pro Leu Gly Pro Ser Gly
1               5

<210> SEQ ID NO 844
<211> LENGTH: 6
<212> TYPE: PRT
<213> ORGANISM: Homo sapiens

<400> SEQUENCE: 844

Ala Ala Gly Pro Ser Gly
1               5

<210> SEQ ID NO 845
<211> LENGTH: 6
<212> TYPE: PRT
<213> ORGANISM: Homo sapiens
<220> FEATURE:
<221> NAME/KEY: MOD_RES
<222> LOCATION: (2)..(2)

```
<223> OTHER INFORMATION: proline or hydroxyproline

<400> SEQUENCE: 845

Pro Xaa Gly Pro Leu Gly
1               5

<210> SEQ ID NO 846
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: proline or hydroxyproline
<220> FEATURE:
<221> NAME/KEY: MOD_RES
<222> LOCATION: (2)..(2)
<223> OTHER INFORMATION: proline or hydroxyproline

<400> SEQUENCE: 846

Xaa Xaa Gly Ser Arg Gly
1               5

<210> SEQ ID NO 847
<211> LENGTH: 6
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: methionine or oxidised methionine

<400> SEQUENCE: 847

Pro Ala Gly Pro Xaa Gly
1               5

<210> SEQ ID NO 848
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 848

Pro Xaa Gly Ser Gly Gly
1               5

<210> SEQ ID NO 849
<211> LENGTH: 6
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: proline or hydroxyproline

<400> SEQUENCE: 849

Gly Leu Xaa Gly Pro Val
1               5

<210> SEQ ID NO 850
<211> LENGTH: 6
<212> TYPE: PRT
<213> ORGANISM: Homo sapiens
<220> FEATURE:
<221> NAME/KEY: MOD_RES
<222> LOCATION: (2)..(2)
```

```
<223> OTHER INFORMATION: proline or hydroxyproline

<400> SEQUENCE: 850

Leu Xaa Gly Pro Val Gly
1               5

<210> SEQ ID NO 851
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 851

Lys Xaa Gly Pro Asp Gly
1               5

<210> SEQ ID NO 852
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline

<400> SEQUENCE: 852

Leu Xaa Gly Pro Gln Gly
1               5

<210> SEQ ID NO 853
<211> LENGTH: 6
<212> TYPE: PRT
<213> ORGANISM: Homo sapiens

<400> SEQUENCE: 853

Val Ile Gln Pro Leu Pro
1               5

<210> SEQ ID NO 854
<211> LENGTH: 6
<212> TYPE: PRT
<213> ORGANISM: Homo sapiens

<400> SEQUENCE: 854

Arg Gly Pro Asn Gly Pro
1               5

<210> SEQ ID NO 855
<211> LENGTH: 6
<212> TYPE: PRT
<213> ORGANISM: Homo sapiens

<400> SEQUENCE: 855

Pro Gly Pro Gln Gly Ser
1               5

<210> SEQ ID NO 856
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Lysine or hydroxylysine
```

```
<400> SEQUENCE: 856

Glu Xaa Gly Pro Leu Gly
1               5

<210> SEQ ID NO 857
<211> LENGTH: 6
<212> TYPE: PRT
<213> ORGANISM: Homo sapiens

<400> SEQUENCE: 857

Gly Pro Pro Gly Ala Ala
1               5

<210> SEQ ID NO 858
<211> LENGTH: 6
<212> TYPE: PRT
<213> ORGANISM: Homo sapiens

<400> SEQUENCE: 858

Thr Gly Pro Lys Gly Glu
1               5

<210> SEQ ID NO 859
<211> LENGTH: 6
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: proline or hydroxyproline

<400> SEQUENCE: 859

Gln Gly Leu Xaa Gly Leu
1               5

<210> SEQ ID NO 860
<211> LENGTH: 6
<212> TYPE: PRT
<213> ORGANISM: Homo sapiens

<400> SEQUENCE: 860

Pro Ser Gly Leu Pro Gly
1               5

<210> SEQ ID NO 861
<211> LENGTH: 6
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: proline or hydroxyproline
<220> FEATURE:
<221> NAME/KEY: MOD_RES
<222> LOCATION: (5)..(5)
<223> OTHER INFORMATION: proline or hydroxyproline

<400> SEQUENCE: 861

Pro Xaa Gly Leu Xaa Gly
1               5

<210> SEQ ID NO 862
<211> LENGTH: 6
<212> TYPE: PRT
<213> ORGANISM: Homo sapiens
<220> FEATURE:
```

```
<221> NAME/KEY: MOD_RES
<222> LOCATION: (2)..(2)
<223> OTHER INFORMATION: proline or hydroxyproline

<400> SEQUENCE: 862

Lys Xaa Gly Pro Arg Gly
1               5

<210> SEQ ID NO 863
<211> LENGTH: 6
<212> TYPE: PRT
<213> ORGANISM: Homo sapiens

<400> SEQUENCE: 863

Pro Leu Gly Pro Leu Gly
1               5

<210> SEQ ID NO 864
<211> LENGTH: 14
<212> TYPE: PRT
<213> ORGANISM: Homo sapiens

<400> SEQUENCE: 864

Gly Tyr Arg Gly Pro Glu Gly Pro Gln Gly Pro Pro Gly His
1               5                   10

<210> SEQ ID NO 865
<211> LENGTH: 16
<212> TYPE: PRT
<213> ORGANISM: Homo sapiens

<400> SEQUENCE: 865

Gly Pro Ile Gly Pro Lys Gly Tyr Arg Gly Asp Glu Gly Pro Pro Gly
1               5                   10                  15

<210> SEQ ID NO 866
<211> LENGTH: 12
<212> TYPE: PRT
<213> ORGANISM: Homo sapiens

<400> SEQUENCE: 866

Ile Gly Ile Gly Ile Gly Asn Ala Asp Ile Thr Glu
1               5                   10

<210> SEQ ID NO 867
<211> LENGTH: 14
<212> TYPE: PRT
<213> ORGANISM: Homo sapiens

<400> SEQUENCE: 867

Gly Ala Gln Gly Pro Ala Gly Pro Ala Gly Pro Pro Gly Leu
1               5                   10

<210> SEQ ID NO 868
<211> LENGTH: 14
<212> TYPE: PRT
<213> ORGANISM: Homo sapiens

<400> SEQUENCE: 868

Gly Leu Ile Gly Glu Gln Gly Ile Ser Gly Pro Arg Gly Ser
1               5                   10

<210> SEQ ID NO 869
<211> LENGTH: 15
<212> TYPE: PRT
```

<213> ORGANISM: Homo sapiens

<400> SEQUENCE: 869

Pro Pro Gly Leu Ile Gly Glu Gln Gly Ile Ser Gly Pro Arg Gly
1               5                   10                  15

<210> SEQ ID NO 870
<211> LENGTH: 16
<212> TYPE: PRT
<213> ORGANISM: Homo sapiens

<400> SEQUENCE: 870

Glu Pro Gly Glu Pro Gly Pro Lys Gly Gly Ile Gly Asn Arg Gly Pro
1               5                   10                  15

<210> SEQ ID NO 871
<211> LENGTH: 26
<212> TYPE: PRT
<213> ORGANISM: Homo sapiens

<400> SEQUENCE: 871

Gly Ile Ser Gly Pro Arg Gly Ser Gly Gly Ala Ala Gly Ala Pro Gly
1               5                   10                  15

Glu Arg Gly Arg Thr Gly Pro Leu Gly Arg
            20                  25

<210> SEQ ID NO 872
<211> LENGTH: 14
<212> TYPE: PRT
<213> ORGANISM: Homo sapiens

<400> SEQUENCE: 872

Pro Gly Pro Ala Gly Pro Pro Gly Asp Pro Gly Leu Met Gly
1               5                   10

<210> SEQ ID NO 873
<211> LENGTH: 28
<212> TYPE: PRT
<213> ORGANISM: Homo sapiens

<400> SEQUENCE: 873

Val Ala Ala Lys Pro Ala Ala Val Arg Pro Ala Ala Ala Ala
1               5                   10                  15

Lys Pro Val Ala Thr Lys Pro Glu Val Pro Arg Pro
            20                  25

<210> SEQ ID NO 874
<211> LENGTH: 14
<212> TYPE: PRT
<213> ORGANISM: Homo sapiens

<400> SEQUENCE: 874

Gly Glu Pro Gly Leu Asn Gly Thr Thr Gly Pro Lys Gly Ile
1               5                   10

<210> SEQ ID NO 875
<211> LENGTH: 17
<212> TYPE: PRT
<213> ORGANISM: Homo sapiens

<400> SEQUENCE: 875

Ile Gly Pro Lys Gly Ile Pro Gly Glu Asp Gly Tyr Arg Gly Tyr Pro
1               5                   10                  15

Gly

<210> SEQ ID NO 876
<211> LENGTH: 26
<212> TYPE: PRT
<213> ORGANISM: Homo sapiens

<400> SEQUENCE: 876

Val Ala Val Val Gln His Ala Pro Ser Glu Ser Val Asp Asn Ala Ser
1               5                   10                  15

Met Pro Pro Val Lys Val Glu Phe Ser Leu
            20                  25

<210> SEQ ID NO 877
<211> LENGTH: 10
<212> TYPE: PRT
<213> ORGANISM: Homo sapiens

<400> SEQUENCE: 877

Leu Gly Pro Met Gly Val Pro Gly Arg Asp
1               5                   10

<210> SEQ ID NO 878
<211> LENGTH: 28
<212> TYPE: PRT
<213> ORGANISM: Homo sapiens

<400> SEQUENCE: 878

Gly Glu Pro Gly Pro Pro Gly Glu Lys Gly Glu Ala Gly Asp Glu Gly
1               5                   10                  15

Asn Pro Gly Pro Asp Gly Ala Pro Gly Glu Arg Gly
            20                  25

<210> SEQ ID NO 879
<211> LENGTH: 28
<212> TYPE: PRT
<213> ORGANISM: Homo sapiens

<400> SEQUENCE: 879

Arg Gly Pro Ile Gly Ser Ile Gly Pro Lys Gly Ile Pro Gly Glu Asp
1               5                   10                  15

Gly Tyr Arg Gly Tyr Pro Gly Asp Glu Gly Gly Pro
            20                  25

<210> SEQ ID NO 880
<211> LENGTH: 11
<212> TYPE: PRT
<213> ORGANISM: Homo sapiens

<400> SEQUENCE: 880

Pro Pro Pro Pro Gln Pro Ala Arg Ser Ala Ser
1               5                   10

<210> SEQ ID NO 881
<211> LENGTH: 12
<212> TYPE: PRT
<213> ORGANISM: Homo sapiens

<400> SEQUENCE: 881

Phe Gly Pro Ser Ala Ala Thr Pro Ala Pro Pro Gly
1               5                   10

<210> SEQ ID NO 882

```
<211> LENGTH: 29
<212> TYPE: PRT
<213> ORGANISM: Homo sapiens

<400> SEQUENCE: 882

Gly Pro Lys Gly Glu Thr Gly Asp Leu Gly Pro Met Gly Val Pro Gly
1               5                   10                  15

Arg Asp Gly Val Pro Gly Gly Pro Gly Glu Thr Gly Lys
            20                  25

<210> SEQ ID NO 883
<211> LENGTH: 6
<212> TYPE: PRT
<213> ORGANISM: Homo sapiens

<400> SEQUENCE: 883

Tyr Arg Gly Pro Glu Gly
1               5

<210> SEQ ID NO 884
<211> LENGTH: 16
<212> TYPE: PRT
<213> ORGANISM: Homo sapiens

<400> SEQUENCE: 884

Ser Ser Gly Ile Glu Asn Gly Ala Phe Gln Gly Met Lys Lys Leu Ser
1               5                   10                  15

<210> SEQ ID NO 885
<211> LENGTH: 6
<212> TYPE: PRT
<213> ORGANISM: Homo sapiens

<400> SEQUENCE: 885

Gly Ile Gly Ile Gly Asn
1               5

<210> SEQ ID NO 886
<211> LENGTH: 6
<212> TYPE: PRT
<213> ORGANISM: Homo sapiens

<400> SEQUENCE: 886

Ile Ser Gly Pro Arg Gly
1               5

<210> SEQ ID NO 887
<211> LENGTH: 6
<212> TYPE: PRT
<213> ORGANISM: Homo sapiens

<400> SEQUENCE: 887

Pro Gly Pro Ala Gly Pro
1               5

<210> SEQ ID NO 888
<211> LENGTH: 6
<212> TYPE: PRT
<213> ORGANISM: Homo sapiens

<400> SEQUENCE: 888

Val Ala Ala Lys Pro Ala
1               5
```

```
<210> SEQ ID NO 889
<211> LENGTH: 6
<212> TYPE: PRT
<213> ORGANISM: Homo sapiens

<400> SEQUENCE: 889

Arg Gly Pro Ile Gly Ser
1               5

<210> SEQ ID NO 890
<211> LENGTH: 6
<212> TYPE: PRT
<213> ORGANISM: Homo sapiens

<400> SEQUENCE: 890

Pro Pro Pro Pro Gln Pro
1               5

<210> SEQ ID NO 891
<211> LENGTH: 6
<212> TYPE: PRT
<213> ORGANISM: Homo sapiens

<400> SEQUENCE: 891

Ala Gln Gly Pro Ala Gly
1               5

<210> SEQ ID NO 892
<211> LENGTH: 6
<212> TYPE: PRT
<213> ORGANISM: Homo sapiens

<400> SEQUENCE: 892

Leu Ile Gly Glu Gln Gly
1               5

<210> SEQ ID NO 893
<211> LENGTH: 6
<212> TYPE: PRT
<213> ORGANISM: Homo sapiens

<400> SEQUENCE: 893

Pro Gly Leu Ile Gly Glu
1               5

<210> SEQ ID NO 894
<211> LENGTH: 6
<212> TYPE: PRT
<213> ORGANISM: Homo sapiens

<400> SEQUENCE: 894

Gly Glu Pro Gly Leu Asn
1               5

<210> SEQ ID NO 895
<211> LENGTH: 6
<212> TYPE: PRT
<213> ORGANISM: Homo sapiens

<400> SEQUENCE: 895

Ile Gly Pro Lys Gly Ile
1               5

<210> SEQ ID NO 896
<211> LENGTH: 6
```

<212> TYPE: PRT
<213> ORGANISM: Homo sapiens

<400> SEQUENCE: 896

Val Ala Val Val Gln His
1               5

<210> SEQ ID NO 897
<211> LENGTH: 6
<212> TYPE: PRT
<213> ORGANISM: Homo sapiens

<400> SEQUENCE: 897

Phe Gly Pro Ser Ala Ala
1               5

<210> SEQ ID NO 898
<211> LENGTH: 6
<212> TYPE: PRT
<213> ORGANISM: Homo sapiens

<400> SEQUENCE: 898

Gly Pro Lys Gly Glu Thr
1               5

<210> SEQ ID NO 899
<211> LENGTH: 6
<212> TYPE: PRT
<213> ORGANISM: Homo sapiens

<400> SEQUENCE: 899

Leu Gly Pro Met Gly Val
1               5

<210> SEQ ID NO 900
<211> LENGTH: 6
<212> TYPE: PRT
<213> ORGANISM: Homo sapiens

<400> SEQUENCE: 900

Gly Asp Glu Gly Pro Pro
1               5

<210> SEQ ID NO 901
<211> LENGTH: 6
<212> TYPE: PRT
<213> ORGANISM: Homo sapiens

<400> SEQUENCE: 901

Gly Asn Ala Asp Ile Thr
1               5

<210> SEQ ID NO 902
<211> LENGTH: 6
<212> TYPE: PRT
<213> ORGANISM: Homo sapiens

<400> SEQUENCE: 902

Asp Pro Gly Leu Met Gly
1               5

<210> SEQ ID NO 903
<211> LENGTH: 6
<212> TYPE: PRT
<213> ORGANISM: Homo sapiens

```
<400> SEQUENCE: 903

Pro Glu Val Pro Arg Pro
1               5

<210> SEQ ID NO 904
<211> LENGTH: 6
<212> TYPE: PRT
<213> ORGANISM: Homo sapiens

<400> SEQUENCE: 904

Thr Gly Pro Lys Gly Ile
1               5

<210> SEQ ID NO 905
<211> LENGTH: 6
<212> TYPE: PRT
<213> ORGANISM: Homo sapiens

<400> SEQUENCE: 905

Gly Asp Glu Gly Gly Pro
1               5

<210> SEQ ID NO 906
<211> LENGTH: 6
<212> TYPE: PRT
<213> ORGANISM: Homo sapiens

<400> SEQUENCE: 906

Pro Ala Arg Ser Ala Ser
1               5

<210> SEQ ID NO 907
<211> LENGTH: 6
<212> TYPE: PRT
<213> ORGANISM: Homo sapiens

<400> SEQUENCE: 907

Gly Ile Ser Gly Pro Arg
1               5

<210> SEQ ID NO 908
<211> LENGTH: 6
<212> TYPE: PRT
<213> ORGANISM: Homo sapiens

<400> SEQUENCE: 908

Gly Ile Gly Asn Arg Gly
1               5

<210> SEQ ID NO 909
<211> LENGTH: 6
<212> TYPE: PRT
<213> ORGANISM: Homo sapiens

<400> SEQUENCE: 909

Tyr Arg Gly Tyr Pro Gly
1               5

<210> SEQ ID NO 910
<211> LENGTH: 6
<212> TYPE: PRT
<213> ORGANISM: Homo sapiens

<400> SEQUENCE: 910
```

Lys Val Glu Phe Ser Leu
1               5

<210> SEQ ID NO 911
<211> LENGTH: 6
<212> TYPE: PRT
<213> ORGANISM: Homo sapiens

<400> SEQUENCE: 911

Gly Val Pro Gly Arg Asp
1               5

<210> SEQ ID NO 912
<211> LENGTH: 6
<212> TYPE: PRT
<213> ORGANISM: Homo sapiens

<400> SEQUENCE: 912

Pro Gly Glu Thr Gly Lys
1               5

<210> SEQ ID NO 913
<211> LENGTH: 6
<212> TYPE: PRT
<213> ORGANISM: Homo sapiens

<400> SEQUENCE: 913

Arg Thr Gly Pro Leu Gly
1               5

<210> SEQ ID NO 914
<211> LENGTH: 6
<212> TYPE: PRT
<213> ORGANISM: Homo sapiens

<400> SEQUENCE: 914

Ala Pro Gly Glu Arg Gly
1               5

<210> SEQ ID NO 915
<211> LENGTH: 6
<212> TYPE: PRT
<213> ORGANISM: Homo sapiens

<400> SEQUENCE: 915

Thr Pro Ala Pro Pro Gly
1               5

<210> SEQ ID NO 916
<211> LENGTH: 22
<212> TYPE: PRT
<213> ORGANISM: Homo sapiens

<400> SEQUENCE: 916

Ser Val Pro Lys Glu Ile Ser Pro Asp Thr Thr Leu Leu Asp Leu Gln
1               5                   10                  15

Asn Asn Asp Ile Ser Glu
            20

<210> SEQ ID NO 917
<211> LENGTH: 23
<212> TYPE: PRT
<213> ORGANISM: Homo sapiens

<400> SEQUENCE: 917

Lys Ser Val Pro Lys Glu Ile Ser Pro Asp Thr Thr Leu Leu Asp Leu
1               5                   10                  15

Gln Asn Asn Asp Ile Ser Glu
            20

<210> SEQ ID NO 918
<211> LENGTH: 23
<212> TYPE: PRT
<213> ORGANISM: Homo sapiens

<400> SEQUENCE: 918

Asn Ser Gly Phe Glu Pro Gly Ala Phe Asp Gly Leu Lys Leu Asn Tyr
1               5                   10                  15

Leu Arg Ile Ser Glu Ala Lys
            20

<210> SEQ ID NO 919
<211> LENGTH: 24
<212> TYPE: PRT
<213> ORGANISM: Homo sapiens

<400> SEQUENCE: 919

Leu Lys Ser Val Pro Lys Glu Ile Ser Pro Asp Thr Thr Leu Leu Asp
1               5                   10                  15

Leu Gln Asn Asn Asp Ile Ser Glu
            20

<210> SEQ ID NO 920
<211> LENGTH: 18
<212> TYPE: PRT
<213> ORGANISM: Homo sapiens

<400> SEQUENCE: 920

Leu Arg Ile Ser Glu Ala Lys Leu Thr Gly Ile Pro Lys Asp Leu Pro
1               5                   10                  15

Glu Thr

<210> SEQ ID NO 921
<211> LENGTH: 26
<212> TYPE: PRT
<213> ORGANISM: Homo sapiens

<400> SEQUENCE: 921

Leu Thr Gly Ile Pro Lys Asp Leu Pro Glu Thr Leu Asn Glu Leu His
1               5                   10                  15

Leu Asp His Asn Lys Ile Gln Ala Ile Glu
            20                  25

<210> SEQ ID NO 922
<211> LENGTH: 20
<212> TYPE: PRT
<213> ORGANISM: Homo sapiens

<400> SEQUENCE: 922

Arg Ile Ser Glu Ala Lys Leu Thr Gly Ile Pro Lys Asp Leu Pro Glu
1               5                   10                  15

Thr Leu Asn Glu
            20

<210> SEQ ID NO 923

```
<211> LENGTH: 12
<212> TYPE: PRT
<213> ORGANISM: Homo sapiens

<400> SEQUENCE: 923

Ala Ile Glu Leu Glu Asp Leu Leu Arg Tyr Ser Lys
1               5                   10

<210> SEQ ID NO 924
<211> LENGTH: 10
<212> TYPE: PRT
<213> ORGANISM: Homo sapiens

<400> SEQUENCE: 924

Ala Ile Glu Leu Glu Asp Leu Leu Arg Tyr
1               5                   10

<210> SEQ ID NO 925
<211> LENGTH: 17
<212> TYPE: PRT
<213> ORGANISM: Homo sapiens

<400> SEQUENCE: 925

Glu Ala Lys Leu Thr Gly Ile Pro Lys Asp Leu Pro Glu Thr Leu Asn
1               5                   10                  15

Glu

<210> SEQ ID NO 926
<211> LENGTH: 24
<212> TYPE: PRT
<213> ORGANISM: Homo sapiens

<400> SEQUENCE: 926

Leu Lys Ala Val Pro Lys Glu Ile Ser Pro Asp Thr Thr Leu Leu Asp
1               5                   10                  15

Leu Gln Asn Asn Asp Ile Ser Glu
            20

<210> SEQ ID NO 927
<211> LENGTH: 16
<212> TYPE: PRT
<213> ORGANISM: Homo sapiens

<400> SEQUENCE: 927

Leu Leu Asp Leu Gln Asn Asn Asp Ile Ser Glu Leu Arg Lys Asp Asp
1               5                   10                  15

<210> SEQ ID NO 928
<211> LENGTH: 10
<212> TYPE: PRT
<213> ORGANISM: Homo sapiens

<400> SEQUENCE: 928

Ile Glu Leu Glu Asp Leu Leu Arg Tyr Ser
1               5                   10

<210> SEQ ID NO 929
<211> LENGTH: 13
<212> TYPE: PRT
<213> ORGANISM: Homo sapiens

<400> SEQUENCE: 929

Asn Ser Gly Phe Glu Pro Gly Ala Phe Asp Gly Leu Lys
1               5                   10
```

<210> SEQ ID NO 930
<211> LENGTH: 11
<212> TYPE: PRT
<213> ORGANISM: Homo sapiens

<400> SEQUENCE: 930

Ile Val Ile Glu Leu Gly Thr Asn Pro Leu Lys
1               5                   10

<210> SEQ ID NO 931
<211> LENGTH: 14
<212> TYPE: PRT
<213> ORGANISM: Homo sapiens

<400> SEQUENCE: 931

Asp Glu Ala Ser Gly Ile Gly Pro Glu Val Pro Asp Asp Arg
1               5                   10

<210> SEQ ID NO 932
<211> LENGTH: 15
<212> TYPE: PRT
<213> ORGANISM: Homo sapiens

<400> SEQUENCE: 932

Leu His Leu Asp Gly Asn Lys Ile Ser Arg Val Asp Ala Ala Ser
1               5                   10                  15

<210> SEQ ID NO 933
<211> LENGTH: 16
<212> TYPE: PRT
<213> ORGANISM: Homo sapiens

<400> SEQUENCE: 933

Val Asn Asn Lys Ile Ser Lys Val Ser Pro Gly Ala Phe Thr Pro Leu
1               5                   10                  15

<210> SEQ ID NO 934
<211> LENGTH: 24
<212> TYPE: PRT
<213> ORGANISM: Homo sapiens

<400> SEQUENCE: 934

Leu Ile Leu Val Asn Asn Lys Ile Ser Lys Val Ser Pro Gly Ala Phe
1               5                   10                  15

Thr Pro Leu Val Lys Leu Glu Arg
                20

<210> SEQ ID NO 935
<211> LENGTH: 15
<212> TYPE: PRT
<213> ORGANISM: Homo sapiens

<400> SEQUENCE: 935

Ser Asn Pro Val Gln Tyr Trp Glu Ile Gln Pro Ser Thr Phe Arg
1               5                   10                  15

<210> SEQ ID NO 936
<211> LENGTH: 11
<212> TYPE: PRT
<213> ORGANISM: Homo sapiens

<400> SEQUENCE: 936

Lys Ile Thr Glu Ile Lys Asp Gly Asp Phe Lys

```
1               5                   10
```

<210> SEQ ID NO 937
<211> LENGTH: 15
<212> TYPE: PRT
<213> ORGANISM: Homo sapiens

<400> SEQUENCE: 937

```
Gly Leu Pro Pro Ser Leu Thr Glu Leu His Leu Asp Gly Asn Lys
1               5                   10                  15
```

<210> SEQ ID NO 938
<211> LENGTH: 10
<212> TYPE: PRT
<213> ORGANISM: Homo sapiens

<400> SEQUENCE: 938

```
Leu Leu Ala Ser Asp Ala Gly Leu Tyr Arg
1               5                   10
```

<210> SEQ ID NO 939
<211> LENGTH: 12
<212> TYPE: PRT
<213> ORGANISM: Homo sapiens

<400> SEQUENCE: 939

```
Leu Ala Thr Val Gly Glu Leu Gln Ala Ala Trp Arg
1               5                   10
```

<210> SEQ ID NO 940
<211> LENGTH: 13
<212> TYPE: PRT
<213> ORGANISM: Homo sapiens

<400> SEQUENCE: 940

```
Glu Thr Thr Val Leu Val Ala Gln Asn Gly Asn Ile Lys
1               5                   10
```

<210> SEQ ID NO 941
<211> LENGTH: 11
<212> TYPE: PRT
<213> ORGANISM: Homo sapiens

<400> SEQUENCE: 941

```
Ser Leu Glu Asp Leu Gln Leu Thr His Asn Lys
1               5                   10
```

<210> SEQ ID NO 942
<211> LENGTH: 11
<212> TYPE: PRT
<213> ORGANISM: Homo sapiens

<400> SEQUENCE: 942

```
Leu Lys Glu Asp Ala Val Ser Ala Ala Phe Lys
1               5                   10
```

<210> SEQ ID NO 943
<211> LENGTH: 14
<212> TYPE: PRT
<213> ORGANISM: Homo sapiens

<400> SEQUENCE: 943

```
Ser Ile Glu Tyr Ser Pro Gln Leu Glu Asp Ala Gly Ser Arg
1               5                   10
```

```
<210> SEQ ID NO 944
<211> LENGTH: 10
<212> TYPE: PRT
<213> ORGANISM: Homo sapiens

<400> SEQUENCE: 944

Leu Glu Gly Asp Thr Leu Ile Ile Pro Arg
1               5                   10

<210> SEQ ID NO 945
<211> LENGTH: 14
<212> TYPE: PRT
<213> ORGANISM: Homo sapiens

<400> SEQUENCE: 945

Val Ser Glu Ala Val Val Glu Lys Leu Glu Pro Glu Tyr Arg
1               5                   10

<210> SEQ ID NO 946
<211> LENGTH: 16
<212> TYPE: PRT
<213> ORGANISM: Homo sapiens

<400> SEQUENCE: 946

Ser Ser Gly Ile Glu Asn Gly Ala Phe Gln Gly Met Lys Lys Leu Ser
1               5                   10                  15

<210> SEQ ID NO 947
<211> LENGTH: 15
<212> TYPE: PRT
<213> ORGANISM: Homo sapiens

<400> SEQUENCE: 947

Glu Val Ser Glu Ala Val Val Glu Lys Leu Glu Pro Glu Tyr Arg
1               5                   10                  15

<210> SEQ ID NO 948
<211> LENGTH: 17
<212> TYPE: PRT
<213> ORGANISM: Homo sapiens

<400> SEQUENCE: 948

Ser Ile Glu Tyr Ser Pro Gln Leu Glu Asp Ala Ser Ala Lys Glu Phe
1               5                   10                  15

Arg

<210> SEQ ID NO 949
<211> LENGTH: 6
<212> TYPE: PRT
<213> ORGANISM: Homo sapiens

<400> SEQUENCE: 949

Ser Val Pro Lys Glu Ile
1               5

<210> SEQ ID NO 950
<211> LENGTH: 6
<212> TYPE: PRT
<213> ORGANISM: Homo sapiens

<400> SEQUENCE: 950

Gly Leu Lys Leu Asn Tyr
1               5
```

```
<210> SEQ ID NO 951
<211> LENGTH: 6
<212> TYPE: PRT
<213> ORGANISM: Homo sapiens

<400> SEQUENCE: 951

Arg Ile Ser Glu Ala Lys
1               5

<210> SEQ ID NO 952
<211> LENGTH: 6
<212> TYPE: PRT
<213> ORGANISM: Homo sapiens

<400> SEQUENCE: 952

Asn Ser Gly Phe Glu Pro
1               5

<210> SEQ ID NO 953
<211> LENGTH: 6
<212> TYPE: PRT
<213> ORGANISM: Homo sapiens

<400> SEQUENCE: 953

Leu Lys Ser Val Pro Lys
1               5

<210> SEQ ID NO 954
<211> LENGTH: 6
<212> TYPE: PRT
<213> ORGANISM: Homo sapiens

<400> SEQUENCE: 954

Ala Ile Glu Leu Glu Asp
1               5

<210> SEQ ID NO 955
<211> LENGTH: 6
<212> TYPE: PRT
<213> ORGANISM: Homo sapiens

<400> SEQUENCE: 955

Gln Cys Ser Asp Leu Gly
1               5

<210> SEQ ID NO 956
<211> LENGTH: 6
<212> TYPE: PRT
<213> ORGANISM: Homo sapiens

<400> SEQUENCE: 956

Glu Ala Lys Leu Thr Gly
1               5

<210> SEQ ID NO 957
<211> LENGTH: 6
<212> TYPE: PRT
<213> ORGANISM: Homo sapiens

<400> SEQUENCE: 957

Ile Glu Leu Glu Asp Leu
1               5

<210> SEQ ID NO 958
```

```
<211> LENGTH: 6
<212> TYPE: PRT
<213> ORGANISM: Homo sapiens

<400> SEQUENCE: 958

Leu Arg Ile Ser Glu Ala
1               5

<210> SEQ ID NO 959
<211> LENGTH: 6
<212> TYPE: PRT
<213> ORGANISM: Homo sapiens

<400> SEQUENCE: 959

Leu Thr Gly Ile Pro Lys
1               5

<210> SEQ ID NO 960
<211> LENGTH: 6
<212> TYPE: PRT
<213> ORGANISM: Homo sapiens

<400> SEQUENCE: 960

Leu Lys Ala Val Pro Lys
1               5

<210> SEQ ID NO 961
<211> LENGTH: 6
<212> TYPE: PRT
<213> ORGANISM: Homo sapiens

<400> SEQUENCE: 961

Leu Leu Asp Leu Gln Asn
1               5

<210> SEQ ID NO 962
<211> LENGTH: 6
<212> TYPE: PRT
<213> ORGANISM: Homo sapiens

<400> SEQUENCE: 962

Ile Val Ile Glu Leu Gly
1               5

<210> SEQ ID NO 963
<211> LENGTH: 6
<212> TYPE: PRT
<213> ORGANISM: Homo sapiens

<400> SEQUENCE: 963

Asp Glu Ala Ser Gly Ile
1               5

<210> SEQ ID NO 964
<211> LENGTH: 6
<212> TYPE: PRT
<213> ORGANISM: Homo sapiens

<400> SEQUENCE: 964

Val Asn Asn Lys Ile Ser
1               5

<210> SEQ ID NO 965
<211> LENGTH: 6
<212> TYPE: PRT
```

<213> ORGANISM: Homo sapiens

<400> SEQUENCE: 965

Asn Gly Leu Asn Gln Met
1               5

<210> SEQ ID NO 966
<211> LENGTH: 6
<212> TYPE: PRT
<213> ORGANISM: Homo sapiens

<400> SEQUENCE: 966

Leu His Leu Asp Gly Asn
1               5

<210> SEQ ID NO 967
<211> LENGTH: 6
<212> TYPE: PRT
<213> ORGANISM: Homo sapiens

<400> SEQUENCE: 967

Leu Ile Leu Val Asn Asn
1               5

<210> SEQ ID NO 968
<211> LENGTH: 6
<212> TYPE: PRT
<213> ORGANISM: Homo sapiens

<400> SEQUENCE: 968

Ser Ser Gly Ile Glu Asn
1               5

<210> SEQ ID NO 969
<211> LENGTH: 6
<212> TYPE: PRT
<213> ORGANISM: Homo sapiens

<400> SEQUENCE: 969

Lys Ile Thr Glu Ile Lys
1               5

<210> SEQ ID NO 970
<211> LENGTH: 6
<212> TYPE: PRT
<213> ORGANISM: Homo sapiens

<400> SEQUENCE: 970

Gly Leu Pro Pro Ser Leu
1               5

<210> SEQ ID NO 971
<211> LENGTH: 6
<212> TYPE: PRT
<213> ORGANISM: Homo sapiens

<400> SEQUENCE: 971

Ser Asn Pro Val Gln Tyr
1               5

<210> SEQ ID NO 972
<211> LENGTH: 6
<212> TYPE: PRT
<213> ORGANISM: Homo sapiens

```
<400> SEQUENCE: 972

Leu Leu Ala Ser Asp Ala
1               5

<210> SEQ ID NO 973
<211> LENGTH: 6
<212> TYPE: PRT
<213> ORGANISM: Homo sapiens

<400> SEQUENCE: 973

Leu Ala Thr Val Gly Glu
1               5

<210> SEQ ID NO 974
<211> LENGTH: 6
<212> TYPE: PRT
<213> ORGANISM: Homo sapiens

<400> SEQUENCE: 974

Glu Thr Thr Val Leu Val
1               5

<210> SEQ ID NO 975
<211> LENGTH: 6
<212> TYPE: PRT
<213> ORGANISM: Homo sapiens

<400> SEQUENCE: 975

Glu Asn Gln Asp Ala Arg
1               5

<210> SEQ ID NO 976
<211> LENGTH: 6
<212> TYPE: PRT
<213> ORGANISM: Homo sapiens

<400> SEQUENCE: 976

Asn Gly Phe Asp Gln Cys
1               5

<210> SEQ ID NO 977
<211> LENGTH: 6
<212> TYPE: PRT
<213> ORGANISM: Homo sapiens

<400> SEQUENCE: 977

Ser Leu Thr Val Val Lys
1               5

<210> SEQ ID NO 978
<211> LENGTH: 6
<212> TYPE: PRT
<213> ORGANISM: Homo sapiens

<400> SEQUENCE: 978

Ser Leu Glu Asp Leu Gln
1               5

<210> SEQ ID NO 979
<211> LENGTH: 6
<212> TYPE: PRT
<213> ORGANISM: Homo sapiens

<400> SEQUENCE: 979
```

Leu Lys Glu Asp Ala Val
1               5

<210> SEQ ID NO 980
<211> LENGTH: 6
<212> TYPE: PRT
<213> ORGANISM: Homo sapiens

<400> SEQUENCE: 980

His Leu Gln His Asn Arg
1               5

<210> SEQ ID NO 981
<211> LENGTH: 6
<212> TYPE: PRT
<213> ORGANISM: Homo sapiens

<400> SEQUENCE: 981

Ser Ile Glu Tyr Ser Pro
1               5

<210> SEQ ID NO 982
<211> LENGTH: 6
<212> TYPE: PRT
<213> ORGANISM: Homo sapiens

<400> SEQUENCE: 982

Leu Val Asn Phe Thr Arg
1               5

<210> SEQ ID NO 983
<211> LENGTH: 6
<212> TYPE: PRT
<213> ORGANISM: Homo sapiens

<400> SEQUENCE: 983

Val Ser Glu Ala Val Val
1               5

<210> SEQ ID NO 984
<211> LENGTH: 6
<212> TYPE: PRT
<213> ORGANISM: Homo sapiens

<400> SEQUENCE: 984

Glu Val Ser Glu Ala Val
1               5

<210> SEQ ID NO 985
<211> LENGTH: 6
<212> TYPE: PRT
<213> ORGANISM: Homo sapiens

<400> SEQUENCE: 985

Leu Gln His Asn Arg Leu
1               5

<210> SEQ ID NO 986
<211> LENGTH: 6
<212> TYPE: PRT
<213> ORGANISM: Homo sapiens

<400> SEQUENCE: 986

Asn Asn Asp Ile Ser Glu
1               5

<210> SEQ ID NO 987
<211> LENGTH: 6
<212> TYPE: PRT
<213> ORGANISM: Homo sapiens

<400> SEQUENCE: 987

Tyr Trp Glu Val Gln Pro
1               5

<210> SEQ ID NO 988
<211> LENGTH: 6
<212> TYPE: PRT
<213> ORGANISM: Homo sapiens

<400> SEQUENCE: 988

Glu Asp Leu Leu Arg Tyr
1               5

<210> SEQ ID NO 989
<211> LENGTH: 6
<212> TYPE: PRT
<213> ORGANISM: Homo sapiens

<400> SEQUENCE: 989

Lys Ile Gln Ala Ile Glu
1               5

<210> SEQ ID NO 990
<211> LENGTH: 6
<212> TYPE: PRT
<213> ORGANISM: Homo sapiens

<400> SEQUENCE: 990

Pro Glu Thr Leu Asn Glu
1               5

<210> SEQ ID NO 991
<211> LENGTH: 6
<212> TYPE: PRT
<213> ORGANISM: Homo sapiens

<400> SEQUENCE: 991

Leu Arg Lys Asp Asp Phe
1               5

<210> SEQ ID NO 992
<211> LENGTH: 6
<212> TYPE: PRT
<213> ORGANISM: Homo sapiens

<400> SEQUENCE: 992

Leu Leu Arg Tyr Ser Lys
1               5

<210> SEQ ID NO 993
<211> LENGTH: 6
<212> TYPE: PRT
<213> ORGANISM: Homo sapiens

<400> SEQUENCE: 993

Glu Leu Arg Lys Asp Asp
1               5

```
<210> SEQ ID NO 994
<211> LENGTH: 6
<212> TYPE: PRT
<213> ORGANISM: Homo sapiens

<400> SEQUENCE: 994

Lys Asp Leu Pro Glu Thr
1               5

<210> SEQ ID NO 995
<211> LENGTH: 6
<212> TYPE: PRT
<213> ORGANISM: Homo sapiens

<400> SEQUENCE: 995

Asp Leu Leu Arg Tyr Ser
1               5

<210> SEQ ID NO 996
<211> LENGTH: 6
<212> TYPE: PRT
<213> ORGANISM: Homo sapiens

<400> SEQUENCE: 996

Ala Phe Asp Gly Leu Lys
1               5

<210> SEQ ID NO 997
<211> LENGTH: 6
<212> TYPE: PRT
<213> ORGANISM: Homo sapiens

<400> SEQUENCE: 997

Leu Asn Glu Leu His Leu
1               5

<210> SEQ ID NO 998
<211> LENGTH: 6
<212> TYPE: PRT
<213> ORGANISM: Homo sapiens

<400> SEQUENCE: 998

Gly Thr Asn Pro Leu Lys
1               5

<210> SEQ ID NO 999
<211> LENGTH: 6
<212> TYPE: PRT
<213> ORGANISM: Homo sapiens

<400> SEQUENCE: 999

Glu Val Pro Asp Asp Arg
1               5

<210> SEQ ID NO 1000
<211> LENGTH: 6
<212> TYPE: PRT
<213> ORGANISM: Homo sapiens

<400> SEQUENCE: 1000

Gly Ala Phe Thr Pro Leu
1               5

<210> SEQ ID NO 1001
<211> LENGTH: 6
```

```
<212> TYPE: PRT
<213> ORGANISM: Homo sapiens

<400> SEQUENCE: 1001

Arg Val Asp Ala Ala Ser
1               5

<210> SEQ ID NO 1002
<211> LENGTH: 6
<212> TYPE: PRT
<213> ORGANISM: Homo sapiens

<400> SEQUENCE: 1002

Leu Val Lys Leu Glu Arg
1               5

<210> SEQ ID NO 1003
<211> LENGTH: 6
<212> TYPE: PRT
<213> ORGANISM: Homo sapiens

<400> SEQUENCE: 1003

Gly Met Lys Lys Leu Ser
1               5

<210> SEQ ID NO 1004
<211> LENGTH: 6
<212> TYPE: PRT
<213> ORGANISM: Homo sapiens

<400> SEQUENCE: 1004

Lys Asp Gly Asp Phe Lys
1               5

<210> SEQ ID NO 1005
<211> LENGTH: 6
<212> TYPE: PRT
<213> ORGANISM: Homo sapiens

<400> SEQUENCE: 1005

His Leu Asp Gly Asn Lys
1               5

<210> SEQ ID NO 1006
<211> LENGTH: 6
<212> TYPE: PRT
<213> ORGANISM: Homo sapiens

<400> SEQUENCE: 1006

Gln Pro Ser Thr Phe Arg
1               5

<210> SEQ ID NO 1007
<211> LENGTH: 6
<212> TYPE: PRT
<213> ORGANISM: Homo sapiens

<400> SEQUENCE: 1007

Ala Phe Gln Gly Met Lys
1               5

<210> SEQ ID NO 1008
<211> LENGTH: 6
<212> TYPE: PRT
<213> ORGANISM: Homo sapiens
```

<400> SEQUENCE: 1008

Cys Asp Val Met Tyr Gly
1               5

<210> SEQ ID NO 1009
<211> LENGTH: 6
<212> TYPE: PRT
<213> ORGANISM: Homo sapiens

<400> SEQUENCE: 1009

Gln Asn Gly Ile Asn Lys
1               5

<210> SEQ ID NO 1010
<211> LENGTH: 6
<212> TYPE: PRT
<213> ORGANISM: Homo sapiens

<400> SEQUENCE: 1010

Ile Gly Gln Asp Tyr Lys
1               5

<210> SEQ ID NO 1011
<211> LENGTH: 6
<212> TYPE: PRT
<213> ORGANISM: Homo sapiens

<400> SEQUENCE: 1011

Gln Leu Thr His Asn Lys
1               5

<210> SEQ ID NO 1012
<211> LENGTH: 6
<212> TYPE: PRT
<213> ORGANISM: Homo sapiens

<400> SEQUENCE: 1012

Val Ser Ala Ala Phe Lys
1               5

<210> SEQ ID NO 1013
<211> LENGTH: 6
<212> TYPE: PRT
<213> ORGANISM: Homo sapiens

<400> SEQUENCE: 1013

Gly Leu Lys Ser Leu Glu
1               5

<210> SEQ ID NO 1014
<211> LENGTH: 6
<212> TYPE: PRT
<213> ORGANISM: Homo sapiens

<400> SEQUENCE: 1014

Glu Asp Ala Gly Ser Arg
1               5

<210> SEQ ID NO 1015
<211> LENGTH: 6
<212> TYPE: PRT
<213> ORGANISM: Homo sapiens

<400> SEQUENCE: 1015

```
Glu Phe Arg Glu Val Ser
1               5

<210> SEQ ID NO 1016
<211> LENGTH: 6
<212> TYPE: PRT
<213> ORGANISM: Homo sapiens

<400> SEQUENCE: 1016

Val Ala Gln Gln Asp Ser
1               5

<210> SEQ ID NO 1017
<211> LENGTH: 6
<212> TYPE: PRT
<213> ORGANISM: Homo sapiens

<400> SEQUENCE: 1017

Ser Ala Lys Glu Phe Arg
1               5

<210> SEQ ID NO 1018
<211> LENGTH: 6
<212> TYPE: PRT
<213> ORGANISM: Homo sapiens

<400> SEQUENCE: 1018

Leu Glu Pro Glu Tyr Arg
1               5

<210> SEQ ID NO 1019
<211> LENGTH: 16
<212> TYPE: PRT
<213> ORGANISM: Homo sapiens

<400> SEQUENCE: 1019

Lys Glu Ser Asp Thr Ser Tyr Val Ser Leu Lys Ala Pro Leu Thr Lys
1               5                   10                  15

<210> SEQ ID NO 1020
<211> LENGTH: 16
<212> TYPE: PRT
<213> ORGANISM: Homo sapiens

<400> SEQUENCE: 1020

Gly Gly Asn Phe Glu Gly Ser Gln Ser Leu Val Gly Asp Ile Gly Asn
1               5                   10                  15

<210> SEQ ID NO 1021
<211> LENGTH: 16
<212> TYPE: PRT
<213> ORGANISM: Homo sapiens

<400> SEQUENCE: 1021

Ala Leu Lys Tyr Glu Val Gln Gly Glu Val Phe Thr Lys Pro Gln Leu
1               5                   10                  15

<210> SEQ ID NO 1022
<211> LENGTH: 14
<212> TYPE: PRT
<213> ORGANISM: Homo sapiens

<400> SEQUENCE: 1022

Gly Ile Val Glu Phe Trp Val Asp Gly Lys Pro Arg Val Arg
```

-continued

```
1               5                   10

<210> SEQ ID NO 1023
<211> LENGTH: 10
<212> TYPE: PRT
<213> ORGANISM: Homo sapiens

<400> SEQUENCE: 1023

Arg Lys Ala Phe Val Phe Pro Lys Glu Ser
1               5                   10

<210> SEQ ID NO 1024
<211> LENGTH: 16
<212> TYPE: PRT
<213> ORGANISM: Homo sapiens

<400> SEQUENCE: 1024

Lys Tyr Glu Val Gln Gly Glu Val Phe Thr Lys Pro Gln Leu Trp Pro
1               5                   10                  15

<210> SEQ ID NO 1025
<211> LENGTH: 13
<212> TYPE: PRT
<213> ORGANISM: Homo sapiens

<400> SEQUENCE: 1025

Asp Ser Phe Gly Gly Asn Phe Glu Gly Ser Gln Ser Leu
1               5                   10

<210> SEQ ID NO 1026
<211> LENGTH: 12
<212> TYPE: PRT
<213> ORGANISM: Homo sapiens

<400> SEQUENCE: 1026

Asp Phe Val Leu Ser Pro Asp Glu Ile Asn Thr Ile
1               5                   10

<210> SEQ ID NO 1027
<211> LENGTH: 13
<212> TYPE: PRT
<213> ORGANISM: Homo sapiens

<400> SEQUENCE: 1027

Ser Leu Lys Lys Gly Tyr Thr Val Gly Ala Glu Ala Ser
1               5                   10

<210> SEQ ID NO 1028
<211> LENGTH: 12
<212> TYPE: PRT
<213> ORGANISM: Homo sapiens

<400> SEQUENCE: 1028

Ala Phe Gly Gln Thr Asp Met Ser Arg Lys Ala Phe
1               5                   10

<210> SEQ ID NO 1029
<211> LENGTH: 14
<212> TYPE: PRT
<213> ORGANISM: Homo sapiens

<400> SEQUENCE: 1029

Ser Leu Lys Lys Gly Tyr Thr Val Gly Ala Glu Ala Ser Ile
1               5                   10
```

```
<210> SEQ ID NO 1030
<211> LENGTH: 11
<212> TYPE: PRT
<213> ORGANISM: Homo sapiens

<400> SEQUENCE: 1030

Gly Glu Val Phe Thr Lys Pro Gln Leu Trp Pro
1               5                   10

<210> SEQ ID NO 1031
<211> LENGTH: 15
<212> TYPE: PRT
<213> ORGANISM: Homo sapiens

<400> SEQUENCE: 1031

Ser Ile Ile Leu Gly Gln Glu Gln Asp Ser Phe Gly Gly Asn Phe
1               5                   10                  15

<210> SEQ ID NO 1032
<211> LENGTH: 14
<212> TYPE: PRT
<213> ORGANISM: Homo sapiens

<400> SEQUENCE: 1032

Lys Tyr Glu Val Gln Gly Glu Val Phe Thr Lys Pro Gln Leu
1               5                   10

<210> SEQ ID NO 1033
<211> LENGTH: 6
<212> TYPE: PRT
<213> ORGANISM: Homo sapiens

<400> SEQUENCE: 1033

Ala Phe Val Phe Pro Lys
1               5

<210> SEQ ID NO 1034
<211> LENGTH: 8
<212> TYPE: PRT
<213> ORGANISM: Homo sapiens

<400> SEQUENCE: 1034

Phe Gly Gln Thr Asp Met Ser Arg
1               5

<210> SEQ ID NO 1035
<211> LENGTH: 9
<212> TYPE: PRT
<213> ORGANISM: Homo sapiens

<400> SEQUENCE: 1035

Phe Gly Gln Thr Asp Met Ser Arg Lys
1               5

<210> SEQ ID NO 1036
<211> LENGTH: 10
<212> TYPE: PRT
<213> ORGANISM: Homo sapiens

<400> SEQUENCE: 1036

Phe Gly Gln Thr Asp Met Ser Arg Lys Ala
1               5                   10

<210> SEQ ID NO 1037
```

```
<211> LENGTH: 11
<212> TYPE: PRT
<213> ORGANISM: Homo sapiens

<400> SEQUENCE: 1037

Phe Gly Gln Thr Asp Met Ser Arg Lys Ala Phe
1               5                   10

<210> SEQ ID NO 1038
<211> LENGTH: 16
<212> TYPE: PRT
<213> ORGANISM: Homo sapiens

<400> SEQUENCE: 1038

Phe Gly Gln Thr Asp Met Ser Arg Lys Ala Phe Val Phe Pro Lys Glu
1               5                   10                  15

<210> SEQ ID NO 1039
<211> LENGTH: 20
<212> TYPE: PRT
<213> ORGANISM: Homo sapiens

<400> SEQUENCE: 1039

Phe Gly Gln Thr Asp Met Ser Arg Lys Ala Phe Val Phe Pro Lys Glu
1               5                   10                  15

Ser Asp Thr Ser
            20

<210> SEQ ID NO 1040
<211> LENGTH: 22
<212> TYPE: PRT
<213> ORGANISM: Homo sapiens

<400> SEQUENCE: 1040

Phe Gly Gln Thr Asp Met Ser Arg Lys Ala Phe Val Phe Pro Lys Glu
1               5                   10                  15

Ser Asp Thr Ser Tyr Val
            20

<210> SEQ ID NO 1041
<211> LENGTH: 23
<212> TYPE: PRT
<213> ORGANISM: Homo sapiens

<400> SEQUENCE: 1041

Phe Gly Gln Thr Asp Met Ser Arg Lys Ala Phe Val Phe Pro Lys Glu
1               5                   10                  15

Ser Asp Thr Ser Tyr Val Ser
            20

<210> SEQ ID NO 1042
<211> LENGTH: 19
<212> TYPE: PRT
<213> ORGANISM: Homo sapiens

<400> SEQUENCE: 1042

Thr Asp Met Ser Arg Lys Ala Phe Val Phe Pro Lys Glu Ser Asp Thr
1               5                   10                  15

Ser Tyr Val

<210> SEQ ID NO 1043
<211> LENGTH: 15
<212> TYPE: PRT
```

<213> ORGANISM: Homo sapiens

<400> SEQUENCE: 1043

Met Ser Arg Lys Ala Phe Val Phe Pro Lys Glu Ser Asp Thr Ser
1               5                   10                  15

<210> SEQ ID NO 1044
<211> LENGTH: 16
<212> TYPE: PRT
<213> ORGANISM: Homo sapiens

<400> SEQUENCE: 1044

Ser Arg Lys Ala Phe Val Phe Pro Lys Glu Ser Asp Thr Ser Tyr Val
1               5                   10                  15

<210> SEQ ID NO 1045
<211> LENGTH: 9
<212> TYPE: PRT
<213> ORGANISM: Homo sapiens

<400> SEQUENCE: 1045

Arg Lys Ala Phe Val Phe Pro Lys Glu
1               5

<210> SEQ ID NO 1046
<211> LENGTH: 15
<212> TYPE: PRT
<213> ORGANISM: Homo sapiens

<400> SEQUENCE: 1046

Arg Lys Ala Phe Val Phe Pro Lys Glu Ser Asp Thr Ser Tyr Val
1               5                   10                  15

<210> SEQ ID NO 1047
<211> LENGTH: 16
<212> TYPE: PRT
<213> ORGANISM: Homo sapiens

<400> SEQUENCE: 1047

Arg Lys Ala Phe Val Phe Pro Lys Glu Ser Asp Thr Ser Tyr Val Ser
1               5                   10                  15

<210> SEQ ID NO 1048
<211> LENGTH: 8
<212> TYPE: PRT
<213> ORGANISM: Homo sapiens

<400> SEQUENCE: 1048

Lys Ala Phe Val Phe Pro Lys Glu
1               5

<210> SEQ ID NO 1049
<211> LENGTH: 10
<212> TYPE: PRT
<213> ORGANISM: Homo sapiens

<400> SEQUENCE: 1049

Lys Ala Phe Val Phe Pro Lys Glu Ser Asp
1               5                   10

<210> SEQ ID NO 1050
<211> LENGTH: 11
<212> TYPE: PRT
<213> ORGANISM: Homo sapiens

<400> SEQUENCE: 1050

Lys Ala Phe Val Phe Pro Lys Glu Ser Asp Thr
1               5                  10

<210> SEQ ID NO 1051
<211> LENGTH: 12
<212> TYPE: PRT
<213> ORGANISM: Homo sapiens

<400> SEQUENCE: 1051

Lys Ala Phe Val Phe Pro Lys Glu Ser Asp Thr Ser
1               5                  10

<210> SEQ ID NO 1052
<211> LENGTH: 14
<212> TYPE: PRT
<213> ORGANISM: Homo sapiens

<400> SEQUENCE: 1052

Lys Ala Phe Val Phe Pro Lys Glu Ser Asp Thr Ser Tyr Val
1               5                  10

<210> SEQ ID NO 1053
<211> LENGTH: 15
<212> TYPE: PRT
<213> ORGANISM: Homo sapiens

<400> SEQUENCE: 1053

Lys Ala Phe Val Phe Pro Lys Glu Ser Asp Thr Ser Tyr Val Ser
1               5                  10                  15

<210> SEQ ID NO 1054
<211> LENGTH: 7
<212> TYPE: PRT
<213> ORGANISM: Homo sapiens

<400> SEQUENCE: 1054

Ala Phe Val Phe Pro Lys Glu
1               5

<210> SEQ ID NO 1055
<211> LENGTH: 10
<212> TYPE: PRT
<213> ORGANISM: Homo sapiens

<400> SEQUENCE: 1055

Ala Phe Val Phe Pro Lys Glu Ser Asp Thr
1               5                  10

<210> SEQ ID NO 1056
<211> LENGTH: 13
<212> TYPE: PRT
<213> ORGANISM: Homo sapiens

<400> SEQUENCE: 1056

Ala Phe Val Phe Pro Lys Glu Ser Asp Thr Ser Tyr Val
1               5                  10

<210> SEQ ID NO 1057
<211> LENGTH: 14
<212> TYPE: PRT
<213> ORGANISM: Homo sapiens

<400> SEQUENCE: 1057

Ala Phe Val Phe Pro Lys Glu Ser Asp Thr Ser Tyr Val Ser
1               5                   10

<210> SEQ ID NO 1058
<211> LENGTH: 15
<212> TYPE: PRT
<213> ORGANISM: Homo sapiens

<400> SEQUENCE: 1058

Ala Phe Val Phe Pro Lys Glu Ser Asp Thr Ser Tyr Val Ser Leu
1               5                   10                  15

<210> SEQ ID NO 1059
<211> LENGTH: 5
<212> TYPE: PRT
<213> ORGANISM: Homo sapiens

<400> SEQUENCE: 1059

Phe Val Phe Pro Lys
1               5

<210> SEQ ID NO 1060
<211> LENGTH: 6
<212> TYPE: PRT
<213> ORGANISM: Homo sapiens

<400> SEQUENCE: 1060

Phe Val Phe Pro Lys Glu
1               5

<210> SEQ ID NO 1061
<211> LENGTH: 8
<212> TYPE: PRT
<213> ORGANISM: Homo sapiens

<400> SEQUENCE: 1061

Phe Val Phe Pro Lys Glu Ser Asp
1               5

<210> SEQ ID NO 1062
<211> LENGTH: 10
<212> TYPE: PRT
<213> ORGANISM: Homo sapiens

<400> SEQUENCE: 1062

Phe Val Phe Pro Lys Glu Ser Asp Thr Ser
1               5                   10

<210> SEQ ID NO 1063
<211> LENGTH: 11
<212> TYPE: PRT
<213> ORGANISM: Homo sapiens

<400> SEQUENCE: 1063

Phe Val Phe Pro Lys Glu Ser Asp Thr Ser Tyr
1               5                   10

<210> SEQ ID NO 1064
<211> LENGTH: 12
<212> TYPE: PRT
<213> ORGANISM: Homo sapiens

<400> SEQUENCE: 1064

Phe Val Phe Pro Lys Glu Ser Asp Thr Ser Tyr Val
1               5                   10

<210> SEQ ID NO 1065
<211> LENGTH: 13
<212> TYPE: PRT
<213> ORGANISM: Homo sapiens

<400> SEQUENCE: 1065

Phe Val Phe Pro Lys Glu Ser Asp Thr Ser Tyr Val Ser
1               5                   10

<210> SEQ ID NO 1066
<211> LENGTH: 14
<212> TYPE: PRT
<213> ORGANISM: Homo sapiens

<400> SEQUENCE: 1066

Phe Val Phe Pro Lys Glu Ser Asp Thr Ser Tyr Val Ser Leu
1               5                   10

<210> SEQ ID NO 1067
<211> LENGTH: 9
<212> TYPE: PRT
<213> ORGANISM: Homo sapiens

<400> SEQUENCE: 1067

Val Phe Pro Lys Glu Ser Asp Thr Ser
1               5

<210> SEQ ID NO 1068
<211> LENGTH: 11
<212> TYPE: PRT
<213> ORGANISM: Homo sapiens

<400> SEQUENCE: 1068

Val Phe Pro Lys Glu Ser Asp Thr Ser Tyr Val
1               5                   10

<210> SEQ ID NO 1069
<211> LENGTH: 12
<212> TYPE: PRT
<213> ORGANISM: Homo sapiens

<400> SEQUENCE: 1069

Val Phe Pro Lys Glu Ser Asp Thr Ser Tyr Val Ser
1               5                   10

<210> SEQ ID NO 1070
<211> LENGTH: 13
<212> TYPE: PRT
<213> ORGANISM: Homo sapiens

<400> SEQUENCE: 1070

Val Phe Pro Lys Glu Ser Asp Thr Ser Tyr Val Ser Leu
1               5                   10

<210> SEQ ID NO 1071
<211> LENGTH: 11
<212> TYPE: PRT
<213> ORGANISM: Homo sapiens

<400> SEQUENCE: 1071

Phe Pro Lys Glu Ser Asp Thr Ser Tyr Val Ser
1               5                   10

```
<210> SEQ ID NO 1072
<211> LENGTH: 17
<212> TYPE: PRT
<213> ORGANISM: Homo sapiens

<400> SEQUENCE: 1072

Lys Glu Ser Asp Thr Ser Tyr Val Ser Leu Lys Ala Pro Leu Thr Lys
1               5                   10                  15
Pro

<210> SEQ ID NO 1073
<211> LENGTH: 15
<212> TYPE: PRT
<213> ORGANISM: Homo sapiens

<400> SEQUENCE: 1073

Ser Asp Thr Ser Tyr Val Ser Leu Lys Ala Pro Leu Thr Lys Pro
1               5                   10                  15

<210> SEQ ID NO 1074
<211> LENGTH: 9
<212> TYPE: PRT
<213> ORGANISM: Homo sapiens

<400> SEQUENCE: 1074

Ser Leu Lys Ala Pro Leu Thr Lys Pro
1               5

<210> SEQ ID NO 1075
<211> LENGTH: 11
<212> TYPE: PRT
<213> ORGANISM: Homo sapiens

<400> SEQUENCE: 1075

Ser Leu Lys Ala Pro Leu Thr Lys Pro Leu Lys
1               5                   10

<210> SEQ ID NO 1076
<211> LENGTH: 10
<212> TYPE: PRT
<213> ORGANISM: Homo sapiens

<400> SEQUENCE: 1076

Leu Lys Ala Pro Leu Thr Lys Pro Leu Lys
1               5                   10

<210> SEQ ID NO 1077
<211> LENGTH: 12
<212> TYPE: PRT
<213> ORGANISM: Homo sapiens

<400> SEQUENCE: 1077

Phe Tyr Thr Glu Leu Ser Ser Thr Arg Gly Tyr Ser
1               5                   10

<210> SEQ ID NO 1078
<211> LENGTH: 8
<212> TYPE: PRT
<213> ORGANISM: Homo sapiens

<400> SEQUENCE: 1078

Leu Ser Ser Thr Arg Gly Tyr Ser
1               5
```

```
<210> SEQ ID NO 1079
<211> LENGTH: 7
<212> TYPE: PRT
<213> ORGANISM: Homo sapiens

<400> SEQUENCE: 1079

Ser Ser Thr Arg Gly Tyr Ser
1               5

<210> SEQ ID NO 1080
<211> LENGTH: 6
<212> TYPE: PRT
<213> ORGANISM: Homo sapiens

<400> SEQUENCE: 1080

Ser Thr Arg Gly Tyr Ser
1               5

<210> SEQ ID NO 1081
<211> LENGTH: 9
<212> TYPE: PRT
<213> ORGANISM: Homo sapiens

<400> SEQUENCE: 1081

Ile Phe Ser Tyr Ala Thr Lys Arg Gln
1               5

<210> SEQ ID NO 1082
<211> LENGTH: 15
<212> TYPE: PRT
<213> ORGANISM: Homo sapiens

<400> SEQUENCE: 1082

Ile Phe Ser Tyr Ala Thr Lys Arg Gln Asp Asn Glu Ile Leu Ile
1               5                   10                  15

<210> SEQ ID NO 1083
<211> LENGTH: 13
<212> TYPE: PRT
<213> ORGANISM: Homo sapiens

<400> SEQUENCE: 1083

Ser Tyr Ala Thr Lys Arg Gln Asp Asn Glu Ile Leu Ile
1               5                   10

<210> SEQ ID NO 1084
<211> LENGTH: 11
<212> TYPE: PRT
<213> ORGANISM: Homo sapiens

<400> SEQUENCE: 1084

Tyr Ala Thr Lys Arg Gln Asp Asn Glu Ile Leu
1               5                   10

<210> SEQ ID NO 1085
<211> LENGTH: 12
<212> TYPE: PRT
<213> ORGANISM: Homo sapiens

<400> SEQUENCE: 1085

Tyr Ala Thr Lys Arg Gln Asp Asn Glu Ile Leu Ile
1               5                   10

<210> SEQ ID NO 1086
<211> LENGTH: 13
```

```
<212> TYPE: PRT
<213> ORGANISM: Homo sapiens

<400> SEQUENCE: 1086

Tyr Ala Thr Lys Arg Gln Asp Asn Glu Ile Leu Ile Phe
1               5                   10

<210> SEQ ID NO 1087
<211> LENGTH: 10
<212> TYPE: PRT
<213> ORGANISM: Homo sapiens

<400> SEQUENCE: 1087

Thr Lys Arg Gln Asp Asn Glu Ile Leu Ile
1               5                   10

<210> SEQ ID NO 1088
<211> LENGTH: 11
<212> TYPE: PRT
<213> ORGANISM: Homo sapiens

<400> SEQUENCE: 1088

Thr Lys Arg Gln Asp Asn Glu Ile Leu Ile Phe
1               5                   10

<210> SEQ ID NO 1089
<211> LENGTH: 16
<212> TYPE: PRT
<213> ORGANISM: Homo sapiens

<400> SEQUENCE: 1089

Thr Lys Arg Gln Asp Asn Glu Ile Leu Ile Phe Trp Ser Lys Asp Ile
1               5                   10                  15

<210> SEQ ID NO 1090
<211> LENGTH: 9
<212> TYPE: PRT
<213> ORGANISM: Homo sapiens

<400> SEQUENCE: 1090

Lys Arg Gln Asp Asn Glu Ile Leu Ile
1               5

<210> SEQ ID NO 1091
<211> LENGTH: 10
<212> TYPE: PRT
<213> ORGANISM: Homo sapiens

<400> SEQUENCE: 1091

Lys Arg Gln Asp Asn Glu Ile Leu Ile Phe
1               5                   10

<210> SEQ ID NO 1092
<211> LENGTH: 8
<212> TYPE: PRT
<213> ORGANISM: Homo sapiens

<400> SEQUENCE: 1092

Trp Ser Lys Asp Ile Gly Tyr Ser
1               5

<210> SEQ ID NO 1093
<211> LENGTH: 7
<212> TYPE: PRT
<213> ORGANISM: Homo sapiens
```

```
<400> SEQUENCE: 1093

Ser Lys Asp Ile Gly Tyr Ser
1               5

<210> SEQ ID NO 1094
<211> LENGTH: 12
<212> TYPE: PRT
<213> ORGANISM: Homo sapiens

<400> SEQUENCE: 1094

Ile Val Glu Phe Trp Val Asp Gly Lys Pro Arg Val
1               5                   10

<210> SEQ ID NO 1095
<211> LENGTH: 9
<212> TYPE: PRT
<213> ORGANISM: Homo sapiens

<400> SEQUENCE: 1095

Glu Phe Trp Val Asp Gly Lys Pro Arg
1               5

<210> SEQ ID NO 1096
<211> LENGTH: 8
<212> TYPE: PRT
<213> ORGANISM: Homo sapiens

<400> SEQUENCE: 1096

Trp Val Asp Gly Lys Pro Arg Val
1               5

<210> SEQ ID NO 1097
<211> LENGTH: 7
<212> TYPE: PRT
<213> ORGANISM: Homo sapiens

<400> SEQUENCE: 1097

Val Asp Gly Lys Pro Arg Val
1               5

<210> SEQ ID NO 1098
<211> LENGTH: 11
<212> TYPE: PRT
<213> ORGANISM: Homo sapiens

<400> SEQUENCE: 1098

Ser Leu Lys Lys Gly Tyr Thr Val Gly Ala Glu
1               5                   10

<210> SEQ ID NO 1099
<211> LENGTH: 12
<212> TYPE: PRT
<213> ORGANISM: Homo sapiens

<400> SEQUENCE: 1099

Ser Leu Lys Lys Gly Tyr Thr Val Gly Ala Glu Ala
1               5                   10

<210> SEQ ID NO 1100
<211> LENGTH: 13
<212> TYPE: PRT
<213> ORGANISM: Homo sapiens

<400> SEQUENCE: 1100
```

-continued

```
Ser Leu Lys Lys Gly Tyr Thr Val Gly Ala Glu Ala Ser
1               5                   10

<210> SEQ ID NO 1101
<211> LENGTH: 7
<212> TYPE: PRT
<213> ORGANISM: Homo sapiens

<400> SEQUENCE: 1101

Leu Lys Lys Gly Tyr Thr Val
1               5

<210> SEQ ID NO 1102
<211> LENGTH: 8
<212> TYPE: PRT
<213> ORGANISM: Homo sapiens

<400> SEQUENCE: 1102

Leu Lys Lys Gly Tyr Thr Val Gly
1               5

<210> SEQ ID NO 1103
<211> LENGTH: 9
<212> TYPE: PRT
<213> ORGANISM: Homo sapiens

<400> SEQUENCE: 1103

Leu Lys Lys Gly Tyr Thr Val Gly Ala
1               5

<210> SEQ ID NO 1104
<211> LENGTH: 10
<212> TYPE: PRT
<213> ORGANISM: Homo sapiens

<400> SEQUENCE: 1104

Leu Lys Lys Gly Tyr Thr Val Gly Ala Glu
1               5                   10

<210> SEQ ID NO 1105
<211> LENGTH: 11
<212> TYPE: PRT
<213> ORGANISM: Homo sapiens

<400> SEQUENCE: 1105

Leu Lys Lys Gly Tyr Thr Val Gly Ala Glu Ala
1               5                   10

<210> SEQ ID NO 1106
<211> LENGTH: 12
<212> TYPE: PRT
<213> ORGANISM: Homo sapiens

<400> SEQUENCE: 1106

Leu Lys Lys Gly Tyr Thr Val Gly Ala Glu Ala Ser
1               5                   10

<210> SEQ ID NO 1107
<211> LENGTH: 13
<212> TYPE: PRT
<213> ORGANISM: Homo sapiens

<400> SEQUENCE: 1107

Leu Lys Lys Gly Tyr Thr Val Gly Ala Glu Ala Ser Ile
```

```
1               5                    10

<210> SEQ ID NO 1108
<211> LENGTH: 14
<212> TYPE: PRT
<213> ORGANISM: Homo sapiens

<400> SEQUENCE: 1108

Ser Ile Ile Leu Gly Gln Glu Gln Asp Ser Phe Gly Gly Asn
1               5                   10

<210> SEQ ID NO 1109
<211> LENGTH: 19
<212> TYPE: PRT
<213> ORGANISM: Homo sapiens

<400> SEQUENCE: 1109

Ser Ile Ile Leu Gly Gln Glu Gln Asp Ser Phe Gly Gly Asn Phe Glu
1               5                   10                  15

Gly Ser Gln

<210> SEQ ID NO 1110
<211> LENGTH: 20
<212> TYPE: PRT
<213> ORGANISM: Homo sapiens

<400> SEQUENCE: 1110

Ser Ile Ile Leu Gly Gln Glu Gln Asp Ser Phe Gly Gly Asn Phe Glu
1               5                   10                  15

Gly Ser Gln Ser
            20

<210> SEQ ID NO 1111
<211> LENGTH: 17
<212> TYPE: PRT
<213> ORGANISM: Homo sapiens

<400> SEQUENCE: 1111

Ile Ile Leu Gly Gln Glu Gln Asp Ser Phe Gly Gly Asn Phe Glu Gly
1               5                   10                  15

Ser

<210> SEQ ID NO 1112
<211> LENGTH: 19
<212> TYPE: PRT
<213> ORGANISM: Homo sapiens

<400> SEQUENCE: 1112

Ile Ile Leu Gly Gln Glu Gln Asp Ser Phe Gly Gly Asn Phe Glu Gly
1               5                   10                  15

Ser Gln Ser

<210> SEQ ID NO 1113
<211> LENGTH: 12
<212> TYPE: PRT
<213> ORGANISM: Homo sapiens

<400> SEQUENCE: 1113

Ile Leu Gly Gln Glu Gln Asp Ser Phe Gly Gly Asn
1               5                   10

<210> SEQ ID NO 1114
```

```
<211> LENGTH: 17
<212> TYPE: PRT
<213> ORGANISM: Homo sapiens

<400> SEQUENCE: 1114

Ile Leu Gly Gln Glu Gln Asp Ser Phe Gly Gly Asn Phe Glu Gly Ser
1               5                   10                  15

Gln

<210> SEQ ID NO 1115
<211> LENGTH: 18
<212> TYPE: PRT
<213> ORGANISM: Homo sapiens

<400> SEQUENCE: 1115

Ile Leu Gly Gln Glu Gln Asp Ser Phe Gly Gly Asn Phe Glu Gly Ser
1               5                   10                  15

Gln Ser

<210> SEQ ID NO 1116
<211> LENGTH: 16
<212> TYPE: PRT
<213> ORGANISM: Homo sapiens

<400> SEQUENCE: 1116

Leu Gly Gln Glu Gln Asp Ser Phe Gly Gly Asn Phe Glu Gly Ser Gln
1               5                   10                  15

<210> SEQ ID NO 1117
<211> LENGTH: 17
<212> TYPE: PRT
<213> ORGANISM: Homo sapiens

<400> SEQUENCE: 1117

Leu Gly Gln Glu Gln Asp Ser Phe Gly Gly Asn Phe Glu Gly Ser Gln
1               5                   10                  15

Ser

<210> SEQ ID NO 1118
<211> LENGTH: 16
<212> TYPE: PRT
<213> ORGANISM: Homo sapiens

<400> SEQUENCE: 1118

Gly Gln Glu Gln Asp Ser Phe Gly Gly Asn Phe Glu Gly Ser Gln Ser
1               5                   10                  15

<210> SEQ ID NO 1119
<211> LENGTH: 11
<212> TYPE: PRT
<213> ORGANISM: Homo sapiens

<400> SEQUENCE: 1119

Ser Phe Gly Gly Asn Phe Glu Gly Ser Gln Ser
1               5                   10

<210> SEQ ID NO 1120
<211> LENGTH: 11
<212> TYPE: PRT
<213> ORGANISM: Homo sapiens

<400> SEQUENCE: 1120

Gln Ser Leu Val Gly Asp Ile Gly Asn Val Asn
```

```
1               5               10

<210> SEQ ID NO 1121
<211> LENGTH: 14
<212> TYPE: PRT
<213> ORGANISM: Homo sapiens

<400> SEQUENCE: 1121

Ile Asn Thr Ile Tyr Leu Gly Gly Pro Phe Ser Pro Asn Val
1               5                   10

<210> SEQ ID NO 1122
<211> LENGTH: 16
<212> TYPE: PRT
<213> ORGANISM: Homo sapiens

<400> SEQUENCE: 1122

Ile Asn Thr Ile Tyr Leu Gly Gly Pro Phe Ser Pro Asn Val Leu Asn
1               5                   10                  15

<210> SEQ ID NO 1123
<211> LENGTH: 13
<212> TYPE: PRT
<213> ORGANISM: Homo sapiens

<400> SEQUENCE: 1123

Ile Tyr Leu Gly Gly Pro Phe Ser Pro Asn Val Leu Asn
1               5                   10

<210> SEQ ID NO 1124
<211> LENGTH: 12
<212> TYPE: PRT
<213> ORGANISM: Homo sapiens

<400> SEQUENCE: 1124

Tyr Leu Gly Gly Pro Phe Ser Pro Asn Val Leu Asn
1               5                   10

<210> SEQ ID NO 1125
<211> LENGTH: 8
<212> TYPE: PRT
<213> ORGANISM: Homo sapiens

<400> SEQUENCE: 1125

Leu Gly Gly Pro Phe Ser Pro Asn
1               5

<210> SEQ ID NO 1126
<211> LENGTH: 26
<212> TYPE: PRT
<213> ORGANISM: Homo sapiens

<400> SEQUENCE: 1126

Ser Pro Asn Val Leu Asn Trp Arg Ala Leu Lys Tyr Glu Val Gln Gly
1               5                   10                  15

Glu Val Phe Thr Lys Pro Gln Leu Trp Pro
            20                  25

<210> SEQ ID NO 1127
<211> LENGTH: 5
<212> TYPE: PRT
<213> ORGANISM: Homo sapiens

<400> SEQUENCE: 1127
```

```
Leu Asn Trp Arg Ala
1               5

<210> SEQ ID NO 1128
<211> LENGTH: 6
<212> TYPE: PRT
<213> ORGANISM: Homo sapiens

<400> SEQUENCE: 1128

Leu Asn Trp Arg Ala Leu
1               5

<210> SEQ ID NO 1129
<211> LENGTH: 7
<212> TYPE: PRT
<213> ORGANISM: Homo sapiens

<400> SEQUENCE: 1129

Leu Asn Trp Arg Ala Leu Lys
1               5

<210> SEQ ID NO 1130
<211> LENGTH: 7
<212> TYPE: PRT
<213> ORGANISM: Homo sapiens

<400> SEQUENCE: 1130

Trp Arg Ala Leu Lys Tyr Glu
1               5

<210> SEQ ID NO 1131
<211> LENGTH: 8
<212> TYPE: PRT
<213> ORGANISM: Homo sapiens

<400> SEQUENCE: 1131

Trp Arg Ala Leu Lys Tyr Glu Val
1               5

<210> SEQ ID NO 1132
<211> LENGTH: 11
<212> TYPE: PRT
<213> ORGANISM: Homo sapiens

<400> SEQUENCE: 1132

Trp Arg Ala Leu Lys Tyr Glu Val Gln Gly Glu
1               5                   10

<210> SEQ ID NO 1133
<211> LENGTH: 6
<212> TYPE: PRT
<213> ORGANISM: Homo sapiens

<400> SEQUENCE: 1133

Ala Leu Lys Tyr Glu Val
1               5

<210> SEQ ID NO 1134
<211> LENGTH: 6
<212> TYPE: PRT
<213> ORGANISM: Homo sapiens

<400> SEQUENCE: 1134

Leu Lys Tyr Glu Val Gln
1               5
```

```
<210> SEQ ID NO 1135
<211> LENGTH: 7
<212> TYPE: PRT
<213> ORGANISM: Homo sapiens

<400> SEQUENCE: 1135

Leu Lys Tyr Glu Val Gln Gly
1               5

<210> SEQ ID NO 1136
<211> LENGTH: 8
<212> TYPE: PRT
<213> ORGANISM: Homo sapiens

<400> SEQUENCE: 1136

Leu Lys Tyr Glu Val Gln Gly Glu
1               5

<210> SEQ ID NO 1137
<211> LENGTH: 13
<212> TYPE: PRT
<213> ORGANISM: Homo sapiens

<400> SEQUENCE: 1137

Leu Lys Tyr Glu Val Gln Gly Glu Val Phe Thr Lys Pro
1               5                   10

<210> SEQ ID NO 1138
<211> LENGTH: 14
<212> TYPE: PRT
<213> ORGANISM: Homo sapiens

<400> SEQUENCE: 1138

Leu Lys Tyr Glu Val Gln Gly Glu Val Phe Thr Lys Pro Gln
1               5                   10

<210> SEQ ID NO 1139
<211> LENGTH: 17
<212> TYPE: PRT
<213> ORGANISM: Homo sapiens

<400> SEQUENCE: 1139

Leu Lys Tyr Glu Val Gln Gly Glu Val Phe Thr Lys Pro Gln Leu Trp
1               5                   10                  15

Pro

<210> SEQ ID NO 1140
<211> LENGTH: 7
<212> TYPE: PRT
<213> ORGANISM: Homo sapiens

<400> SEQUENCE: 1140

Lys Tyr Glu Val Gln Gly Glu
1               5

<210> SEQ ID NO 1141
<211> LENGTH: 13
<212> TYPE: PRT
<213> ORGANISM: Homo sapiens

<400> SEQUENCE: 1141

Lys Tyr Glu Val Gln Gly Glu Val Phe Thr Lys Pro Gln
1               5                   10
```

```
<210> SEQ ID NO 1142
<211> LENGTH: 16
<212> TYPE: PRT
<213> ORGANISM: Homo sapiens

<400> SEQUENCE: 1142

Lys Tyr Glu Val Gln Gly Glu Val Phe Thr Lys Pro Gln Leu Trp Pro
1               5                   10                  15

<210> SEQ ID NO 1143
<211> LENGTH: 11
<212> TYPE: PRT
<213> ORGANISM: Homo sapiens

<400> SEQUENCE: 1143

Tyr Glu Val Gln Gly Glu Val Phe Thr Lys Pro
1               5                   10

<210> SEQ ID NO 1144
<211> LENGTH: 12
<212> TYPE: PRT
<213> ORGANISM: Homo sapiens

<400> SEQUENCE: 1144

Tyr Glu Val Gln Gly Glu Val Phe Thr Lys Pro Gln
1               5                   10

<210> SEQ ID NO 1145
<211> LENGTH: 15
<212> TYPE: PRT
<213> ORGANISM: Homo sapiens

<400> SEQUENCE: 1145

Tyr Glu Val Gln Gly Glu Val Phe Thr Lys Pro Gln Leu Trp Pro
1               5                   10                  15

<210> SEQ ID NO 1146
<211> LENGTH: 10
<212> TYPE: PRT
<213> ORGANISM: Homo sapiens

<400> SEQUENCE: 1146

Val Gln Gly Glu Val Phe Thr Lys Pro Gln
1               5                   10

<210> SEQ ID NO 1147
<211> LENGTH: 13
<212> TYPE: PRT
<213> ORGANISM: Homo sapiens

<400> SEQUENCE: 1147

Val Gln Gly Glu Val Phe Thr Lys Pro Gln Leu Trp Pro
1               5                   10

<210> SEQ ID NO 1148
<211> LENGTH: 9
<212> TYPE: PRT
<213> ORGANISM: Homo sapiens

<400> SEQUENCE: 1148

Gln Gly Glu Val Phe Thr Lys Pro Gln
1               5
```

```
<210> SEQ ID NO 1149
<211> LENGTH: 7
<212> TYPE: PRT
<213> ORGANISM: Homo sapiens

<400> SEQUENCE: 1149

Gly Glu Val Phe Thr Lys Pro
1               5

<210> SEQ ID NO 1150
<211> LENGTH: 8
<212> TYPE: PRT
<213> ORGANISM: Homo sapiens

<400> SEQUENCE: 1150

Gly Glu Val Phe Thr Lys Pro Gln
1               5

<210> SEQ ID NO 1151
<211> LENGTH: 7
<212> TYPE: PRT
<213> ORGANISM: Homo sapiens

<400> SEQUENCE: 1151

Glu Val Phe Thr Lys Pro Gln
1               5

<210> SEQ ID NO 1152
<211> LENGTH: 10
<212> TYPE: PRT
<213> ORGANISM: Homo sapiens

<400> SEQUENCE: 1152

Glu Val Phe Thr Lys Pro Gln Leu Trp Pro
1               5                   10

<210> SEQ ID NO 1153
<211> LENGTH: 6
<212> TYPE: PRT
<213> ORGANISM: Homo sapiens

<400> SEQUENCE: 1153

Val Phe Thr Lys Pro Gln
1               5

<210> SEQ ID NO 1154
<211> LENGTH: 5
<212> TYPE: PRT
<213> ORGANISM: Homo sapiens

<400> SEQUENCE: 1154

Phe Thr Lys Pro Gln
1               5

<210> SEQ ID NO 1155
<211> LENGTH: 8
<212> TYPE: PRT
<213> ORGANISM: Homo sapiens

<400> SEQUENCE: 1155

Phe Thr Lys Pro Gln Leu Trp Pro
1               5

<210> SEQ ID NO 1156
<211> LENGTH: 7
```

<212> TYPE: PRT
<213> ORGANISM: Homo sapiens

<400> SEQUENCE: 1156

Thr Lys Pro Gln Leu Trp Pro
1               5

<210> SEQ ID NO 1157
<211> LENGTH: 6
<212> TYPE: PRT
<213> ORGANISM: Homo sapiens

<400> SEQUENCE: 1157

Lys Pro Gln Leu Trp Pro
1               5

<210> SEQ ID NO 1158
<211> LENGTH: 9
<212> TYPE: PRT
<213> ORGANISM: Homo sapiens

<400> SEQUENCE: 1158

Met Ser Arg Lys Ala Phe Val Phe Pro
1               5

<210> SEQ ID NO 1159
<211> LENGTH: 11
<212> TYPE: PRT
<213> ORGANISM: Homo sapiens

<400> SEQUENCE: 1159

Met Ser Arg Lys Ala Phe Val Phe Pro Lys Glu
1               5                   10

<210> SEQ ID NO 1160
<211> LENGTH: 13
<212> TYPE: PRT
<213> ORGANISM: Homo sapiens

<400> SEQUENCE: 1160

Met Ser Arg Lys Ala Phe Val Phe Pro Lys Glu Ser Asp
1               5                   10

<210> SEQ ID NO 1161
<211> LENGTH: 18
<212> TYPE: PRT
<213> ORGANISM: Homo sapiens

<400> SEQUENCE: 1161

Met Ser Arg Lys Ala Phe Val Phe Pro Lys Glu Ser Asp Thr Ser Tyr
1               5                   10                  15

Val Ser

<210> SEQ ID NO 1162
<211> LENGTH: 8
<212> TYPE: PRT
<213> ORGANISM: Homo sapiens

<400> SEQUENCE: 1162

Ser Arg Lys Ala Phe Val Phe Pro
1               5

<210> SEQ ID NO 1163
<211> LENGTH: 12

```
<212> TYPE: PRT
<213> ORGANISM: Homo sapiens

<400> SEQUENCE: 1163

Ser Arg Lys Ala Phe Val Phe Pro Lys Glu Ser Asp
1               5                   10

<210> SEQ ID NO 1164
<211> LENGTH: 14
<212> TYPE: PRT
<213> ORGANISM: Homo sapiens

<400> SEQUENCE: 1164

Ser Arg Lys Ala Phe Val Phe Pro Lys Glu Ser Asp Thr Ser
1               5                   10

<210> SEQ ID NO 1165
<211> LENGTH: 7
<212> TYPE: PRT
<213> ORGANISM: Homo sapiens

<400> SEQUENCE: 1165

Arg Lys Ala Phe Val Phe Pro
1               5

<210> SEQ ID NO 1166
<211> LENGTH: 11
<212> TYPE: PRT
<213> ORGANISM: Homo sapiens

<400> SEQUENCE: 1166

Arg Lys Ala Phe Val Phe Pro Lys Glu Ser Asp
1               5                   10

<210> SEQ ID NO 1167
<211> LENGTH: 6
<212> TYPE: PRT
<213> ORGANISM: Homo sapiens

<400> SEQUENCE: 1167

Lys Ala Phe Val Phe Pro
1               5

<210> SEQ ID NO 1168
<211> LENGTH: 11
<212> TYPE: PRT
<213> ORGANISM: Homo sapiens

<400> SEQUENCE: 1168

Ala Phe Val Phe Pro Lys Glu Ser Asp Thr Ser
1               5                   10

<210> SEQ ID NO 1169
<211> LENGTH: 7
<212> TYPE: PRT
<213> ORGANISM: Homo sapiens

<400> SEQUENCE: 1169

Val Phe Pro Lys Glu Ser Asp
1               5

<210> SEQ ID NO 1170
<211> LENGTH: 7
<212> TYPE: PRT
<213> ORGANISM: Homo sapiens
```

<400> SEQUENCE: 1170

Lys Glu Ser Asp Thr Ser Tyr
1               5

<210> SEQ ID NO 1171
<211> LENGTH: 9
<212> TYPE: PRT
<213> ORGANISM: Homo sapiens

<400> SEQUENCE: 1171

Lys Glu Ser Asp Thr Ser Tyr Val Ser
1               5

<210> SEQ ID NO 1172
<211> LENGTH: 6
<212> TYPE: PRT
<213> ORGANISM: Homo sapiens

<400> SEQUENCE: 1172

Val Ser Leu Lys Ala Pro
1               5

<210> SEQ ID NO 1173
<211> LENGTH: 6
<212> TYPE: PRT
<213> ORGANISM: Homo sapiens

<400> SEQUENCE: 1173

Leu Lys Ala Pro Leu Thr
1               5

<210> SEQ ID NO 1174
<211> LENGTH: 8
<212> TYPE: PRT
<213> ORGANISM: Homo sapiens

<400> SEQUENCE: 1174

Leu Lys Ala Pro Leu Thr Lys Pro
1               5

<210> SEQ ID NO 1175
<211> LENGTH: 11
<212> TYPE: PRT
<213> ORGANISM: Homo sapiens

<400> SEQUENCE: 1175

Tyr Thr Glu Leu Ser Ser Thr Arg Gly Tyr Ser
1               5                   10

<210> SEQ ID NO 1176
<211> LENGTH: 9
<212> TYPE: PRT
<213> ORGANISM: Homo sapiens

<400> SEQUENCE: 1176

Tyr Ala Thr Lys Arg Gln Asp Asn Glu
1               5

<210> SEQ ID NO 1177
<211> LENGTH: 10
<212> TYPE: PRT
<213> ORGANISM: Homo sapiens

<400> SEQUENCE: 1177

Tyr Ala Thr Lys Arg Gln Asp Asn Glu Ile
1               5                   10

<210> SEQ ID NO 1178
<211> LENGTH: 9
<212> TYPE: PRT
<213> ORGANISM: Homo sapiens

<400> SEQUENCE: 1178

Thr Lys Arg Gln Asp Asn Glu Ile Leu
1               5

<210> SEQ ID NO 1179
<211> LENGTH: 8
<212> TYPE: PRT
<213> ORGANISM: Homo sapiens

<400> SEQUENCE: 1179

Lys Arg Gln Asp Asn Glu Ile Leu
1               5

<210> SEQ ID NO 1180
<211> LENGTH: 8
<212> TYPE: PRT
<213> ORGANISM: Homo sapiens

<400> SEQUENCE: 1180

Ile Leu Ile Phe Trp Ser Lys Asp
1               5

<210> SEQ ID NO 1181
<211> LENGTH: 6
<212> TYPE: PRT
<213> ORGANISM: Homo sapiens

<400> SEQUENCE: 1181

Ile Phe Trp Ser Lys Asp
1               5

<210> SEQ ID NO 1182
<211> LENGTH: 9
<212> TYPE: PRT
<213> ORGANISM: Homo sapiens

<400> SEQUENCE: 1182

Trp Val Asp Gly Lys Pro Arg Val Arg
1               5

<210> SEQ ID NO 1183
<211> LENGTH: 16
<212> TYPE: PRT
<213> ORGANISM: Homo sapiens

<400> SEQUENCE: 1183

Val Arg Lys Ser Leu Lys Lys Gly Tyr Thr Val Gly Ala Glu Ala Ser
1               5                   10                  15

<210> SEQ ID NO 1184
<211> LENGTH: 7
<212> TYPE: PRT
<213> ORGANISM: Homo sapiens

<400> SEQUENCE: 1184

Ser Leu Lys Lys Gly Tyr Thr
1               5

<210> SEQ ID NO 1185
<211> LENGTH: 9
<212> TYPE: PRT
<213> ORGANISM: Homo sapiens

<400> SEQUENCE: 1185

Ser Leu Lys Lys Gly Tyr Thr Val Gly
1               5

<210> SEQ ID NO 1186
<211> LENGTH: 10
<212> TYPE: PRT
<213> ORGANISM: Homo sapiens

<400> SEQUENCE: 1186

Ser Leu Lys Lys Gly Tyr Thr Val Gly Ala
1               5                   10

<210> SEQ ID NO 1187
<211> LENGTH: 14
<212> TYPE: PRT
<213> ORGANISM: Homo sapiens

<400> SEQUENCE: 1187

Ser Leu Lys Lys Gly Tyr Thr Val Gly Ala Glu Ala Ser Ile
1               5                   10

<210> SEQ ID NO 1188
<211> LENGTH: 11
<212> TYPE: PRT
<213> ORGANISM: Homo sapiens

<400> SEQUENCE: 1188

Lys Lys Gly Tyr Thr Val Gly Ala Glu Ala Ser
1               5                   10

<210> SEQ ID NO 1189
<211> LENGTH: 10
<212> TYPE: PRT
<213> ORGANISM: Homo sapiens

<400> SEQUENCE: 1189

Lys Gly Tyr Thr Val Gly Ala Glu Ala Ser
1               5                   10

<210> SEQ ID NO 1190
<211> LENGTH: 11
<212> TYPE: PRT
<213> ORGANISM: Homo sapiens

<400> SEQUENCE: 1190

Lys Gly Tyr Thr Val Gly Ala Glu Ala Ser Ile
1               5                   10

<210> SEQ ID NO 1191
<211> LENGTH: 8
<212> TYPE: PRT
<213> ORGANISM: Homo sapiens

<400> SEQUENCE: 1191

Ile Ile Leu Gly Gln Glu Gln Asp
1               5

```
<210> SEQ ID NO 1192
<211> LENGTH: 13
<212> TYPE: PRT
<213> ORGANISM: Homo sapiens

<400> SEQUENCE: 1192

Ile Ile Leu Gly Gln Glu Gln Asp Ser Phe Gly Gly Asn
1               5                   10

<210> SEQ ID NO 1193
<211> LENGTH: 12
<212> TYPE: PRT
<213> ORGANISM: Homo sapiens

<400> SEQUENCE: 1193

Leu Val Gly Asp Ile Gly Asn Val Asn Met Trp Asp
1               5                   10

<210> SEQ ID NO 1194
<211> LENGTH: 10
<212> TYPE: PRT
<213> ORGANISM: Homo sapiens

<400> SEQUENCE: 1194

Ile Tyr Leu Gly Gly Pro Phe Ser Pro Asn
1               5                   10

<210> SEQ ID NO 1195
<211> LENGTH: 13
<212> TYPE: PRT
<213> ORGANISM: Homo sapiens

<400> SEQUENCE: 1195

Ile Tyr Leu Gly Gly Pro Phe Ser Pro Asn Val Leu Asn
1               5                   10

<210> SEQ ID NO 1196
<211> LENGTH: 11
<212> TYPE: PRT
<213> ORGANISM: Homo sapiens

<400> SEQUENCE: 1196

Leu Gly Gly Pro Phe Ser Pro Asn Val Leu Asn
1               5                   10

<210> SEQ ID NO 1197
<211> LENGTH: 10
<212> TYPE: PRT
<213> ORGANISM: Homo sapiens

<400> SEQUENCE: 1197

Glu Val Gln Gly Glu Val Phe Thr Lys Pro
1               5                   10

<210> SEQ ID NO 1198
<211> LENGTH: 14
<212> TYPE: PRT
<213> ORGANISM: Homo sapiens

<400> SEQUENCE: 1198

Glu Val Gln Gly Glu Val Phe Thr Lys Pro Gln Leu Trp Pro
1               5                   10

<210> SEQ ID NO 1199
```

```
<211> LENGTH: 9
<212> TYPE: PRT
<213> ORGANISM: Homo sapiens

<400> SEQUENCE: 1199

Val Gln Gly Glu Val Phe Thr Lys Pro
1               5

<210> SEQ ID NO 1200
<211> LENGTH: 11
<212> TYPE: PRT
<213> ORGANISM: Homo sapiens

<400> SEQUENCE: 1200

Gly Glu Val Phe Thr Lys Pro Gln Leu Trp Pro
1               5                   10

<210> SEQ ID NO 1201
<211> LENGTH: 6
<212> TYPE: PRT
<213> ORGANISM: Homo sapiens

<400> SEQUENCE: 1201

Glu Val Phe Thr Lys Pro
1               5

<210> SEQ ID NO 1202
<211> LENGTH: 7
<212> TYPE: PRT
<213> ORGANISM: Homo sapiens

<400> SEQUENCE: 1202

Val Phe Thr Lys Pro Gln Leu
1               5

<210> SEQ ID NO 1203
<211> LENGTH: 9
<212> TYPE: PRT
<213> ORGANISM: Homo sapiens

<400> SEQUENCE: 1203

Val Phe Thr Lys Pro Gln Leu Trp Pro
1               5

<210> SEQ ID NO 1204
<211> LENGTH: 7
<212> TYPE: PRT
<213> ORGANISM: Homo sapiens

<400> SEQUENCE: 1204

Lys Ala Phe Val Phe Pro Lys
1               5

<210> SEQ ID NO 1205
<211> LENGTH: 6
<212> TYPE: PRT
<213> ORGANISM: Homo sapiens

<400> SEQUENCE: 1205

Val Arg Lys Ser Leu Lys
1               5

<210> SEQ ID NO 1206
<211> LENGTH: 17
<212> TYPE: PRT
```

<210> SEQ ID NO 1206
<211> LENGTH: 16
<212> TYPE: PRT
<213> ORGANISM: Homo sapiens

<400> SEQUENCE: 1206

Met Ser Arg Lys Ala Phe Val Phe Pro Lys Glu Ser Asp Thr Ser Tyr
1               5                   10                  15
Val

<210> SEQ ID NO 1207
<211> LENGTH: 17
<212> TYPE: PRT
<213> ORGANISM: Homo sapiens

<400> SEQUENCE: 1207

Ser Arg Lys Ala Phe Val Phe Pro Lys Glu Ser Asp Thr Ser Tyr Val
1               5                   10                  15
Ser

<210> SEQ ID NO 1208
<211> LENGTH: 16
<212> TYPE: PRT
<213> ORGANISM: Homo sapiens

<400> SEQUENCE: 1208

Lys Ala Phe Val Phe Pro Lys Glu Ser Asp Thr Ser Tyr Val Ser Leu
1               5                   10                  15

<210> SEQ ID NO 1209
<211> LENGTH: 17
<212> TYPE: PRT
<213> ORGANISM: Homo sapiens

<400> SEQUENCE: 1209

Lys Ala Phe Val Phe Pro Lys Glu Ser Asp Thr Ser Tyr Val Ser Leu
1               5                   10                  15
Lys

<210> SEQ ID NO 1210
<211> LENGTH: 18
<212> TYPE: PRT
<213> ORGANISM: Homo sapiens

<400> SEQUENCE: 1210

Ala Phe Val Phe Pro Lys Glu Ser Asp Thr Ser Tyr Val Ser Leu Lys
1               5                   10                  15
Ala Pro

<210> SEQ ID NO 1211
<211> LENGTH: 15
<212> TYPE: PRT
<213> ORGANISM: Homo sapiens

<400> SEQUENCE: 1211

Phe Val Phe Pro Lys Glu Ser Asp Thr Ser Tyr Val Ser Leu Lys
1               5                   10                  15

<210> SEQ ID NO 1212
<211> LENGTH: 14
<212> TYPE: PRT
<213> ORGANISM: Homo sapiens

<400> SEQUENCE: 1212

Val Phe Pro Lys Glu Ser Asp Thr Ser Tyr Val Ser Leu Lys

```
1               5                   10
```

<210> SEQ ID NO 1213
<211> LENGTH: 13
<212> TYPE: PRT
<213> ORGANISM: Homo sapiens

<400> SEQUENCE: 1213

```
Lys Glu Ser Asp Thr Ser Tyr Val Ser Leu Lys Ala Pro
1               5                   10
```

<210> SEQ ID NO 1214
<211> LENGTH: 12
<212> TYPE: PRT
<213> ORGANISM: Homo sapiens

<400> SEQUENCE: 1214

```
Thr Lys Arg Gln Asp Asn Glu Ile Leu Ile Phe Trp
1               5                   10
```

<210> SEQ ID NO 1215
<211> LENGTH: 15
<212> TYPE: PRT
<213> ORGANISM: Homo sapiens

<400> SEQUENCE: 1215

```
Ile Val Glu Phe Trp Val Asp Gly Lys Pro Arg Val Arg Lys Ser
1               5                   10                  15
```

<210> SEQ ID NO 1216
<211> LENGTH: 14
<212> TYPE: PRT
<213> ORGANISM: Homo sapiens

<400> SEQUENCE: 1216

```
Leu Lys Lys Gly Tyr Thr Val Gly Ala Glu Ala Ser Ile Ile
1               5                   10
```

<210> SEQ ID NO 1217
<211> LENGTH: 15
<212> TYPE: PRT
<213> ORGANISM: Homo sapiens

<400> SEQUENCE: 1217

```
Gln Glu Gln Asp Ser Phe Gly Gly Asn Phe Glu Gly Ser Gln Ser
1               5                   10                  15
```

<210> SEQ ID NO 1218
<211> LENGTH: 10
<212> TYPE: PRT
<213> ORGANISM: Homo sapiens

<400> SEQUENCE: 1218

```
Phe Val Leu Ser Pro Asp Glu Ile Asn Thr
1               5                   10
```

<210> SEQ ID NO 1219
<211> LENGTH: 15
<212> TYPE: PRT
<213> ORGANISM: Homo sapiens

<400> SEQUENCE: 1219

```
Ser Lys Asp Ile Gly Tyr Ser Phe Thr Val Gly Gly Ser Glu Ile
1               5                   10                  15
```

<210> SEQ ID NO 1220
<211> LENGTH: 12
<212> TYPE: PRT
<213> ORGANISM: Homo sapiens

<400> SEQUENCE: 1220

Phe Gly Gln Thr Asp Met Ser Arg Lys Ala Phe Val
1               5                   10

<210> SEQ ID NO 1221
<211> LENGTH: 10
<212> TYPE: PRT
<213> ORGANISM: Homo sapiens

<400> SEQUENCE: 1221

Phe Pro Lys Glu Ser Asp Thr Ser Tyr Val
1               5                   10

<210> SEQ ID NO 1222
<211> LENGTH: 6
<212> TYPE: PRT
<213> ORGANISM: Homo sapiens

<400> SEQUENCE: 1222

Ser Leu Lys Ala Pro Leu
1               5

<210> SEQ ID NO 1223
<211> LENGTH: 12
<212> TYPE: PRT
<213> ORGANISM: Homo sapiens

<400> SEQUENCE: 1223

Ser Leu Lys Ala Pro Leu Thr Lys Pro Leu Lys Ala
1               5                   10

<210> SEQ ID NO 1224
<211> LENGTH: 9
<212> TYPE: PRT
<213> ORGANISM: Homo sapiens

<400> SEQUENCE: 1224

Arg Gly Tyr Ser Ile Phe Ser Tyr Ala
1               5

<210> SEQ ID NO 1225
<211> LENGTH: 14
<212> TYPE: PRT
<213> ORGANISM: Homo sapiens

<400> SEQUENCE: 1225

Phe Ser Tyr Ala Thr Lys Arg Gln Asp Asn Glu Ile Leu Ile
1               5                   10

<210> SEQ ID NO 1226
<211> LENGTH: 11
<212> TYPE: PRT
<213> ORGANISM: Homo sapiens

<400> SEQUENCE: 1226

Ala Thr Lys Arg Gln Asp Asn Glu Ile Leu Ile
1               5                   10

<210> SEQ ID NO 1227

```
<211> LENGTH: 9
<212> TYPE: PRT
<213> ORGANISM: Homo sapiens

<400> SEQUENCE: 1227

Phe Trp Ser Lys Asp Ile Gly Tyr Ser
1               5

<210> SEQ ID NO 1228
<211> LENGTH: 11
<212> TYPE: PRT
<213> ORGANISM: Homo sapiens

<400> SEQUENCE: 1228

Phe Trp Ser Lys Asp Ile Gly Tyr Ser Phe Thr
1               5                   10

<210> SEQ ID NO 1229
<211> LENGTH: 12
<212> TYPE: PRT
<213> ORGANISM: Homo sapiens

<400> SEQUENCE: 1229

Phe Trp Ser Lys Asp Ile Gly Tyr Ser Phe Thr Val
1               5                   10

<210> SEQ ID NO 1230
<211> LENGTH: 11
<212> TYPE: PRT
<213> ORGANISM: Homo sapiens

<400> SEQUENCE: 1230

Trp Ser Lys Asp Ile Gly Tyr Ser Phe Thr Val
1               5                   10

<210> SEQ ID NO 1231
<211> LENGTH: 13
<212> TYPE: PRT
<213> ORGANISM: Homo sapiens

<400> SEQUENCE: 1231

Lys Ser Leu Lys Lys Gly Tyr Thr Val Gly Ala Glu Ala
1               5                   10

<210> SEQ ID NO 1232
<211> LENGTH: 10
<212> TYPE: PRT
<213> ORGANISM: Homo sapiens

<400> SEQUENCE: 1232

Lys Lys Gly Tyr Thr Val Gly Ala Glu Ala
1               5                   10

<210> SEQ ID NO 1233
<211> LENGTH: 11
<212> TYPE: PRT
<213> ORGANISM: Homo sapiens

<400> SEQUENCE: 1233

Gly Ala Glu Ala Ser Ile Ile Leu Gly Gln Glu
1               5                   10

<210> SEQ ID NO 1234
<211> LENGTH: 13
<212> TYPE: PRT
```

```
<213> ORGANISM: Homo sapiens

<400> SEQUENCE: 1234

Gly Ala Glu Ala Ser Ile Ile Leu Gly Gln Glu Gln Asp
1               5                   10

<210> SEQ ID NO 1235
<211> LENGTH: 9
<212> TYPE: PRT
<213> ORGANISM: Homo sapiens

<400> SEQUENCE: 1235

Ser Ile Ile Leu Gly Gln Glu Gln Asp
1               5

<210> SEQ ID NO 1236
<211> LENGTH: 18
<212> TYPE: PRT
<213> ORGANISM: Homo sapiens

<400> SEQUENCE: 1236

Ile Ile Leu Gly Gln Glu Gln Asp Ser Phe Gly Gly Asn Phe Glu Gly
1               5                   10                  15

Ser Gln

<210> SEQ ID NO 1237
<211> LENGTH: 16
<212> TYPE: PRT
<213> ORGANISM: Homo sapiens

<400> SEQUENCE: 1237

Ile Leu Gly Gln Glu Gln Asp Ser Phe Gly Gly Asn Phe Glu Gly Ser
1               5                   10                  15

<210> SEQ ID NO 1238
<211> LENGTH: 11
<212> TYPE: PRT
<213> ORGANISM: Homo sapiens

<400> SEQUENCE: 1238

Leu Gly Gln Glu Gln Asp Ser Phe Gly Gly Asn
1               5                   10

<210> SEQ ID NO 1239
<211> LENGTH: 15
<212> TYPE: PRT
<213> ORGANISM: Homo sapiens

<400> SEQUENCE: 1239

Leu Gly Gln Glu Gln Asp Ser Phe Gly Gly Asn Phe Glu Gly Ser
1               5                   10                  15

<210> SEQ ID NO 1240
<211> LENGTH: 18
<212> TYPE: PRT
<213> ORGANISM: Homo sapiens

<400> SEQUENCE: 1240

Leu Gly Gln Glu Gln Asp Ser Phe Gly Gly Asn Phe Glu Gly Ser Gln
1               5                   10                  15

Ser Leu

<210> SEQ ID NO 1241
```

<211> LENGTH: 19
<212> TYPE: PRT
<213> ORGANISM: Homo sapiens

<400> SEQUENCE: 1241

Leu Gly Gln Glu Gln Asp Ser Phe Gly Gly Asn Phe Glu Gly Ser Gln
1               5                   10                  15

Ser Leu Val

<210> SEQ ID NO 1242
<211> LENGTH: 13
<212> TYPE: PRT
<213> ORGANISM: Homo sapiens

<400> SEQUENCE: 1242

Gln Asp Ser Phe Gly Gly Asn Phe Glu Gly Ser Gln Ser
1               5                   10

<210> SEQ ID NO 1243
<211> LENGTH: 10
<212> TYPE: PRT
<213> ORGANISM: Homo sapiens

<400> SEQUENCE: 1243

Ser Phe Gly Gly Asn Phe Glu Gly Ser Gln
1               5                   10

<210> SEQ ID NO 1244
<211> LENGTH: 13
<212> TYPE: PRT
<213> ORGANISM: Homo sapiens

<400> SEQUENCE: 1244

Ser Phe Gly Gly Asn Phe Glu Gly Ser Gln Ser Leu Val
1               5                   10

<210> SEQ ID NO 1245
<211> LENGTH: 11
<212> TYPE: PRT
<213> ORGANISM: Homo sapiens

<400> SEQUENCE: 1245

Leu Val Gly Asp Ile Gly Asn Val Asn Met Trp
1               5                   10

<210> SEQ ID NO 1246
<211> LENGTH: 13
<212> TYPE: PRT
<213> ORGANISM: Homo sapiens

<400> SEQUENCE: 1246

Ile Asn Thr Ile Tyr Leu Gly Gly Pro Phe Ser Pro Asn
1               5                   10

<210> SEQ ID NO 1247
<211> LENGTH: 11
<212> TYPE: PRT
<213> ORGANISM: Homo sapiens

<400> SEQUENCE: 1247

Thr Ile Tyr Leu Gly Gly Pro Phe Ser Pro Asn
1               5                   10

<210> SEQ ID NO 1248

```
<211> LENGTH: 13
<212> TYPE: PRT
<213> ORGANISM: Homo sapiens

<400> SEQUENCE: 1248

Tyr Leu Gly Gly Pro Phe Ser Pro Asn Val Ser Glu Gln
1               5                   10

<210> SEQ ID NO 1249
<211> LENGTH: 6
<212> TYPE: PRT
<213> ORGANISM: Homo sapiens

<400> SEQUENCE: 1249

Val Leu Asn Trp Arg Ala
1               5

<210> SEQ ID NO 1250
<211> LENGTH: 7
<212> TYPE: PRT
<213> ORGANISM: Homo sapiens

<400> SEQUENCE: 1250

Val Leu Asn Trp Arg Ala Leu
1               5

<210> SEQ ID NO 1251
<211> LENGTH: 8
<212> TYPE: PRT
<213> ORGANISM: Homo sapiens

<400> SEQUENCE: 1251

Val Leu Asn Trp Arg Ala Leu Lys
1               5

<210> SEQ ID NO 1252
<211> LENGTH: 10
<212> TYPE: PRT
<213> ORGANISM: Homo sapiens

<400> SEQUENCE: 1252

Leu Asn Trp Arg Ala Leu Lys Tyr Glu Val
1               5                   10

<210> SEQ ID NO 1253
<211> LENGTH: 5
<212> TYPE: PRT
<213> ORGANISM: Homo sapiens

<400> SEQUENCE: 1253

Asn Trp Arg Ala Leu
1               5

<210> SEQ ID NO 1254
<211> LENGTH: 7
<212> TYPE: PRT
<213> ORGANISM: Homo sapiens

<400> SEQUENCE: 1254

Asn Trp Arg Ala Leu Lys Tyr
1               5

<210> SEQ ID NO 1255
<211> LENGTH: 9
<212> TYPE: PRT
```

<213> ORGANISM: Homo sapiens

<400> SEQUENCE: 1255

Asn Trp Arg Ala Leu Lys Tyr Glu Val
1               5

<210> SEQ ID NO 1256
<211> LENGTH: 10
<212> TYPE: PRT
<213> ORGANISM: Homo sapiens

<400> SEQUENCE: 1256

Asn Trp Arg Ala Leu Lys Tyr Glu Val Gln
1               5                   10

<210> SEQ ID NO 1257
<211> LENGTH: 9
<212> TYPE: PRT
<213> ORGANISM: Homo sapiens

<400> SEQUENCE: 1257

Trp Arg Ala Leu Lys Tyr Glu Val Gln
1               5

<210> SEQ ID NO 1258
<211> LENGTH: 7
<212> TYPE: PRT
<213> ORGANISM: Homo sapiens

<400> SEQUENCE: 1258

Arg Ala Leu Lys Tyr Glu Val
1               5

<210> SEQ ID NO 1259
<211> LENGTH: 8
<212> TYPE: PRT
<213> ORGANISM: Homo sapiens

<400> SEQUENCE: 1259

Arg Ala Leu Lys Tyr Glu Val Gln
1               5

<210> SEQ ID NO 1260
<211> LENGTH: 10
<212> TYPE: PRT
<213> ORGANISM: Homo sapiens

<400> SEQUENCE: 1260

Arg Ala Leu Lys Tyr Glu Val Gln Gly Glu
1               5                   10

<210> SEQ ID NO 1261
<211> LENGTH: 15
<212> TYPE: PRT
<213> ORGANISM: Homo sapiens

<400> SEQUENCE: 1261

Ala Leu Lys Tyr Glu Val Gln Gly Glu Val Phe Thr Lys Pro Gln
1               5                   10                  15

<210> SEQ ID NO 1262
<211> LENGTH: 11
<212> TYPE: PRT
<213> ORGANISM: Homo sapiens

<400> SEQUENCE: 1262

Glu Val Gln Gly Glu Val Phe Thr Lys Pro Gln
1               5                   10

<210> SEQ ID NO 1263
<211> LENGTH: 10
<212> TYPE: PRT
<213> ORGANISM: Homo sapiens

<400> SEQUENCE: 1263

Gln Gly Glu Val Phe Thr Lys Pro Gln Leu
1               5                   10

<210> SEQ ID NO 1264
<211> LENGTH: 12
<212> TYPE: PRT
<213> ORGANISM: Homo sapiens

<400> SEQUENCE: 1264

Gln Gly Glu Val Phe Thr Lys Pro Gln Leu Trp Pro
1               5                   10

<210> SEQ ID NO 1265
<211> LENGTH: 10
<212> TYPE: PRT
<213> ORGANISM: Homo sapiens

<400> SEQUENCE: 1265

Glu Ser Asp Thr Ser Tyr Val Ser Leu Lys
1               5                   10

<210> SEQ ID NO 1266
<211> LENGTH: 14
<212> TYPE: PRT
<213> ORGANISM: Homo sapiens

<400> SEQUENCE: 1266

Gln Glu Gln Asp Ser Phe Gly Gly Asn Phe Glu Gly Ser Gln
1               5                   10

<210> SEQ ID NO 1267
<211> LENGTH: 18
<212> TYPE: PRT
<213> ORGANISM: Homo sapiens

<400> SEQUENCE: 1267

Gln Glu Gln Asp Ser Phe Gly Gly Asn Phe Glu Gly Ser Gln Ser Leu
1               5                   10                  15

Val Gly

<210> SEQ ID NO 1268
<211> LENGTH: 11
<212> TYPE: PRT
<213> ORGANISM: Homo sapiens

<400> SEQUENCE: 1268

Gly Asn Phe Glu Gly Ser Gln Ser Leu Val Gly
1               5                   10

<210> SEQ ID NO 1269
<211> LENGTH: 9
<212> TYPE: PRT
<213> ORGANISM: Homo sapiens -continued

```
<400> SEQUENCE: 1269

Tyr Glu Val Gln Gly Glu Val Phe Thr
1               5

<210> SEQ ID NO 1270
<211> LENGTH: 7
<212> TYPE: PRT
<213> ORGANISM: Homo sapiens

<400> SEQUENCE: 1270

Glu Ile Asn Thr Ile Tyr Leu
1               5

<210> SEQ ID NO 1271
<211> LENGTH: 5
<212> TYPE: PRT
<213> ORGANISM: Homo sapiens

<400> SEQUENCE: 1271

Lys Tyr Glu Val Gln
1               5

<210> SEQ ID NO 1272
<211> LENGTH: 14
<212> TYPE: PRT
<213> ORGANISM: Homo sapiens

<400> SEQUENCE: 1272

Glu Ser Asp Thr Ser Tyr Val Ser Leu Lys Ala Pro Leu Thr
1               5                   10

<210> SEQ ID NO 1273
<211> LENGTH: 9
<212> TYPE: PRT
<213> ORGANISM: Homo sapiens

<400> SEQUENCE: 1273

Ser Asp Thr Ser Tyr Val Ser Leu Lys
1               5

<210> SEQ ID NO 1274
<211> LENGTH: 8
<212> TYPE: PRT
<213> ORGANISM: Homo sapiens

<400> SEQUENCE: 1274

Asp Thr Ser Tyr Val Ser Leu Lys
1               5

<210> SEQ ID NO 1275
<211> LENGTH: 8
<212> TYPE: PRT
<213> ORGANISM: Homo sapiens

<400> SEQUENCE: 1275

Ile Phe Trp Ser Lys Asp Ile Gly
1               5

<210> SEQ ID NO 1276
<211> LENGTH: 8
<212> TYPE: PRT
<213> ORGANISM: Homo sapiens

<400> SEQUENCE: 1276
```

```
Lys Gly Tyr Thr Val Gly Ala Glu
1               5
```

<210> SEQ ID NO 1277
<211> LENGTH: 15
<212> TYPE: PRT
<213> ORGANISM: Homo sapiens

<400> SEQUENCE: 1277

```
Ala Glu Ala Ser Ile Ile Leu Gly Gln Glu Gln Asp Ser Phe Gly
1               5                   10                  15
```

<210> SEQ ID NO 1278
<211> LENGTH: 9
<212> TYPE: PRT
<213> ORGANISM: Homo sapiens

<400> SEQUENCE: 1278

```
Leu Gly Gln Glu Gln Asp Ser Phe Gly
1               5
```

<210> SEQ ID NO 1279
<211> LENGTH: 13
<212> TYPE: PRT
<213> ORGANISM: Homo sapiens

<400> SEQUENCE: 1279

```
Leu Gly Gln Glu Gln Asp Ser Phe Gly Gly Asn Phe Glu
1               5                   10
```

<210> SEQ ID NO 1280
<211> LENGTH: 8
<212> TYPE: PRT
<213> ORGANISM: Homo sapiens

<400> SEQUENCE: 1280

```
Gly Gln Glu Gln Asp Ser Phe Gly
1               5
```

<210> SEQ ID NO 1281
<211> LENGTH: 12
<212> TYPE: PRT
<213> ORGANISM: Homo sapiens

<400> SEQUENCE: 1281

```
Gly Gln Glu Gln Asp Ser Phe Gly Gly Asn Phe Glu
1               5                   10
```

<210> SEQ ID NO 1282
<211> LENGTH: 15
<212> TYPE: PRT
<213> ORGANISM: Homo sapiens

<400> SEQUENCE: 1282

```
Gly Gln Glu Gln Asp Ser Phe Gly Gly Asn Phe Glu Gly Ser Gln
1               5                   10                  15
```

<210> SEQ ID NO 1283
<211> LENGTH: 9
<212> TYPE: PRT
<213> ORGANISM: Homo sapiens

<400> SEQUENCE: 1283

```
Gln Glu Gln Asp Ser Phe Gly Gly Asn
1               5
```

<210> SEQ ID NO 1284
<211> LENGTH: 11
<212> TYPE: PRT
<213> ORGANISM: Homo sapiens

<400> SEQUENCE: 1284

Gln Glu Gln Asp Ser Phe Gly Gly Asn Phe Glu
1               5                   10

<210> SEQ ID NO 1285
<211> LENGTH: 12
<212> TYPE: PRT
<213> ORGANISM: Homo sapiens

<400> SEQUENCE: 1285

Gln Glu Gln Asp Ser Phe Gly Gly Asn Phe Glu Gly
1               5                   10

<210> SEQ ID NO 1286
<211> LENGTH: 13
<212> TYPE: PRT
<213> ORGANISM: Homo sapiens

<400> SEQUENCE: 1286

Gln Glu Gln Asp Ser Phe Gly Gly Asn Phe Glu Gly Ser
1               5                   10

<210> SEQ ID NO 1287
<211> LENGTH: 10
<212> TYPE: PRT
<213> ORGANISM: Homo sapiens

<400> SEQUENCE: 1287

Gly Asn Phe Glu Gly Ser Gln Ser Leu Val
1               5                   10

<210> SEQ ID NO 1288
<211> LENGTH: 14
<212> TYPE: PRT
<213> ORGANISM: Homo sapiens

<400> SEQUENCE: 1288

Gly Asn Phe Glu Gly Ser Gln Ser Leu Val Gly Asp Ile Gly
1               5                   10

<210> SEQ ID NO 1289
<211> LENGTH: 10
<212> TYPE: PRT
<213> ORGANISM: Homo sapiens

<400> SEQUENCE: 1289

Gly Ser Gln Ser Leu Val Gly Asp Ile Gly
1               5                   10

<210> SEQ ID NO 1290
<211> LENGTH: 13
<212> TYPE: PRT
<213> ORGANISM: Homo sapiens

<400> SEQUENCE: 1290

Gly Ser Gln Ser Leu Val Gly Asp Ile Gly Asn Val Asn
1               5                   10

```
<210> SEQ ID NO 1291
<211> LENGTH: 9
<212> TYPE: PRT
<213> ORGANISM: Homo sapiens

<400> SEQUENCE: 1291

Val Leu Ser Pro Asp Glu Ile Asn Thr
1               5

<210> SEQ ID NO 1292
<211> LENGTH: 9
<212> TYPE: PRT
<213> ORGANISM: Homo sapiens

<400> SEQUENCE: 1292

Gly Pro Phe Ser Pro Asn Val Leu Asn
1               5

<210> SEQ ID NO 1293
<211> LENGTH: 8
<212> TYPE: PRT
<213> ORGANISM: Homo sapiens

<400> SEQUENCE: 1293

Ser Pro Asn Val Leu Asn Trp Arg
1               5

<210> SEQ ID NO 1294
<211> LENGTH: 6
<212> TYPE: PRT
<213> ORGANISM: Homo sapiens

<400> SEQUENCE: 1294

Lys Tyr Glu Val Gln Gly
1               5

<210> SEQ ID NO 1295
<211> LENGTH: 11
<212> TYPE: PRT
<213> ORGANISM: Homo sapiens

<400> SEQUENCE: 1295

Thr Ser Trp Glu Ser Ala Ser Gly Ile Val Glu
1               5                   10

<210> SEQ ID NO 1296
<211> LENGTH: 6
<212> TYPE: PRT
<213> ORGANISM: Homo sapiens

<400> SEQUENCE: 1296

Lys Gly Tyr Thr Val Gly
1               5

<210> SEQ ID NO 1297
<211> LENGTH: 17
<212> TYPE: PRT
<213> ORGANISM: Homo sapiens

<400> SEQUENCE: 1297

Gln Glu Gln Asp Ser Phe Gly Gly Asn Phe Glu Gly Ser Gln Ser Leu
1               5                   10                  15

Val
```

```
<210> SEQ ID NO 1298
<211> LENGTH: 14
<212> TYPE: PRT
<213> ORGANISM: Homo sapiens

<400> SEQUENCE: 1298

Ser Phe Gly Gly Asn Phe Glu Gly Ser Gln Ser Leu Val Gly
1               5                   10

<210> SEQ ID NO 1299
<211> LENGTH: 10
<212> TYPE: PRT
<213> ORGANISM: Homo sapiens

<400> SEQUENCE: 1299

Ser Pro Asp Glu Ile Asn Thr Ile Tyr Leu
1               5                   10

<210> SEQ ID NO 1300
<211> LENGTH: 11
<212> TYPE: PRT
<213> ORGANISM: Homo sapiens

<400> SEQUENCE: 1300

Ser Pro Asp Glu Ile Asn Thr Ile Tyr Leu Gly
1               5                   10

<210> SEQ ID NO 1301
<211> LENGTH: 10
<212> TYPE: PRT
<213> ORGANISM: Homo sapiens

<400> SEQUENCE: 1301

Gly Gly Pro Phe Ser Pro Asn Val Leu Asn
1               5                   10

<210> SEQ ID NO 1302
<211> LENGTH: 5
<212> TYPE: PRT
<213> ORGANISM: Homo sapiens

<400> SEQUENCE: 1302

Ala Leu Lys Tyr Glu
1               5

<210> SEQ ID NO 1303
<211> LENGTH: 7
<212> TYPE: PRT
<213> ORGANISM: Homo sapiens

<400> SEQUENCE: 1303

Ala Leu Lys Tyr Glu Val Gln
1               5

<210> SEQ ID NO 1304
<211> LENGTH: 8
<212> TYPE: PRT
<213> ORGANISM: Homo sapiens

<400> SEQUENCE: 1304

Tyr Glu Val Gln Gly Glu Val Phe
1               5

<210> SEQ ID NO 1305
<211> LENGTH: 6
```

```
<212> TYPE: PRT
<213> ORGANISM: Homo sapiens

<400> SEQUENCE: 1305

Ser Phe Gly Gly Asn Phe
1               5

<210> SEQ ID NO 1306
<211> LENGTH: 6
<212> TYPE: PRT
<213> ORGANISM: Homo sapiens

<400> SEQUENCE: 1306

Phe Gly Gln Thr Asp Met
1               5

<210> SEQ ID NO 1307
<211> LENGTH: 6
<212> TYPE: PRT
<213> ORGANISM: Homo sapiens

<400> SEQUENCE: 1307

Thr Asp Met Ser Arg Lys
1               5

<210> SEQ ID NO 1308
<211> LENGTH: 6
<212> TYPE: PRT
<213> ORGANISM: Homo sapiens

<400> SEQUENCE: 1308

Met Ser Arg Lys Ala Phe
1               5

<210> SEQ ID NO 1309
<211> LENGTH: 6
<212> TYPE: PRT
<213> ORGANISM: Homo sapiens

<400> SEQUENCE: 1309

Ser Arg Lys Ala Phe Val
1               5

<210> SEQ ID NO 1310
<211> LENGTH: 6
<212> TYPE: PRT
<213> ORGANISM: Homo sapiens

<400> SEQUENCE: 1310

Val Phe Pro Lys Glu Ser
1               5

<210> SEQ ID NO 1311
<211> LENGTH: 6
<212> TYPE: PRT
<213> ORGANISM: Homo sapiens

<400> SEQUENCE: 1311

Phe Pro Lys Glu Ser Asp
1               5

<210> SEQ ID NO 1312
<211> LENGTH: 6
<212> TYPE: PRT
<213> ORGANISM: Homo sapiens
```

<400> SEQUENCE: 1312

Lys Glu Ser Asp Thr Ser
1               5

<210> SEQ ID NO 1313
<211> LENGTH: 6
<212> TYPE: PRT
<213> ORGANISM: Homo sapiens

<400> SEQUENCE: 1313

Leu Ser Ser Thr Arg Gly
1               5

<210> SEQ ID NO 1314
<211> LENGTH: 6
<212> TYPE: PRT
<213> ORGANISM: Homo sapiens

<400> SEQUENCE: 1314

Ser Ser Thr Arg Gly Tyr
1               5

<210> SEQ ID NO 1315
<211> LENGTH: 6
<212> TYPE: PRT
<213> ORGANISM: Homo sapiens

<400> SEQUENCE: 1315

Lys Arg Gln Asp Asn Glu
1               5

<210> SEQ ID NO 1316
<211> LENGTH: 6
<212> TYPE: PRT
<213> ORGANISM: Homo sapiens

<400> SEQUENCE: 1316

Trp Ser Lys Asp Ile Gly
1               5

<210> SEQ ID NO 1317
<211> LENGTH: 6
<212> TYPE: PRT
<213> ORGANISM: Homo sapiens

<400> SEQUENCE: 1317

Ser Lys Asp Ile Gly Tyr
1               5

<210> SEQ ID NO 1318
<211> LENGTH: 6
<212> TYPE: PRT
<213> ORGANISM: Homo sapiens

<400> SEQUENCE: 1318

Ser Ile Ile Leu Gly Gln
1               5

<210> SEQ ID NO 1319
<211> LENGTH: 6
<212> TYPE: PRT
<213> ORGANISM: Homo sapiens

<400> SEQUENCE: 1319

Ile Ile Leu Gly Gln Glu
1               5

<210> SEQ ID NO 1320
<211> LENGTH: 6
<212> TYPE: PRT
<213> ORGANISM: Homo sapiens

<400> SEQUENCE: 1320

Ile Leu Gly Gln Glu Gln
1               5

<210> SEQ ID NO 1321
<211> LENGTH: 6
<212> TYPE: PRT
<213> ORGANISM: Homo sapiens

<400> SEQUENCE: 1321

Ile Tyr Leu Gly Gly Pro
1               5

<210> SEQ ID NO 1322
<211> LENGTH: 6
<212> TYPE: PRT
<213> ORGANISM: Homo sapiens

<400> SEQUENCE: 1322

Tyr Leu Gly Gly Pro Phe
1               5

<210> SEQ ID NO 1323
<211> LENGTH: 6
<212> TYPE: PRT
<213> ORGANISM: Homo sapiens

<400> SEQUENCE: 1323

Leu Gly Gly Pro Phe Ser
1               5

<210> SEQ ID NO 1324
<211> LENGTH: 6
<212> TYPE: PRT
<213> ORGANISM: Homo sapiens

<400> SEQUENCE: 1324

Val Gln Gly Glu Val Phe
1               5

<210> SEQ ID NO 1325
<211> LENGTH: 6
<212> TYPE: PRT
<213> ORGANISM: Homo sapiens

<400> SEQUENCE: 1325

Tyr Thr Glu Leu Ser Ser
1               5

<210> SEQ ID NO 1326
<211> LENGTH: 6
<212> TYPE: PRT
<213> ORGANISM: Homo sapiens

<400> SEQUENCE: 1326

Ile Leu Ile Phe Trp Ser

```
<210> SEQ ID NO 1327
<211> LENGTH: 6
<212> TYPE: PRT
<213> ORGANISM: Homo sapiens

<400> SEQUENCE: 1327

Leu Val Gly Asp Ile Gly
1               5

<210> SEQ ID NO 1328
<211> LENGTH: 6
<212> TYPE: PRT
<213> ORGANISM: Homo sapiens

<400> SEQUENCE: 1328

Gln Glu Gln Asp Ser Phe
1               5

<210> SEQ ID NO 1329
<211> LENGTH: 6
<212> TYPE: PRT
<213> ORGANISM: Homo sapiens

<400> SEQUENCE: 1329

Arg Gly Tyr Ser Ile Phe
1               5

<210> SEQ ID NO 1330
<211> LENGTH: 6
<212> TYPE: PRT
<213> ORGANISM: Homo sapiens

<400> SEQUENCE: 1330

Gly Ala Glu Ala Ser Ile
1               5

<210> SEQ ID NO 1331
<211> LENGTH: 6
<212> TYPE: PRT
<213> ORGANISM: Homo sapiens

<400> SEQUENCE: 1331

Gln Asp Ser Phe Gly Gly
1               5

<210> SEQ ID NO 1332
<211> LENGTH: 6
<212> TYPE: PRT
<213> ORGANISM: Homo sapiens

<400> SEQUENCE: 1332

Thr Ile Tyr Leu Gly Gly
1               5

<210> SEQ ID NO 1333
<211> LENGTH: 6
<212> TYPE: PRT
<213> ORGANISM: Homo sapiens

<400> SEQUENCE: 1333

Glu Ile Asn Thr Ile Tyr
1               5
```

<210> SEQ ID NO 1334
<211> LENGTH: 6
<212> TYPE: PRT
<213> ORGANISM: Homo sapiens

<400> SEQUENCE: 1334

Asp Thr Ser Tyr Val Ser
1               5

<210> SEQ ID NO 1335
<211> LENGTH: 6
<212> TYPE: PRT
<213> ORGANISM: Homo sapiens

<400> SEQUENCE: 1335

Ala Glu Ala Ser Ile Ile
1               5

<210> SEQ ID NO 1336
<211> LENGTH: 6
<212> TYPE: PRT
<213> ORGANISM: Homo sapiens

<400> SEQUENCE: 1336

Thr Ser Trp Glu Ser Ala
1               5

<210> SEQ ID NO 1337
<211> LENGTH: 6
<212> TYPE: PRT
<213> ORGANISM: Homo sapiens

<400> SEQUENCE: 1337

Ser Pro Asp Glu Ile Asn
1               5

<210> SEQ ID NO 1338
<211> LENGTH: 6
<212> TYPE: PRT
<213> ORGANISM: Homo sapiens

<400> SEQUENCE: 1338

Gly Gly Pro Phe Ser Pro
1               5

<210> SEQ ID NO 1339
<211> LENGTH: 6
<212> TYPE: PRT
<213> ORGANISM: Homo sapiens

<400> SEQUENCE: 1339

Tyr Glu Val Gln Gly Glu
1               5

<210> SEQ ID NO 1340
<211> LENGTH: 6
<212> TYPE: PRT
<213> ORGANISM: Homo sapiens

<400> SEQUENCE: 1340

Phe Val Leu Ser Pro Asp
1               5

<210> SEQ ID NO 1341

```
<211> LENGTH: 6
<212> TYPE: PRT
<213> ORGANISM: Homo sapiens

<400> SEQUENCE: 1341

Leu Lys Lys Gly Tyr Thr
1               5

<210> SEQ ID NO 1342
<211> LENGTH: 6
<212> TYPE: PRT
<213> ORGANISM: Homo sapiens

<400> SEQUENCE: 1342

Arg Lys Ala Phe Val Phe
1               5

<210> SEQ ID NO 1343
<211> LENGTH: 6
<212> TYPE: PRT
<213> ORGANISM: Homo sapiens

<400> SEQUENCE: 1343

Ile Val Glu Phe Trp Val
1               5

<210> SEQ ID NO 1344
<211> LENGTH: 6
<212> TYPE: PRT
<213> ORGANISM: Homo sapiens

<400> SEQUENCE: 1344

Glu Ser Asp Thr Ser Tyr
1               5

<210> SEQ ID NO 1345
<211> LENGTH: 6
<212> TYPE: PRT
<213> ORGANISM: Homo sapiens

<400> SEQUENCE: 1345

Thr Lys Pro Gln Leu Trp
1               5

<210> SEQ ID NO 1346
<211> LENGTH: 6
<212> TYPE: PRT
<213> ORGANISM: Homo sapiens

<400> SEQUENCE: 1346

Glu Val Gln Gly Glu Val
1               5

<210> SEQ ID NO 1347
<211> LENGTH: 6
<212> TYPE: PRT
<213> ORGANISM: Homo sapiens

<400> SEQUENCE: 1347

Ser Asp Thr Ser Tyr Val
1               5

<210> SEQ ID NO 1348
<211> LENGTH: 6
<212> TYPE: PRT
```

```
<213> ORGANISM: Homo sapiens

<400> SEQUENCE: 1348

Ile Phe Ser Tyr Ala Thr
1               5

<210> SEQ ID NO 1349
<211> LENGTH: 6
<212> TYPE: PRT
<213> ORGANISM: Homo sapiens

<400> SEQUENCE: 1349

Ser Tyr Ala Thr Lys Arg
1               5

<210> SEQ ID NO 1350
<211> LENGTH: 6
<212> TYPE: PRT
<213> ORGANISM: Homo sapiens

<400> SEQUENCE: 1350

Tyr Ala Thr Lys Arg Gln
1               5

<210> SEQ ID NO 1351
<211> LENGTH: 6
<212> TYPE: PRT
<213> ORGANISM: Homo sapiens

<400> SEQUENCE: 1351

Glu Phe Trp Val Asp Gly
1               5

<210> SEQ ID NO 1352
<211> LENGTH: 6
<212> TYPE: PRT
<213> ORGANISM: Homo sapiens

<400> SEQUENCE: 1352

Trp Val Asp Gly Lys Pro
1               5

<210> SEQ ID NO 1353
<211> LENGTH: 6
<212> TYPE: PRT
<213> ORGANISM: Homo sapiens

<400> SEQUENCE: 1353

Val Asp Gly Lys Pro Arg
1               5

<210> SEQ ID NO 1354
<211> LENGTH: 6
<212> TYPE: PRT
<213> ORGANISM: Homo sapiens

<400> SEQUENCE: 1354

Leu Gly Gln Glu Gln Asp
1               5

<210> SEQ ID NO 1355
<211> LENGTH: 6
<212> TYPE: PRT
<213> ORGANISM: Homo sapiens
```

```
<400> SEQUENCE: 1355

Gly Gln Glu Gln Asp Ser
1               5

<210> SEQ ID NO 1356
<211> LENGTH: 6
<212> TYPE: PRT
<213> ORGANISM: Homo sapiens

<400> SEQUENCE: 1356

Gln Ser Leu Val Gly Asp
1               5

<210> SEQ ID NO 1357
<211> LENGTH: 6
<212> TYPE: PRT
<213> ORGANISM: Homo sapiens

<400> SEQUENCE: 1357

Ser Pro Asn Val Leu Asn
1               5

<210> SEQ ID NO 1358
<211> LENGTH: 6
<212> TYPE: PRT
<213> ORGANISM: Homo sapiens

<400> SEQUENCE: 1358

Gln Gly Glu Val Phe Thr
1               5

<210> SEQ ID NO 1359
<211> LENGTH: 6
<212> TYPE: PRT
<213> ORGANISM: Homo sapiens

<400> SEQUENCE: 1359

Gly Glu Val Phe Thr Lys
1               5

<210> SEQ ID NO 1360
<211> LENGTH: 6
<212> TYPE: PRT
<213> ORGANISM: Homo sapiens

<400> SEQUENCE: 1360

Lys Lys Gly Tyr Thr Val
1               5

<210> SEQ ID NO 1361
<211> LENGTH: 6
<212> TYPE: PRT
<213> ORGANISM: Homo sapiens

<400> SEQUENCE: 1361

Phe Ser Tyr Ala Thr Lys
1               5

<210> SEQ ID NO 1362
<211> LENGTH: 6
<212> TYPE: PRT
<213> ORGANISM: Homo sapiens

<400> SEQUENCE: 1362
```

Ala Thr Lys Arg Gln Asp
1               5

<210> SEQ ID NO 1363
<211> LENGTH: 6
<212> TYPE: PRT
<213> ORGANISM: Homo sapiens

<400> SEQUENCE: 1363

Phe Trp Ser Lys Asp Ile
1               5

<210> SEQ ID NO 1364
<211> LENGTH: 6
<212> TYPE: PRT
<213> ORGANISM: Homo sapiens

<400> SEQUENCE: 1364

Asn Trp Arg Ala Leu Lys
1               5

<210> SEQ ID NO 1365
<211> LENGTH: 6
<212> TYPE: PRT
<213> ORGANISM: Homo sapiens

<400> SEQUENCE: 1365

Gly Ser Gln Ser Leu Val
1               5

<210> SEQ ID NO 1366
<211> LENGTH: 6
<212> TYPE: PRT
<213> ORGANISM: Homo sapiens

<400> SEQUENCE: 1366

Asp Phe Val Leu Ser Pro
1               5

<210> SEQ ID NO 1367
<211> LENGTH: 6
<212> TYPE: PRT
<213> ORGANISM: Homo sapiens

<400> SEQUENCE: 1367

Val Leu Ser Pro Asp Glu
1               5

<210> SEQ ID NO 1368
<211> LENGTH: 6
<212> TYPE: PRT
<213> ORGANISM: Homo sapiens

<400> SEQUENCE: 1368

Thr Lys Arg Gln Asp Asn
1               5

<210> SEQ ID NO 1369
<211> LENGTH: 6
<212> TYPE: PRT
<213> ORGANISM: Homo sapiens

<400> SEQUENCE: 1369

Gly Asn Phe Glu Gly Ser
1               5

```
<210> SEQ ID NO 1370
<211> LENGTH: 6
<212> TYPE: PRT
<213> ORGANISM: Homo sapiens

<400> SEQUENCE: 1370

Ser Leu Lys Lys Gly Tyr
1               5

<210> SEQ ID NO 1371
<211> LENGTH: 6
<212> TYPE: PRT
<213> ORGANISM: Homo sapiens

<400> SEQUENCE: 1371

Lys Ser Leu Lys Lys Gly
1               5

<210> SEQ ID NO 1372
<211> LENGTH: 6
<212> TYPE: PRT
<213> ORGANISM: Homo sapiens

<400> SEQUENCE: 1372

Ile Asn Thr Ile Tyr Leu
1               5

<210> SEQ ID NO 1373
<211> LENGTH: 6
<212> TYPE: PRT
<213> ORGANISM: Homo sapiens

<400> SEQUENCE: 1373

Arg Ala Leu Lys Tyr Glu
1               5

<210> SEQ ID NO 1374
<211> LENGTH: 6
<212> TYPE: PRT
<213> ORGANISM: Homo sapiens

<400> SEQUENCE: 1374

Phe Tyr Thr Glu Leu Ser
1               5

<210> SEQ ID NO 1375
<211> LENGTH: 6
<212> TYPE: PRT
<213> ORGANISM: Homo sapiens

<400> SEQUENCE: 1375

Trp Arg Ala Leu Lys Tyr
1               5

<210> SEQ ID NO 1376
<211> LENGTH: 6
<212> TYPE: PRT
<213> ORGANISM: Homo sapiens

<400> SEQUENCE: 1376

Gly Pro Phe Ser Pro Asn
1               5
```

```
<210> SEQ ID NO 1377
<211> LENGTH: 6
<212> TYPE: PRT
<213> ORGANISM: Homo sapiens

<400> SEQUENCE: 1377

Pro Asp Glu Ile Asn Thr
1               5

<210> SEQ ID NO 1378
<211> LENGTH: 6
<212> TYPE: PRT
<213> ORGANISM: Homo sapiens

<400> SEQUENCE: 1378

Asp Ser Phe Gly Gly Asn
1               5

<210> SEQ ID NO 1379
<211> LENGTH: 6
<212> TYPE: PRT
<213> ORGANISM: Homo sapiens

<400> SEQUENCE: 1379

Leu Thr Lys Pro Leu Lys
1               5

<210> SEQ ID NO 1380
<211> LENGTH: 6
<212> TYPE: PRT
<213> ORGANISM: Homo sapiens

<400> SEQUENCE: 1380

Lys Asp Ile Gly Tyr Ser
1               5

<210> SEQ ID NO 1381
<211> LENGTH: 6
<212> TYPE: PRT
<213> ORGANISM: Homo sapiens

<400> SEQUENCE: 1381

Asp Gly Lys Pro Arg Val
1               5

<210> SEQ ID NO 1382
<211> LENGTH: 6
<212> TYPE: PRT
<213> ORGANISM: Homo sapiens

<400> SEQUENCE: 1382

Asn Phe Glu Gly Ser Gln
1               5

<210> SEQ ID NO 1383
<211> LENGTH: 6
<212> TYPE: PRT
<213> ORGANISM: Homo sapiens

<400> SEQUENCE: 1383

Asn Val Asn Met Trp Asp
1               5

<210> SEQ ID NO 1384
<211> LENGTH: 6
```

```
<212> TYPE: PRT
<213> ORGANISM: Homo sapiens

<400> SEQUENCE: 1384

Pro Arg Val Arg Lys Ser
1               5

<210> SEQ ID NO 1385
<211> LENGTH: 6
<212> TYPE: PRT
<213> ORGANISM: Homo sapiens

<400> SEQUENCE: 1385

Thr Val Gly Ser Glu Ile
1               5

<210> SEQ ID NO 1386
<211> LENGTH: 6
<212> TYPE: PRT
<213> ORGANISM: Homo sapiens

<400> SEQUENCE: 1386

Gly Tyr Ser Phe Thr Val
1               5

<210> SEQ ID NO 1387
<211> LENGTH: 6
<212> TYPE: PRT
<213> ORGANISM: Homo sapiens

<400> SEQUENCE: 1387

Glu Gly Ser Gln Ser Leu
1               5

<210> SEQ ID NO 1388
<211> LENGTH: 6
<212> TYPE: PRT
<213> ORGANISM: Homo sapiens

<400> SEQUENCE: 1388

Glu Gln Asp Ser Phe Gly
1               5

<210> SEQ ID NO 1389
<211> LENGTH: 6
<212> TYPE: PRT
<213> ORGANISM: Homo sapiens

<400> SEQUENCE: 1389

Asn Val Leu Asn Trp Arg
1               5

<210> SEQ ID NO 1390
<211> LENGTH: 6
<212> TYPE: PRT
<213> ORGANISM: Homo sapiens

<400> SEQUENCE: 1390

Ala Ser Gly Ile Val Glu
1               5

<210> SEQ ID NO 1391
<211> LENGTH: 6
<212> TYPE: PRT
<213> ORGANISM: Homo sapiens
```

<400> SEQUENCE: 1391

Asn Thr Ile Tyr Leu Gly
1               5

<210> SEQ ID NO 1392
<211> LENGTH: 6
<212> TYPE: PRT
<213> ORGANISM: Homo sapiens

<400> SEQUENCE: 1392

Val Gly Ala Glu Ala Ser
1               5

<210> SEQ ID NO 1393
<211> LENGTH: 6
<212> TYPE: PRT
<213> ORGANISM: Homo sapiens

<400> SEQUENCE: 1393

Ala Pro Leu Thr Lys Pro
1               5

<210> SEQ ID NO 1394
<211> LENGTH: 6
<212> TYPE: PRT
<213> ORGANISM: Homo sapiens

<400> SEQUENCE: 1394

Gln Thr Asp Met Ser Arg
1               5

<210> SEQ ID NO 1395
<211> LENGTH: 6
<212> TYPE: PRT
<213> ORGANISM: Homo sapiens

<400> SEQUENCE: 1395

Pro Lys Glu Ser Asp Thr
1               5

<210> SEQ ID NO 1396
<211> LENGTH: 6
<212> TYPE: PRT
<213> ORGANISM: Homo sapiens

<400> SEQUENCE: 1396

Thr Ser Tyr Val Ser Leu
1               5

<210> SEQ ID NO 1397
<211> LENGTH: 6
<212> TYPE: PRT
<213> ORGANISM: Homo sapiens

<400> SEQUENCE: 1397

Asp Asn Glu Ile Leu Ile
1               5

<210> SEQ ID NO 1398
<211> LENGTH: 6
<212> TYPE: PRT
<213> ORGANISM: Homo sapiens

<400> SEQUENCE: 1398

Gln Asp Asn Glu Ile Leu
1               5

<210> SEQ ID NO 1399
<211> LENGTH: 6
<212> TYPE: PRT
<213> ORGANISM: Homo sapiens

<400> SEQUENCE: 1399

Asn Glu Ile Leu Ile Phe
1               5

<210> SEQ ID NO 1400
<211> LENGTH: 6
<212> TYPE: PRT
<213> ORGANISM: Homo sapiens

<400> SEQUENCE: 1400

Tyr Thr Val Gly Ala Glu
1               5

<210> SEQ ID NO 1401
<211> LENGTH: 6
<212> TYPE: PRT
<213> ORGANISM: Homo sapiens

<400> SEQUENCE: 1401

Thr Val Gly Ala Glu Ala
1               5

<210> SEQ ID NO 1402
<211> LENGTH: 6
<212> TYPE: PRT
<213> ORGANISM: Homo sapiens

<400> SEQUENCE: 1402

Pro Phe Ser Pro Asn Val
1               5

<210> SEQ ID NO 1403
<211> LENGTH: 6
<212> TYPE: PRT
<213> ORGANISM: Homo sapiens

<400> SEQUENCE: 1403

Phe Glu Gly Ser Gln Ser
1               5

<210> SEQ ID NO 1404
<211> LENGTH: 6
<212> TYPE: PRT
<213> ORGANISM: Homo sapiens

<400> SEQUENCE: 1404

Asp Ile Gly Asn Val Asn
1               5

<210> SEQ ID NO 1405
<211> LENGTH: 6
<212> TYPE: PRT
<213> ORGANISM: Homo sapiens

<400> SEQUENCE: 1405

Arg Gln Asp Asn Glu Ile

-continued

```
1               5

<210> SEQ ID NO 1406
<211> LENGTH: 6
<212> TYPE: PRT
<213> ORGANISM: Homo sapiens

<400> SEQUENCE: 1406

Phe Thr Lys Pro Gln Leu
1               5

<210> SEQ ID NO 1407
<211> LENGTH: 6
<212> TYPE: PRT
<213> ORGANISM: Homo sapiens

<400> SEQUENCE: 1407

Ser Tyr Val Ser Leu Lys
1               5

<210> SEQ ID NO 1408
<211> LENGTH: 6
<212> TYPE: PRT
<213> ORGANISM: Homo sapiens

<400> SEQUENCE: 1408

Thr Lys Pro Leu Lys Ala
1               5

<210> SEQ ID NO 1409
<211> LENGTH: 6
<212> TYPE: PRT
<213> ORGANISM: Homo sapiens

<400> SEQUENCE: 1409

Ser Ile Phe Ser Tyr Ala
1               5

<210> SEQ ID NO 1410
<211> LENGTH: 6
<212> TYPE: PRT
<213> ORGANISM: Homo sapiens

<400> SEQUENCE: 1410

Gly Asn Val Asn Met Trp
1               5

<210> SEQ ID NO 1411
<211> LENGTH: 6
<212> TYPE: PRT
<213> ORGANISM: Homo sapiens

<400> SEQUENCE: 1411

Ser Gln Ser Leu Val Gly
1               5

<210> SEQ ID NO 1412
<211> LENGTH: 6
<212> TYPE: PRT
<213> ORGANISM: Homo sapiens

<400> SEQUENCE: 1412

Phe Gly Gly Asn Phe Glu
1               5
```

<210> SEQ ID NO 1413
<211> LENGTH: 6
<212> TYPE: PRT
<213> ORGANISM: Homo sapiens

<400> SEQUENCE: 1413

Gly Gly Asn Phe Glu Gly
1               5

<210> SEQ ID NO 1414
<211> LENGTH: 6
<212> TYPE: PRT
<213> ORGANISM: Homo sapiens

<400> SEQUENCE: 1414

Gly Lys Pro Arg Val Arg
1               5

<210> SEQ ID NO 1415
<211> LENGTH: 6
<212> TYPE: PRT
<213> ORGANISM: Homo sapiens

<400> SEQUENCE: 1415

Asp Met Ser Arg Lys Ala
1               5

<210> SEQ ID NO 1416
<211> LENGTH: 6
<212> TYPE: PRT
<213> ORGANISM: Homo sapiens

<400> SEQUENCE: 1416

Glu Ile Leu Ile Phe Trp
1               5

<210> SEQ ID NO 1417
<211> LENGTH: 6
<212> TYPE: PRT
<213> ORGANISM: Homo sapiens

<400> SEQUENCE: 1417

Ile Gly Tyr Ser Phe Thr
1               5

<210> SEQ ID NO 1418
<211> LENGTH: 12
<212> TYPE: PRT
<213> ORGANISM: Homo sapiens

<400> SEQUENCE: 1418

Gly Val Pro Gly Ala Ile Pro Gly Gly Val Pro Gly
1               5                   10

<210> SEQ ID NO 1419
<211> LENGTH: 18
<212> TYPE: PRT
<213> ORGANISM: Homo sapiens

<400> SEQUENCE: 1419

Ala Ile Pro Gly Gly Val Pro Gly Gly Val Phe Tyr Pro Gly Ala Gly
1               5                   10                  15

Leu Gly

<210> SEQ ID NO 1420
<211> LENGTH: 19
<212> TYPE: PRT
<213> ORGANISM: Homo sapiens

<400> SEQUENCE: 1420

Ala Ile Pro Gly Gly Val Pro Gly Gly Val Phe Tyr Pro Gly Ala Gly
1               5                   10                  15

Leu Gly Ala

<210> SEQ ID NO 1421
<211> LENGTH: 15
<212> TYPE: PRT
<213> ORGANISM: Homo sapiens

<400> SEQUENCE: 1421

Gly Val Pro Gly Gly Val Phe Tyr Pro Gly Ala Gly Leu Gly Ala
1               5                   10                  15

<210> SEQ ID NO 1422
<211> LENGTH: 17
<212> TYPE: PRT
<213> ORGANISM: Homo sapiens

<400> SEQUENCE: 1422

Gly Val Pro Gly Gly Val Phe Tyr Pro Gly Ala Gly Leu Gly Ala Leu
1               5                   10                  15

Gly

<210> SEQ ID NO 1423
<211> LENGTH: 17
<212> TYPE: PRT
<213> ORGANISM: Homo sapiens

<400> SEQUENCE: 1423

Val Pro Gly Gly Val Phe Tyr Pro Gly Ala Gly Leu Gly Ala Leu Gly
1               5                   10                  15

Gly

<210> SEQ ID NO 1424
<211> LENGTH: 21
<212> TYPE: PRT
<213> ORGANISM: Homo sapiens

<400> SEQUENCE: 1424

Gly Val Phe Tyr Pro Gly Ala Gly Leu Gly Ala Leu Gly Gly Gly Ala
1               5                   10                  15

Leu Gly Pro Gly Gly
            20

<210> SEQ ID NO 1425
<211> LENGTH: 9
<212> TYPE: PRT
<213> ORGANISM: Homo sapiens

<400> SEQUENCE: 1425

Val Phe Tyr Pro Gly Ala Gly Leu Gly
1               5

<210> SEQ ID NO 1426
<211> LENGTH: 10
<212> TYPE: PRT

<213> ORGANISM: Homo sapiens

<400> SEQUENCE: 1426

Val Phe Tyr Pro Gly Ala Gly Leu Gly Ala
1               5                   10

<210> SEQ ID NO 1427
<211> LENGTH: 11
<212> TYPE: PRT
<213> ORGANISM: Homo sapiens

<400> SEQUENCE: 1427

Val Phe Tyr Pro Gly Ala Gly Leu Gly Ala Leu
1               5                   10

<210> SEQ ID NO 1428
<211> LENGTH: 12
<212> TYPE: PRT
<213> ORGANISM: Homo sapiens

<400> SEQUENCE: 1428

Val Phe Tyr Pro Gly Ala Gly Leu Gly Ala Leu Gly
1               5                   10

<210> SEQ ID NO 1429
<211> LENGTH: 13
<212> TYPE: PRT
<213> ORGANISM: Homo sapiens

<400> SEQUENCE: 1429

Val Phe Tyr Pro Gly Ala Gly Leu Gly Ala Leu Gly Gly
1               5                   10

<210> SEQ ID NO 1430
<211> LENGTH: 14
<212> TYPE: PRT
<213> ORGANISM: Homo sapiens

<400> SEQUENCE: 1430

Val Phe Tyr Pro Gly Ala Gly Leu Gly Ala Leu Gly Gly Gly
1               5                   10

<210> SEQ ID NO 1431
<211> LENGTH: 16
<212> TYPE: PRT
<213> ORGANISM: Homo sapiens

<400> SEQUENCE: 1431

Val Phe Tyr Pro Gly Ala Gly Leu Gly Ala Leu Gly Gly Gly Ala Leu
1               5                   10                  15

<210> SEQ ID NO 1432
<211> LENGTH: 17
<212> TYPE: PRT
<213> ORGANISM: Homo sapiens

<400> SEQUENCE: 1432

Val Phe Tyr Pro Gly Ala Gly Leu Gly Ala Leu Gly Gly Gly Ala Leu
1               5                   10                  15

Gly

<210> SEQ ID NO 1433
<211> LENGTH: 19
<212> TYPE: PRT

-continued

<213> ORGANISM: Homo sapiens

<400> SEQUENCE: 1433

Val Phe Tyr Pro Gly Ala Gly Leu Gly Ala Leu Gly Gly Ala Leu
1               5                   10                  15

Gly Pro Gly

<210> SEQ ID NO 1434
<211> LENGTH: 20
<212> TYPE: PRT
<213> ORGANISM: Homo sapiens

<400> SEQUENCE: 1434

Val Phe Tyr Pro Gly Ala Gly Leu Gly Ala Leu Gly Gly Ala Leu
1               5                   10                  15

Gly Pro Gly Gly
            20

<210> SEQ ID NO 1435
<211> LENGTH: 29
<212> TYPE: PRT
<213> ORGANISM: Homo sapiens

<400> SEQUENCE: 1435

Val Phe Tyr Pro Gly Ala Gly Leu Gly Ala Leu Gly Gly Ala Leu
1               5                   10                  15

Gly Pro Gly Gly Lys Pro Leu Lys Pro Val Pro Gly Gly
            20                  25

<210> SEQ ID NO 1436
<211> LENGTH: 22
<212> TYPE: PRT
<213> ORGANISM: Homo sapiens

<400> SEQUENCE: 1436

Leu Gly Ala Leu Gly Gly Ala Leu Gly Pro Gly Gly Lys Pro Leu
1               5                   10                  15

Lys Pro Val Pro Gly Gly
            20

<210> SEQ ID NO 1437
<211> LENGTH: 20
<212> TYPE: PRT
<213> ORGANISM: Homo sapiens

<400> SEQUENCE: 1437

Ala Leu Gly Gly Gly Ala Leu Gly Pro Gly Gly Lys Pro Leu Lys Pro
1               5                   10                  15

Val Pro Gly Gly
            20

<210> SEQ ID NO 1438
<211> LENGTH: 18
<212> TYPE: PRT
<213> ORGANISM: Homo sapiens

<400> SEQUENCE: 1438

Leu Gly Gly Gly Ala Leu Gly Pro Gly Gly Lys Pro Leu Lys Pro Val
1               5                   10                  15

Pro Gly

```
<210> SEQ ID NO 1439
<211> LENGTH: 19
<212> TYPE: PRT
<213> ORGANISM: Homo sapiens

<400> SEQUENCE: 1439

Leu Gly Gly Gly Ala Leu Gly Pro Gly Gly Lys Pro Leu Lys Pro Val
1               5                   10                  15

Pro Gly Gly

<210> SEQ ID NO 1440
<211> LENGTH: 17
<212> TYPE: PRT
<213> ORGANISM: Homo sapiens

<400> SEQUENCE: 1440

Gly Gly Ala Leu Gly Pro Gly Gly Lys Pro Leu Lys Pro Val Pro Gly
1               5                   10                  15

Gly

<210> SEQ ID NO 1441
<211> LENGTH: 14
<212> TYPE: PRT
<213> ORGANISM: Homo sapiens

<400> SEQUENCE: 1441

Leu Gly Pro Gly Gly Lys Pro Leu Lys Pro Val Pro Gly Gly
1               5                   10

<210> SEQ ID NO 1442
<211> LENGTH: 13
<212> TYPE: PRT
<213> ORGANISM: Homo sapiens

<400> SEQUENCE: 1442

Gly Pro Gly Gly Lys Pro Leu Lys Pro Val Pro Gly Gly
1               5                   10

<210> SEQ ID NO 1443
<211> LENGTH: 12
<212> TYPE: PRT
<213> ORGANISM: Homo sapiens

<400> SEQUENCE: 1443

Pro Gly Gly Lys Pro Leu Lys Pro Val Pro Gly Gly
1               5                   10

<210> SEQ ID NO 1444
<211> LENGTH: 10
<212> TYPE: PRT
<213> ORGANISM: Homo sapiens

<400> SEQUENCE: 1444

Gly Lys Pro Leu Lys Pro Val Pro Gly Gly
1               5                   10

<210> SEQ ID NO 1445
<211> LENGTH: 8
<212> TYPE: PRT
<213> ORGANISM: Homo sapiens

<400> SEQUENCE: 1445

Pro Leu Lys Pro Val Pro Gly Gly
1               5
```

```
<210> SEQ ID NO 1446
<211> LENGTH: 7
<212> TYPE: PRT
<213> ORGANISM: Homo sapiens

<400> SEQUENCE: 1446

Leu Lys Pro Val Pro Gly Gly
1               5

<210> SEQ ID NO 1447
<211> LENGTH: 15
<212> TYPE: PRT
<213> ORGANISM: Homo sapiens

<400> SEQUENCE: 1447

Gly Leu Ala Gly Ala Gly Leu Gly Ala Gly Leu Gly Ala Phe Pro
1               5                   10                  15

<210> SEQ ID NO 1448
<211> LENGTH: 16
<212> TYPE: PRT
<213> ORGANISM: Homo sapiens

<400> SEQUENCE: 1448

Gly Leu Ala Gly Ala Gly Leu Gly Ala Gly Leu Gly Ala Phe Pro Ala
1               5                   10                  15

<210> SEQ ID NO 1449
<211> LENGTH: 11
<212> TYPE: PRT
<213> ORGANISM: Homo sapiens

<400> SEQUENCE: 1449

Leu Ala Gly Ala Gly Leu Gly Ala Gly Leu Gly
1               5                   10

<210> SEQ ID NO 1450
<211> LENGTH: 14
<212> TYPE: PRT
<213> ORGANISM: Homo sapiens

<400> SEQUENCE: 1450

Leu Ala Gly Ala Gly Leu Gly Ala Gly Leu Gly Ala Phe Pro
1               5                   10

<210> SEQ ID NO 1451
<211> LENGTH: 15
<212> TYPE: PRT
<213> ORGANISM: Homo sapiens

<400> SEQUENCE: 1451

Leu Ala Gly Ala Gly Leu Gly Ala Gly Leu Gly Ala Phe Pro Ala
1               5                   10                  15

<210> SEQ ID NO 1452
<211> LENGTH: 17
<212> TYPE: PRT
<213> ORGANISM: Homo sapiens

<400> SEQUENCE: 1452

Leu Ala Gly Ala Gly Leu Gly Ala Gly Leu Gly Ala Phe Pro Ala Val
1               5                   10                  15

Thr
```

<210> SEQ ID NO 1453
<211> LENGTH: 20
<212> TYPE: PRT
<213> ORGANISM: Homo sapiens

<400> SEQUENCE: 1453

Leu Ala Gly Ala Gly Leu Gly Ala Gly Leu Gly Ala Phe Pro Ala Val
1               5                   10                  15

Thr Phe Pro Gly
            20

<210> SEQ ID NO 1454
<211> LENGTH: 21
<212> TYPE: PRT
<213> ORGANISM: Homo sapiens

<400> SEQUENCE: 1454

Leu Ala Gly Ala Gly Leu Gly Ala Gly Leu Gly Ala Phe Pro Ala Val
1               5                   10                  15

Thr Phe Pro Gly Ala
            20

<210> SEQ ID NO 1455
<211> LENGTH: 26
<212> TYPE: PRT
<213> ORGANISM: Homo sapiens

<400> SEQUENCE: 1455

Leu Ala Gly Ala Gly Leu Gly Ala Gly Leu Gly Ala Phe Pro Ala Val
1               5                   10                  15

Thr Phe Pro Gly Ala Leu Val Pro Gly Gly
            20                  25

<210> SEQ ID NO 1456
<211> LENGTH: 28
<212> TYPE: PRT
<213> ORGANISM: Homo sapiens

<400> SEQUENCE: 1456

Leu Ala Gly Ala Gly Leu Gly Ala Gly Leu Gly Ala Phe Pro Ala Val
1               5                   10                  15

Thr Phe Pro Gly Ala Leu Val Pro Gly Gly Val Ala
            20                  25

<210> SEQ ID NO 1457
<211> LENGTH: 33
<212> TYPE: PRT
<213> ORGANISM: Homo sapiens

<400> SEQUENCE: 1457

Leu Ala Gly Ala Gly Leu Gly Ala Gly Leu Gly Ala Phe Pro Ala Val
1               5                   10                  15

Thr Phe Pro Gly Ala Leu Val Pro Gly Gly Val Ala Asp Ala Ala Ala
            20                  25                  30

Ala

<210> SEQ ID NO 1458
<211> LENGTH: 25
<212> TYPE: PRT
<213> ORGANISM: Homo sapiens -continued

<400> SEQUENCE: 1458

Ala Gly Ala Gly Leu Gly Ala Gly Leu Gly Ala Phe Pro Ala Val Thr
1               5                   10                  15

Phe Pro Gly Ala Leu Val Pro Gly Gly
            20                  25

<210> SEQ ID NO 1459
<211> LENGTH: 13
<212> TYPE: PRT
<213> ORGANISM: Homo sapiens

<400> SEQUENCE: 1459

Gly Ala Gly Leu Gly Ala Gly Leu Gly Ala Phe Pro Ala
1               5                   10

<210> SEQ ID NO 1460
<211> LENGTH: 19
<212> TYPE: PRT
<213> ORGANISM: Homo sapiens

<400> SEQUENCE: 1460

Gly Ala Gly Leu Gly Ala Gly Leu Gly Ala Phe Pro Ala Val Thr Phe
1               5                   10                  15

Pro Gly Ala

<210> SEQ ID NO 1461
<211> LENGTH: 12
<212> TYPE: PRT
<213> ORGANISM: Homo sapiens

<400> SEQUENCE: 1461

Ala Gly Leu Gly Ala Gly Leu Gly Ala Phe Pro Ala
1               5                   10

<210> SEQ ID NO 1462
<211> LENGTH: 11
<212> TYPE: PRT
<213> ORGANISM: Homo sapiens

<400> SEQUENCE: 1462

Gly Leu Gly Ala Gly Leu Gly Ala Phe Pro Ala
1               5                   10

<210> SEQ ID NO 1463
<211> LENGTH: 10
<212> TYPE: PRT
<213> ORGANISM: Homo sapiens

<400> SEQUENCE: 1463

Leu Gly Ala Gly Leu Gly Ala Phe Pro Ala
1               5                   10

<210> SEQ ID NO 1464
<211> LENGTH: 16
<212> TYPE: PRT
<213> ORGANISM: Homo sapiens

<400> SEQUENCE: 1464

Leu Gly Ala Gly Leu Gly Ala Phe Pro Ala Val Thr Phe Pro Gly Ala
1               5                   10                  15

<210> SEQ ID NO 1465
<211> LENGTH: 21

```
<212> TYPE: PRT
<213> ORGANISM: Homo sapiens

<400> SEQUENCE: 1465

Leu Gly Ala Gly Leu Gly Ala Phe Pro Ala Val Thr Phe Pro Gly Ala
1               5                   10                  15

Leu Val Pro Gly Gly
            20

<210> SEQ ID NO 1466
<211> LENGTH: 28
<212> TYPE: PRT
<213> ORGANISM: Homo sapiens

<400> SEQUENCE: 1466

Leu Gly Ala Gly Leu Gly Ala Phe Pro Ala Val Thr Phe Pro Gly Ala
1               5                   10                  15

Leu Val Pro Gly Gly Val Ala Asp Ala Ala Ala Ala
            20                  25

<210> SEQ ID NO 1467
<211> LENGTH: 13
<212> TYPE: PRT
<213> ORGANISM: Homo sapiens

<400> SEQUENCE: 1467

Ala Gly Leu Gly Ala Phe Pro Ala Val Thr Phe Pro Gly
1               5                   10

<210> SEQ ID NO 1468
<211> LENGTH: 12
<212> TYPE: PRT
<213> ORGANISM: Homo sapiens

<400> SEQUENCE: 1468

Leu Gly Ala Phe Pro Ala Val Thr Phe Pro Gly Ala
1               5                   10

<210> SEQ ID NO 1469
<211> LENGTH: 19
<212> TYPE: PRT
<213> ORGANISM: Homo sapiens

<400> SEQUENCE: 1469

Leu Gly Ala Phe Pro Ala Val Thr Phe Pro Gly Ala Leu Val Pro Gly
1               5                   10                  15

Gly Val Ala

<210> SEQ ID NO 1470
<211> LENGTH: 24
<212> TYPE: PRT
<213> ORGANISM: Homo sapiens

<400> SEQUENCE: 1470

Leu Gly Ala Phe Pro Ala Val Thr Phe Pro Gly Ala Leu Val Pro Gly
1               5                   10                  15

Gly Val Ala Asp Ala Ala Ala Ala
            20

<210> SEQ ID NO 1471
<211> LENGTH: 15
<212> TYPE: PRT
<213> ORGANISM: Homo sapiens
```

-continued

<400> SEQUENCE: 1471

Ala Phe Pro Ala Val Thr Phe Pro Gly Ala Leu Val Pro Gly Gly
1               5                   10                  15

<210> SEQ ID NO 1472
<211> LENGTH: 12
<212> TYPE: PRT
<213> ORGANISM: Homo sapiens

<400> SEQUENCE: 1472

Ala Val Thr Phe Pro Gly Ala Leu Val Pro Gly Gly
1               5                   10

<210> SEQ ID NO 1473
<211> LENGTH: 19
<212> TYPE: PRT
<213> ORGANISM: Homo sapiens

<400> SEQUENCE: 1473

Ala Val Thr Phe Pro Gly Ala Leu Val Pro Gly Gly Val Ala Asp Ala
1               5                   10                  15

Ala Ala Ala

<210> SEQ ID NO 1474
<211> LENGTH: 11
<212> TYPE: PRT
<213> ORGANISM: Homo sapiens

<400> SEQUENCE: 1474

Val Thr Phe Pro Gly Ala Leu Val Pro Gly Gly
1               5                   10

<210> SEQ ID NO 1475
<211> LENGTH: 18
<212> TYPE: PRT
<213> ORGANISM: Homo sapiens

<400> SEQUENCE: 1475

Val Thr Phe Pro Gly Ala Leu Val Pro Gly Gly Val Ala Asp Ala Ala
1               5                   10                  15

Ala Ala

<210> SEQ ID NO 1476
<211> LENGTH: 12
<212> TYPE: PRT
<213> ORGANISM: Homo sapiens

<400> SEQUENCE: 1476

Leu Val Pro Gly Gly Val Ala Asp Ala Ala Ala Ala
1               5                   10

<210> SEQ ID NO 1477
<211> LENGTH: 14
<212> TYPE: PRT
<213> ORGANISM: Homo sapiens

<400> SEQUENCE: 1477

Leu Val Pro Gly Gly Val Ala Asp Ala Ala Ala Ala Tyr Lys
1               5                   10

<210> SEQ ID NO 1478
<211> LENGTH: 9

```
<212> TYPE: PRT
<213> ORGANISM: Homo sapiens

<400> SEQUENCE: 1478

Val Ala Asp Ala Ala Ala Ala Tyr Lys
1               5

<210> SEQ ID NO 1479
<211> LENGTH: 7
<212> TYPE: PRT
<213> ORGANISM: Homo sapiens

<400> SEQUENCE: 1479

Lys Ala Ala Lys Ala Gly Ala
1               5

<210> SEQ ID NO 1480
<211> LENGTH: 14
<212> TYPE: PRT
<213> ORGANISM: Homo sapiens

<400> SEQUENCE: 1480

Leu Gly Val Ser Ala Gly Ala Val Val Pro Gln Pro Gly Ala
1               5                   10

<210> SEQ ID NO 1481
<211> LENGTH: 19
<212> TYPE: PRT
<213> ORGANISM: Homo sapiens

<400> SEQUENCE: 1481

Val Pro Gly Val Gly Leu Pro Gly Val Tyr Pro Gly Gly Val Leu Pro
1               5                   10                  15

Gly Ala Arg

<210> SEQ ID NO 1482
<211> LENGTH: 18
<212> TYPE: PRT
<213> ORGANISM: Homo sapiens

<400> SEQUENCE: 1482

Pro Gly Val Gly Leu Pro Gly Val Tyr Pro Gly Gly Val Leu Pro Gly
1               5                   10                  15

Ala Arg

<210> SEQ ID NO 1483
<211> LENGTH: 15
<212> TYPE: PRT
<213> ORGANISM: Homo sapiens

<400> SEQUENCE: 1483

Gly Leu Pro Gly Val Tyr Pro Gly Gly Val Leu Pro Gly Ala Arg
1               5                   10                  15

<210> SEQ ID NO 1484
<211> LENGTH: 13
<212> TYPE: PRT
<213> ORGANISM: Homo sapiens

<400> SEQUENCE: 1484

Pro Gly Val Tyr Pro Gly Gly Val Leu Pro Gly Ala Arg
1               5                   10
```

```
<210> SEQ ID NO 1485
<211> LENGTH: 7
<212> TYPE: PRT
<213> ORGANISM: Homo sapiens

<400> SEQUENCE: 1485

Ala Arg Phe Pro Gly Val Gly
1               5

<210> SEQ ID NO 1486
<211> LENGTH: 11
<212> TYPE: PRT
<213> ORGANISM: Homo sapiens

<400> SEQUENCE: 1486

Ala Arg Phe Pro Gly Val Gly Val Leu Pro Gly
1               5                   10

<210> SEQ ID NO 1487
<211> LENGTH: 16
<212> TYPE: PRT
<213> ORGANISM: Homo sapiens

<400> SEQUENCE: 1487

Arg Phe Pro Gly Val Gly Val Leu Pro Gly Val Pro Thr Gly Ala Gly
1               5                   10                  15

<210> SEQ ID NO 1488
<211> LENGTH: 13
<212> TYPE: PRT
<213> ORGANISM: Homo sapiens

<400> SEQUENCE: 1488

Phe Pro Gly Val Gly Val Leu Pro Gly Val Pro Thr Gly
1               5                   10

<210> SEQ ID NO 1489
<211> LENGTH: 14
<212> TYPE: PRT
<213> ORGANISM: Homo sapiens

<400> SEQUENCE: 1489

Phe Pro Gly Val Gly Val Leu Pro Gly Val Pro Thr Gly Ala
1               5                   10

<210> SEQ ID NO 1490
<211> LENGTH: 16
<212> TYPE: PRT
<213> ORGANISM: Homo sapiens

<400> SEQUENCE: 1490

Phe Pro Gly Val Gly Val Leu Pro Gly Val Pro Thr Gly Ala Gly Val
1               5                   10                  15

<210> SEQ ID NO 1491
<211> LENGTH: 19
<212> TYPE: PRT
<213> ORGANISM: Homo sapiens

<400> SEQUENCE: 1491

Phe Pro Gly Val Gly Val Leu Pro Gly Val Pro Thr Gly Ala Gly Val
1               5                   10                  15

Lys Pro Lys
```

<210> SEQ ID NO 1492
<211> LENGTH: 7
<212> TYPE: PRT
<213> ORGANISM: Homo sapiens

<400> SEQUENCE: 1492

Lys Pro Lys Ala Pro Gly Val
1               5

<210> SEQ ID NO 1493
<211> LENGTH: 6
<212> TYPE: PRT
<213> ORGANISM: Homo sapiens

<400> SEQUENCE: 1493

Pro Lys Ala Pro Gly Val
1               5

<210> SEQ ID NO 1494
<211> LENGTH: 13
<212> TYPE: PRT
<213> ORGANISM: Homo sapiens

<400> SEQUENCE: 1494

Gly Ala Phe Ala Gly Ile Pro Gly Val Gly Pro Phe Gly
1               5                   10

<210> SEQ ID NO 1495
<211> LENGTH: 16
<212> TYPE: PRT
<213> ORGANISM: Homo sapiens

<400> SEQUENCE: 1495

Val Gly Pro Phe Gly Gly Pro Gln Pro Gly Val Pro Leu Gly Tyr Pro
1               5                   10                  15

<210> SEQ ID NO 1496
<211> LENGTH: 11
<212> TYPE: PRT
<213> ORGANISM: Homo sapiens

<400> SEQUENCE: 1496

Gly Pro Gln Pro Gly Val Pro Leu Gly Tyr Pro
1               5                   10

<210> SEQ ID NO 1497
<211> LENGTH: 10
<212> TYPE: PRT
<213> ORGANISM: Homo sapiens

<400> SEQUENCE: 1497

Pro Gln Pro Gly Val Pro Leu Gly Tyr Pro
1               5                   10

<210> SEQ ID NO 1498
<211> LENGTH: 8
<212> TYPE: PRT
<213> ORGANISM: Homo sapiens

<400> SEQUENCE: 1498

Pro Gly Val Pro Leu Gly Tyr Pro
1               5

<210> SEQ ID NO 1499
<211> LENGTH: 8

```
<212> TYPE: PRT
<213> ORGANISM: Homo sapiens

<400> SEQUENCE: 1499

Gly Tyr Pro Ile Lys Ala Pro Lys
1               5

<210> SEQ ID NO 1500
<211> LENGTH: 7
<212> TYPE: PRT
<213> ORGANISM: Homo sapiens

<400> SEQUENCE: 1500

Pro Lys Leu Pro Gly Gly Tyr
1               5

<210> SEQ ID NO 1501
<211> LENGTH: 13
<212> TYPE: PRT
<213> ORGANISM: Homo sapiens

<400> SEQUENCE: 1501

Tyr Thr Thr Gly Lys Leu Pro Tyr Gly Tyr Gly Pro Gly
1               5                   10

<210> SEQ ID NO 1502
<211> LENGTH: 21
<212> TYPE: PRT
<213> ORGANISM: Homo sapiens

<400> SEQUENCE: 1502

Tyr Thr Thr Gly Lys Leu Pro Tyr Gly Tyr Gly Pro Gly Gly Val Ala
1               5                   10                  15

Gly Ala Ala Gly Lys
            20

<210> SEQ ID NO 1503
<211> LENGTH: 10
<212> TYPE: PRT
<213> ORGANISM: Homo sapiens

<400> SEQUENCE: 1503

Thr Thr Gly Lys Leu Pro Tyr Gly Tyr Gly
1               5                   10

<210> SEQ ID NO 1504
<211> LENGTH: 20
<212> TYPE: PRT
<213> ORGANISM: Homo sapiens

<400> SEQUENCE: 1504

Thr Thr Gly Lys Leu Pro Tyr Gly Tyr Gly Pro Gly Gly Val Ala Gly
1               5                   10                  15

Ala Ala Gly Lys
            20

<210> SEQ ID NO 1505
<211> LENGTH: 16
<212> TYPE: PRT
<213> ORGANISM: Homo sapiens

<400> SEQUENCE: 1505

Leu Pro Tyr Gly Tyr Gly Pro Gly Gly Val Ala Gly Ala Ala Gly Lys
1               5                   10                  15
```

<210> SEQ ID NO 1506
<211> LENGTH: 13
<212> TYPE: PRT
<213> ORGANISM: Homo sapiens

<400> SEQUENCE: 1506

Gly Tyr Gly Pro Gly Gly Val Ala Gly Ala Ala Gly Lys
1               5                   10

<210> SEQ ID NO 1507
<211> LENGTH: 12
<212> TYPE: PRT
<213> ORGANISM: Homo sapiens

<400> SEQUENCE: 1507

Tyr Gly Pro Gly Gly Val Ala Gly Ala Ala Gly Lys
1               5                   10

<210> SEQ ID NO 1508
<211> LENGTH: 20
<212> TYPE: PRT
<213> ORGANISM: Homo sapiens

<400> SEQUENCE: 1508

Ala Gly Tyr Pro Thr Gly Thr Gly Val Gly Pro Gln Ala Ala Ala
1               5                   10                  15

Ala Ala Ala Lys
            20

<210> SEQ ID NO 1509
<211> LENGTH: 14
<212> TYPE: PRT
<213> ORGANISM: Homo sapiens

<400> SEQUENCE: 1509

Thr Gly Val Gly Pro Gln Ala Ala Ala Ala Ala Ala Ala Lys
1               5                   10

<210> SEQ ID NO 1510
<211> LENGTH: 10
<212> TYPE: PRT
<213> ORGANISM: Homo sapiens

<400> SEQUENCE: 1510

Pro Gln Ala Ala Ala Ala Ala Ala Ala Lys
1               5                   10

<210> SEQ ID NO 1511
<211> LENGTH: 29
<212> TYPE: PRT
<213> ORGANISM: Homo sapiens

<400> SEQUENCE: 1511

Phe Gly Ala Gly Ala Ala Gly Val Leu Pro Gly Val Gly Gly Ala Gly
1               5                   10                  15

Val Pro Gly Val Pro Gly Ala Ile Pro Gly Ile Gly Gly
            20                  25

<210> SEQ ID NO 1512
<211> LENGTH: 38
<212> TYPE: PRT
<213> ORGANISM: Homo sapiens -continued

<400> SEQUENCE: 1512

Phe Gly Ala Gly Ala Ala Gly Val Leu Pro Gly Val Gly Ala Gly
1               5                   10                  15

Val Pro Gly Val Pro Gly Ala Ile Pro Gly Ile Gly Ile Ala Gly
            20                  25                  30

Val Gly Thr Pro Ala Ala
            35

<210> SEQ ID NO 1513
<211> LENGTH: 16
<212> TYPE: PRT
<213> ORGANISM: Homo sapiens

<400> SEQUENCE: 1513

Gly Val Leu Pro Gly Val Gly Gly Ala Gly Val Pro Gly Val Pro Gly
1               5                   10                  15

<210> SEQ ID NO 1514
<211> LENGTH: 22
<212> TYPE: PRT
<213> ORGANISM: Homo sapiens

<400> SEQUENCE: 1514

Val Leu Pro Gly Val Gly Gly Ala Gly Val Pro Gly Val Pro Gly Ala
1               5                   10                  15

Ile Pro Gly Ile Gly Gly
            20

<210> SEQ ID NO 1515
<211> LENGTH: 30
<212> TYPE: PRT
<213> ORGANISM: Homo sapiens

<400> SEQUENCE: 1515

Val Leu Pro Gly Val Gly Gly Ala Gly Val Pro Gly Val Pro Gly Ala
1               5                   10                  15

Ile Pro Gly Ile Gly Gly Ile Ala Gly Val Gly Thr Pro Ala
            20                  25                  30

<210> SEQ ID NO 1516
<211> LENGTH: 31
<212> TYPE: PRT
<213> ORGANISM: Homo sapiens

<400> SEQUENCE: 1516

Val Leu Pro Gly Val Gly Gly Ala Gly Val Pro Gly Val Pro Gly Ala
1               5                   10                  15

Ile Pro Gly Ile Gly Gly Ile Ala Gly Val Gly Thr Pro Ala Ala
            20                  25                  30

<210> SEQ ID NO 1517
<211> LENGTH: 13
<212> TYPE: PRT
<213> ORGANISM: Homo sapiens

<400> SEQUENCE: 1517

Gly Ala Gly Val Pro Gly Val Pro Gly Ala Ile Pro Gly
1               5                   10

<210> SEQ ID NO 1518
<211> LENGTH: 14
<212> TYPE: PRT

<213> ORGANISM: Homo sapiens

<400> SEQUENCE: 1518

Ala Gly Val Pro Gly Val Pro Gly Ala Ile Pro Gly Ile Gly
1               5                   10

<210> SEQ ID NO 1519
<211> LENGTH: 14
<212> TYPE: PRT
<213> ORGANISM: Homo sapiens

<400> SEQUENCE: 1519

Ala Gly Val Pro Gly Val Pro Gly Ala Ile Pro Gly Ile Gly
1               5                   10

<210> SEQ ID NO 1520
<211> LENGTH: 15
<212> TYPE: PRT
<213> ORGANISM: Homo sapiens

<400> SEQUENCE: 1520

Ala Gly Val Pro Gly Val Pro Gly Ala Ile Pro Gly Ile Gly Gly
1               5                   10                  15

<210> SEQ ID NO 1521
<211> LENGTH: 18
<212> TYPE: PRT
<213> ORGANISM: Homo sapiens

<400> SEQUENCE: 1521

Ala Gly Val Pro Gly Val Pro Gly Ala Ile Pro Gly Ile Gly Gly Ile
1               5                   10                  15
Ala Gly

<210> SEQ ID NO 1522
<211> LENGTH: 23
<212> TYPE: PRT
<213> ORGANISM: Homo sapiens

<400> SEQUENCE: 1522

Ala Gly Val Pro Gly Val Pro Gly Ala Ile Pro Gly Ile Gly Gly Ile
1               5                   10                  15
Ala Gly Val Gly Thr Pro Ala
            20

<210> SEQ ID NO 1523
<211> LENGTH: 14
<212> TYPE: PRT
<213> ORGANISM: Homo sapiens

<400> SEQUENCE: 1523

Gly Val Pro Gly Val Pro Gly Ala Ile Pro Gly Ile Gly Gly
1               5                   10

<210> SEQ ID NO 1524
<211> LENGTH: 16
<212> TYPE: PRT
<213> ORGANISM: Homo sapiens

<400> SEQUENCE: 1524

Gly Val Pro Gly Val Pro Gly Ala Ile Pro Gly Ile Gly Gly Ile Ala
1               5                   10                  15

```
<210> SEQ ID NO 1525
<211> LENGTH: 19
<212> TYPE: PRT
<213> ORGANISM: Homo sapiens

<400> SEQUENCE: 1525

Gly Val Pro Gly Val Pro Gly Ala Ile Pro Gly Ile Gly Gly Ile Ala
1               5                   10                  15

Gly Val Gly

<210> SEQ ID NO 1526
<211> LENGTH: 13
<212> TYPE: PRT
<213> ORGANISM: Homo sapiens

<400> SEQUENCE: 1526

Val Pro Gly Val Pro Gly Ala Ile Pro Gly Ile Gly Gly
1               5                   10

<210> SEQ ID NO 1527
<211> LENGTH: 19
<212> TYPE: PRT
<213> ORGANISM: Homo sapiens

<400> SEQUENCE: 1527

Gly Val Pro Gly Ala Ile Pro Gly Ile Gly Gly Ile Ala Gly Val Gly
1               5                   10                  15

Thr Pro Ala

<210> SEQ ID NO 1528
<211> LENGTH: 15
<212> TYPE: PRT
<213> ORGANISM: Homo sapiens

<400> SEQUENCE: 1528

Val Pro Gly Ala Ile Pro Gly Ile Gly Gly Ile Ala Gly Val Gly
1               5                   10                  15

<210> SEQ ID NO 1529
<211> LENGTH: 18
<212> TYPE: PRT
<213> ORGANISM: Homo sapiens

<400> SEQUENCE: 1529

Val Pro Gly Ala Ile Pro Gly Ile Gly Gly Ile Ala Gly Val Gly Thr
1               5                   10                  15

Pro Ala

<210> SEQ ID NO 1530
<211> LENGTH: 20
<212> TYPE: PRT
<213> ORGANISM: Homo sapiens

<400> SEQUENCE: 1530

Val Pro Gly Ala Ile Pro Gly Ile Gly Gly Ile Ala Gly Val Gly Thr
1               5                   10                  15

Pro Ala Ala Ala
            20

<210> SEQ ID NO 1531
<211> LENGTH: 28
<212> TYPE: PRT
<213> ORGANISM: Homo sapiens
```

```
<400> SEQUENCE: 1531

Val Pro Gly Ala Ile Pro Gly Ile Gly Ile Ala Gly Val Gly Thr
1               5                   10                  15

Pro Ala Ala Ala Ala Ala Ala Ala Ala Ala Lys
            20                  25

<210> SEQ ID NO 1532
<211> LENGTH: 12
<212> TYPE: PRT
<213> ORGANISM: Homo sapiens

<400> SEQUENCE: 1532

Ala Ile Pro Gly Ile Gly Gly Ile Ala Gly Val Gly
1               5                   10

<210> SEQ ID NO 1533
<211> LENGTH: 15
<212> TYPE: PRT
<213> ORGANISM: Homo sapiens

<400> SEQUENCE: 1533

Ala Ile Pro Gly Ile Gly Gly Ile Ala Gly Val Gly Thr Pro Ala
1               5                   10                  15

<210> SEQ ID NO 1534
<211> LENGTH: 16
<212> TYPE: PRT
<213> ORGANISM: Homo sapiens

<400> SEQUENCE: 1534

Ala Ile Pro Gly Ile Gly Gly Ile Ala Gly Val Gly Thr Pro Ala Ala
1               5                   10                  15

<210> SEQ ID NO 1535
<211> LENGTH: 17
<212> TYPE: PRT
<213> ORGANISM: Homo sapiens

<400> SEQUENCE: 1535

Ala Ile Pro Gly Ile Gly Gly Ile Ala Gly Val Gly Thr Pro Ala Ala
1               5                   10                  15

Ala

<210> SEQ ID NO 1536
<211> LENGTH: 20
<212> TYPE: PRT
<213> ORGANISM: Homo sapiens

<400> SEQUENCE: 1536

Ala Ile Pro Gly Ile Gly Gly Ile Ala Gly Val Gly Thr Pro Ala Ala
1               5                   10                  15

Ala Ala Ala Ala
            20

<210> SEQ ID NO 1537
<211> LENGTH: 25
<212> TYPE: PRT
<213> ORGANISM: Homo sapiens

<400> SEQUENCE: 1537

Ala Ile Pro Gly Ile Gly Gly Ile Ala Gly Val Gly Thr Pro Ala Ala
1               5                   10                  15
```

Ala Ala Ala Ala Ala Ala Ala Ala Lys
            20                  25

<210> SEQ ID NO 1538
<211> LENGTH: 16
<212> TYPE: PRT
<213> ORGANISM: Homo sapiens

<400> SEQUENCE: 1538

Ile Pro Gly Ile Gly Gly Ile Ala Gly Val Gly Thr Pro Ala Ala Ala
1               5                   10                  15

<210> SEQ ID NO 1539
<211> LENGTH: 14
<212> TYPE: PRT
<213> ORGANISM: Homo sapiens

<400> SEQUENCE: 1539

Ile Gly Gly Ile Ala Gly Val Gly Thr Pro Ala Ala Ala Ala
1               5                   10

<210> SEQ ID NO 1540
<211> LENGTH: 12
<212> TYPE: PRT
<213> ORGANISM: Homo sapiens

<400> SEQUENCE: 1540

Gly Ile Ala Gly Val Gly Thr Pro Ala Ala Ala Ala
1               5                   10

<210> SEQ ID NO 1541
<211> LENGTH: 16
<212> TYPE: PRT
<213> ORGANISM: Homo sapiens

<400> SEQUENCE: 1541

Gly Ile Ala Gly Val Gly Thr Pro Ala Ala Ala Ala Ala Ala Ala Ala
1               5                   10                  15

<210> SEQ ID NO 1542
<211> LENGTH: 19
<212> TYPE: PRT
<213> ORGANISM: Homo sapiens

<400> SEQUENCE: 1542

Gly Ile Ala Gly Val Gly Thr Pro Ala Ala Ala Ala Ala Ala Ala Ala
1               5                   10                  15

Ala Ala Lys

<210> SEQ ID NO 1543
<211> LENGTH: 15
<212> TYPE: PRT
<213> ORGANISM: Homo sapiens

<400> SEQUENCE: 1543

Ile Ala Gly Val Gly Thr Pro Ala Ala Ala Ala Ala Ala Ala Ala
1               5                   10                  15

<210> SEQ ID NO 1544
<211> LENGTH: 16
<212> TYPE: PRT
<213> ORGANISM: Homo sapiens

<400> SEQUENCE: 1544

Ile Ala Gly Val Gly Thr Pro Ala Ala Ala Ala Ala Ala Ala Ala
1               5                   10                  15

<210> SEQ ID NO 1545
<211> LENGTH: 18
<212> TYPE: PRT
<213> ORGANISM: Homo sapiens

<400> SEQUENCE: 1545

Ile Ala Gly Val Gly Thr Pro Ala Ala Ala Ala Ala Ala Ala Ala
1               5                   10                  15

Ala Lys

<210> SEQ ID NO 1546
<211> LENGTH: 13
<212> TYPE: PRT
<213> ORGANISM: Homo sapiens

<400> SEQUENCE: 1546

Thr Pro Ala Ala Ala Ala Ala Ala Ala Ala Ala Ala Lys
1               5                   10

<210> SEQ ID NO 1547
<211> LENGTH: 12
<212> TYPE: PRT
<213> ORGANISM: Homo sapiens

<400> SEQUENCE: 1547

Pro Ala Ala Ala Ala Ala Ala Ala Ala Ala Ala Lys
1               5                   10

<210> SEQ ID NO 1548
<211> LENGTH: 11
<212> TYPE: PRT
<213> ORGANISM: Homo sapiens

<400> SEQUENCE: 1548

Ala Ala Ala Ala Ala Ala Ala Ala Ala Ala Lys
1               5                   10

<210> SEQ ID NO 1549
<211> LENGTH: 10
<212> TYPE: PRT
<213> ORGANISM: Homo sapiens

<400> SEQUENCE: 1549

Ala Ala Ala Ala Ala Ala Ala Ala Ala Lys
1               5                   10

<210> SEQ ID NO 1550
<211> LENGTH: 9
<212> TYPE: PRT
<213> ORGANISM: Homo sapiens

<400> SEQUENCE: 1550

Ala Ala Ala Ala Ala Ala Ala Ala Lys
1               5

<210> SEQ ID NO 1551
<211> LENGTH: 10
<212> TYPE: PRT
<213> ORGANISM: Homo sapiens

<400> SEQUENCE: 1551

Ala Ala Ala Ala Ala Ala Ala Lys Ala
1               5                   10

<210> SEQ ID NO 1552
<211> LENGTH: 8
<212> TYPE: PRT
<213> ORGANISM: Homo sapiens

<400> SEQUENCE: 1552

Ala Ala Ala Ala Ala Ala Ala Lys
1               5

<210> SEQ ID NO 1553
<211> LENGTH: 18
<212> TYPE: PRT
<213> ORGANISM: Homo sapiens

<400> SEQUENCE: 1553

Leu Val Pro Gly Gly Pro Gly Phe Gly Pro Gly Val Val Gly Val Pro
1               5                   10                  15

Gly Ala

<210> SEQ ID NO 1554
<211> LENGTH: 13
<212> TYPE: PRT
<213> ORGANISM: Homo sapiens

<400> SEQUENCE: 1554

Gly Pro Gly Phe Gly Pro Gly Val Val Gly Val Pro Gly
1               5                   10

<210> SEQ ID NO 1555
<211> LENGTH: 20
<212> TYPE: PRT
<213> ORGANISM: Homo sapiens

<400> SEQUENCE: 1555

Gly Pro Gly Phe Gly Pro Gly Val Val Gly Val Pro Gly Ala Gly Val
1               5                   10                  15

Pro Gly Val Gly
            20

<210> SEQ ID NO 1556
<211> LENGTH: 31
<212> TYPE: PRT
<213> ORGANISM: Homo sapiens

<400> SEQUENCE: 1556

Gly Pro Gly Phe Gly Pro Gly Val Val Gly Val Pro Gly Ala Gly Val
1               5                   10                  15

Pro Gly Val Gly Val Pro Gly Ala Gly Ile Pro Val Val Pro Gly
            20                  25                  30

<210> SEQ ID NO 1557
<211> LENGTH: 12
<212> TYPE: PRT
<213> ORGANISM: Homo sapiens

<400> SEQUENCE: 1557

Pro Gly Phe Gly Pro Gly Val Val Gly Val Pro Gly
1               5                   10

<210> SEQ ID NO 1558
<211> LENGTH: 13
<212> TYPE: PRT
<213> ORGANISM: Homo sapiens

<400> SEQUENCE: 1558

Pro Gly Phe Gly Pro Gly Val Val Gly Val Pro Gly Ala
1               5                   10

<210> SEQ ID NO 1559
<211> LENGTH: 14
<212> TYPE: PRT
<213> ORGANISM: Homo sapiens

<400> SEQUENCE: 1559

Pro Gly Phe Gly Pro Gly Val Val Gly Val Pro Gly Ala Gly
1               5                   10

<210> SEQ ID NO 1560
<211> LENGTH: 13
<212> TYPE: PRT
<213> ORGANISM: Homo sapiens

<400> SEQUENCE: 1560

Pro Gly Val Val Gly Val Pro Gly Ala Gly Val Pro Gly
1               5                   10

<210> SEQ ID NO 1561
<211> LENGTH: 18
<212> TYPE: PRT
<213> ORGANISM: Homo sapiens

<400> SEQUENCE: 1561

Pro Gly Val Val Gly Val Pro Gly Ala Gly Val Pro Gly Val Gly
1               5                   10                  15

Pro Gly

<210> SEQ ID NO 1562
<211> LENGTH: 27
<212> TYPE: PRT
<213> ORGANISM: Homo sapiens

<400> SEQUENCE: 1562

Pro Gly Val Val Gly Val Pro Gly Ala Gly Val Pro Gly Val Gly Val
1               5                   10                  15

Pro Gly Ala Gly Ile Pro Val Val Pro Gly Ala
            20                  25

<210> SEQ ID NO 1563
<211> LENGTH: 17
<212> TYPE: PRT
<213> ORGANISM: Homo sapiens

<400> SEQUENCE: 1563

Val Val Gly Val Pro Gly Ala Gly Val Pro Gly Val Gly Val Pro Gly
1               5                   10                  15

Ala

<210> SEQ ID NO 1564
<211> LENGTH: 39
<212> TYPE: PRT
<213> ORGANISM: Homo sapiens

<400> SEQUENCE: 1564

Val Gly Val Pro Gly Ala Gly Val Pro Gly Val Gly Val Pro Gly Ala
1               5                   10                  15

Gly Ile Pro Val Val Pro Gly Ala Gly Ile Pro Gly Ala Ala Val Pro
            20                  25                  30

Gly Val Val Ser Pro Glu Ala
        35

<210> SEQ ID NO 1565
<211> LENGTH: 18
<212> TYPE: PRT
<213> ORGANISM: Homo sapiens

<400> SEQUENCE: 1565

Ala Gly Val Pro Gly Val Gly Val Pro Gly Ala Gly Ile Pro Val Val
1               5                   10                  15

Pro Gly

<210> SEQ ID NO 1566
<211> LENGTH: 17
<212> TYPE: PRT
<213> ORGANISM: Homo sapiens

<400> SEQUENCE: 1566

Gly Val Pro Gly Val Gly Val Pro Gly Ala Gly Ile Pro Val Val Pro
1               5                   10                  15

Gly

<210> SEQ ID NO 1567
<211> LENGTH: 18
<212> TYPE: PRT
<213> ORGANISM: Homo sapiens

<400> SEQUENCE: 1567

Gly Val Pro Gly Val Gly Val Pro Gly Ala Gly Ile Pro Val Val Pro
1               5                   10                  15

Gly Ala

<210> SEQ ID NO 1568
<211> LENGTH: 16
<212> TYPE: PRT
<213> ORGANISM: Homo sapiens

<400> SEQUENCE: 1568

Val Pro Gly Val Gly Val Pro Gly Ala Gly Ile Pro Val Val Pro Gly
1               5                   10                  15

<210> SEQ ID NO 1569
<211> LENGTH: 13
<212> TYPE: PRT
<213> ORGANISM: Homo sapiens

<400> SEQUENCE: 1569

Val Gly Val Pro Gly Ala Gly Ile Pro Val Val Pro Gly
1               5                   10

<210> SEQ ID NO 1570
<211> LENGTH: 18
<212> TYPE: PRT
<213> ORGANISM: Homo sapiens

<400> SEQUENCE: 1570

Val Gly Val Pro Gly Ala Gly Ile Pro Val Val Pro Gly Ala Gly Ile
1               5                   10                  15

Pro Gly

<210> SEQ ID NO 1571
<211> LENGTH: 11
<212> TYPE: PRT
<213> ORGANISM: Homo sapiens

<400> SEQUENCE: 1571

Val Pro Gly Ala Gly Ile Pro Val Val Pro Gly
1               5                   10

<210> SEQ ID NO 1572
<211> LENGTH: 13
<212> TYPE: PRT
<213> ORGANISM: Homo sapiens

<400> SEQUENCE: 1572

Ala Gly Ile Pro Val Val Pro Gly Ala Gly Ile Pro Gly
1               5                   10

<210> SEQ ID NO 1573
<211> LENGTH: 27
<212> TYPE: PRT
<213> ORGANISM: Homo sapiens

<400> SEQUENCE: 1573

Ala Gly Ile Pro Val Val Pro Gly Ala Gly Ile Pro Gly Ala Ala Val
1               5                   10                  15

Pro Gly Val Val Ser Pro Glu Ala Ala Ala Lys
            20                  25

<210> SEQ ID NO 1574
<211> LENGTH: 12
<212> TYPE: PRT
<213> ORGANISM: Homo sapiens

<400> SEQUENCE: 1574

Gly Ile Pro Val Val Pro Gly Ala Gly Ile Pro Gly
1               5                   10

<210> SEQ ID NO 1575
<211> LENGTH: 17
<212> TYPE: PRT
<213> ORGANISM: Homo sapiens

<400> SEQUENCE: 1575

Ile Pro Gly Ala Ala Val Pro Gly Val Val Ser Pro Glu Ala Ala Ala
1               5                   10                  15

Lys

<210> SEQ ID NO 1576
<211> LENGTH: 15
<212> TYPE: PRT
<213> ORGANISM: Homo sapiens

<400> SEQUENCE: 1576

Gly Ala Ala Val Pro Gly Val Val Ser Pro Glu Ala Ala Ala Lys
1               5                   10                  15

<210> SEQ ID NO 1577
<211> LENGTH: 13

<212> TYPE: PRT
<213> ORGANISM: Homo sapiens

<400> SEQUENCE: 1577

Ala Val Pro Gly Val Val Ser Pro Glu Ala Ala Ala Lys
1               5                   10

<210> SEQ ID NO 1578
<211> LENGTH: 12
<212> TYPE: PRT
<213> ORGANISM: Homo sapiens

<400> SEQUENCE: 1578

Val Pro Gly Val Val Ser Pro Glu Ala Ala Ala Lys
1               5                   10

<210> SEQ ID NO 1579
<211> LENGTH: 8
<212> TYPE: PRT
<213> ORGANISM: Homo sapiens

<400> SEQUENCE: 1579

Tyr Gly Ala Arg Pro Gly Val Gly
1               5

<210> SEQ ID NO 1580
<211> LENGTH: 10
<212> TYPE: PRT
<213> ORGANISM: Homo sapiens

<400> SEQUENCE: 1580

Tyr Gly Ala Arg Pro Gly Val Gly Val Gly
1               5                   10

<210> SEQ ID NO 1581
<211> LENGTH: 14
<212> TYPE: PRT
<213> ORGANISM: Homo sapiens

<400> SEQUENCE: 1581

Tyr Gly Ala Arg Pro Gly Val Gly Val Gly Gly Ile Pro Thr
1               5                   10

<210> SEQ ID NO 1582
<211> LENGTH: 15
<212> TYPE: PRT
<213> ORGANISM: Homo sapiens

<400> SEQUENCE: 1582

Tyr Gly Ala Arg Pro Gly Val Gly Val Gly Gly Ile Pro Thr Tyr
1               5                   10                  15

<210> SEQ ID NO 1583
<211> LENGTH: 16
<212> TYPE: PRT
<213> ORGANISM: Homo sapiens

<400> SEQUENCE: 1583

Tyr Gly Ala Arg Pro Gly Val Gly Val Gly Gly Ile Pro Thr Tyr Gly
1               5                   10                  15

<210> SEQ ID NO 1584
<211> LENGTH: 18
<212> TYPE: PRT
<213> ORGANISM: Homo sapiens

<400> SEQUENCE: 1584

Tyr Gly Ala Arg Pro Gly Val Gly Val Gly Gly Ile Pro Thr Tyr Gly
1               5                   10                  15

Val Gly

<210> SEQ ID NO 1585
<211> LENGTH: 19
<212> TYPE: PRT
<213> ORGANISM: Homo sapiens

<400> SEQUENCE: 1585

Tyr Gly Ala Arg Pro Gly Val Gly Val Gly Gly Ile Pro Thr Tyr Gly
1               5                   10                  15

Val Gly Ala

<210> SEQ ID NO 1586
<211> LENGTH: 20
<212> TYPE: PRT
<213> ORGANISM: Homo sapiens

<400> SEQUENCE: 1586

Tyr Gly Ala Arg Pro Gly Val Gly Val Gly Gly Ile Pro Thr Tyr Gly
1               5                   10                  15

Val Gly Ala Gly
            20

<210> SEQ ID NO 1587
<211> LENGTH: 8
<212> TYPE: PRT
<213> ORGANISM: Homo sapiens

<400> SEQUENCE: 1587

Gly Ala Arg Pro Gly Val Gly Val
1               5

<210> SEQ ID NO 1588
<211> LENGTH: 10
<212> TYPE: PRT
<213> ORGANISM: Homo sapiens

<400> SEQUENCE: 1588

Gly Ala Arg Pro Gly Val Gly Val Gly Gly
1               5                   10

<210> SEQ ID NO 1589
<211> LENGTH: 12
<212> TYPE: PRT
<213> ORGANISM: Homo sapiens

<400> SEQUENCE: 1589

Gly Ala Arg Pro Gly Val Gly Val Gly Gly Ile Pro
1               5                   10

<210> SEQ ID NO 1590
<211> LENGTH: 14
<212> TYPE: PRT
<213> ORGANISM: Homo sapiens

<400> SEQUENCE: 1590

Gly Ala Arg Pro Gly Val Gly Val Gly Gly Ile Pro Thr Tyr
1               5                   10

<210> SEQ ID NO 1591
<211> LENGTH: 16
<212> TYPE: PRT
<213> ORGANISM: Homo sapiens

<400> SEQUENCE: 1591

Gly Ala Arg Pro Gly Val Gly Val Gly Gly Ile Pro Thr Tyr Gly Val
1               5                   10                  15

<210> SEQ ID NO 1592
<211> LENGTH: 17
<212> TYPE: PRT
<213> ORGANISM: Homo sapiens

<400> SEQUENCE: 1592

Gly Ala Arg Pro Gly Val Gly Val Gly Gly Ile Pro Thr Tyr Gly Val
1               5                   10                  15

Gly

<210> SEQ ID NO 1593
<211> LENGTH: 21
<212> TYPE: PRT
<213> ORGANISM: Homo sapiens

<400> SEQUENCE: 1593

Gly Ala Arg Pro Gly Val Gly Val Gly Gly Ile Pro Thr Tyr Gly Val
1               5                   10                  15

Gly Ala Gly Gly Phe
            20

<210> SEQ ID NO 1594
<211> LENGTH: 24
<212> TYPE: PRT
<213> ORGANISM: Homo sapiens

<400> SEQUENCE: 1594

Gly Ala Arg Pro Gly Val Gly Val Gly Gly Ile Pro Thr Tyr Gly Val
1               5                   10                  15

Gly Ala Gly Gly Phe Pro Gly Phe
            20

<210> SEQ ID NO 1595
<211> LENGTH: 25
<212> TYPE: PRT
<213> ORGANISM: Homo sapiens

<400> SEQUENCE: 1595

Gly Ala Arg Pro Gly Val Gly Val Gly Gly Ile Pro Thr Tyr Gly Val
1               5                   10                  15

Gly Ala Gly Gly Phe Pro Gly Phe Gly
            20                  25

<210> SEQ ID NO 1596
<211> LENGTH: 29
<212> TYPE: PRT
<213> ORGANISM: Homo sapiens

<400> SEQUENCE: 1596

Gly Ala Arg Pro Gly Val Gly Val Gly Gly Ile Pro Thr Tyr Gly Val
1               5                   10                  15

Gly Ala Gly Gly Phe Pro Gly Phe Gly Val Gly Val Gly
            20                  25

<210> SEQ ID NO 1597
<211> LENGTH: 9
<212> TYPE: PRT
<213> ORGANISM: Homo sapiens

<400> SEQUENCE: 1597

Ala Arg Pro Gly Val Gly Val Gly Gly
1               5

<210> SEQ ID NO 1598
<211> LENGTH: 11
<212> TYPE: PRT
<213> ORGANISM: Homo sapiens

<400> SEQUENCE: 1598

Ala Arg Pro Gly Val Gly Val Gly Gly Ile Pro
1               5                   10

<210> SEQ ID NO 1599
<211> LENGTH: 13
<212> TYPE: PRT
<213> ORGANISM: Homo sapiens

<400> SEQUENCE: 1599

Ala Arg Pro Gly Val Gly Val Gly Gly Ile Pro Thr Tyr
1               5                   10

<210> SEQ ID NO 1600
<211> LENGTH: 17
<212> TYPE: PRT
<213> ORGANISM: Homo sapiens

<400> SEQUENCE: 1600

Ala Arg Pro Gly Val Gly Val Gly Gly Ile Pro Thr Tyr Gly Val Gly
1               5                   10                  15

Ala

<210> SEQ ID NO 1601
<211> LENGTH: 19
<212> TYPE: PRT
<213> ORGANISM: Homo sapiens

<400> SEQUENCE: 1601

Ala Arg Pro Gly Val Gly Val Gly Gly Ile Pro Thr Tyr Gly Val Gly
1               5                   10                  15

Ala Gly Gly

<210> SEQ ID NO 1602
<211> LENGTH: 22
<212> TYPE: PRT
<213> ORGANISM: Homo sapiens

<400> SEQUENCE: 1602

Ala Arg Pro Gly Val Gly Val Gly Gly Ile Pro Thr Tyr Gly Val Gly
1               5                   10                  15

Ala Gly Gly Phe Pro Gly
            20

<210> SEQ ID NO 1603
<211> LENGTH: 23
<212> TYPE: PRT
<213> ORGANISM: Homo sapiens

<400> SEQUENCE: 1603

Ala Arg Pro Gly Val Gly Val Gly Gly Ile Pro Thr Tyr Gly Val Gly
1               5                   10                  15
Ala Gly Gly Phe Pro Gly Phe
            20

<210> SEQ ID NO 1604
<211> LENGTH: 7
<212> TYPE: PRT
<213> ORGANISM: Homo sapiens

<400> SEQUENCE: 1604

Arg Pro Gly Val Gly Val Gly
1               5

<210> SEQ ID NO 1605
<211> LENGTH: 8
<212> TYPE: PRT
<213> ORGANISM: Homo sapiens

<400> SEQUENCE: 1605

Arg Pro Gly Val Gly Val Gly Gly
1               5

<210> SEQ ID NO 1606
<211> LENGTH: 11
<212> TYPE: PRT
<213> ORGANISM: Homo sapiens

<400> SEQUENCE: 1606

Pro Gly Val Gly Val Gly Gly Ile Pro Thr Tyr
1               5                   10

<210> SEQ ID NO 1607
<211> LENGTH: 12
<212> TYPE: PRT
<213> ORGANISM: Homo sapiens

<400> SEQUENCE: 1607

Pro Gly Val Gly Val Gly Gly Ile Pro Thr Tyr Gly
1               5                   10

<210> SEQ ID NO 1608
<211> LENGTH: 16
<212> TYPE: PRT
<213> ORGANISM: Homo sapiens

<400> SEQUENCE: 1608

Pro Gly Val Gly Val Gly Gly Ile Pro Thr Tyr Gly Val Gly Ala Gly
1               5                   10                  15

<210> SEQ ID NO 1609
<211> LENGTH: 12
<212> TYPE: PRT
<213> ORGANISM: Homo sapiens

<400> SEQUENCE: 1609

Val Gly Gly Ile Pro Thr Tyr Gly Val Gly Ala Gly
1               5                   10

<210> SEQ ID NO 1610
<211> LENGTH: 21
<212> TYPE: PRT

-continued

<213> ORGANISM: Homo sapiens

<400> SEQUENCE: 1610

Gly Val Gly Ala Gly Gly Phe Pro Gly Phe Gly Val Gly Val Gly Gly
1               5                   10                  15

Ile Pro Gly Val Ala
            20

<210> SEQ ID NO 1611
<211> LENGTH: 14
<212> TYPE: PRT
<213> ORGANISM: Homo sapiens

<400> SEQUENCE: 1611

Val Gly Ala Gly Gly Phe Pro Gly Phe Gly Val Gly Val Gly
1               5                   10

<210> SEQ ID NO 1612
<211> LENGTH: 33
<212> TYPE: PRT
<213> ORGANISM: Homo sapiens

<400> SEQUENCE: 1612

Val Gly Val Gly Gly Ile Pro Gly Val Ala Gly Val Pro Ser Val Gly
1               5                   10                  15

Gly Val Pro Gly Val Gly Gly Val Pro Gly Val Gly Ile Ser Pro Glu
            20                  25                  30

Ala

<210> SEQ ID NO 1613
<211> LENGTH: 18
<212> TYPE: PRT
<213> ORGANISM: Homo sapiens

<400> SEQUENCE: 1613

Val Ala Gly Val Pro Ser Val Gly Gly Val Pro Gly Val Gly Gly Val
1               5                   10                  15

Pro Gly

<210> SEQ ID NO 1614
<211> LENGTH: 25
<212> TYPE: PRT
<213> ORGANISM: Homo sapiens

<400> SEQUENCE: 1614

Val Ala Gly Val Pro Ser Val Gly Gly Val Pro Gly Val Gly Gly Val
1               5                   10                  15

Pro Gly Val Gly Ile Ser Pro Glu Ala
            20                  25

<210> SEQ ID NO 1615
<211> LENGTH: 20
<212> TYPE: PRT
<213> ORGANISM: Homo sapiens

<400> SEQUENCE: 1615

Ser Val Gly Gly Val Pro Gly Val Gly Gly Val Pro Gly Val Gly Ile
1               5                   10                  15

Ser Pro Glu Ala
            20

<210> SEQ ID NO 1616
<211> LENGTH: 19
<212> TYPE: PRT
<213> ORGANISM: Homo sapiens

<400> SEQUENCE: 1616

Val Gly Gly Val Pro Gly Val Gly Gly Val Pro Gly Val Gly Ile Ser
1               5                   10                  15

Pro Glu Ala

<210> SEQ ID NO 1617
<211> LENGTH: 14
<212> TYPE: PRT
<213> ORGANISM: Homo sapiens

<400> SEQUENCE: 1617

Gly Val Pro Gly Val Gly Gly Val Pro Gly Val Gly Ile Ser
1               5                   10

<210> SEQ ID NO 1618
<211> LENGTH: 17
<212> TYPE: PRT
<213> ORGANISM: Homo sapiens

<400> SEQUENCE: 1618

Gly Val Pro Gly Val Gly Gly Val Pro Gly Val Gly Ile Ser Pro Glu
1               5                   10                  15

Ala

<210> SEQ ID NO 1619
<211> LENGTH: 19
<212> TYPE: PRT
<213> ORGANISM: Homo sapiens

<400> SEQUENCE: 1619

Gly Val Pro Gly Val Gly Gly Val Pro Gly Val Gly Ile Ser Pro Glu
1               5                   10                  15

Ala Gln Ala

<210> SEQ ID NO 1620
<211> LENGTH: 18
<212> TYPE: PRT
<213> ORGANISM: Homo sapiens

<400> SEQUENCE: 1620

Gly Val Pro Gly Val Gly Ile Ser Pro Glu Ala Gln Ala Ala Ala Ala
1               5                   10                  15

Ala Lys

<210> SEQ ID NO 1621
<211> LENGTH: 11
<212> TYPE: PRT
<213> ORGANISM: Homo sapiens

<400> SEQUENCE: 1621

Gly Val Gly Thr Pro Ala Ala Ala Ala Ala Lys
1               5                   10

<210> SEQ ID NO 1622
<211> LENGTH: 8
<212> TYPE: PRT
<213> ORGANISM: Homo sapiens

```
<400> SEQUENCE: 1622

Thr Pro Ala Ala Ala Ala Ala Lys
1               5

<210> SEQ ID NO 1623
<211> LENGTH: 14
<212> TYPE: PRT
<213> ORGANISM: Homo sapiens

<400> SEQUENCE: 1623

Phe Gly Leu Val Pro Gly Val Gly Val Ala Pro Gly Val Gly
1               5                   10

<210> SEQ ID NO 1624
<211> LENGTH: 18
<212> TYPE: PRT
<213> ORGANISM: Homo sapiens

<400> SEQUENCE: 1624

Phe Gly Leu Val Pro Gly Val Gly Val Ala Pro Gly Val Gly Val Ala
1               5                   10                  15

Pro Gly

<210> SEQ ID NO 1625
<211> LENGTH: 24
<212> TYPE: PRT
<213> ORGANISM: Homo sapiens

<400> SEQUENCE: 1625

Phe Gly Leu Val Pro Gly Val Gly Val Ala Pro Gly Val Gly Val Ala
1               5                   10                  15

Pro Gly Val Gly Val Ala Pro Gly
            20

<210> SEQ ID NO 1626
<211> LENGTH: 26
<212> TYPE: PRT
<213> ORGANISM: Homo sapiens

<400> SEQUENCE: 1626

Phe Gly Leu Val Pro Gly Val Gly Val Ala Pro Gly Val Gly Val Ala
1               5                   10                  15

Pro Gly Val Gly Val Ala Pro Gly Val Gly
            20                  25

<210> SEQ ID NO 1627
<211> LENGTH: 30
<212> TYPE: PRT
<213> ORGANISM: Homo sapiens

<400> SEQUENCE: 1627

Phe Gly Leu Val Pro Gly Val Gly Val Ala Pro Gly Val Gly Val Ala
1               5                   10                  15

Pro Gly Val Gly Val Ala Pro Gly Val Gly Leu Ala Pro Gly
            20                  25                  30

<210> SEQ ID NO 1628
<211> LENGTH: 36
<212> TYPE: PRT
<213> ORGANISM: Homo sapiens

<400> SEQUENCE: 1628
```

```
Phe Gly Leu Val Pro Gly Val Gly Val Ala Pro Gly Val Gly Val Ala
1               5                   10                  15

Pro Gly Val Gly Val Ala Pro Gly Val Gly Leu Ala Pro Gly Val Gly
                20                  25                  30

Val Ala Pro Gly
        35
```

<210> SEQ ID NO 1629
<211> LENGTH: 37
<212> TYPE: PRT
<213> ORGANISM: Homo sapiens

<400> SEQUENCE: 1629

```
Phe Gly Leu Val Pro Gly Val Gly Val Ala Pro Gly Val Gly Val Ala
1               5                   10                  15

Pro Gly Val Gly Val Ala Pro Gly Val Gly Leu Ala Pro Gly Val Gly
                20                  25                  30

Val Ala Pro Gly Val
        35
```

<210> SEQ ID NO 1630
<211> LENGTH: 42
<212> TYPE: PRT
<213> ORGANISM: Homo sapiens

<400> SEQUENCE: 1630

```
Phe Gly Leu Val Pro Gly Val Gly Val Ala Pro Gly Val Gly Val Ala
1               5                   10                  15

Pro Gly Val Gly Val Ala Pro Gly Val Gly Leu Ala Pro Gly Val Gly
                20                  25                  30

Val Ala Pro Gly Val Gly Val Ala Pro Gly
        35                  40
```

<210> SEQ ID NO 1631
<211> LENGTH: 11
<212> TYPE: PRT
<213> ORGANISM: Homo sapiens

<400> SEQUENCE: 1631

```
Gly Leu Val Pro Gly Val Gly Val Ala Pro Gly
1               5                   10
```

<210> SEQ ID NO 1632
<211> LENGTH: 12
<212> TYPE: PRT
<213> ORGANISM: Homo sapiens

<400> SEQUENCE: 1632

```
Gly Leu Val Pro Gly Val Gly Val Ala Pro Gly Val
1               5                   10
```

<210> SEQ ID NO 1633
<211> LENGTH: 15
<212> TYPE: PRT
<213> ORGANISM: Homo sapiens

<400> SEQUENCE: 1633

```
Gly Leu Val Pro Gly Val Gly Val Ala Pro Gly Val Gly Val Ala
1               5                   10                  15
```

<210> SEQ ID NO 1634
<211> LENGTH: 16

```
<212> TYPE: PRT
<213> ORGANISM: Homo sapiens

<400> SEQUENCE: 1634

Gly Leu Val Pro Gly Val Gly Val Ala Pro Gly Val Gly Val Ala Pro
1               5                   10                  15

<210> SEQ ID NO 1635
<211> LENGTH: 17
<212> TYPE: PRT
<213> ORGANISM: Homo sapiens

<400> SEQUENCE: 1635

Gly Leu Val Pro Gly Val Gly Val Ala Pro Gly Val Gly Val Ala Pro
1               5                   10                  15

Gly

<210> SEQ ID NO 1636
<211> LENGTH: 19
<212> TYPE: PRT
<213> ORGANISM: Homo sapiens

<400> SEQUENCE: 1636

Gly Leu Val Pro Gly Val Gly Val Ala Pro Gly Val Gly Val Ala Pro
1               5                   10                  15

Gly Val Gly

<210> SEQ ID NO 1637
<211> LENGTH: 23
<212> TYPE: PRT
<213> ORGANISM: Homo sapiens

<400> SEQUENCE: 1637

Gly Leu Val Pro Gly Val Gly Val Ala Pro Gly Val Gly Val Ala Pro
1               5                   10                  15

Gly Val Gly Val Ala Pro Gly
            20

<210> SEQ ID NO 1638
<211> LENGTH: 26
<212> TYPE: PRT
<213> ORGANISM: Homo sapiens

<400> SEQUENCE: 1638

Gly Leu Val Pro Gly Val Gly Val Ala Pro Gly Val Gly Val Ala Pro
1               5                   10                  15

Gly Val Gly Val Ala Pro Gly Val Gly Leu
            20                  25

<210> SEQ ID NO 1639
<211> LENGTH: 27
<212> TYPE: PRT
<213> ORGANISM: Homo sapiens

<400> SEQUENCE: 1639

Gly Leu Val Pro Gly Val Gly Val Ala Pro Gly Val Gly Val Ala Pro
1               5                   10                  15

Gly Val Gly Val Ala Pro Gly Val Gly Leu Ala
            20                  25

<210> SEQ ID NO 1640
<211> LENGTH: 29
```

```
<212> TYPE: PRT
<213> ORGANISM: Homo sapiens

<400> SEQUENCE: 1640

Gly Leu Val Pro Gly Val Gly Val Ala Pro Gly Val Gly Val Ala Pro
1               5                   10                  15

Gly Val Gly Val Ala Pro Gly Val Gly Leu Ala Pro Gly
            20                  25

<210> SEQ ID NO 1641
<211> LENGTH: 31
<212> TYPE: PRT
<213> ORGANISM: Homo sapiens

<400> SEQUENCE: 1641

Gly Leu Val Pro Gly Val Gly Val Ala Pro Gly Val Gly Val Ala Pro
1               5                   10                  15

Gly Val Gly Val Ala Pro Gly Val Gly Leu Ala Pro Gly Val Gly
            20                  25                  30

<210> SEQ ID NO 1642
<211> LENGTH: 33
<212> TYPE: PRT
<213> ORGANISM: Homo sapiens

<400> SEQUENCE: 1642

Gly Leu Val Pro Gly Val Gly Val Ala Pro Gly Val Gly Val Ala Pro
1               5                   10                  15

Gly Val Gly Val Ala Pro Gly Val Gly Leu Ala Pro Gly Val Gly Val
            20                  25                  30

Ala

<210> SEQ ID NO 1643
<211> LENGTH: 35
<212> TYPE: PRT
<213> ORGANISM: Homo sapiens

<400> SEQUENCE: 1643

Gly Leu Val Pro Gly Val Gly Val Ala Pro Gly Val Gly Val Ala Pro
1               5                   10                  15

Gly Val Gly Val Ala Pro Gly Val Gly Leu Ala Pro Gly Val Gly Val
            20                  25                  30

Ala Pro Gly
        35

<210> SEQ ID NO 1644
<211> LENGTH: 12
<212> TYPE: PRT
<213> ORGANISM: Homo sapiens

<400> SEQUENCE: 1644

Leu Val Pro Gly Val Gly Val Ala Pro Gly Val Gly
1               5                   10

<210> SEQ ID NO 1645
<211> LENGTH: 16
<212> TYPE: PRT
<213> ORGANISM: Homo sapiens

<400> SEQUENCE: 1645

Leu Val Pro Gly Val Gly Val Ala Pro Gly Val Gly Val Ala Pro Gly
1               5                   10                  15
```

<210> SEQ ID NO 1646
<211> LENGTH: 18
<212> TYPE: PRT
<213> ORGANISM: Homo sapiens

<400> SEQUENCE: 1646

Leu Val Pro Gly Val Gly Val Ala Pro Gly Val Gly Val Ala Pro Gly
1               5                   10                  15

Val Gly

<210> SEQ ID NO 1647
<211> LENGTH: 24
<212> TYPE: PRT
<213> ORGANISM: Homo sapiens

<400> SEQUENCE: 1647

Leu Val Pro Gly Val Gly Val Ala Pro Gly Val Gly Val Ala Pro Gly
1               5                   10                  15

Val Gly Val Ala Pro Gly Val Gly
            20

<210> SEQ ID NO 1648
<211> LENGTH: 36
<212> TYPE: PRT
<213> ORGANISM: Homo sapiens

<400> SEQUENCE: 1648

Leu Val Pro Gly Val Gly Val Ala Pro Gly Val Gly Val Ala Pro Gly
1               5                   10                  15

Val Gly Val Ala Pro Gly Val Gly Leu Ala Pro Gly Val Gly Val Ala
            20                  25                  30

Pro Gly Val Gly
        35

<210> SEQ ID NO 1649
<211> LENGTH: 14
<212> TYPE: PRT
<213> ORGANISM: Homo sapiens

<400> SEQUENCE: 1649

Pro Gly Val Gly Val Ala Pro Gly Val Gly Val Ala Pro Gly
1               5                   10

<210> SEQ ID NO 1650
<211> LENGTH: 15
<212> TYPE: PRT
<213> ORGANISM: Homo sapiens

<400> SEQUENCE: 1650

Val Gly Val Ala Pro Gly Val Gly Val Ala Pro Gly Val Gly Val
1               5                   10                  15

<210> SEQ ID NO 1651
<211> LENGTH: 20
<212> TYPE: PRT
<213> ORGANISM: Homo sapiens

<400> SEQUENCE: 1651

Val Gly Val Ala Pro Gly Val Gly Val Ala Pro Gly Val Gly Val Ala
1               5                   10                  15

Pro Gly Val Gly

<210> SEQ ID NO 1652
<211> LENGTH: 30
<212> TYPE: PRT
<213> ORGANISM: Homo sapiens

<400> SEQUENCE: 1652

Val Gly Val Ala Pro Gly Val Gly Val Ala Pro Gly Val Gly Val Ala
1               5                   10                  15
Pro Gly Val Gly Leu Ala Pro Gly Val Gly Val Ala Pro Gly
            20                  25                  30

<210> SEQ ID NO 1653
<211> LENGTH: 16
<212> TYPE: PRT
<213> ORGANISM: Homo sapiens

<400> SEQUENCE: 1653

Val Ala Pro Gly Val Gly Val Ala Pro Gly Val Gly Val Ala Pro Gly
1               5                   10                  15

<210> SEQ ID NO 1654
<211> LENGTH: 18
<212> TYPE: PRT
<213> ORGANISM: Homo sapiens

<400> SEQUENCE: 1654

Val Ala Pro Gly Val Gly Val Ala Pro Gly Val Gly Val Ala Pro Gly
1               5                   10                  15
Val Gly

<210> SEQ ID NO 1655
<211> LENGTH: 24
<212> TYPE: PRT
<213> ORGANISM: Homo sapiens

<400> SEQUENCE: 1655

Val Ala Pro Gly Val Gly Val Ala Pro Gly Val Gly Val Ala Pro Gly
1               5                   10                  15
Val Gly Leu Ala Pro Gly Val Gly
            20

<210> SEQ ID NO 1656
<211> LENGTH: 28
<212> TYPE: PRT
<213> ORGANISM: Homo sapiens

<400> SEQUENCE: 1656

Val Ala Pro Gly Val Gly Val Ala Pro Gly Val Gly Val Ala Pro Gly
1               5                   10                  15
Val Gly Leu Ala Pro Gly Val Gly Val Ala Pro Gly
            20                  25

<210> SEQ ID NO 1657
<211> LENGTH: 16
<212> TYPE: PRT
<213> ORGANISM: Homo sapiens

<400> SEQUENCE: 1657

Val Gly Val Ala Pro Gly Val Gly Val Ala Pro Gly Val Gly Leu Ala
1               5                   10                  15

<210> SEQ ID NO 1658
<211> LENGTH: 24
<212> TYPE: PRT
<213> ORGANISM: Homo sapiens

<400> SEQUENCE: 1658

Val Gly Val Ala Pro Gly Val Gly Val Ala Pro Gly Val Gly Leu Ala
1               5                   10                  15

Pro Gly Val Gly Val Ala Pro Gly
            20

<210> SEQ ID NO 1659
<211> LENGTH: 41
<212> TYPE: PRT
<213> ORGANISM: Homo sapiens

<400> SEQUENCE: 1659

Val Gly Val Ala Pro Gly Val Gly Val Ala Pro Gly Val Gly Leu Ala
1               5                   10                  15

Pro Gly Val Gly Val Ala Pro Gly Val Gly Val Ala Pro Gly Val Gly
            20                  25                  30

Val Ala Pro Gly Ile Gly Pro Gly Gly
        35                  40

<210> SEQ ID NO 1660
<211> LENGTH: 24
<212> TYPE: PRT
<213> ORGANISM: Homo sapiens

<400> SEQUENCE: 1660

Val Ala Pro Gly Val Gly Val Ala Pro Gly Val Gly Leu Ala Pro Gly
1               5                   10                  15

Val Gly Val Ala Pro Gly Val Gly
            20

<210> SEQ ID NO 1661
<211> LENGTH: 26
<212> TYPE: PRT
<213> ORGANISM: Homo sapiens

<400> SEQUENCE: 1661

Val Ala Pro Gly Val Gly Val Ala Pro Gly Val Gly Leu Ala Pro Gly
1               5                   10                  15

Val Gly Val Ala Pro Gly Val Gly Val Ala
            20                  25

<210> SEQ ID NO 1662
<211> LENGTH: 28
<212> TYPE: PRT
<213> ORGANISM: Homo sapiens

<400> SEQUENCE: 1662

Val Ala Pro Gly Val Gly Val Ala Pro Gly Val Gly Leu Ala Pro Gly
1               5                   10                  15

Val Gly Val Ala Pro Gly Val Gly Val Ala Pro Gly
            20                  25

<210> SEQ ID NO 1663
<211> LENGTH: 37
<212> TYPE: PRT
<213> ORGANISM: Homo sapiens -continued

<400> SEQUENCE: 1663

Val Ala Pro Gly Val Gly Val Ala Pro Gly Val Gly Leu Ala Pro Gly
1               5                   10                  15

Val Gly Val Ala Pro Gly Val Gly Val Ala Pro Gly Val Gly Val Ala
            20                  25                  30

Pro Gly Ile Gly Pro
        35

<210> SEQ ID NO 1664
<211> LENGTH: 39
<212> TYPE: PRT
<213> ORGANISM: Homo sapiens

<400> SEQUENCE: 1664

Val Ala Pro Gly Val Gly Val Ala Pro Gly Val Gly Leu Ala Pro Gly
1               5                   10                  15

Val Gly Val Ala Pro Gly Val Gly Val Ala Pro Gly Val Gly Val Ala
            20                  25                  30

Pro Gly Ile Gly Pro Gly Gly
        35

<210> SEQ ID NO 1665
<211> LENGTH: 14
<212> TYPE: PRT
<213> ORGANISM: Homo sapiens

<400> SEQUENCE: 1665

Pro Gly Val Gly Val Ala Pro Gly Val Gly Leu Ala Pro Gly
1               5                   10

<210> SEQ ID NO 1666
<211> LENGTH: 19
<212> TYPE: PRT
<213> ORGANISM: Homo sapiens

<400> SEQUENCE: 1666

Pro Gly Val Gly Val Ala Pro Gly Val Gly Leu Ala Pro Gly Val Gly
1               5                   10                  15

Val Ala Pro

<210> SEQ ID NO 1667
<211> LENGTH: 22
<212> TYPE: PRT
<213> ORGANISM: Homo sapiens

<400> SEQUENCE: 1667

Pro Gly Val Gly Val Ala Pro Gly Val Gly Leu Ala Pro Gly Val Gly
1               5                   10                  15

Val Ala Pro Gly Val Gly
            20

<210> SEQ ID NO 1668
<211> LENGTH: 16
<212> TYPE: PRT
<213> ORGANISM: Homo sapiens

<400> SEQUENCE: 1668

Val Gly Val Ala Pro Gly Val Gly Leu Ala Pro Gly Val Gly Val Ala
1               5                   10                  15

<210> SEQ ID NO 1669

-continued

```
<211> LENGTH: 17
<212> TYPE: PRT
<213> ORGANISM: Homo sapiens

<400> SEQUENCE: 1669

Val Gly Val Ala Pro Gly Val Gly Leu Ala Pro Gly Val Gly Val Ala
1               5                   10                  15

Pro

<210> SEQ ID NO 1670
<211> LENGTH: 24
<212> TYPE: PRT
<213> ORGANISM: Homo sapiens

<400> SEQUENCE: 1670

Val Gly Val Ala Pro Gly Val Gly Leu Ala Pro Gly Val Gly Val Ala
1               5                   10                  15

Pro Gly Val Gly Val Ala Pro Gly
            20

<210> SEQ ID NO 1671
<211> LENGTH: 26
<212> TYPE: PRT
<213> ORGANISM: Homo sapiens

<400> SEQUENCE: 1671

Val Gly Val Ala Pro Gly Val Gly Leu Ala Pro Gly Val Gly Val Ala
1               5                   10                  15

Pro Gly Val Gly Val Ala Pro Gly Val Gly
            20                  25

<210> SEQ ID NO 1672
<211> LENGTH: 30
<212> TYPE: PRT
<213> ORGANISM: Homo sapiens

<400> SEQUENCE: 1672

Val Gly Val Ala Pro Gly Val Gly Leu Ala Pro Gly Val Gly Val Ala
1               5                   10                  15

Pro Gly Val Gly Val Ala Pro Gly Val Gly Val Ala Pro Gly
            20                  25                  30

<210> SEQ ID NO 1673
<211> LENGTH: 35
<212> TYPE: PRT
<213> ORGANISM: Homo sapiens

<400> SEQUENCE: 1673

Val Gly Val Ala Pro Gly Val Gly Leu Ala Pro Gly Val Gly Val Ala
1               5                   10                  15

Pro Gly Val Gly Val Ala Pro Gly Val Gly Val Ala Pro Gly Ile Gly
            20                  25                  30

Pro Gly Gly
        35

<210> SEQ ID NO 1674
<211> LENGTH: 34
<212> TYPE: PRT
<213> ORGANISM: Homo sapiens

<400> SEQUENCE: 1674

Gly Val Ala Pro Gly Val Gly Leu Ala Pro Gly Val Gly Val Ala Pro
```

```
                1               5                   10                  15
Gly Val Gly Val Ala Pro Gly Val Gly Val Ala Pro Gly Ile Gly Pro
            20                  25                  30

Gly Gly

<210> SEQ ID NO 1675
<211> LENGTH: 14
<212> TYPE: PRT
<213> ORGANISM: Homo sapiens

<400> SEQUENCE: 1675

Val Ala Pro Gly Val Gly Leu Ala Pro Gly Val Gly Val Ala
1               5                   10

<210> SEQ ID NO 1676
<211> LENGTH: 16
<212> TYPE: PRT
<213> ORGANISM: Homo sapiens

<400> SEQUENCE: 1676

Val Ala Pro Gly Val Gly Leu Ala Pro Gly Val Gly Val Ala Pro Gly
1               5                   10                  15

<210> SEQ ID NO 1677
<211> LENGTH: 18
<212> TYPE: PRT
<213> ORGANISM: Homo sapiens

<400> SEQUENCE: 1677

Val Ala Pro Gly Val Gly Leu Ala Pro Gly Val Gly Val Ala Pro Gly
1               5                   10                  15

Val Gly

<210> SEQ ID NO 1678
<211> LENGTH: 20
<212> TYPE: PRT
<213> ORGANISM: Homo sapiens

<400> SEQUENCE: 1678

Val Ala Pro Gly Val Gly Leu Ala Pro Gly Val Gly Val Ala Pro Gly
1               5                   10                  15

Val Gly Val Ala
            20

<210> SEQ ID NO 1679
<211> LENGTH: 22
<212> TYPE: PRT
<213> ORGANISM: Homo sapiens

<400> SEQUENCE: 1679

Val Ala Pro Gly Val Gly Leu Ala Pro Gly Val Gly Val Ala Pro Gly
1               5                   10                  15

Val Gly Val Ala Pro Gly
            20

<210> SEQ ID NO 1680
<211> LENGTH: 26
<212> TYPE: PRT
<213> ORGANISM: Homo sapiens

<400> SEQUENCE: 1680

Val Ala Pro Gly Val Gly Leu Ala Pro Gly Val Gly Val Ala Pro Gly
```

```
                1               5                   10                  15
Val Gly Val Ala Pro Gly Val Gly Val Ala
            20                  25

<210> SEQ ID NO 1681
<211> LENGTH: 33
<212> TYPE: PRT
<213> ORGANISM: Homo sapiens

<400> SEQUENCE: 1681

Val Ala Pro Gly Val Gly Leu Ala Pro Gly Val Gly Val Ala Pro Gly
1               5                   10                  15

Val Gly Val Ala Pro Gly Val Gly Val Ala Pro Gly Ile Gly Pro Gly
            20                  25                  30

Gly

<210> SEQ ID NO 1682
<211> LENGTH: 14
<212> TYPE: PRT
<213> ORGANISM: Homo sapiens

<400> SEQUENCE: 1682

Pro Gly Val Gly Leu Ala Pro Gly Val Gly Val Ala Pro Gly
1               5                   10

<210> SEQ ID NO 1683
<211> LENGTH: 19
<212> TYPE: PRT
<213> ORGANISM: Homo sapiens

<400> SEQUENCE: 1683

Gly Val Gly Leu Ala Pro Gly Val Gly Val Ala Pro Gly Val Gly Val
1               5                   10                  15

Ala Pro Gly

<210> SEQ ID NO 1684
<211> LENGTH: 14
<212> TYPE: PRT
<213> ORGANISM: Homo sapiens

<400> SEQUENCE: 1684

Val Gly Leu Ala Pro Gly Val Gly Val Ala Pro Gly Val Gly
1               5                   10

<210> SEQ ID NO 1685
<211> LENGTH: 18
<212> TYPE: PRT
<213> ORGANISM: Homo sapiens

<400> SEQUENCE: 1685

Val Gly Leu Ala Pro Gly Val Gly Val Ala Pro Gly Val Gly Val Ala
1               5                   10                  15

Pro Gly

<210> SEQ ID NO 1686
<211> LENGTH: 26
<212> TYPE: PRT
<213> ORGANISM: Homo sapiens

<400> SEQUENCE: 1686

Val Gly Leu Ala Pro Gly Val Gly Val Ala Pro Gly Val Gly Val Ala
1               5                   10                  15
```

```
Pro Gly Val Gly Val Ala Pro Gly Ile Gly
            20                  25

<210> SEQ ID NO 1687
<211> LENGTH: 29
<212> TYPE: PRT
<213> ORGANISM: Homo sapiens

<400> SEQUENCE: 1687

Val Gly Leu Ala Pro Gly Val Gly Val Ala Pro Gly Val Gly Val Ala
1               5                   10                  15

Pro Gly Val Gly Val Ala Pro Gly Ile Gly Pro Gly Gly
            20                  25

<210> SEQ ID NO 1688
<211> LENGTH: 28
<212> TYPE: PRT
<213> ORGANISM: Homo sapiens

<400> SEQUENCE: 1688

Val Gly Leu Ala Pro Gly Val Gly Val Ala Pro Gly Val Gly Val Ala
1               5                   10                  15

Pro Gly Val Gly Val Ala Pro Gly Ile Gly Pro Gly
            20                  25

<210> SEQ ID NO 1689
<211> LENGTH: 33
<212> TYPE: PRT
<213> ORGANISM: Homo sapiens

<400> SEQUENCE: 1689

Val Gly Leu Ala Pro Gly Val Gly Val Ala Pro Gly Val Gly Val Ala
1               5                   10                  15

Pro Gly Val Gly Val Ala Pro Gly Ile Gly Pro Gly Gly Val Ala Ala
            20                  25                  30

Ala

<210> SEQ ID NO 1690
<211> LENGTH: 18
<212> TYPE: PRT
<213> ORGANISM: Homo sapiens

<400> SEQUENCE: 1690

Leu Ala Pro Gly Val Gly Val Ala Pro Gly Val Gly Val Ala Pro Gly
1               5                   10                  15

Val Gly

<210> SEQ ID NO 1691
<211> LENGTH: 20
<212> TYPE: PRT
<213> ORGANISM: Homo sapiens

<400> SEQUENCE: 1691

Leu Ala Pro Gly Val Gly Val Ala Pro Gly Val Gly Val Ala Pro Gly
1               5                   10                  15

Val Gly Val Ala
            20

<210> SEQ ID NO 1692
<211> LENGTH: 25
<212> TYPE: PRT
```

<213> ORGANISM: Homo sapiens

<400> SEQUENCE: 1692

Leu Ala Pro Gly Val Gly Val Ala Pro Gly Val Gly Val Ala Pro Gly
1               5                   10                  15

Val Gly Val Ala Pro Gly Ile Gly Pro
            20                  25

<210> SEQ ID NO 1693
<211> LENGTH: 27
<212> TYPE: PRT
<213> ORGANISM: Homo sapiens

<400> SEQUENCE: 1693

Leu Ala Pro Gly Val Gly Val Ala Pro Gly Val Gly Val Ala Pro Gly
1               5                   10                  15

Val Gly Val Ala Pro Gly Ile Gly Pro Gly Gly
            20                  25

<210> SEQ ID NO 1694
<211> LENGTH: 24
<212> TYPE: PRT
<213> ORGANISM: Homo sapiens

<400> SEQUENCE: 1694

Gly Val Gly Val Ala Pro Gly Val Gly Val Ala Pro Gly Val Gly Val
1               5                   10                  15

Ala Pro Gly Ile Gly Pro Gly Gly
            20

<210> SEQ ID NO 1695
<211> LENGTH: 16
<212> TYPE: PRT
<213> ORGANISM: Homo sapiens

<400> SEQUENCE: 1695

Val Gly Val Ala Pro Gly Val Gly Val Ala Pro Gly Val Gly Val Ala
1               5                   10                  15

<210> SEQ ID NO 1696
<211> LENGTH: 18
<212> TYPE: PRT
<213> ORGANISM: Homo sapiens

<400> SEQUENCE: 1696

Val Gly Val Ala Pro Gly Val Gly Val Ala Pro Gly Val Gly Val Ala
1               5                   10                  15

Pro Gly

<210> SEQ ID NO 1697
<211> LENGTH: 22
<212> TYPE: PRT
<213> ORGANISM: Homo sapiens

<400> SEQUENCE: 1697

Val Gly Val Ala Pro Gly Val Gly Val Ala Pro Gly Val Gly Val Ala
1               5                   10                  15

Pro Gly Ile Gly Pro Gly
            20

<210> SEQ ID NO 1698
<211> LENGTH: 23

```
<212> TYPE: PRT
<213> ORGANISM: Homo sapiens

<400> SEQUENCE: 1698

Val Gly Val Ala Pro Gly Val Gly Val Ala Pro Gly Val Gly Val Ala
1               5                   10                  15

Pro Gly Ile Gly Pro Gly Gly
            20

<210> SEQ ID NO 1699
<211> LENGTH: 27
<212> TYPE: PRT
<213> ORGANISM: Homo sapiens

<400> SEQUENCE: 1699

Val Gly Val Ala Pro Gly Val Gly Val Ala Pro Gly Val Gly Val Ala
1               5                   10                  15

Pro Gly Ile Gly Pro Gly Gly Val Ala Ala Ala
            20                  25

<210> SEQ ID NO 1700
<211> LENGTH: 15
<212> TYPE: PRT
<213> ORGANISM: Homo sapiens

<400> SEQUENCE: 1700

Val Ala Pro Gly Val Gly Val Ala Pro Gly Val Gly Val Ala Pro
1               5                   10                  15

<210> SEQ ID NO 1701
<211> LENGTH: 18
<212> TYPE: PRT
<213> ORGANISM: Homo sapiens

<400> SEQUENCE: 1701

Val Ala Pro Gly Val Gly Val Ala Pro Gly Val Gly Val Ala Pro Gly
1               5                   10                  15

Ile Gly

<210> SEQ ID NO 1702
<211> LENGTH: 21
<212> TYPE: PRT
<213> ORGANISM: Homo sapiens

<400> SEQUENCE: 1702

Val Ala Pro Gly Val Gly Val Ala Pro Gly Val Gly Val Ala Pro Gly
1               5                   10                  15

Ile Gly Pro Gly Gly
            20

<210> SEQ ID NO 1703
<211> LENGTH: 18
<212> TYPE: PRT
<213> ORGANISM: Homo sapiens

<400> SEQUENCE: 1703

Pro Gly Val Gly Val Ala Pro Gly Val Gly Val Ala Pro Gly Ile Gly
1               5                   10                  15

Pro Gly

<210> SEQ ID NO 1704
<211> LENGTH: 19
```

<212> TYPE: PRT
<213> ORGANISM: Homo sapiens

<400> SEQUENCE: 1704

Pro Gly Val Gly Val Ala Pro Gly Val Gly Val Ala Pro Gly Ile Gly
1               5                   10                  15

Pro Gly Gly

<210> SEQ ID NO 1705
<211> LENGTH: 17
<212> TYPE: PRT
<213> ORGANISM: Homo sapiens

<400> SEQUENCE: 1705

Val Gly Val Ala Pro Gly Val Gly Val Ala Pro Gly Ile Gly Pro Gly
1               5                   10                  15

Gly

<210> SEQ ID NO 1706
<211> LENGTH: 20
<212> TYPE: PRT
<213> ORGANISM: Homo sapiens

<400> SEQUENCE: 1706

Val Gly Val Ala Pro Gly Val Gly Val Ala Pro Gly Ile Gly Pro Gly
1               5                   10                  15

Gly Val Ala Ala
            20

<210> SEQ ID NO 1707
<211> LENGTH: 14
<212> TYPE: PRT
<213> ORGANISM: Homo sapiens

<400> SEQUENCE: 1707

Val Ala Pro Gly Val Gly Val Ala Pro Gly Ile Gly Pro Gly
1               5                   10

<210> SEQ ID NO 1708
<211> LENGTH: 12
<212> TYPE: PRT
<213> ORGANISM: Homo sapiens

<400> SEQUENCE: 1708

Pro Gly Val Gly Val Ala Pro Gly Ile Gly Pro Gly
1               5                   10

<210> SEQ ID NO 1709
<211> LENGTH: 14
<212> TYPE: PRT
<213> ORGANISM: Homo sapiens

<400> SEQUENCE: 1709

Val Gly Val Ala Pro Gly Ile Gly Pro Gly Gly Val Ala Ala
1               5                   10

<210> SEQ ID NO 1710
<211> LENGTH: 9
<212> TYPE: PRT
<213> ORGANISM: Homo sapiens

<400> SEQUENCE: 1710

Pro Gly Gly Val Ala Ala Ala Ala Lys

```
1               5

<210> SEQ ID NO 1711
<211> LENGTH: 7
<212> TYPE: PRT
<213> ORGANISM: Homo sapiens

<400> SEQUENCE: 1711

Leu Arg Ala Ala Ala Gly Leu
1               5

<210> SEQ ID NO 1712
<211> LENGTH: 8
<212> TYPE: PRT
<213> ORGANISM: Homo sapiens

<400> SEQUENCE: 1712

Leu Arg Ala Ala Ala Gly Leu Gly
1               5

<210> SEQ ID NO 1713
<211> LENGTH: 9
<212> TYPE: PRT
<213> ORGANISM: Homo sapiens

<400> SEQUENCE: 1713

Leu Arg Ala Ala Ala Gly Leu Gly Ala
1               5

<210> SEQ ID NO 1714
<211> LENGTH: 15
<212> TYPE: PRT
<213> ORGANISM: Homo sapiens

<400> SEQUENCE: 1714

Ala Ala Ala Gly Leu Gly Ala Gly Ile Pro Gly Leu Gly Val Gly
1               5                   10                  15

<210> SEQ ID NO 1715
<211> LENGTH: 17
<212> TYPE: PRT
<213> ORGANISM: Homo sapiens

<400> SEQUENCE: 1715

Ala Ala Ala Gly Leu Gly Ala Gly Ile Pro Gly Leu Gly Val Gly Val
1               5                   10                  15

Gly

<210> SEQ ID NO 1716
<211> LENGTH: 11
<212> TYPE: PRT
<213> ORGANISM: Homo sapiens

<400> SEQUENCE: 1716

Leu Gly Ala Gly Ile Pro Gly Leu Gly Val Gly
1               5                   10

<210> SEQ ID NO 1717
<211> LENGTH: 13
<212> TYPE: PRT
<213> ORGANISM: Homo sapiens

<400> SEQUENCE: 1717

Leu Gly Ala Gly Ile Pro Gly Leu Gly Val Gly Val Gly
```

```
1               5                   10
```

<210> SEQ ID NO 1718
<211> LENGTH: 20
<212> TYPE: PRT
<213> ORGANISM: Homo sapiens

<400> SEQUENCE: 1718

```
Leu Gly Ala Gly Ile Pro Gly Leu Gly Val Gly Val Gly Val Pro Gly
1               5                   10                  15

Leu Gly Val Gly
            20
```

<210> SEQ ID NO 1719
<211> LENGTH: 16
<212> TYPE: PRT
<213> ORGANISM: Homo sapiens

<400> SEQUENCE: 1719

```
Leu Gly Ala Gly Ile Pro Gly Leu Gly Val Gly Val Gly Val Pro Gly
1               5                   10                  15
```

<210> SEQ ID NO 1720
<211> LENGTH: 21
<212> TYPE: PRT
<213> ORGANISM: Homo sapiens

<400> SEQUENCE: 1720

```
Leu Gly Ala Gly Ile Pro Gly Leu Gly Val Gly Val Gly Val Pro Gly
1               5                   10                  15

Leu Gly Val Gly Ala
            20
```

<210> SEQ ID NO 1721
<211> LENGTH: 17
<212> TYPE: PRT
<213> ORGANISM: Homo sapiens

<400> SEQUENCE: 1721

```
Leu Gly Ala Gly Ile Pro Gly Leu Gly Val Gly Val Gly Val Pro Gly
1               5                   10                  15

Leu
```

<210> SEQ ID NO 1722
<211> LENGTH: 18
<212> TYPE: PRT
<213> ORGANISM: Homo sapiens

<400> SEQUENCE: 1722

```
Leu Gly Ala Gly Ile Pro Gly Leu Gly Val Gly Val Gly Val Pro Gly
1               5                   10                  15

Leu Gly
```

<210> SEQ ID NO 1723
<211> LENGTH: 25
<212> TYPE: PRT
<213> ORGANISM: Homo sapiens

<400> SEQUENCE: 1723

```
Leu Gly Ala Gly Ile Pro Gly Leu Gly Val Gly Val Gly Val Pro Gly
1               5                   10                  15

Leu Gly Val Gly Ala Gly Val Pro Gly
```

```
            20                  25

<210> SEQ ID NO 1724
<211> LENGTH: 27
<212> TYPE: PRT
<213> ORGANISM: Homo sapiens

<400> SEQUENCE: 1724

Leu Gly Ala Gly Ile Pro Gly Leu Gly Val Gly Val Gly Val Pro Gly
1               5                   10                  15

Leu Gly Val Gly Ala Gly Val Pro Gly Leu Gly
            20                  25

<210> SEQ ID NO 1725
<211> LENGTH: 29
<212> TYPE: PRT
<213> ORGANISM: Homo sapiens

<400> SEQUENCE: 1725

Leu Gly Ala Gly Ile Pro Gly Leu Gly Val Gly Val Gly Val Pro Gly
1               5                   10                  15

Leu Gly Val Gly Ala Gly Val Pro Gly Leu Gly Val Gly
            20                  25

<210> SEQ ID NO 1726
<211> LENGTH: 36
<212> TYPE: PRT
<213> ORGANISM: Homo sapiens

<400> SEQUENCE: 1726

Leu Gly Ala Gly Ile Pro Gly Leu Gly Val Gly Val Gly Val Pro Gly
1               5                   10                  15

Leu Gly Val Gly Ala Gly Val Pro Gly Leu Gly Val Gly Ala Gly Val
            20                  25                  30

Pro Gly Phe Gly
        35

<210> SEQ ID NO 1727
<211> LENGTH: 17
<212> TYPE: PRT
<213> ORGANISM: Homo sapiens

<400> SEQUENCE: 1727

Gly Ala Gly Ile Pro Gly Leu Gly Val Gly Val Gly Val Pro Gly Leu
1               5                   10                  15

Gly

<210> SEQ ID NO 1728
<211> LENGTH: 14
<212> TYPE: PRT
<213> ORGANISM: Homo sapiens

<400> SEQUENCE: 1728

Ala Gly Ile Pro Gly Leu Gly Val Gly Val Gly Val Pro Gly
1               5                   10

<210> SEQ ID NO 1729
<211> LENGTH: 18
<212> TYPE: PRT
<213> ORGANISM: Homo sapiens

<400> SEQUENCE: 1729
```

```
Gly Ile Pro Gly Leu Gly Val Gly Val Pro Gly Leu Gly Val
1               5                   10                  15

Gly Ala

<210> SEQ ID NO 1730
<211> LENGTH: 14
<212> TYPE: PRT
<213> ORGANISM: Homo sapiens

<400> SEQUENCE: 1730

Leu Gly Val Gly Val Gly Val Pro Gly Leu Gly Val Gly Ala
1               5                   10

<210> SEQ ID NO 1731
<211> LENGTH: 14
<212> TYPE: PRT
<213> ORGANISM: Homo sapiens

<400> SEQUENCE: 1731

Val Gly Val Pro Gly Leu Gly Val Gly Ala Gly Val Pro Gly
1               5                   10

<210> SEQ ID NO 1732
<211> LENGTH: 15
<212> TYPE: PRT
<213> ORGANISM: Homo sapiens

<400> SEQUENCE: 1732

Val Gly Val Pro Gly Leu Gly Val Gly Ala Gly Val Pro Gly Leu
1               5                   10                  15

<210> SEQ ID NO 1733
<211> LENGTH: 16
<212> TYPE: PRT
<213> ORGANISM: Homo sapiens

<400> SEQUENCE: 1733

Val Gly Val Pro Gly Leu Gly Val Gly Ala Gly Val Pro Gly Leu Gly
1               5                   10                  15

<210> SEQ ID NO 1734
<211> LENGTH: 18
<212> TYPE: PRT
<213> ORGANISM: Homo sapiens

<400> SEQUENCE: 1734

Val Gly Val Pro Gly Leu Gly Val Gly Ala Gly Val Pro Gly Leu Gly
1               5                   10                  15

Val Gly

<210> SEQ ID NO 1735
<211> LENGTH: 19
<212> TYPE: PRT
<213> ORGANISM: Homo sapiens

<400> SEQUENCE: 1735

Val Gly Val Pro Gly Leu Gly Val Gly Ala Gly Val Pro Gly Leu Gly
1               5                   10                  15

Val Gly Ala

<210> SEQ ID NO 1736
<211> LENGTH: 18
<212> TYPE: PRT
```

```
<213> ORGANISM: Homo sapiens

<400> SEQUENCE: 1736

Val Gly Ala Gly Val Pro Gly Leu Gly Val Gly Ala Gly Val Pro Gly
1               5                   10                  15

Phe Gly

<210> SEQ ID NO 1737
<211> LENGTH: 8
<212> TYPE: PRT
<213> ORGANISM: Homo sapiens

<400> SEQUENCE: 1737

Pro Gly Ala Leu Ala Ala Ala Lys
1               5

<210> SEQ ID NO 1738
<211> LENGTH: 16
<212> TYPE: PRT
<213> ORGANISM: Homo sapiens

<400> SEQUENCE: 1738

Ala Lys Tyr Gly Ala Ala Val Pro Gly Val Leu Gly Gly Leu Gly Ala
1               5                   10                  15

<210> SEQ ID NO 1739
<211> LENGTH: 11
<212> TYPE: PRT
<213> ORGANISM: Homo sapiens

<400> SEQUENCE: 1739

Tyr Gly Ala Ala Val Pro Gly Val Leu Gly Gly
1               5                   10

<210> SEQ ID NO 1740
<211> LENGTH: 13
<212> TYPE: PRT
<213> ORGANISM: Homo sapiens

<400> SEQUENCE: 1740

Tyr Gly Ala Ala Val Pro Gly Val Leu Gly Gly Leu Gly
1               5                   10

<210> SEQ ID NO 1741
<211> LENGTH: 14
<212> TYPE: PRT
<213> ORGANISM: Homo sapiens

<400> SEQUENCE: 1741

Tyr Gly Ala Ala Val Pro Gly Val Leu Gly Gly Leu Gly Ala
1               5                   10

<210> SEQ ID NO 1742
<211> LENGTH: 16
<212> TYPE: PRT
<213> ORGANISM: Homo sapiens

<400> SEQUENCE: 1742

Tyr Gly Ala Ala Val Pro Gly Val Leu Gly Gly Leu Gly Ala Leu Gly
1               5                   10                  15

<210> SEQ ID NO 1743
<211> LENGTH: 23
<212> TYPE: PRT
```

-continued

<213> ORGANISM: Homo sapiens

<400> SEQUENCE: 1743

Tyr Gly Ala Ala Val Pro Gly Val Leu Gly Gly Leu Gly Ala Leu Gly
1               5                   10                  15

Gly Val Gly Ile Pro Gly Gly
            20

<210> SEQ ID NO 1744
<211> LENGTH: 31
<212> TYPE: PRT
<213> ORGANISM: Homo sapiens

<400> SEQUENCE: 1744

Tyr Gly Ala Ala Val Pro Gly Val Leu Gly Gly Leu Gly Ala Leu Gly
1               5                   10                  15

Gly Val Gly Ile Pro Gly Gly Val Val Gly Ala Gly Pro Ala Ala
            20                  25                  30

<210> SEQ ID NO 1745
<211> LENGTH: 12
<212> TYPE: PRT
<213> ORGANISM: Homo sapiens

<400> SEQUENCE: 1745

Gly Ala Ala Val Pro Gly Val Leu Gly Gly Leu Gly
1               5                   10

<210> SEQ ID NO 1746
<211> LENGTH: 22
<212> TYPE: PRT
<213> ORGANISM: Homo sapiens

<400> SEQUENCE: 1746

Gly Ala Ala Val Pro Gly Val Leu Gly Gly Leu Gly Ala Leu Gly Gly
1               5                   10                  15

Val Gly Ile Pro Gly Gly
            20

<210> SEQ ID NO 1747
<211> LENGTH: 11
<212> TYPE: PRT
<213> ORGANISM: Homo sapiens

<400> SEQUENCE: 1747

Ala Val Pro Gly Val Leu Gly Gly Leu Gly Ala
1               5                   10

<210> SEQ ID NO 1748
<211> LENGTH: 20
<212> TYPE: PRT
<213> ORGANISM: Homo sapiens

<400> SEQUENCE: 1748

Ala Val Pro Gly Val Leu Gly Gly Leu Gly Ala Leu Gly Gly Val Gly
1               5                   10                  15

Ile Pro Gly Gly
            20

<210> SEQ ID NO 1749
<211> LENGTH: 16
<212> TYPE: PRT
<213> ORGANISM: Homo sapiens

```
<400> SEQUENCE: 1749

Val Leu Gly Gly Leu Gly Ala Leu Gly Gly Val Gly Ile Pro Gly Gly
1               5                   10                  15

<210> SEQ ID NO 1750
<211> LENGTH: 21
<212> TYPE: PRT
<213> ORGANISM: Homo sapiens

<400> SEQUENCE: 1750

Gly Gly Leu Gly Ala Leu Gly Gly Val Gly Ile Pro Gly Gly Val Val
1               5                   10                  15

Gly Ala Gly Pro Ala
            20

<210> SEQ ID NO 1751
<211> LENGTH: 23
<212> TYPE: PRT
<213> ORGANISM: Homo sapiens

<400> SEQUENCE: 1751

Gly Gly Leu Gly Ala Leu Gly Gly Val Gly Ile Pro Gly Gly Val Val
1               5                   10                  15

Gly Ala Gly Pro Ala Ala Ala
            20

<210> SEQ ID NO 1752
<211> LENGTH: 12
<212> TYPE: PRT
<213> ORGANISM: Homo sapiens

<400> SEQUENCE: 1752

Leu Gly Ala Leu Gly Gly Val Gly Ile Pro Gly Gly
1               5                   10

<210> SEQ ID NO 1753
<211> LENGTH: 19
<212> TYPE: PRT
<213> ORGANISM: Homo sapiens

<400> SEQUENCE: 1753

Leu Gly Ala Leu Gly Gly Val Gly Ile Pro Gly Gly Val Val Gly Ala
1               5                   10                  15

Gly Pro Ala

<210> SEQ ID NO 1754
<211> LENGTH: 20
<212> TYPE: PRT
<213> ORGANISM: Homo sapiens

<400> SEQUENCE: 1754

Leu Gly Ala Leu Gly Gly Val Gly Ile Pro Gly Gly Val Val Gly Ala
1               5                   10                  15

Gly Pro Ala Ala
            20

<210> SEQ ID NO 1755
<211> LENGTH: 21
<212> TYPE: PRT
<213> ORGANISM: Homo sapiens

<400> SEQUENCE: 1755
```

```
Leu Gly Ala Leu Gly Gly Val Gly Ile Pro Gly Gly Val Val Gly Ala
1               5                   10                  15

Gly Pro Ala Ala Ala
            20

<210> SEQ ID NO 1756
<211> LENGTH: 22
<212> TYPE: PRT
<213> ORGANISM: Homo sapiens

<400> SEQUENCE: 1756

Leu Gly Ala Leu Gly Gly Val Gly Ile Pro Gly Gly Val Val Gly Ala
1               5                   10                  15

Gly Pro Ala Ala Ala Ala
            20

<210> SEQ ID NO 1757
<211> LENGTH: 18
<212> TYPE: PRT
<213> ORGANISM: Homo sapiens

<400> SEQUENCE: 1757

Ala Leu Gly Gly Val Gly Ile Pro Gly Gly Val Val Gly Ala Gly Pro
1               5                   10                  15

Ala Ala

<210> SEQ ID NO 1758
<211> LENGTH: 19
<212> TYPE: PRT
<213> ORGANISM: Homo sapiens

<400> SEQUENCE: 1758

Ala Leu Gly Gly Val Gly Ile Pro Gly Gly Val Val Gly Ala Gly Pro
1               5                   10                  15

Ala Ala Ala

<210> SEQ ID NO 1759
<211> LENGTH: 13
<212> TYPE: PRT
<213> ORGANISM: Homo sapiens

<400> SEQUENCE: 1759

Leu Gly Gly Val Gly Ile Pro Gly Gly Val Ser Glu Gln
1               5                   10

<210> SEQ ID NO 1760
<211> LENGTH: 16
<212> TYPE: PRT
<213> ORGANISM: Homo sapiens

<400> SEQUENCE: 1760

Leu Gly Gly Val Gly Ile Pro Gly Gly Val Val Gly Ala Gly Pro Ala
1               5                   10                  15

<210> SEQ ID NO 1761
<211> LENGTH: 18
<212> TYPE: PRT
<213> ORGANISM: Homo sapiens

<400> SEQUENCE: 1761

Leu Gly Gly Val Gly Ile Pro Gly Gly Val Val Gly Ala Gly Pro Ala
1               5                   10                  15
```

Ala Ala

<210> SEQ ID NO 1762
<211> LENGTH: 20
<212> TYPE: PRT
<213> ORGANISM: Homo sapiens

<400> SEQUENCE: 1762

Leu Gly Gly Val Gly Ile Pro Gly Gly Val Val Gly Ala Gly Pro Ala
1               5                   10                  15

Ala Ala Ala Ala
        20

<210> SEQ ID NO 1763
<211> LENGTH: 23
<212> TYPE: PRT
<213> ORGANISM: Homo sapiens

<400> SEQUENCE: 1763

Leu Gly Gly Val Gly Ile Pro Gly Gly Val Val Gly Ala Gly Pro Ala
1               5                   10                  15

Ala Ala Ala Ala Ala Ala Lys
        20

<210> SEQ ID NO 1764
<211> LENGTH: 17
<212> TYPE: PRT
<213> ORGANISM: Homo sapiens

<400> SEQUENCE: 1764

Gly Val Gly Ile Pro Gly Gly Val Val Gly Ala Gly Pro Ala Ala Ala
1               5                   10                  15

Ala

<210> SEQ ID NO 1765
<211> LENGTH: 21
<212> TYPE: PRT
<213> ORGANISM: Homo sapiens

<400> SEQUENCE: 1765

Gly Val Gly Ile Pro Gly Gly Val Val Gly Ala Gly Pro Ala Ala Ala
1               5                   10                  15

Ala Ala Ala Ala Lys
        20

<210> SEQ ID NO 1766
<211> LENGTH: 15
<212> TYPE: PRT
<213> ORGANISM: Homo sapiens

<400> SEQUENCE: 1766

Val Gly Ile Pro Gly Gly Val Val Gly Ala Gly Pro Ala Ala Ala
1               5                   10                  15

<210> SEQ ID NO 1767
<211> LENGTH: 20
<212> TYPE: PRT
<213> ORGANISM: Homo sapiens

<400> SEQUENCE: 1767

Val Gly Ile Pro Gly Gly Val Val Gly Ala Gly Pro Ala Ala Ala Ala
1               5                   10                  15

Ala Ala Ala Lys
        20

<210> SEQ ID NO 1768
<211> LENGTH: 14
<212> TYPE: PRT
<213> ORGANISM: Homo sapiens

<400> SEQUENCE: 1768

Ile Pro Gly Gly Val Val Gly Ala Gly Pro Ala Ala Ala Ala
1               5                   10

<210> SEQ ID NO 1769
<211> LENGTH: 14
<212> TYPE: PRT
<213> ORGANISM: Homo sapiens

<400> SEQUENCE: 1769

Val Val Gly Ala Gly Pro Ala Ala Ala Ala Ala Ala Ala Lys
1               5                   10

<210> SEQ ID NO 1770
<211> LENGTH: 13
<212> TYPE: PRT
<213> ORGANISM: Homo sapiens

<400> SEQUENCE: 1770

Val Gly Ala Gly Pro Ala Ala Ala Ala Ala Ala Ala Lys
1               5                   10

<210> SEQ ID NO 1771
<211> LENGTH: 11
<212> TYPE: PRT
<213> ORGANISM: Homo sapiens

<400> SEQUENCE: 1771

Ala Gly Pro Ala Ala Ala Ala Ala Ala Ala Lys
1               5                   10

<210> SEQ ID NO 1772
<211> LENGTH: 10
<212> TYPE: PRT
<213> ORGANISM: Homo sapiens

<400> SEQUENCE: 1772

Gly Pro Ala Ala Ala Ala Ala Ala Ala Lys
1               5                   10

<210> SEQ ID NO 1773
<211> LENGTH: 9
<212> TYPE: PRT
<213> ORGANISM: Homo sapiens

<400> SEQUENCE: 1773

Pro Ala Ala Ala Ala Ala Ala Ala Lys
1               5

<210> SEQ ID NO 1774
<211> LENGTH: 24
<212> TYPE: PRT
<213> ORGANISM: Homo sapiens

<400> SEQUENCE: 1774

Phe Gly Leu Val Gly Ala Ala Gly Leu Gly Gly Leu Gly Val Gly Gly

```
1               5                  10                 15
Leu Gly Val Pro Gly Val Gly Gly
            20

<210> SEQ ID NO 1775
<211> LENGTH: 12
<212> TYPE: PRT
<213> ORGANISM: Homo sapiens

<400> SEQUENCE: 1775

Gly Leu Val Gly Ala Ala Gly Leu Gly Gly Leu Gly
1               5                  10

<210> SEQ ID NO 1776
<211> LENGTH: 15
<212> TYPE: PRT
<213> ORGANISM: Homo sapiens

<400> SEQUENCE: 1776

Gly Leu Val Gly Ala Ala Gly Leu Gly Gly Leu Gly Val Gly Gly
1               5                  10                 15

<210> SEQ ID NO 1777
<211> LENGTH: 22
<212> TYPE: PRT
<213> ORGANISM: Homo sapiens

<400> SEQUENCE: 1777

Gly Leu Val Gly Ala Ala Gly Leu Gly Gly Leu Gly Val Gly Gly Leu
1               5                  10                 15

Gly Val Pro Gly Val Gly
            20

<210> SEQ ID NO 1778
<211> LENGTH: 23
<212> TYPE: PRT
<213> ORGANISM: Homo sapiens

<400> SEQUENCE: 1778

Gly Leu Val Gly Ala Ala Gly Leu Gly Gly Leu Gly Val Gly Gly Leu
1               5                  10                 15

Gly Val Pro Gly Val Gly Gly
            20

<210> SEQ ID NO 1779
<211> LENGTH: 13
<212> TYPE: PRT
<213> ORGANISM: Homo sapiens

<400> SEQUENCE: 1779

Leu Val Gly Ala Ala Gly Leu Gly Gly Leu Gly Val Gly
1               5                  10

<210> SEQ ID NO 1780
<211> LENGTH: 13
<212> TYPE: PRT
<213> ORGANISM: Homo sapiens

<400> SEQUENCE: 1780

Leu Val Gly Ala Ala Gly Leu Gly Gly Leu Gly Val Gly
1               5                  10

<210> SEQ ID NO 1781
```

```
<211> LENGTH: 15
<212> TYPE: PRT
<213> ORGANISM: Homo sapiens

<400> SEQUENCE: 1781

Leu Val Gly Ala Ala Gly Leu Gly Gly Leu Gly Val Gly Gly Leu
1               5                   10                  15

<210> SEQ ID NO 1782
<211> LENGTH: 24
<212> TYPE: PRT
<213> ORGANISM: Homo sapiens

<400> SEQUENCE: 1782

Leu Val Gly Ala Ala Gly Leu Gly Gly Leu Gly Val Gly Gly Leu Gly
1               5                   10                  15

Val Pro Gly Val Gly Gly Leu Gly
            20

<210> SEQ ID NO 1783
<211> LENGTH: 31
<212> TYPE: PRT
<213> ORGANISM: Homo sapiens

<400> SEQUENCE: 1783

Leu Val Gly Ala Ala Gly Leu Gly Gly Leu Gly Val Gly Gly Leu Gly
1               5                   10                  15

Val Pro Gly Val Gly Gly Leu Gly Gly Ile Pro Pro Ala Ala Ala
            20                  25                  30

<210> SEQ ID NO 1784
<211> LENGTH: 13
<212> TYPE: PRT
<213> ORGANISM: Homo sapiens

<400> SEQUENCE: 1784

Val Gly Ala Ala Gly Leu Gly Gly Leu Gly Val Gly Gly
1               5                   10

<210> SEQ ID NO 1785
<211> LENGTH: 13
<212> TYPE: PRT
<213> ORGANISM: Homo sapiens

<400> SEQUENCE: 1785

Leu Gly Gly Leu Gly Val Gly Gly Leu Gly Val Pro Gly
1               5                   10

<210> SEQ ID NO 1786
<211> LENGTH: 15
<212> TYPE: PRT
<213> ORGANISM: Homo sapiens

<400> SEQUENCE: 1786

Leu Gly Gly Leu Gly Val Gly Gly Leu Gly Val Pro Gly Val Gly
1               5                   10                  15

<210> SEQ ID NO 1787
<211> LENGTH: 17
<212> TYPE: PRT
<213> ORGANISM: Homo sapiens

<400> SEQUENCE: 1787

Leu Gly Gly Leu Gly Val Gly Gly Leu Gly Val Pro Gly Val Gly Gly
```

-continued

```
1               5                   10                  15

Leu

<210> SEQ ID NO 1788
<211> LENGTH: 18
<212> TYPE: PRT
<213> ORGANISM: Homo sapiens

<400> SEQUENCE: 1788

Leu Gly Gly Leu Gly Val Gly Gly Leu Gly Val Pro Gly Val Gly Gly
1               5                   10                  15

Leu Gly

<210> SEQ ID NO 1789
<211> LENGTH: 15
<212> TYPE: PRT
<213> ORGANISM: Homo sapiens

<400> SEQUENCE: 1789

Leu Gly Val Gly Gly Leu Gly Val Pro Gly Val Gly Gly Leu Gly
1               5                   10                  15

<210> SEQ ID NO 1790
<211> LENGTH: 20
<212> TYPE: PRT
<213> ORGANISM: Homo sapiens

<400> SEQUENCE: 1790

Gly Leu Gly Val Pro Gly Val Gly Gly Leu Gly Gly Ile Pro Pro Ala
1               5                   10                  15

Ala Ala Ala Lys
            20

<210> SEQ ID NO 1791
<211> LENGTH: 11
<212> TYPE: PRT
<213> ORGANISM: Homo sapiens

<400> SEQUENCE: 1791

Leu Gly Gly Ile Pro Pro Ala Ala Ala Ala Lys
1               5                   10

<210> SEQ ID NO 1792
<211> LENGTH: 13
<212> TYPE: PRT
<213> ORGANISM: Homo sapiens

<400> SEQUENCE: 1792

Leu Gly Gly Val Leu Gly Gly Ala Gly Gln Phe Pro Leu
1               5                   10

<210> SEQ ID NO 1793
<211> LENGTH: 19
<212> TYPE: PRT
<213> ORGANISM: Homo sapiens

<400> SEQUENCE: 1793

Leu Gly Gly Val Leu Gly Gly Ala Gly Gln Phe Pro Leu Gly Gly Val
1               5                   10                  15

Ala Ala Arg

<210> SEQ ID NO 1794
```

<211> LENGTH: 21
<212> TYPE: PRT
<213> ORGANISM: Homo sapiens

<400> SEQUENCE: 1794

Leu Gly Gly Val Leu Gly Gly Ala Gly Gln Phe Pro Leu Gly Gly Val
1               5                   10                  15

Ala Ala Arg Pro Gly
            20

<210> SEQ ID NO 1795
<211> LENGTH: 23
<212> TYPE: PRT
<213> ORGANISM: Homo sapiens

<400> SEQUENCE: 1795

Leu Gly Gly Val Leu Gly Gly Ala Gly Gln Phe Pro Leu Gly Gly Val
1               5                   10                  15

Ala Ala Arg Pro Gly Phe Gly
            20

<210> SEQ ID NO 1796
<211> LENGTH: 20
<212> TYPE: PRT
<213> ORGANISM: Homo sapiens

<400> SEQUENCE: 1796

Gly Gly Val Leu Gly Gly Ala Gly Gln Phe Pro Leu Gly Gly Val Ala
1               5                   10                  15

Ala Arg Pro Gly
            20

<210> SEQ ID NO 1797
<211> LENGTH: 13
<212> TYPE: PRT
<213> ORGANISM: Homo sapiens

<400> SEQUENCE: 1797

Gly Ala Gly Gln Phe Pro Leu Gly Gly Val Ala Ala Arg
1               5                   10

<210> SEQ ID NO 1798
<211> LENGTH: 17
<212> TYPE: PRT
<213> ORGANISM: Homo sapiens

<400> SEQUENCE: 1798

Gly Ala Gly Gln Phe Pro Leu Gly Gly Val Ala Ala Arg Pro Gly Phe
1               5                   10                  15

Gly

<210> SEQ ID NO 1799
<211> LENGTH: 16
<212> TYPE: PRT
<213> ORGANISM: Homo sapiens

<400> SEQUENCE: 1799

Ala Gly Gln Phe Pro Leu Gly Gly Val Ala Ala Arg Pro Gly Phe Gly
1               5                   10                  15

<210> SEQ ID NO 1800
<211> LENGTH: 11
<212> TYPE: PRT

<213> ORGANISM: Homo sapiens

<400> SEQUENCE: 1800

Phe Pro Leu Gly Gly Val Ala Ala Arg Pro Gly
1               5                   10

<210> SEQ ID NO 1801
<211> LENGTH: 8
<212> TYPE: PRT
<213> ORGANISM: Homo sapiens

<400> SEQUENCE: 1801

Pro Leu Gly Gly Val Ala Ala Arg
1               5

<210> SEQ ID NO 1802
<211> LENGTH: 10
<212> TYPE: PRT
<213> ORGANISM: Homo sapiens

<400> SEQUENCE: 1802

Pro Leu Gly Gly Val Ala Ala Arg Pro Gly
1               5                   10

<210> SEQ ID NO 1803
<211> LENGTH: 12
<212> TYPE: PRT
<213> ORGANISM: Homo sapiens

<400> SEQUENCE: 1803

Pro Leu Gly Gly Val Ala Ala Arg Pro Gly Phe Gly
1               5                   10

<210> SEQ ID NO 1804
<211> LENGTH: 13
<212> TYPE: PRT
<213> ORGANISM: Homo sapiens

<400> SEQUENCE: 1804

Pro Leu Gly Gly Val Ala Ala Arg Pro Gly Phe Gly Leu
1               5                   10

<210> SEQ ID NO 1805
<211> LENGTH: 19
<212> TYPE: PRT
<213> ORGANISM: Homo sapiens

<400> SEQUENCE: 1805

Pro Leu Gly Gly Val Ala Ala Arg Pro Gly Phe Gly Leu Ser Pro Ile
1               5                   10                  15

Phe Pro Gly

<210> SEQ ID NO 1806
<211> LENGTH: 7
<212> TYPE: PRT
<213> ORGANISM: Homo sapiens

<400> SEQUENCE: 1806

Leu Gly Gly Val Ala Ala Arg
1               5

<210> SEQ ID NO 1807
<211> LENGTH: 8
<212> TYPE: PRT

<213> ORGANISM: Homo sapiens

<400> SEQUENCE: 1807

Leu Gly Gly Val Ala Ala Arg Pro
1               5

<210> SEQ ID NO 1808
<211> LENGTH: 9
<212> TYPE: PRT
<213> ORGANISM: Homo sapiens

<400> SEQUENCE: 1808

Leu Gly Gly Val Ala Ala Arg Pro Gly
1               5

<210> SEQ ID NO 1809
<211> LENGTH: 10
<212> TYPE: PRT
<213> ORGANISM: Homo sapiens

<400> SEQUENCE: 1809

Leu Gly Gly Val Ala Ala Arg Pro Gly Phe
1               5                   10

<210> SEQ ID NO 1810
<211> LENGTH: 11
<212> TYPE: PRT
<213> ORGANISM: Homo sapiens

<400> SEQUENCE: 1810

Leu Gly Gly Val Ala Ala Arg Pro Gly Phe Gly
1               5                   10

<210> SEQ ID NO 1811
<211> LENGTH: 12
<212> TYPE: PRT
<213> ORGANISM: Homo sapiens

<400> SEQUENCE: 1811

Leu Gly Gly Val Ala Ala Arg Pro Gly Phe Gly Leu
1               5                   10

<210> SEQ ID NO 1812
<211> LENGTH: 14
<212> TYPE: PRT
<213> ORGANISM: Homo sapiens

<400> SEQUENCE: 1812

Leu Gly Gly Val Ala Ala Arg Pro Gly Phe Gly Leu Ser Pro
1               5                   10

<210> SEQ ID NO 1813
<211> LENGTH: 18
<212> TYPE: PRT
<213> ORGANISM: Homo sapiens

<400> SEQUENCE: 1813

Leu Gly Gly Val Ala Ala Arg Pro Gly Phe Gly Leu Ser Pro Ile Phe
1               5                   10                  15

Pro Gly

<210> SEQ ID NO 1814
<211> LENGTH: 19
<212> TYPE: PRT

<213> ORGANISM: Homo sapiens

<400> SEQUENCE: 1814

Leu Gly Gly Val Ala Ala Arg Pro Gly Phe Gly Leu Ser Pro Ile Phe
1               5                   10                  15

Pro Gly Gly

<210> SEQ ID NO 1815
<211> LENGTH: 20
<212> TYPE: PRT
<213> ORGANISM: Homo sapiens

<400> SEQUENCE: 1815

Leu Gly Gly Val Ala Ala Arg Pro Gly Phe Gly Leu Ser Pro Ile Phe
1               5                   10                  15

Pro Gly Gly Ala
            20

<210> SEQ ID NO 1816
<211> LENGTH: 10
<212> TYPE: PRT
<213> ORGANISM: Homo sapiens

<400> SEQUENCE: 1816

Gly Gly Val Ala Ala Arg Pro Gly Phe Gly
1               5                   10

<210> SEQ ID NO 1817
<211> LENGTH: 11
<212> TYPE: PRT
<213> ORGANISM: Homo sapiens

<400> SEQUENCE: 1817

Gly Gly Val Ala Ala Arg Pro Gly Phe Gly Leu
1               5                   10

<210> SEQ ID NO 1818
<211> LENGTH: 19
<212> TYPE: PRT
<213> ORGANISM: Homo sapiens

<400> SEQUENCE: 1818

Gly Gly Val Ala Ala Arg Pro Gly Phe Gly Leu Ser Pro Ile Phe Pro
1               5                   10                  15

Gly Gly Ala

<210> SEQ ID NO 1819
<211> LENGTH: 14
<212> TYPE: PRT
<213> ORGANISM: Homo sapiens

<400> SEQUENCE: 1819

Gly Val Ala Ala Arg Pro Gly Phe Gly Leu Ser Pro Ile Phe
1               5                   10

<210> SEQ ID NO 1820
<211> LENGTH: 15
<212> TYPE: PRT
<213> ORGANISM: Homo sapiens

<400> SEQUENCE: 1820

Gly Val Ala Ala Arg Pro Gly Phe Gly Leu Ser Pro Ile Phe Pro
1               5                   10                  15

```
<210> SEQ ID NO 1821
<211> LENGTH: 8
<212> TYPE: PRT
<213> ORGANISM: Homo sapiens

<400> SEQUENCE: 1821

Val Ala Ala Arg Pro Gly Phe Gly
1               5

<210> SEQ ID NO 1822
<211> LENGTH: 14
<212> TYPE: PRT
<213> ORGANISM: Homo sapiens

<400> SEQUENCE: 1822

Val Ala Ala Arg Pro Gly Phe Gly Leu Ser Pro Ile Phe Pro
1               5                   10

<210> SEQ ID NO 1823
<211> LENGTH: 15
<212> TYPE: PRT
<213> ORGANISM: Homo sapiens

<400> SEQUENCE: 1823

Val Ala Ala Arg Pro Gly Phe Gly Leu Ser Pro Ile Phe Pro Gly
1               5                   10                  15

<210> SEQ ID NO 1824
<211> LENGTH: 12
<212> TYPE: PRT
<213> ORGANISM: Homo sapiens

<400> SEQUENCE: 1824

Arg Pro Gly Phe Gly Leu Ser Pro Ile Phe Pro Gly
1               5                   10

<210> SEQ ID NO 1825
<211> LENGTH: 12
<212> TYPE: PRT
<213> ORGANISM: Homo sapiens

<400> SEQUENCE: 1825

Pro Gly Phe Gly Leu Ser Pro Ile Phe Pro Gly Gly
1               5                   10

<210> SEQ ID NO 1826
<211> LENGTH: 13
<212> TYPE: PRT
<213> ORGANISM: Homo sapiens

<400> SEQUENCE: 1826

Pro Gly Phe Gly Leu Ser Pro Ile Phe Pro Gly Gly Ala
1               5                   10

<210> SEQ ID NO 1827
<211> LENGTH: 19
<212> TYPE: PRT
<213> ORGANISM: Homo sapiens

<400> SEQUENCE: 1827

Pro Gly Val Gly Leu Pro Gly Val Tyr Pro Gly Gly Val Leu Pro Gly
1               5                   10                  15

Ala Arg Phe
```

<210> SEQ ID NO 1828
<211> LENGTH: 18
<212> TYPE: PRT
<213> ORGANISM: Homo sapiens

<400> SEQUENCE: 1828

Gly Val Gly Leu Pro Gly Val Tyr Pro Gly Gly Val Leu Pro Gly Ala
1               5                   10                  15

Arg Phe

<210> SEQ ID NO 1829
<211> LENGTH: 16
<212> TYPE: PRT
<213> ORGANISM: Homo sapiens

<400> SEQUENCE: 1829

Gly Leu Pro Gly Val Tyr Pro Gly Gly Val Leu Pro Gly Ala Arg Phe
1               5                   10                  15

<210> SEQ ID NO 1830
<211> LENGTH: 14
<212> TYPE: PRT
<213> ORGANISM: Homo sapiens

<400> SEQUENCE: 1830

Pro Gly Val Tyr Pro Gly Gly Val Leu Pro Gly Ala Arg Phe
1               5                   10

<210> SEQ ID NO 1831
<211> LENGTH: 22
<212> TYPE: PRT
<213> ORGANISM: Homo sapiens

<400> SEQUENCE: 1831

Lys Ala Gly Tyr Pro Thr Gly Thr Gly Val Gly Pro Gln Ala Ala Ala
1               5                   10                  15

Ala Ala Ala Ala Lys Ala
            20

<210> SEQ ID NO 1832
<211> LENGTH: 26
<212> TYPE: PRT
<213> ORGANISM: Homo sapiens

<400> SEQUENCE: 1832

Gly Gly Pro Gly Phe Gly Pro Gly Val Val Gly Val Pro Gly Ala Gly
1               5                   10                  15

Val Pro Gly Val Gly Val Pro Gly Ala Gly
            20                  25

<210> SEQ ID NO 1833
<211> LENGTH: 22
<212> TYPE: PRT
<213> ORGANISM: Homo sapiens

<400> SEQUENCE: 1833

Gly Phe Gly Pro Gly Val Val Gly Val Pro Gly Ala Gly Val Pro Gly
1               5                   10                  15

Val Gly Val Pro Gly Ala
            20

```
<210> SEQ ID NO 1834
<211> LENGTH: 21
<212> TYPE: PRT
<213> ORGANISM: Homo sapiens

<400> SEQUENCE: 1834

Phe Gly Pro Gly Val Val Gly Val Pro Gly Ala Gly Val Pro Gly Val
1               5                   10                  15

Gly Val Pro Gly Ala
            20

<210> SEQ ID NO 1835
<211> LENGTH: 18
<212> TYPE: PRT
<213> ORGANISM: Homo sapiens

<400> SEQUENCE: 1835

Gly Val Pro Gly Val Gly Val Pro Gly Ala Gly Ile Pro Val Val Pro
1               5                   10                  15

Gly Ala

<210> SEQ ID NO 1836
<211> LENGTH: 18
<212> TYPE: PRT
<213> ORGANISM: Homo sapiens

<400> SEQUENCE: 1836

Gly Ala Arg Pro Gly Val Gly Val Gly Gly Ile Pro Thr Tyr Gly Val
1               5                   10                  15

Gly Ala

<210> SEQ ID NO 1837
<211> LENGTH: 21
<212> TYPE: PRT
<213> ORGANISM: Homo sapiens

<400> SEQUENCE: 1837

Gly Ala Arg Pro Gly Val Gly Val Gly Gly Ile Pro Thr Tyr Gly Val
1               5                   10                  15

Gly Ala Gly Gly Phe
            20

<210> SEQ ID NO 1838
<211> LENGTH: 19
<212> TYPE: PRT
<213> ORGANISM: Homo sapiens

<400> SEQUENCE: 1838

Ala Arg Pro Gly Val Gly Val Gly Gly Ile Pro Thr Tyr Gly Val Gly
1               5                   10                  15

Ala Gly Gly

<210> SEQ ID NO 1839
<211> LENGTH: 24
<212> TYPE: PRT
<213> ORGANISM: Homo sapiens

<400> SEQUENCE: 1839

Gly Gly Val Pro Gly Val Gly Gly Val Pro Gly Val Gly Ile Ser Pro
1               5                   10                  15

Glu Ala Gln Ala Ala Ala Ala Ala
            20
```

-continued

<210> SEQ ID NO 1840
<211> LENGTH: 19
<212> TYPE: PRT
<213> ORGANISM: Homo sapiens

<400> SEQUENCE: 1840

Gly Val Pro Gly Val Gly Ile Ser Pro Glu Ala Gln Ala Ala Ala
1               5                   10                  15

Ala Lys Ala

<210> SEQ ID NO 1841
<211> LENGTH: 16
<212> TYPE: PRT
<213> ORGANISM: Homo sapiens

<400> SEQUENCE: 1841

Gly Val Gly Ile Ser Pro Glu Ala Gln Ala Ala Ala Ala Lys Ala
1               5                   10                  15

<210> SEQ ID NO 1842
<211> LENGTH: 25
<212> TYPE: PRT
<213> ORGANISM: Homo sapiens

<400> SEQUENCE: 1842

Val Pro Gly Val Gly Val Ala Pro Gly Val Gly Val Ala Pro Gly Val
1               5                   10                  15

Gly Val Ala Pro Gly Val Gly Leu Ala
            20                  25

<210> SEQ ID NO 1843
<211> LENGTH: 30
<212> TYPE: PRT
<213> ORGANISM: Homo sapiens

<400> SEQUENCE: 1843

Gly Val Ala Pro Gly Val Gly Val Ala Pro Gly Val Gly Val Ala Pro
1               5                   10                  15

Gly Val Gly Leu Ala Pro Gly Val Gly Val Ala Pro Gly Val
            20                  25                  30

<210> SEQ ID NO 1844
<211> LENGTH: 22
<212> TYPE: PRT
<213> ORGANISM: Homo sapiens

<400> SEQUENCE: 1844

Gly Val Gly Val Ala Pro Gly Val Gly Val Ala Pro Gly Val Gly Leu
1               5                   10                  15

Ala Pro Gly Val Gly Val
            20

<210> SEQ ID NO 1845
<211> LENGTH: 28
<212> TYPE: PRT
<213> ORGANISM: Homo sapiens

<400> SEQUENCE: 1845

Gly Val Gly Val Ala Pro Gly Val Gly Val Ala Pro Gly Val Gly Leu
1               5                   10                  15

Ala Pro Gly Val Gly Val Ala Pro Gly Val Gly Val

-continued

```
              20                  25
```

<210> SEQ ID NO 1846
<211> LENGTH: 26
<212> TYPE: PRT
<213> ORGANISM: Homo sapiens

<400> SEQUENCE: 1846

```
Ala Pro Gly Val Gly Val Ala Pro Gly Val Gly Val Ala Pro Gly Val
1               5                   10                  15

Gly Val Ala Pro Gly Ile Gly Pro Gly Gly
            20                  25
```

<210> SEQ ID NO 1847
<211> LENGTH: 22
<212> TYPE: PRT
<213> ORGANISM: Homo sapiens

<400> SEQUENCE: 1847

```
Gly Val Ala Pro Gly Val Gly Val Ala Pro Gly Val Gly Val Ala Pro
1               5                   10                  15

Gly Ile Gly Pro Gly Gly
            20
```

<210> SEQ ID NO 1848
<211> LENGTH: 21
<212> TYPE: PRT
<213> ORGANISM: Homo sapiens

<400> SEQUENCE: 1848

```
Ala Ala Val Pro Gly Val Leu Gly Gly Leu Gly Ala Leu Gly Gly Val
1               5                   10                  15

Gly Ile Pro Gly Gly
            20
```

<210> SEQ ID NO 1849
<211> LENGTH: 23
<212> TYPE: PRT
<213> ORGANISM: Homo sapiens

<400> SEQUENCE: 1849

```
Gly Ala Ala Gly Leu Gly Gly Leu Gly Val Gly Gly Leu Gly Val Pro
1               5                   10                  15

Gly Val Gly Gly Leu Gly Gly
            20
```

<210> SEQ ID NO 1850
<211> LENGTH: 23
<212> TYPE: PRT
<213> ORGANISM: Homo sapiens

<400> SEQUENCE: 1850

```
Gly Gly Ala Gly Val Pro Gly Val Pro Gly Ala Ile Pro Gly Ile Gly
1               5                   10                  15

Gly Ile Ala Gly Val Gly Thr
            20
```

<210> SEQ ID NO 1851
<211> LENGTH: 22
<212> TYPE: PRT
<213> ORGANISM: Homo sapiens

<400> SEQUENCE: 1851

```
Gly Ala Gly Val Pro Gly Val Pro Gly Ala Ile Pro Gly Ile Gly
1               5                   10                  15

Ile Ala Gly Val Gly Thr
                20

<210> SEQ ID NO 1852
<211> LENGTH: 18
<212> TYPE: PRT
<213> ORGANISM: Homo sapiens

<400> SEQUENCE: 1852

Ala Gly Val Gly Thr Pro Ala Ala Ala Ala Ala Ala Ala Ala Ala
1               5                   10                  15

Lys Ala

<210> SEQ ID NO 1853
<211> LENGTH: 17
<212> TYPE: PRT
<213> ORGANISM: Homo sapiens

<400> SEQUENCE: 1853

Gly Val Gly Thr Pro Ala Ala Ala Ala Ala Ala Ala Ala Ala Lys
1               5                   10                  15

Ala

<210> SEQ ID NO 1854
<211> LENGTH: 25
<212> TYPE: PRT
<213> ORGANISM: Homo sapiens

<400> SEQUENCE: 1854

Gly Gly Pro Gly Phe Gly Pro Gly Val Val Gly Val Pro Gly Ala Gly
1               5                   10                  15

Val Pro Gly Val Gly Val Pro Gly Ala
                20                  25

<210> SEQ ID NO 1855
<211> LENGTH: 19
<212> TYPE: PRT
<213> ORGANISM: Homo sapiens

<400> SEQUENCE: 1855

Gly Ala Arg Pro Gly Val Gly Val Gly Ile Pro Thr Tyr Gly Val
1               5                   10                  15

Gly Ala Gly

<210> SEQ ID NO 1856
<211> LENGTH: 20
<212> TYPE: PRT
<213> ORGANISM: Homo sapiens

<400> SEQUENCE: 1856

Ala Arg Pro Gly Val Gly Val Gly Gly Ile Pro Thr Tyr Val Gly
1               5                   10                  15

Ala Gly Gly Phe
            20

<210> SEQ ID NO 1857
<211> LENGTH: 28
<212> TYPE: PRT
<213> ORGANISM: Homo sapiens
```

```
<400> SEQUENCE: 1857

Gly Val Gly Val Ala Pro Gly Val Gly Val Ala Pro Gly Val Gly Val
1               5                   10                  15

Ala Pro Gly Val Gly Leu Ala Pro Gly Val Gly Val
            20                  25

<210> SEQ ID NO 1858
<211> LENGTH: 26
<212> TYPE: PRT
<213> ORGANISM: Homo sapiens

<400> SEQUENCE: 1858

Ala Pro Gly Val Gly Val Ala Pro Gly Val Gly Leu Ala Pro Gly Val
1               5                   10                  15

Gly Val Ala Pro Gly Val Gly Val Ala Pro
            20                  25

<210> SEQ ID NO 1859
<211> LENGTH: 22
<212> TYPE: PRT
<213> ORGANISM: Homo sapiens

<400> SEQUENCE: 1859

Gly Val Gly Val Ala Pro Gly Val Gly Leu Ala Pro Gly Val Gly Val
1               5                   10                  15

Ala Pro Gly Val Gly Val
            20

<210> SEQ ID NO 1860
<211> LENGTH: 27
<212> TYPE: PRT
<213> ORGANISM: Homo sapiens

<400> SEQUENCE: 1860

Leu Ala Pro Gly Val Gly Val Ala Pro Gly Val Gly Val Ala Pro Gly
1               5                   10                  15

Val Gly Val Ala Pro Gly Ile Gly Pro Gly Gly
            20                  25

<210> SEQ ID NO 1861
<211> LENGTH: 23
<212> TYPE: PRT
<213> ORGANISM: Homo sapiens

<400> SEQUENCE: 1861

Tyr Gly Ala Ala Val Pro Gly Val Leu Gly Gly Leu Gly Ala Leu Gly
1               5                   10                  15

Gly Val Gly Ile Pro Gly Gly
            20

<210> SEQ ID NO 1862
<211> LENGTH: 20
<212> TYPE: PRT
<213> ORGANISM: Homo sapiens

<400> SEQUENCE: 1862

Gly Gly Ala Gly Gln Phe Pro Leu Gly Val Ala Ala Arg Pro Gly
1               5                   10                  15

Phe Gly Leu Ser
            20
```

<210> SEQ ID NO 1863
<211> LENGTH: 15
<212> TYPE: PRT
<213> ORGANISM: Homo sapiens

<400> SEQUENCE: 1863

Leu Val Pro Gly Gly Val Ala Asp Ala Ala Ala Ala Tyr Lys Ala
1               5                   10                  15

<210> SEQ ID NO 1864
<211> LENGTH: 12
<212> TYPE: PRT
<213> ORGANISM: Homo sapiens

<400> SEQUENCE: 1864

Val Tyr Pro Gly Gly Val Leu Pro Gly Ala Arg Phe
1               5                   10

<210> SEQ ID NO 1865
<211> LENGTH: 26
<212> TYPE: PRT
<213> ORGANISM: Homo sapiens

<400> SEQUENCE: 1865

Val Ala Pro Gly Val Gly Val Ala Pro Gly Val Gly Val Ala Pro Gly
1               5                   10                  15

Val Gly Leu Ala Pro Gly Val Gly Val Ala
            20                  25

<210> SEQ ID NO 1866
<211> LENGTH: 20
<212> TYPE: PRT
<213> ORGANISM: Homo sapiens

<400> SEQUENCE: 1866

Leu Ala Pro Gly Val Gly Val Ala Pro Gly Val Gly Val Ala Pro Gly
1               5                   10                  15

Val Gly Val Ala
            20

<210> SEQ ID NO 1867
<211> LENGTH: 23
<212> TYPE: PRT
<213> ORGANISM: Homo sapiens

<400> SEQUENCE: 1867

Leu Ala Pro Gly Val Gly Val Ala Pro Gly Val Gly Val Ala Pro Gly
1               5                   10                  15

Val Gly Val Ala Pro Gly Ile
            20

<210> SEQ ID NO 1868
<211> LENGTH: 25
<212> TYPE: PRT
<213> ORGANISM: Homo sapiens

<400> SEQUENCE: 1868

Leu Ala Pro Gly Val Gly Val Ala Pro Gly Val Gly Val Ala Pro Gly
1               5                   10                  15

Val Gly Val Ala Pro Gly Ile Gly Pro
            20                  25

<210> SEQ ID NO 1869
<211> LENGTH: 26
<212> TYPE: PRT
<213> ORGANISM: Homo sapiens

<400> SEQUENCE: 1869

Leu Ala Pro Gly Val Gly Val Ala Pro Gly Val Gly Val Ala Pro Gly
1               5                   10                  15

Val Gly Val Ala Pro Gly Ile Gly Pro Gly
            20                  25

<210> SEQ ID NO 1870
<211> LENGTH: 31
<212> TYPE: PRT
<213> ORGANISM: Homo sapiens

<400> SEQUENCE: 1870

Leu Ala Pro Gly Val Gly Val Ala Pro Gly Val Gly Val Ala Pro Gly
1               5                   10                  15

Val Gly Val Ala Pro Gly Ile Gly Pro Gly Gly Val Ala Ala Ala
            20                  25                  30

<210> SEQ ID NO 1871
<211> LENGTH: 24
<212> TYPE: PRT
<213> ORGANISM: Homo sapiens

<400> SEQUENCE: 1871

Gly Val Gly Val Ala Pro Gly Val Gly Val Ala Pro Gly Val Gly Val
1               5                   10                  15

Ala Pro Gly Ile Gly Pro Gly Gly
            20

<210> SEQ ID NO 1872
<211> LENGTH: 23
<212> TYPE: PRT
<213> ORGANISM: Homo sapiens

<400> SEQUENCE: 1872

Gly Ala Ala Val Pro Gly Val Leu Gly Gly Leu Gly Ala Leu Gly Gly
1               5                   10                  15

Val Gly Ile Pro Gly Gly Val
            20

<210> SEQ ID NO 1873
<211> LENGTH: 21
<212> TYPE: PRT
<213> ORGANISM: Homo sapiens

<400> SEQUENCE: 1873

Ala Ala Val Pro Gly Val Leu Gly Gly Leu Gly Ala Leu Gly Gly Val
1               5                   10                  15

Gly Ile Pro Gly Gly
            20

<210> SEQ ID NO 1874
<211> LENGTH: 21
<212> TYPE: PRT
<213> ORGANISM: Homo sapiens

<400> SEQUENCE: 1874

Ala Val Pro Gly Val Leu Gly Gly Leu Gly Ala Leu Gly Gly Val Gly
1               5                   10                  15

-continued

```
Ile Pro Gly Gly Val
            20

<210> SEQ ID NO 1875
<211> LENGTH: 18
<212> TYPE: PRT
<213> ORGANISM: Homo sapiens

<400> SEQUENCE: 1875

Ala Gly Gln Phe Pro Leu Gly Gly Val Ala Ala Arg Pro Gly Phe Gly
1               5                   10                  15

Leu Ser

<210> SEQ ID NO 1876
<211> LENGTH: 17
<212> TYPE: PRT
<213> ORGANISM: Homo sapiens

<400> SEQUENCE: 1876

Gly Ala Leu Val Pro Gly Gly Val Ala Asp Ala Ala Ala Ala Tyr Lys
1               5                   10                  15

Ala

<210> SEQ ID NO 1877
<211> LENGTH: 17
<212> TYPE: PRT
<213> ORGANISM: Homo sapiens

<400> SEQUENCE: 1877

Gly Leu Pro Tyr Thr Thr Gly Lys Leu Pro Tyr Gly Tyr Gly Pro Gly
1               5                   10                  15

Gly

<210> SEQ ID NO 1878
<211> LENGTH: 16
<212> TYPE: PRT
<213> ORGANISM: Homo sapiens

<400> SEQUENCE: 1878

Ala Ala Ala Ala Ala Ala Ala Lys Ala Ala Lys Phe Gly Ala Gly
1               5                   10                  15

<210> SEQ ID NO 1879
<211> LENGTH: 18
<212> TYPE: PRT
<213> ORGANISM: Homo sapiens

<400> SEQUENCE: 1879

Ala Ala Ala Ala Ala Ala Ala Ala Lys Ala Ala Lys Tyr Gly
1               5                   10                  15

Ala Ala

<210> SEQ ID NO 1880
<211> LENGTH: 26
<212> TYPE: PRT
<213> ORGANISM: Homo sapiens

<400> SEQUENCE: 1880

Gly Val Ala Pro Gly Val Gly Val Ala Pro Gly Val Gly Val Ala Pro
1               5                   10                  15

Gly Val Gly Leu Ala Pro Gly Val Gly Val
```

```
                    20                  25

<210> SEQ ID NO 1881
<211> LENGTH: 20
<212> TYPE: PRT
<213> ORGANISM: Homo sapiens

<400> SEQUENCE: 1881

Thr Phe Pro Gly Ala Leu Val Pro Gly Val Ala Asp Ala Ala Ala
1               5                   10                  15

Ala Tyr Lys Ala
            20

<210> SEQ ID NO 1882
<211> LENGTH: 21
<212> TYPE: PRT
<213> ORGANISM: Homo sapiens

<400> SEQUENCE: 1882

Gly Leu Pro Gly Val Tyr Pro Gly Gly Val Leu Pro Gly Ala Arg Phe
1               5                   10                  15

Pro Gly Val Gly Val
            20

<210> SEQ ID NO 1883
<211> LENGTH: 20
<212> TYPE: PRT
<213> ORGANISM: Homo sapiens

<400> SEQUENCE: 1883

Gly Tyr Pro Thr Gly Thr Gly Val Gly Pro Gln Ala Ala Ala Ala
1               5                   10                  15

Ala Ala Lys Ala
            20

<210> SEQ ID NO 1884
<211> LENGTH: 18
<212> TYPE: PRT
<213> ORGANISM: Homo sapiens

<400> SEQUENCE: 1884

Gly Thr Pro Ala Ala Ala Ala Ala Ala Ala Ala Ala Lys Ala Ala
1               5                   10                  15

Lys Tyr

<210> SEQ ID NO 1885
<211> LENGTH: 22
<212> TYPE: PRT
<213> ORGANISM: Homo sapiens

<400> SEQUENCE: 1885

Gly Val Pro Gly Ala Gly Val Pro Gly Val Gly Val Pro Gly Ala Gly
1               5                   10                  15

Ile Pro Val Val Pro Gly
            20

<210> SEQ ID NO 1886
<211> LENGTH: 28
<212> TYPE: PRT
<213> ORGANISM: Homo sapiens

<400> SEQUENCE: 1886
```

```
Gly Val Pro Gly Ala Gly Val Pro Gly Val Gly Pro Gly Ala Gly
1               5                  10                 15

Ile Pro Val Val Pro Gly Ala Gly Ile Pro Gly Ala
            20                  25
```

<210> SEQ ID NO 1887
<211> LENGTH: 17
<212> TYPE: PRT
<213> ORGANISM: Homo sapiens

<400> SEQUENCE: 1887

```
Gly Ile Ser Pro Glu Ala Gln Ala Ala Ala Ala Lys Ala Ala Lys
1               5                  10                 15

Tyr
```

<210> SEQ ID NO 1888
<211> LENGTH: 20
<212> TYPE: PRT
<213> ORGANISM: Homo sapiens

<400> SEQUENCE: 1888

```
Val Pro Gly Val Gly Val Ala Pro Gly Val Gly Val Ala Pro Gly Val
1               5                  10                 15

Gly Val Ala Pro
            20
```

<210> SEQ ID NO 1889
<211> LENGTH: 25
<212> TYPE: PRT
<213> ORGANISM: Homo sapiens

<400> SEQUENCE: 1889

```
Gly Val Ala Pro Gly Val Gly Val Ala Pro Gly Val Gly Val Ala Pro
1               5                  10                 15

Gly Ile Gly Pro Gly Gly Val Ala Ala
            20                  25
```

<210> SEQ ID NO 1890
<211> LENGTH: 20
<212> TYPE: PRT
<213> ORGANISM: Homo sapiens

<400> SEQUENCE: 1890

```
Gly Ile Pro Gly Gly Val Val Gly Ala Gly Pro Ala Ala Ala Ala Ala
1               5                  10                 15

Ala Ala Lys Ala
            20
```

<210> SEQ ID NO 1891
<211> LENGTH: 23
<212> TYPE: PRT
<213> ORGANISM: Homo sapiens

<400> SEQUENCE: 1891

```
Gly Gly Val Leu Pro Gly Ala Arg Phe Pro Gly Val Gly Val Leu Pro
1               5                  10                 15

Gly Val Pro Thr Gly Ala Gly
            20
```

<210> SEQ ID NO 1892
<211> LENGTH: 19
<212> TYPE: PRT

-continued

<213> ORGANISM: Homo sapiens

<400> SEQUENCE: 1892

Gly Gly Val Pro Gly Val Gly Val Pro Gly Val Gly Ile Ser Pro
1               5                   10                  15

Glu Ala Gln

<210> SEQ ID NO 1893
<211> LENGTH: 22
<212> TYPE: PRT
<213> ORGANISM: Homo sapiens

<400> SEQUENCE: 1893

Gly Val Gly Val Ala Pro Gly Val Gly Val Ala Pro Gly Val Gly Val
1               5                   10                  15

Ala Pro Gly Val Gly Leu
            20

<210> SEQ ID NO 1894
<211> LENGTH: 20
<212> TYPE: PRT
<213> ORGANISM: Homo sapiens

<400> SEQUENCE: 1894

Gly Val Pro Gly Val Pro Gly Ala Ile Pro Gly Ile Gly Gly Ile Ala
1               5                   10                  15

Gly Val Gly Thr
            20

<210> SEQ ID NO 1895
<211> LENGTH: 22
<212> TYPE: PRT
<213> ORGANISM: Homo sapiens

<400> SEQUENCE: 1895

Phe Gly Pro Gly Val Val Gly Val Pro Gly Ala Gly Val Pro Gly Val
1               5                   10                  15

Gly Val Pro Gly Ala Gly
            20

<210> SEQ ID NO 1896
<211> LENGTH: 19
<212> TYPE: PRT
<213> ORGANISM: Homo sapiens

<400> SEQUENCE: 1896

Gly Val Pro Gly Val Gly Val Pro Gly Ala Gly Ile Pro Val Val Pro
1               5                   10                  15

Gly Ala Gly

<210> SEQ ID NO 1897
<211> LENGTH: 19
<212> TYPE: PRT
<213> ORGANISM: Homo sapiens

<400> SEQUENCE: 1897

Gly Val Gly Val Ala Pro Gly Val Gly Val Ala Pro Gly Val Gly Val
1               5                   10                  15

Ala Pro Gly

<210> SEQ ID NO 1898

```
<211> LENGTH: 6
<212> TYPE: PRT
<213> ORGANISM: Homo sapiens

<400> SEQUENCE: 1898

Gly Val Pro Gly Ala Ile
1               5

<210> SEQ ID NO 1899
<211> LENGTH: 6
<212> TYPE: PRT
<213> ORGANISM: Homo sapiens

<400> SEQUENCE: 1899

Ala Ile Pro Gly Gly Val
1               5

<210> SEQ ID NO 1900
<211> LENGTH: 6
<212> TYPE: PRT
<213> ORGANISM: Homo sapiens

<400> SEQUENCE: 1900

Gly Val Pro Gly Gly Val
1               5

<210> SEQ ID NO 1901
<211> LENGTH: 6
<212> TYPE: PRT
<213> ORGANISM: Homo sapiens

<400> SEQUENCE: 1901

Ala Leu Gly Gly Gly Ala
1               5

<210> SEQ ID NO 1902
<211> LENGTH: 6
<212> TYPE: PRT
<213> ORGANISM: Homo sapiens

<400> SEQUENCE: 1902

Leu Gly Gly Gly Ala Leu
1               5

<210> SEQ ID NO 1903
<211> LENGTH: 6
<212> TYPE: PRT
<213> ORGANISM: Homo sapiens

<400> SEQUENCE: 1903

Gly Gly Ala Leu Gly Pro
1               5

<210> SEQ ID NO 1904
<211> LENGTH: 6
<212> TYPE: PRT
<213> ORGANISM: Homo sapiens

<400> SEQUENCE: 1904

Pro Leu Lys Pro Val Pro
1               5

<210> SEQ ID NO 1905
<211> LENGTH: 6
<212> TYPE: PRT
```

<213> ORGANISM: Homo sapiens

<400> SEQUENCE: 1905

Leu Lys Pro Val Pro Gly
1               5

<210> SEQ ID NO 1906
<211> LENGTH: 6
<212> TYPE: PRT
<213> ORGANISM: Homo sapiens

<400> SEQUENCE: 1906

Gly Leu Ala Gly Ala Gly
1               5

<210> SEQ ID NO 1907
<211> LENGTH: 6
<212> TYPE: PRT
<213> ORGANISM: Homo sapiens

<400> SEQUENCE: 1907

Gly Leu Gly Ala Gly Leu
1               5

<210> SEQ ID NO 1908
<211> LENGTH: 6
<212> TYPE: PRT
<213> ORGANISM: Homo sapiens

<400> SEQUENCE: 1908

Leu Gly Ala Gly Leu Gly
1               5

<210> SEQ ID NO 1909
<211> LENGTH: 6
<212> TYPE: PRT
<213> ORGANISM: Homo sapiens

<400> SEQUENCE: 1909

Ala Gly Leu Gly Ala Phe
1               5

<210> SEQ ID NO 1910
<211> LENGTH: 6
<212> TYPE: PRT
<213> ORGANISM: Homo sapiens

<400> SEQUENCE: 1910

Leu Val Pro Gly Gly Val
1               5

<210> SEQ ID NO 1911
<211> LENGTH: 6
<212> TYPE: PRT
<213> ORGANISM: Homo sapiens

<400> SEQUENCE: 1911

Val Ala Asp Ala Ala Ala
1               5

<210> SEQ ID NO 1912
<211> LENGTH: 6
<212> TYPE: PRT
<213> ORGANISM: Homo sapiens

```
<400> SEQUENCE: 1912

Lys Ala Ala Lys Ala Gly
1               5

<210> SEQ ID NO 1913
<211> LENGTH: 6
<212> TYPE: PRT
<213> ORGANISM: Homo sapiens

<400> SEQUENCE: 1913

Pro Val Gly Tyr Pro Gly
1               5

<210> SEQ ID NO 1914
<211> LENGTH: 6
<212> TYPE: PRT
<213> ORGANISM: Homo sapiens

<400> SEQUENCE: 1914

Ala Arg Phe Pro Gly Val
1               5

<210> SEQ ID NO 1915
<211> LENGTH: 6
<212> TYPE: PRT
<213> ORGANISM: Homo sapiens

<400> SEQUENCE: 1915

Arg Phe Pro Gly Val Gly
1               5

<210> SEQ ID NO 1916
<211> LENGTH: 6
<212> TYPE: PRT
<213> ORGANISM: Homo sapiens

<400> SEQUENCE: 1916

Val Gly Pro Phe Gly Gly
1               5

<210> SEQ ID NO 1917
<211> LENGTH: 6
<212> TYPE: PRT
<213> ORGANISM: Homo sapiens

<400> SEQUENCE: 1917

Gly Pro Gln Pro Gly Val
1               5

<210> SEQ ID NO 1918
<211> LENGTH: 6
<212> TYPE: PRT
<213> ORGANISM: Homo sapiens

<400> SEQUENCE: 1918

Pro Gln Pro Gly Val Pro
1               5

<210> SEQ ID NO 1919
<211> LENGTH: 6
<212> TYPE: PRT
<213> ORGANISM: Homo sapiens

<400> SEQUENCE: 1919
```

Thr Thr Gly Lys Leu Pro
1               5

<210> SEQ ID NO 1920
<211> LENGTH: 6
<212> TYPE: PRT
<213> ORGANISM: Homo sapiens

<400> SEQUENCE: 1920

Leu Pro Tyr Gly Tyr Gly
1               5

<210> SEQ ID NO 1921
<211> LENGTH: 6
<212> TYPE: PRT
<213> ORGANISM: Homo sapiens

<400> SEQUENCE: 1921

Gly Tyr Gly Pro Gly Gly
1               5

<210> SEQ ID NO 1922
<211> LENGTH: 6
<212> TYPE: PRT
<213> ORGANISM: Homo sapiens

<400> SEQUENCE: 1922

Phe Gly Ala Gly Ala Ala
1               5

<210> SEQ ID NO 1923
<211> LENGTH: 6
<212> TYPE: PRT
<213> ORGANISM: Homo sapiens

<400> SEQUENCE: 1923

Gly Val Leu Pro Gly Val
1               5

<210> SEQ ID NO 1924
<211> LENGTH: 6
<212> TYPE: PRT
<213> ORGANISM: Homo sapiens

<400> SEQUENCE: 1924

Val Leu Pro Gly Val Gly
1               5

<210> SEQ ID NO 1925
<211> LENGTH: 6
<212> TYPE: PRT
<213> ORGANISM: Homo sapiens

<400> SEQUENCE: 1925

Ala Gly Ile Pro Gly Leu
1               5

<210> SEQ ID NO 1926
<211> LENGTH: 6
<212> TYPE: PRT
<213> ORGANISM: Homo sapiens

<400> SEQUENCE: 1926

Val Pro Gly Ala Ile Pro
1               5

```
<210> SEQ ID NO 1927
<211> LENGTH: 6
<212> TYPE: PRT
<213> ORGANISM: Homo sapiens

<400> SEQUENCE: 1927

Ala Ile Pro Gly Ile Gly
1               5

<210> SEQ ID NO 1928
<211> LENGTH: 6
<212> TYPE: PRT
<213> ORGANISM: Homo sapiens

<400> SEQUENCE: 1928

Thr Pro Ala Ala Ala Ala
1               5

<210> SEQ ID NO 1929
<211> LENGTH: 6
<212> TYPE: PRT
<213> ORGANISM: Homo sapiens

<400> SEQUENCE: 1929

Pro Ala Ala Ala Ala Ala
1               5

<210> SEQ ID NO 1930
<211> LENGTH: 6
<212> TYPE: PRT
<213> ORGANISM: Homo sapiens

<400> SEQUENCE: 1930

Ala Ala Ala Ala Ala Ala
1               5

<210> SEQ ID NO 1931
<211> LENGTH: 6
<212> TYPE: PRT
<213> ORGANISM: Homo sapiens

<400> SEQUENCE: 1931

Val Gly Val Pro Gly Ala
1               5

<210> SEQ ID NO 1932
<211> LENGTH: 6
<212> TYPE: PRT
<213> ORGANISM: Homo sapiens

<400> SEQUENCE: 1932

Ala Val Gly Pro Gly Val
1               5

<210> SEQ ID NO 1933
<211> LENGTH: 6
<212> TYPE: PRT
<213> ORGANISM: Homo sapiens

<400> SEQUENCE: 1933

Gly Val Pro Gly Val Gly
1               5
```

```
<210> SEQ ID NO 1934
<211> LENGTH: 6
<212> TYPE: PRT
<213> ORGANISM: Homo sapiens

<400> SEQUENCE: 1934

Gly Ile Pro Val Val Pro
1               5

<210> SEQ ID NO 1935
<211> LENGTH: 6
<212> TYPE: PRT
<213> ORGANISM: Homo sapiens

<400> SEQUENCE: 1935

Ile Pro Gly Ala Ala Val
1               5

<210> SEQ ID NO 1936
<211> LENGTH: 6
<212> TYPE: PRT
<213> ORGANISM: Homo sapiens

<400> SEQUENCE: 1936

Gly Ala Ala Val Pro Gly
1               5

<210> SEQ ID NO 1937
<211> LENGTH: 6
<212> TYPE: PRT
<213> ORGANISM: Homo sapiens

<400> SEQUENCE: 1937

Ala Arg Pro Gly Val Gly
1               5

<210> SEQ ID NO 1938
<211> LENGTH: 6
<212> TYPE: PRT
<213> ORGANISM: Homo sapiens

<400> SEQUENCE: 1938

Arg Pro Gly Val Gly Val
1               5

<210> SEQ ID NO 1939
<211> LENGTH: 6
<212> TYPE: PRT
<213> ORGANISM: Homo sapiens

<400> SEQUENCE: 1939

Val Gly Gly Ile Pro Thr
1               5

<210> SEQ ID NO 1940
<211> LENGTH: 6
<212> TYPE: PRT
<213> ORGANISM: Homo sapiens

<400> SEQUENCE: 1940

Ser Val Gly Gly Val Pro
1               5

<210> SEQ ID NO 1941
<211> LENGTH: 6
```

```
<212> TYPE: PRT
<213> ORGANISM: Homo sapiens

<400> SEQUENCE: 1941

Val Gly Gly Val Pro Gly
1               5

<210> SEQ ID NO 1942
<211> LENGTH: 6
<212> TYPE: PRT
<213> ORGANISM: Homo sapiens

<400> SEQUENCE: 1942

Gly Val Gly Thr Pro Ala
1               5

<210> SEQ ID NO 1943
<211> LENGTH: 6
<212> TYPE: PRT
<213> ORGANISM: Homo sapiens

<400> SEQUENCE: 1943

Val Gly Val Ala Pro Gly
1               5

<210> SEQ ID NO 1944
<211> LENGTH: 6
<212> TYPE: PRT
<213> ORGANISM: Homo sapiens

<400> SEQUENCE: 1944

Val Ala Pro Gly Val Gly
1               5

<210> SEQ ID NO 1945
<211> LENGTH: 6
<212> TYPE: PRT
<213> ORGANISM: Homo sapiens

<400> SEQUENCE: 1945

Gly Val Ala Pro Gly Val
1               5

<210> SEQ ID NO 1946
<211> LENGTH: 6
<212> TYPE: PRT
<213> ORGANISM: Homo sapiens

<400> SEQUENCE: 1946

Gly Val Pro Val Ala Pro
1               5

<210> SEQ ID NO 1947
<211> LENGTH: 6
<212> TYPE: PRT
<213> ORGANISM: Homo sapiens

<400> SEQUENCE: 1947

Gly Ala Gly Ile Pro Gly
1               5

<210> SEQ ID NO 1948
<211> LENGTH: 6
<212> TYPE: PRT
<213> ORGANISM: Homo sapiens
```

<400> SEQUENCE: 1948

Pro Gly Gly Val Ala Ala
1               5

<210> SEQ ID NO 1949
<211> LENGTH: 6
<212> TYPE: PRT
<213> ORGANISM: Homo sapiens

<400> SEQUENCE: 1949

Leu Gly Ala Gly Ile Pro
1               5

<210> SEQ ID NO 1950
<211> LENGTH: 6
<212> TYPE: PRT
<213> ORGANISM: Homo sapiens

<400> SEQUENCE: 1950

Pro Gly Phe Gly Pro Gly
1               5

<210> SEQ ID NO 1951
<211> LENGTH: 6
<212> TYPE: PRT
<213> ORGANISM: Homo sapiens

<400> SEQUENCE: 1951

Pro Gly Val Val Gly Val
1               5

<210> SEQ ID NO 1952
<211> LENGTH: 6
<212> TYPE: PRT
<213> ORGANISM: Homo sapiens

<400> SEQUENCE: 1952

Pro Gly Ala Leu Ala Ala
1               5

<210> SEQ ID NO 1953
<211> LENGTH: 6
<212> TYPE: PRT
<213> ORGANISM: Homo sapiens

<400> SEQUENCE: 1953

Ala Lys Tyr Gly Ala Ala
1               5

<210> SEQ ID NO 1954
<211> LENGTH: 6
<212> TYPE: PRT
<213> ORGANISM: Homo sapiens

<400> SEQUENCE: 1954

Tyr Gly Ala Ala Val Pro
1               5

<210> SEQ ID NO 1955
<211> LENGTH: 6
<212> TYPE: PRT
<213> ORGANISM: Homo sapiens

<400> SEQUENCE: 1955

Ala Leu Gly Gly Val Gly
1               5

<210> SEQ ID NO 1956
<211> LENGTH: 6
<212> TYPE: PRT
<213> ORGANISM: Homo sapiens

<400> SEQUENCE: 1956

Leu Gly Gly Val Gly Ile
1               5

<210> SEQ ID NO 1957
<211> LENGTH: 6
<212> TYPE: PRT
<213> ORGANISM: Homo sapiens

<400> SEQUENCE: 1957

Gly Val Gly Ile Pro Gly
1               5

<210> SEQ ID NO 1958
<211> LENGTH: 6
<212> TYPE: PRT
<213> ORGANISM: Homo sapiens

<400> SEQUENCE: 1958

Ala Gly Pro Ala Ala Ala
1               5

<210> SEQ ID NO 1959
<211> LENGTH: 6
<212> TYPE: PRT
<213> ORGANISM: Homo sapiens

<400> SEQUENCE: 1959

Gly Pro Ala Ala Ala Ala
1               5

<210> SEQ ID NO 1960
<211> LENGTH: 6
<212> TYPE: PRT
<213> ORGANISM: Homo sapiens

<400> SEQUENCE: 1960

Phe Gly Leu Val Gly Ala
1               5

<210> SEQ ID NO 1961
<211> LENGTH: 6
<212> TYPE: PRT
<213> ORGANISM: Homo sapiens

<400> SEQUENCE: 1961

Gly Leu Gly Val Pro Gly
1               5

<210> SEQ ID NO 1962
<211> LENGTH: 6
<212> TYPE: PRT
<213> ORGANISM: Homo sapiens

<400> SEQUENCE: 1962

Leu Gly Gly Ile Pro Pro

```
1               5

<210> SEQ ID NO 1963
<211> LENGTH: 6
<212> TYPE: PRT
<213> ORGANISM: Homo sapiens

<400> SEQUENCE: 1963

Leu Gly Gly Val Leu Gly
1               5

<210> SEQ ID NO 1964
<211> LENGTH: 6
<212> TYPE: PRT
<213> ORGANISM: Homo sapiens

<400> SEQUENCE: 1964

Pro Leu Gly Gly Val Ala
1               5

<210> SEQ ID NO 1965
<211> LENGTH: 6
<212> TYPE: PRT
<213> ORGANISM: Homo sapiens

<400> SEQUENCE: 1965

Leu Gly Gly Val Ala Ala
1               5

<210> SEQ ID NO 1966
<211> LENGTH: 6
<212> TYPE: PRT
<213> ORGANISM: Homo sapiens

<400> SEQUENCE: 1966

Gly Gly Val Ala Ala Arg
1               5

<210> SEQ ID NO 1967
<211> LENGTH: 6
<212> TYPE: PRT
<213> ORGANISM: Homo sapiens

<400> SEQUENCE: 1967

Gly Val Gly Leu Pro Gly
1               5

<210> SEQ ID NO 1968
<211> LENGTH: 6
<212> TYPE: PRT
<213> ORGANISM: Homo sapiens

<400> SEQUENCE: 1968

Val Gly Leu Pro Gly Val
1               5

<210> SEQ ID NO 1969
<211> LENGTH: 6
<212> TYPE: PRT
<213> ORGANISM: Homo sapiens

<400> SEQUENCE: 1969

Leu Pro Gly Val Tyr Pro
1               5
```

<210> SEQ ID NO 1970
<211> LENGTH: 6
<212> TYPE: PRT
<213> ORGANISM: Homo sapiens

<400> SEQUENCE: 1970

Val Pro Gly Val Pro Val
1               5

<210> SEQ ID NO 1971
<211> LENGTH: 6
<212> TYPE: PRT
<213> ORGANISM: Homo sapiens

<400> SEQUENCE: 1971

Val Pro Gly Val Gly Ile
1               5

<210> SEQ ID NO 1972
<211> LENGTH: 6
<212> TYPE: PRT
<213> ORGANISM: Homo sapiens

<400> SEQUENCE: 1972

Val Gly Ile Ser Pro Glu
1               5

<210> SEQ ID NO 1973
<211> LENGTH: 6
<212> TYPE: PRT
<213> ORGANISM: Homo sapiens

<400> SEQUENCE: 1973

Ala Pro Gly Val Gly Val
1               5

<210> SEQ ID NO 1974
<211> LENGTH: 6
<212> TYPE: PRT
<213> ORGANISM: Homo sapiens

<400> SEQUENCE: 1974

Val Pro Gly Gly Val Ala
1               5

<210> SEQ ID NO 1975
<211> LENGTH: 6
<212> TYPE: PRT
<213> ORGANISM: Homo sapiens

<400> SEQUENCE: 1975

Tyr Pro Gly Gly Val Leu
1               5

<210> SEQ ID NO 1976
<211> LENGTH: 6
<212> TYPE: PRT
<213> ORGANISM: Homo sapiens

<400> SEQUENCE: 1976

Gly Pro Gly Phe Gly Pro
1               5

<210> SEQ ID NO 1977

```
<211> LENGTH: 6
<212> TYPE: PRT
<213> ORGANISM: Homo sapiens

<400> SEQUENCE: 1977

Tyr Pro Thr Gly Thr Gly
1               5

<210> SEQ ID NO 1978
<211> LENGTH: 6
<212> TYPE: PRT
<213> ORGANISM: Homo sapiens

<400> SEQUENCE: 1978

Val Pro Gly Ala Gly Val
1               5

<210> SEQ ID NO 1979
<211> LENGTH: 6
<212> TYPE: PRT
<213> ORGANISM: Homo sapiens

<400> SEQUENCE: 1979

Val Pro Gly Gly Val Phe
1               5

<210> SEQ ID NO 1980
<211> LENGTH: 6
<212> TYPE: PRT
<213> ORGANISM: Homo sapiens

<400> SEQUENCE: 1980

Gly Val Phe Tyr Pro Gly
1               5

<210> SEQ ID NO 1981
<211> LENGTH: 6
<212> TYPE: PRT
<213> ORGANISM: Homo sapiens

<400> SEQUENCE: 1981

Val Phe Tyr Pro Gly Ala
1               5

<210> SEQ ID NO 1982
<211> LENGTH: 6
<212> TYPE: PRT
<213> ORGANISM: Homo sapiens

<400> SEQUENCE: 1982

Leu Gly Pro Gly Gly Lys
1               5

<210> SEQ ID NO 1983
<211> LENGTH: 6
<212> TYPE: PRT
<213> ORGANISM: Homo sapiens

<400> SEQUENCE: 1983

Gly Pro Gly Gly Lys Pro
1               5

<210> SEQ ID NO 1984
<211> LENGTH: 6
<212> TYPE: PRT
```

<213> ORGANISM: Homo sapiens

<400> SEQUENCE: 1984

Pro Gly Gly Lys Pro Leu
1               5

<210> SEQ ID NO 1985
<211> LENGTH: 6
<212> TYPE: PRT
<213> ORGANISM: Homo sapiens

<400> SEQUENCE: 1985

Leu Ala Gly Ala Gly Leu
1               5

<210> SEQ ID NO 1986
<211> LENGTH: 6
<212> TYPE: PRT
<213> ORGANISM: Homo sapiens

<400> SEQUENCE: 1986

Ala Gly Ala Gly Leu Gly
1               5

<210> SEQ ID NO 1987
<211> LENGTH: 6
<212> TYPE: PRT
<213> ORGANISM: Homo sapiens

<400> SEQUENCE: 1987

Gly Ala Gly Leu Gly Ala
1               5

<210> SEQ ID NO 1988
<211> LENGTH: 6
<212> TYPE: PRT
<213> ORGANISM: Homo sapiens

<400> SEQUENCE: 1988

Leu Gly Ala Phe Pro Ala
1               5

<210> SEQ ID NO 1989
<211> LENGTH: 6
<212> TYPE: PRT
<213> ORGANISM: Homo sapiens

<400> SEQUENCE: 1989

Ala Phe Pro Ala Val Thr
1               5

<210> SEQ ID NO 1990
<211> LENGTH: 6
<212> TYPE: PRT
<213> ORGANISM: Homo sapiens

<400> SEQUENCE: 1990

Ala Val Thr Phe Pro Gly
1               5

<210> SEQ ID NO 1991
<211> LENGTH: 6
<212> TYPE: PRT
<213> ORGANISM: Homo sapiens

<400> SEQUENCE: 1991

Leu Gly Val Ser Ala Gly
1               5

<210> SEQ ID NO 1992
<211> LENGTH: 6
<212> TYPE: PRT
<213> ORGANISM: Homo sapiens

<400> SEQUENCE: 1992

Val Pro Gly Val Gly Leu
1               5

<210> SEQ ID NO 1993
<211> LENGTH: 6
<212> TYPE: PRT
<213> ORGANISM: Homo sapiens

<400> SEQUENCE: 1993

Pro Gly Val Gly Leu Pro
1               5

<210> SEQ ID NO 1994
<211> LENGTH: 6
<212> TYPE: PRT
<213> ORGANISM: Homo sapiens

<400> SEQUENCE: 1994

Phe Pro Gly Val Gly Val
1               5

<210> SEQ ID NO 1995
<211> LENGTH: 6
<212> TYPE: PRT
<213> ORGANISM: Homo sapiens

<400> SEQUENCE: 1995

Lys Pro Gly Ala Pro Gly
1               5

<210> SEQ ID NO 1996
<211> LENGTH: 6
<212> TYPE: PRT
<213> ORGANISM: Homo sapiens

<400> SEQUENCE: 1996

Pro Gly Val Pro Leu Gly
1               5

<210> SEQ ID NO 1997
<211> LENGTH: 6
<212> TYPE: PRT
<213> ORGANISM: Homo sapiens

<400> SEQUENCE: 1997

Gly Tyr Pro Ile Lys Ala
1               5

<210> SEQ ID NO 1998
<211> LENGTH: 6
<212> TYPE: PRT
<213> ORGANISM: Homo sapiens

<400> SEQUENCE: 1998

```
Pro Lys Leu Pro Gly Gly
1               5

<210> SEQ ID NO 1999
<211> LENGTH: 6
<212> TYPE: PRT
<213> ORGANISM: Homo sapiens

<400> SEQUENCE: 1999

Tyr Gly Pro Gly Gly Val
1               5

<210> SEQ ID NO 2000
<211> LENGTH: 6
<212> TYPE: PRT
<213> ORGANISM: Homo sapiens

<400> SEQUENCE: 2000

Ala Gly Tyr Pro Thr Gly
1               5

<210> SEQ ID NO 2001
<211> LENGTH: 6
<212> TYPE: PRT
<213> ORGANISM: Homo sapiens

<400> SEQUENCE: 2001

Thr Gly Val Gly Pro Gln
1               5

<210> SEQ ID NO 2002
<211> LENGTH: 6
<212> TYPE: PRT
<213> ORGANISM: Homo sapiens

<400> SEQUENCE: 2002

Gly Ala Gly Val Pro Gly
1               5

<210> SEQ ID NO 2003
<211> LENGTH: 6
<212> TYPE: PRT
<213> ORGANISM: Homo sapiens

<400> SEQUENCE: 2003

Ala Gly Val Pro Gly Val
1               5

<210> SEQ ID NO 2004
<211> LENGTH: 6
<212> TYPE: PRT
<213> ORGANISM: Homo sapiens

<400> SEQUENCE: 2004

Gly Val Pro Gly Val Pro
1               5

<210> SEQ ID NO 2005
<211> LENGTH: 6
<212> TYPE: PRT
<213> ORGANISM: Homo sapiens

<400> SEQUENCE: 2005

Ile Pro Gly Ile Gly Gly
1               5
```

<210> SEQ ID NO 2006
<211> LENGTH: 6
<212> TYPE: PRT
<213> ORGANISM: Homo sapiens

<400> SEQUENCE: 2006

Ile Gly Gly Ile Ala Gly
1               5

<210> SEQ ID NO 2007
<211> LENGTH: 6
<212> TYPE: PRT
<213> ORGANISM: Homo sapiens

<400> SEQUENCE: 2007

Gly Ile Ala Gly Val Gly
1               5

<210> SEQ ID NO 2008
<211> LENGTH: 6
<212> TYPE: PRT
<213> ORGANISM: Homo sapiens

<400> SEQUENCE: 2008

Val Pro Gly Val Gly Val
1               5

<210> SEQ ID NO 2009
<211> LENGTH: 6
<212> TYPE: PRT
<213> ORGANISM: Homo sapiens

<400> SEQUENCE: 2009

Val Pro Val Gly Val Ala
1               5

<210> SEQ ID NO 2010
<211> LENGTH: 6
<212> TYPE: PRT
<213> ORGANISM: Homo sapiens

<400> SEQUENCE: 2010

Val Pro Gly Ala Gly Ile
1               5

<210> SEQ ID NO 2011
<211> LENGTH: 6
<212> TYPE: PRT
<213> ORGANISM: Homo sapiens

<400> SEQUENCE: 2011

Ala Val Pro Gly Val Val
1               5

<210> SEQ ID NO 2012
<211> LENGTH: 6
<212> TYPE: PRT
<213> ORGANISM: Homo sapiens

<400> SEQUENCE: 2012

Val Pro Gly Val Val Ser
1               5

<210> SEQ ID NO 2013
<211> LENGTH: 6
<212> TYPE: PRT
<213> ORGANISM: Homo sapiens

<400> SEQUENCE: 2013

Tyr Gly Ala Arg Pro Gly
1               5

<210> SEQ ID NO 2014
<211> LENGTH: 6
<212> TYPE: PRT
<213> ORGANISM: Homo sapiens

<400> SEQUENCE: 2014

Gly Val Gly Ala Gly Gly
1               5

<210> SEQ ID NO 2015
<211> LENGTH: 6
<212> TYPE: PRT
<213> ORGANISM: Homo sapiens

<400> SEQUENCE: 2015

Val Gly Ala Gly Gly Phe
1               5

<210> SEQ ID NO 2016
<211> LENGTH: 6
<212> TYPE: PRT
<213> ORGANISM: Homo sapiens

<400> SEQUENCE: 2016

Val Gly Val Gly Gly Ile
1               5

<210> SEQ ID NO 2017
<211> LENGTH: 6
<212> TYPE: PRT
<213> ORGANISM: Homo sapiens

<400> SEQUENCE: 2017

Phe Gly Leu Val Pro Gly
1               5

<210> SEQ ID NO 2018
<211> LENGTH: 6
<212> TYPE: PRT
<213> ORGANISM: Homo sapiens

<400> SEQUENCE: 2018

Gly Leu Val Pro Gly Val
1               5

<210> SEQ ID NO 2019
<211> LENGTH: 6
<212> TYPE: PRT
<213> ORGANISM: Homo sapiens

<400> SEQUENCE: 2019

Leu Val Pro Gly Val Gly
1               5

<210> SEQ ID NO 2020
<211> LENGTH: 6

```
<212> TYPE: PRT
<213> ORGANISM: Homo sapiens

<400> SEQUENCE: 2020

Pro Gly Val Gly Leu Ala
1               5

<210> SEQ ID NO 2021
<211> LENGTH: 6
<212> TYPE: PRT
<213> ORGANISM: Homo sapiens

<400> SEQUENCE: 2021

Gly Val Gly Leu Ala Pro
1               5

<210> SEQ ID NO 2022
<211> LENGTH: 6
<212> TYPE: PRT
<213> ORGANISM: Homo sapiens

<400> SEQUENCE: 2022

Val Gly Leu Ala Pro Gly
1               5

<210> SEQ ID NO 2023
<211> LENGTH: 6
<212> TYPE: PRT
<213> ORGANISM: Homo sapiens

<400> SEQUENCE: 2023

Leu Arg Ala Ala Ala Gly
1               5

<210> SEQ ID NO 2024
<211> LENGTH: 6
<212> TYPE: PRT
<213> ORGANISM: Homo sapiens

<400> SEQUENCE: 2024

Leu Val Gly Ala Ala Gly
1               5

<210> SEQ ID NO 2025
<211> LENGTH: 6
<212> TYPE: PRT
<213> ORGANISM: Homo sapiens

<400> SEQUENCE: 2025

Leu Val Pro Gly Gly Pro
1               5

<210> SEQ ID NO 2026
<211> LENGTH: 6
<212> TYPE: PRT
<213> ORGANISM: Homo sapiens

<400> SEQUENCE: 2026

Gly Ile Pro Gly Leu Gly
1               5

<210> SEQ ID NO 2027
<211> LENGTH: 6
<212> TYPE: PRT
<213> ORGANISM: Homo sapiens
```

```
<400> SEQUENCE: 2027

Leu Gly Val Gly Val Gly
1               5

<210> SEQ ID NO 2028
<211> LENGTH: 6
<212> TYPE: PRT
<213> ORGANISM: Homo sapiens

<400> SEQUENCE: 2028

Val Gly Val Pro Gly Leu
1               5

<210> SEQ ID NO 2029
<211> LENGTH: 6
<212> TYPE: PRT
<213> ORGANISM: Homo sapiens

<400> SEQUENCE: 2029

Ala Ala Ala Gly Leu Gly
1               5

<210> SEQ ID NO 2030
<211> LENGTH: 6
<212> TYPE: PRT
<213> ORGANISM: Homo sapiens

<400> SEQUENCE: 2030

Ala Val Pro Gly Val Leu
1               5

<210> SEQ ID NO 2031
<211> LENGTH: 6
<212> TYPE: PRT
<213> ORGANISM: Homo sapiens

<400> SEQUENCE: 2031

Val Leu Gly Gly Leu Gly
1               5

<210> SEQ ID NO 2032
<211> LENGTH: 6
<212> TYPE: PRT
<213> ORGANISM: Homo sapiens

<400> SEQUENCE: 2032

Val Gly Ile Pro Gly Gly
1               5

<210> SEQ ID NO 2033
<211> LENGTH: 6
<212> TYPE: PRT
<213> ORGANISM: Homo sapiens

<400> SEQUENCE: 2033

Ile Pro Gly Gly Val Val
1               5

<210> SEQ ID NO 2034
<211> LENGTH: 6
<212> TYPE: PRT
<213> ORGANISM: Homo sapiens

<400> SEQUENCE: 2034
```

Val Val Gly Ala Gly Pro
1               5

<210> SEQ ID NO 2035
<211> LENGTH: 6
<212> TYPE: PRT
<213> ORGANISM: Homo sapiens

<400> SEQUENCE: 2035

Gly Leu Val Gly Ala Ala
1               5

<210> SEQ ID NO 2036
<211> LENGTH: 6
<212> TYPE: PRT
<213> ORGANISM: Homo sapiens

<400> SEQUENCE: 2036

Val Gly Ala Ala Gly Leu
1               5

<210> SEQ ID NO 2037
<211> LENGTH: 6
<212> TYPE: PRT
<213> ORGANISM: Homo sapiens

<400> SEQUENCE: 2037

Leu Gly Gly Leu Gly Val
1               5

<210> SEQ ID NO 2038
<211> LENGTH: 6
<212> TYPE: PRT
<213> ORGANISM: Homo sapiens

<400> SEQUENCE: 2038

Gly Gly Val Leu Gly Gly
1               5

<210> SEQ ID NO 2039
<211> LENGTH: 6
<212> TYPE: PRT
<213> ORGANISM: Homo sapiens

<400> SEQUENCE: 2039

Gly Ala Gly Gln Phe Pro
1               5

<210> SEQ ID NO 2040
<211> LENGTH: 6
<212> TYPE: PRT
<213> ORGANISM: Homo sapiens

<400> SEQUENCE: 2040

Ala Phe Gln Phe Pro Leu
1               5

<210> SEQ ID NO 2041
<211> LENGTH: 6
<212> TYPE: PRT
<213> ORGANISM: Homo sapiens

<400> SEQUENCE: 2041

Gly Val Ala Ala Arg Pro

```
1               5

<210> SEQ ID NO 2042
<211> LENGTH: 6
<212> TYPE: PRT
<213> ORGANISM: Homo sapiens

<400> SEQUENCE: 2042

Val Ala Ala Arg Pro Gly
1               5

<210> SEQ ID NO 2043
<211> LENGTH: 6
<212> TYPE: PRT
<213> ORGANISM: Homo sapiens

<400> SEQUENCE: 2043

Arg Pro Gly Phe Gly Leu
1               5

<210> SEQ ID NO 2044
<211> LENGTH: 6
<212> TYPE: PRT
<213> ORGANISM: Homo sapiens

<400> SEQUENCE: 2044

Gly Val Tyr Pro Gly Gly
1               5

<210> SEQ ID NO 2045
<211> LENGTH: 6
<212> TYPE: PRT
<213> ORGANISM: Homo sapiens

<400> SEQUENCE: 2045

Leu Pro Tyr Thr Thr Gly
1               5

<210> SEQ ID NO 2046
<211> LENGTH: 6
<212> TYPE: PRT
<213> ORGANISM: Homo sapiens

<400> SEQUENCE: 2046

Phe Gly Pro Gly Val Val
1               5

<210> SEQ ID NO 2047
<211> LENGTH: 6
<212> TYPE: PRT
<213> ORGANISM: Homo sapiens

<400> SEQUENCE: 2047

Ala Ala Val Pro Gly Val
1               5

<210> SEQ ID NO 2048
<211> LENGTH: 6
<212> TYPE: PRT
<213> ORGANISM: Homo sapiens

<400> SEQUENCE: 2048

Ala Ala Gly Leu Gly Gly
1               5
```

<210> SEQ ID NO 2049
<211> LENGTH: 6
<212> TYPE: PRT
<213> ORGANISM: Homo sapiens

<400> SEQUENCE: 2049

Phe Pro Gly Ala Leu Val
1               5

<210> SEQ ID NO 2050
<211> LENGTH: 6
<212> TYPE: PRT
<213> ORGANISM: Homo sapiens

<400> SEQUENCE: 2050

Val Pro Gly Val Leu Gly
1               5

<210> SEQ ID NO 2051
<211> LENGTH: 6
<212> TYPE: PRT
<213> ORGANISM: Homo sapiens

<400> SEQUENCE: 2051

Gly Gln Phe Pro Leu Gly
1               5

<210> SEQ ID NO 2052
<211> LENGTH: 6
<212> TYPE: PRT
<213> ORGANISM: Homo sapiens

<400> SEQUENCE: 2052

Ala Leu Val Pro Gly Gly
1               5

<210> SEQ ID NO 2053
<211> LENGTH: 6
<212> TYPE: PRT
<213> ORGANISM: Homo sapiens

<400> SEQUENCE: 2053

Ile Ser Pro Glu Ala Gln
1               5

<210> SEQ ID NO 2054
<211> LENGTH: 6
<212> TYPE: PRT
<213> ORGANISM: Homo sapiens

<400> SEQUENCE: 2054

Gly Val Leu Pro Gly Ala
1               5

<210> SEQ ID NO 2055
<211> LENGTH: 6
<212> TYPE: PRT
<213> ORGANISM: Homo sapiens

<400> SEQUENCE: 2055

Val Gly Ala Gly Val Pro
1               5

<210> SEQ ID NO 2056

```
<211> LENGTH: 6
<212> TYPE: PRT
<213> ORGANISM: Homo sapiens

<400> SEQUENCE: 2056

Leu Gly Ala Leu Gly Gly
1               5

<210> SEQ ID NO 2057
<211> LENGTH: 6
<212> TYPE: PRT
<213> ORGANISM: Homo sapiens

<400> SEQUENCE: 2057

Val Pro Gly Val Pro Gly
1               5

<210> SEQ ID NO 2058
<211> LENGTH: 6
<212> TYPE: PRT
<213> ORGANISM: Homo sapiens

<400> SEQUENCE: 2058

Gly Gly Leu Gly Ala Leu
1               5

<210> SEQ ID NO 2059
<211> LENGTH: 6
<212> TYPE: PRT
<213> ORGANISM: Homo sapiens

<400> SEQUENCE: 2059

Gly Lys Pro Leu Lys Pro
1               5

<210> SEQ ID NO 2060
<211> LENGTH: 6
<212> TYPE: PRT
<213> ORGANISM: Homo sapiens

<400> SEQUENCE: 2060

Ile Ala Gly Val Gly Thr
1               5

<210> SEQ ID NO 2061
<211> LENGTH: 6
<212> TYPE: PRT
<213> ORGANISM: Homo sapiens

<400> SEQUENCE: 2061

Val Gly Ala Gly Pro Ala
1               5

<210> SEQ ID NO 2062
<211> LENGTH: 6
<212> TYPE: PRT
<213> ORGANISM: Homo sapiens

<400> SEQUENCE: 2062

Ala Gly Leu Gly Ala Gly
1               5

<210> SEQ ID NO 2063
<211> LENGTH: 6
<212> TYPE: PRT
```

<213> ORGANISM: Homo sapiens

<400> SEQUENCE: 2063

Val Val Gly Val Pro Gly
1               5

<210> SEQ ID NO 2064
<211> LENGTH: 6
<212> TYPE: PRT
<213> ORGANISM: Homo sapiens

<400> SEQUENCE: 2064

Leu Gly Val Gly Gly Leu
1               5

<210> SEQ ID NO 2065
<211> LENGTH: 6
<212> TYPE: PRT
<213> ORGANISM: Homo sapiens

<400> SEQUENCE: 2065

Val Thr Phe Pro Gly Ala
1               5

<210> SEQ ID NO 2066
<211> LENGTH: 6
<212> TYPE: PRT
<213> ORGANISM: Homo sapiens

<400> SEQUENCE: 2066

Ala Gly Ile Pro Val Val
1               5

<210> SEQ ID NO 2067
<211> LENGTH: 6
<212> TYPE: PRT
<213> ORGANISM: Homo sapiens

<400> SEQUENCE: 2067

Phe Pro Leu Gly Gly Val
1               5

<210> SEQ ID NO 2068
<211> LENGTH: 6
<212> TYPE: PRT
<213> ORGANISM: Homo sapiens

<400> SEQUENCE: 2068

Gly Leu Pro Gly Val Tyr
1               5

<210> SEQ ID NO 2069
<211> LENGTH: 6
<212> TYPE: PRT
<213> ORGANISM: Homo sapiens

<400> SEQUENCE: 2069

Gly Ala Arg Pro Gly Val
1               5

<210> SEQ ID NO 2070
<211> LENGTH: 6
<212> TYPE: PRT
<213> ORGANISM: Homo sapiens

```
<400> SEQUENCE: 2070

Pro Gly Phe Gly Leu Ser
1               5

<210> SEQ ID NO 2071
<211> LENGTH: 6
<212> TYPE: PRT
<213> ORGANISM: Homo sapiens

<400> SEQUENCE: 2071

Gly Ala Phe Ala Gly Ile
1               5

<210> SEQ ID NO 2072
<211> LENGTH: 6
<212> TYPE: PRT
<213> ORGANISM: Homo sapiens

<400> SEQUENCE: 2072

Val Ala Gly Val Pro Ser
1               5

<210> SEQ ID NO 2073
<211> LENGTH: 6
<212> TYPE: PRT
<213> ORGANISM: Homo sapiens

<400> SEQUENCE: 2073

Gly Pro Gly Val Val Gly
1               5

<210> SEQ ID NO 2074
<211> LENGTH: 6
<212> TYPE: PRT
<213> ORGANISM: Homo sapiens

<400> SEQUENCE: 2074

Tyr Thr Thr Gly Lys Leu
1               5

<210> SEQ ID NO 2075
<211> LENGTH: 6
<212> TYPE: PRT
<213> ORGANISM: Homo sapiens

<400> SEQUENCE: 2075

Pro Gly Val Gly Val Ala
1               5

<210> SEQ ID NO 2076
<211> LENGTH: 6
<212> TYPE: PRT
<213> ORGANISM: Homo sapiens

<400> SEQUENCE: 2076

Val Gly Thr Pro Ala Ala
1               5

<210> SEQ ID NO 2077
<211> LENGTH: 6
<212> TYPE: PRT
<213> ORGANISM: Homo sapiens

<400> SEQUENCE: 2077
```

Pro Gln Ala Ala Ala Ala
1               5

<210> SEQ ID NO 2078
<211> LENGTH: 6
<212> TYPE: PRT
<213> ORGANISM: Homo sapiens

<400> SEQUENCE: 2078

Leu Ala Pro Gly Val Gly
1               5

<210> SEQ ID NO 2079
<211> LENGTH: 6
<212> TYPE: PRT
<213> ORGANISM: Homo sapiens

<400> SEQUENCE: 2079

Pro Gly Gly Val Pro Gly
1               5

<210> SEQ ID NO 2080
<211> LENGTH: 6
<212> TYPE: PRT
<213> ORGANISM: Homo sapiens

<400> SEQUENCE: 2080

Pro Gly Ala Gly Leu Gly
1               5

<210> SEQ ID NO 2081
<211> LENGTH: 6
<212> TYPE: PRT
<213> ORGANISM: Homo sapiens

<400> SEQUENCE: 2081

Gly Ala Leu Gly Gly Gly
1               5

<210> SEQ ID NO 2082
<211> LENGTH: 6
<212> TYPE: PRT
<213> ORGANISM: Homo sapiens

<400> SEQUENCE: 2082

Gly Gly Gly Ala Leu Gly
1               5

<210> SEQ ID NO 2083
<211> LENGTH: 6
<212> TYPE: PRT
<213> ORGANISM: Homo sapiens

<400> SEQUENCE: 2083

Gly Leu Gly Ala Phe Pro
1               5

<210> SEQ ID NO 2084
<211> LENGTH: 6
<212> TYPE: PRT
<213> ORGANISM: Homo sapiens

<400> SEQUENCE: 2084

Ala Asp Ala Ala Ala Ala
1               5

<210> SEQ ID NO 2085
<211> LENGTH: 6
<212> TYPE: PRT
<213> ORGANISM: Homo sapiens

<400> SEQUENCE: 2085

Pro Gly Val Leu Gly Gly
1               5

<210> SEQ ID NO 2086
<211> LENGTH: 6
<212> TYPE: PRT
<213> ORGANISM: Homo sapiens

<400> SEQUENCE: 2086

Val Gly Val Leu Pro Gly
1               5

<210> SEQ ID NO 2087
<211> LENGTH: 6
<212> TYPE: PRT
<213> ORGANISM: Homo sapiens

<400> SEQUENCE: 2087

Val Pro Thr Gly Ala Gly
1               5

<210> SEQ ID NO 2088
<211> LENGTH: 6
<212> TYPE: PRT
<213> ORGANISM: Homo sapiens

<400> SEQUENCE: 2088

Gly Val Gly Pro Phe Gly
1               5

<210> SEQ ID NO 2089
<211> LENGTH: 6
<212> TYPE: PRT
<213> ORGANISM: Homo sapiens

<400> SEQUENCE: 2089

Val Pro Leu Gly Tyr Pro
1               5

<210> SEQ ID NO 2090
<211> LENGTH: 6
<212> TYPE: PRT
<213> ORGANISM: Homo sapiens

<400> SEQUENCE: 2090

Ala Ala Ala Ala Ala Lys
1               5

<210> SEQ ID NO 2091
<211> LENGTH: 6
<212> TYPE: PRT
<213> ORGANISM: Homo sapiens

<400> SEQUENCE: 2091

Ala Ala Ala Ala Lys Ala
1               5

```
<210> SEQ ID NO 2092
<211> LENGTH: 6
<212> TYPE: PRT
<213> ORGANISM: Homo sapiens

<400> SEQUENCE: 2092

Gly Val Gly Val Pro Gly
1               5

<210> SEQ ID NO 2093
<211> LENGTH: 6
<212> TYPE: PRT
<213> ORGANISM: Homo sapiens

<400> SEQUENCE: 2093

Pro Val Val Pro Gly Ala
1               5

<210> SEQ ID NO 2094
<211> LENGTH: 6
<212> TYPE: PRT
<213> ORGANISM: Homo sapiens

<400> SEQUENCE: 2094

Val Val Ser Pro Glu Ala
1               5

<210> SEQ ID NO 2095
<211> LENGTH: 6
<212> TYPE: PRT
<213> ORGANISM: Homo sapiens

<400> SEQUENCE: 2095

Gly Gly Ile Pro Thr Tyr
1               5

<210> SEQ ID NO 2096
<211> LENGTH: 6
<212> TYPE: PRT
<213> ORGANISM: Homo sapiens

<400> SEQUENCE: 2096

Gly Ile Pro Thr Tyr Gly
1               5

<210> SEQ ID NO 2097
<211> LENGTH: 6
<212> TYPE: PRT
<213> ORGANISM: Homo sapiens

<400> SEQUENCE: 2097

Gly Val Gly Val Gly Gly
1               5

<210> SEQ ID NO 2098
<211> LENGTH: 6
<212> TYPE: PRT
<213> ORGANISM: Homo sapiens

<400> SEQUENCE: 2098

Gly Val Gly Gly Ile Pro
1               5

<210> SEQ ID NO 2099
<211> LENGTH: 6
```

```
<212> TYPE: PRT
<213> ORGANISM: Homo sapiens

<400> SEQUENCE: 2099

Gly Phe Pro Gly Phe Gly
1               5

<210> SEQ ID NO 2100
<211> LENGTH: 6
<212> TYPE: PRT
<213> ORGANISM: Homo sapiens

<400> SEQUENCE: 2100

Phe Gly Val Gly Val Gly
1               5

<210> SEQ ID NO 2101
<211> LENGTH: 6
<212> TYPE: PRT
<213> ORGANISM: Homo sapiens

<400> SEQUENCE: 2101

Pro Gly Val Gly Ile Ser
1               5

<210> SEQ ID NO 2102
<211> LENGTH: 6
<212> TYPE: PRT
<213> ORGANISM: Homo sapiens

<400> SEQUENCE: 2102

Ser Pro Glu Ala Gln Ala
1               5

<210> SEQ ID NO 2103
<211> LENGTH: 6
<212> TYPE: PRT
<213> ORGANISM: Homo sapiens

<400> SEQUENCE: 2103

Gly Val Gly Val Ala Pro
1               5

<210> SEQ ID NO 2104
<211> LENGTH: 6
<212> TYPE: PRT
<213> ORGANISM: Homo sapiens

<400> SEQUENCE: 2104

Ala Pro Gly Val Gly Leu
1               5

<210> SEQ ID NO 2105
<211> LENGTH: 6
<212> TYPE: PRT
<213> ORGANISM: Homo sapiens

<400> SEQUENCE: 2105

Gly Ile Gly Pro Gly Gly
1               5

<210> SEQ ID NO 2106
<211> LENGTH: 6
<212> TYPE: PRT
<213> ORGANISM: Homo sapiens
```

<400> SEQUENCE: 2106

Ala Pro Gly Ile Gly Pro
1               5

<210> SEQ ID NO 2107
<211> LENGTH: 6
<212> TYPE: PRT
<213> ORGANISM: Homo sapiens

<400> SEQUENCE: 2107

Val Ala Pro Gly Ile Gly
1               5

<210> SEQ ID NO 2108
<211> LENGTH: 6
<212> TYPE: PRT
<213> ORGANISM: Homo sapiens

<400> SEQUENCE: 2108

Arg Ala Ala Ala Gly Leu
1               5

<210> SEQ ID NO 2109
<211> LENGTH: 6
<212> TYPE: PRT
<213> ORGANISM: Homo sapiens

<400> SEQUENCE: 2109

Ala Ala Gly Leu Gly Ala
1               5

<210> SEQ ID NO 2110
<211> LENGTH: 6
<212> TYPE: PRT
<213> ORGANISM: Homo sapiens

<400> SEQUENCE: 2110

Gly Val Pro Gly Leu Gly
1               5

<210> SEQ ID NO 2111
<211> LENGTH: 6
<212> TYPE: PRT
<213> ORGANISM: Homo sapiens

<400> SEQUENCE: 2111

Gly Val Pro Gly Phe Gly
1               5

<210> SEQ ID NO 2112
<211> LENGTH: 6
<212> TYPE: PRT
<213> ORGANISM: Homo sapiens

<400> SEQUENCE: 2112

Ala Gly Val Pro Gly Leu
1               5

<210> SEQ ID NO 2113
<211> LENGTH: 6
<212> TYPE: PRT
<213> ORGANISM: Homo sapiens

<400> SEQUENCE: 2113

Gly Ala Gly Pro Ala Ala
1               5

<210> SEQ ID NO 2114
<211> LENGTH: 6
<212> TYPE: PRT
<213> ORGANISM: Homo sapiens

<400> SEQUENCE: 2114

Val Pro Gly Val Gly Gly
1               5

<210> SEQ ID NO 2115
<211> LENGTH: 6
<212> TYPE: PRT
<213> ORGANISM: Homo sapiens

<400> SEQUENCE: 2115

Gly Leu Gly Gly Leu Gly
1               5

<210> SEQ ID NO 2116
<211> LENGTH: 6
<212> TYPE: PRT
<213> ORGANISM: Homo sapiens

<400> SEQUENCE: 2116

Pro Gly Val Gly Gly Leu
1               5

<210> SEQ ID NO 2117
<211> LENGTH: 6
<212> TYPE: PRT
<213> ORGANISM: Homo sapiens

<400> SEQUENCE: 2117

Pro Ala Ala Ala Ala Lys
1               5

<210> SEQ ID NO 2118
<211> LENGTH: 6
<212> TYPE: PRT
<213> ORGANISM: Homo sapiens

<400> SEQUENCE: 2118

Ala Ala Arg Pro Gly Phe
1               5

<210> SEQ ID NO 2119
<211> LENGTH: 6
<212> TYPE: PRT
<213> ORGANISM: Homo sapiens

<400> SEQUENCE: 2119

Leu Ser Pro Ile Phe Pro
1               5

<210> SEQ ID NO 2120
<211> LENGTH: 6
<212> TYPE: PRT
<213> ORGANISM: Homo sapiens

<400> SEQUENCE: 2120

Ala Gln Ala Ala Ala Ala

```
1               5

<210> SEQ ID NO 2121
<211> LENGTH: 6
<212> TYPE: PRT
<213> ORGANISM: Homo sapiens

<400> SEQUENCE: 2121

Gly Pro Gly Ile Pro Gly
1               5

<210> SEQ ID NO 2122
<211> LENGTH: 6
<212> TYPE: PRT
<213> ORGANISM: Homo sapiens

<400> SEQUENCE: 2122

Gly Pro Gly Gly Val Ala
1               5

<210> SEQ ID NO 2123
<211> LENGTH: 6
<212> TYPE: PRT
<213> ORGANISM: Homo sapiens

<400> SEQUENCE: 2123

Gly Leu Gly Ala Leu Gly
1               5

<210> SEQ ID NO 2124
<211> LENGTH: 6
<212> TYPE: PRT
<213> ORGANISM: Homo sapiens

<400> SEQUENCE: 2124

Ala Leu Gly Pro Gly Gly
1               5

<210> SEQ ID NO 2125
<211> LENGTH: 6
<212> TYPE: PRT
<213> ORGANISM: Homo sapiens

<400> SEQUENCE: 2125

Gly Ala Leu Gly Pro Gly
1               5

<210> SEQ ID NO 2126
<211> LENGTH: 6
<212> TYPE: PRT
<213> ORGANISM: Homo sapiens

<400> SEQUENCE: 2126

Val Ala Pro Val Gly Val
1               5

<210> SEQ ID NO 2127
<211> LENGTH: 6
<212> TYPE: PRT
<213> ORGANISM: Homo sapiens

<400> SEQUENCE: 2127

Lys Pro Val Pro Gly Gly
1               5
```

<210> SEQ ID NO 2128
<211> LENGTH: 6
<212> TYPE: PRT
<213> ORGANISM: Homo sapiens

<400> SEQUENCE: 2128

Ala Ala Ala Ala Tyr Lys
1               5

<210> SEQ ID NO 2129
<211> LENGTH: 6
<212> TYPE: PRT
<213> ORGANISM: Homo sapiens

<400> SEQUENCE: 2129

Ala Ala Lys Ala Gly Ala
1               5

<210> SEQ ID NO 2130
<211> LENGTH: 6
<212> TYPE: PRT
<213> ORGANISM: Homo sapiens

<400> SEQUENCE: 2130

Val Pro Gln Pro Gly Ala
1               5

<210> SEQ ID NO 2131
<211> LENGTH: 6
<212> TYPE: PRT
<213> ORGANISM: Homo sapiens

<400> SEQUENCE: 2131

Pro Gly Val Pro Thr Gly
1               5

<210> SEQ ID NO 2132
<211> LENGTH: 6
<212> TYPE: PRT
<213> ORGANISM: Homo sapiens

<400> SEQUENCE: 2132

Gly Val Pro Thr Gly Ala
1               5

<210> SEQ ID NO 2133
<211> LENGTH: 6
<212> TYPE: PRT
<213> ORGANISM: Homo sapiens

<400> SEQUENCE: 2133

Ala Gly Val Lys Pro Lys
1               5

<210> SEQ ID NO 2134
<211> LENGTH: 6
<212> TYPE: PRT
<213> ORGANISM: Homo sapiens

<400> SEQUENCE: 2134

Pro Ile Lys Ala Pro Lys
1               5

<210> SEQ ID NO 2135

```
<211> LENGTH: 6
<212> TYPE: PRT
<213> ORGANISM: Homo sapiens

<400> SEQUENCE: 2135

Lys Leu Pro Gly Gly Tyr
1               5

<210> SEQ ID NO 2136
<211> LENGTH: 6
<212> TYPE: PRT
<213> ORGANISM: Homo sapiens

<400> SEQUENCE: 2136

Tyr Gly Tyr Gly Pro Gly
1               5

<210> SEQ ID NO 2137
<211> LENGTH: 6
<212> TYPE: PRT
<213> ORGANISM: Homo sapiens

<400> SEQUENCE: 2137

Gly Ile Gly Gly Ile Ala
1               5

<210> SEQ ID NO 2138
<211> LENGTH: 6
<212> TYPE: PRT
<213> ORGANISM: Homo sapiens

<400> SEQUENCE: 2138

Gly Thr Pro Ala Ala Ala
1               5

<210> SEQ ID NO 2139
<211> LENGTH: 6
<212> TYPE: PRT
<213> ORGANISM: Homo sapiens

<400> SEQUENCE: 2139

Ile Pro Val Val Pro Gly
1               5

<210> SEQ ID NO 2140
<211> LENGTH: 6
<212> TYPE: PRT
<213> ORGANISM: Homo sapiens

<400> SEQUENCE: 2140

Gly Val Pro Gly Ala Gly
1               5

<210> SEQ ID NO 2141
<211> LENGTH: 6
<212> TYPE: PRT
<213> ORGANISM: Homo sapiens

<400> SEQUENCE: 2141

Pro Glu Ala Ala Ala Lys
1               5

<210> SEQ ID NO 2142
<211> LENGTH: 6
<212> TYPE: PRT
```

<213> ORGANISM: Homo sapiens

<400> SEQUENCE: 2142

Pro Thr Tyr Gly Val Gly
1               5

<210> SEQ ID NO 2143
<211> LENGTH: 6
<212> TYPE: PRT
<213> ORGANISM: Homo sapiens

<400> SEQUENCE: 2143

Thr Tyr Gly Val Gly Ala
1               5

<210> SEQ ID NO 2144
<211> LENGTH: 6
<212> TYPE: PRT
<213> ORGANISM: Homo sapiens

<400> SEQUENCE: 2144

Tyr Gly Val Gly Ala Gly
1               5

<210> SEQ ID NO 2145
<211> LENGTH: 6
<212> TYPE: PRT
<213> ORGANISM: Homo sapiens

<400> SEQUENCE: 2145

Ile Pro Thr Tyr Gly Val
1               5

<210> SEQ ID NO 2146
<211> LENGTH: 6
<212> TYPE: PRT
<213> ORGANISM: Homo sapiens

<400> SEQUENCE: 2146

Pro Gly Ala Ile Pro Gly
1               5

<210> SEQ ID NO 2147
<211> LENGTH: 6
<212> TYPE: PRT
<213> ORGANISM: Homo sapiens

<400> SEQUENCE: 2147

Ala Gly Gly Phe Pro Gly
1               5

<210> SEQ ID NO 2148
<211> LENGTH: 6
<212> TYPE: PRT
<213> ORGANISM: Homo sapiens

<400> SEQUENCE: 2148

Gly Ile Pro Gly Val Ala
1               5

<210> SEQ ID NO 2149
<211> LENGTH: 6
<212> TYPE: PRT
<213> ORGANISM: Homo sapiens

<400> SEQUENCE: 2149

Gly Ile Ser Pro Glu Ala
1               5

<210> SEQ ID NO 2150
<211> LENGTH: 6
<212> TYPE: PRT
<213> ORGANISM: Homo sapiens

<400> SEQUENCE: 2150

Val Pro Gly Ala Pro Gly
1               5

<210> SEQ ID NO 2151
<211> LENGTH: 6
<212> TYPE: PRT
<213> ORGANISM: Homo sapiens

<400> SEQUENCE: 2151

Gly Gly Val Ala Ala Ala
1               5

<210> SEQ ID NO 2152
<211> LENGTH: 6
<212> TYPE: PRT
<213> ORGANISM: Homo sapiens

<400> SEQUENCE: 2152

Pro Gly Ile Gly Pro Gly
1               5

<210> SEQ ID NO 2153
<211> LENGTH: 6
<212> TYPE: PRT
<213> ORGANISM: Homo sapiens

<400> SEQUENCE: 2153

Gly Leu Gly Val Gly Gly
1               5

<210> SEQ ID NO 2154
<211> LENGTH: 6
<212> TYPE: PRT
<213> ORGANISM: Homo sapiens

<400> SEQUENCE: 2154

Pro Gly Leu Gly Val Gly
1               5

<210> SEQ ID NO 2155
<211> LENGTH: 6
<212> TYPE: PRT
<213> ORGANISM: Homo sapiens

<400> SEQUENCE: 2155

Gly Leu Gly Val Gly Ala
1               5

<210> SEQ ID NO 2156
<211> LENGTH: 6
<212> TYPE: PRT
<213> ORGANISM: Homo sapiens

<400> SEQUENCE: 2156

Ala Leu Ala Ala Ala Lys
1               5

<210> SEQ ID NO 2157
<211> LENGTH: 6
<212> TYPE: PRT
<213> ORGANISM: Homo sapiens

<400> SEQUENCE: 2157

Leu Gly Gly Leu Gly Ala
1               5

<210> SEQ ID NO 2158
<211> LENGTH: 6
<212> TYPE: PRT
<213> ORGANISM: Homo sapiens

<400> SEQUENCE: 2158

Gly Gly Leu Gly Val Gly
1               5

<210> SEQ ID NO 2159
<211> LENGTH: 6
<212> TYPE: PRT
<213> ORGANISM: Homo sapiens

<400> SEQUENCE: 2159

Gly Val Gly Gly Leu Gly
1               5

<210> SEQ ID NO 2160
<211> LENGTH: 6
<212> TYPE: PRT
<213> ORGANISM: Homo sapiens

<400> SEQUENCE: 2160

Ala Gly Gln Phe Pro Leu
1               5

<210> SEQ ID NO 2161
<211> LENGTH: 6
<212> TYPE: PRT
<213> ORGANISM: Homo sapiens

<400> SEQUENCE: 2161

Gly Phe Gly Leu Ser Pro
1               5

<210> SEQ ID NO 2162
<211> LENGTH: 6
<212> TYPE: PRT
<213> ORGANISM: Homo sapiens

<400> SEQUENCE: 2162

Pro Ile Phe Pro Gly Gly
1               5

<210> SEQ ID NO 2163
<211> LENGTH: 6
<212> TYPE: PRT
<213> ORGANISM: Homo sapiens

<400> SEQUENCE: 2163

Ile Phe Pro Gly Gly Ala
1               5

```
<210> SEQ ID NO 2164
<211> LENGTH: 6
<212> TYPE: PRT
<213> ORGANISM: Homo sapiens

<400> SEQUENCE: 2164

Ala Ala Lys Phe Gly Ala
1               5

<210> SEQ ID NO 2165
<211> LENGTH: 6
<212> TYPE: PRT
<213> ORGANISM: Homo sapiens

<400> SEQUENCE: 2165

Ala Ala Lys Tyr Gly Ala
1               5

<210> SEQ ID NO 2166
<211> LENGTH: 6
<212> TYPE: PRT
<213> ORGANISM: Homo sapiens

<400> SEQUENCE: 2166

Ala Ala Lys Ala Ala Lys
1               5

<210> SEQ ID NO 2167
<211> LENGTH: 6
<212> TYPE: PRT
<213> ORGANISM: Homo sapiens

<400> SEQUENCE: 2167

Ala Gly Leu Gly Ala Leu
1               5

<210> SEQ ID NO 2168
<211> LENGTH: 6
<212> TYPE: PRT
<213> ORGANISM: Homo sapiens

<400> SEQUENCE: 2168

Gly Ile Pro Gly Gly Val
1               5

<210> SEQ ID NO 2169
<211> LENGTH: 6
<212> TYPE: PRT
<213> ORGANISM: Homo sapiens

<400> SEQUENCE: 2169

Pro Gly Val Gly Val Gly
1               5

<210> SEQ ID NO 2170
<211> LENGTH: 6
<212> TYPE: PRT
<213> ORGANISM: Homo sapiens

<400> SEQUENCE: 2170

Ile Pro Pro Ala Ala Ala
1               5
```

<210> SEQ ID NO 2171
<211> LENGTH: 6
<212> TYPE: PRT
<213> ORGANISM: Homo sapiens

<400> SEQUENCE: 2171

Ala Arg Pro Gly Phe Gly
1               5

<210> SEQ ID NO 2172
<211> LENGTH: 6
<212> TYPE: PRT
<213> ORGANISM: Homo sapiens

<400> SEQUENCE: 2172

Val Leu Pro Gly Ala Arg
1               5

<210> SEQ ID NO 2173
<211> LENGTH: 6
<212> TYPE: PRT
<213> ORGANISM: Homo sapiens

<400> SEQUENCE: 2173

Gly Gly Phe Pro Gly Phe
1               5

<210> SEQ ID NO 2174
<211> LENGTH: 6
<212> TYPE: PRT
<213> ORGANISM: Homo sapiens

<400> SEQUENCE: 2174

Gly Leu Ser Pro Ile Phe
1               5

<210> SEQ ID NO 2175
<211> LENGTH: 6
<212> TYPE: PRT
<213> ORGANISM: Homo sapiens

<400> SEQUENCE: 2175

Pro Thr Gly Ala Gly Val
1               5

<210> SEQ ID NO 2176
<211> LENGTH: 6
<212> TYPE: PRT
<213> ORGANISM: Homo sapiens

<400> SEQUENCE: 2176

Ala Gly Ala Ala Gly Lys
1               5

<210> SEQ ID NO 2177
<211> LENGTH: 10
<212> TYPE: PRT
<213> ORGANISM: Homo sapiens

<400> SEQUENCE: 2177

Arg Leu Arg Ser Ser Val Pro Gly Val Arg
1               5                   10

<210> SEQ ID NO 2178
<211> LENGTH: 10

<212> TYPE: PRT
<213> ORGANISM: Homo sapiens

<400> SEQUENCE: 2178

Arg Leu Arg Ser Ser Val Pro Gly Val Leu
1               5                   10

<210> SEQ ID NO 2179
<211> LENGTH: 10
<212> TYPE: PRT
<213> ORGANISM: Homo sapiens

<400> SEQUENCE: 2179

Leu Leu Gln Asp Ser Val Asp Phe Ser Leu
1               5                   10

<210> SEQ ID NO 2180
<211> LENGTH: 10
<212> TYPE: PRT
<213> ORGANISM: Homo sapiens

<400> SEQUENCE: 2180

Phe Ala Asp Leu Ser Glu Ala Ala Asn Arg
1               5                   10

<210> SEQ ID NO 2181
<211> LENGTH: 10
<212> TYPE: PRT
<213> ORGANISM: Homo sapiens

<400> SEQUENCE: 2181

Ile Ser Leu Pro Leu Pro Thr Phe Ser Ser
1               5                   10

<210> SEQ ID NO 2182
<211> LENGTH: 6
<212> TYPE: PRT
<213> ORGANISM: Homo sapiens

<400> SEQUENCE: 2182

Leu Leu Gln Asp Ser Val
1               5

<210> SEQ ID NO 2183
<211> LENGTH: 6
<212> TYPE: PRT
<213> ORGANISM: Homo sapiens

<400> SEQUENCE: 2183

Phe Ala Asp Leu Ser Glu
1               5

<210> SEQ ID NO 2184
<211> LENGTH: 6
<212> TYPE: PRT
<213> ORGANISM: Homo sapiens

<400> SEQUENCE: 2184

Ile Ser Leu Pro Leu Pro
1               5

<210> SEQ ID NO 2185
<211> LENGTH: 6
<212> TYPE: PRT
<213> ORGANISM: Homo sapiens

```
<400> SEQUENCE: 2185

Ser Val Pro Gly Val Arg
1               5

<210> SEQ ID NO 2186
<211> LENGTH: 6
<212> TYPE: PRT
<213> ORGANISM: Homo sapiens

<400> SEQUENCE: 2186

Ser Val Pro Gly Val Leu
1               5

<210> SEQ ID NO 2187
<211> LENGTH: 6
<212> TYPE: PRT
<213> ORGANISM: Homo sapiens

<400> SEQUENCE: 2187

Gly Pro Pro Gly Ile Cys
1               5

<210> SEQ ID NO 2188
<211> LENGTH: 6
<212> TYPE: PRT
<213> ORGANISM: Homo sapiens

<400> SEQUENCE: 2188

Leu Pro Gly Ala Ala Gly
1               5

<210> SEQ ID NO 2189
<211> LENGTH: 6
<212> TYPE: PRT
<213> ORGANISM: Homo sapiens

<400> SEQUENCE: 2189

Ala Pro Gly Pro Leu Gly
1               5

<210> SEQ ID NO 2190
<211> LENGTH: 9
<212> TYPE: PRT
<213> ORGANISM: Homo sapiens

<400> SEQUENCE: 2190

Ile Leu Gly His Val Pro Gly Met Leu
1               5

<210> SEQ ID NO 2191
<211> LENGTH: 17
<212> TYPE: PRT
<213> ORGANISM: Homo sapiens

<400> SEQUENCE: 2191

Pro Gly Leu Pro Gly Gln Pro Gly Pro Pro Gly Leu Pro Val Pro Gly
1               5                   10                  15

Gln

<210> SEQ ID NO 2192
<211> LENGTH: 42
<212> TYPE: PRT
<213> ORGANISM: Homo sapiens
```

<400> SEQUENCE: 2192

Ser Gly Tyr Pro Gly Asn Pro Gly Leu Pro Gly Ile Pro Gly Gln Asp
1               5                   10                  15

Gly Pro Pro Gly Pro Pro Gly Ile Pro Gly Cys Asn Gly Thr Lys Gly
            20                  25                  30

Glu Arg Gly Pro Leu Gly Pro Pro Gly Leu
        35                  40

<210> SEQ ID NO 2193
<211> LENGTH: 11
<212> TYPE: PRT
<213> ORGANISM: Homo sapiens

<400> SEQUENCE: 2193

Val Ser Gly Pro Pro Gly Val Pro Gly Gln Ala
1               5                   10

<210> SEQ ID NO 2194
<211> LENGTH: 12
<212> TYPE: PRT
<213> ORGANISM: Homo sapiens

<400> SEQUENCE: 2194

Val Ser Gly Pro Pro Gly Val Pro Gly Gln Ala Gln
1               5                   10

<210> SEQ ID NO 2195
<211> LENGTH: 20
<212> TYPE: PRT
<213> ORGANISM: Homo sapiens

<400> SEQUENCE: 2195

Lys Arg Gly Pro Pro Gly Pro Pro Gly Leu Pro Gly Pro Gly Pro
1               5                   10                  15

Asp Gly Phe Leu
            20

<210> SEQ ID NO 2196
<211> LENGTH: 15
<212> TYPE: PRT
<213> ORGANISM: Homo sapiens

<400> SEQUENCE: 2196

Leu His Gly Phe Pro Gly Ala Pro Gly Gln Glu Gly Pro Leu Gly
1               5                   10                  15

<210> SEQ ID NO 2197
<211> LENGTH: 18
<212> TYPE: PRT
<213> ORGANISM: Homo sapiens

<400> SEQUENCE: 2197

Leu Pro Gly Pro Asp Gly Pro Pro Gly Glu Arg Gly Leu Pro Gly Glu
1               5                   10                  15

Val Leu

<210> SEQ ID NO 2198
<211> LENGTH: 7
<212> TYPE: PRT
<213> ORGANISM: Homo sapiens

<400> SEQUENCE: 2198

Leu Arg Gly Ile Pro Gly Phe
1               5

<210> SEQ ID NO 2199
<211> LENGTH: 21
<212> TYPE: PRT
<213> ORGANISM: Homo sapiens

<400> SEQUENCE: 2199

Pro Gly Phe Pro Gly Ala Pro Gly Thr Val Gly Ala Pro Gly Ile Ala
1               5                   10                  15

Gly Ile Pro Gln Lys
            20

<210> SEQ ID NO 2200
<211> LENGTH: 9
<212> TYPE: PRT
<213> ORGANISM: Homo sapiens

<400> SEQUENCE: 2200

Gln Gln Gly Asn Arg Gly Leu Gly Phe
1               5

<210> SEQ ID NO 2201
<211> LENGTH: 14
<212> TYPE: PRT
<213> ORGANISM: Homo sapiens

<400> SEQUENCE: 2201

Val Gly Gln Pro Gly Pro Asn Gly Ile Pro Ser Asp Thr Leu
1               5                   10

<210> SEQ ID NO 2202
<211> LENGTH: 43
<212> TYPE: PRT
<213> ORGANISM: Homo sapiens

<400> SEQUENCE: 2202

Gly Glu Pro Gly Met Gln Gly Glu Pro Gly Pro Pro Gly Pro Pro Gly
1               5                   10                  15

Asn Leu Gly Pro Cys Gly Pro Arg Gly Lys Pro Gly Lys Asp Gly Lys
            20                  25                  30

Pro Gly Thr Pro Gly Pro Ala Gly Glu Lys Gly
        35                  40

<210> SEQ ID NO 2203
<211> LENGTH: 39
<212> TYPE: PRT
<213> ORGANISM: Homo sapiens

<400> SEQUENCE: 2203

Gly Glu Pro Gly Pro Pro Gly Pro Gly Asn Leu Gly Pro Cys Gly
1               5                   10                  15

Pro Arg Gly Lys Pro Gly Lys Asp Gly Lys Pro Gly Thr Pro Gly Pro
            20                  25                  30

Ala Gly Glu Lys Gly Asn Lys
        35

<210> SEQ ID NO 2204
<211> LENGTH: 23
<212> TYPE: PRT
<213> ORGANISM: Homo sapiens

<400> SEQUENCE: 2204

Pro Gly Ile Pro Gly Thr Pro Gly Pro Gly Leu Pro Gly Leu Gln
1               5                   10                  15

Gly Pro Val Gly Pro Pro Gly
            20

<210> SEQ ID NO 2205
<211> LENGTH: 8
<212> TYPE: PRT
<213> ORGANISM: Homo sapiens

<400> SEQUENCE: 2205

Pro Gly Asp Ile Val Phe Arg Lys
1               5

<210> SEQ ID NO 2206
<211> LENGTH: 17
<212> TYPE: PRT
<213> ORGANISM: Homo sapiens

<400> SEQUENCE: 2206

Gly Asn Lys Gly Asp Pro Ala Ser His Phe Gly Pro Gly Pro Lys
1               5                   10                  15

Gly

<210> SEQ ID NO 2207
<211> LENGTH: 9
<212> TYPE: PRT
<213> ORGANISM: Homo sapiens

<400> SEQUENCE: 2207

Pro Gly Pro Arg Gly Lys Pro Gly Met
1               5

<210> SEQ ID NO 2208
<211> LENGTH: 12
<212> TYPE: PRT
<213> ORGANISM: Homo sapiens

<400> SEQUENCE: 2208

Pro Gly Leu Pro Gly Gln Pro Gly Thr Arg Gly Leu
1               5                   10

<210> SEQ ID NO 2209
<211> LENGTH: 40
<212> TYPE: PRT
<213> ORGANISM: Homo sapiens

<400> SEQUENCE: 2209

Pro Gly Pro Pro Gly Pro Leu Gly Ile Pro Gly Arg Ser Gly Val Pro
1               5                   10                  15

Gly Leu Lys Gly Asp Asp Gly Leu Gln Gly Gln Pro Gly Leu Pro Gly
            20                  25                  30

Pro Thr Gly Glu Lys Gly Ser Lys
        35                  40

<210> SEQ ID NO 2210
<211> LENGTH: 41
<212> TYPE: PRT
<213> ORGANISM: Homo sapiens

<400> SEQUENCE: 2210

```
Pro Gly Pro Pro Gly Pro Leu Gly Ile Pro Gly Arg Ser Gly Val Pro
1               5                   10                  15

Gly Leu Lys Gly Asp Asp Gly Leu Gln Gly Gln Pro Gly Leu Pro Gly
            20                  25                  30

Pro Thr Gly Glu Lys Gly Ser Lys Gly
        35                  40

<210> SEQ ID NO 2211
<211> LENGTH: 40
<212> TYPE: PRT
<213> ORGANISM: Homo sapiens

<400> SEQUENCE: 2211

Ser Lys Gly Glu Lys Gly Glu Pro Gly Leu Pro Gly Ile Pro Gly Val
1               5                   10                  15

Ser Gly Pro Lys Gly Tyr Gln Gly Leu Pro Gly Asp Pro Gly Gln Pro
            20                  25                  30

Gly Leu Ser Gly Gln Pro Gly Leu
        35                  40

<210> SEQ ID NO 2212
<211> LENGTH: 6
<212> TYPE: PRT
<213> ORGANISM: Homo sapiens

<400> SEQUENCE: 2212

Ile Leu Gly His Val Pro
1               5

<210> SEQ ID NO 2213
<211> LENGTH: 6
<212> TYPE: PRT
<213> ORGANISM: Homo sapiens

<400> SEQUENCE: 2213

Pro Gly Leu Pro Gly Gln
1               5

<210> SEQ ID NO 2214
<211> LENGTH: 6
<212> TYPE: PRT
<213> ORGANISM: Homo sapiens

<400> SEQUENCE: 2214

Leu Pro Gly Pro Asp Gly
1               5

<210> SEQ ID NO 2215
<211> LENGTH: 6
<212> TYPE: PRT
<213> ORGANISM: Homo sapiens

<400> SEQUENCE: 2215

Pro Gly Asp Ile Val Phe
1               5

<210> SEQ ID NO 2216
<211> LENGTH: 6
<212> TYPE: PRT
<213> ORGANISM: Homo sapiens

<400> SEQUENCE: 2216
```

Gly Asn Lys Gly Asp Pro
1               5

<210> SEQ ID NO 2217
<211> LENGTH: 6
<212> TYPE: PRT
<213> ORGANISM: Homo sapiens

<400> SEQUENCE: 2217

Ser Gly Tyr Pro Gly Asn
1               5

<210> SEQ ID NO 2218
<211> LENGTH: 6
<212> TYPE: PRT
<213> ORGANISM: Homo sapiens

<400> SEQUENCE: 2218

Pro Gly Phe Pro Gly Ala
1               5

<210> SEQ ID NO 2219
<211> LENGTH: 6
<212> TYPE: PRT
<213> ORGANISM: Homo sapiens

<400> SEQUENCE: 2219

Pro Gly Pro Arg Gly Lys
1               5

<210> SEQ ID NO 2220
<211> LENGTH: 6
<212> TYPE: PRT
<213> ORGANISM: Homo sapiens

<400> SEQUENCE: 2220

Val Ser Gly Pro Pro Gly
1               5

<210> SEQ ID NO 2221
<211> LENGTH: 6
<212> TYPE: PRT
<213> ORGANISM: Homo sapiens

<400> SEQUENCE: 2221

Gln Gln Gly Asn Arg Gly
1               5

<210> SEQ ID NO 2222
<211> LENGTH: 6
<212> TYPE: PRT
<213> ORGANISM: Homo sapiens

<400> SEQUENCE: 2222

Val Gly Gln Pro Gly Pro
1               5

<210> SEQ ID NO 2223
<211> LENGTH: 6
<212> TYPE: PRT
<213> ORGANISM: Homo sapiens

<400> SEQUENCE: 2223

Lys Arg Gly Pro Pro Gly
1               5

<210> SEQ ID NO 2224
<211> LENGTH: 6
<212> TYPE: PRT
<213> ORGANISM: Homo sapiens

<400> SEQUENCE: 2224

Gly Glu Pro Gly Met Gln
1               5

<210> SEQ ID NO 2225
<211> LENGTH: 6
<212> TYPE: PRT
<213> ORGANISM: Homo sapiens

<400> SEQUENCE: 2225

Leu His Gly Phe Pro Gly
1               5

<210> SEQ ID NO 2226
<211> LENGTH: 6
<212> TYPE: PRT
<213> ORGANISM: Homo sapiens

<400> SEQUENCE: 2226

Ser Lys Gly Glu Lys Gly
1               5

<210> SEQ ID NO 2227
<211> LENGTH: 6
<212> TYPE: PRT
<213> ORGANISM: Homo sapiens

<400> SEQUENCE: 2227

Pro Gly Ile Pro Gly Thr
1               5

<210> SEQ ID NO 2228
<211> LENGTH: 6
<212> TYPE: PRT
<213> ORGANISM: Homo sapiens

<400> SEQUENCE: 2228

His Val Pro Gly Met Leu
1               5

<210> SEQ ID NO 2229
<211> LENGTH: 6
<212> TYPE: PRT
<213> ORGANISM: Homo sapiens

<400> SEQUENCE: 2229

Leu Pro Val Pro Gly Gln
1               5

<210> SEQ ID NO 2230
<211> LENGTH: 6
<212> TYPE: PRT
<213> ORGANISM: Homo sapiens

<400> SEQUENCE: 2230

Leu Gly Pro Pro Gly Leu
1               5

```
<210> SEQ ID NO 2231
<211> LENGTH: 6
<212> TYPE: PRT
<213> ORGANISM: Homo sapiens

<400> SEQUENCE: 2231

Gly Val Pro Gly Gln Ala
1               5

<210> SEQ ID NO 2232
<211> LENGTH: 6
<212> TYPE: PRT
<213> ORGANISM: Homo sapiens

<400> SEQUENCE: 2232

Val Pro Gly Gln Ala Gln
1               5

<210> SEQ ID NO 2233
<211> LENGTH: 6
<212> TYPE: PRT
<213> ORGANISM: Homo sapiens

<400> SEQUENCE: 2233

Gly Pro Asp Gly Phe Leu
1               5

<210> SEQ ID NO 2234
<211> LENGTH: 6
<212> TYPE: PRT
<213> ORGANISM: Homo sapiens

<400> SEQUENCE: 2234

Gln Glu Gly Pro Leu Gly
1               5

<210> SEQ ID NO 2235
<211> LENGTH: 6
<212> TYPE: PRT
<213> ORGANISM: Homo sapiens

<400> SEQUENCE: 2235

Leu Pro Gly Glu Val Leu
1               5

<210> SEQ ID NO 2236
<211> LENGTH: 6
<212> TYPE: PRT
<213> ORGANISM: Homo sapiens

<400> SEQUENCE: 2236

Arg Gly Ile Pro Gly Phe
1               5

<210> SEQ ID NO 2237
<211> LENGTH: 6
<212> TYPE: PRT
<213> ORGANISM: Homo sapiens

<400> SEQUENCE: 2237

Ala Gly Ile Pro Gln Lys
1               5

<210> SEQ ID NO 2238
<211> LENGTH: 6
```

```
<212> TYPE: PRT
<213> ORGANISM: Homo sapiens

<400> SEQUENCE: 2238

Asn Arg Gly Leu Gly Phe
1               5

<210> SEQ ID NO 2239
<211> LENGTH: 6
<212> TYPE: PRT
<213> ORGANISM: Homo sapiens

<400> SEQUENCE: 2239

Ile Pro Ser Asp Thr Leu
1               5

<210> SEQ ID NO 2240
<211> LENGTH: 6
<212> TYPE: PRT
<213> ORGANISM: Homo sapiens

<400> SEQUENCE: 2240

Pro Ala Gly Glu Lys Gly
1               5

<210> SEQ ID NO 2241
<211> LENGTH: 6
<212> TYPE: PRT
<213> ORGANISM: Homo sapiens

<400> SEQUENCE: 2241

Gly Glu Lys Gly Asn Lys
1               5

<210> SEQ ID NO 2242
<211> LENGTH: 6
<212> TYPE: PRT
<213> ORGANISM: Homo sapiens

<400> SEQUENCE: 2242

Pro Val Gly Pro Pro Gly
1               5

<210> SEQ ID NO 2243
<211> LENGTH: 6
<212> TYPE: PRT
<213> ORGANISM: Homo sapiens

<400> SEQUENCE: 2243

Asp Ile Val Phe Arg Lys
1               5

<210> SEQ ID NO 2244
<211> LENGTH: 6
<212> TYPE: PRT
<213> ORGANISM: Homo sapiens

<400> SEQUENCE: 2244

Arg Gly Lys Pro Gly Met
1               5

<210> SEQ ID NO 2245
<211> LENGTH: 6
<212> TYPE: PRT
<213> ORGANISM: Homo sapiens
```

<400> SEQUENCE: 2245

Pro Gly Thr Arg Gly Leu
1               5

<210> SEQ ID NO 2246
<211> LENGTH: 6
<212> TYPE: PRT
<213> ORGANISM: Homo sapiens

<400> SEQUENCE: 2246

Gly Glu Lys Gly Ser Lys
1               5

<210> SEQ ID NO 2247
<211> LENGTH: 6
<212> TYPE: PRT
<213> ORGANISM: Homo sapiens

<400> SEQUENCE: 2247

Glu Lys Gly Ser Lys Gly
1               5

<210> SEQ ID NO 2248
<211> LENGTH: 6
<212> TYPE: PRT
<213> ORGANISM: Homo sapiens

<400> SEQUENCE: 2248

Ser Gly Gln Pro Gly Leu
1               5

<210> SEQ ID NO 2249
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Leucine or Isoleucine

<400> SEQUENCE: 2249

Xaa Tyr Asp Gly Lys Gly Val Gly
1               5

<210> SEQ ID NO 2250
<211> LENGTH: 8
<212> TYPE: PRT
<213> ORGANISM: Homo sapiens

<400> SEQUENCE: 2250

Glu Lys Ala His Asp Gly Gly Arg
1               5

<210> SEQ ID NO 2251
<211> LENGTH: 8
<212> TYPE: PRT
<213> ORGANISM: Homo sapiens

<400> SEQUENCE: 2251

Lys Asn Gly Glu Thr Gly Pro Gln
1               5

<210> SEQ ID NO 2252
<211> LENGTH: 13

```
<212> TYPE: PRT
<213> ORGANISM: Homo sapiens

<400> SEQUENCE: 2252

Lys Asn Gly Glu Thr Gly Pro Gln Gly Pro Gly Gly Cys
1               5                   10

<210> SEQ ID NO 2253
<211> LENGTH: 13
<212> TYPE: PRT
<213> ORGANISM: Homo sapiens

<400> SEQUENCE: 2253

Lys Asn Gly Glu Thr Gly Pro Gln Gly Pro Pro Gly Lys
1               5                   10

<210> SEQ ID NO 2254
<211> LENGTH: 13
<212> TYPE: PRT
<213> ORGANISM: Homo sapiens

<400> SEQUENCE: 2254

Lys Asp Gly Glu Thr Gly Ala Ala Gly Pro Pro Gly Lys
1               5                   10

<210> SEQ ID NO 2255
<211> LENGTH: 13
<212> TYPE: PRT
<213> ORGANISM: Homo sapiens

<400> SEQUENCE: 2255

Lys Asp Gly Glu Ala Gly Ala Gln Gly Pro Pro Gly Lys
1               5                   10

<210> SEQ ID NO 2256
<211> LENGTH: 10
<212> TYPE: PRT
<213> ORGANISM: Homo sapiens

<400> SEQUENCE: 2256

Lys Asn Gly Glu Thr Gly Pro Gln Gly Pro
1               5                   10
```